United States Patent
Xu

(10) Patent No.: US 9,745,321 B2
(45) Date of Patent: *Aug. 29, 2017

(54) FUSED PYRIMIDINE COMPOUND, INTERMEDIATE, PREPARATION METHOD THEREFOR, AND COMPOSITION AND APPLICATION THEREOF

(71) Applicant: SHANGHAI YINGLI PHARMACEUTICAL CO., LTD, Shanghai (CN)

(72) Inventor: Zusheng Xu, Shanghai (CN)

(73) Assignee: SHANGHAI YINGLI PHARMACEUTICAL CO., LTD, Shanghai (CN)

( * ) Notice: Subject to any disclaimer, the term of this patent is extended or adjusted under 35 U.S.C. 154(b) by 0 days.

This patent is subject to a terminal disclaimer.

(21) Appl. No.: 15/025,618

(22) PCT Filed: Sep. 17, 2014

(86) PCT No.: PCT/CN2014/086683
§ 371 (c)(1),
(2) Date: Mar. 29, 2016

(87) PCT Pub. No.: WO2015/043398
PCT Pub. Date: Apr. 2, 2015

(65) Prior Publication Data
US 2016/0214994 A1 Jul. 28, 2016

(30) Foreign Application Priority Data
Sep. 30, 2013 (CN) .......................... 2013 1 0461133

(51) Int. Cl.
| C07D 495/04 | (2006.01) |
| C07D 493/04 | (2006.01) |
| C07D 491/04 | (2006.01) |
| C07D 491/048 | (2006.01) |
| C07D 519/00 | (2006.01) |

(52) U.S. Cl.
CPC ....... *C07D 495/04* (2013.01); *C07D 491/048* (2013.01); *C07D 493/04* (2013.01); *C07D 519/00* (2013.01)

(58) Field of Classification Search
CPC . C07D 493/04; C07D 495/04; C07D 491/048
See application file for complete search history.

(56) References Cited

U.S. PATENT DOCUMENTS

| 3,475,429 A * | 10/1969 | Eberhard ............. C07D 495/04 514/822 |
| 8,129,371 B2 | 3/2012 | Zask et al. |
| 8,153,639 B2 | 4/2012 | Chuckowree et al. |
| 2004/0266780 A1 | 12/2004 | Sadhu et al. |
| 2005/0153964 A1 | 7/2005 | Leach et al. |
| 2007/0185075 A1 | 8/2007 | Bell et al. |
| 2008/0076758 A1 | 3/2008 | Folkes et al. |
| 2008/0207609 A1 | 8/2008 | Shuttleworth et al. |
| 2008/0207611 A1 | 8/2008 | Shuttleworth et al. |
| 2008/0269210 A1 | 10/2008 | Castanedo et al. |
| 2009/0098086 A1 | 4/2009 | Zask et al. |
| 2009/0131429 A1 | 5/2009 | Shutteleworth et al. |

(Continued)

FOREIGN PATENT DOCUMENTS

| CN | 101675053 A | 3/2010 |
| CN | 102014914 A1 | 4/2011 |

(Continued)

OTHER PUBLICATIONS

International Search Report and Written Opinion from PCT/CN2014/086683 dated Dec. 24, 2014.
Gary A. Molander et al., "Synthesis of Functionalized Organotrifluoroborates via Halomethyltrifluoroborates," Org. Lett., 2006 vol. 8 (10), pp. 2031-2034.
Jessica Raushel et al., "Reinvestigation of Aminomethyltrifluoroborates and Their Application in Suzuki-Miyaura Cross-Coupling Reactions," J. Org. Chem., 2011, 76, pp. 2762-2769.
Hello A. Stefani et al., "Recent advances in organotrifluoroborates chemistry," Tetrahedron 63 (2007), pp. 3623-3658.
Sylvain Darses et al., "Potassium Organotrifluoroborates: New Perspectives in Organic Synthesis," Chem. Rev. 2008, 108, pp. 288-325.

(Continued)

*Primary Examiner* — Nyeemah A Grazier
(74) *Attorney, Agent, or Firm* — Millen White Zelano and Branigan, PC; John Sopp; Anthony Zelano

(57) ABSTRACT

Disclosed are a fused pyrimidine compound, an intermediate, a preparation method therefor, and a composition and an application thereof. The present invention provides a fused pyrimidine compound shown in formula I, pharmaceutically acceptable salt, hydrate, solvate, and an optical isomer or prodrug of the compound. The present invention further provides applications of the fused pyrimidine compound shown in formula I, the pharmaceutically acceptable salt, the hydrate, solvate, and the optical isomer or the prodrug of the compound in the preparing drugs for curing and/or preventing a kinase-related disease. The fused pyrimidine compound I of the present invention is an efficient PI3 kinase depressor, and can be used to prepare drugs for preventing and/or curing cell-proliferation diseases such as cancer, infection, inflammation, and an autoimmune disease.

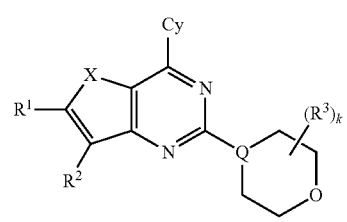

45 Claims, No Drawings

(56) References Cited

U.S. PATENT DOCUMENTS

| | | |
|---|---|---|
| 2009/0181963 A1 | 7/2009 | Dehnhardt et al. |
| 2009/0209559 A1 | 8/2009 | Chuckowree et al. |
| 2010/0234370 A1 | 9/2010 | Shuttleworth et al. |
| 2010/0280027 A1 | 11/2010 | Shuttleworth et al. |
| 2011/0105464 A1 | 5/2011 | Castanedo et al. |
| 2011/0112070 A1 | 5/2011 | Baldwin et al. |
| 2011/0118246 A1 | 5/2011 | Baldwin et al. |
| 2011/0123434 A1 | 5/2011 | Lamb et al. |
| 2011/0130395 A1 | 6/2011 | Liang et al. |
| 2011/0178070 A1 | 7/2011 | Gong et al. |
| 2011/0207712 A1 | 8/2011 | Bajjalieh et al. |
| 2012/0015931 A1 | 1/2012 | Li et al. |
| 2012/0252802 A1 | 10/2012 | Brown et al. |
| 2012/0258966 A1 | 10/2012 | Shuttleworth et al. |
| 2012/0309773 A1 | 12/2012 | Babu et al. |
| 2013/0102595 A1 | 4/2013 | Bao et al. |
| 2013/0165433 A1 | 6/2013 | Baldwin et al. |
| 2013/0165441 A1 | 6/2013 | Hamblin et al. |
| 2013/0289064 A1 | 10/2013 | Stowasser et al. |
| 2013/0317017 A1 | 11/2013 | Shuttleworth et al. |
| 2013/0324561 A1 | 12/2013 | Evarts et al. |
| 2014/0005163 A1 | 1/2014 | Furet et al. |
| 2014/0051699 A1 | 2/2014 | Liang |
| 2014/0058103 A1 | 2/2014 | Kearney |
| 2014/0221367 A1 | 8/2014 | Chuckowree et al. |
| 2014/0294946 A1 | 10/2014 | Shuttleworth et al. |
| 2014/0309216 A1 | 10/2014 | Folkes et al. |
| 2015/0246929 A1 | 9/2015 | Xu |

FOREIGN PATENT DOCUMENTS

| | | |
|---|---|---|
| CN | 103242341 A | 8/2013 |
| CN | 104513254 A | 4/2015 |
| WO | 03087088 A2 | 10/2003 |
| WO | 2006/046031 A1 | 5/2006 |
| WO | 2007023382 A2 | 3/2007 |
| WO | 2007044729 A2 | 4/2007 |
| WO | 2007072163 A2 | 6/2007 |
| WO | 2007/127175 A2 | 11/2007 |
| WO | 2007127183 A1 | 11/2007 |
| WO | 2007129161 A2 | 11/2007 |
| WO | 2007132171 A1 | 11/2007 |
| WO | 2008064093 A2 | 5/2008 |
| WO | 2008127594 A2 | 10/2008 |
| WO | 2009052145 A1 | 4/2009 |
| WO | 2009147187 A1 | 12/2009 |
| WO | 2009147190 A1 | 12/2009 |
| WO | 2010/005558 A2 | 1/2010 |
| WO | 2010008847 A2 | 1/2010 |
| WO | 2010091808 A1 | 8/2010 |
| WO | 2010120987 A1 | 10/2010 |
| WO | 2010120994 A2 | 10/2010 |
| WO | 2010139731 A1 | 12/2010 |
| WO | 2011041399 A2 | 4/2011 |
| WO | 2011079230 A2 | 6/2011 |
| WO | 2011101429 A1 | 8/2011 |
| WO | 2012007493 A1 | 1/2012 |
| WO | 2012032065 A1 | 3/2012 |
| WO | 2012032067 A1 | 3/2012 |
| WO | 2012037108 A1 | 3/2012 |
| WO | 2012037226 A1 | 3/2012 |
| WO | 2012040634 A1 | 3/2012 |
| WO | 2012135160 A1 | 10/2012 |
| WO | 2013152717 A1 | 10/2013 |

OTHER PUBLICATIONS

Norio Miyaura et al., "Palladium-Catalyzed Cross-Coupling Reactions of Organoboron Compounds," Chem. Rev. 1995 95,pp. 2457-2483.

Paul Knocher, et al., "Organozinc Mediated Reactions," Tetrahedron 54 (1998) pp. 8275-8319.

Alexey G. Sergeev et al., "Palladium-Catalyzed Hydroxylation of Aryl Halides under Ambient Conditions," Angew. Chem. Int. Ed. 2009, 48, pp. 7595-7599.

Roger J. Gillespie et al., "Antagonists of the human adenosine A2A receptor. Part 2: Design and synthesis of 4-arylthieno[3,2-d]pyrimidine derivatives," Bioorganic & Medicinal Chemistry Letters 18 (2008) pp. 2920-2923.

Roger J. Gillespie et al., "Antagonists of the human adenosine A2A receptor. Part 3: Design and synthesis of pyrazolo [3,4-d]pyrimidines, pyrrolo[2,3-d]pyrimidines and 6-arylpurines," Bioorganic & Medicinal Chemistry Letters 18 (2008) pp. 2924-2929.

Jelena Dodonova et al., "Synthesis of 4-aryl-, 2,4-diaryl- and 2,4,7-triarylpyrrolo[2,3-d]pyrimidines by a combination of the Suzuki cross-coupling and N-arylation reactions," Tetrahedron 68 (2012) pp. 329-339.

Yitzhak Tor et al., "Designing new isomorphic fluorescent nucleobase analogues: the thieno[3,2-d]pyrimidine core," Tetrahedron 2007, 63, pp. 3608-3614.

Brian S. Safina et al., "Discovery of Novel PI3-Kinase δ Specific Inhibitors for the Treatment of Rheumatoid Arthritis: Taming CYP3A4 Time-Dependent Inhibition," Journal of Medicinal Chemistry, 2011, pp. 5887-5900.

Albrecht Metzger et al., "Polyfunctional benzylic zinc chlorides by the direct insertion of magnesium into benzylic chlorides in the presence of LiCl and ZnCl2," Chemical Communication, 2008, pp. 5824-5826.

Chinese Patent Application CN201310461133A (not published).

Japanese Patent Application JP2016-519343 (not published).

European Patent Application EP14847916.5 (not published).

English translation of CN104513254A published Apr. 15, 2015, 194 pages.

Amancio Camera "Novel inhibitors of the PI3K family", Expert Opinion On Investigational Drugs, vol. 18, No. 9, Sep. 2009 (Sep. 2009), pp. 1265-1277, XP055004998.

Machine Translation of CN 103242341 A, Publication Date: Aug. 14, 2013.

Supplementary European Search Report, Annex To The European Search Report corresponding to EP 14 84 7916, dated Mar. 31, 2017: Date of Completion of the Search: Mar. 22, 2017.

\* cited by examiner

FUSED PYRIMIDINE COMPOUND, INTERMEDIATE, PREPARATION METHOD THEREFOR, AND COMPOSITION AND APPLICATION THEREOF

The application claims priority of Chinese Patent Application CN201310461133.4 filed on Sep. 30, 2013, the disclosure of which is incorporated herein by reference in its entirety.

FIELD OF INVENTION

The present invention relates to a fused pyrimidine compound, an intermediate, a preparation method, a composition and a use thereof.

PRIOR ARTS

Phosphoinositide 3-kinase (PI3K) is an intracellular phosphatidylinositol kinase which can catalyze the phosphorylation of hydroxyl group at 3-position of the phosphatidylinositol. The PI3K may be classified into Class I, Class II and Class III kinase and the most extensively studied one is the Class I PI3K which can be activated by cell surface receptors. The Class I PI3K in mammalian cells is further divided into Class Ia and Class Ib based on structure and receptor, which transducts signals from tyrosine kinase-coupled receptors and G protein-coupled receptors, respectively. The Class Ia PI3K includes PI3Kα, PI3Kβ and PI3Kδ subtypes, and the Class Ib PI3K includes PI3Kγ subtype (*Trends Biochem. Sci.*, 1997, 22, 267-272). The Class Ia PI3K is a dimeric protein consisting of a p110 catalytic subunit and a p85 regulatory subunit and having dual activities of a lipid kinase and a protein kinase (*Nat. Rev. Cancer* 2002, 2, 489-501), and is considered to be correlated with cell proliferation and cancer development, immune diseases and inflammation related diseases.

Some compounds as PI3K inhibitors have been disclosed by prior art, such as: WO2008064093, WO2007044729, WO2008127594, WO2007127183, WO2007129161, US20040266780, WO2007072163, WO2009147187, WO2009147190, WO2010120987, WO2010120994, WO2010091808, WO2011101429, WO2011041399, WO2012040634, WO2012037226, WO2012032065, WO2012007493, WO2012135160, etc.

Currently there is no small molecule PI3Kδ selective available yet on the market, one object of the present invention is to provide a potent and low-toxicity medicament of PI3Kδ selective inhibitor for treating cell proliferation diseases such as cancer, infection, inflammation and autoimmune disease, etc.

CONTENT OF THE PRESENT INVENTION

The technical problem to be solved by the present invention is to provide a fused pyrimidine compound, an intermediate, a preparation method, a composition and a use thereof which is completely different from the prior art. The fused pyrimidine compound of the present invention is an inhibitor selective for PI3Kδ, and can be used for preparing a medicament for preventing and/or treating cell proliferation diseases such as cancer, infection, inflammation and autoimmune disease, etc.

The present invention provides a fused pyrimidine compound represented by formula I, a pharmaceutically acceptable salt, a hydrate, a solvate, an optical isomer or a prodrug thereof,

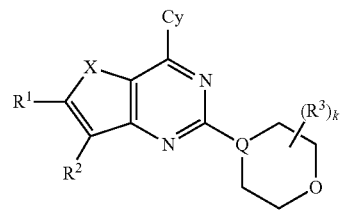

I wherein:

X is S or O; Q is C or N;

$R^1$ is selected from a hydrogen, a deuterium, a halogen, an alkyl (e.g., an unsubstituted $C_1$-$C_6$ alkyl; the unsubstituted $C_1$-$C_6$ alkyl is preferably a methyl, an ethyl, a propyl or an isopropyl), an alkoxy, an alkenyl, an alkynyl, a cycloalkyl, a heterocycloalkyl, an aryl or a heteroaryl; preferably a hydrogen or an alkyl (e.g., an unsubstituted $C_1$-$C_6$ alkyl; the unsubstituted $C_1$-$C_6$ alkyl is preferably a methyl, an ethyl, a propyl or an isopropyl);

$R^2$ is selected from a hydrogen, a deuterium, a halogen, CN, —$(CR^8R^9)_m$—$NR^5R^6$, —$(CR^8R^9)_m NR^7C(=Y)R^5$, —$(CR^8R^9)_m NR^7S(O)_2R^5$, —$(CR^8R^9)_m OR^5$, —$(CR^8R^9)_m S(O)_2R^5$, —$(CR^8R^9)_m S(O)_2NR^5R^6$, —$C(OR^5)R^6R^8$, —$C(=Y)R^5$, —$C(=Y)OR^5$, —$C(=Y)NR^5R^6$, —$C(=Y)NR^7OR^5$, —$C(=O)NR^7S(O)_2R^5$, —$C(=O)NR^7(CR^8R^9)_m NR^5R^6$, —$NR^7C(=Y)R^6$, —$NR^7C(=Y)OR^6$, —$NR^7C(=Y)NR^5R^6$, —$NR^7S(O)_2R^5$, —$NR^7S(O)_2NR^5R^6$, —$SR^5$, —$S(O)_2R^5$, —$S(O)_2NR^5R^6$, —$SC(=Y)R^5$, —$SC(=Y)OR^5$, a $C_1$-$C_{12}$ alkyl (e.g., a substituted or an unsubstituted $C_1$-$C_4$ alkyl, in which the "$C_1$-$C_4$ alkyl" is preferably a methyl, and the "substituted" means being substituted by substituted or unsubstituted aryl, and the "substituted" in the "substituted or unsubstituted aryl" means that it may be substituted by a halogen (preferably F, Cl or Br, more preferably Cl) and/or an unsubstituted $C_1$-$C_6$ alkyl (which may be a methyl, an ethyl, a propyl, an isopropyl, a butyl, an isobutyl or a tert-butyl) and the aryl in the "substituted or unsubstituted aryl" is preferably a phenyl, an example of the "substituted aryl" is

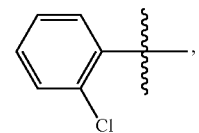 [SMILES: *c1ccccc1Cl]

an example of the "substituted $C_1$-$C_4$ alkyl" is

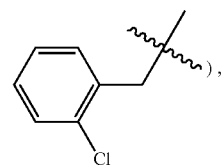 [SMILES: *Cc1ccccc1Cl]

a $C_2$-$C_8$ alkenyl, a $C_2$-$C_8$ alkynyl, a $C_3$-$C_{12}$ carbocyclyl, a $C_2$-$C_{20}$ heterocyclyl, a $C_6$-$C_{20}$ aryl or a $C_1$-$C_{20}$ heteroaryl;

$(R^3)_k$ represents that a hydrogen on the heterocycle to which it is attached is substituted by 0 to k occurrences of $R^3$, and at each occurrence $R^3$ is the same or different from one another, and is independently selected from a hydrogen, a deuterium, a halogen, a $C_1$-$C_6$ alkyl, or any two of R³ are linked together by a single bond, a C₁-C₆ alkyl or a C₁-C₆ alkylene substituted by one or more heteroatoms, with the heteroatom being O, N or S; preferably k is 0;

Cy is a heterocyclyl which is selected from:

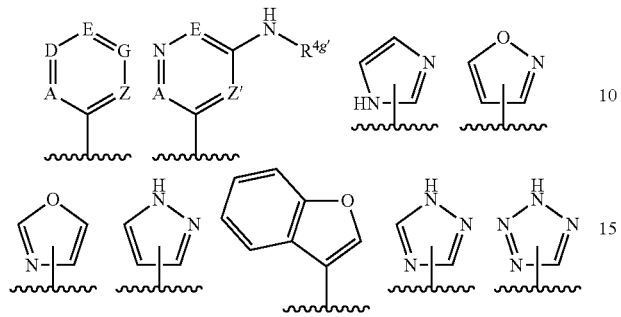

A is N or CR^{4a};
D is N or CR^{4d};
E is N or CR^{4e};
G is N or CR^{4g};
Z is N or CR⁴;
Z' is N or CR^{4'};
A, D, E, Z and G are not N at the same time;
each of R^{4a}, R^{4d}, R^{4e} and R^{4'} are independently selected from a hydrogen, a halogen, —CN, an alkyl, an alkoxy, an alkenyl, —NR⁵R⁶, —OR⁵, —SR⁵, —C(O)R⁵, —NR⁵C(O)R⁶, —N(C(O)R⁶)₂, —NR⁵'C(O)NR⁵R⁶, —S(O)R⁵, —S(O)₂R⁵, —S(O)₂NR⁵R⁶, —NR⁷S(O)₂R⁵, —NR⁵'S(O)₂NR⁵R⁶, —C(=O)OR⁵ or —C(=O)NR⁵R⁶;
R^{4g'} is —S(O)R⁵, —S(O)₂R⁵ (which may be

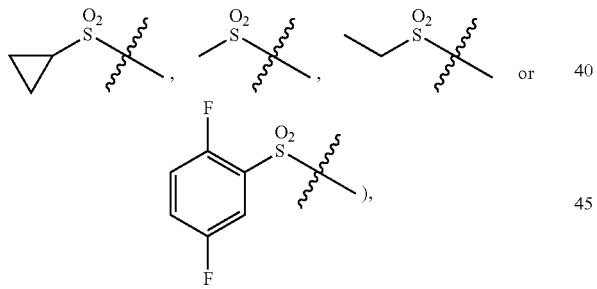

—S(O)₂NR⁵R⁶ (which may be

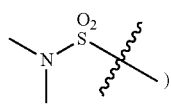 [SMILES: *S(=O)(=O)N(C)C]

or —C(O)R⁵;

R⁴ and R^{4g}, together with the atoms to which they are attached form a saturated, unsaturated or partially unsaturated 5-membered or 6-membered heterocycle, and only one of the ring atoms of the 5-membered or 6-membered heterocycle is a heteroatom, and the heteroatom is selected from O, N and S, and the 5-membered or 6-membered heterocycle is fused to the 6-membered ring containing A, D, E, Z and G (preferably

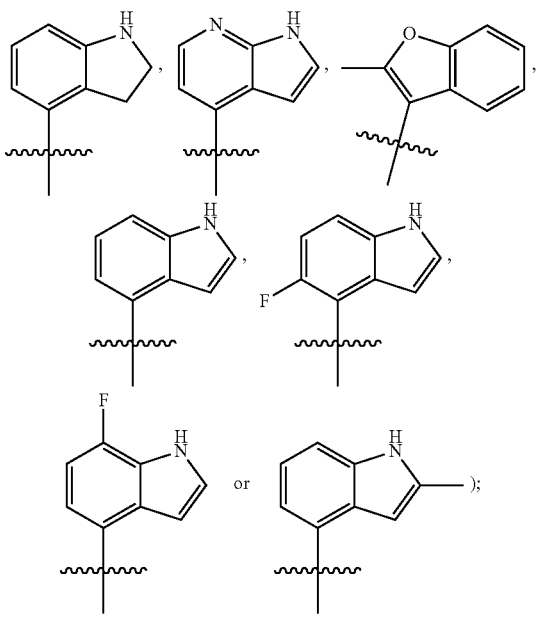

each of R⁵, R^{5'}, R⁶, R⁷ and R^{7'} are independently a hydrogen, a C₁-C₁₂ alkyl (preferably substituted or unsubstituted C₁-C₅ alkyl in which the "unsubstituted" means not being substituted by a substituent other than an alkyl, and the "C₁-C₅ alkyl" is preferably a methyl, an ethyl, a propyl, an isopropyl, a n-butyl, an isobutyl, a tert-butyl, a n-pentyl, an isopentyl or a neo-pentyl, more preferably a methyl, an ethyl, a propyl, an isopropyl or a tert-butyl, and the "substituted" in the "substituted or unsubstituted C₁-C₅ alkyl" means that it may be substituted by a hydroxyl and/or an unsubstituted C₁-C₃ alkoxy such as a methoxy, an example of the "substituted C₁-C₅ alkyl" is

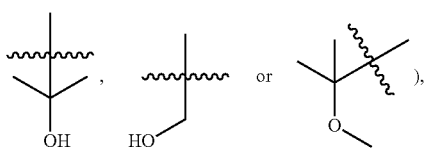

a C₂-C₈ alkenyl (preferably substituted or unsubstituted C₂-C₄ alkenyl in which the "substituted" means being substituted by one or more unsubstituted C₁-C₆ alkyl which may be a methyl, an ethyl, a propyl, an isopropyl, a n-butyl, an isobutyl or a tert-butyl; when being substituted by the ethyl, the "substituted or unsubstituted C₂-C₄ alkenyl" may be

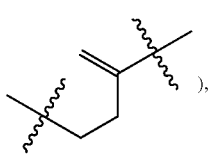 [SMILES: *CCC(*)=C]

a C₂-C₈ alkynyl, a C₃-C₁₂ carbocyclyl (preferably substituted or unsubstituted C₃-C₆ saturated carbocyclyl in which the "substituted" means being substituted by one or more unsubstituted C₁-C₆ alkyl and/or C₃-C₆ heterocyclyl containing O or N as heteroatoms with a heteroatom number of 1-2, and the "unsubstituted $C_1$-$C_6$ alkyl" may be a methyl, an ethyl, a propyl, an isopropyl, a n-butyl, an isobutyl or a tert-butyl, and the "$C_3$-$C_6$ heterocyclyl containing O or N as heteroatoms with a heteroatom number of 1-2" may be "$C_5$-$C_6$ heterocyclyl containing N as a heteroatom with a heteroatom number of 1" which may be a piperidyl, and the "piperidyl" may be as

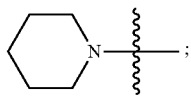 [SMILES: *N1CCCCC1]

when the "substituted" means being substituted by a methyl and/or an ethyl, the "substituted $C_3$-$C_6$ saturated carbocyclyl" is preferably

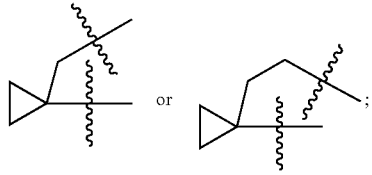 [SMILES: *CC1(*)CC1 ; *CCC1(*)CC1]

when the "substituted" means being substituted by

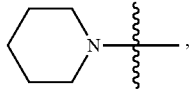

the "substituted $C_3$-$C_6$ saturated carbocyclyl" is preferably

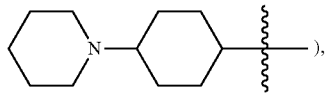 [SMILES: *C1CCC(N2CCCCC2)CC1]

a $C_2$-$C_{20}$ heterocyclyl (preferably substituted or unsubstituted $C_1$-$C_9$ heterocyclyl containing the heteroatom selected from the group consisting of O, S and N with a heteroatom number of 1-3 in which the "substituted" means preferably being substituted by the substituents selected from the group consisting of an unsubstituted $C_1$-$C_6$ alkyl (preferably a methyl, an ethyl, a propyl, an isopropyl, a n-butyl, an isobutyl or a tert-butyl), a halogen (e.g., F, Cl or Br), a halogen-substituted alkyl (e.g., trifluoromethyl), a hydroxyl-substituted alkyl (e.g., hydroxymethyl or

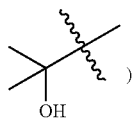

and "$C_2$-$C_4$ heterocyclyl containing O, S or N as a heteroatom with a heteroatom number of 1-2" (in which the "$C_2$-$C_4$ heterocyclyl" is preferably a $C_3$ heterocyclyl; and which is preferably "$C_3$ heterocyclyl containing O as a heteroatom with a heteroatom number of 1," more preferably oxacyclobutyl such as

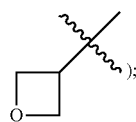 [SMILES: *C1COC1]

and the "substituted or unsubstituted $C_1$-$C_9$ heterocyclyl containing the heteroatom selected from the group consisting of O, S and N with a heteroatom number of 1-3" is more preferably substituted or unsubstituted $C_4$-$C_5$ heterocyclyl containing O or N as heteroatom with a heteroatom number of 1-2, e.g., substituted or unsubstituted tetrahydropyranyl (an example of the "unsubstituted tetrahydropyranyl" is

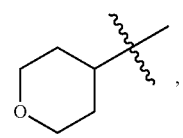

an example of the "substituted tetrahydropyranyl" is

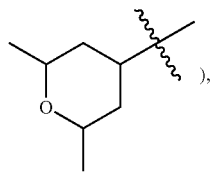 [SMILES: *C1CC(C)OC(C)C1]

substituted or unsubstituted morpholinyl (the substituted morpholinyl is preferably

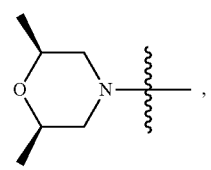 [SMILES: *N1C[C@@H](C)O[C@@H](C)C1]

and the unsubstituted morpholinyl may be

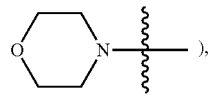

substituted or unsubstituted pyrrolidyl (the substituted pyrrolidyl is preferably

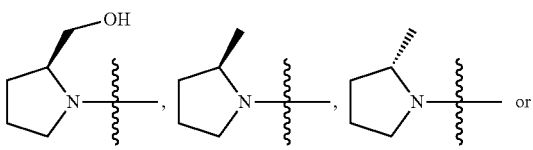

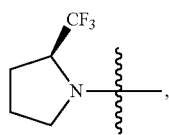

the unsubstituted pyrrolidyl may be

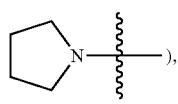

substituted or unsubstituted piperidyl (the "substituted piperidyl" is preferably

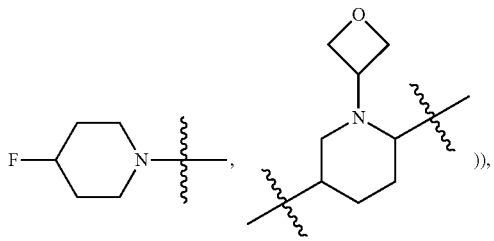 [SMILES: *N1CCC(F)CC1 ; *C1CCC(*)N(C2COC2)C1]

a $C_6$-$C_{20}$ aryl, a $C_1$-$C_{20}$ heteroaryl, or a heterocycle formed by $R^5$, $R^6$ together with the nitrogen to which they are directly attached, a spiro ring further formed by the heterocycle and a $C_2$-$C_6$ heterocycle (preferably the "$C_2$-$C_6$ heterocycle" is "$C_2$-$C_6$ heterocycle containing O, S or N as heteroatom with a heteroatom number of 1-2", for example

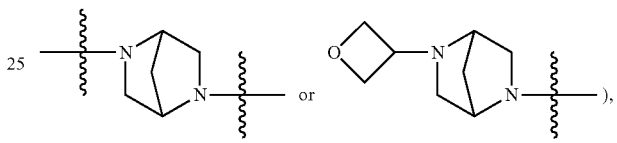

a spiro ring further formed by the heterocycle formed by $R^5$, $R^6$ together with the nitrogen to which they are directly attached and the $C_2$-$C_6$ carbocycle (for example

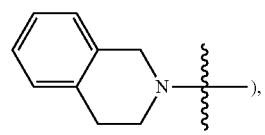 [SMILES: *N1CCc2ccccc2C1]

a fused ring further formed by the heterocycle formed by $R^5$, $R^6$ together with the nitrogen to which they are directly attached and a $C_2$-$C_6$ heteroaromatic ring (the "$C_2$-$C_6$ heteroaromatic ring" is preferably "$C_2$-$C_6$ heteroaromatic ring containing O, S or N as heteroatom with a heteroatom number of 1-2", an example of the fused ring is

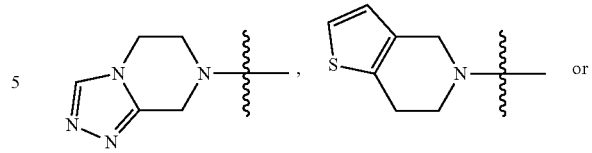

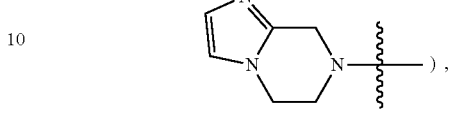

a bridged ring further formed by the heterocycle formed by $R^5$, $R^6$ together with the nitrogen to which they are directly attached and a $C_2$-$C_6$ heteroaromatic ring (the "$C_2$-$C_6$ heteroaromatic ring" is preferably "$C_2$-$C_6$ heteroaromatic ring containing O, S or N as heteroatom with a heteroatom number of 1-2", an example of the bridged ring is

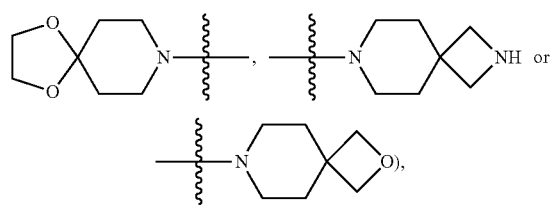

a fused ring further formed by the heterocycle formed by $R^5$, $R^6$ together with the nitrogen to which they are directly attached and a $C_2$-$C_6$ aromatic ring (the "$C_2$-$C_6$ aromatic ring" is preferably a benzene ring, an example of the fused ring is

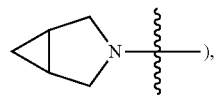 [SMILES: *N1CC2CC2C1]

a fused ring further formed by the heterocycle formed by $R^5$, $R^6$ together with the nitrogen to which they are directly attached and a $C_2$-$C_6$ carbocycle (for example

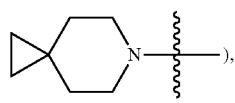

or a heterocycle formed by $R^5$, $R^6$ together with the nitrogen to which they are directly attached which may be optionally substituted by the substituent selected from the group consisting of: oxo, —$(CH_2)_m OR^7$ (for example

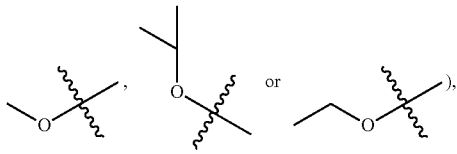

—NR⁷R⁷'

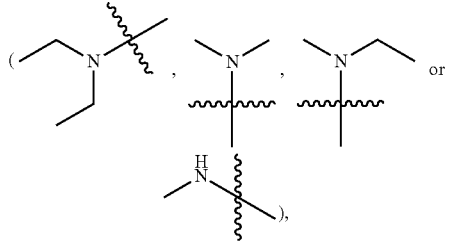
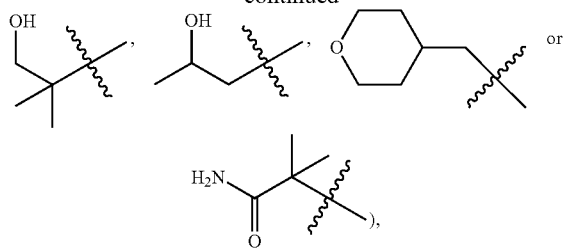

a deuterium, a halogen (for example F, Cl, Br or I, preferably F), —SO₂R⁷ (for example

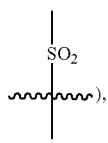

),

—C(=O)R⁷, —NR⁷C(=Y)R⁷', —NR⁷S(O)₂R⁷', —C(=Y)NR⁷R⁷', a C₁-C₁₂ alkyl (preferably a substituted or an unsubstituted C₁-C₆ alkyl in which the "unsubstituted" means not being substituted by a substituent other than an alkyl, preferably a methyl, an ethyl, a propyl, an isopropyl, a n-butyl, an isobutyl, a tert-butyl, a n-pentyl, an isopentyl or a neo-pentyl, more preferably a methyl, an ethyl, a propyl or an isopropyl; and the "substituted" means that it may be substituted by the substituent selected from the group consisting of: a hydroxyl,

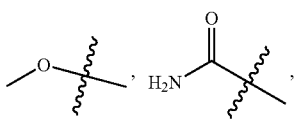

F and a C₂-C₆ heterocyclyl; the "C₂-C₆ heterocyclyl" refers to a C₂-C₆ heterocyclyl containing O, S or N as heteroatom with a heteroatom number of 1-2, preferably a tetrahydropyranyl; and the substituted C₁-C₆ alkyl is preferably trifluoromethyl,

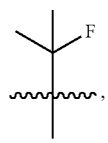

trifluoroethyl,

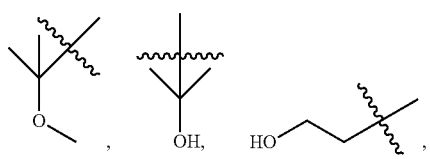

a C₂-C₈ alkenyl (preferably substituted or unsubstituted C₂-C₄ alkenyl in which the "substituted" means being substituted by one or more unsubstituted C₁-C₆ alkyl, the "unsubstituted C₁-C₆ alkyl" is preferably a methyl, an ethyl, a propyl, an isopropyl, a n-butyl, an isobutyl or a tert-butyl, example of the "unsubstituted C₂-C₄ alkenyl" is

an example of the "substituted C₂-C₄ alkenyl" is

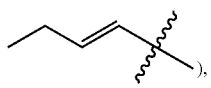 [SMILES: */C=C/CC]

a C₂-C₈ alkynyl, a hydroxyl, a C₃-C₁₂ carbocyclyl (preferably unsubstituted C₃-C₆ saturated carbocyclyl, for example cyclopropyl), a C₂-C₂₀ heterocyclyl (preferably substituted or unsubstituted C₁-C₉ heterocyclyl containing the heteroatom selected from O, S and N with a heteroatom number of 1-3 in which the "substituted" means being preferably substituted by the substituents selected from the group consisting of an unsubstituted C₁-C₆ alkyl (preferably a methyl, an ethyl, a propyl, an isopropyl, a n-butyl, an isobutyl or a tert-butyl), a halogen (e.g., F, Cl or Br), a halogen substituted alkyl (e.g., trifluoromethyl), oxo and a hydroxyl-substituted alkyl (e.g., hydroxymethyl or

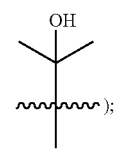 [SMILES: *C(C)(C)O]

);

and which is preferably substituted or unsubstituted C₃-C₅ heterocyclyl containing O or N as heteroatom with a heteroatom number of 1-2, for example, substituted or unsubstituted tetrahydropyranyl (an example of the unsubstituted tetrahydropyranyl is

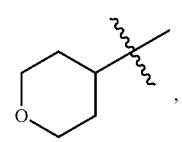

an example of the substituted tetrahydropyranyl is

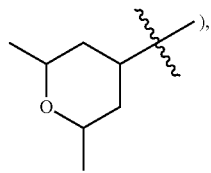 [SMILES: *C1CC(C)OC(C)C1]

substituted or unsubstituted oxacyclobutyl (an example of the unsubstituted oxacyclobutyl is

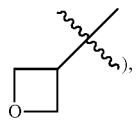

substituted or unsubstituted morpholinyl (the unsubstituted morpholinyl is preferably

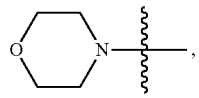

and the substituted morpholinyl is preferably

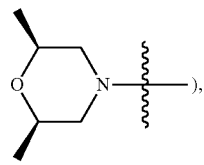 [SMILES: *N1C[C@@H](C)O[C@@H](C)C1]

substituted or unsubstituted pyrrolidyl (the substituted pyrrolidyl is preferably

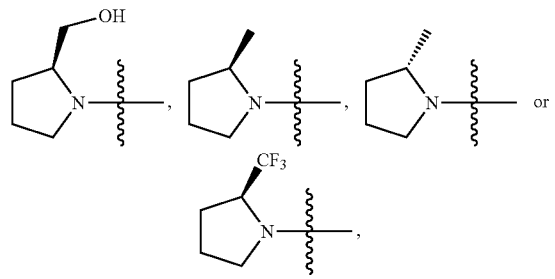

and the unsubstituted pyrrolidyl may be

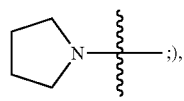

substituted or unsubstituted piperidyl (the substituted piperidyl is preferably

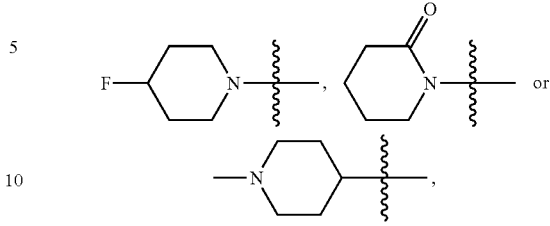

and the unsubstituted piperidyl may be

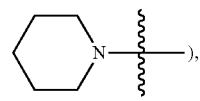

substituted or unsubstituted azetidinyl (an example of the substituted azetidinyl is

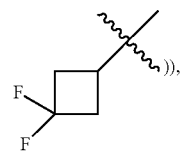

methylsulfonyl

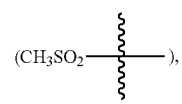

a $C_3$-$C_{20}$ heterocycloalkenyl (preferably a $C_3$-$C_5$ heterocycloalkenyl having N, O or S as heteroatom with a heteroatom number of 1 or 2 which is preferably

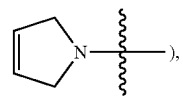 [SMILES: *N1CC=CC1]

a $C_6$-$C_{20}$ aryl and a $C_1$-$C_{20}$ heteroaryl (preferably a substituted or unsubstituted $C_2$-$C_6$ heteroaryl containing O, S or N as heteroatom with a heteroatom number of 1 or 2, in which the "substituted" means that may be substituted by the substituents selected from the group consisting of a methyl, an ethyl and a propyl; which is preferably a $C_3$ heteroaryl containing S and/or N as heteroatom with a heteroatom number of 2 with a preference to substituted thiazolyl such as

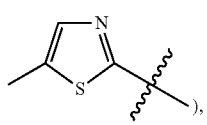 [SMILES: *c1ncc(C)s1]

an amino (which may be substituted by the substituent selected from the group consisting of a methyl, an ethyl, a propyl, an isopropyl, a n-butyl, an isobutyl, a tert-butyl and a tert-butoxycarbonyl, preferably

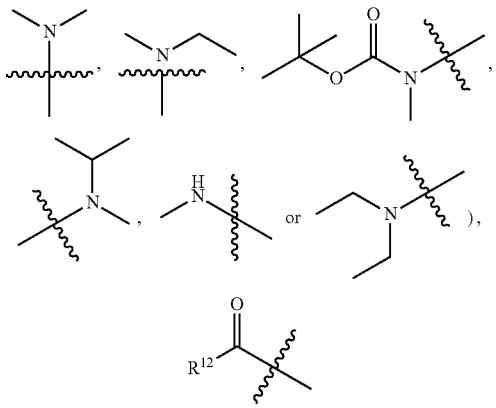

(in which R¹² is preferably unsubstituted $C_1$-$C_4$ alkyl (for example methyl, ethyl, propyl, isopropyl or tert-butyl), a halogen-substituted $C_1$-$C_4$ alkyl (for example trifluoromethyl), a cyano-substituted $C_1$-$C_4$ alkyl (for example

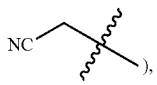

a pyrrolidyl, a hydroxyl-substituted $C_1$-$C_4$ alkyl (for example hydroxyethyl), an unsubstituted $C_1$-$C_4$ alkoxy (for example a methoxy or a tert-butoxy) or an unsubstituted $C_3$-$C_6$ saturated carbocyclyl (for example a cyclopropyl or a cyclohexyl), and

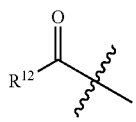

is preferably

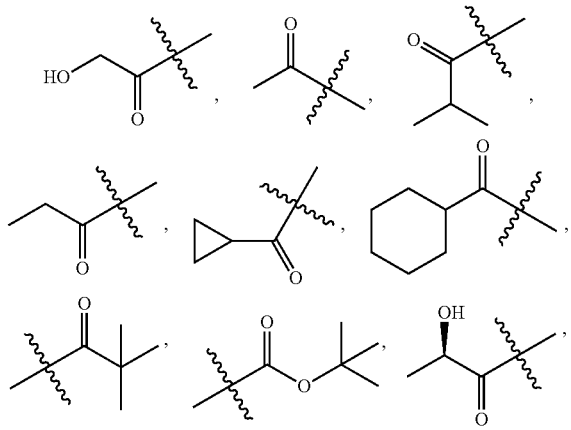

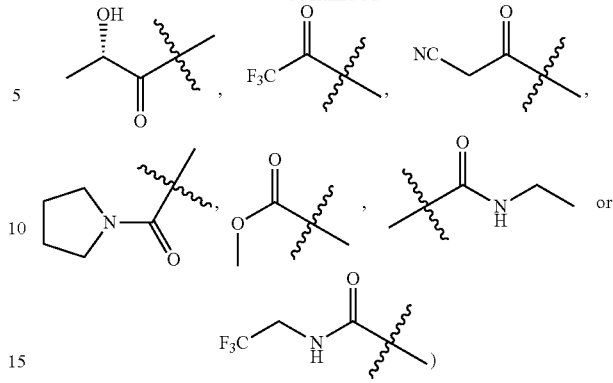

or substituted or unsubstituted $C_1$-$C_3$ amido (in which the "substituted" means being substituted by an unsubstituted $C_1$-$C_6$ alkoxy such as a methoxy, an ethoxy, a propoxy, an isopropoxy or a tert-butoxy; an example of the "substituted $C_1$-$C_3$ amido" is

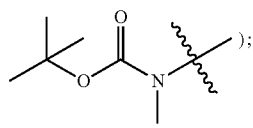 [SMILES: *N(C)C(=O)OC(C)(C)C]

each of $R^8$ and $R^9$ are independently a hydrogen, a deuterium, a halogen, —CN, a hydroxyl, an alkoxy, a cycloalkoxy, a $C_1$-$C_{12}$ alkyl (preferably an unsubstituted $C_1$-$C_6$ alkyl which is preferably a methyl, an ethyl, a propyl, an isopropyl, a n-butyl, an isobutyl, a tert-butyl, a n-pentyl, an isopentyl or a neo-pentyl, more preferably a methyl, an ethyl, a propyl or an isopropyl), a $C_2$-$C_{12}$ alkenyl, a $C_2$-$C_{12}$ alkynyl, a $C_3$-$C_{12}$ cycloalkyl, a $C_6$-$C_{12}$ aryl, a 3-12 membered heterocycloalkyl or a 5-12 membered heteroaryl; preferably a hydrogen or a $C_1$-$C_{12}$ alkyl (preferably an unsubstituted $C_1$-$C_6$ alkyl which is preferably a methyl, an ethyl, a propyl, an isopropyl, a n-butyl, an isobutyl, a tert-butyl, a n-pentyl, an isopentyl or a neo-pentyl, more preferably a methyl, an ethyl, a propyl or an isopropyl).

$(CR^8R^9)_m$ represents that m number of $(CR^8R^9)$ are linked together, in which each of $R^8$ and $R^9$ are the same or different from one another, and independently are a hydrogen, a deuterium, a halogen, —CN, a hydroxyl, an alkoxy, a $C_1$-$C_{12}$ alkyl, a $C_2$-$C_{12}$ alkenyl, a $C_2$-$C_{12}$ alkynyl, a $C_3$-$C_{12}$ cycloalkyl, a $C_6$-$C_{12}$ aryl, a 3-12 membered heterocycloalkyl or a 5-12 membered heteroaryl; or a saturated or partially unsaturated $C_3$-$C_{12}$ carbocycle or $C_2$-$C_{20}$ heterocycle formed by $R^8$, $R^9$ together with the atoms to which they are attached;

wherein the alkyl, alkenyl, alkynyl, cycloalkyl, carbocycle, heterocycle, heterocycloalkyl, aryl, or heterocyclyl may optionally be substituted by the substituent selected from the group consisting of: a deuterium, a halogen, —CN, —CF₃, —NO₂, oxo, $R^5$, —C(=Y)$R^5$, —C(=Y)O$R^5$, —C(=Y)N$R^5R^6$, —(C$R^8R^9$)$_m$N$R^5R^6$, —(C$R^8R^9$)$_m$O$R^5$, —N$R^5R^6$, —N$R^7$C(=Y)$R^5$, —N$R^7$C(=Y)O$R^6$, —N$R^7$C(=Y)N$R^5R^6$, —(C$R^8R^9$)$_m$N$R^7$SO$_2R^5$, =NR', OR⁵, —OC(=Y)$R^5$, —OC(=Y)O$R^5$, —OC(=Y)N$R^5R^6$, —OS(O)$_2$(O$R^5$), —OP(=Y)(O$R^5$)(O$R^6$), —OP(O$R^5$)(O$R^6$), —S$R^5$, —S(O)$R^5$, —S(O)$_2R^5$, —S(O)$_2$N$R^5R^6$, —S(O)(O$R^5$), —S(O)$_2$(O$R^5$), —SC(=Y)$R^5$, —SC(=Y)O$R^5$, —SC(=Y)N$R^5R^6$, a $C_2$-$C_8$ alkenyl, a $C_2$-$C_8$ alkynyl, a $C_3$-$C_{12}$ carbocyclyl, a $C_2$-$C_{20}$ heterocyclyl, a $C_6$-$C_{20}$ aryl or a $C_1$-$C_{12}$ heteroaryl;

Y is O, S or $NR^7$;

m and k independently are 0, 1, 2, 3, 4, 5 or 6, and k is preferably 0.

In the present invention, the fused pyrimidine compound represented by formula I, the pharmaceutically acceptable salt, hydrate, solvate, optical isomer or prodrug thereof, is preferably selected from the compound represented by formula 2, 3, 4 or 5,

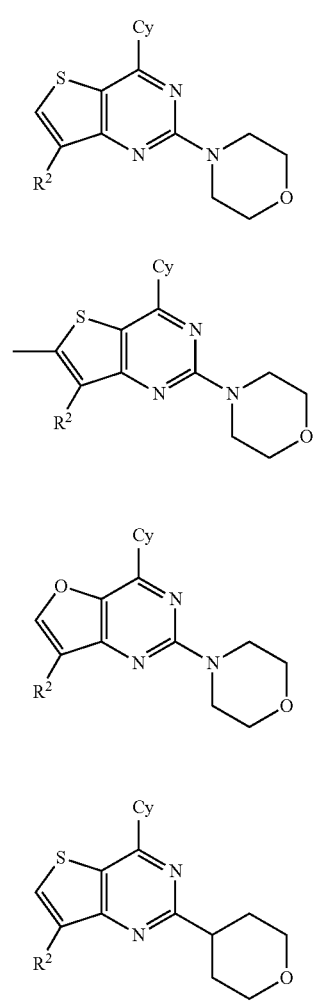

In the compound represented by formula 2 or the compound represented by formula 3, Cy is preferably a substituent selected from the group consisting ofs:

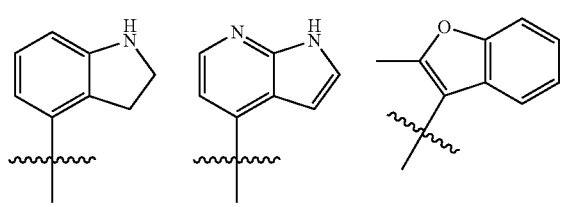

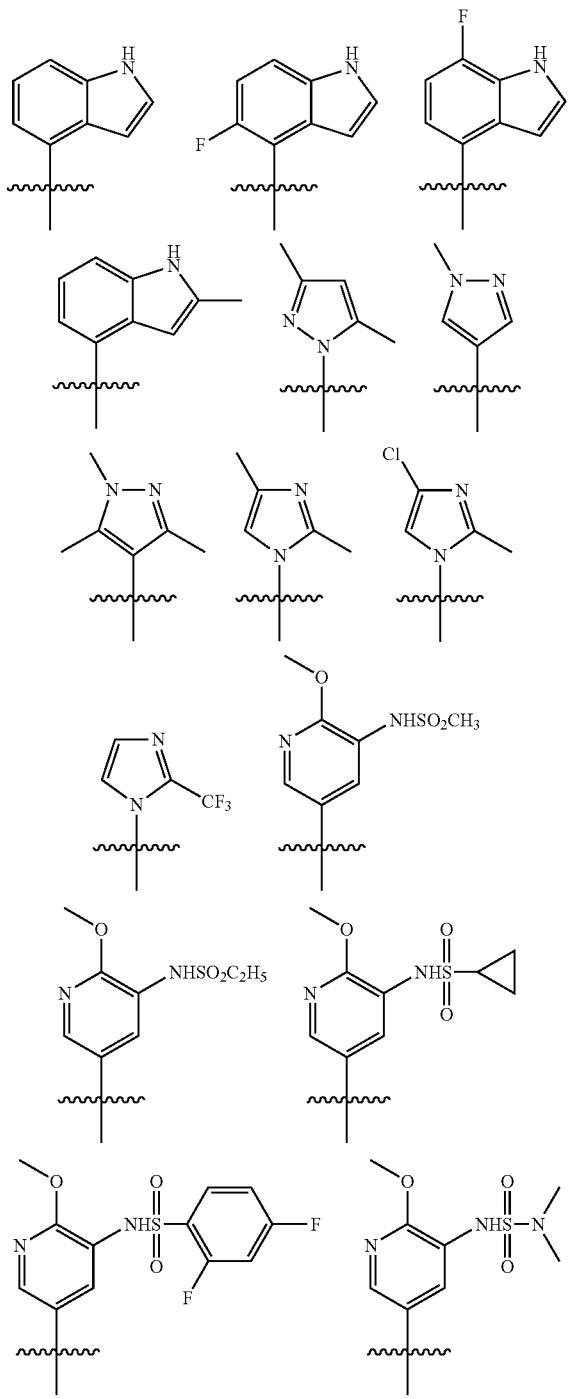

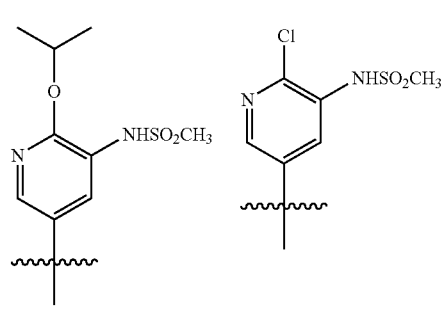

-continued
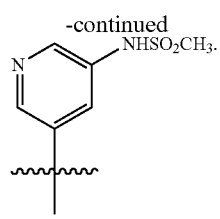
In the compound represented by formula 4 or 5, preferably, Cy may be the following substituent:
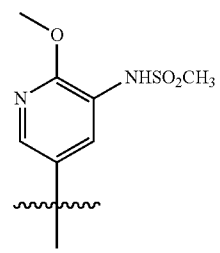
In the present invention, the compound I is more preferably a compound selected from the group consisting of:
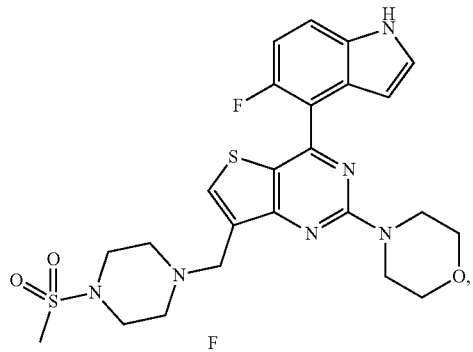
1
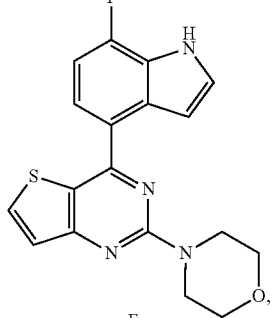
2
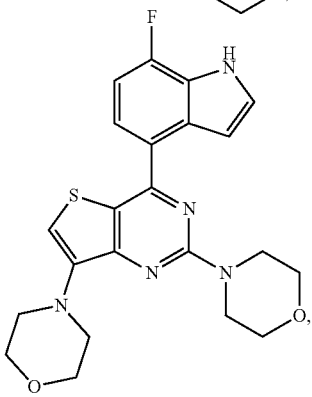
3
-continued
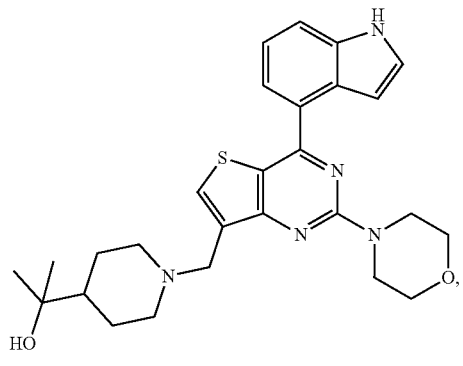
4
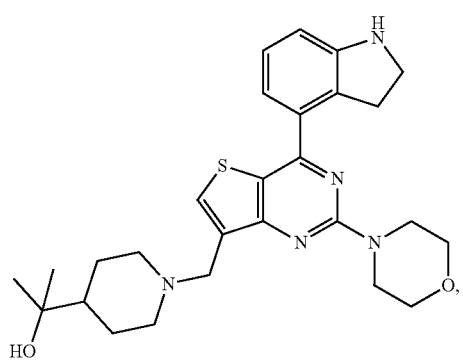
5
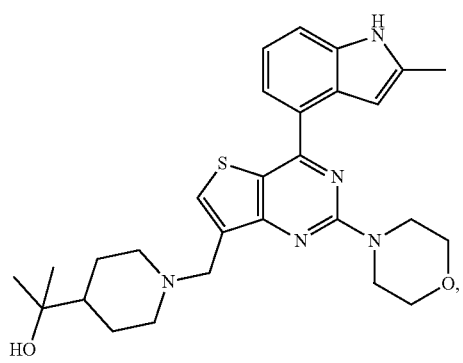
6
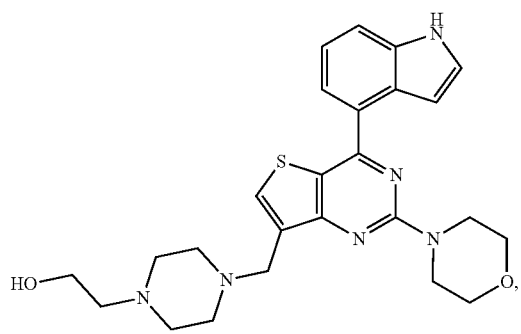
7

-continued
8
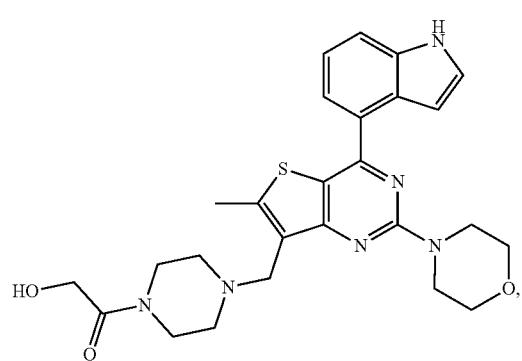
9
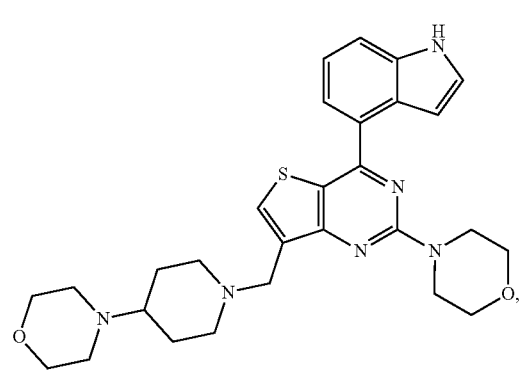
10
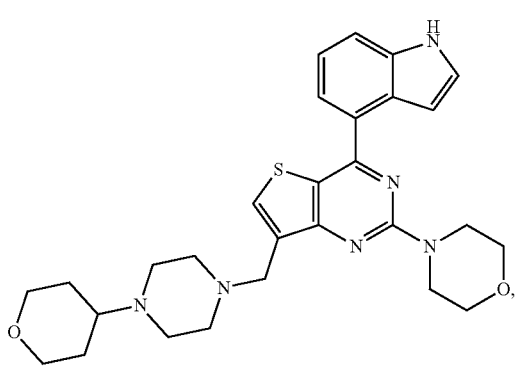
11
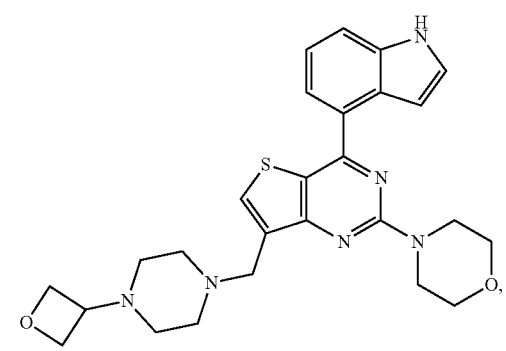
-continued
12
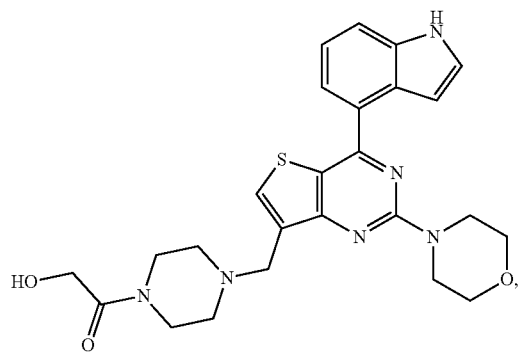
13
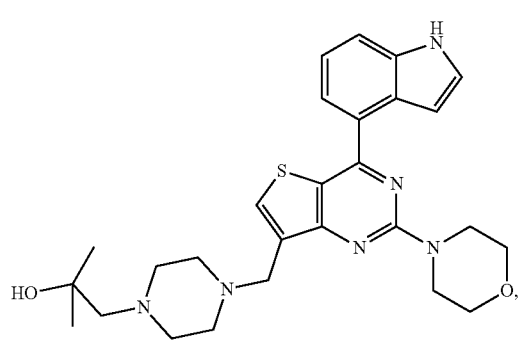
14
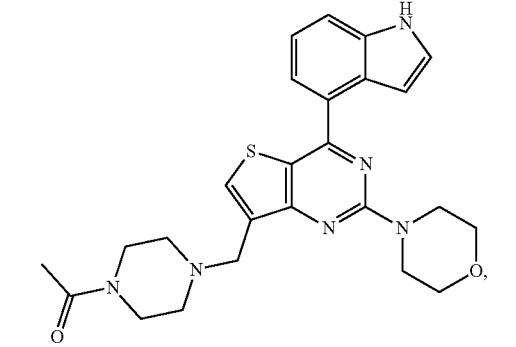
15
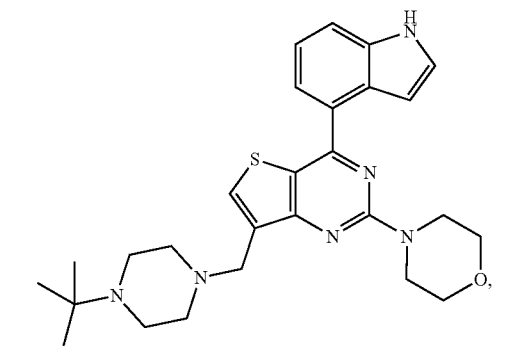

-continued
16
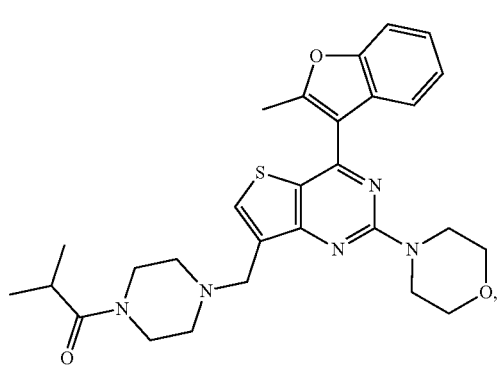
17
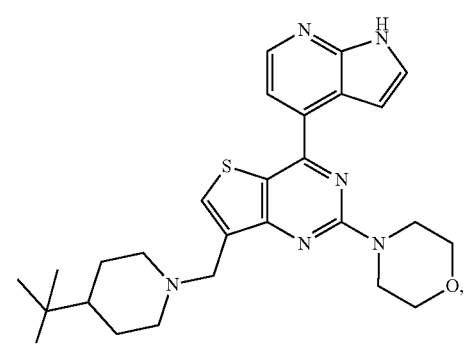
18
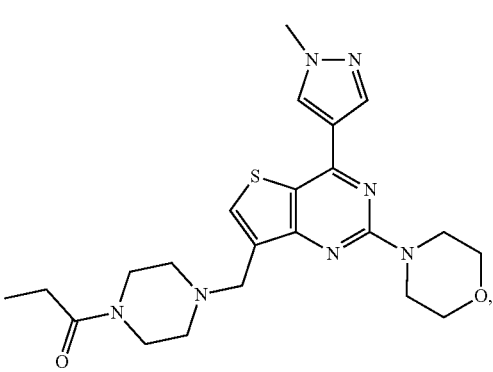
19
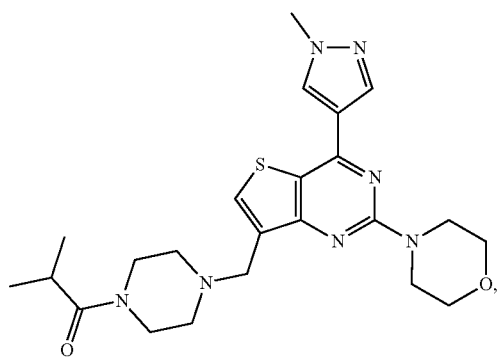
-continued
20
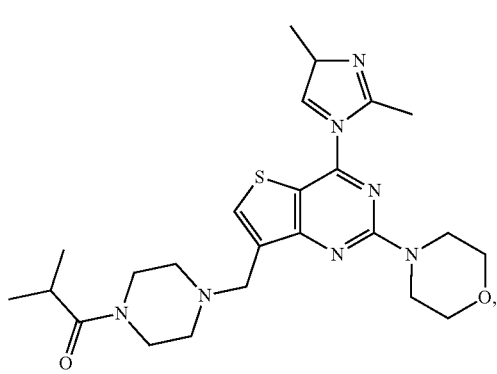
21
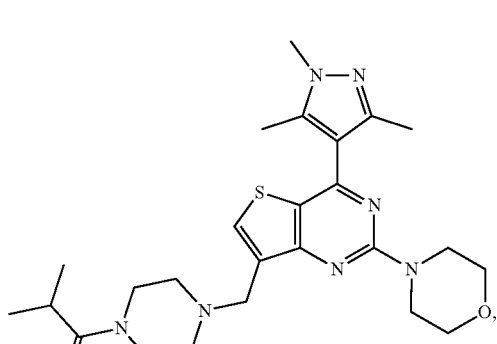
22
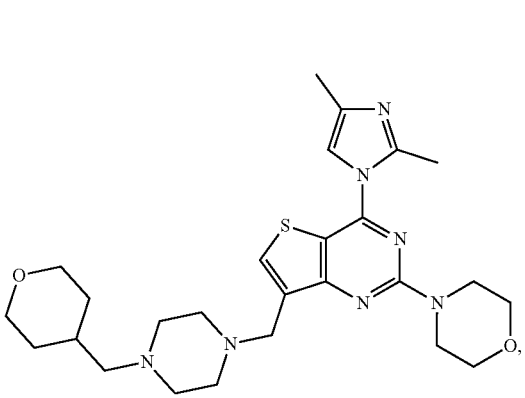
23
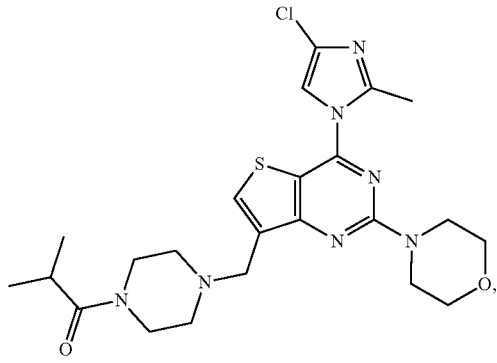

23
-continued
24
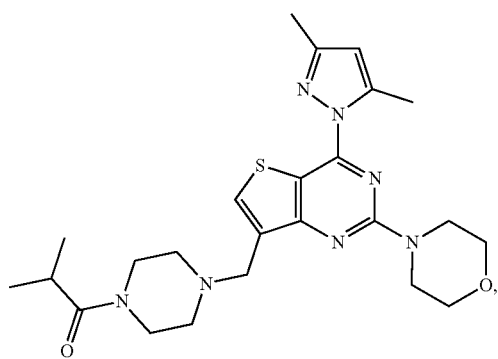
25
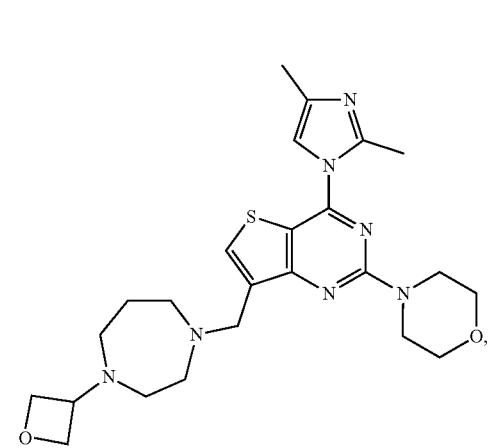
26
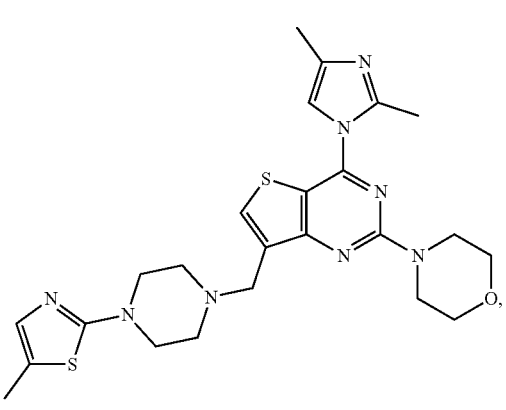
27
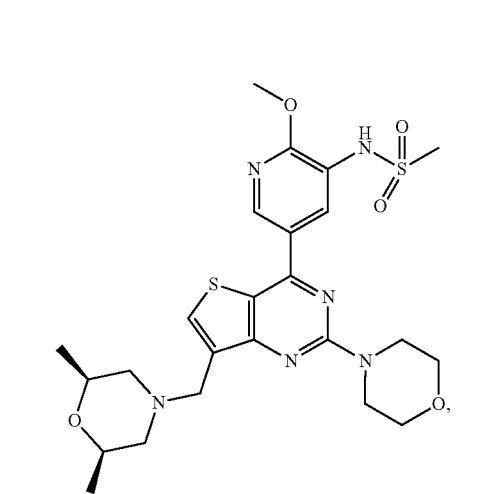
24
-continued
28
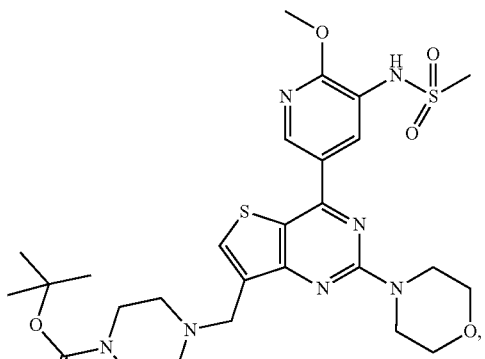
29
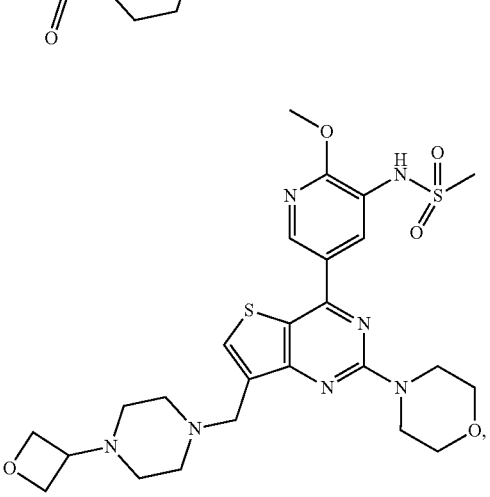
30
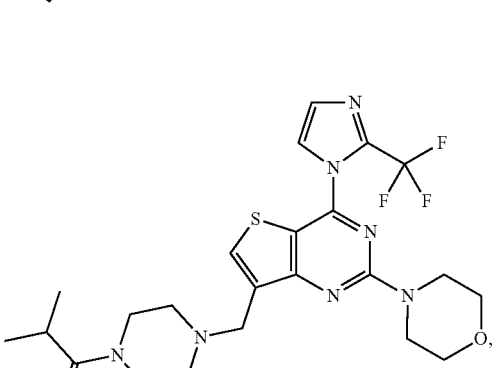
31
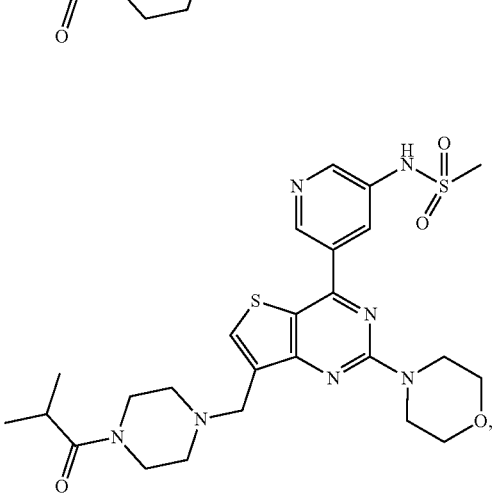

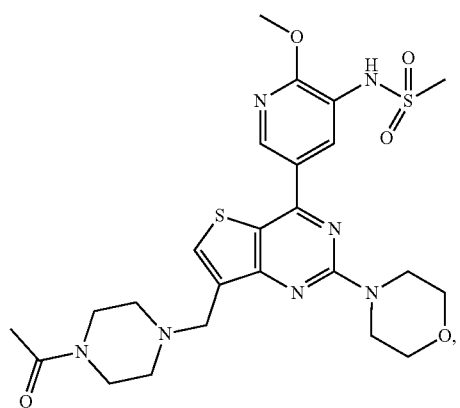
32
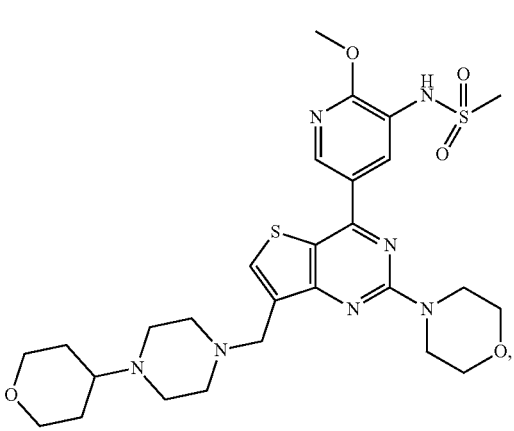
33
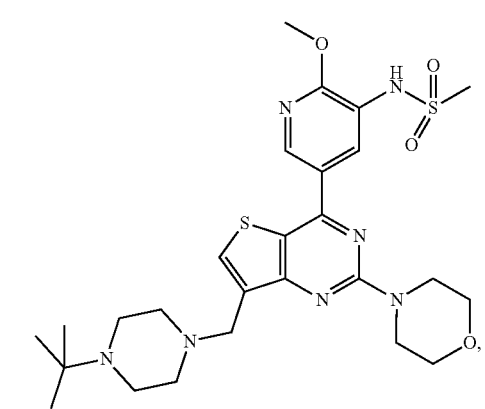
34
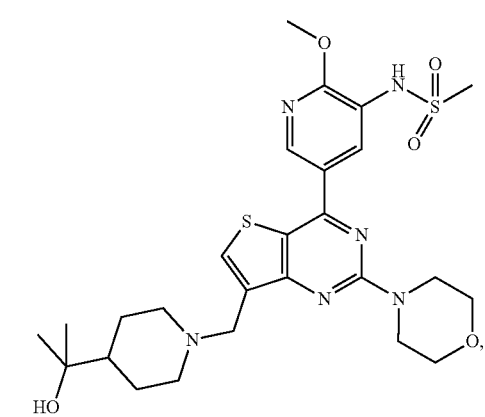
35
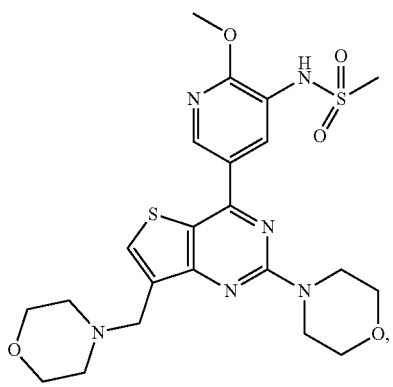
36
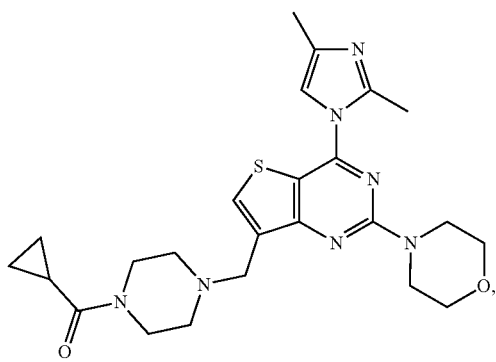
37
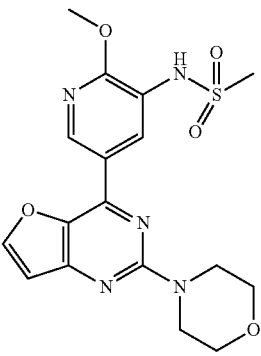
38
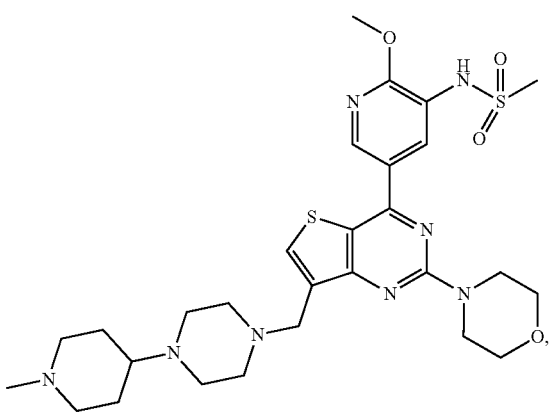
39

40
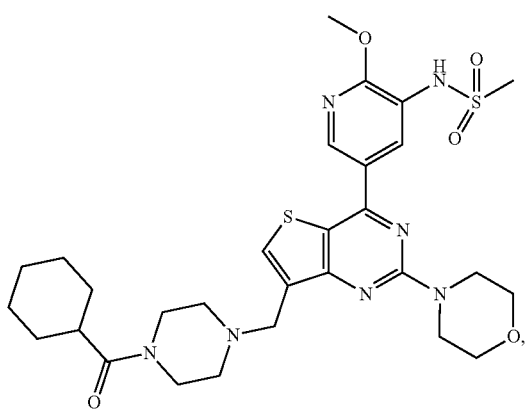
41
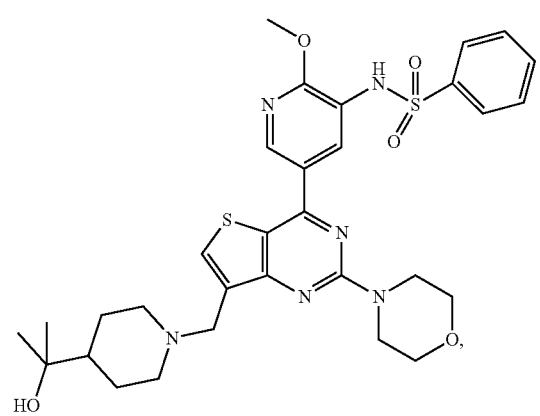
42
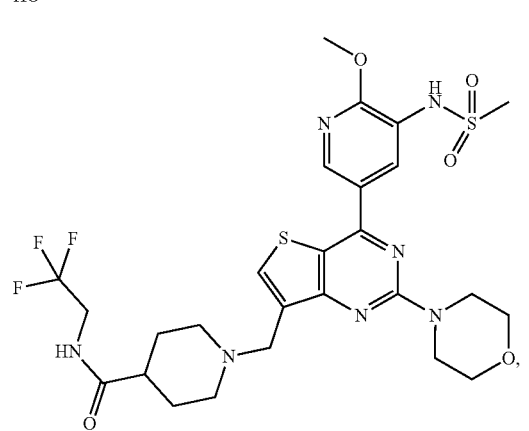
43
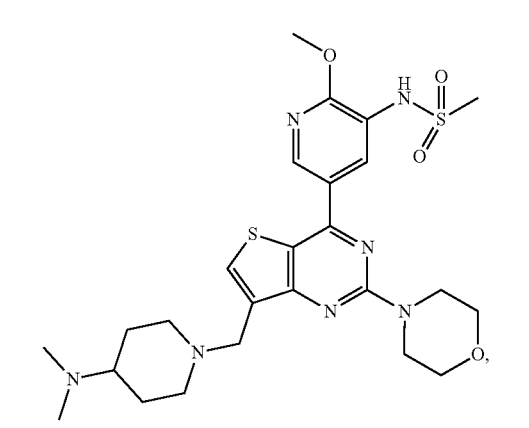
44
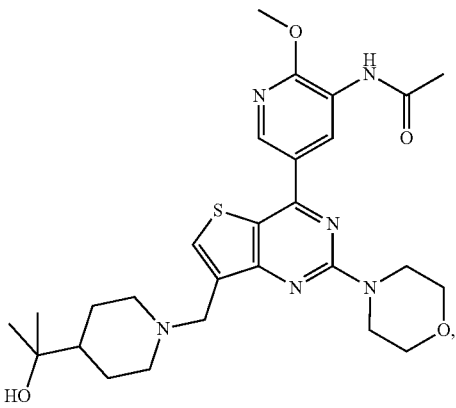
45
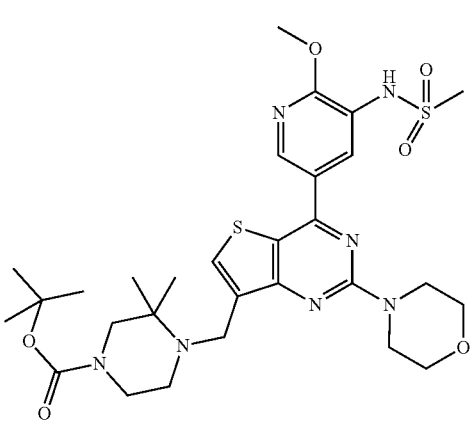
46
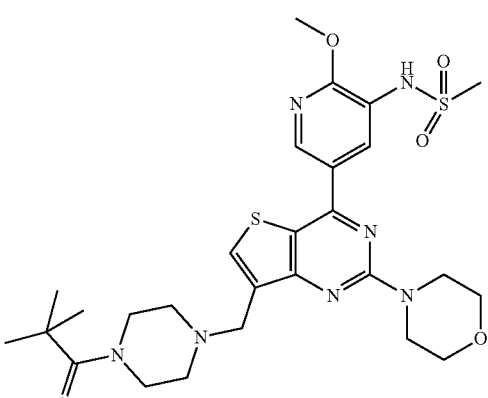
47
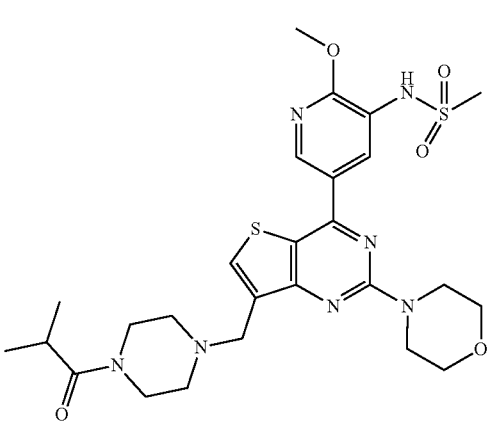

48
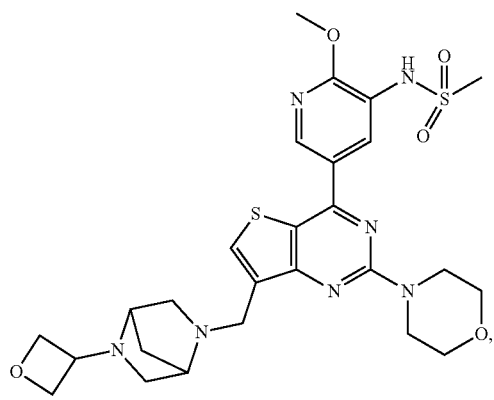
49
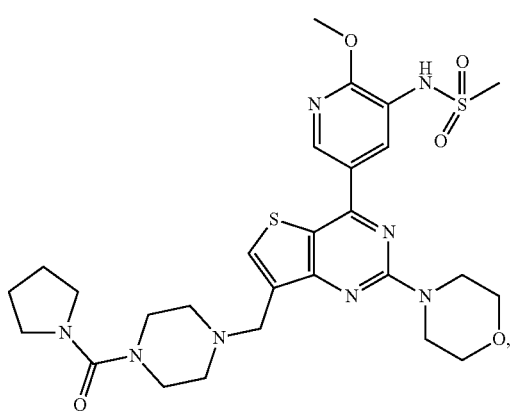
50
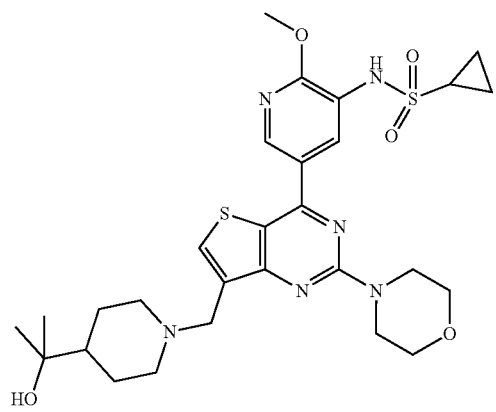
51
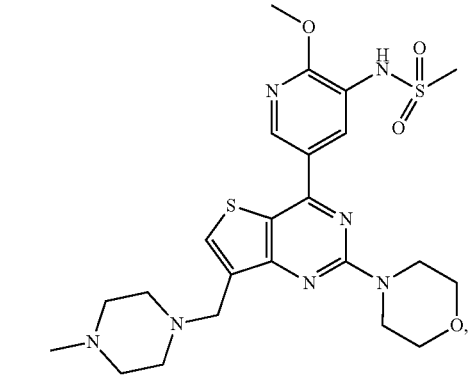
52
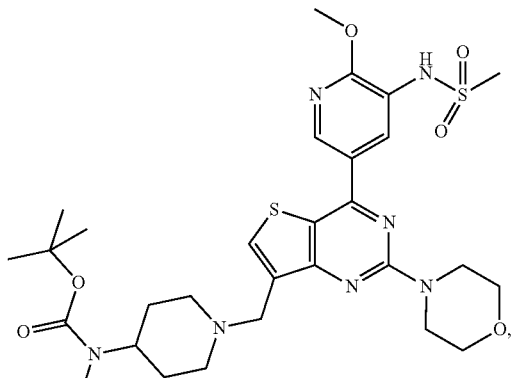
53
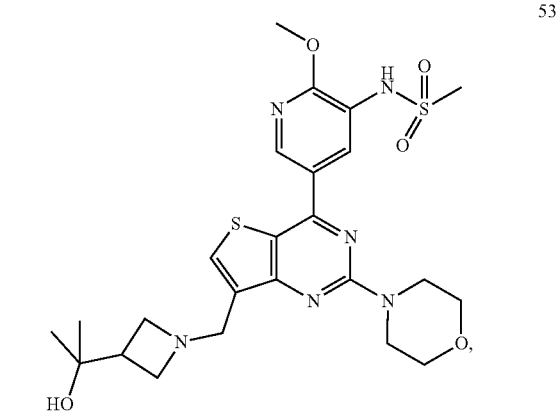
54
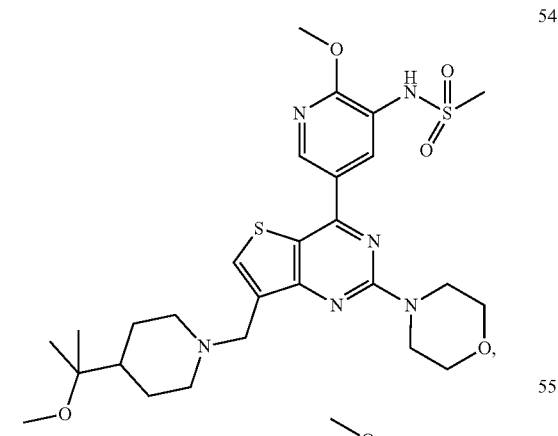
55
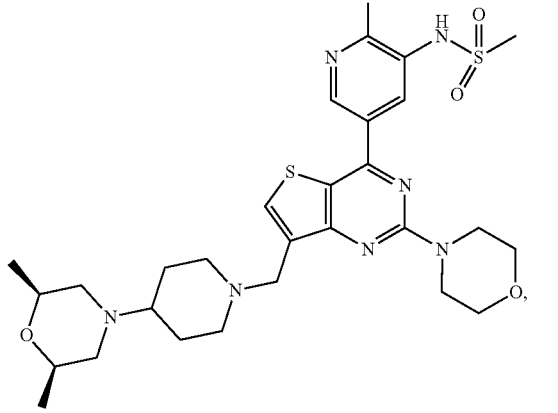

56 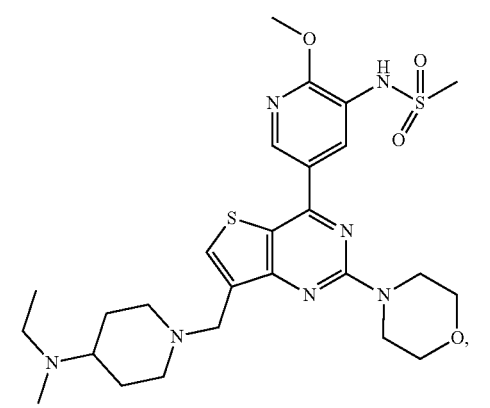
57 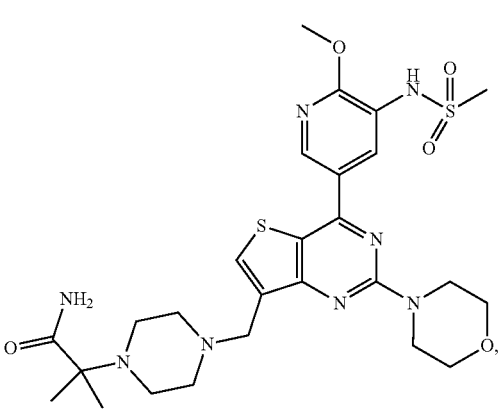
58 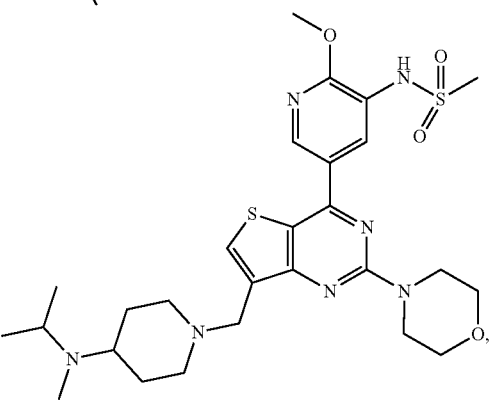
59 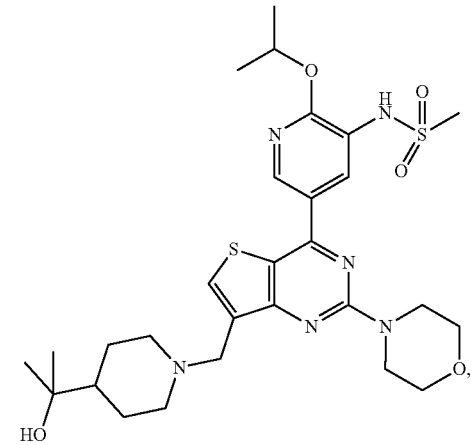
60 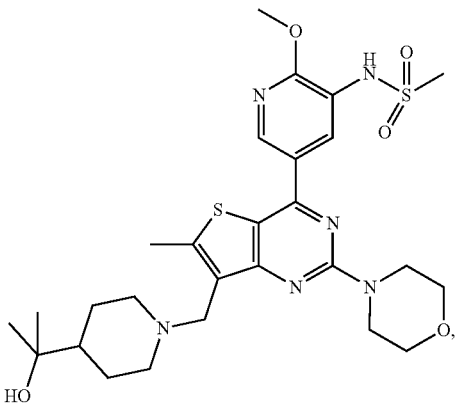
61 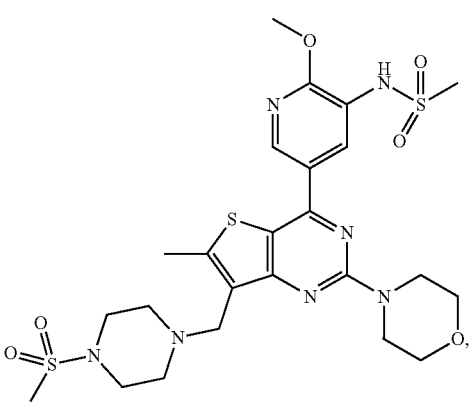
62 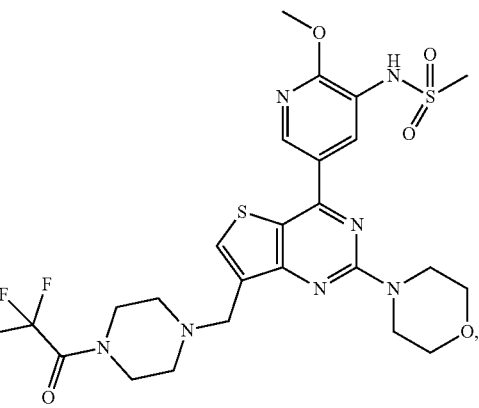
63 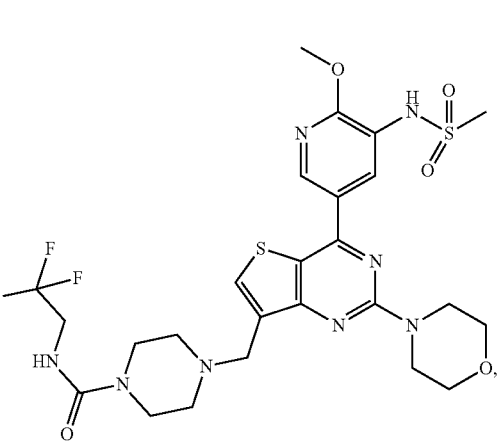

33
-continued
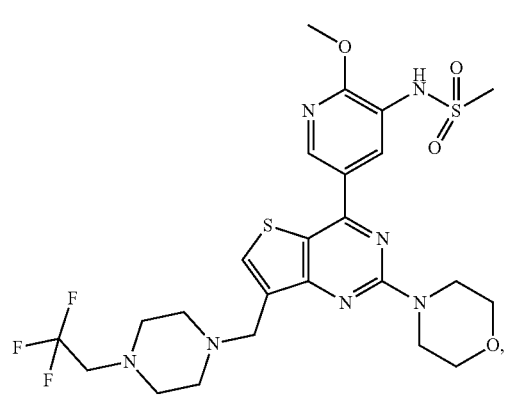
64
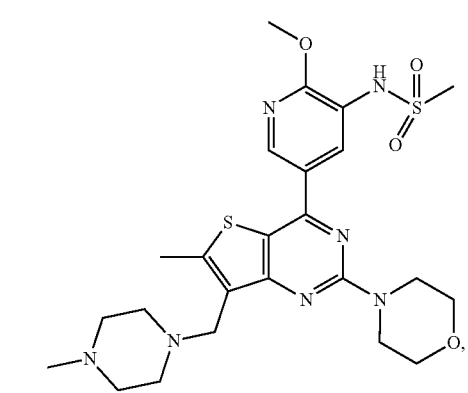
65
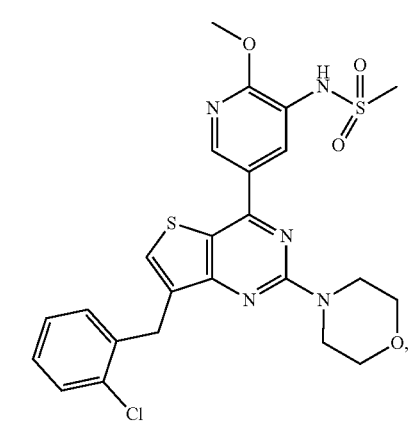
66
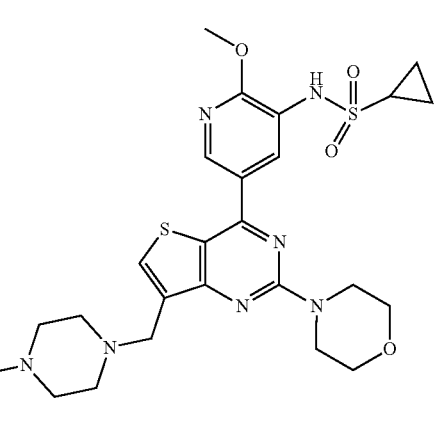
67
34
-continued
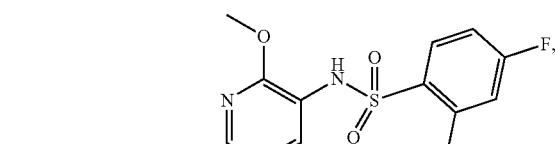
68
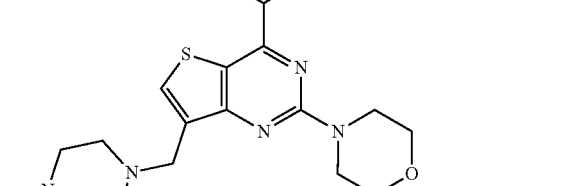
69
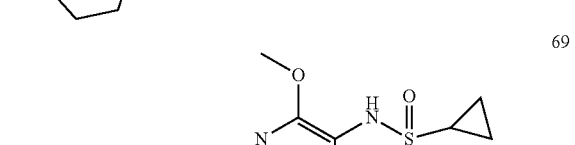
70
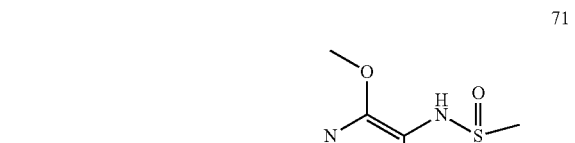
71
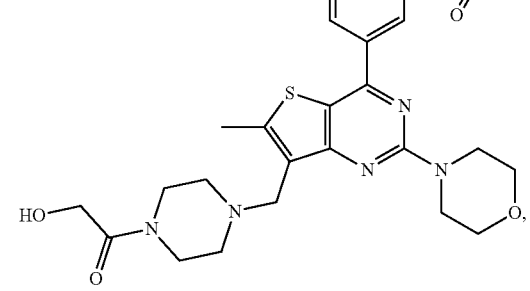

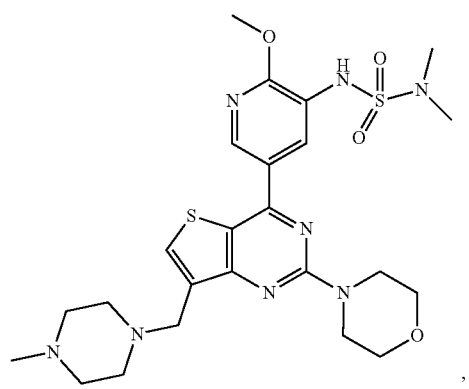
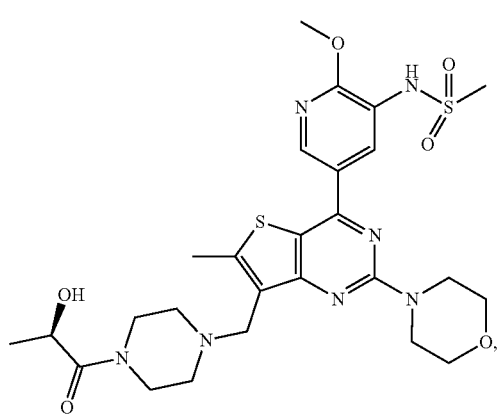
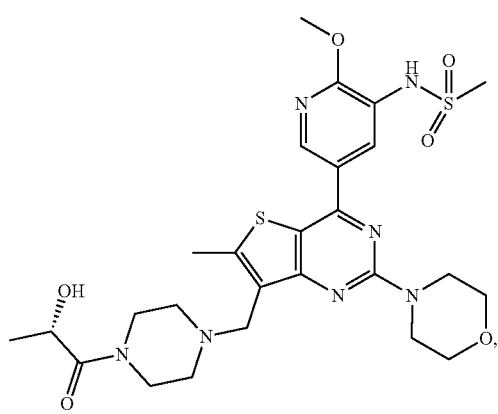
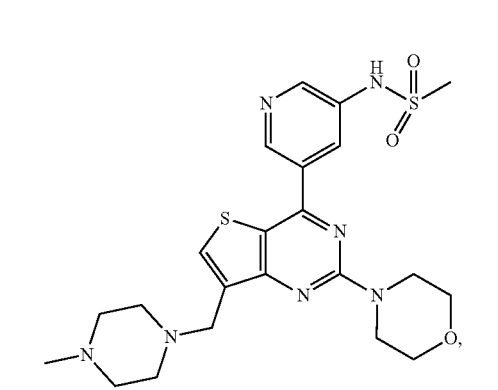
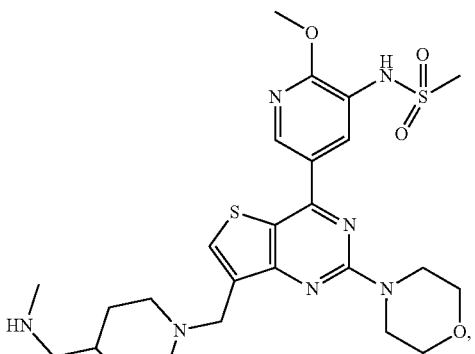
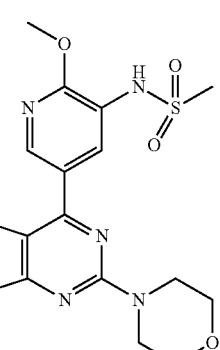
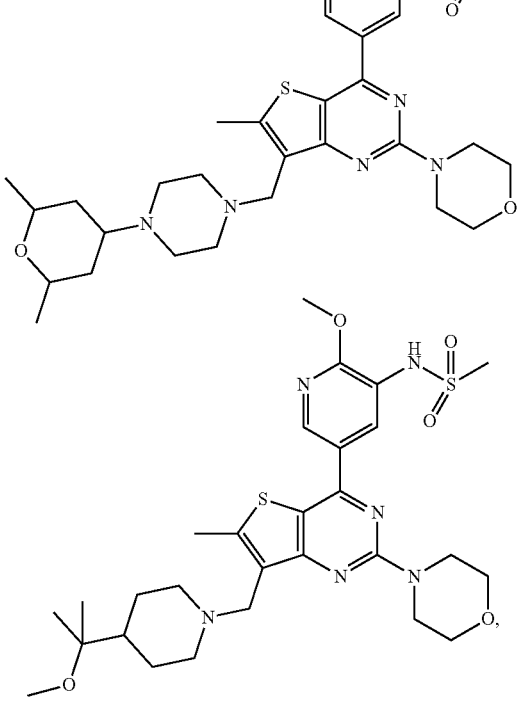
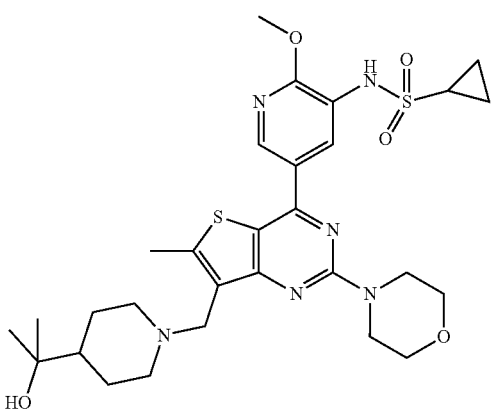

80
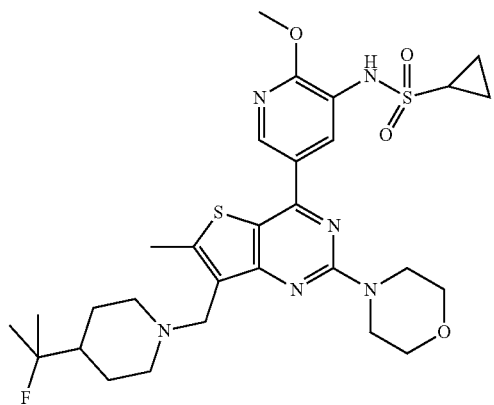
,
81
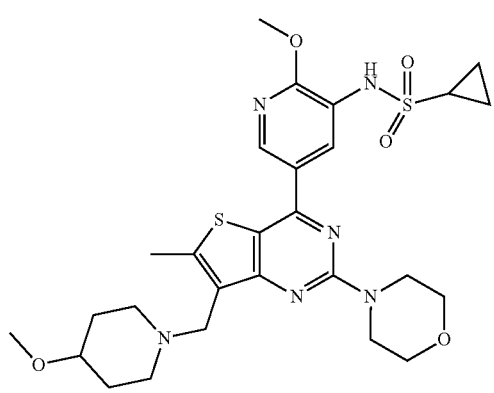
,
82
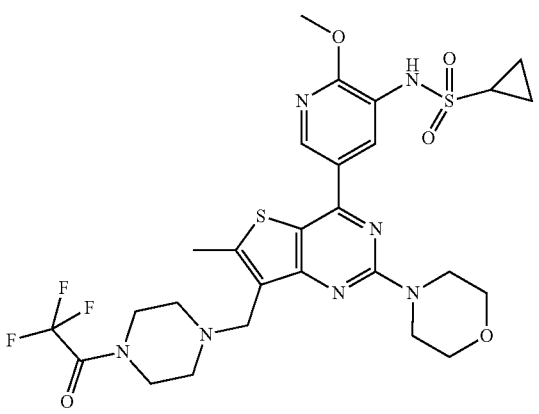
,
83
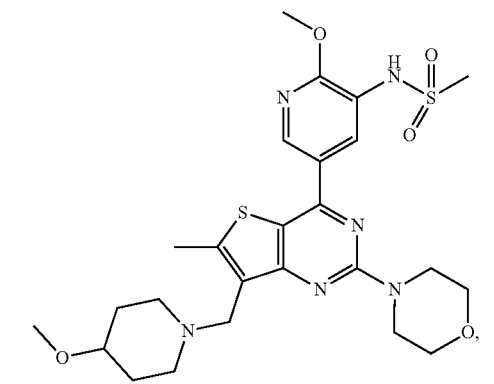
,
84
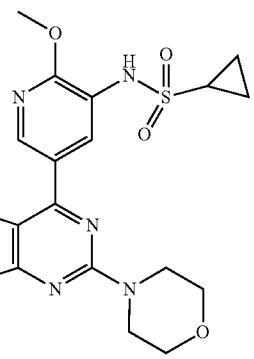
,
85
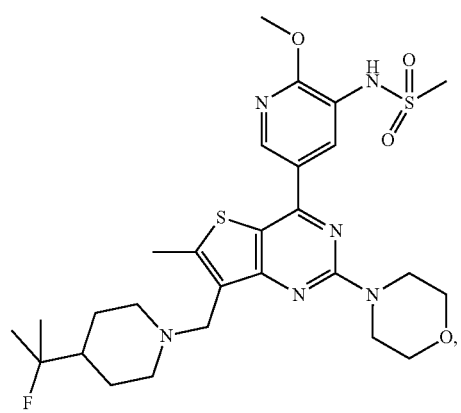
,
86
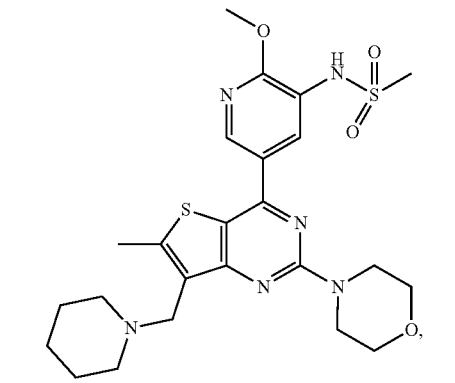
,
87
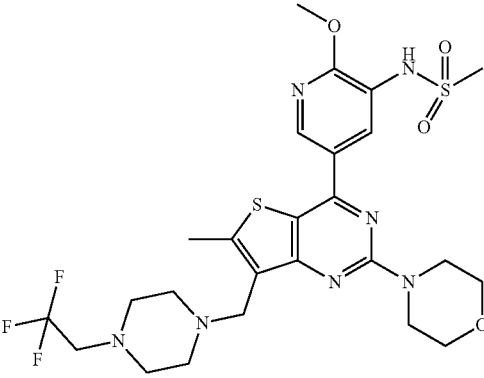
, 88 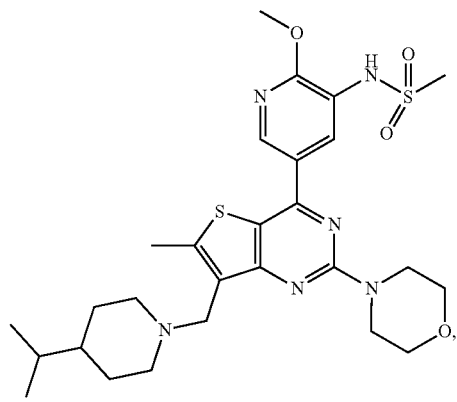
89 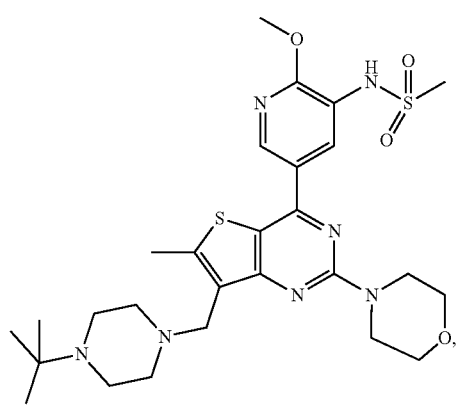
90 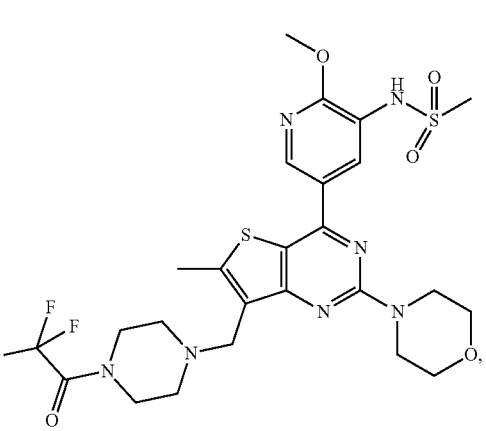
91 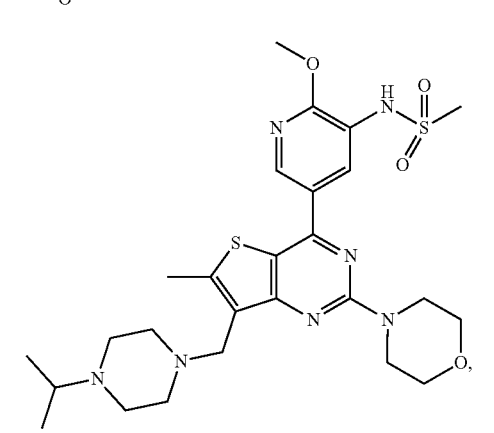
92 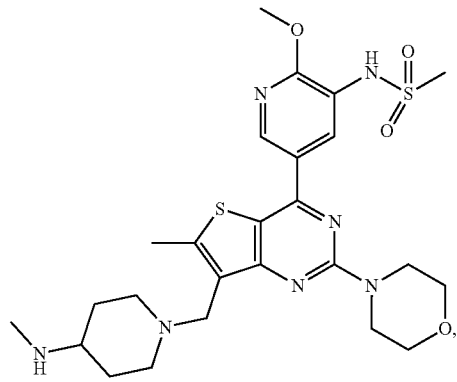
93 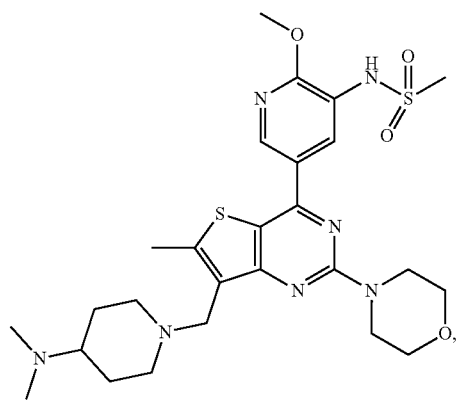
94 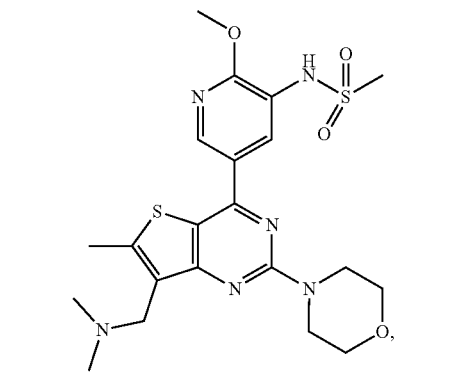
95 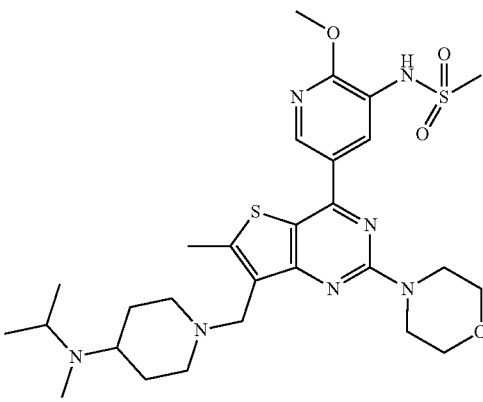

96 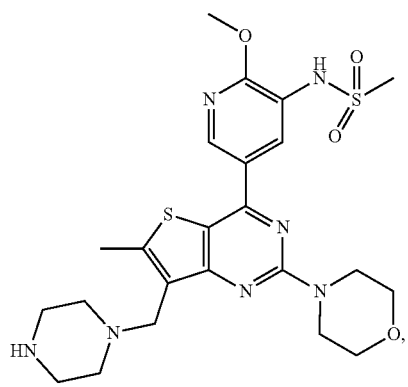
97 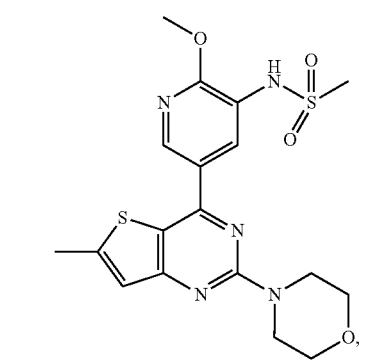
98 
99 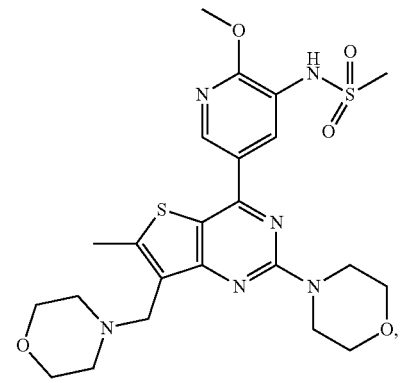
100 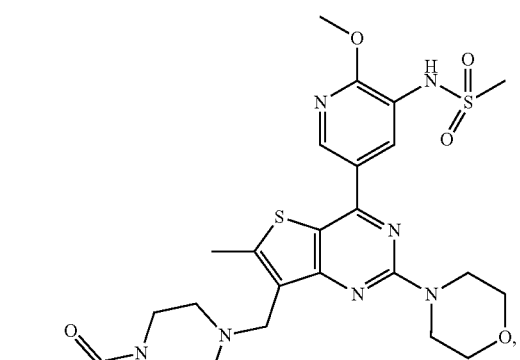
101 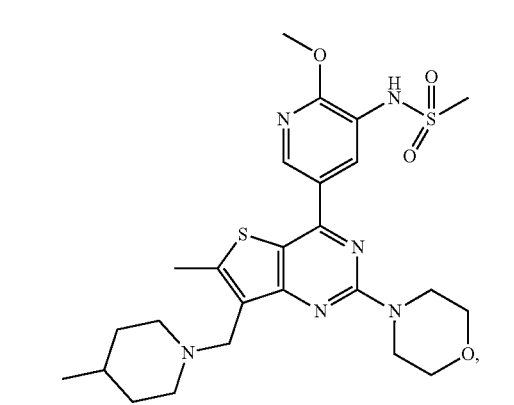
102 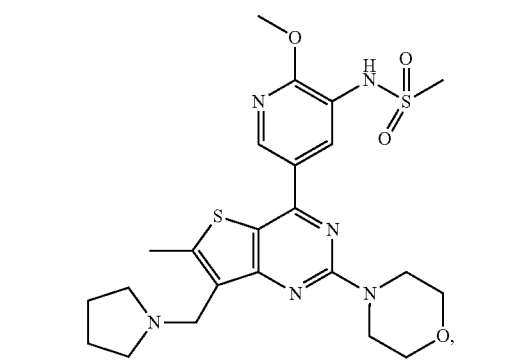
103 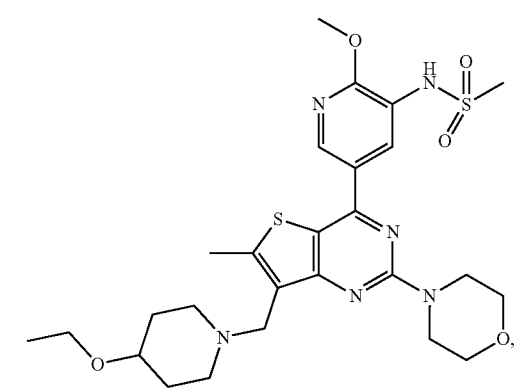

104
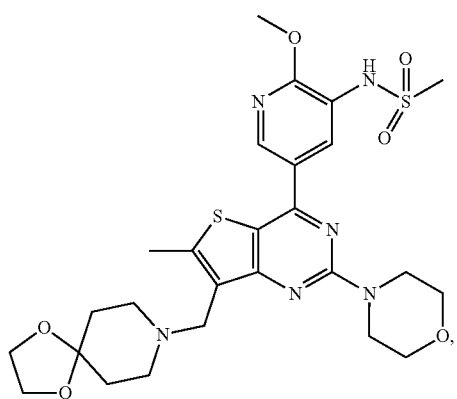
105
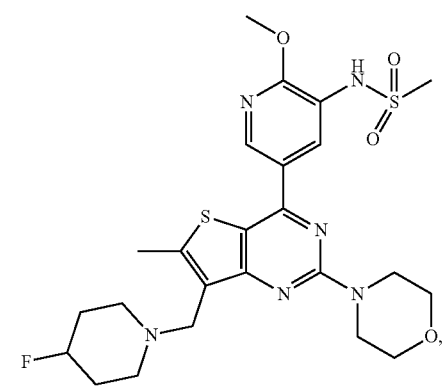
106
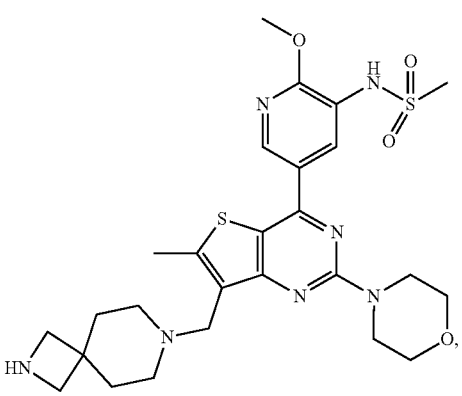
107
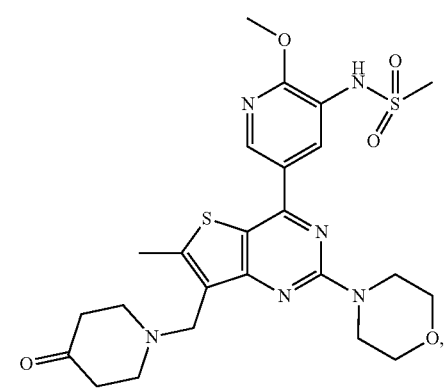
108
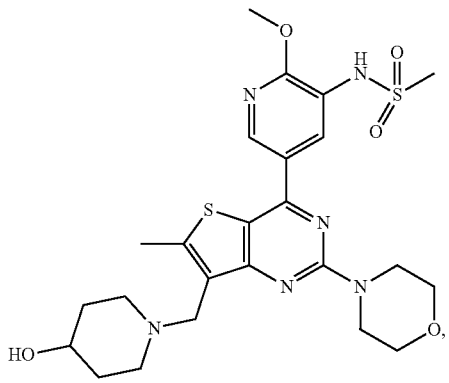
109
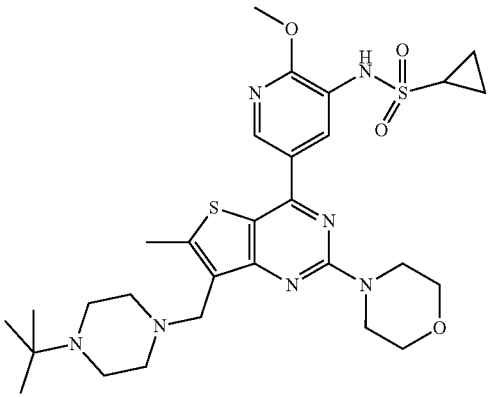
110
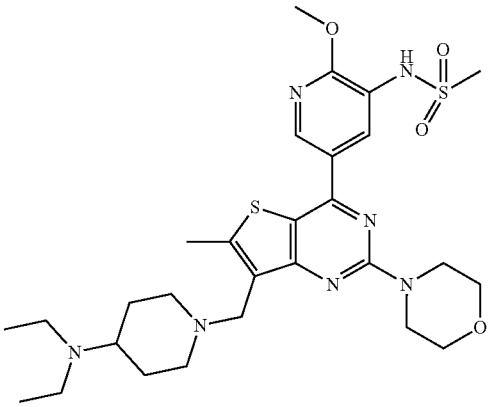
111
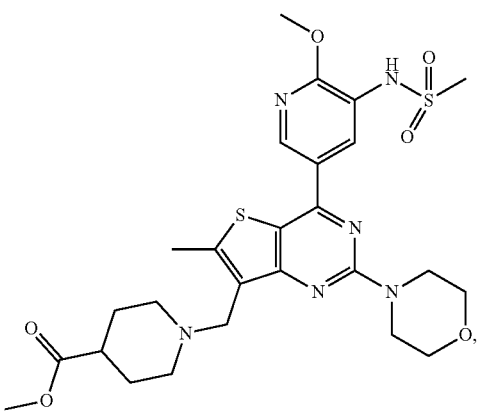

-continued
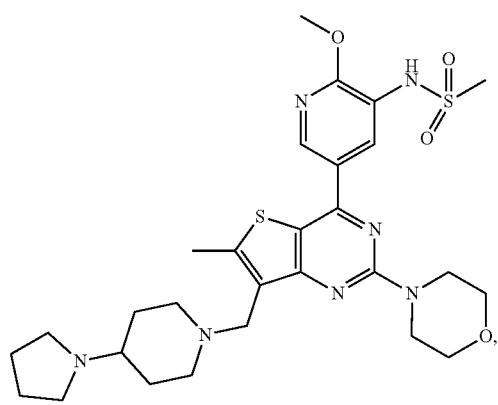
112
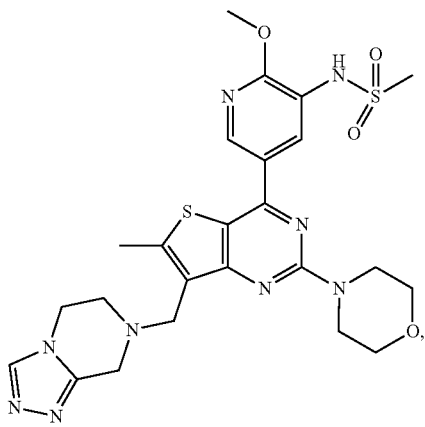
116
113
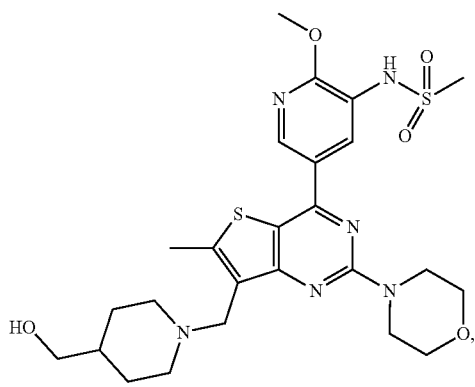
117
114
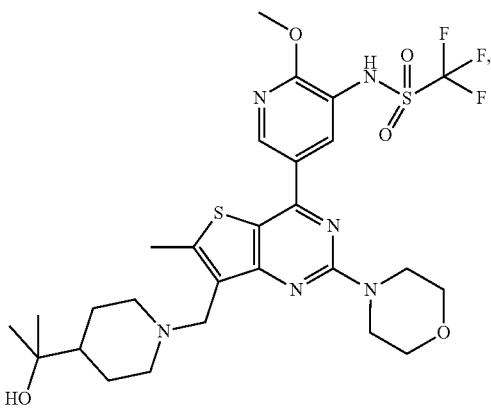
118
115
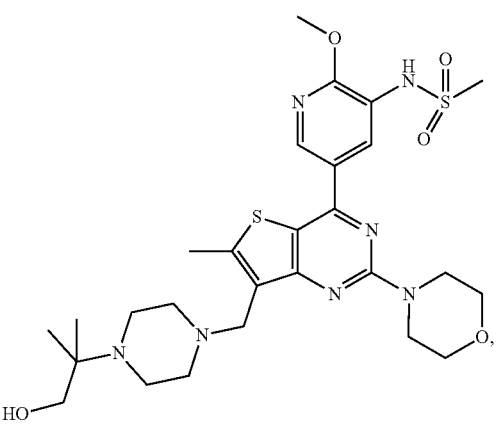
119

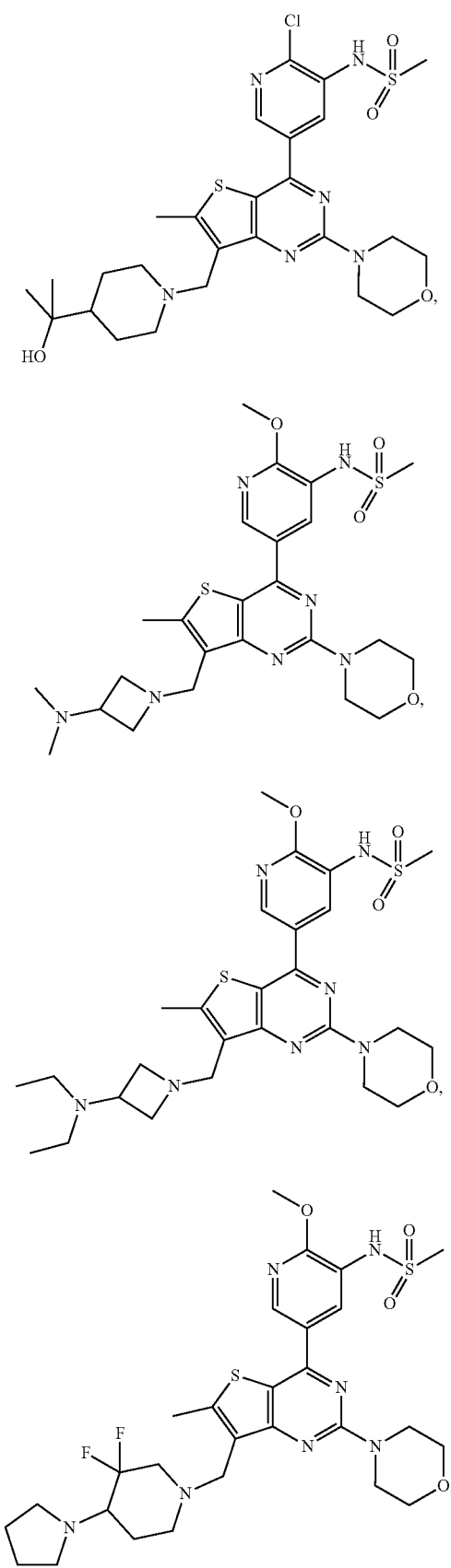
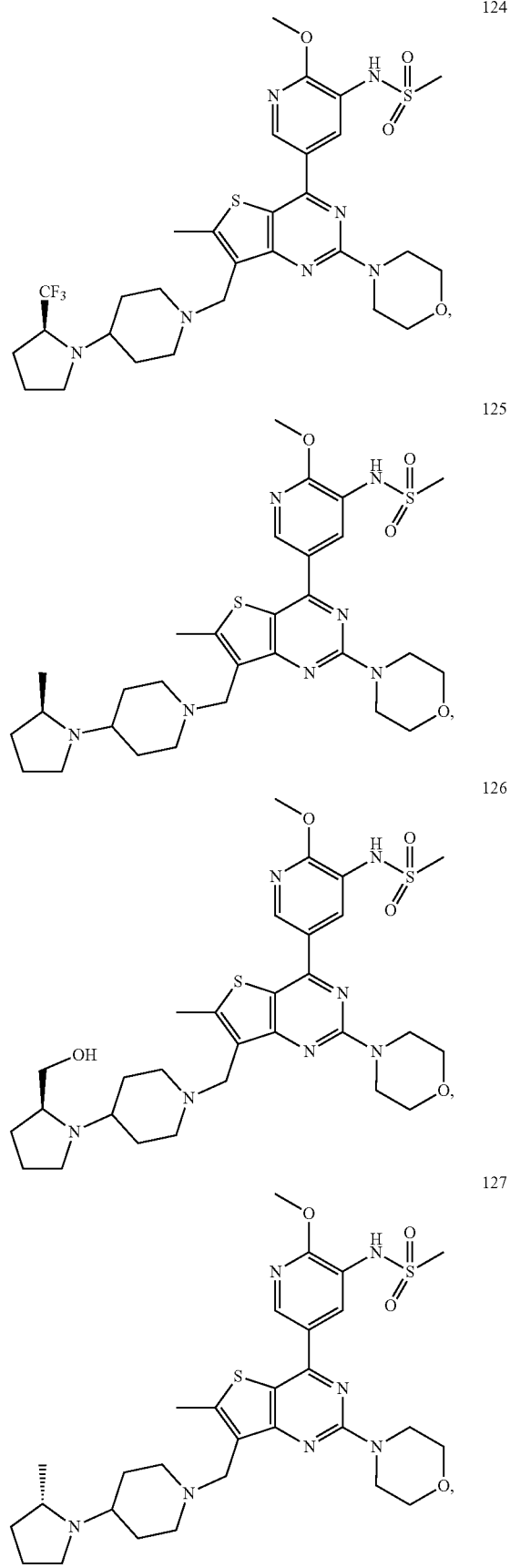

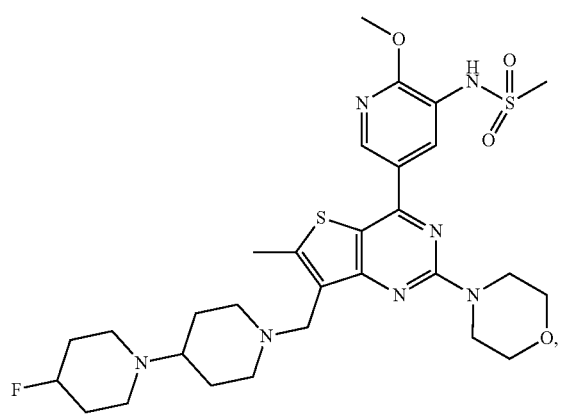
128
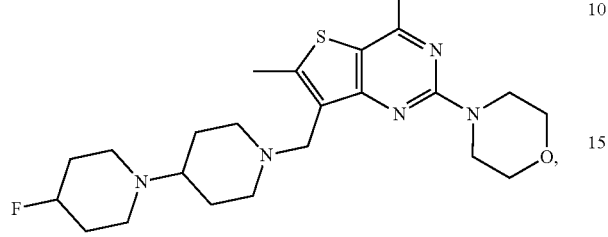
129
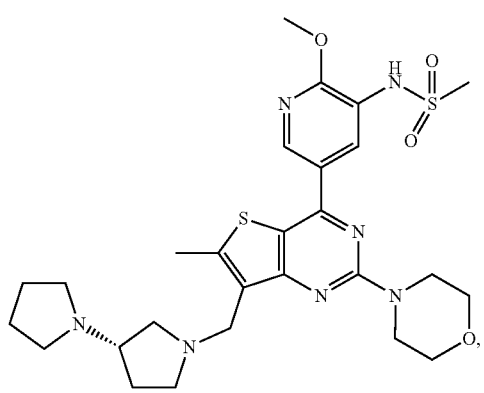
130
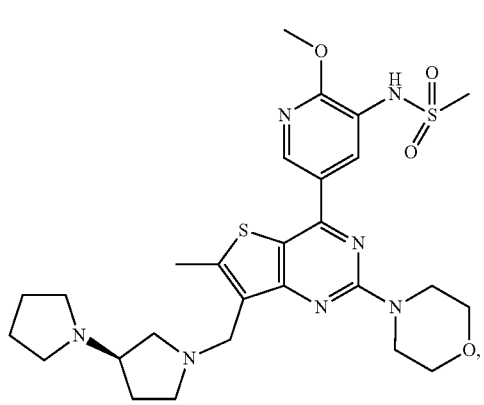
131
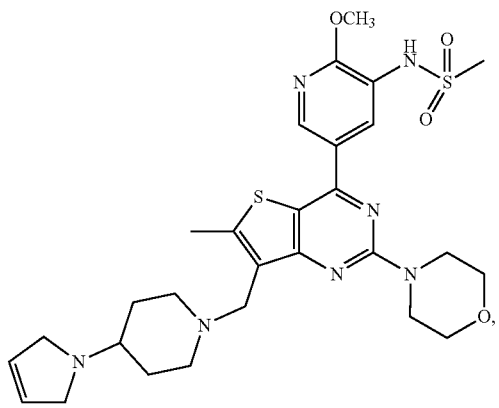
132
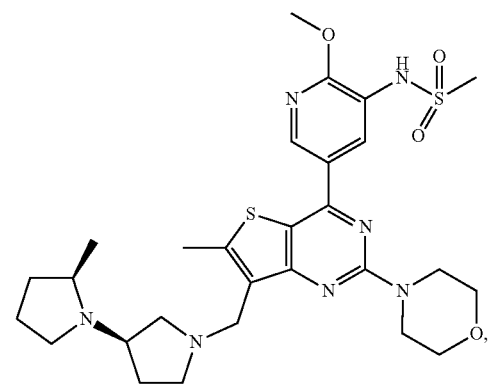
133
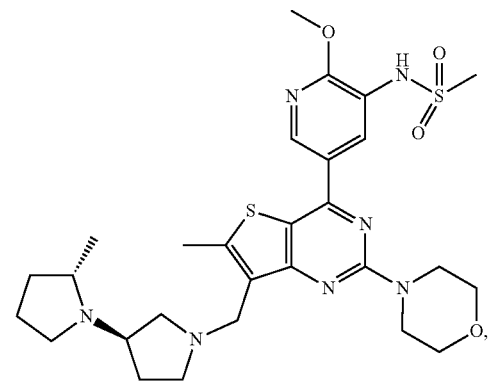
134
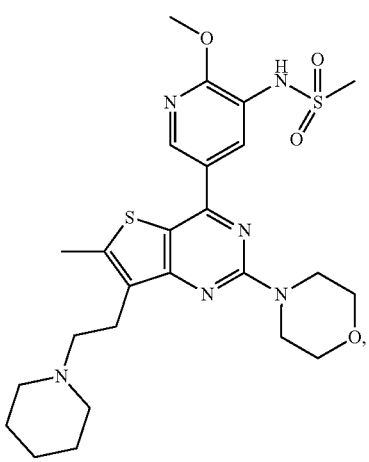
135

136 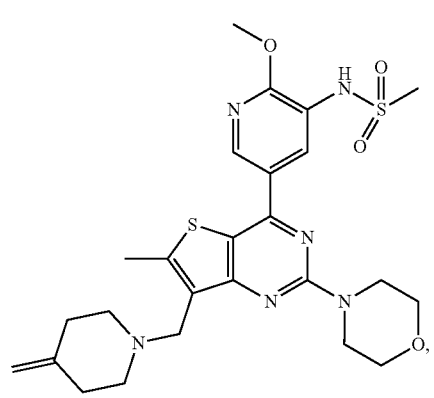
137 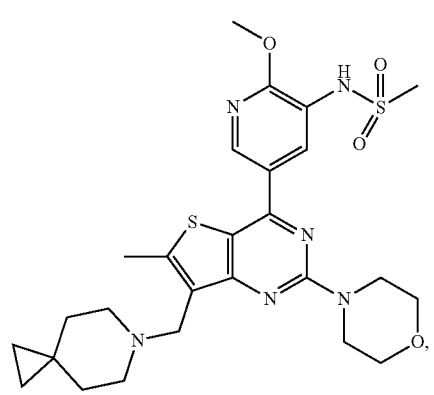
138 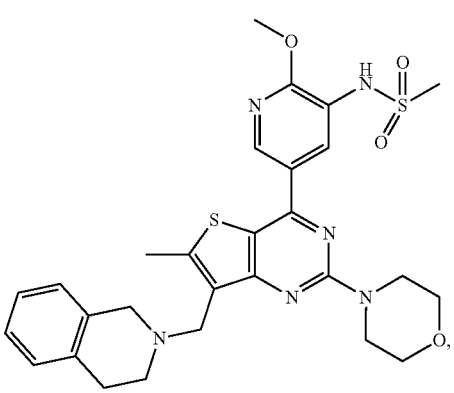
139 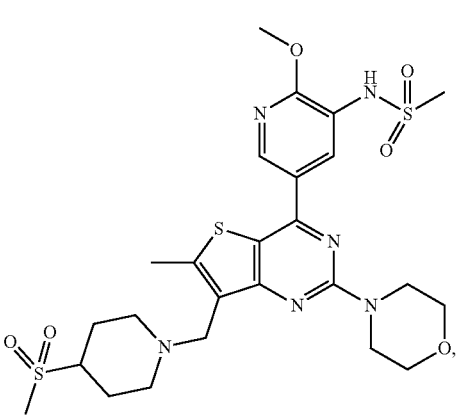
140 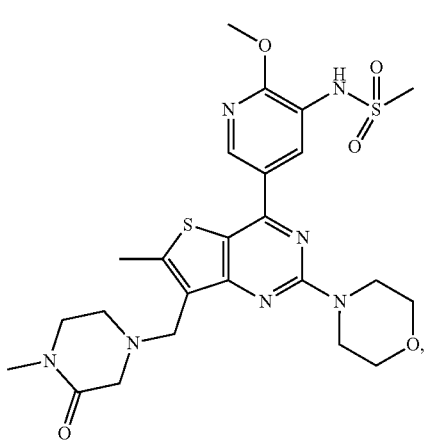
141 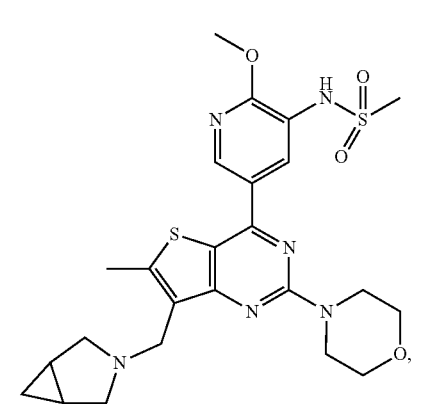
142 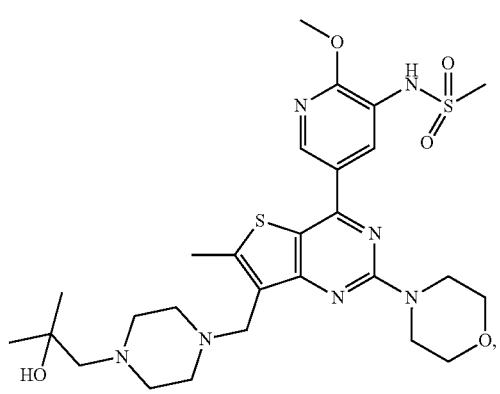
143 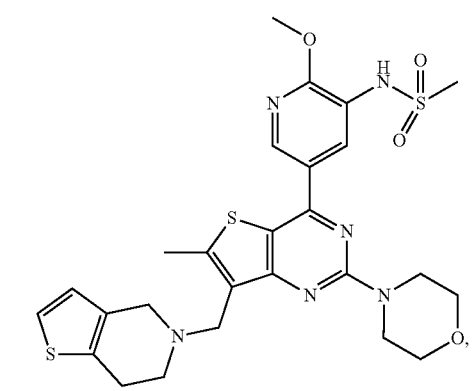

144 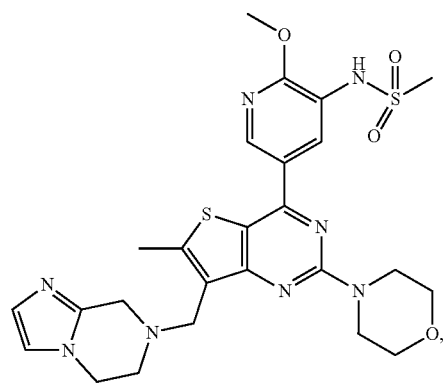
145 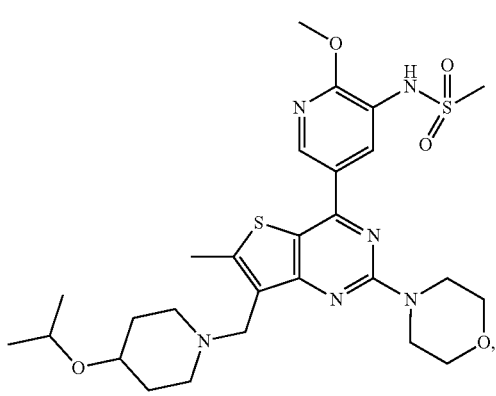
146 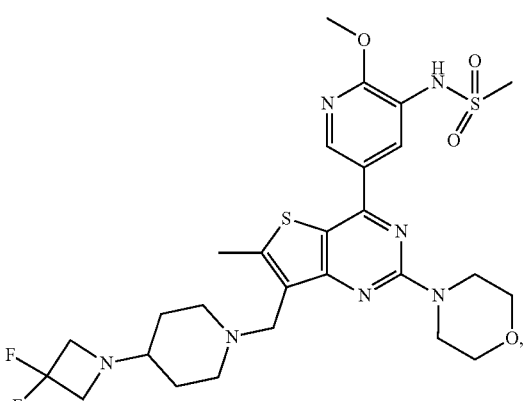
147 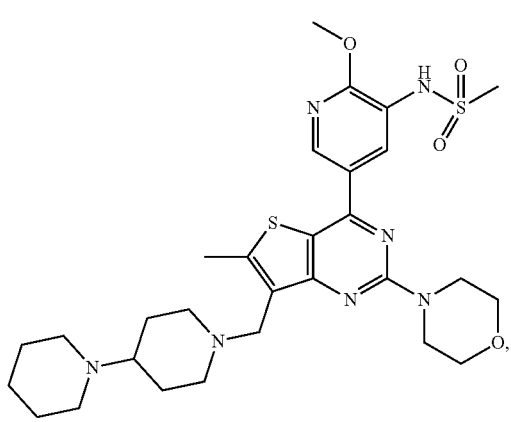
148 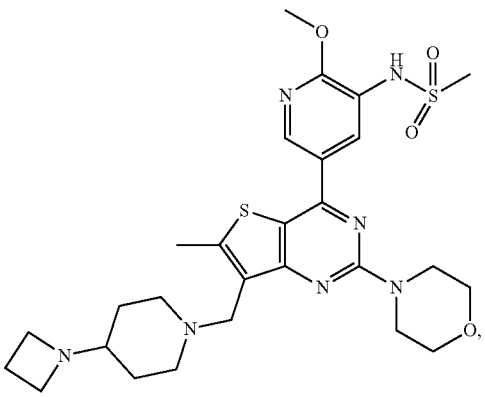
149 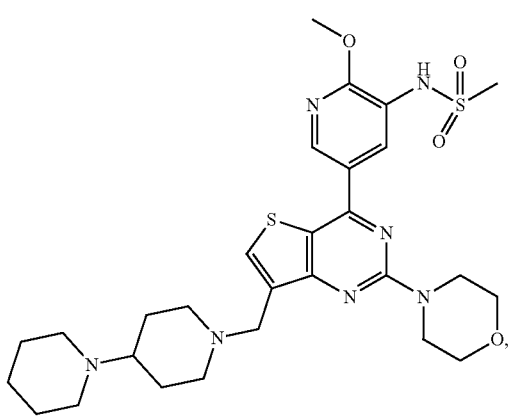
150 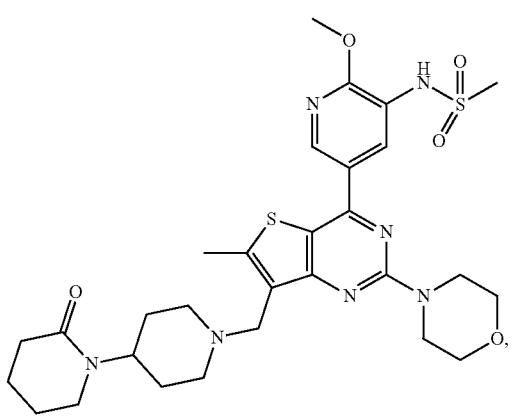
151 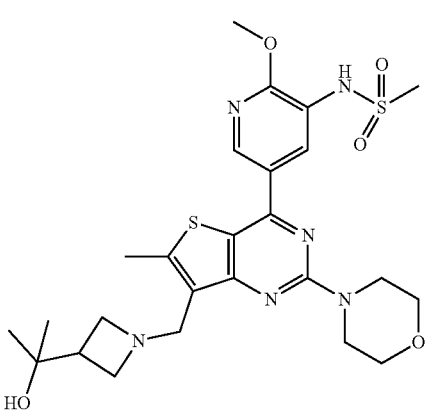

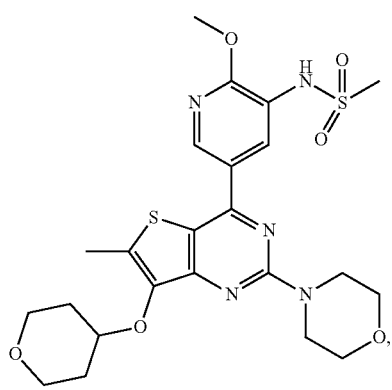

152

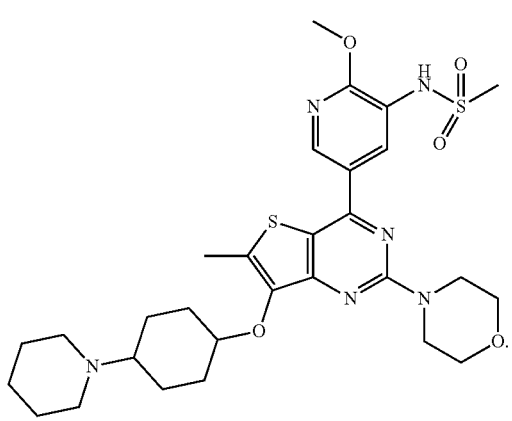

153

The present invention also provides a preparation method for compound I which is any of the following methods:

Method I, reacting compound I-a with $R^2BF_3K$, $R^2B(OR^{10})_2$, $R^2ZnX^1$ or $R^2MgX^1$ as the coupling reaction shown below to obtain compound I;

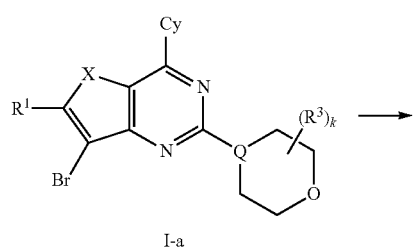

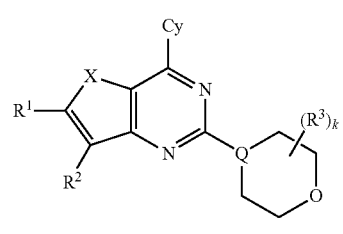

wherein $R^{10}$ is a hydrogen, a $C_1$-$C_6$ alkyl, or a pinacol borate group formed by two $OR^{10}$ groups together with the boron atom to which they are attached as shown below; $X^1$ is Cl, Br or I; $R^1$, $R^2$, $R^3$, Cy, Q, X and k are defined as above;

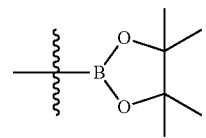 [SMILES: *B1OC(C)(C)C(C)(C)O1]

Wherein the coupling reaction is a type of organic chemistry reaction well-known to the person skilled in the art, and the reaction therefore can be performed according to the methods of coupling reaction in references: *Org. Lett.,* 2006, 8(10), 2031-2034; or *J. Org. Chem.* 2011, 76, 2762-2769; or *Tetrahedron* 63(2007) 3623-3658; or *Chem. Rev.* 2008, 108, 288-325; or *Chem. Rev.* 1995, 95, 2457-2483; or *Tetrahedron* 54(1998) 8275-8319.

Method II: further derivatizing compound I, i.e., deprotecting —$CO_2$t-Bu or after the deprotection, undergoing N-alkylation, N-arylation, reductive amination, or N-acylation reaction well-known to the person skilled in the art, to obtain the target compound I;

the general formula of compound I is as below:

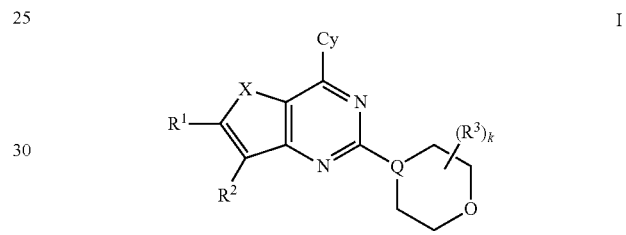

Wherein in the case of compound I as a starting material, $R^2$ is the group shown below, and each of $n_1$ and $n_2$ are independently 0, 1 or 2;

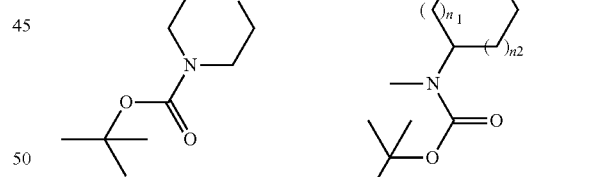

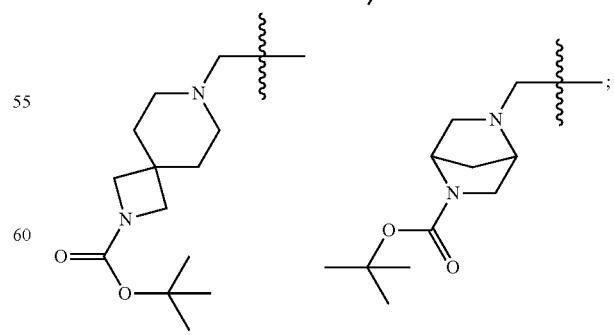

in the case of compound I as a product, $R^2$ is the group shown below:

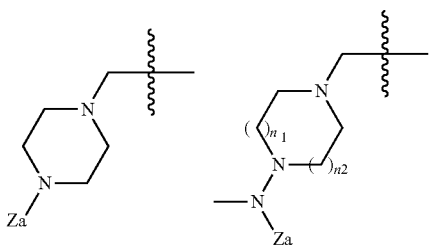

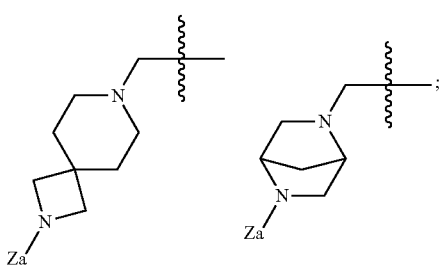

Za is a hydrogen, —C(=Y)R$^5$, —C(=Y)NR$^5$R$^6$, —S(O)R$^5$, —S(O)$_2$R$^5$, a C$_1$-C$_{12}$ alkyl, a C$_3$-C$_{12}$ carbocyclyl, a C$_2$-C$_{20}$ heterocyclyl, a C$_6$-C$_{20}$ aryl or a C$_1$-C$_{20}$ heteroaryl; R$^1$, R$^2$, R$^3$, Cy, Q, X, k, R$^5$ and R$^6$ are defined as above;

Method III: further derivatizing compound I, i.e., via reduction or reductive amination reaction well-known to the person skilled in the art, to obtain the target compound I;

the general formula of compound I is as below:

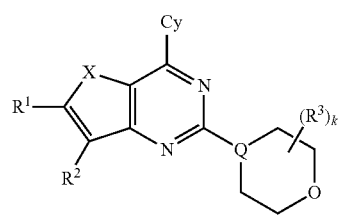

I wherein in the case of compound I as a starting material, R$^2$ is the group shown below, and each of n$_1$ and n$_2$ are independently 0, 1 or 2;

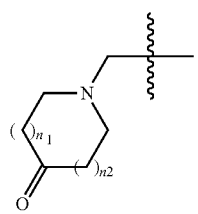

in the case of compound I as a product, R$^2$ is the group shown below: each of n$_1$ and n$_2$ are independently 0, 1 or 2; R$^1$, R$^2$, R$^3$, Cy, Q, X, k, R$^5$ and R$^6$ are defined as above;

method IV, allowing compound I-a to undergo Pd-catalyzed hydroxylation reaction to obtain a phenol intermediate I-a', followed by a nucleophilic substitution reaction between I-a' and R$^5$—OTs, R$^5$—OMs or R$^5$—X$^1$ well-known to the person skilled in the art, to obtain the target compound I;

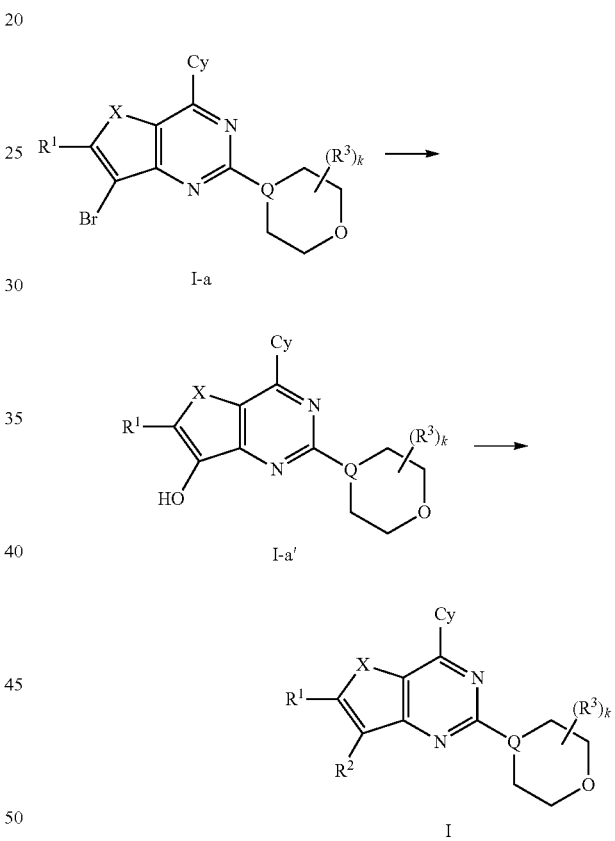

Wherein R$^2$ is —(CR$^8$R$^9$)$_m$OR$^5$, m is 0; X$^1$ is Cl, Br or I; R$^1$, R$^3$, Cy, Q, X and k are defined as above; R$^5$ is a C$_1$-C$_{12}$ alkyl (preferably substituted or unsubstituted C$_1$-C$_5$ alkyl in which the "unsubstituted" means not being substituted by a substituent other than an alkyl; the "C$_1$-C$_5$ alkyl" is preferably a methyl, an ethyl, a propyl, an isopropyl, a n-butyl, an isobutyl, a tert-butyl, a n-pentyl, an isopentyl or a neopentyl, more preferably a methyl, an ethyl, a propyl, an isopropyl or a tert-butyl; and the "substituted" means that it may be substituted by a hydroxyl and/or an unsubstituted C$_1$-C$_3$ alkoxy such as a methoxy, an example of the "substituted C$_1$-C$_5$ alkyl" is

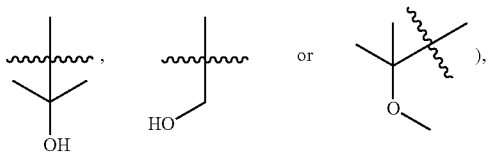

a C$_3$-C$_{12}$ carbocyclyl (preferably substituted or unsubstituted C$_3$-C$_6$ saturated carbocyclyl in which the "substituted" means being substituted by one or more unsubstituted C$_1$-C$_6$ alkyl and/or "C$_3$-C$_6$ heterocyclyl containing O or N as heteroatom with a heteroatom number of 1-2", the "unsubstituted C$_1$-C$_6$ alkyl" may be a methyl, an ethyl, a propyl, an isopropyl, a n-butyl, an isobutyl or a tert-butyl, and the "C$_3$-C$_6$heterocyclyl containing O or N as heteroatom with a heteroatom number of 1-2" may be "C$_5$-C$_6$heterocyclyl containing N as heteroatom with a heteroatom number of 1" which may be a piperidyl, and the "piperidyl" may be

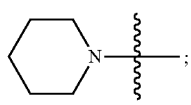

in the case that the "substituted" in the "substituted or unsubstituted C$_3$-C$_6$ saturated carboncyclyl" means being substituted by a methyl and/or an ethyl, the "substituted C$_3$-C$_6$ saturated carbocyclyl" is preferably

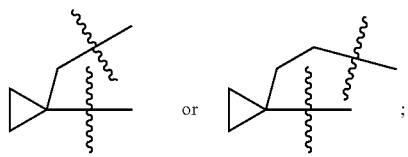 [SMILES: *CC1(*)CC1 ; *CCC1(*)CC1]

in the case that the "substituted" in the "substituted or unsubstituted C$_3$-C$_6$ saturated carboncyclyl" means being substituted by

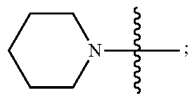

the "substituted C$_3$-C$_6$ saturated carbocyclyl" is preferably

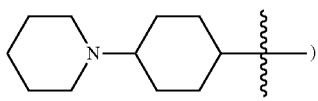 [SMILES: *C1CCC(N2CCCCC2)CC1]

or a C$_2$-C$_{20}$ heterocyclyl (preferably substituted or unsubstituted C$_1$-C$_9$ heterocyclyl containing the heteroatom selected from the group consisting of O, S and N with a heteroatom number of 1-3, in which the "substituted" means being substituted preferably by the substituent selected from the group consisting of unsubstituted C$_1$-C$_6$ alkyl (preferably a methyl, an ethyl, a propyl, an isopropyl, a n-butyl, an isobutyl or a tert-butyl), a halogen (e.g., F, Cl or Br), a halogen-substituted alkyl(e.g., trifluoromethyl), a hydroxyl-substituted alkyl (e.g., hydroxymethyl or

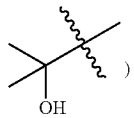

and "C$_2$-C$_4$ heterocyclyl containing O, S or N as heteroatom with a heteroatom number of 1-2" (in which the "C$_2$-C$_4$ heterocyclyl" is preferably a C$_3$ heterocyclyl; and the "C$_2$-C$_4$ heterocyclyl containing O, S or N as heteroatom with a heteroatom number of 1-2" is preferably a "C$_3$ heterocyclyl containing O as heteroatom with a heteroatom number of 1" with a preference to oxacyclobutyl which may be

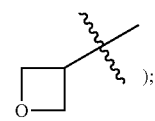 [SMILES: *C1COC1]

the "substituted or unsubstituted C$_1$-C$_9$ heterocyclyl containing the heteroatom selected from the group consisting of O, S and N with a heteroatom number of 1-3" is more preferably substituted or unsubstituted C$_4$-C$_5$ heterocyclyl containing O or N as heteroatom with a heteroatom number of 1-2, for example, substituted or unsubstituted tetrahydropyranyl (an example of the "unsubstituted tetrahydropyranyl" is

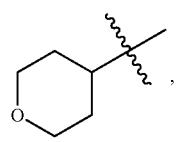 [SMILES: *C1CCOCC1]

an example of the "substituted trtrahydropyranyl" is

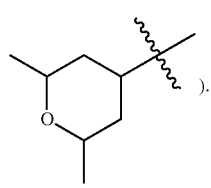 [SMILES: *C1CC(C)OC(C)C1]

a substituted or unsubstituted pyrrolidyl (in which the substituted pyrrolidyl may be

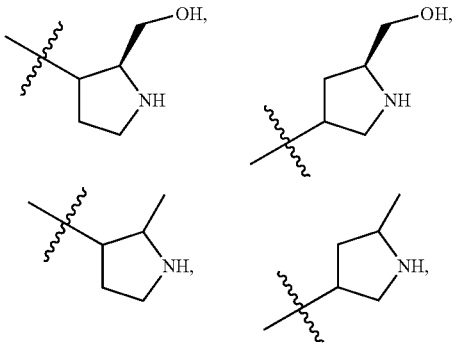

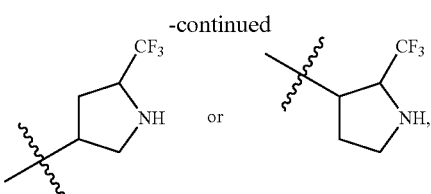

and the unsubstituted pyrrolidyl may be

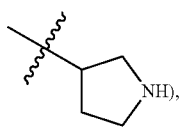

a substituted or unsubstituted piperidyl (the "substituted piperidyl" is preferably

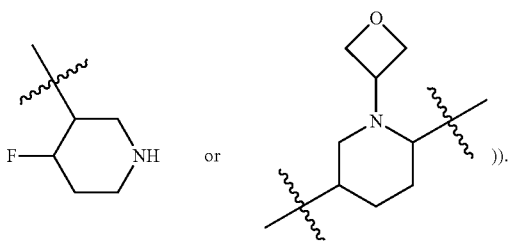 [SMILES: *C1CNCCC1F ; *C1CCC(*)N(C2COC2)C1]

In $R^5$ the carbon atom other than the one at α-position of the heteroatom is linked with the oxygen atom in "—$(CR^8R^9)_mOR^5$".

Wherein, the Pd-catalyzed hydroxylation reaction may be performed according to the method in reference of Angew. Chem. Int. Ed. 2009, 48, 7595-7599.

In the present invention, the compound I-a may be prepared by the following method: allowing compound I-c and compound I-b to undergo a nucleophilic substitution reaction to obtain compound I-a;

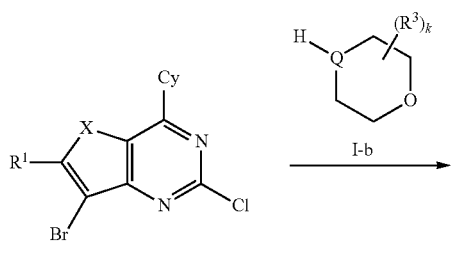

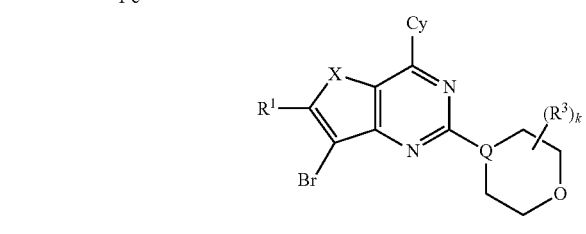

wherein Q is N; $R_1$, $R_2$, $R_3$, Cy, X and k are defined as above.

wherein the nucleophilic substitution reaction is a type of organic chemistry reaction well-known to the person skilled in the art, and thus the reaction may be performed according to the method of the nucleophilic substitution reaction in references of *Bioorganic & Medicinal Chemistry Letters* 18(2008) 2920-2923; or *Bioorganic & Medicinal Chemistry Letters* 18(2008) 2924-2929.

In the present invention, the compound I-c may be prepared by the following method: allowing compounds I-e and I-d to undergo a coupling reaction, or allowing compound I-e and NH-containing Cy to undergo a nucleophilic substitution reaction;

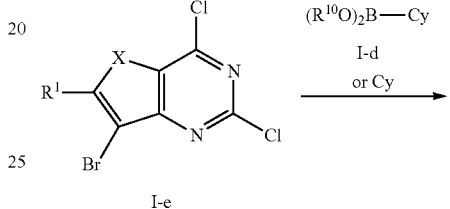

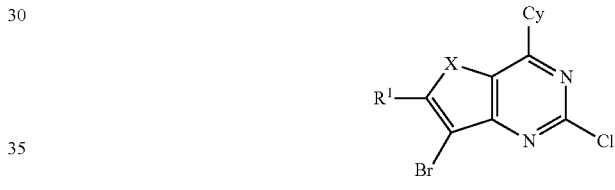

Wherein $R^{10}$ is a hydrogen or a $C_1$-$C_6$ alkyl, or a pinacol borate group formed by two $OR^{10}$ groups together with the boron atom to which they are attached (as shown below); each of the other groups and alphabets are defined as above.

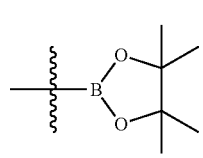

Wherein the coupling reaction is a type of organic chemistry reaction well-known to the person skilled in the art, and thus the reaction may be performed according to the method of the coupling reaction in references of *Chem. Rev.* 1995, 95, 2457-2483; or *Tetrahedron* 68(2012) 329-339; or *Bioorganic & Medicinal Chemistry Letters* 18(2008) 2920-2923; or *Bioorganic & Medicinal Chemistry Letters* 18(2008) 2924-2929.

Therefore, in the present invention, the reaction route of the preparation method of the compound I is preferably shown as below:

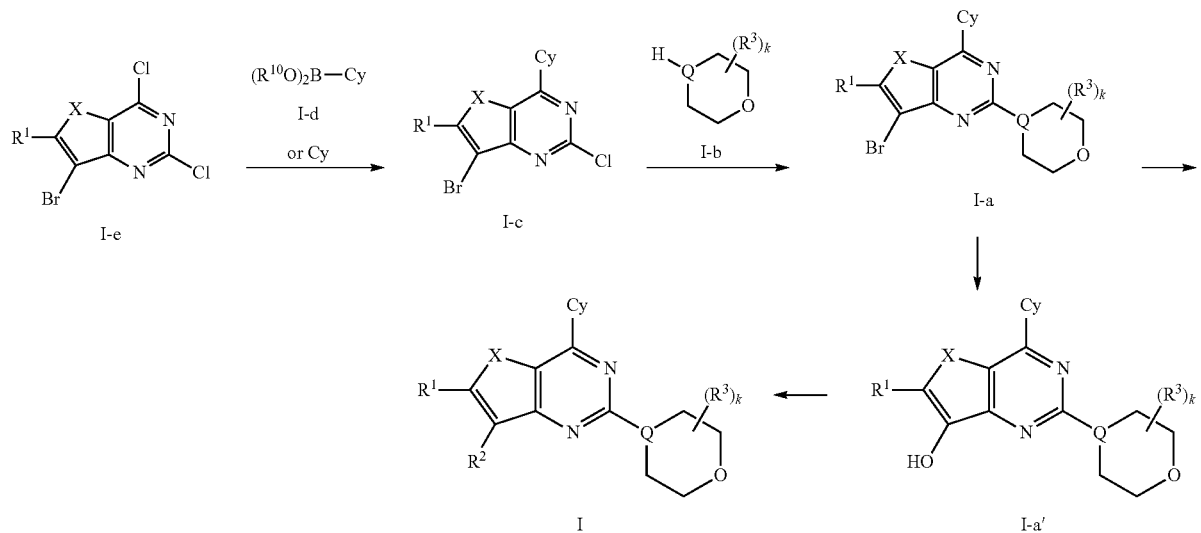

wherein Q is N; $R^1$, $R^2$, $R^3$, Cy, X and k are defined as above.

Wherein the route takes compound I-e as a starting material, allows compound I-e and compound I-d to undergo the coupling reaction, or allows compound I-e and NH-containing Cy to undergo a selective nucleophilic substitution reaction to obtain compound I-c; allows compound I-b and compound I-c to undergo the nucleophilic substitution reaction to obtain compound I-a, carries on coupling reaction with compound I-a to yield the compound of general formula I; or first carrying on Pd-catalyzed hydroxylation reaction on compound I-a to yield compound I-a' and followed by undergoing a nucleophilic substitution reaction with compound I-a' to yield the compound of general formula I.

wherein the coupling reaction and nucleophilic substitution reaction are all organic chemistry reactions well-known to the person skilled in the art.

wherein the starting material of compound I-e ($R^1$=H) may be prepared according to the method disclosed in reference (Tetrahedron 2007, 63, 3608-3614); and compound I-e ($R^1$≠H) may be prepared by the following method: allowing compound I-f to undergo a bromination reaction as shown by the route below:

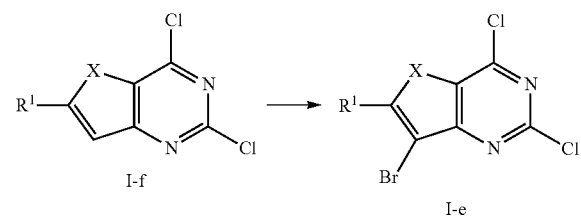

wherein $R^1$ is the same as previously defined, but is not a hydrogen; and X is the same as previously defined.

Wherein, the methods and conditions of the bromination reaction may all be conventional methods and conditions of this type of reaction in the art, the following methods and conditions are particularly preferred in the present invention: reacting compound I-f with bromine in the presence of a Lewis acid in a solvent. Wherein, the solvent is preferably acetic acid, propionic acid, more preferably acetic acid. The volume-mass ratio of the solvent and compound I-f is preferably 2 mL/g-20 mL/g. The Lewis acid is preferably selected from the group consisting of aluminum trichloride, titanium tetrachloride and tin chloride, more preferably aluminum trichloride. The usage of the bromine is preferably 1-6 times, more preferably 2-4 times as much as the molar amount of compound I-f. The temperature of the reaction is preferably 0° C.-120° C., more preferably 20° C.-100° C. The duration of the reaction is preferably until the reaction is complete by detection, generally 3 hrs to 20 hrs.

Wherein, compound I-f may be prepared by a method known in the art of organic chemistry, such as the method described in references (WO2007/023382; CN101675053).

According to the above-described preparation method disclosed by the present invention, the person skilled in the art can utilize the same principle and method to prepare each specific compound covered by the compound represented by general formula I of the present invention.

Unless otherwise specified or providing a preparation method, the starting materials used for preparing the compounds of the present invention or the intermediates thereof are all known in the art or commercially available.

The present invention also provides an intermediate compound for preparing the above compound I which is selected from the group consisting of:

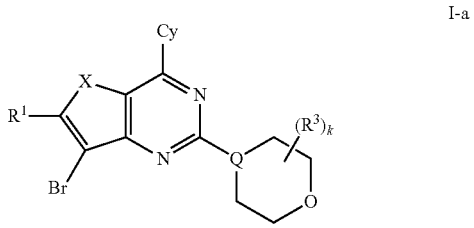

-continued
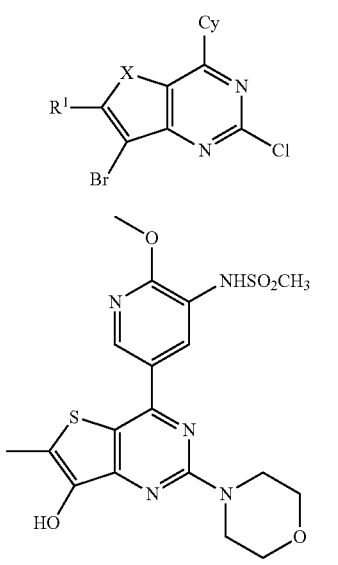
Wherein Q is N; $R^1$, $R^3$, Cy, X and k are defined as above.
In the present invention, the intermediate compound I-a is preferably a specific compound selected from the group consisting of:

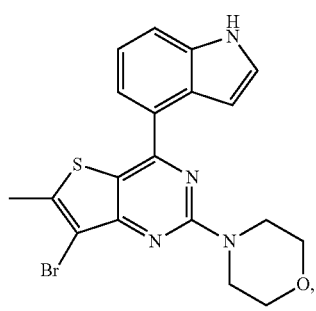
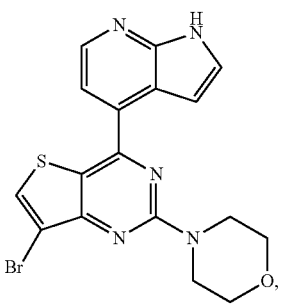
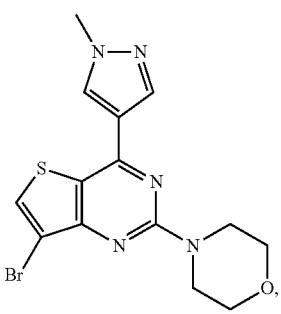
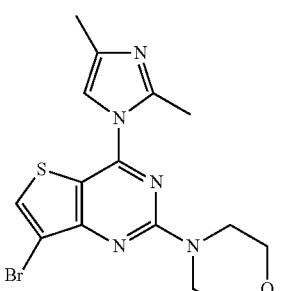
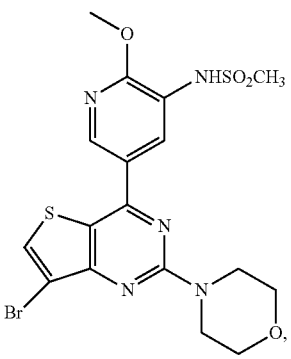

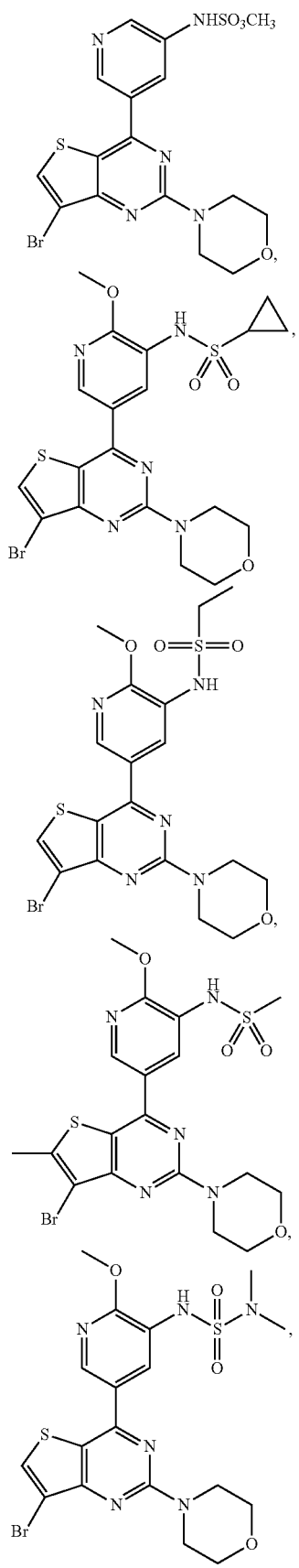
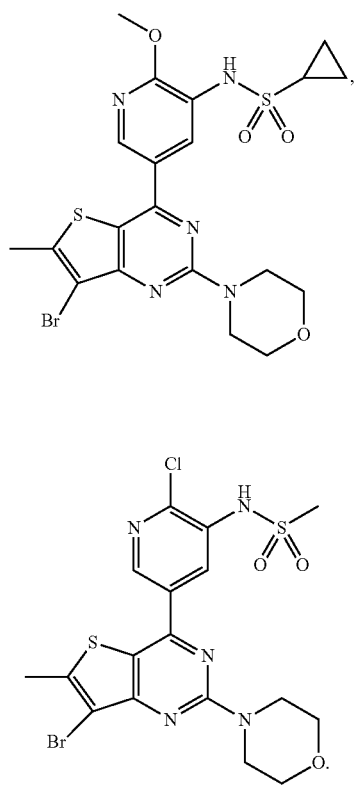
In the present invention, the intermediate compound I-c is preferably a specific compound selected from the group consisting of:
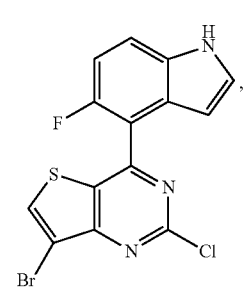

4-b

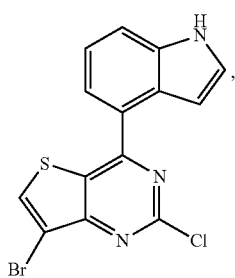

8-e

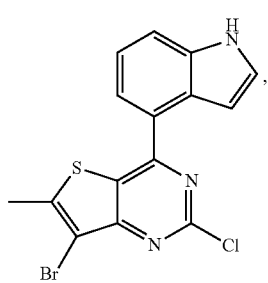

17-b

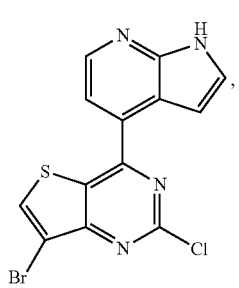

18-d

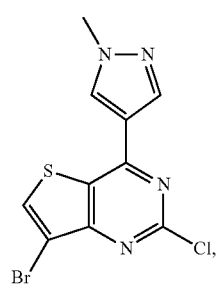

27-b

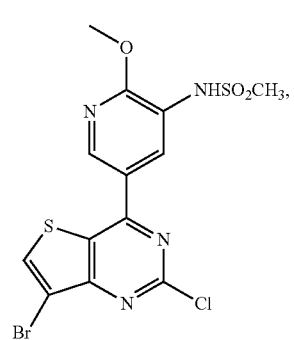

31-d

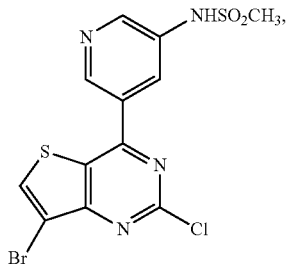

50-b

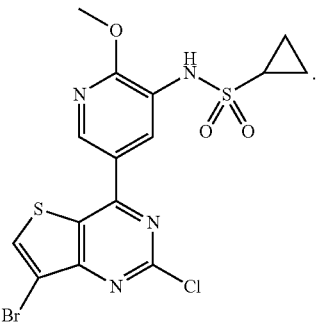

The chemical general formula involved in the present invention may exhibit tautomerism, structural isomerism and stereoisomerism. The present invention includes any tautomeric or structural isomeric or stereoisomeric form as well as the mixture thereof, and they have the ability to modulate kinase activity which is not limited to any form of the isomer or the mixture thereof.

The present invention provides a use of the fused pyrimidine compound represented by formula I, the pharmaceutically acceptable salt, hydrate, solvate, optical isomer or prodrug thereof in manufacturing a kinase inhibitor.

The present invention also provides a use of the fused pyrimidine compound represented by formula I, the pharmaceutically acceptable salt, hydrate, solvate, optical isomer or prodrug thereof in manufacturing a medicament for treating and/or preventing a disease associated with kinase.

In the present invention, the kinase is preferably PI3 kinase (PI3K), more preferably p110 δ subtype of PI3 kinase (PI3K).

The present invention also provides a pharmaceutical composition comprising a therapeutically effective amount of the fused pyrimidine compound represented by formula I, the pharmaceutically acceptable salt, hydrate, solvate, optical isomer or prodrug thereof, and a pharmaceutically acceptable carrier.

In the present invention, the "therapeutically effective amount" represents (i) an amount of the compound in the present invention for preventing or treating the specific diseases or disorders described in the application, (ii) an amount of the compound in the present invention for reducing, ameliorating or eliminating one or more symptoms associated with the specific diseases or disorders described in the application, or (iii) an amount of the compound in the present invention for preventing or delaying the onset of one or more symptoms associated with the specific diseases or disorders described in the application. The dosage for treating human patient may be in a range of 0.0001 mg/kg-50 mg/kg, most often 0.001 mg/kg-10 mg/kg body weight, for example 0.01 mg/kg-1 mg/kg. Such a dosage may be administered for example 1-5 times a day.

The present invention further provides a use of the pharmaceutical composition in manufacturing a kinase inhibitor.

The present invention also provides a use of the pharmaceutical composition in manufacturing a medicament for treating and/or preventing a disease associated with kinase.

In the present invention, the "kinase" in the "disease associated with kinase" is preferably a PI3 kinase.

In the present invention, the "disease associated a kinase" includes, but are not limited to, a disease selected from the group consisting of cancer, immune disease, metabolism and/or endocrine disorder, cardiovascular disease, viral infection and inflammation, and neurological disease, preferably cancer and/or immune disease. The immune disease includes, but not limited to, a disease selected from the group consisting of rheumatoid arthritis, psoriasis, ulcerative colitis, Crohn's disease and systemic lupus erythematosus; the cardiovascular disease includes, but not limited to, a disease selected from the group consisting of blood tumor; and the viral infection and inflammation include, but not limited to, asthma and/or atopic dermatitis.

The present invention also provides a method for treating and/or preventing a disease associated with kinase, which comprises: administering an effective dosage of the pharmaceutical composition to a patient.

Unless otherwise specified, the following terms in the specification and claims of the invention have the meaning as follows:

As used herein, the "alkyl" (including used alone and contained in other groups) intends to encompass a saturated straight- or branched-chain aliphatic hydrocarbyl containing 1 to 20 carbon atoms, preferably 1 to 12 carbon atoms, more preferably 1 to 6 carbon atoms, such as methyl, ethyl, n-propyl, isopropyl, n-butyl, tert-butyl, isobutyl, pentyl, hexyl, heptyl, octyl, nonyl, decyl, 4,4-dimethylpentyl, 2,2,4-trimethylpentyl, undecyl, dodecyl, and various isomers thereof etc.; as well as the above alkyl group containing the substituent selected from the group consisting of: a deuterium, a halogen (preferably F, Br, Cl or I), an alkoxy, an aryl, an aryloxy, an aryl-substituted aryl or diaryl, an arylalkoxy, an alkenyl, an alkynyl, a cycloalkyl, a cycloalkenyl, a cycloalkylalkoxy, an amino, optionally substituted amino (such as an amino substituted by one to two unsubstituted $C_1$-$C_3$ alkyl, or —$NR^7C(=Y)R^5$ mentioned above), a hydroxyl, an acyl, an aldehyde group, a heteroaryl, a heteroaryloxy, a heterocycloalkyl, a heterocycloalkoxy, an aryl-heteroaryl, an arylalkoxycarbonyl, a heteroarylalkoxy, an aryloxyaryl, an alkylamino, an amido, an arylcarbonylamino, a $C_2$-$C_{20}$ heterocyclyl, a nitro, a cyano, a mercapto, and an alkylmercapto. "$C_{x1}$-$C_{y1}$" alkyl (with x1 and y1 being integers) with the specified range of carbon number described in the present invention, such as "$C_1$-$C_{12}$ alkyl", is the same as defined except that the range of carbon number differs from the range of carbon number of "alkyl" defined in this paragraph.

As used herein, the "alkylene" (including used alone and contained in other groups) intends to encompass a subsaturated straight- or branched-chain aliphatic hydrocarbyl containing 1 to 20 carbon atoms, preferably 1 to 12 carbon atoms, more preferably 1 to 6 carbon atoms, such as a methylene, an ethylene, a n-propylene, an isopropylene, a n-butylene, a tert-butylene, an isobutylene, a pentylene, a hexylene, a heptylene, an octylene, a nonylene, a decylene, 4,4-dimethylpentylene, 2,2,4-trimethylpentylene, an undecylene, a dodecylene, and various isomers thereof etc.; the alkylene may be substituted by any 1 to 4 substituents selected from the group consisting of: a deuterium, a halogen (preferably F, Br, Cl or I), an alkoxy, an aryl, an aryloxy, an aryl-substituted aryl or diaryl, an arylalkoxy, an alkenyl, an alkynyl, a cycloalkyl, a cycloalkenyl, a cycloalkylalkoxy, an amino, optionally substituted amino (such as an amino substituted by one to two unsubstituted $C_1$-$C_3$ alkyl), a hydroxyl, an acyl, an aldehyde group, a heteroaryl, a heteroaryloxy, a heterocycloalkyl, a heterocycloalkoxy, an aryl-heteroaryl, an arylalkoxycarbonyl, a heteroarylalkoxy, an aryloxyaryl, an alkylamino, an amido, an arylcarbonylamino, a nitro, a cyano, a mercapto, and an alkylmercapto; the substituent selected from the above together with the alkylene may also be linked to form a ring, and thereby to form a fused ring or a spiro ring.

The term "alicyclyl," "carbocyclyl," or "cycloalkyl" (including used alone or contained in other groups) includes saturated or partially unsaturated (containing 1 or 2 double bonds) cyclic hydrocarbon groups containing 1 to 3 rings, including monocyclic alkyl, bicyclic alkyl and tricyclic alkyl, containing 3 to 20 ring-forming carbon atoms, preferably 3 to 12 carbon atoms, for example: a cyclopropyl, a cyclobutyl, a cyclopentyl, a cyclohexyl, a cycloheptyl, a cyclooctyl, a cyclodecyl and a cyclododecyl, a cyclohexenyl; the cycloalkyl may be substituted by any 1 to 4 substituents selected from the group consisting of: a deuterium, a halogen, an alkyl, an alkoxy, a hydroxyl, an aryl, an aryloxy, an arylalkyl, an alkylamino, an amido, oxo, an acyl, an arylcarbonylamino, an amino, a nitro, a cyano, a mercapto, and an alkylmercapto. In addition, any cycloalkyl ring may be fused to a cycloalkyl, aryl, heteroaryl or heterocycloalkyl ring so as to form a fused ring, bridged ring or a spiro ring.

The term "alkoxy" represents a cyclic or non-cyclic alkyl group having the indicated number of carbon atoms and linked via an oxygen bridge. Thus, "alkoxy" includes the above definitions of "alkyl" and "cycloalkyl".

The term "alkenyl" refers to a straight-chain, branched-chain or cyclic non-aromatic hydrocarbyl having the indicated number of carbon atoms and at least one carbon-carbon double bond. Preferably there is one carbon-carbon double bond, and may have up to four non-aromatic carbon-carbon double bonds. Thus, "$C_2$-$C_{12}$ alkenyl" refers to an alkenyl group having 2 to 12 carbon atoms. "$C_2$-$C_6$ alkenyl" refers to an alkenyl group having 2 to 6 carbon atoms, including a vinyl, a propenyl, a butenyl, 2-methylbutenyl and a cyclohexenyl. The straight-, branched-chain or cyclic part of the alkenyl group may include a double bond and, where the substituted alkenyl is specified, the alkenyl group may be substituted.

The term "alkynyl" refers to a straight-chain, branched-chain or cyclic hydrocarbyl having the indicated number of carbon atoms and at least one carbon-carbon triple bond. It may have up to three carbon-carbon triple bonds. Thus, "$C_2$-$C_{12}$ alkynyl" refers to an alkynyl group having 2 to 12 carbon atoms. "$C_2$-$C_6$ alkynyl" refers to an alkynyl group having 2 to 6 carbon atoms, including an ethynyl, a propynyl, a butynyl and 3-methylbutynyl and the like.

As used herein, the "aryl" refers to any stable monocyclic or bicyclic carbocycle with up to 7 atoms in each ring, wherein at least one ring is an aromatic ring. Examples of the above-mentioned aryl unit include phenyl, naphthyl, tetrahydronaphthyl, 2,3-dihydroindenyl, biphenyl, phenanthryl, anthryl or acenaphthenyl. It would be understood that if an aryl substituent is a bicyclic substituent and one ring is non-aromatic ring, then the linkage is through the aromatic ring. The above-mentioned aryl may be substituted by any 1 to 4 substituents selected from the group consisting of: a deuterium, a halogen (F, Br, Cl or I), an alkyl, an alkoxy, an aryloxy, a diaryl, an arylalkyl, an arylalkoxy, an alkenyl, an alkynyl, a cycloalkyl, a cycloalkenyl, a cycloalkylalkyl, a cycloalkylalkoxy, optionally substituted amino, a hydroxyl, a hydroxyalkyl, an acyl, an aldehyde group, a heteroaryl, a heteroaryloxy, a heterocycloalkyl, a heterocycloalkyloxy, an arylheteroaryl, an arylalkoxycarbonyl, a heteroarylalkyl, a heteroarylalkoxy, an aryloxyalkyl, an alkylamino, an amido, an arylcarbonylamino, a nitro, a cyano, a mercapto, a haloalkyl, a trihaloalkyl, and an alkylmercapto.

The term "alkylmercapto" represents a cyclic or non-cyclic alkyl group containing the indicated number of carbon atoms and linked via a sulfur-bridge. Thus, "alkylmercapto" includes the above definitions of alkyl and cycloalkyl.

The term "halogen" represents fluorine, chlorine, bromine, iodine, or astatine.

The term "haloalkyl" represents a halogen-substituted alkyl group at arbitrary position(s). Thus, "haloalkyl" includes the above definitions of halogen and alkyl.

The term "haloalkoxy" represents to a halogen-substituted alkoxy group at arbitrary position(s). Thus, the "haloalkoxy" includes the above definitions of halogen and alkoxy.

The term "aryloxy" represents an aryl group having the indicated number of carbon atoms and linked via an oxygen-bridge. Thus, "aryloxy" includes the above definition of aryl.

As used herein, the term "arylhetero" or "heteroaryl" represents a stable monocycle or bicycle which may be with up to 7 atoms in each ring, wherein at least one ring is an aromatic ring and contains 1 to 4 heteroatoms selected from O, N, and S. Heteroaryl groups within the scope of this definition include, but not limited to, acridinyl, carbazolyl, cinnolinyl, quinoxalinyl, pyrazolyl, imidazolyl, indolyl, indazolyl, triazolyl, tetrazolyl, benzotriazolyl, benzimidazolyl, benzoxazolyl, benzothiazolyl, benzisoxazolyl, benzisothiazolyl, purinyl, furyl, thienyl, thiazolyl, benzothienyl, benzofuranyl, quinolinyl, isoquinolinyl, oxazolyl, oxdiazolyl, isoxazolyl, triazinyl, pyrazinyl, pyridazinyl, pyridinyl, pyrimidinyl, pyrrolyl, tetrahydroquinolinyl. As the heterocycle defined below, "heteroaryl" should also be understood to include N-oxide derivatives of any nitrogen-containing heteroaryl group. In the case where the heteroaryl substituent is a bicyclic substituent and one ring is a non-aromatic ring or is without any heteroatom, it is understandable that a linkage is established via the aromatic ring or the heteroatom contained in the ring. The heteroaryl group may be substituted by any 1 to 4 substituents selected from the group consisting of: a deuterium, a halogen, an alkyl, an alkoxy, a hydroxyl, an aryl, an aryloxy, an arylalkyl, a cycloalkyl, an alkylamino, an amido, an acyl, an arylcarbonylamino, an amino, a nitro, a cyano, a mercapto and an alkylmercapto.

As used herein, the term "heterocycle" or "heterocyclyl" represents a 5 to 10 membered aromatic or non-aromatic heterocycle containing 1 to 4 heteroatoms selected from O, N, and S, and includes bicyclic groups. Therefore, the "heterocyclyl" includes the above heteroaryl groups, as well as dihydro- or tetrahydro-analogs thereof. Other examples of "heterocyclyl" include, but are not limited to, benzimidazolyl, benzofuranyl, benzofurazanyl, benzopyrazolyl, benzotriazolyl, benzothienyl, benzoxazolyl, carbazolyl, carbolinyl, cinnolinyl, furyl, imidazolyl, dihydroindolyl, indolyl, indazolyl, isobenzofuranyl, pseudoindolyl, isoquinolinyl, isothiazolyl, isoxazolyl, naphthalene pyrimidinyl, oxadiazolyl, oxazolyl, oxazoline, isoxazoline, oxetanyl, pyranyl, pyrazinyl, pyrazolyl, pyridazinyl, pyridopyridyl, pyridazinyl, pyridinyl, pyrimidinyl, pyrrolyl, quinazolinyl, quinolyl, quinoxalinyl, tetrahydropyranyl, tetrazolyl, tetrazopyridyl, thiadiazolyl, thiazolyl, thienyl, triazolyl, azetidinyl, 1,4-dioxanyl, hexahydrodiazepinyl, piperazinyl, piperidinyl, pyrrolidinyl, morpholinyl, thio-morpholinyl, dihydrobenzimidazolyl, dihydrobenzofuranyl, dihydrobenzothienyl, dihydrobenzoxazolyl, dihydrofuryl, dihydroimidazolyl, dihydroindolyl, dihydroisoxazolyl, dihydroisothiazolyl, dihydrooxadiazolyl, dihydrooxazolyl, dihydropyrazinyl, dihydropyrazolyl, dihydropyridyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl and tetrahydrothienyl and N-oxides thereof. The heterocyclyl substituent can be linked with other groups via a carbon atom or a heteroatom therein. $C_2$-$C_{20}$heterocyclyl is preferably $C_2$-$C_8$ saturated heterocyclyl, more preferably $C_4$-$C_5$ saturated heterocyclyl, in which the heteroatom is N, O or S, more preferably $C_4$-$C_5$ saturated heterocyclyl with a heteroatom number of 2, e.g., piperazinyl or piperidyl. Where there is one heteroatom in the $C_2$-$C_{20}$ heterocyclyl, the substitution position is preferably at a carbon atom or a heteroatom; and where there are two or more than two heteroatoms, the substitution position is preferably at the heteroatom.

The term "heteroalicyclyl" or "heterocycloalkyl" used herein alone or as a part of another group refers to a 4 to 12 membered saturated or partially unsaturated ring containing 1 to 4 heteroatoms (such as nitrogen, oxygen and/or sulphur). The heterocycloalkyl group may include one or more than one substituent, such as an alkyl, a halogen, oxo and the alkyl substituent listed above. In addition, the heterocycloalkyl ring can be fused to a cycloalkyl, aryl, heteroaryl or heterocycloalkyl ring to form a fused ring, a bridged ring or a spiro ring. The heterocycloalkyl substituent can be linked with other groups via a carbon atom or a heteroatom therein.

The above various preferred conditions can be combined randomly without departing from common knowledge in the art to obtain various preferred embodiments of the present invention.

The reagents and starting materials used in the present invention are all commercially available.

The room temperature described in the present invention refers to ambient temperature within a range of 10° C.-35° C.

The positive effect of the present invention is that: the fused pyrimidine compound I of the present invention is a potent, low toxic PI3 kinase (especially PI3Kδ-oriented) inhibitor which can be used in manufacturing a medicament for preventing and/or treating cell proliferation diseases such as cancer, infections, inflammation and autoimmune diseases.

DETAILED DESCRIPTION OF THE PREFERRED EMBODIMENT

Now the present invention will be further illustrated below by way of examples, and however the present invention is not therefore limited within the scope of the examples. The experimental method without particular conditions being specified in the following examples is chosen according to conventional methods and conditions, or product instructions.

Synthetic Route of Compound 1

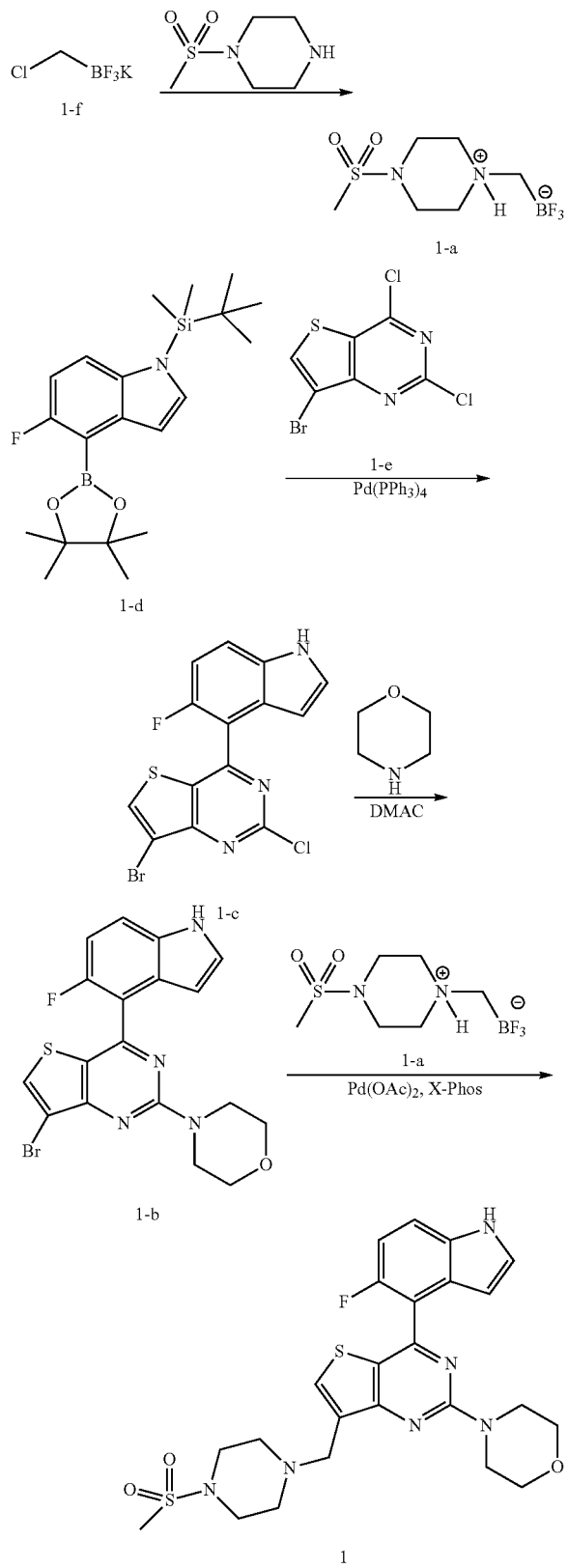

Synthesis of Compound 1-c

A mixture of compound 1-d (prepared according to the method disclosed in reference: Journal of Medicinal Chemistry, 2012, 5887-5900) (338 mg), compound 1-e (prepared according to the method disclosed in reference: Tetrahedron 2007, 63, 3608-3614) (540 mg), tetrakis(triphenylphosphine)palladium (139 mg, 0.12 mmol), cesium carbonate (782 mg, 2.4 mmol), dioxane (25 mL) and water (10 mL) was heated to 100° C. under nitrogen atmosphere overnight. The reaction solution was cooled, and concentrated under reduced pressure. The residue was diluted with ethyl acetate, and washed sequentially with water and saturated brine. The separated organic phase was dried over anhydrous sodium sulfate, and concentrated under reduced pressure. The residue was purified by silica gel column chromatography (elution system: petroleum ether/ethyl acetate=6/1) to yield compound 1-c (98 mg, 21%). LC-MS ESI:m/z=382(M+H)$^+$.

Synthesis of Compound 1-b

To a reaction flask were added 1-c (98 mg), morpholine (90 mg) and N,N-dimethylacetamide (DMAC) (5 mL). The reaction solution was stirred under nitrogen atmosphere at 95° C. overnight. The reactants were cooled to room temperature, and concentrated under reduced pressure. The residue was diluted with ethyl acetate, and washed sequentially with water and saturated brine, the separated organic phase was dried over anhydrous sodium sulfate, and concentrated under reduced pressure. The residue was purified by Prep-TLC (developing system: petroleum ether/ethyl acetate=2/1), to yield compound 1-b (63 mg, 47%). LC-MS (ESI): m/z=433(M+H)$^+$.

Synthesis of Compound 1-a

To a sealed tube were added compound 1-f (prepared according to the method disclosed in reference: J. Org. Chem. 2011, 76, 2762-2769) (5.5 g, 35.17 mmol), 1-methylsulfonyl piperazine (5.67 g, 34.52 mmol), cyclopentyl methyl ether (CPME) (26 mL) and tert-butanol (9 mL). The reaction solution was stirred under nitrogen atmosphere at 110° C. overnight. The reaction solution was cooled, and concentrated under reduced pressure. To the residue was added acetone (100 mL), refluxed and filtered off potassium chloride. The filtrate was concentrated, and then the residue was dissolved in acetone (50 mL), followed by a slow addition of diethyl ether (80 mL) to precipitate, and further addition of diethyl ether (250 mL). After filtration, the filter cake was dried to yield compound 1-a (7 g, yield 62%). $^1$H NMR (500 MHz, DMSO-d$_6$): δ 8.94(1H, brs), 3.51-3.69 (2H, m), 3.37-3.50(2H, m), 3.06-3.22(2H, m), 2.89-3.04(2H, m), 2.97(3H, s), 2.03(2H, q, J=5.0 Hz).

Synthesis of Compound 1

A mixture of compound 1-b (63 mg, 0.145 mmol), compound 1-a (46 mg, 0.189 mmol), palladium acetate (10 mg), X-Phos (4 mg), cesium carbonate (142 mg, 0.435 mmol), tetrahydrofuran (1.2 mL) and water (0.3 mL) was heated under nitrogen atmosphere to 80° C. and stirred overnight. The reaction liquid was cooled, diluted with tetrahydrofuran, and filtered, the filtrate was concentrated under reduced pressure. The residue was purified by HPLC to yield compound 1 (16 mg, 21%). LC-MS(ESI): m/z=531(M+H)$^+$; $^1$HNMR (500 MHz, CDCl$_3$) δ 8.41(s, 1H), 7.72(s, 1H), 7.47(dd, J=3.5 Hz, 8.5 Hz, 1H), 7.29(t, J=3.0 Hz, 1H), 7.10(t, J=4.5 Hz, 1H), 6.60(s, 1H), 3.93(t, J=4.5 Hz, 4H), 3.88(s, 2H), 3.83(t, J=5.0 Hz, 4H), 3.28(t, J=4.5 Hz, 4H), 2.78(s, 3H), 2.73(t, J=4.5 Hz, 4H).

Synthetic Route of Compound 2

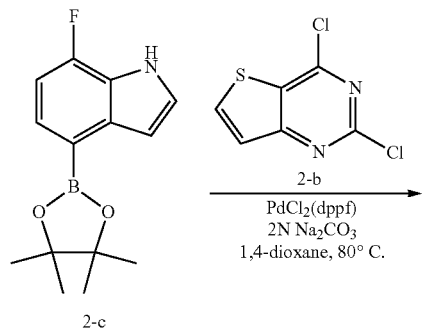

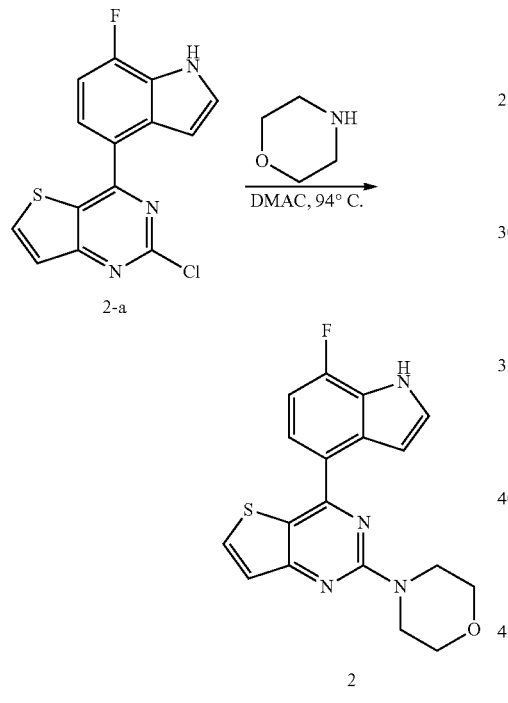

Synthesis of Compound 2-a

To a reaction flask were added purchased compound 2-c (200 mg, 0.77 mmol), purchased compound 2-b (144 mg, 0.7 mmol), PdCl$_2$(dppf) (26 mg, 0.035 mmol), 2 N sodium carbonate aqueous solution (1.05 mL) and 1,4-dioxane (10 mL). The mixture was stirred under nitrogen atmosphere at 80° C. overnight. The mixed liquid was cooled, and filtered through celite. The filtrate was concentrated under reduced pressure. The residue was purified by silica gel preparation plate chromatography (developing system: petroleum ether/ethyl acetate=3/1), to obtain compound 2-a (184 mg, 69%). LC-MS(ESI): m/z=304(M+H)$^+$.

Synthesis of Compound 2

A mixture of compound 2-a (184 mg, 0.48 mmol), morpholine (209 mg, 2.4 mmol) and N, N-dimethylacetamide (10 mL) was heated to 94° C. and reacted overnight. The reactants were cooled to room temperature, and concentrated under reduced pressure. The residue was diluted with ethyl acetate and neutralized with saturated sodium carbonate, and the organic phase was washed sequentially with water and saturated brine, the separated organic phase was dried over anhydrous sodium sulfate, and concentrated under reduced pressure. The residue was purified by silica gel preparation plate chromatography (developing system: petroleum ether/ethyl acetate=2/1) to obtain compound 2 (110 mg, 65%). LC-MS (ESI): m/z=449.0, 451.0 (M+H)$^+$.
$^1$H NMR (400 MHz, CDCl$_3$): δ 8.62(1H, s), 7.84(1H, d, J=5.6 Hz), 7.76-7.73(1H, m), 7.35(1H, t, J=2.8 Hz), 7.30 (1H, d, J=5.6 Hz), 7.10-7.03(2H, m), 3.97(4H, t, J=4.8 Hz), 3.85(4H, t, J=5.2 Hz).

Synthetic Route of Compound 3

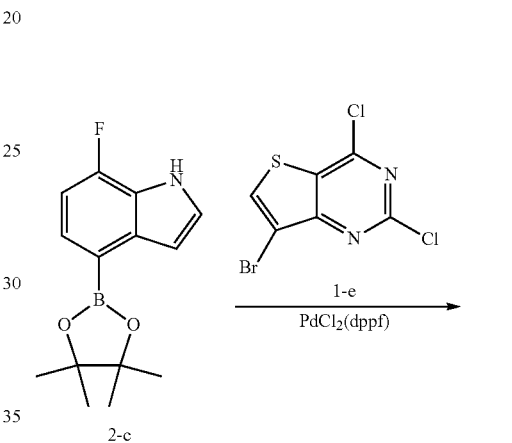

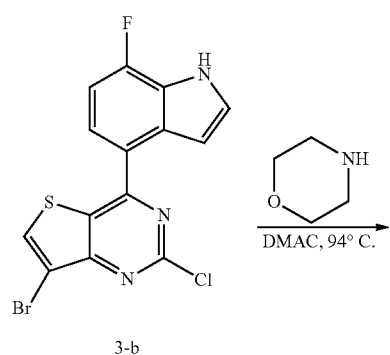

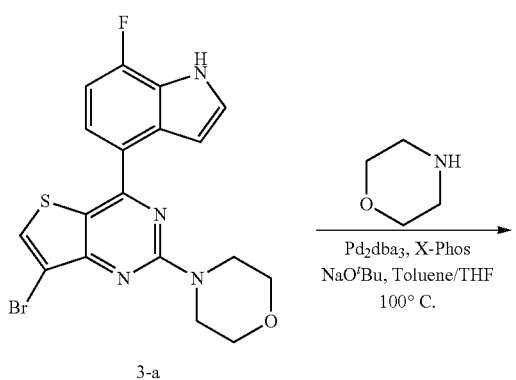

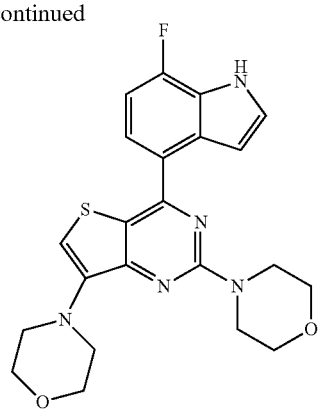

3

Synthesis of Compound 3-b

To a reaction flask were added compound 2-c (997 mg, 3.8 mmol), Compound 1-e (994 mg, 3.5 mmol), PdCl₂(dppf) (128 mg, 0.175 mmol), 2 N sodium carbonate aqueous solution (5.3 mL) and 1, 4-dioxane (30 mL). The mixture was stirred under nitrogen atmosphere at 80° C. overnight. The reaction mixture was concentrated under reduced pressure, and then diluted with ethyl acetate, and filtered, the filtrate was concentrated under reduced pressure. The residue was purified by silica gel column chromatography (elution system: petroleum ether/ethyl acetate=10/1~dichloromethane/tetrahydrofuran=100/1), to obtain 3-b (885 mg, 66%). LC-MS (ESI): m/z=382 (M+H)⁺.

Synthesis of Compound 3-a

A mixture of compound 3-b (885 mg, 2.31 mmol), morpholine (1000 mg, 11.55 mmol) and N, N-dimethylacetamide (20 mL) was heated to 94° C. and reacted overnight. The reactants were cooled to room temperature, and then concentrated, the residue was diluted with ethyl acetate, and neutralized with saturated sodium carbonate, the separated organic phase was dried over anhydrous sodium sulfate, and concentrated under reduced pressure. The residue was purified by silica gel preparation plate chromatography (developing system: petroleum ether/ethyl acetate=10/1~8/1) to obtain compound 3-a (498 mg, 50%). LC-MS (ESI): m/z=433 (M+H)⁺.

Synthesis of Compound 3

To a microwave tube was added compound 3-a (100 mg, 0.23 mmol), morpholine (120 mg, 0.69 mmol), Pd₂dba₃ (21 mg, 0.023 mmol), X-Phos (33 mg, 0.069 mmol), sodium tert-butoxide (132 mg, 1.38 mmol), tetrahydrofuran (1.0 mL) and toluene (1.0 mL). The mixture was stirred under nitrogen atmosphere at 100° C. overnight. The reaction solution was cooled to room temperature, and filtered, the filtrate was concentrated under reduced pressure. The residue was purified by Prep-HPLC to yield compound 3 (23 mg, 23%). LC-MS (ESI): m/z=440 (M+H)⁺. ¹H NMR (400 MHz, CDCl₃): δ 8.74(1H, s), 7.74(1H, q, J=4.8, 8.4 Hz), 7.33(1H, t, J=2.8 Hz), 7.06-6.99(2H, m), 6.80(1H, s), 3.99 (4H, t, J=4.0 Hz), 3.93(4H, t, J=4.0 Hz), 3.85(4H, t, J=4.4 Hz), 3.43(4H, t, J=4.4 Hz).

Synthetic Route of Compound 4

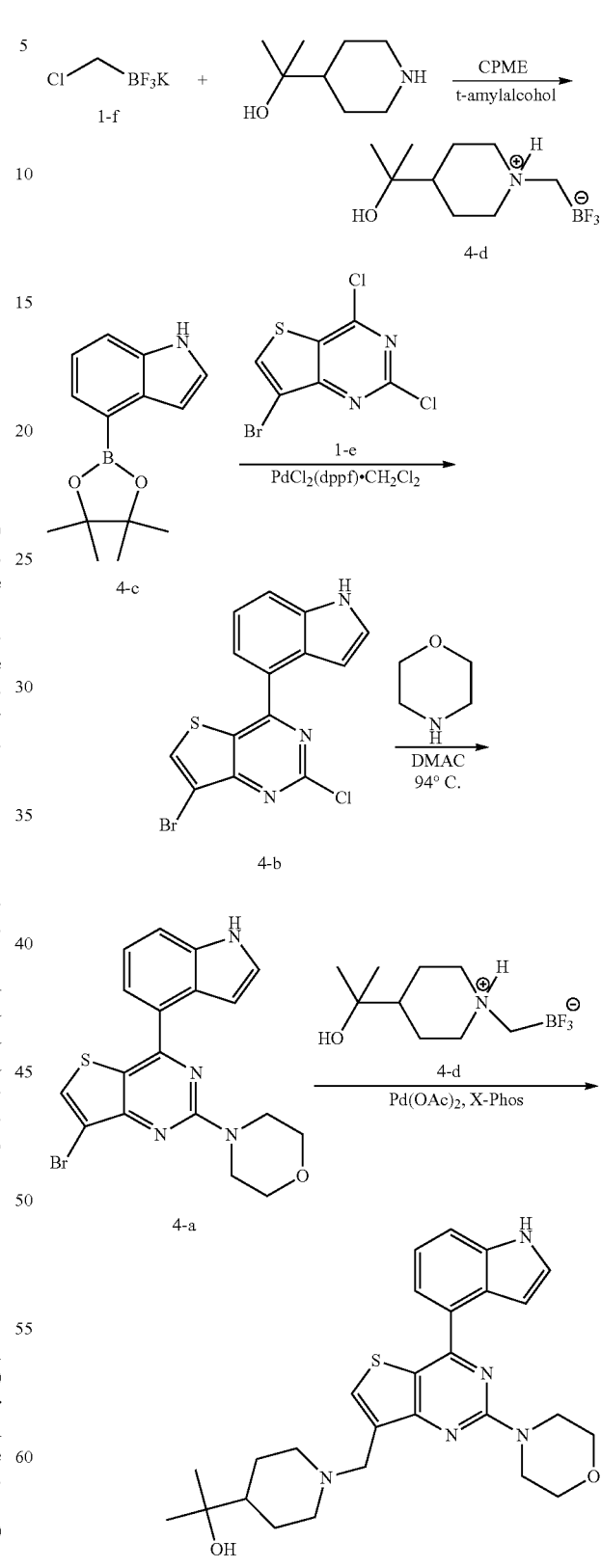

Synthesis of Compound 4-d

To a reaction tube were added compound 1-f (0.5 g, 3.2 mmol), 2-(4-piperidyl)-2-propanol (0.46 g, 3.23 mmol), cyclopentyl methyl ether (CPME) (2.1 mL) and tert-amyl alcohol (0.7 mL). The reaction solution was stirred under nitrogen atmosphere at 110° C. overnight. The reaction solution was cooled, and concentrated under reduced pressure. To the remains was added acetone (6 mL) and refluxed, followed by slow addition of diethyl ether (10 mL) to allow precipitation, and further addition of diethyl ether (90 mL). The mixture was cooled to room temperature, and filtered. The filter cake was dried to obtain compound 4-d (0.77 g, yield 100%). $^1$H NMR (500 MHz, DMSO-$d_6$): δ 9.19(s, 1H), 4.25(s, 1H), 3.38(d, J=12.5 Hz, 2H), 2.67(t, J=12.5 Hz, 2H), 1.90(d, J=5.0 Hz, 2H), 1.74(d, J=13.5 Hz, 2H), 1.44-1.57(m, 2H), 1.36(t, J=12.0 Hz, 1H), 1.02(s, 6H).

Synthesis of Compound 4-b

To a reaction flask were added purchased compound 4-c (1.0 g, 4.11 mmol), compound 1-e (1.06 g, 3.74 mmol), PdCl$_2$(dppf)CH$_2$Cl$_2$ (137 mg, 0.187 mmol), 2 N sodium carbonate aqueous solution (5.6 mL) and 1, 4-dioxane (25 mL). The reaction solution was stirred under nitrogen atmosphere at 80° C. overnight. The reaction mixture was concentrated and then dissolved with ethyl acetate, after filtration through celite, the organic phase was sequentially washed with water, saturated brine, and dried over anhydrous sodium sulfate, and concentrated under reduced pressure. The residue was purified by silica gel preparation plate chromatography (developing system: dichloromethane/petroleum ether=4/1), to yield compound 4-b (658 mg, 52%).

Synthesis of Compound 4-a

A mixture of compound 4-b (658 mg, 1.8 mmol), morpholine (790 mg, 9.1 mmol) and N, N-dimethylacetamide (12 mL) was heated to 94° C. to react overnight. The reactants were cooled to room temperature and then concentrated, the residue was diluted with ethyl acetate, and washed with aqueous ammonia, the separated organic phase was dried over anhydrous sodium sulfate, and concentrated under reduced pressure, the residue was purified by silica gel preparation plate chromatography (developing system: petroleum ether/ethyl acetate=8/1), to obtain compound 4-a (500 mg, 46%). LC-MS(ESI): m/z=415(M+H)$^+$.

Synthesis of Compound 4

To a microwave tube were added compound 4-a (100 mg, 0.24 mmol), compound 4-d (127 mg, 0.48 mmol), cesium carbonate (235 mg, 0.72 mmol), X-Phos (23 mg, 0.048 mmol), palladium acetate (5 mg, 0.024 mmol) and a mixed liquid of THF and water (10/1 v/v, 2 mL). The reaction solution was stirred under nitrogen atmosphere at 80° C. overnight. The reaction solution was cooled, and filtered. The filter cake was washed with tetrahydrofuran. The filtrate was concentrated under reduced pressure. The residue was purified by Prep-HPLC to yield compound 4(36 mg, 30%). LC-MS(ESI): m/z=492.3(M+H)$^+$. $^1$H NMR (500 MHz, CDCl$_3$): δ 8.38(1H, s), 7.74(1H, d, J=7.5 Hz), 7.68(1H, s), 7.48(1H, d, J=8.0 Hz), 7.25-7.29(2H, m), 6.98(1H, s), 3.90-3.92(4H, m), 3.77-3.79(6H, m), 3.08(2H, d, J=11.5 Hz), 2.04 (2H, t, J=11.5 Hz), 1.69 (2H, d, J=12.0 Hz), 1.35-1.40 (2H, m), 1.23-1.25 (1H, m), 1.11 (6H, s).

Synthetic Route of Compound 5

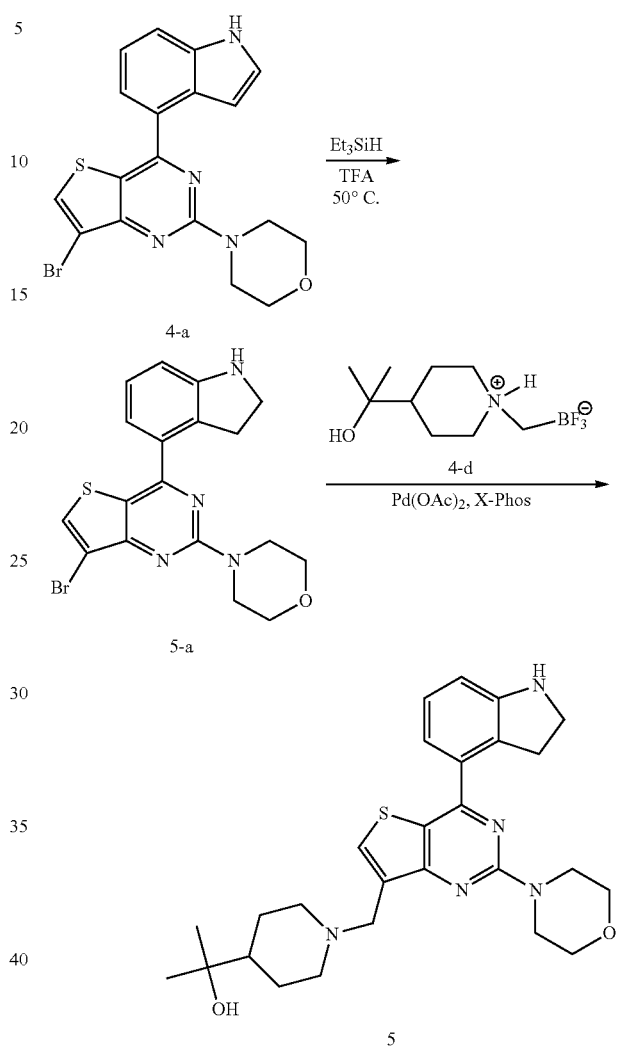

Synthesis of Compound 5-a

Compound 4-a (100 mg, 0.24 mmol) was dissolved in trifluoroacetic acid (2.5 mL). To the solution was slowly added dropwise triethylsilane (46 mg, 0.63 mmol), and the mixture under nitrogen atmosphere was heated to 50° C. to react for 3 hrs. The reactants were cooled to room temperature, and concentrated under reduced pressure. The residue was diluted with ethyl acetate, and washed with saturated sodium carbonate aqueous solution, the separated organic phase was dried over anhydrous sodium sulfate, and concentrated under reduced pressure. The residue was purified by silica gel preparation plate chromatography (developing system: dichloromethane/tetrahydrofuran=100/3), to obtain 5-a (90 mg, 75%). LC-MS (ESI): m/z=419 (M+H)$^+$.

Synthesis of Compound 5

To a microwave tube were added compound 5-a (95 mg, 0.23 mmol), compound 4-d (120 mg, 0.46 mmol), cesium carbonate (225 mg, 0.69 mmol), X-Phos (22 mg, 0.046 mmol), palladium acetate (5 mg, 0.023 mmol) and a mixed liquid of THF and water (10/1, v/v, 2 mL). The mixture was stirred under nitrogen atmosphere at 80° C. overnight. The reaction solution was cooled to room temperature, and filtered, the filter cake was washed with THF. The filtrate was concentrated under reduced pressure. The residue was purified by Prep-HPLC to yield compound 5 (20 mg, 18%). LC-MS (ESI): m/z=494.2 (M+H)$^+$. $^1$H NMR (500 MHz, CDCl$_3$): δ 7.84 (1H, s), 7.18 (1H, d, J=7.5 Hz), 7.10 (1H, t, J=8.0 Hz), 6.70 (1H, d, J=14.0 Hz), 3.82-3.85 (6H, m), 3.74-3.76 (4H, m), 3.51 (2H, t, J=8.5 Hz), 3.22 (2H, t, J=8.5 Hz), 3.13 (2H, d, J=11.0 Hz), 2.14 (2H, t, J=11.5 Hz), 1.71 (2H, d, J=13.0 Hz), 1.44-1.51 (2H, m), 1.23-1.28 (1H, m), 1.11 (6H, s).

Synthetic Route of Compound 6

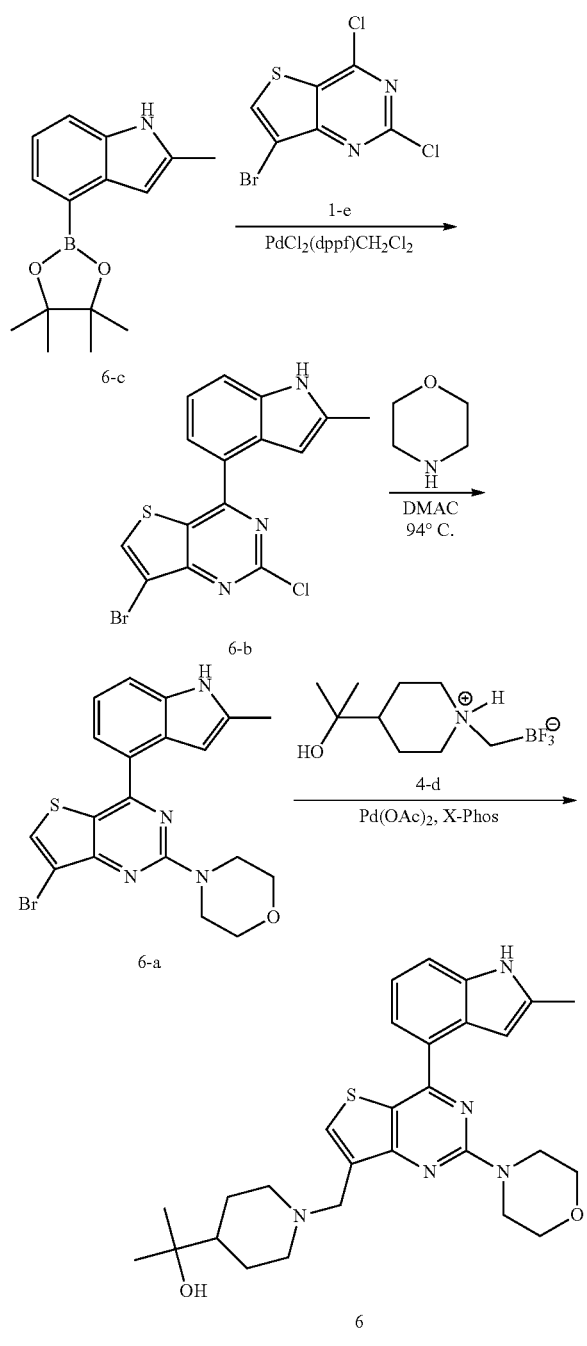

Synthesis of Compound 6-b

To a reaction flask were added purchased compound 6-c (300 mg, 1.16 mmol), compound 1-e (331 mg, 1.16 mmol), PdCl$_2$(dppf) CH$_2$Cl$_2$ (42 mg, 0.058 mmol), 2 N sodium carbonate aqueous solution (1.74 mL) and 1,4-dioxane (8 mL). The mixture was stirred under nitrogen atmosphere at 80° C. overnight. The reaction mixed liquid was concentrated under reduced pressure, and then dissolved in ethyl acetate, and filtered through celite. The filtrate was washed sequentially with water, saturated brine, and dried over anhydrous sodium sulfate, and concentrated under reduced pressure. The residue was purified by silica gel preparation plate chromatography (developing system: dichloromethane/ethyl acetate/petroleum ether=1/1/2), to yield compound 6-b (220 mg, 50%). LC-MS (ESI): m/z=379 (M+H)$^+$.

Synthesis of Compound 6-a

A mixture of compound 6-b (220 mg, 0.58 mmol), morpholine (254 mg, 2.92 mmol) and N, N-dimethylacetamide (6 mL) was heated to 94° C. and reacted overnight. The reactants were cooled, and concentrated under reduced pressure. The residue was diluted with ethyl acetate, and washed with aqueous ammonia, the separated organic phase was dried over anhydrous sodium sulfate, and concentrated under reduced pressure. The residue was purified by preparation plate chromatograph (developing system: petroleum ether/ethyl acetate=3/2), to yield compound 6-a (85 mg, 33.5%). LC-MS (ESI): m/z=429.0 (M+H)$^+$.

Synthesis of Compound 6

To a microwave tube were added compound 6-a (88 mg, 0.20 mmol), compound 4-d (108 mg, 0.41 mmol), cesium carbonate (196 mg, 0.60 mmol), X-Phos (20 mg, 0.041 mmol), palladium acetate (5 mg, 0.020 mmol) and a mixed liquid of THF and water (10/1, v/v, 1.1 mL). The mixture was stirred under nitrogen atmosphere at 80° C. overnight. The reaction solution was cooled, filtered, and the filter cake was washed with THF. The filtrate was concentrated under reduced pressure. The residue was purified by Prep-HPLC to yield compound 6 (76 mg, 73%). LC-MS (ESI): m/z=506.2 (M+H)$^+$. $^1$H NMR (500 MHz, CDCl$_3$): δ 8.03 (1H, s), 7.65-7.67 (2H, m), 7.36 (1H, d, J=8.0 Hz), 7.18 (1H, t, J=7.0 Hz), 6.62 (1H, s), 3.90-3.92 (4H, m), 3.77-3.79 (6H, m), 3.07 (2H, d, J=11.0 Hz), 2.41 (3H, s), 2.03 (2H, t, J=10.5 Hz), 1.68 (2H, d, J=12.0 Hz), 1.34-1.40 (2H, m), 1.22-1.25 (1H, m), 1.11 (6H, s).

Synthetic Route of Compound 7

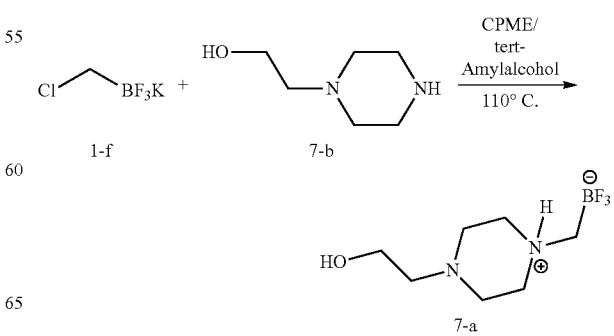

85

-continued

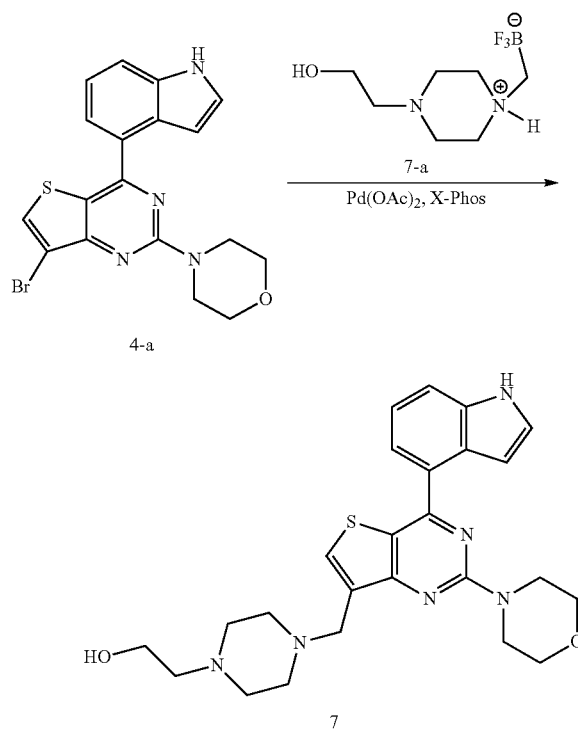

Synthesis of Compound 7-a

To a sealed tube were added compound 1-f (1.26 g, 8.07 mmol), compound 7-b (1.05 g, 8.07 mmol), cyclopentyl methyl ether (CPME) (24 mL) and tert-amyl alcohol (8 mL). The reaction solution was stirred under nitrogen atmosphere at 110° C. overnight. The reaction solution was cooled, and concentrated under reduced pressure. To the residue was added acetone and refluxed, followed by slow addition of diethyl ether to allow precipitation, and filtered. The filter cake was dried to obtain compound 7-a (1.04 g, 45%) which is directly used in the next reaction.

Synthesis of Compound 7

To a microwave tube were added compound 4-a (100 mg, 0.24 mmol), compound 7-a (102 mg, 0.48 mmol), cesium carbonate (235 mg, 0.72 mmol), X-Phos (23 mg, 0.048 mmol), palladium acetate (5 mg, 0.024 mmol), THF (0.9 mL) and water (0.09 mL). The mixture was stirred under nitrogen atmosphere at 80° C. overnight. The reaction solution was cooled to room temperature and filtered, and the filter cake was washed with THF. The filtrate was concentrated under reduced pressure. The residue was purified by Prep-HPLC to yield compound 7 (17 mg, 15%). LC-MS (ESI): m/z=479 (M+H)$^+$. $^1$H NMR (400 MHz, CDCl$_3$): δ 8.58 (1H, s), 7.80 (1H, d, J=7.2 Hz), 7.75 (1H, s), 7.54 (1H, d, J=8.4 Hz), 7.35-7.30 (2H, m), 7.04 (1H, s), 3.98 (4H, t, J=4.4 Hz), 3.87-3.84 (6H, m), 3.62 (2H, t, J=5.2 Hz), 2.67-2.55 (10H, m).

86

Synthetic Route of Compound 8

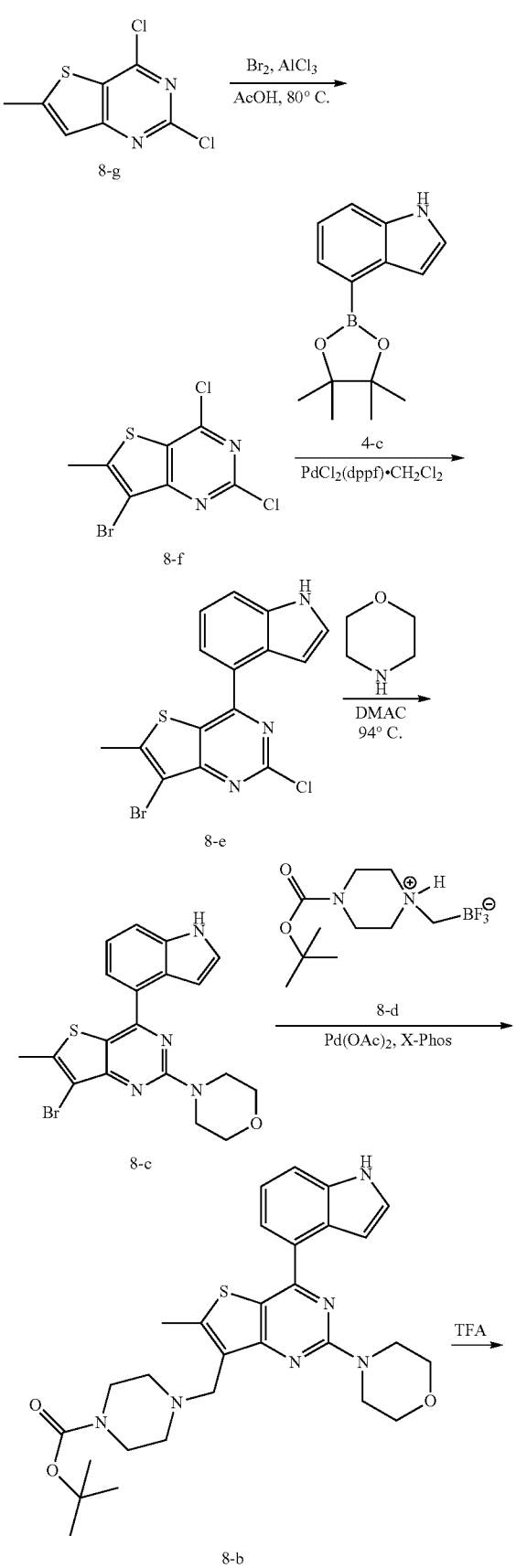

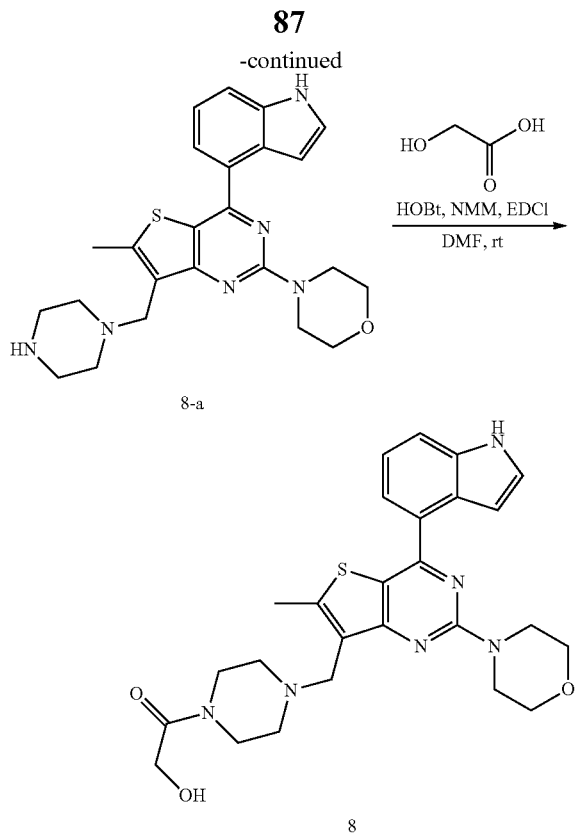

Synthesis of Compound 8-f

At normal temperature a solution of bromine (1.44 mL, 27.6 mmol) in acetic acid (10 mL) was slowly added dropwise into a solution of 8-g (prepared according to the method of patent: WO 2007/023382 A2) (1.984 g, 9.2 mmol) and aluminum trichloride (2.46 g, 18.4 mmol) in acetic acid (30 mL). The mixture was heated to 80° C. to react for 6 hrs after the addition was completed. The reaction mixture was cooled, and then partitioned between ethyl acetate (80 mL) and water (80 mL). The organic layer was separated and washed with 5% sodium thiosulfate solution (2×80 mL). The aqueous phase was extracted with ethyl acetate (×2), the combined organic phase was washed sequentially with saturated sodium bicarbonate solution (200 mL) and saturated brine (400 mL), dried over anhydrous sodium sulfate, and concentrated under reduced pressure, to yield target compound 8-f (1.035 g, yield 76%) as a pale yellow solid. LC-MS (ESI): m/z 296.9 (M+H)$^+$.

Synthesis of Compound 8-e

To a reaction flask were added compound 4-c (400 mg, 1.65 mmol), compound 8-f (344 mg, 1.155 mmol), PdCl$_2$(dppf) CH$_2$Cl$_2$ (60 mg, 0.0825 mmol), 2 N sodium carbonate aqueous solution (2.48 mL) and 1,4-dioxane (8 mL). The mixture was stirred under nitrogen atmosphere at 80° C. overnight. The reaction mixed liquid was concentrated and then dissolved in ethyl acetate, followed by filtration through celite. The organic phase was washed sequentially with water, saturated brine, dried over anhydrous sodium sulfate, and concentrated under reduced pressure. The residue was purified by silica gel preparation plate chromatography (developing system: dichloromethane/ethyl acetate=100/1), to yield compound 8-e (260 mg, 59.7%). LC-MS (ESI): m/z=379.9 (M+H)$^+$.

Synthesis of Compound 8-c

A mixture of compound 8-e (260 mg, 0.688 mmol), morpholine (299 mg, 3.44 mmol) and N,N-dimethylacetamide (6 mL) was heated to 94° C. and react overnight. The reactants were cooled to room temperature, and concentrated, the residue was diluted with ethyl acetate, and washed with aqueous ammonia, the separated organic phase was dried over anhydrous sodium sulfate, and concentrated under reduced pressure. The residue was purified by silica gel preparation plate chromatography (developing system: dichloromethane/ethyl acetate=100/1), to obtain compound 8-c (206 mg, 70.1%). LC-MS (ESI): m/z=429 (M+H)$^+$.

Synthesis of Compound 8-b

To a microwave tube were added compound 8-c (105 mg, 0.245 mmol), compound 8-d (prepared according to the method disclosed in reference: J. Org. Chem. 2011, 76, 2762-2769) (0.49 mmol), cesium carbonate (240 mg, 0.735 mmol), X-Phos (24 mg, 0.049 mmol), palladium acetate (5.5 mg, 0.0245 mmol), and a mixed liquid of THF and water (10/1, v/v, 1.1 mL). The mixture was stirred under nitrogen atmosphere at 80° C. overnight. The reaction liquid was cooled to room temperature and filtered, and the filter cake was washed with THF. The filtrate was concentrated under reduced pressure. The residue was purified by silica gel preparation plate chromatography (developing system: petroleum ether/ethyl acetate=2/3), to yield compound 8-b (90 mg, 67%). LC-MS(ESI): m/z=549.3(M+H)$^+$.

Synthesis of Compound 8-a

Compound 8-b (90 mg, 0.164 mmol) was dissolved in dichloromethane (1.1 mL), and trifluoroacetic acid (187 mg, 1.64 mmol) was added dropwise slowly thereto. The reaction solution was stirred at room temperature overnight. The reactants were concentrated and the residue was neutralized with saturated sodium bicarbonate (50 mL), and extracted with ethyl acetate. The separated organic phase was dried over anhydrous sodium sulfate, and concentrated under reduced pressure, to obtain compound 8-a (70 mg, 95%). LC-MS(ESI): m/z=449.2(M+H)$^+$.

Synthesis of Compound 8

Compound 8-a (90 mg, 0.164 mmol), hydroxyl acetic acid (14 mg, 0.188 mmol), NMM (0.052 mL, 0.468 mmol) were dissolved in DMF (2.0 mL), and to the mixture were added HOBt (32 mg, 0.234 mmol), EDCI (45 mg, 0.234 mmol), the reaction solution was stirred at room temperature overnight. The reactants were diluted with ethyl acetate, and washed with water, the separated organic phase was dried over anhydrous sodium sulfate, and concentrated under reduced pressure. The residue was purified by Prep-HPLC to obtain compound 8 (36 mg, 46%). LC-MS(ESI): m/z=507.2(M+H)$^+$. $^1$H NMR (400 MHz, CDCl$_3$): δ 8.46(1H, s), 7.67(1H, d, J=7.2 Hz), 7.54(1H, d, J=8.4 Hz), 7.31-7.34(2H, m), 7.05(1H, s), 4.14(2H, s), 3.93-3.95(4H, m), 3.84-3.86(4H, m), 3.80(2H, s), 3.67(2H, t, J=4.6 Hz), 3.25(2H, t, J=4.8 Hz), 2.61(3H, s), 2.58(2H, t, J=5.2 Hz), 2.54(2H, t, J=5.2 Hz), 1.26(1H, t, J=7.2 Hz).

Synthetic Route of Compound 9

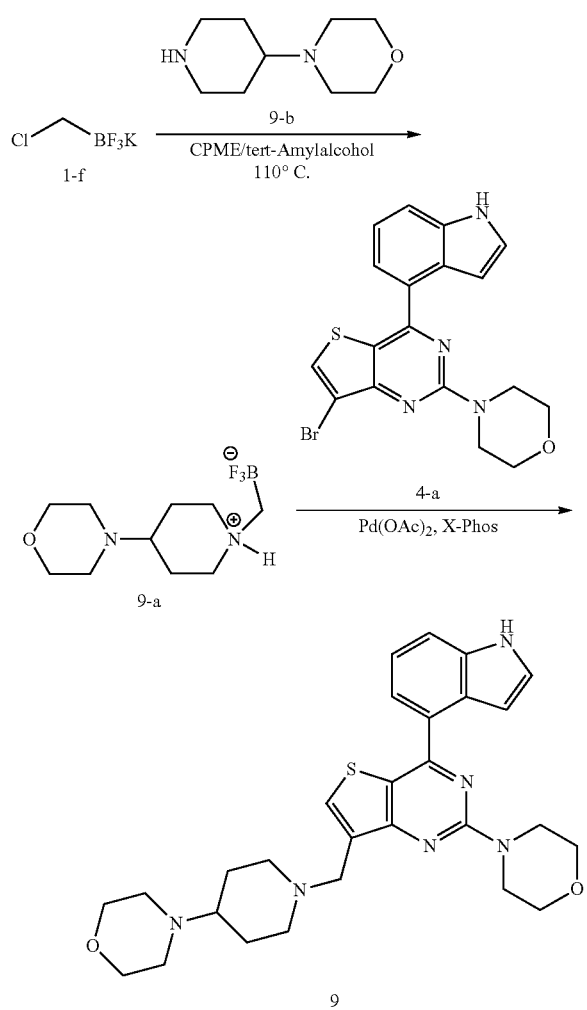

Synthesis of Compound 9-a

To a sealed tube were added purchased compound 9-b (1.377 g, 8.1 mmol), compound 1-f (1.248 g, 8.0 mmol), cyclopentyl methyl ether (CPME) (15 mL) and tert-amyl alcohol (5 mL). The reaction solution was stirred under nitrogen atmosphere at 110° C. overnight. The reaction solution was cooled to room temperature, and concentrated under reduced pressure, to the remains was added acetone and refluxed, followed by slow addition of diethyl ether to allow precipitation, and filtered. The filter cake was dried to obtain compound 9-a (2.16 g, 100%).

Synthesis of Compound 9

To a microwave tube were added compound 4-a (207 mg, 0.5 mmol), compound 9-a (416 mg, 1.65 mmol), cesium carbonate (489 mg, 1.5 mmol), X-Phos (48 mg, 0.1 mmol), palladium acetate (11 mg, 0.05 mmol), THF (1.8 mL) and water (0.18 mL). The mixture was stirred under nitrogen atmosphere at 80° C. overnight. The reaction solution was cooled to room temperature and filtered, and the filter cake was washed with THF. The filtrate was concentrated under reduced pressure. The residue was purified by Prep-HPLC to yield compound 9 (33 mg, 13%). LC-MS(ESI): m/z=519 (M+H)$^+$. $^1$H NMR (400 MHz, CDCl$_3$): δ 8.41(1H, s), 7.81(1H, d, J=7.2 Hz), 7.74(1H, s), 7.56(1H, d, J=8.0 Hz), 7.37-7.33(2H, m), 7.06(1H, s), 3.98(4H, t, J=4.0 Hz), 3.86-3.85(6H, m), 3.72(4H, t, J=4.0 Hz), 3.11(2H, d, J=11.6 Hz), 2.56(4H, t, J=4.8 Hz), 2.25-2.12(3H, m), 1.84(2H, d, J=12 Hz), 1.34-1.26(2H, m).

Synthetic Route of Compound 10

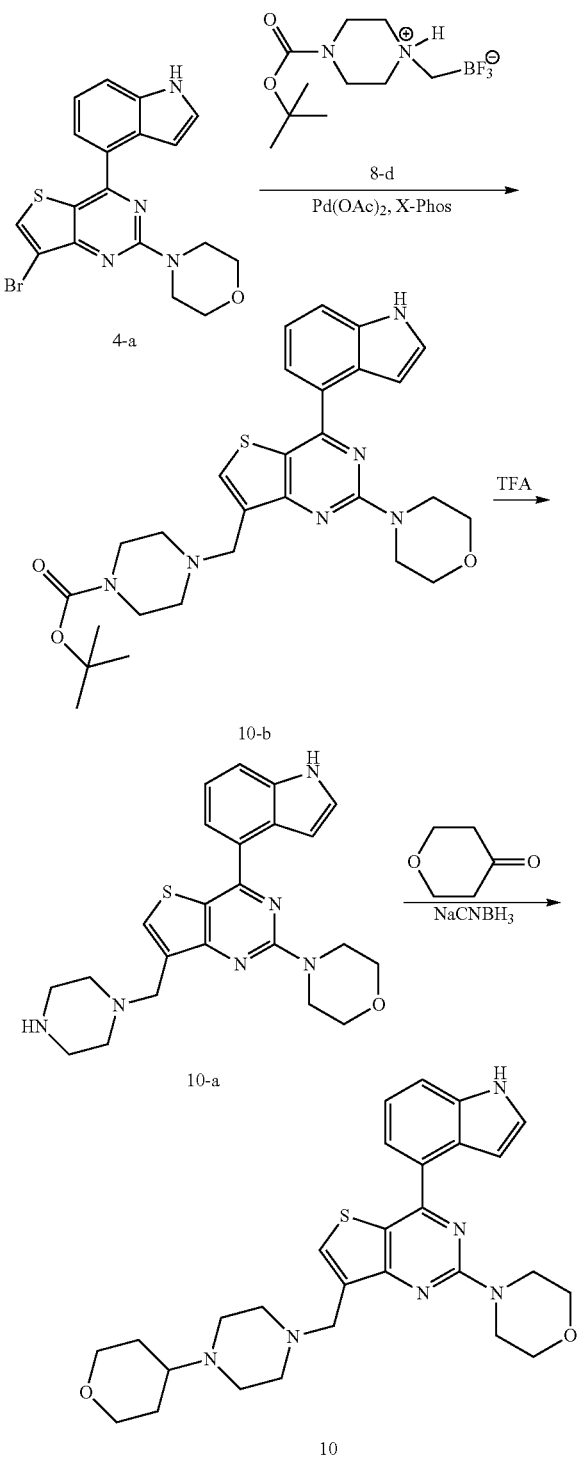

Synthesis of Compound 10-b

To a microwave tube were added compound 4-a (400 mg, 0.97 mmol), compound 8-d (1.94 mmol), cesium carbonate (632 mg, 1.94 mmol), X-Phos (94 mg, 0.194 mmol), palladium acetate (22 mg, 0.097 mmol) and a mixed liquid of THF and water (10/1, v/v, 4.4 mL). The mixture was stirred under nitrogen atmosphere at 80° C. overnight. The reaction solution was cooled to room temperature and filtered, and the filter cake was washed with THF. The filtrate was concentrated under reduced pressure. The residue was separated and purified by silica gel column chromatography (elution system: petroleum ether/ethyl acetate=4/1~1/1), to yield compound 10-b (400 mg, 78%). LC-MS(ESI): m/z=535.2(M+H)+.

Synthesis of Compound 10-a

Compound 10-b (400 mg, 0.94 mmol) was dissolved in dichloromethane (10.0 mL), and trifluoroacetic acid (2.0 mL) was slowly added dropwise thereto. The reaction liquid was stirred at room temperature for 2 hrs. The reactants were concentrated and the residue was neutralized with saturated sodium bicarbonate (150 mL), and extracted with ethyl acetate. The separated organic phase was dried over anhydrous sodium sulfate, and concentrated under reduced pressure to obtain compound 10-a (300 mg, 92%). LC-MS(ESI): m/z=435.2(M+H)+.

Synthesis of Compound 10

Compound 10-a (60 mg, 0.14 mmol), 4-oxacyclohexanone (98 mg, 0.98 mmol) were dissolved in a mixed liquid of THF and methanol and acetic acid (5/5/1, v/v/v, 3 mL), to which was added slowly sodium cyanoborohydride (62 mg, 0.98 mmol). The reaction solution was stirred at room temperature overnight. The reaction solution was quenched with saturated sodium bicarbonate (30.0 mL), and then extracted with ethyl acetate. The separated organic phase was dried over anhydrous sodium sulfate, and concentrated under reduced pressure. The residue was purified by Prep-HPLC to obtain compound 10(28 mg, 39%). LC-MS(ESI): m/z=519.3(M+H)+. 1H NMR (400 MHz, CDCl3): δ 8.30(1H, s), 7.72(1H, d, J=7.6 Hz), 7.68(1H, s), 7.49(1H, d, J=8.0 Hz), 7.26-7.29(2H, m), 6.98(1H, s), 3.90-3.97(6H, m), 3.76-3.80(6H, m), 3.30 (2H, t, J=11.2 Hz), 2.57(8H, brs), 2.30-2.37(1H, m), 1.71(2H, d, J=12.4 Hz), 1.44-1.49 (2H, m).

Synthetic Route of Compound 11

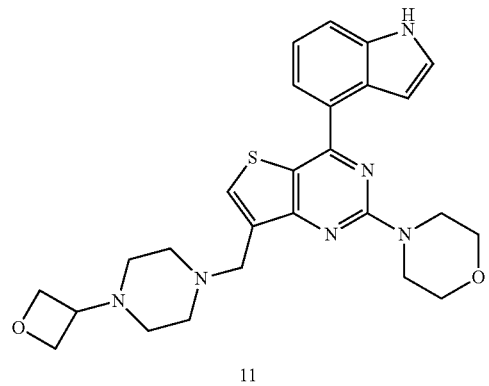

Synthesis of Compound 11

Compound 10-a (60 mg, 0.14 mmol), 3-oxacyclobutanone (70 mg, 0.98 mmol) were dissolved in a mixed liquid of THF and methanol and acetic acid (5/5/1, v/v/v, 3 mL), and to which was slowly added sodium cyanoborohydride (62 mg, 0.98 mmol). The reaction solution was stirred at room temperature overnight. The reaction solution was quenched with saturated sodium bicarbonate (30.0 mL), and then extracted with ethyl acetate. The separated organic phase was dried over anhydrous sodium sulfate, and concentrated under reduced pressure. The residue was purified by Prep-HPLC to obtain compound 11 (12 mg, 18%). LC-MS (ESI): m/z=491.2 (M+H)+. 1H NMR (400 MHz, CDCl3): δ8.46 (1H, s), 7.79 (1H, d, J=7.2 Hz), 7.75 (1H, s), 7.55 (1H, d, J=8.8 Hz), 7.32-7.36 (2H, m), 7.04 (1H, s), 4.60-4.68 (4H, m), 3.97-3.99 (4H, m), 3.89 (s, 2H), 8.84-3.86 (4H, m), 3.48-3.53 (1H, m), 2.70 (4H, s), 2.42 (4H, s).

Synthetic Route of Compound 12

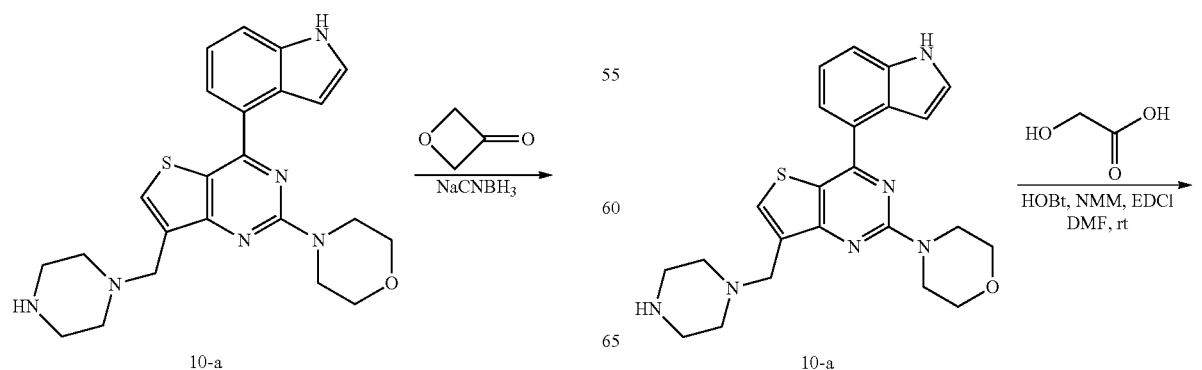

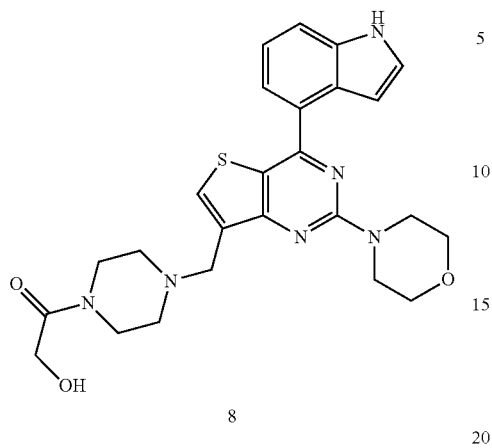

8

Synthesis of Compound 12

Compound 10-a (47 mg, 0.108 mmol), hydroxyl acetic acid (10 mg, 0.13 mmol), NMM (0.036 mL, 0.324 mmol) were dissolved in DMF (2.0 mL), and to which were added HOBt (22 mg, 0.16 mmol), EDCI (31 mg, 0.16 mmol), and the reaction solution was stirred at room temperature overnight. The reactants were diluted with ethyl acetate, and washed with water. The separated organic phase was dried over anhydrous sodium sulfate, and concentrated under reduced pressure. The residue was purified by Prep-HPLC to obtain compound 12 (30 mg, 57%). LC-MS (ESI): m/z=493.2 (M+H)$^+$. $^1$H NMR (400 MHz, CDCl$_3$): δ 8.32 (1H, s), 7.73 (1H, d, J=7.2 Hz), 7.68 (1H, s), 7.50 1H, d, J=8.4 Hz), 7.27-7.30 (2H, m), 6.98 (1H, s), 4.08 (2H, s), 3.89-3.92 (4H, m), 3.82 (2H, s), 3.77-3.79 (4H, m), 3.65 (2H, t, J=4.8 Hz), 3.24 (2H, t, J=4.8 Hz), 2.52-2.57 (4H, m), 1.25 (1H, brs).

Synthetic Route of Compound 13

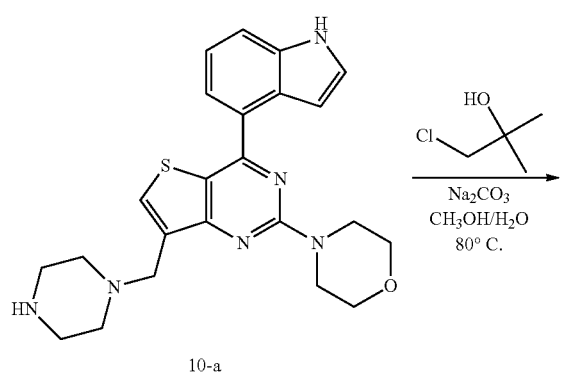

10-a

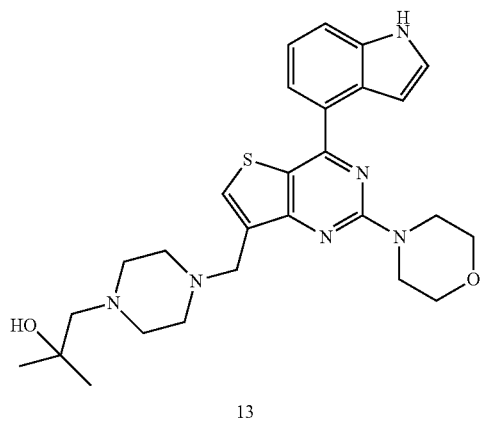

13

Synthesis of Compound 13

Compound 10-a (77 mg, 0.177 mmol) was dissolved in a mixed liquid of methanol and water (1/1, v/v, 5 mL), and to the solution were added sodium carbonate (28 mg, 0.266 mmol) and 1-chloro-2-methyl-propan-2-ol (28 mg, 0.266 mmol). The reaction solution was stirred at 80° C. overnight. The reaction mixture was diluted with saturated brine, and the aqueous layer was extracted with ethyl acetate. The separated organic phase was dried over anhydrous sodium sulfate, and concentrated under reduced pressure. The residue was purified by Prep-HPLC to obtain compound 13 (35 mg, 39%). LC-MS (ESI): m/z=507.3 (M+H)$^+$. $^1$H NMR (400 MHz, CDCl$_3$): δ 8.32 (1H, s), 7.74 (1H, s), 7.68 (1H, s), 7.49 (1H, d, J=8.0 Hz), 7.26-7.29 (2H, m), 6.98 (1H, s), 3.91 (4H, d, J=4.8 Hz), 3.77-3.90 (6H, m), 2.58-2.64 (8H, m), 2.27 (2H, s), 1.09 (6H, s).

Synthetic Route of Compound 14

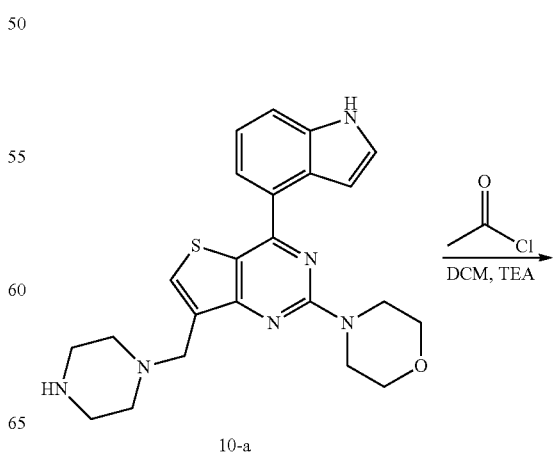

10-a

95

-continued

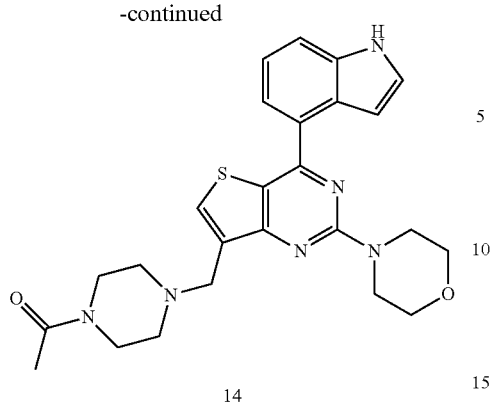

14

Synthesis of Compound 14

Compound 10-a (77 mg, 0.177 mmol), triethylamine (0.123 mL, 0.885 mmol) were dissolved in dichloromethane (5 mL), and in an ice bath to the mixed liquid was slowly added acetyl chloride (42 mg, 0.531 mmol). The reaction solution was stirred at room temperature for 2 hrs, diluted with saturated sodium bicarbonate (30.0 mL), and then extracted with ethyl acetate. The combined organic phase was dried over anhydrous sodium sulfate, and concentrated under reduced pressure. The residue was separated and purified by silica gel preparation plate chromatography (developing system: dichloromethane/methanol=10/1) to obtain compound 14 (40 mg, 48%). LC-MS (ESI): m/z=477.2 (M+H)$^+$. $^1$H NMR (400 MHz, CDCl$_3$): δ 8.31 (1H, s), 7.73 (1H, d, J=6.8 Hz), 7.68 (1H, s), 7.50 (1H, d, J=8.0 Hz), 7.26-7.30 (2H, m), 6.98 (1H, s), 3.91 (4H, t, J=4.8 Hz), 3.77-3.81 (6H, m), 3.60 (2H, t, J=4.8 Hz), 3.43 (2H, t, J=4.8 Hz), 2.52 (4H, s), 2.01 (3H, s).

Synthetic Route of Compound 15

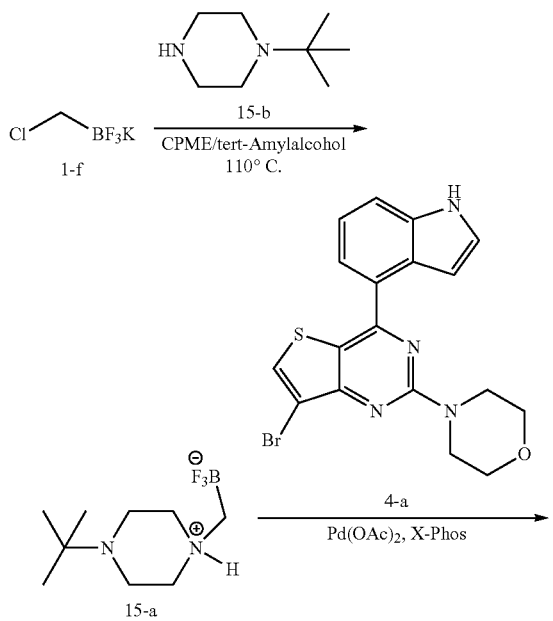

96

-continued

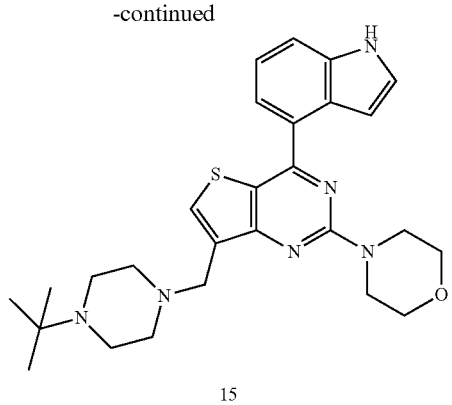

15

Synthesis of Compound 15-a

To a sealed tube were added purchased compound 15-b (1.15 g, 8.1 mmol), compound 1-f (1.248 g, 8.0 mmol), cyclopentyl methyl ether (CPME) (15 mL) and tert-amyl alcohol (5 mL). The mixture was stirred under nitrogen atmosphere at 110° C. overnight. The reaction solution was cooled to room temperature, and concentrated under reduced pressure. To the residue was added acetone and refluxed, followed by slow addition of diethyl ether to allow precipitation, and filtration. The filter cake was dried to obtain compound 15-a (1.37 g, 76%).

Synthesis of Compound 15

Compound 4-a (120 mg, 0.289 mmol), compound 15-a (259 mg, 1.156 mmol), cesium carbonate (283 mg, 0.867 mmol), X-Phos (28 mg, 0.0578 mmol), palladium acetate (7 mg, 0.029 mmol), THF (1 mL) and water (0.1 mL) were added into a microwave tube. The mixture was stirred under nitrogen atmosphere at 80° C. overnight. The reaction solution was cooled to room temperature, and filtered through celite. The filter cake was washed with THF, and concentrated under reduced pressure. The residue was separated and purified by silica gel preparation plate chromatography (developing system: ethyl acetate/methanol=6/1) to yield compound 15 (85 mg, 60%). LC-MS (ESI): m/z=491 (M+H)$^+$. $^1$H NMR (400 MHz, CDCl$_3$): δ 8.44 (1H, s), 7.79 (2H, d, J=6.8 Hz), 7.56 (1H, d, J=7.6 Hz), 7.36-7.33 (2H, m), 7.04 (1H, s), 3.98 (4H, t, J=4.4 Hz), 3.91 (2H, s), 3.85 (4H, t, J=5.2 Hz), 2.83 (8H, brs), 1.18 (9H, s).

Synthetic Route of Compound 16

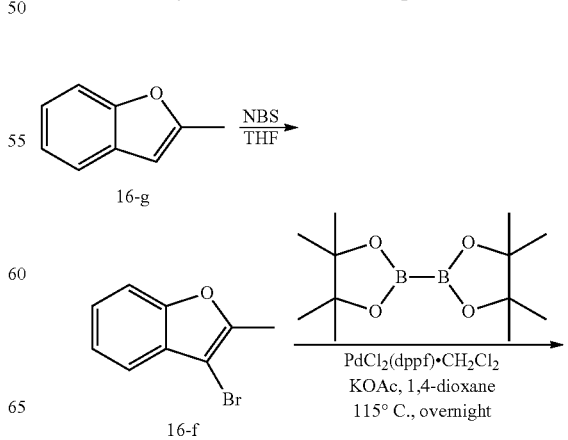

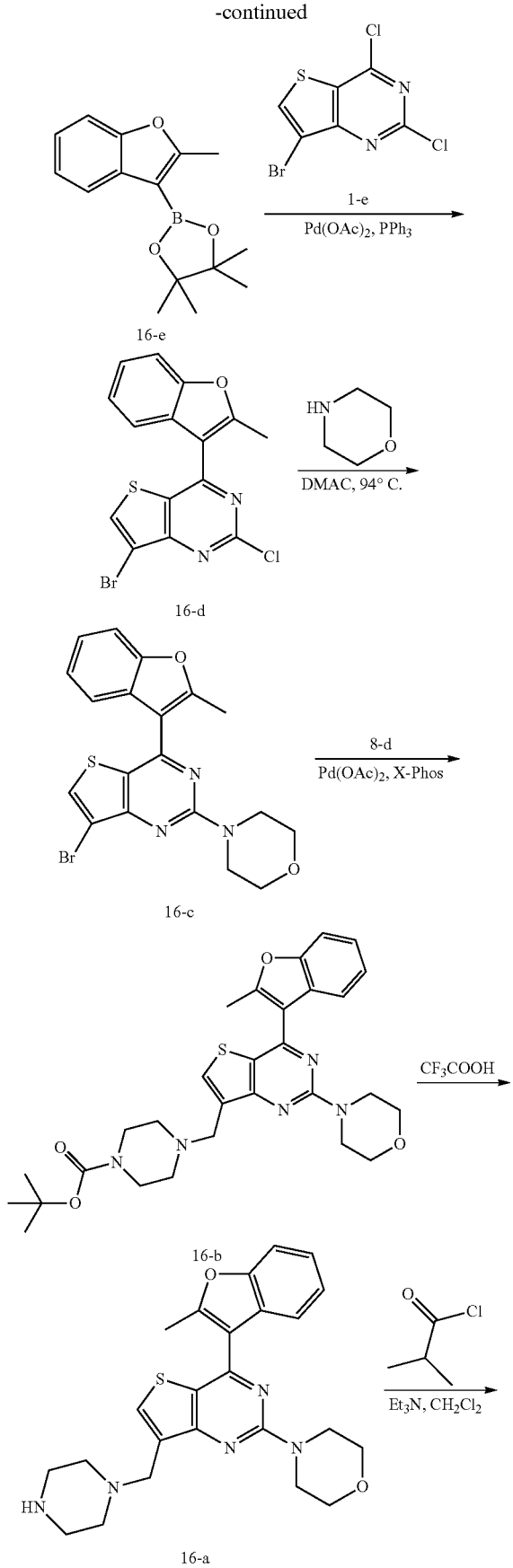

Synthesis of Compound 16-f

A solution of 16-g (2.89 g, 21.91 mmol) dissolved in tetrahydrofuran (80 mL) was cooled to 5° C., and then NBS (4.68 g, 26.29 mmol) was slowly added thereto. The reaction solution was reacted at normal temperature overnight, and then poured into sodium thiosulfate solution, and extracted with ethyl acetate (80 mL×3). The combined organic phase was dried over anhydrous magnesium sulfate, and concentrated under reduced pressure. The residue was purified by silica gel column chromatography (eluted with petroleum ether) to obtain compound 16-f (2.57 g, yield 56%) as a colourless liquid. $^1$H NMR (400 MHz, CDCl$_3$-MeOD): δ 7.37-7.31 (m, 2H), 7.20-7.18 (m, 2H), 2.40 (s, 3H).

Synthesis of Compound 16-e

To a dry 250 mL flask were added 16-f (3.25 g, 15.4 mmol), pinacol borate (4.3 g, 16.9 mmol), PdCl$_2$(dppf) CH$_2$Cl$_2$ (629 mg, 0.77 mmol), KOAc (4.53 g, 46.2 mmol) and 1,4-dioxane (100 mL). The reaction solution was refluxed under nitrogen atmosphere at 115° C. overnight. The reaction solution was cooled to room temperature, added to ethyl acetate (200 mL) and filtered. The filtrate was sequentially washed with water (100 mL×2), dried over anhydrous sodium sulfate, and concentrated under reduced pressure. The residue was purified by silica gel column chromatography (eluted with petroleum ether) to obtain compound 16-e (893 mg, yield 23%), as a pale yellow solid. LC-MS (ESI): m/z 259.1 (M+H)$^+$.

Synthesis of Compound 16-d 1-e (328 mg, 1.16 mmol), Pd (OAc)$_2$ (27 mg, 0.116 mmol) and triphenylphosphine (61 mg, 0.232 mmol) were dissolved in tetrahydrofuran (20 mL) and stirred at normal temperature for 5 minutes, and then 16-e (600 mg, 2.32 mmol) and sodium bicarbonate saturated solution (2.0 mL) were added. The mixture was stirred under nitrogen atmosphere at 90° C. overnight. The reaction solution was cooled to room temperature, and filtered through celite, the filter cake was washed with THF. The filtrate was concentrated under reduced pressure. The residue was dissolved in ethyl acetate (40 mL), sequentially washed with water (20 mL), dried over anhydrous sodium sulfate, and concentrated under reduced pressure to obtain compound 16-d (560 mg, yield 100%), as a dark red solid. LC-MS (ESI): m/z 378.9 (M+H)$^+$.

Synthesis of Compound 16-c 16-d (560 mg, 1.48 mmol) and morpholine (286 •L, 3.26 mmol) were dissolved in DMAC (6 mL). The mixture was stirred under nitrogen atmosphere at 94° C. overnight. The reaction liquid was cooled to room temperature, added to water (12 mL), and solid precipitated out, filtered, and washed with water. The filter cake was dissolved in dichloromethane (50 mL), washed with water (25 mL×2), dried over anhydrous sodium sulfate, and concentrated under reduced pressure to obtain compound 16-c (512 mg, yield 81%), as a yellow solid. LC-MS (ESI): m/z 430.0 (M+H)$^+$.

Synthesis of Compound 16-b 16-c (512 mg, 1.19 mmol), 8-d (480 mg, 1.79 mmol), palladium acetate (627 mg, 0.119 mmol), X-Phos (57 mg, 0.119 mmol), cesium carbonate (1.163 g, 3.57 mmol), THF (6.0 mL) and water (0.6 mL) were added into a microwave tube. The mixture was stirred under nitrogen atmosphere at 80° C. overnight. The reaction solution was cooled to room temperature and filtered through celite, and the filter cake was washed with THF, and concentrated under reduced pressure. The residue was purified by silica gel preparation plate chromatography (developing system: dichloromethane/methanol=20/1), to yield target compound 16-b (133 mg, yield 20%), as a yellow solid. LC-MS (ESI): m/z 550.2 (M+H)$^+$.

Synthesis of Compound 16-a

CF$_3$COOH (2 mL) was added dropwise slowly into a solution of compound 16-b (153 mg, 0.28 mmol) in dichloromethane (8 mL). The reaction mixture was stirred at normal temperature for 1 hr, and then the reaction solution was concentrated, and the residue was partitioned between sodium carbonate saturated solution and dichloromethane. The organic layer was separated, and the aqueous layer was extracted with dichloromethane (×2). The organic phases were combined, washed with brine (×2), and then dried over (Na$_2$SO$_4$), and concentrated under reduced pressure, to yield target compound 16-a (125 mg, yield 100%), as a yellow solid. LC-MS (ESI): m/z 450.2 (M+H)$^+$.

Synthesis of Compound 16

Triethylamine (60 μL, 0.435 mmol) was dripped into a solution of 16-a (65 mg, 0.145 mmol) in dichloromethane (5 mL), and the reaction liquid was cooled to 0° C., then isobutyryl chloride (30 μL, 0.29 mmol) was slowly added thereto. The reaction solution was warmed to normal temperature and stirred overnight. The reaction solution was concentrated under reduced pressure. The residue was purified by Prep-HPLC to obtain target compound 16 (66 mg, yield 88%), as a pale yellow solid. LC-MS (ESI): m/z 520.2 (M+H)$^+$. $^1$H NMR (500 MHz, CDCl$_3$): δ 7.73 (s, 1H), 7.68 (d, 1H, J=8.0 Hz), 7.49 (d, 1H, J=8.5 Hz), 7.31 (t, 1H, J=7.0 Hz), 7.24 (t, 1H, J=7.5 Hz), 3.93 (t, 4H, J=5.0 Hz), 3.88 (s, 2H), 3.84 (t, 4H, J=5.0 Hz), 3.67 (s, 2H), 3.55 (s, 2H), 2.80 (m, 1H), 2.63 (s, 3H), 2.59 (t, 4H, J=3.5 Hz), 1.12 (d, 6H, J=6.5 Hz).

Synthetic Route of Compound 17

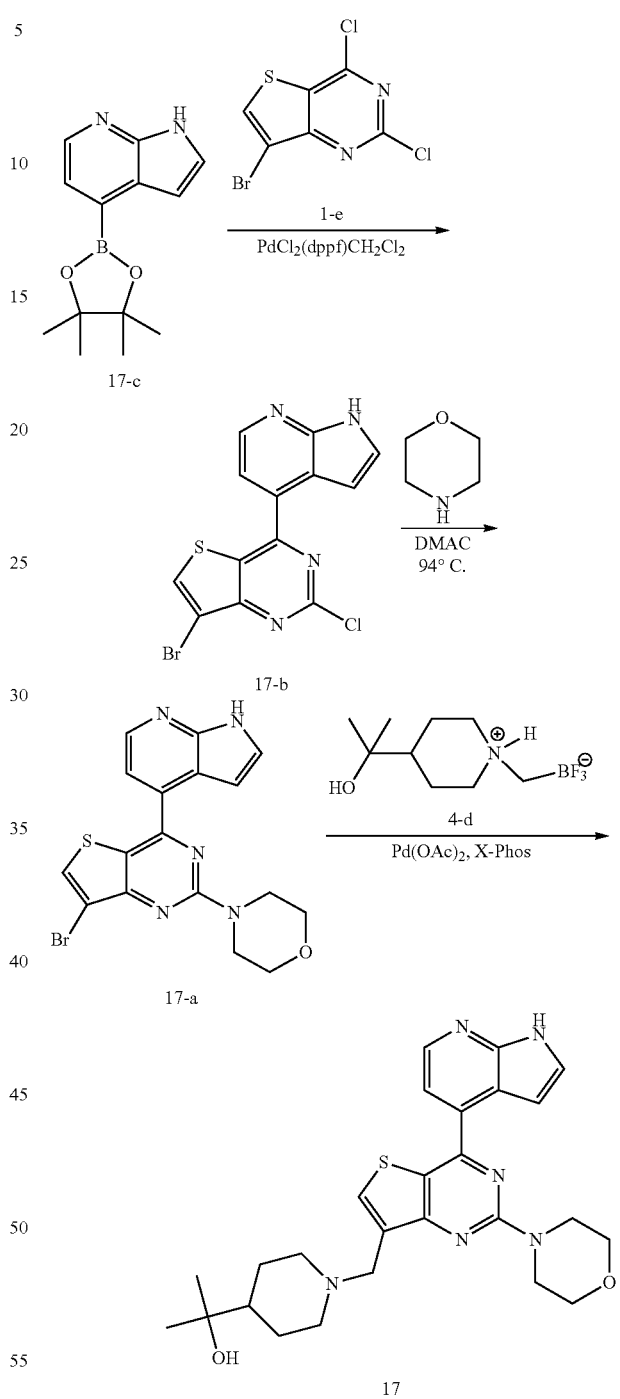

Synthesis of Compound 17-b

To a reaction flask were added compound 1-e (140 mg, 0.497 mmol), purchased compound 17-c (146 mg, 0.596 mmol), PdCl$_2$(dppf) (33 mg, 0.0398 mmol), potassium phosphate (317 mg, 1.461 mmol), dioxane (20 mL) and water (2.5 mL). The reaction solution was reacted under nitrogen atmosphere at 90° C. for 3 hrs. Then the reaction mixture was cooled to room temperature, and concentrated under reduced pressure. The residue was partitioned between water (100 mL) and ethyl acetate (100 mL). The organic layer was separated, and the aqueous layer was extracted with ethyl acetate (2×100 mL). The combined organic phase was sequentially washed with water (300 mL), brine (300 mL), and then dried over (Na₂SO₄), and concentrated under reduced pressure, to obtain target compound 17-b (176 mg, yield 97%), as a yellow solid. LC-MS (ESI): m/z 364.9 (M+H)⁺.

Synthesis of Compound 17-a

A mixture of compound 17-b (176 mg, 0.48 mmol), morpholine (1.45 mmol) and N, N-dimethylacetamide (6 mL) was heated to 94° C. to react overnight. The reaction mixture was cooled, and then partitioned between water (15 mL) and ethyl acetate (15 mL). The organic layer was separated, and the aqueous layer was extracted with ethyl acetate (2×15 mL). The combined organic phase was washed with brine (2×30 mL), and then dried over (Na₂SO₄), and concentrated under reduced pressure, to obtain target compound 17-a (177 mg, 88%), as a dark yellow solid. LC-MS (ESI): m/z 416.0 (M+H)⁺.

Synthesis of Compound 17

Compound 17-a (89 mg, 0.22 mmol), compound 4-d (0.44 mmol), cesium carbonate (215 mg, 0.66 mmol), X-Phos (10 mg, 0.022 mmol), palladium acetate (5 mg, 0.022 mmol) and a mixed liquid of THF and water (10/1, v/v, 1.1 mL) were added into a microwave tube. The mixture was stirred under nitrogen atmosphere at 80° C. overnight. The reaction solution was cooled to room temperature, filtered through celite, and the filter cake was washed with THF, and concentrated under reduced pressure. The residue was purified by Prep-HPLC to yield compound 17 (12 mg, 12%), as a yellow solid. LC-MS (ESI): m/z 493.2 (M+H)⁺. ¹H NMR (400 MHz, CDCl₃): δ 10.15 (s, 1H), 8.48 (d, 1H, J=5.2 Hz), 7.96 (s, 1H), 7.70 (d, 1H, J=5.2 Hz), 7.47 (d, 1H, J=2.8 Hz), 6.94 (d, 1H, J=3.2 Hz), 3.99 (t, 6H, J=5.6 Hz), 3.86 (t, 4H, J=5.2 Hz), 3.24 (d, 2H, J=11.2 Hz), 2.26 (t, 2H, J=11.2 Hz), 1.81 (d, 2H, J=12.8 Hz), 1.61 (d, 2H, J=11.6 Hz), 1.37-1.33 (m, 1H), 1.19 (s, 6H).

Synthetic Route of Compound 18

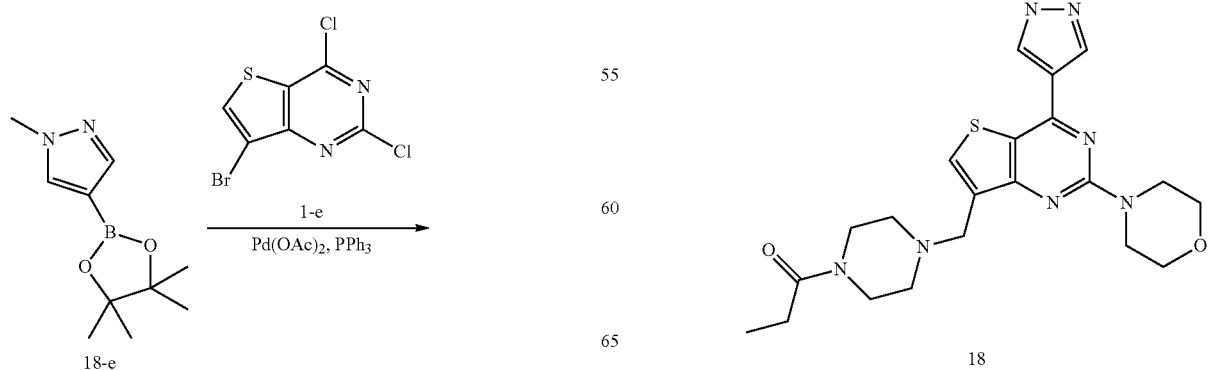

Synthesis of Compound 18-d

To a reaction flask were added compound 18-e (350 mg, 1.68 mmol), compound 1-e (477 mg, 1.68 mmol), PdCl$_2$ (dppf) (61 mg, 0.084 mmol), 2 N sodium carbonate aqueous solution (2.52 mL) and 1,4-dioxane (10 mL). The mixture was stirred under nitrogen atmosphere at 80° C. overnight. The reaction solution was cooled to room temperature, filtered through celite, and the filter cake was washed with 1,4-dioxane. The filtrate was concentrated under reduced pressure to obtain compound 18-d directly used in the next reaction. LC-MS (ESI): m/z 330 (M+H)$^+$.

Synthesis of Compound 18-c

A mixture of the above crude product 18-d, morpholine (731 mg) and N, N-dimethylacetamide (5 mL) was heated to 94° C. to react overnight. The reaction mixture was cooled, and diluted with ethyl acetate, the organic phase was washed with saturated NaHCO$_3$ and brine, dried over anhydrous sodium sulfate, and concentrated under reduced pressure. The residue was purified by silica gel column chromatography (elution system: petroleum ether/ethyl acetate/dichloromethane=4/1/1) to obtain compound 18-c (214 mg, two-step yield: 34%). LC-MS (ESI): m/z=380 (M+H)$^+$.

Synthesis of Compound 18-b

To a reaction flask were added compound 18-c (272 mg, 0.72 mmol), compound 8-d (2.87 mmol), cesium carbonate (704 mg, 2.16 mmol), X-Phos (69 mg, 0.144 mmol), palladium acetate (16 mg, 0.072 mmol), THF (2.60 mL) and water (0.26 mL). The mixture was stirred at 80° C. overnight. The reaction solution was cooled, and then diluted with ethyl acetate and tetrahydrofuran. The organic phase was washed with water and brine, dried over anhydrous sodium sulfate, and concentrated under reduced pressure. The residue was purified by silica gel column chromatography (elution system: petroleum ether/ethyl acetate=1/1), to obtain compound 18-b (322 mg, 89%). LC-MS (ESI): m/z=500 (M+H)$^+$.

Synthesis of Compound 18-a

A mixture of compound 18-b (322 mg, 0.64 mmol), CF$_3$COOH (2 mL) and dichloromethane (10 mL) was reacted at normal temperature overnight, and then diluted with ethyl acetate. The organic phase was neutralized with saturated Na$_2$CO$_3$ and washed with brine, dried over anhydrous sodium sulfate, and concentrated under reduced pressure, to obtain compound 18-a (219 mg, 86%). LC-MS (ESI): m/z=400 (M+H)$^+$.

Synthesis of Compound 18

A mixture of compound 18-a (73 mg, 0.18 mmol), propionyl chloride (0.063 mL, 0.72 mmol), triethylamine (0.10 mL, 0.72 mmol) and dichloromethane (5 mL) was reacted at normal temperature for 1.5 hrs, and then diluted with ethyl acetate. The organic phase was washed with saturated Na$_2$CO$_3$ and brine, dried over anhydrous sodium sulfate, and concentrated under reduced pressure. The residue was purified by silica gel preparation plate chromatography (developing system: ethyl acetate/methanol=30/1) to obtain compound 18 (67 mg, 82%). LC-MS (ESI): m/z=456 (M+H)$^+$. $^1$H NMR (400 MHz, CDCl$_3$): δ 8.21 (1H, s), 8.12 (1H, s), 7.68 (1H, s), 3.98 (3H, s), 3.88 (4H, t, J=4.0 Hz), 3.81-3.79 (6H, m), 3.64-3.61 (2H, m), 3.46-3.44 (2H, m), 2.53-2.51 (4H, m), 2.29 (2H, q, J=7.6 Hz), 1.10 (3H, t, J=7.6 Hz).

Synthetic Route of Compound 19

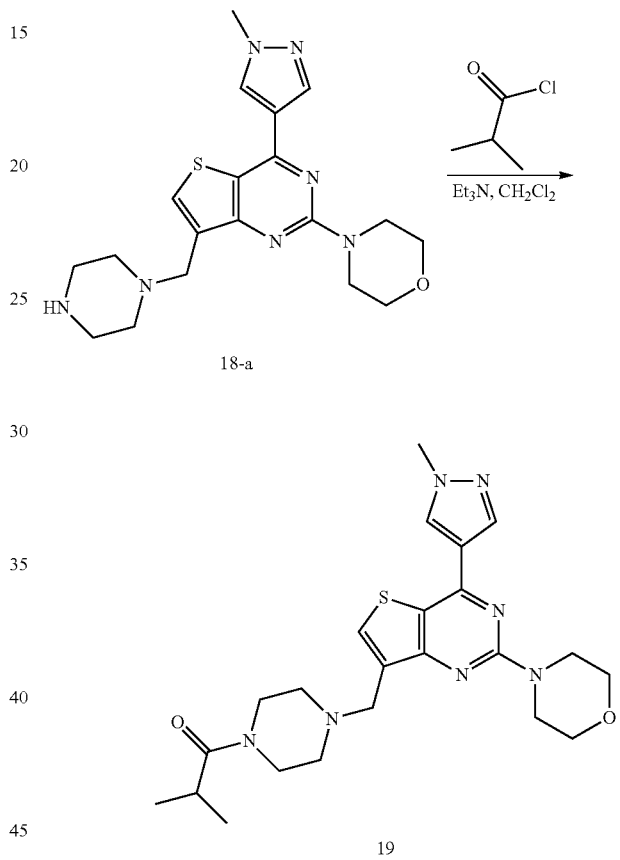

Synthesis of Compound 19

A mixture of compound 18-a (73 mg, 0.18 mmol), isobutyryl chloride (0.075 mL, 0.72 mmol), triethylamine (0.10 mL, 0.72 mmol) and dichloromethane (5 mL) was reacted at normal temperature for 1.5 hrs, and then diluted with ethyl acetate. The organic phase was washed with saturated Na$_2$CO$_3$ and brine, dried over anhydrous sodium sulfate, and concentrated under reduced pressure. The residue was purified by silica gel preparation plate chromatography (developing system: ethyl acetate/methanol=30/1) to obtain compound 19 (61 mg, 72%). LC-MS (ESI): m/z=470 (M+H)$^+$. $^1$H NMR (400 MHz, CDCl$_3$): δ 8.22 (1H, s), 8.13 (1H, s), 7.71 (1H, s), 4.00 (3H, s), 3.89 (4H, t, J=4.4 Hz), 3.82-3.80 (6H, m), 3.65 (2H, s), 3.53 (2H, s), 2.78-2.69 (1H, m), 2.56-2.55 (4H, m), 1.09 (6H, d, J=6.8 Hz).

Synthetic Route of Compound 20

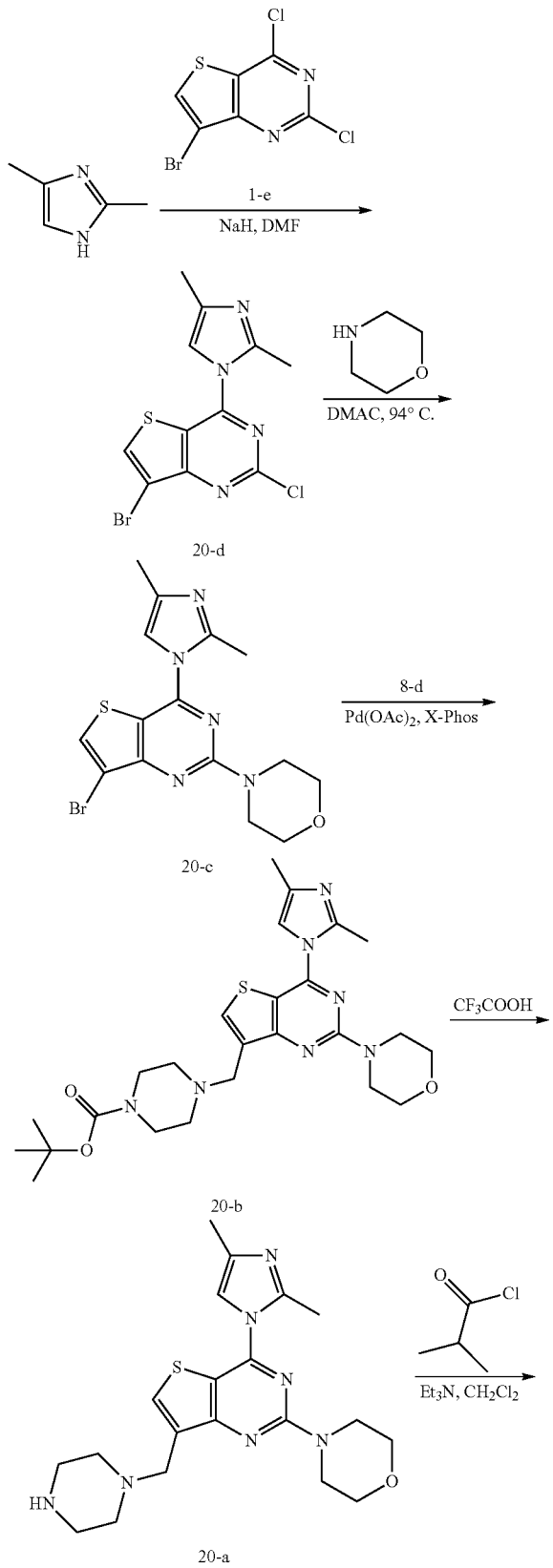

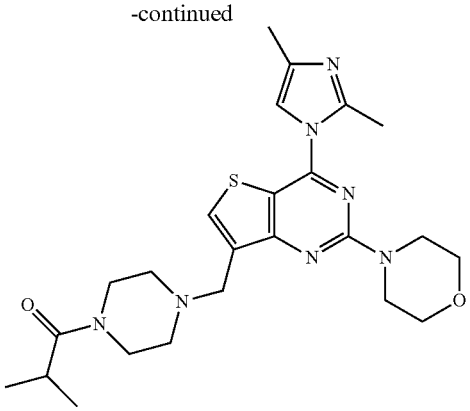

Synthesis of Compound 20-d 2,4-dimethylimidazole (1.58 g, 16.45 mmol) was dissolved in N,N-dimethylamine (60 mL). In an ice bath, to the solution was added sodium hydride (60% in mineral oil) (1.05 g, 26.3 mmol) slowly. The reaction mixture was reacted for 30 minutes in an ice bath, and then in an ice bath the reaction solution was added dropwise to a solution of compound 1-e (5.0 g, 17.6 mmol) in N,N-dimethylformamide (100 mL) slowly. The reaction mixture was reacted at 0° C. for 10 minutes, and then diluted with ethyl acetate (300 mL). The organic layer was separated, washed with water, dried over anhydrous sodium sulfate, and concentrated under reduced pressure, to obtain 20-d (4.0 g, 71.0%). LC-MS (ESI): m/z=342.9, 344.9 (M+H)$^+$.

Synthesis of Compound 20-c

A mixture of compound 20-d (4.0 g, 11.69 mmol), morpholine (5.09 g, 58.48 mmol) and N,N-dimethylacetamide (20 mL) was heated to 94° C. to react overnight. The reactants were diluted with ethyl acetate (400 mL). The organic layer was separated, sequentially washed with saturated sodium bicarbonate, saturated brine, dried over anhydrous sodium sulfate, and concentrated under reduced pressure. The residue was separated and purified by silica gel column chromatography (elution system: ethyl acetate/dichloromethane=1/4) to obtain compound 20-c (2.1 g, 46.5%). LC-MS (ESI): m/z=394.0 (M+H)$^+$.

Synthesis of Compound 20-b

To a microwave tube were added compound 20-c (1.9 g, 4.82 mmol), Compound 8-d (14.46 mmol), cesium carbonate (4.71 g, 14.46 mmol), X-Phos (459 mg, 0.964 mmol), palladium acetate (108 mg, 0.482 mmol), and a mixed liquid of THF and water (10/1, v/v, 20 mL). The reaction mixture was stirred under nitrogen atmosphere at 80° C. overnight. The reaction solution was cooled, diluted with water (80 mL), and extracted with ethyl acetate (2×100 mL). The organic layer was separated, dried over anhydrous sodium sulfate, and concentrated under reduced pressure. The residue was separated and purified by silica gel column chromatography (elution system: ethyl acetate/petroleum ether=3/1~1/1) to obtain compound 20-b (2.0 g, 81%). LC-MS (ESI): m/z=514.3 (M+H)$^+$.

Synthesis of Compound 20-a

Trifluoroacetic acid (9.0 mL) was added dropwise to a solution of compound 20-b (2.0 g, 3.90 mmol) in dichloromethane (36.0 mL) slowly. The mixture was stirred at room temperature overnight, and then the reaction mixture was concentrated under reduced pressure, the residue was neutralized with saturated sodium bicarbonate (80 mL), and extracted with ethyl acetate (2×100 mL). The organic layers were combined, dried over anhydrous sodium sulfate, and concentrated under reduced pressure to obtain compound 20-a (1.23 g, 76.4%). LC-MS (ESI): m/z=414.2 (M+H)$^+$.

Synthesis of Compound 20

In an ice-water bath, to a solution of compound 20-a (0.21 mmol) in dichloromethane (4 mL) were sequentially added triethylamine (0.15 mL, 1.05 mmol) and isobutyryl chloride (40 μL, 0.38 mmol). Then the reaction solution was warmed to room temperature and stirred overnight. The reaction solution was diluted with dichloromethane, and the organic layer was sequentially washed with saturated sodium bicarbonate, water, saturated sodium chloride, dried over anhydrous sodium sulfate, and concentrated under reduced pressure. The residue was purified by Prep-TLC to obtain compound 20 (50 mg, two-step yield 48%), as a yellow solid. LC-MS (ESI): m/z=484.3 (M+H)$^+$; $^1$H NMR (400 MHz, CDCl$_3$): δ 7.77 (1H, s), 7.22 (1H, s), 3.80-3.90 (4H, m), 3.71-3.80 (6H, m), 3.57-3.67 (2H, m), 3.46-3.56 (2H, m), 2.69-2.79 (1H, m), 2.62 (3H, s), 2.46-2.58 (4H, m), 2.24 (3H, s), 1.09 (6H, d, J=6.4 Hz).

Synthetic Route of Compound 21

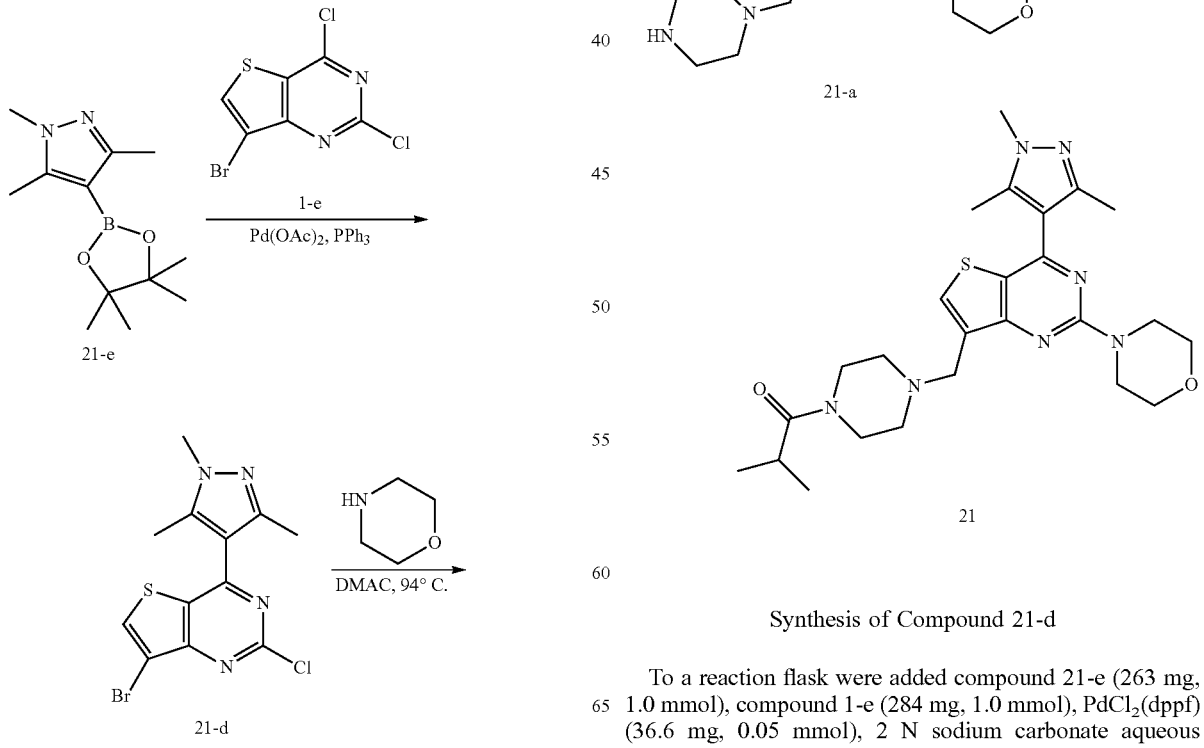

Synthesis of Compound 21-d

To a reaction flask were added compound 21-e (263 mg, 1.0 mmol), compound 1-e (284 mg, 1.0 mmol), PdCl$_2$(dppf) (36.6 mg, 0.05 mmol), 2 N sodium carbonate aqueous solution (1.5 mL) and 1,4-dioxane (8 mL). The mixture was stirred under nitrogen atmosphere at 80° C. overnight. The reaction mixture was cooled to room temperature, filtered through celite, and the filter cake was washed with 1,4-dioxane, and concentrated under reduced pressure. The residue was purified by silica gel preparation plate chromatography (developing system: dichloromethane/ethyl acetate=6/1) to obtain compound 21-d (130 mg, 36.5%). LC-MS (ESI): m/z=357 (M+H)$^+$.

Synthesis of Compound 21-c

A mixture of compound 21-d (130 mg, 0.365 mmol), morpholine (159 mg, 1.82 mmol) and N,N-dimethylacetamide (8 mL) was heated to 94° C. to react overnight. The reaction mixture was cooled and diluted with ethyl acetate, the organic phase was washed with saturated NaHCO$_3$ and brine, dried over anhydrous sodium sulfate, and concentrated under reduced pressure. The residue was washed with petroleum ether/ethyl acetate (3/1, v/v, 8 mL), to obtain compound 21-c (110 mg, 74%). LC-MS (ESI): m/z=408.0 (M+H)$^+$.

Synthesis of Compound 21-b

To a reaction flask were added compound 21-c (110 mg, 0.27 mmol), compound 8-d (0.81 mmol), cesium carbonate (264 mg, 0.81 mmol), X-Phos (26 mg, 0.054 mmol), palladium acetate (6 mg, 0.027 mmol), THF (1.0 mL) and water (0.1 mL). The mixture was stirred at 80° C. overnight. The reaction solution was cooled, and then diluted with ethyl acetate and tetrahydrofuran. The organic phase was washed with water and brine, dried over anhydrous sodium sulfate, and concentrated under reduced pressure. The residue was purified by silica gel preparation plate chromatography (developing system: ethyl acetate), to obtain compound 21-b (110 mg, 77.5%). LC-MS (ESI): m/z=528.3 (M+H)$^+$.

Synthesis of Compound 21-a

A mixture of compound 21-b (98 mg, 0.186 mmol), CF$_3$COOH (2 mL) and dichloromethane (6 mL) was reacted at normal temperature overnight, and then diluted with ethyl acetate. The organic phase was neutralized with saturated NaHCO$_3$ and washed with brine, dried over anhydrous sodium sulfate, and concentrated under reduced pressure, to obtain compound 21-a (77 mg, 96.9%). LC-MS (ESI): m/z=428.3 (M+H)$^+$.

Synthesis of Compound 21

A mixture of compound 21-a (77 mg, 0.18 mmol), isobutyryl chloride (0.54 mmol), triethylamine (0.10 mL, 0.72 mmol) and dichloromethane (5 mL) was reacted at normal temperature for 2 hrs, and then diluted with ethyl acetate. The organic phase was washed with saturated NaHCO$_3$ and brine, dried over anhydrous sodium sulfate, and concentrated under reduced pressure. The residue was purified by Prep-HPLC to obtain compound 21 (35 mg, 39%). LC-MS (ESI): m/z=498.2 (M+H)$^+$. $^1$H NMR (400 MHz, CDCl$_3$): δ 7.71 (1H, s), 3.87-3.89 (4H, m), 3.79-3.82 (9H, m), 3.66 (2H, s), 3.55 (2H, s), 2.74-2.80 (1H, m), 2.58 (4H, s), 2.31 (6H, d, J=2.0 Hz), 1.11 (6H, d, J=6.4 Hz).

Synthetic Route of Compound 22

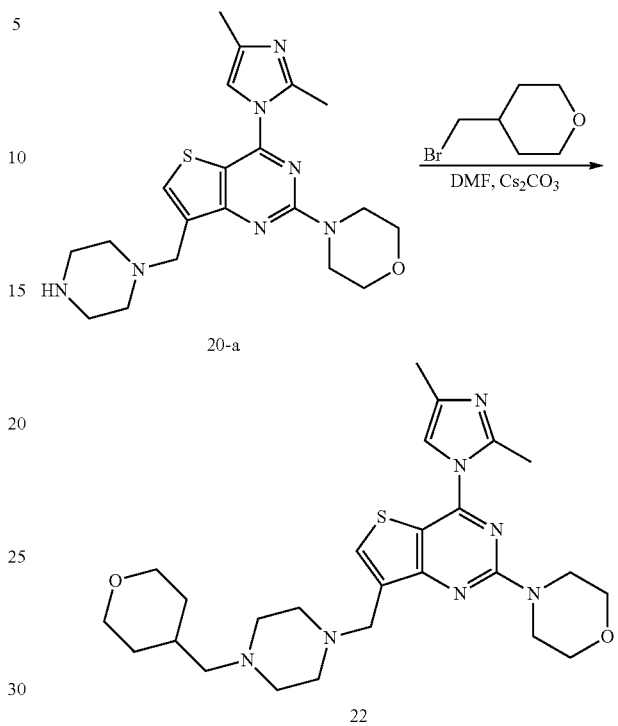

Synthesis of Compound 22

Compound 20-a (80 mg, 0.194 mmol) was dissolved in DMF (5 mL), and to the solution were sequentially added cesium carbonate (190 mg, 0.582 mmol) and 4-bromomethyl tetrahydropyrane (45 mg, 0.252 mmol). The reaction mixture was heated to 70° C. and stirred overnight. The reactants were cooled to room temperature, and then diluted with ethyl acetate (50 mL), and washed with water (2×50 mL). The organic layer was separated, dried over anhydrous sodium sulfate, and concentrated under reduced pressure. The residue was purified by Prep-HPLC to obtain compound 22 (24 mg, 24%). LC-MS (ESI): m/z=512.3 (M+H)$^+$. $^1$H NMR (400 MHz, CDCl$_3$): δ 7.77 (1H, s), 7.25 (1H, s), 3.93-3.97 (2H, m), 3.86-3.88 (4H, m), 3.80-3.82 (6H, m), 3.37 (2H, J=7.2 Hz, t), 2.65 (3H, s), 2.60 (4H, s), 2.47 (4H, s), 2.28 (3H, s), 2.20 (2H, J=7.2 Hz, d), 1.71-1.74 (1H, m), 1.66 (1H, s), 1.63 (1H, s), 1.21-1.31 (2H, m).

Synthesis of Compound 23

According to the method for preparing compound 20, 2-methyl-4-chloroimidazole (prepared according to the method disclosed in: WO 2003/87088 A2) was used in the preparation to yield compound 23, as a pale yellow solid. LC-MS (ESI): m/z 504.2 (M+H)$^+$. $^1$H NMR (400 MHz, CDCl$_3$): δ 7.83 (s, 1H), 7.40 (s, 1H), 3.87 (t, 4H, J=5.2 Hz), 3.82 (t, 6H, J=5.2 Hz), 3.66 (s, 2H), 3.55 (d, 2H, J=4.4 Hz), 2.76-2.72 (m, 1H), 2.63 (s, 3H), 2.56 (s, 4H), 1.12 (d, 6H, J=6.8 Hz).

Synthesis of Compound 24

According to the method for preparing compound 20, 2,5-dimethylpyrazole was used in the preparation to yield compound 24, as a yellow solid. LC-MS (ESI): m/z 484.3 (M+H)⁺. ¹H NMR (400 MHz, CDCl₃): δ 7.77 (s, 1H), 6.06 (s, 1H), 3.83 (s, 8H), 3.82 (s, 2H), 3.65 (s, 2H), 3.53 (t, 2H, J=4.4 Hz), 2.77-2.74 (m, 4H), 2.55 (t, 4H, J=5.2 Hz), 2.35 (s, 3H), 1.11 (d, 6H, J=6.8 Hz).

Synthetic Route of Compound 25

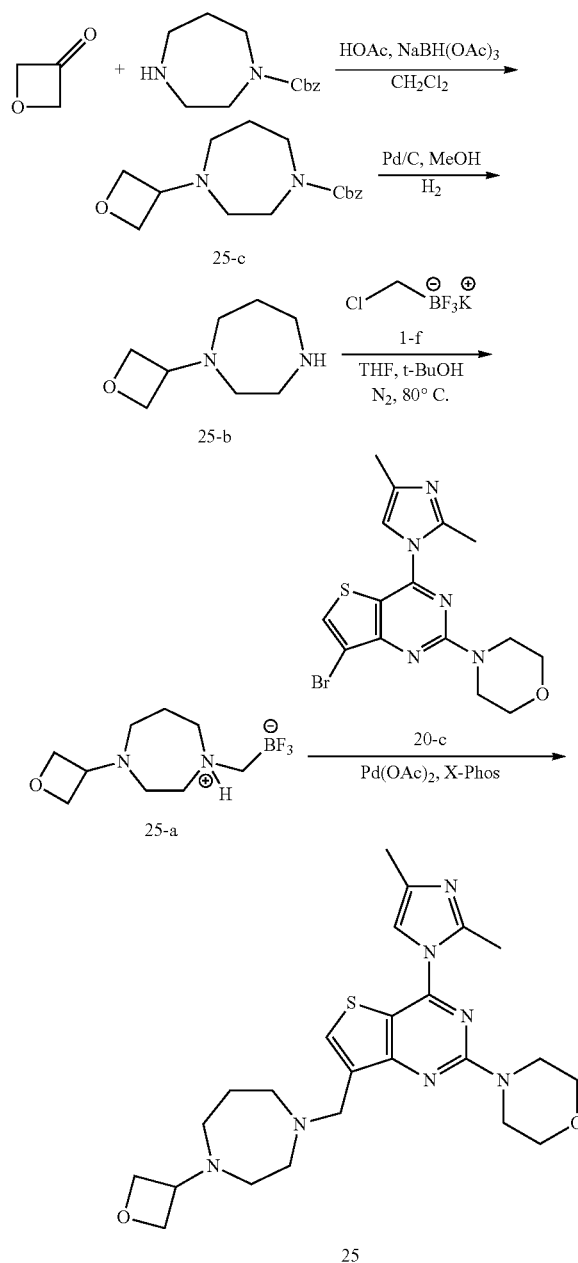

Synthesis of Compound 25-c

3-Oxacyclobutanone (480 mg, 6.66 mmol) and N-benzoxycarbonyl homopiperazine (520 mg, 2.22 mmol) were dissolved in DCE (10 mL), and then dripped into acetic acid (66 mg, 1.11 mmol). The reaction solution was stirred at normal temperature for 2 hrs, and then NaBH(OAc)₃ (1.41 g, 6.66 mmol) was added and at normal temperature reacted for 48 hrs. The reaction solution was diluted with dichloromethane (20 mL), and sequentially washed with sodium bicarbonate saturated solution (20 mL) and brine (2×20 mL). The organic layer was separated, dried over anhydrous sodium sulfate, and concentrated under reduced pressure. The residue was purified by silica gel column chromatography (elution system: dichloroethane/methanol=50/1~20/1) to obtain target compound 25-c (650 mg, yield 100%), as colorless liquid. LC-MS (ESI): m/z 291.1 (M+H)⁺.

Synthesis of Compound 25-b

Compound 25-c (650 mg, 2.24 mmol) was dissolved in methanol (6 mL), and Pd/C (65 mg) was added. The reaction mixture was reacted under hydrogen atmosphere at room temperature overnight, then filtered through celite, and rinsed with ethyl acetate. The filtrate was concentrated under reduced pressure to obtain target compound 25-b (359 mg, yield 100%), as pale yellow liquid. LC-MS (ESI): m/z 157.2 (M+H)⁺.

Synthesis of Compound 25-a

Compound 25-c (359 mg, 2.30 mmol), 1-f (300 mg, 1.92 mmol), tetrahydrofuran (1.83 mL) and tert-butanol (0.83 mL) were placed into a microwave tube. The reaction mixture was reacted under nitrogen atmosphere at 80° C. overnight. The reaction solution was concentrated to obtain a crude product of target compound 25-a directly used in the next reaction.

Synthesis of Compound 25

Compound 20-c (100 mg, 0.25 mmol), the above crude product 25-a (595 mg, 2.5 mmol), palladium acetate (6 mg, 0.025 mmol), X-Phos (12 mg, 0.025 mmol), cesium carbonate (245 mg, 0.75 mmol), THF (1.0 mL) and water (0.1 mL) were added into a microwave tube, and reacted under nitrogen atmosphere with microwave at 120° C. for 1 hr. The reaction mixture was filtered through celite, and rinsed with THF. The filtrate was concentrated under reduced pressure. The residue was purified by silica gel column chromatography (elution system: dichloroethane/methanol=50/1~10/1) to obtain target compound 25 (30 mg, yield 25%), as a pale yellow solid. LC-MS (ESI): m/z 484.1 (M+H)⁺. ¹H NMR (400 MHz, CDCl₃): δ 7.81 (s, 1H), 7.25 (s, 1H), 4.66 (t, 2H, J=6.4 Hz), 4.58 (t, 2H, J=6.4 Hz), 3.94 (s, 2H), 3.88 (t, 4H, J=4.0 Hz), 3.82 (t, 4H, J=4.0 Hz), 3.75-3.71 (m, 1H), 2.89 (t, 4H, J=5.6 Hz), 2.65 (s, 3H), 2.57 (t, 4H, J=5.6 Hz), 2.27 (s, 3H), 1.88-1.85 (m, 2H).

Synthetic Route of Compound 26

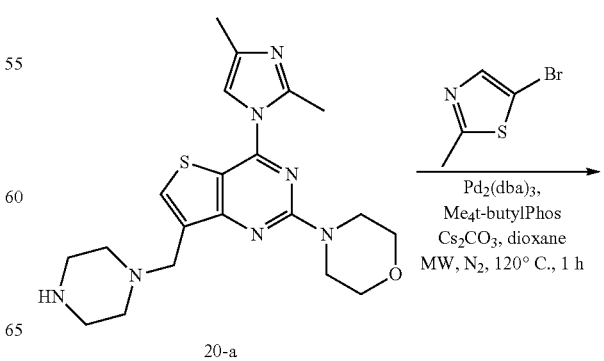

113

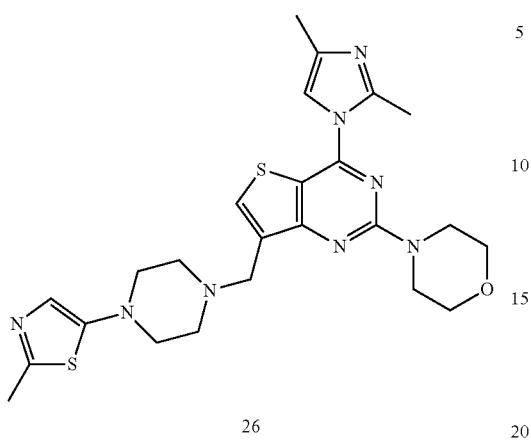

26

Synthesis of Compound 26

Compound 20-a (100 mg, 0.242 mmol), 2-bromo-4-methylthiazole (87 mg, 0.484 mmol), Pd$_2$(dba)$_3$ (11 mg, 0.0121 mmol), Me$_4$t-butylPhos (12 mg, 0.0242 mmol), cesium carbonate (237 mg, 0.726 mmol) and 1,4-dioxane (1.0 mL) were added into a microwave tube, and reacted under nitrogen in microwave at 120° C. for 1 hr. The reaction mixture was filtered through celite, and rinsed with dichloromethane. The filtrate was concentrated under reduced pressure. The residue was purified by Prep-HPLC to obtain target compound 26 (63 mg, yield 51%), as a yellow solid. LC-MS (ESI): m/z 511.2 (M+H)$^+$. $^1$H NMR (400 MHz, CDCl$_3$): δ 7.81 (s, 1H), 7.26 (s, 1H), 6.81 (s, 1H), 3.89 (t, 4H, J=5.2 Hz), 3.84 (s, 2H), 3.82 (t, 4H, J=4.8 Hz), 3.48 (t, 4H, J=4.8 Hz), 2.70 (t, 4H, J=4.8 Hz), 2.66 (s, 3H), 2.29 (s, 3H), 2.28 (s, 3H).

Synthetic Route of Compound 27

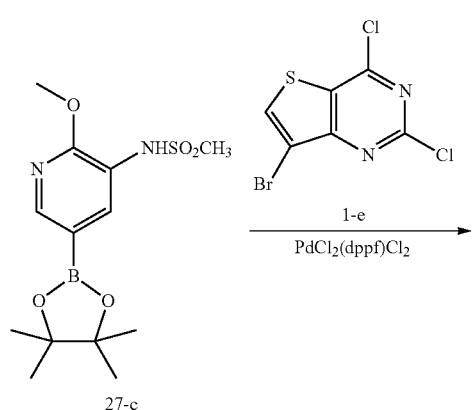

114

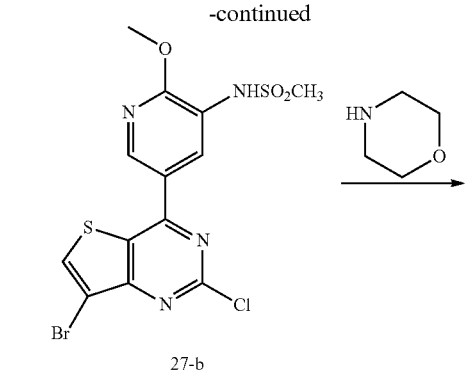

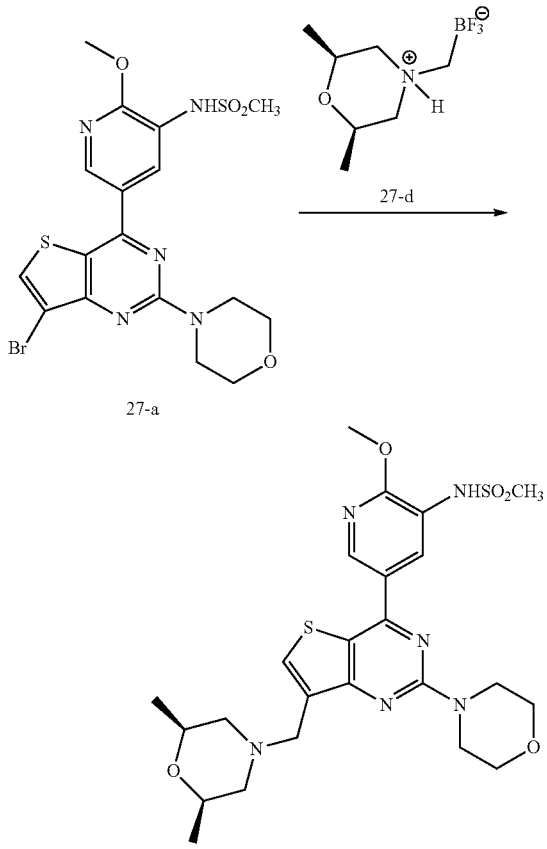

Synthesis of Compound 27-d

According to the method for preparing compound 1-a,(2S,6R)-2,6-dimethyl morpholine was used in the preparation to yield compound 27-d (4 g, 74%), as a white solid. $^1$H NMR (400 MHz, CDCl$_3$): δ 9.04 (1H, brs), 3.73-3.91 (2H, m), 3.26 (2H, d, J=12.4 Hz), 2.39-2.49 (2H, m), 1.88-2.05 (2H, m), 1.09 (6H, d, J=6.4 Hz).

Synthesis of Compound 27-b

Compound 1-e (1.5 g, 6.09 mmol), compound 27-c (prepared according to the method disclosed in: WO 2012/032067 A1) (2 g, 6.09 mmol), anhydrous sodium carbonate (1.94 g, 18.27 mmol), dioxane/water (20 mL/20 mL) and Pd(dppf)Cl$_2$CH$_2$Cl$_2$ (500 mg, 0.6 mmol) were placed into a reaction flask. The reaction mixture was heated under nitrogen atmosphere to 80° C. overnight. The reaction mixture was concentrated under reduced pressure, and then partitioned between dichloromethane (50 mL) and water (50 mL). The organic layer was separated, dried over anhydrous sodium sulfate, and concentrated under reduced pressure. The residue was purified by silica gel column chromatography to obtain compound 27-b (1.05 g, 44.1%), as a light brown solid. LC-MS (ESI): m/z=449 (M+H)+.

Synthesis of Compound 27-a

Compound 27-b (1.05 g, 2.35 mmol) was dissolved in N,N-dimethylacetamide (15 mL), and morpholine (1 mL) was added. The reaction mixture was heated to 90° C. to react for 5 hrs. The reaction solution was concentrated under reduced pressure. The residue was purified by silica gel column chromatography to obtain compound 27-a (520 mg, 44.5%), as a pale yellow solid. LC-MS (ESI): m/z=500 (M+H)+.

Synthesis of Compound 27

Compound 27-a (70 mg, 0.14 mmol), 27-d (55 mg, 0.28 mmol), palladium acetate (5 mg, 0.03 mmol), X-Phos (10 mg, 0.037 mmol) and cesium carbonate (137 mg, 0.42 mmol) were added into a microwave tube containing THF (2.0 mL) and water (0.2 mL), and reacted under nitrogen atmosphere at 80° C. overnight. The reaction mixture was filtered through celite, and rinsed with tetrahydrofuran. The filtrate was concentrated under reduced pressure. The residue was purified by Prep-HPLC to obtain target compound 27 (15 mg, yield 20%), as a yellow solid. LC-MS (ESI): m/z 549 (M+H)+. 1H-NMR (400 MHz, CDCl3): δ 8.79 (d, J=2.0 Hz, 1H), 8.59 (d, J=2.0 Hz, 1H), 7.78 (s, 1H), 6.82 (s, 1H), 4.12 (s, 3H), 3.93-3.95 (m, 4H), 3.82-3.84 (m, 6H), 3.71 (br,2H), 3.08 (s, 3H), 2.82-2.85 (m, 2H), 1.91-1.93 (m, 2H), 1.15 (d, J=6.0 Hz, 6H).

Synthetic Route of Compound 28

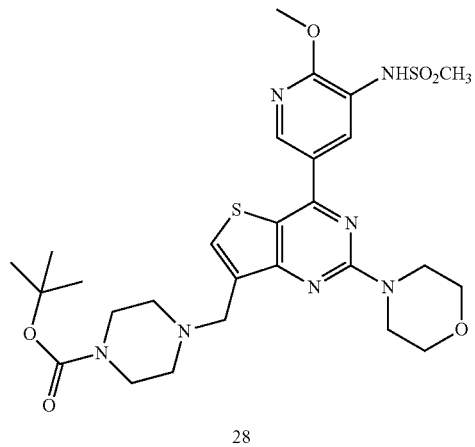

28

Synthesis of Compound 28

Compound 27-a (420 mg, 1.68 mmol), 8-d (905 mg, 3.37 mmol), palladium acetate (42 mg, 0.18 mmol), X-Phos (82 mg, 0.18 mmol) and cesium carbonate (1.65 g, 2.52 mmol) were added into a microwave tube containing THF (10 mL). The mixture was under nitrogen atmosphere and microwave heated to 85° C. to react for 30 minutes. The reaction mixture was filtered through celite, and rinsed with tetrahydrofuran. The filtrate was concentrated under reduced pressure. The residue was purified by silica gel column chromatography (eluted with ethyl acetate) to obtain target compound 28 (430 mg, yield 70%), as a yellow solid. LC-MS (ESI): m/z 620 (M+H) +.

Synthetic Route of Compound 29

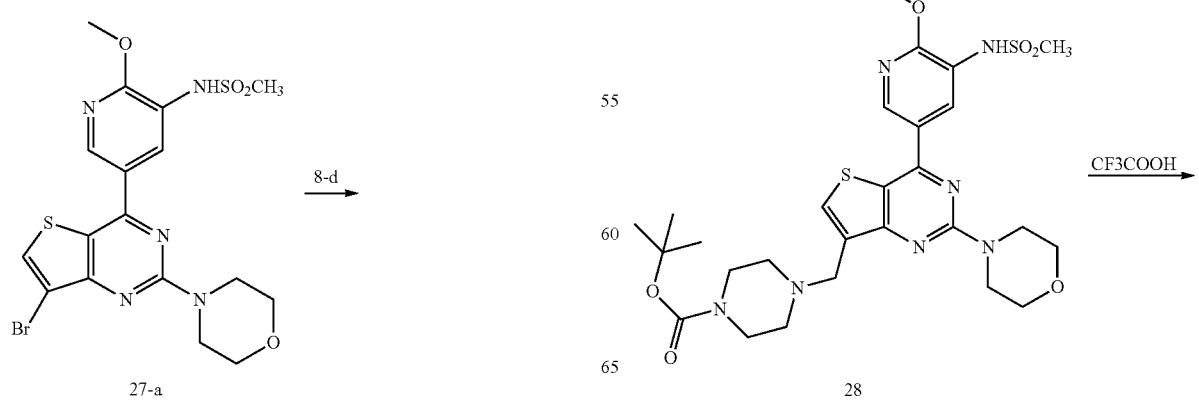

-continued

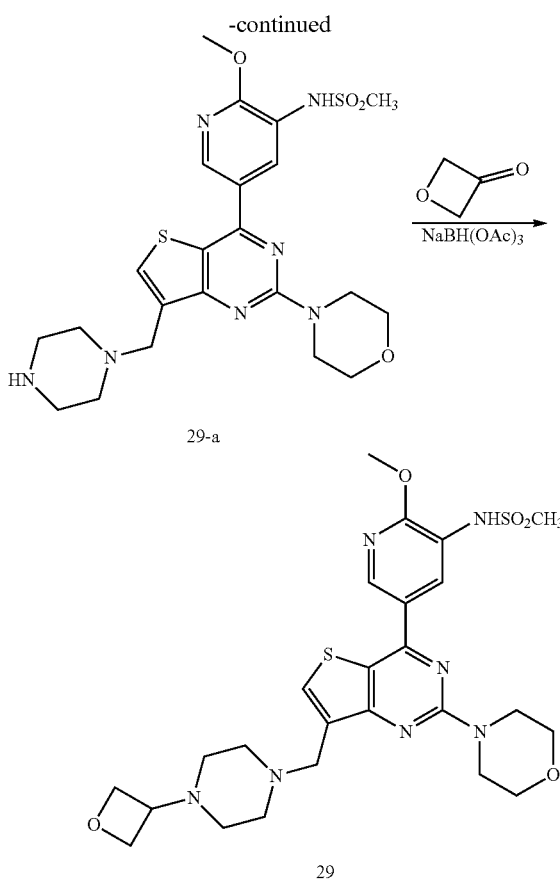

Synthesis of Compound 29-a

Trifluoroacetic acid (0.5 mL) was dripped into a solution of compound 28 (200 mg, 0.33 mmol) in dichloromethane (3 mL), and was stirred at room temperature for 3 hrs. The reaction mixture was concentrated under reduced pressure, and then partitioned between dichloromethane (50 mL) and saturated sodium carbonate (5 mL). The organic layer was separated, dried over anhydrous sodium sulfate, and concentrated under reduced pressure to obtain compound 29-a (160 mg, yield 95%), as a pale yellow solid. LC-MS (ESI): m/z 520 (M+H)$^+$.

Synthesis of Compound 29

Compound 29-a (70 mg, 0.135 mmol), 3-oxacyclobutanone (195 mg, 2.69 mmol) were dissolved in dichloromethane (5 mL), and then a drop of acetic acid and sodium triacetoxyborohydride (570 mg, 2.69 mmol) was added, and was stirred at room temperature overnight. The reaction solution was partitioned between dichloromethane (50 mL) and water (10 mL). The organic layer was separated, dried over anhydrous sodium sulfate, and concentrated under reduced pressure. The residue was purified by Prep-HPLC to obtain target compound 29 (23 mg, 30%), as a yellow solid. LC-MS (ESI): m/z 576 (M+H)$^+$. $^1$H-NMR (400 MHz, CDCl$_3$): δ 8.78 (d, J=2.0 Hz, 1H), 8.59 (d, J=2.0 Hz, 1H), 7.77 (s, 1H), 4.59-4.67 (m, 4H), 4.12 (s, 3H), 3.94 (d, J=4.4 Hz, 4H), 3.82-3.88 (m, 6H), 3.49-3.52 (m, 1H), 3.08 (s, 3H), 2.65 (br, 4H), 2.39 (br, 4H).

Synthesis of Compound 30

According to the method for preparing compound 20, 2-trifluoromethylimidazole was used in the preparation to yield compound 30, as a white solid. LC-MS (ESI): m/z=524.2 [M+H]$^+$. $^1$H NMR (400 MHz, CDCl$_3$): δ 7.83 (1H, s), 7.66 (1H, s), 7.32 (1H, s), 3.84-3.93 (4H, m), 3.73-3.83 (6H, m), 3.62-3.71 (2H, m), 3.50-3.60 (2H, m), 2.69-2.84 (1H, m), 2.46-2.62 (4H, m), 1.11 (6H, d, J=6.8 Hz).

Synthetic Route of Compound 31

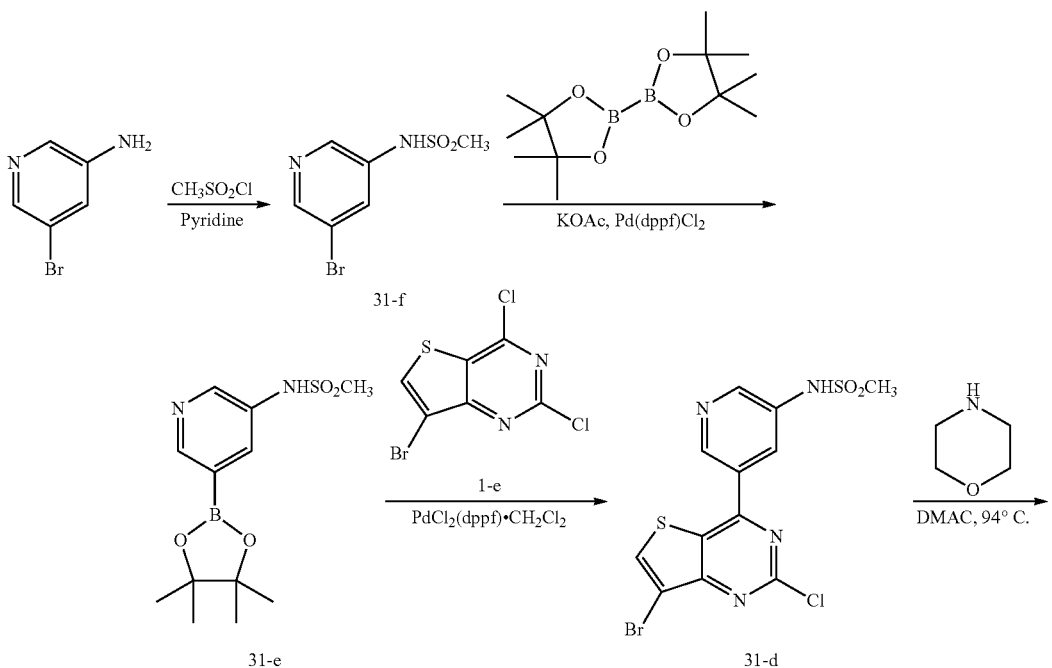

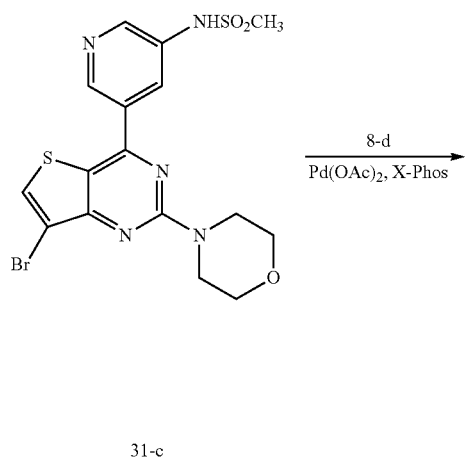

31-c

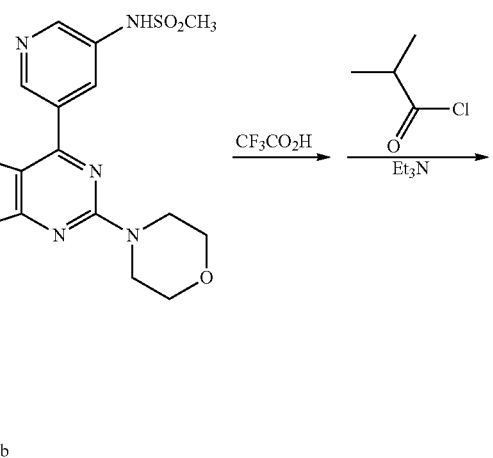

31-b

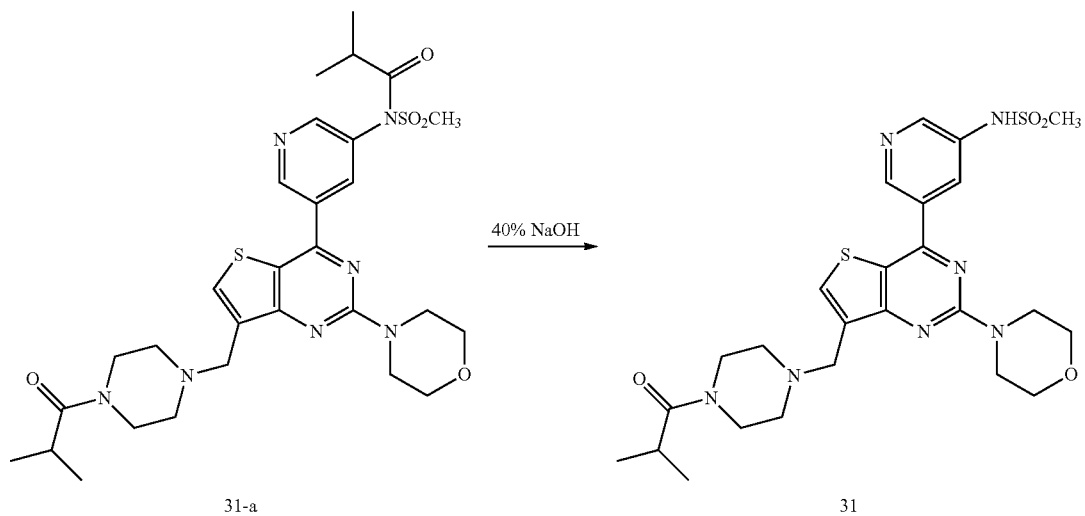

31-a → 31

Synthesis of Compound 31-f

5-Bromo-3-aminopyridine (2.12 g, 11.84 mmol) was dissolved in dichloromethane (100.0 mL) and pyridine (20.0 mL). The solution was cooled with an ice bath, and methylsulfonyl chloride (0.9 mL, 11.84 mmol) was slowly added dropwise. The reaction solution was stirred at room temperature overnight, and then partitioned between water and dichloromethane. The organic layer was separated, dried over anhydrous sodium sulfate, and concentrated under reduced pressure to obtain compound 31-f (2.9 g, 97.3%). LC-MS (ESI): m/z=250.9 (M+H)$^+$.

Synthesis of Compound 31-e

To a reaction flask were added compound 31-f (867 mg, 3.44 mmol), PdCl$_2$(dppf) (126 mg, 0.172 mmol), bis(pinacolato)diboron (961 g, 3.78 mmol), potassium acetate (1.01 g, 10.32 mmol) and 1, 4-dioxane (87 mL). The mixture was stirred under nitrogen atmosphere at 115° C. overnight, and then concentrated under reduced pressure. The residue was dissolved in ethyl acetate (250 mL), and filtered through celite. The filtrate was concentrated under reduced pressure to obtain 31-e (1.6 g), and crude product was used directly in the next step without further purification. LC-MS (ESI): m/z=299.1 (M+H)$^+$.

Synthesis of Compound 31-d

To a reaction flask were added compound 1-e (977 mg, 3.44 mmol), compound 31-e (1.6 g, 3.44 mmol), PdCl$_2$(dppf) (126 mg, 0.172 mmol), 2 N sodium carbonate aqueous solution (5.2 mL, 10.32 mmol), 1, 4-dioxane (25 mL). The mixture was stirred under nitrogen atmosphere at 80° C. overnight. The reaction solution was concentrated under reduced pressure. The residue was dissolved in a mixed solvent of tetrahydrofuran (20 mL) and dichloromethane (100 mL), and filtered through celite. The filtrate was concentrated under reduced pressure. The residue was separated and purified by silica gel column chromatography (elution system: dichloromethane/ethyl acetate=1/1) to obtain compound 31-d (820 mg, 56.9%). LC-MS (ESI): m/z=420.9 (M+H)$^+$.

Synthesis of Compound 31-c

A mixture of compound 31-d (800 mg, 1.89 mmol), morpholine (825 mg, 9.48 mmol) and N,N-dimethylacetamide (8 mL) was heated to 94° C. to react overnight. The reactants were cooled to room temperature, and concentrated under reduced pressure. The residue was diluted with ethyl acetate, and washed with aqueous ammonia. The organic layer was separated, dried over anhydrous sodium sulfate, and concentrated under reduced pressure. The residue was purified by Prep-HPLC to obtain target compound 31-c (100 mg, 11.2%). LC-MS (ESI): m/z=470.0 (M+H)$^+$.

Synthesis of Compound 31-b

To a microwave tube were added compound 31-c (100 mg, 0.213 mmol), compound 8-d (130 mg, 0.426 mmol), cesium carbonate (208 mg, 0.693 mmol), X-Phos (20 mg, 0.0426 mmol), palladium acetate (5 mg, 0.0213 mmol), THF (2.0 mL) and water (0.2 mL). The mixture was stirred under nitrogen atmosphere at 80° C. overnight. The reaction solution was cooled to room temperature and filtered, and the filter cake was eluted with THF. The residue after the filtrate being concentrated under reduced pressure was purified by silica gel preparation plate chromatography (developing system: dichloromethane/methanol=10/1), to yield compound 31-b (37 mg, 29.6%). LC-MS (ESI): m/z=590.2 (M+H)$^+$.

Synthesis of Compound 31-a

Compound 31-b (37 mg, 0.0628 mmol) was dissolved in dichloromethane (3.0 mL), and trifluoroacetic acid (1.0 mL) was slowly added dropwise. The reaction solution was stirred at room temperature overnight, and then concentrated under reduced pressure. The residue was dissolved in dichloromethane (3 mL), and cooled in an ice bath, and sequentially triethylamine (31 mg, 0.307 mmol) and isobutyryl chloride (20 mg, 0.184 mmol) were added dropwise. The reaction solution was stirred at room temperature for 2 hrs. The reaction solution was diluted with saturated sodium bicarbonate (20.0 mL), and extracted with dichloromethane (2×20.0 mL). The organic layers were combined, dried over anhydrous sodium sulfate, and concentrated under reduced pressure, to obtain compound 31-a (38 mg, 98%). LC-MS (ESI): m/z=630.3 (M+H)$^+$.

Synthesis of Compound 31

Compound 31-a (38 mg, 0.06 mmol) was dissolved in tetrahydrofuran (4 mL), and to the solution was slowly added 40% sodium hydroxide solution (0.1 mL). The reaction solution was stirred at room temperature overnight, and the solution was adjusted to acidic with 1 N HCl, and then saturated sodium bicarbonate solution (5 mL) and water (15 mL) were added, and extracted with dichloromethane (2×). The organic layers were combined, dried over anhydrous sodium sulfate, and concentrated under reduced pressure. The residue was purified by Prep-HPLC to obtain target compound 31 (13 mg, 50.6%). LC-MS (ESI): m/z=560.3 (M+H)$^+$. $^1$H NMR (500 MHz, CDCl$_3$): δ 9.13 (1H, J=1.5 Hz, d), 8.54 (1H, J=2.5 Hz, d), 8.38 (1H, J=2.5 Hz, t), 7.47 (1H, s), 3.86-3.88 (4H, m), 3.76-3.81 (6H, m), 3.60 (2H, s), 3.48 (2H, s), 3.06 (3H, s), 2.68-2.74 (1H, m), 2.50 (4H, s), 1.05 (6H, J=6.0 Hz, d).

Synthetic Route of Compound 32

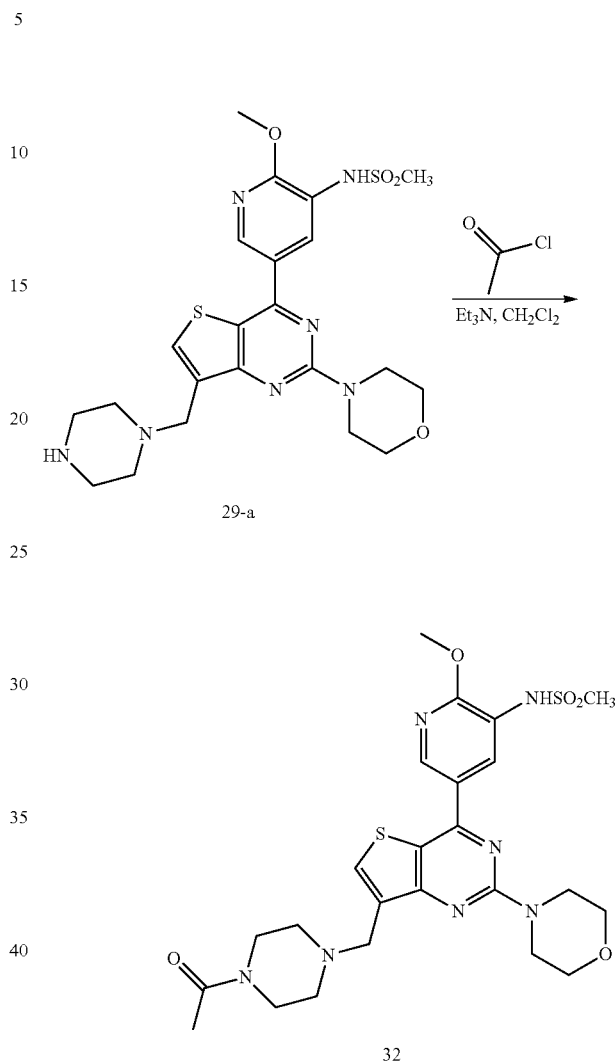

Synthesis of Compound 32

Triethylamine (30 μL) was dripped into a solution of compound 29-a (50 mg, 0.096 mmol) in dichloromethane (1 mL). The reaction solution was cooled to 0° C., and acetyl chloride (10 mg, 0.115 mmol) was added dropwise. The reaction mixture was stirred 30 minutes, and quenched with water (5 mL), and extracted with dichloromethane (15 mL). The organic layer was dried over anhydrous sodium sulfate, and concentrated under reduced pressure. The residue was purified by Prep-HPLC to obtain target compound 32 (13 mg, 24%), as a yellow solid. LC-MS (ESI): m/z 562 (M+H)$^+$. $^1$H-NMR (400 MHz, CDCl$_3$): δ 8.78 (d, J=2.0 Hz, 1H), 8.59 (d, J=2.0 Hz, 1H), 7.78 (s, 1H), 4.12 (s, 3H), 3.92-3.94 (m, 4H), 3.82-3.86 (m, 6H), 3.64-3.66 (m, 2H), 3.48-3.50 (m, 2H), 3.08 (s, 3H), 2.54-2.58 (m, 4H), 2.08 (s, 3H).

123
Synthetic Route of Compound 33

124
Synthetic Route of Compound 34

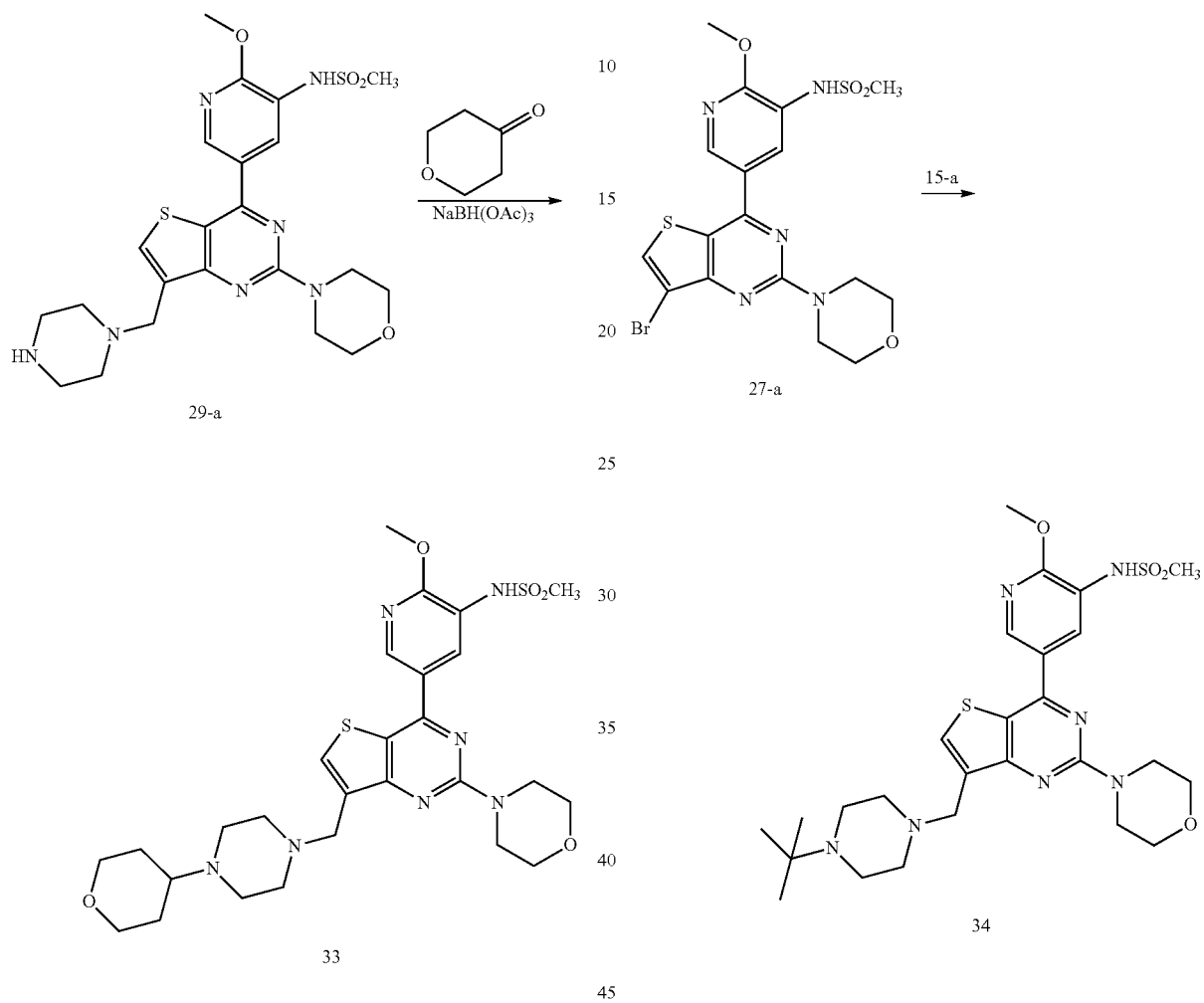

Synthesis of Compound 33

Compound 29-a (100 mg, 0.193 mmol), 4-oxotetrahydropyranone (385 mg, 3.85 mmol) were dissolved in dichloromethane (10 mL), and a drop of acetic acid and sodium triacetoxyborohydride (818 mg, 3.85 mmol) were added. The reaction mixture was stirred at room temperature overnight, diluted with dichloromethane (50 mL), and washed with water (10 mL). The organic layer was separated, dried over anhydrous sodium sulfate, and concentrated under reduced pressure. The residue was purified by Prep-HPLC to obtain target compound 33 (28 mg, 24%), as a yellow solid. LC-MS (ESI): m/z 604 (M+H)$^+$. $^1$H-NMR (400 MHz, CDCl$_3$): δ 8.78 (d, J=2.0 Hz, 1H), 8.58 (d, J=2.0 Hz, 1H), 7.78 (s, 1H), 4.12 (s, 3H), 3.99-4.03 (m, 2H), 3.92-3.94 (m, 4H), 3.82-3.85 (m, 6H), 3.34-3.39 (m, 2H), 3.08 (s, 3H), 2.63 (br, 8H), 2.40-2.44 (m, 1H), 1.75-1.78 (m, 2H), 1.58-1.60 (m, 2H).

Synthesis of Compound 34

Compound 27-a (60 mg, 0.12 mmol), compound 15-a (54 mg, 0.24 mmol), cesium carbonate (117 mg, 0.36 mmol), X-Phos (10 mg, 0.04 mmol), palladium acetate (5 mg, 0.02 mmol), THF(1 mL) and water(0.1 mL) were added into a microwave tube. The mixture was stirred under nitrogen atmosphere at 80° C. overnight. The reaction solution was cooled to room temperature, filtered through celite, and the filter cake was washed with THF, and concentrated under reduced pressure. The residue was purified by Prep-HPLC to obtain target compound 34(10 mg, 15%), as a yellow solid. LC-MS(ESI): m/z 576(M+H)$^+$; $^1$H-NMR (400 MHz, CDCl$_3$): δ 8.79(d, J=2.0 Hz, 1H), 8.57(d, J=2.0 Hz, 1H), 7.76(s, 1H), 4.12(s, 3H), 3.92-3.94(m, 4H), 3.82-3.85(m, 6H), 3.71(br, 2H), 3.08(s, 3H), 2.64(br, 8H), 1.07(s, 9H).

125
Synthetic Route of Compound 35

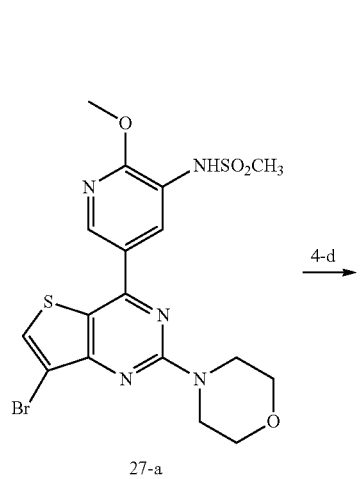

Synthesis of Compound 35

Compound 27-a (300 mg, 0.6 mmol), compound 4-d (360 mg, 1.6 mmol), cesium carbonate (600 mg, 1.84 mmol), X-Phos (120 mg, 0.26 mmol), palladium acetate (60 mg, 0.26 mmol), THF (10 mL) and water (1 mL) were added into a microwave tube. The mixture was stirred under nitrogen atmosphere at 80° C. overnight. The reaction solution was cooled to room temperature, filtered through celite, and the filter cake was washed with THF, and concentrated under reduced pressure. The residue was purified by Prep-HPLC to obtain target compound 35 (23 mg, 7%), as a yellow solid. LC-MS (ESI): m/z 578 (M+H)$^+$; $^1$H-NMR (400 MHz, CDCl$_3$): δ 8.78 (d, J=2.0 Hz, 1H), 8.59 (d, J=2.0 Hz, 1H), 7.82 (s, 1H), 4.12 (s, 3H), 3.92-3.95 (m, 4H), 3.82-3.85 (m, 6H), 3.11-3.14 (m, 2H), 3.08 (s, 3H), 2.08-2.13 (m, 2H), 1.74-1.77 (m, 2H), 1.45-1.48 (m, 2H), 1.29-1.32 (m, 2H), 1.18 (s, 6H).

126
Synthetic Route of Compound 36

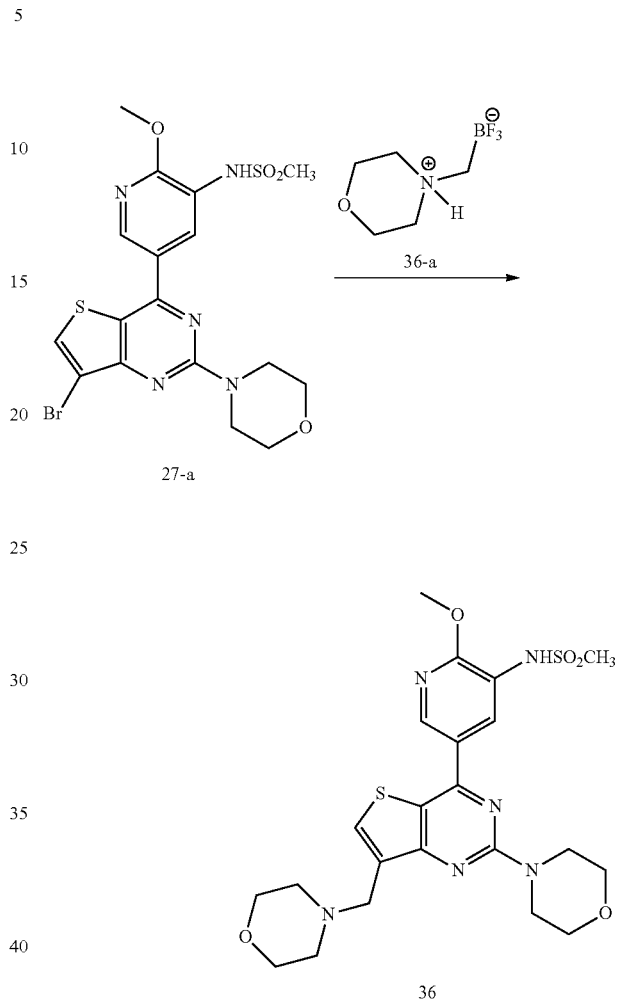

Synthesis of Compound 36

Compound 27-a (100 mg, 0.2 mmol), compound 36-a (prepared according to the method disclosed in reference: J. Org. Chem. 2011, 76, 2762-2769) (68 mg, 0.4 mmol), cesium carbonate (200 mg, 0.61 mmol), X-Phos (20 mg, 0.1 mmol), palladium acetate (10 mg, 0.05 mmol), THF (3 mL) and water (0.3 mL) were added into a microwave tube. The mixture was stirred under nitrogen atmosphere at 80° C. overnight. The reaction solution was cooled to room temperature, filtered through celite, and the filter cake was washed with THF, and concentrated under reduced pressure. The residue was purified by Prep-HPLC to obtain target compound 36 (24 mg, 23%), as a yellow solid. LC-MS (ESI): m/z 521 (M+H)$^+$; $^1$H-NMR (400 MHz, CDCl$_3$): δ 8.78 (d, J=2.0 Hz, 1H), 8.59 (d, J=2.0 Hz, 1H), 7.79 (s, 1H), 6.85 (br, 1H), 4.12 (s, 3H), 3.92-3.95 (m, 4H), 3.82-3.85 (m, 6H), 3.74-3.76 (m, 4H), 3.08 (s, 3H), 2.59 (s, 4H).

Synthetic Route of Compound 37

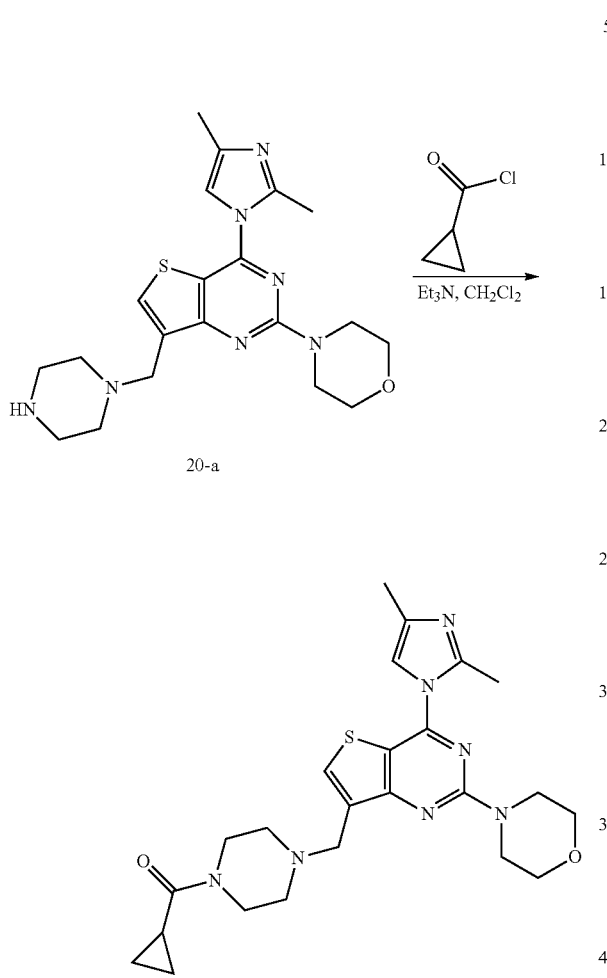

Synthesis of Compound 37

In an ice-water bath, to a solution of compound 20-a (98 mg, 0.237 mmol) in dichloromethane (5 mL) were sequentially added triethylamine (1.18 mmol) and cyclopropylformyl chloride (0.712 mmol). Then the reaction solution was warmed to room temperature and stirred for 2 hrs. The reaction solution was diluted with dichloromethane, and the organic layer was sequentially washed with saturated sodium bicarbonate, water, saturated sodium chloride, dried over anhydrous sodium sulfate, and concentrated under reduced pressure. The residue was purified by Prep-HPLC to obtain target compound 37 (65 mg, 57%). LC-MS (ESI): m/z=482.2 (M+H)$^+$. $^1$H NMR (400 MHz, CDCl$_3$): δ7.72 (1H, s), 7.18 (1H, s), 3.79-3.82 (4H, m), 3.72-3.76 (6H, m), 3.61-3.65 (4H, m), 2.59 (3H, s), 2.49-2.54 (4H, m), 2.21 (3H, s), 1.62-1.68 (1H, m), 0.89-0.93 (2H, m), 0.66-0.70 (2H, m).

Synthetic Route of Compound 38

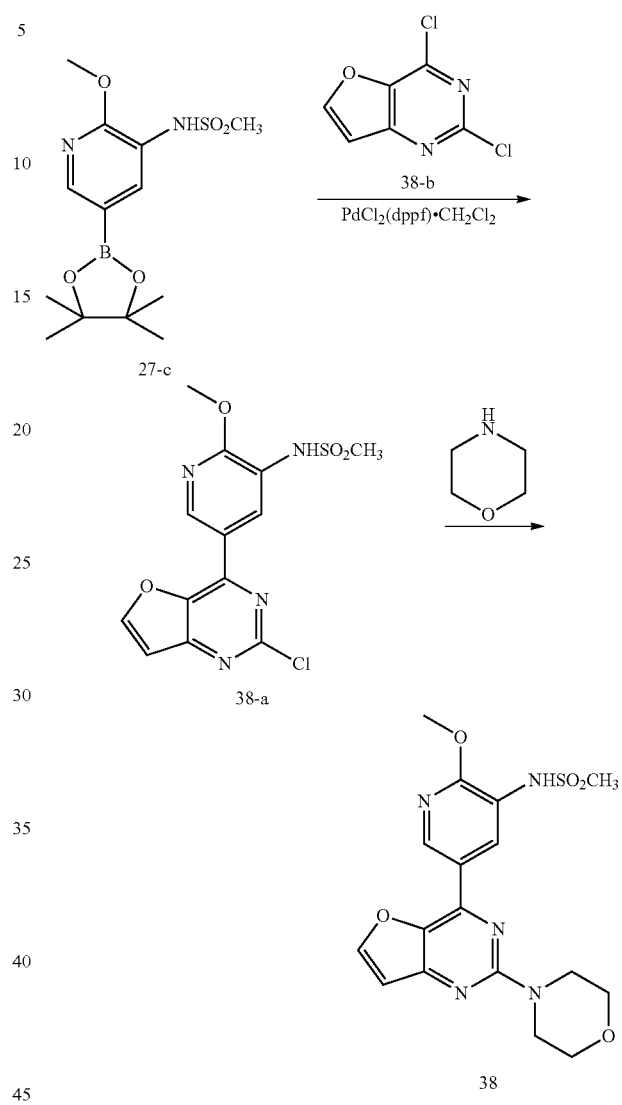

Synthesis of Compound 38-a

To a reaction flask were added compound 27-c (36 mg, 0.106 mmol), compound 38-b (prepared according to the method disclosed in: WO 2011/079230 A2) (20 mg, 0.106 mmol), PdCl$_2$(dppf) (4 mg, 0.005 mmol), 2 N sodium carbonate aqueous solution (0.16 mL, 0.32 mmol, 3.0 equiv.) and 1,4-dioxane (1 mL). The mixture was stirred under nitrogen atmosphere at 80° C. overnight. The reaction mixture was concentrated under reduced pressure, and then partitioned between water (15 mL) and dichloromethane (20 mL). The organic phase was separated out, dried over anhydrous sodium sulfate, and concentrated under reduced pressure, to obtain compound 38-a (40 mg). LC-MS (ESI): m/z=354.7 (M+H)$^+$.

Synthesis of Compound 38

A mixture of compound 38-a (40 mg, 0.113 mmol), morpholine (98 mg, 1.13 mmol) and N,N-dimethylacetamide (2 mL) was heated to 94° C. to react overnight. The reactants were cooled to room temperature, and concentrated under reduced pressure. The residue was purified by Prep-HPLC to obtain target compound 38 (4 mg, 9.0%). LC-MS (ESI): m/z=405.8 (M+H)$^+$. $^1$H NMR (400 MHz, CDCl$_3$): δ 9.00 (2H, s), 8.76 (1H, d, J=2.0 Hz), 7.81 (1H, d, J=2.4 Hz), 6.70 (1H, d, J=2.0 Hz), 4.05 (3H, s), 3.75-3.83 (8H, m), 2.99 (3H, s).

Synthetic Route of Compound 39

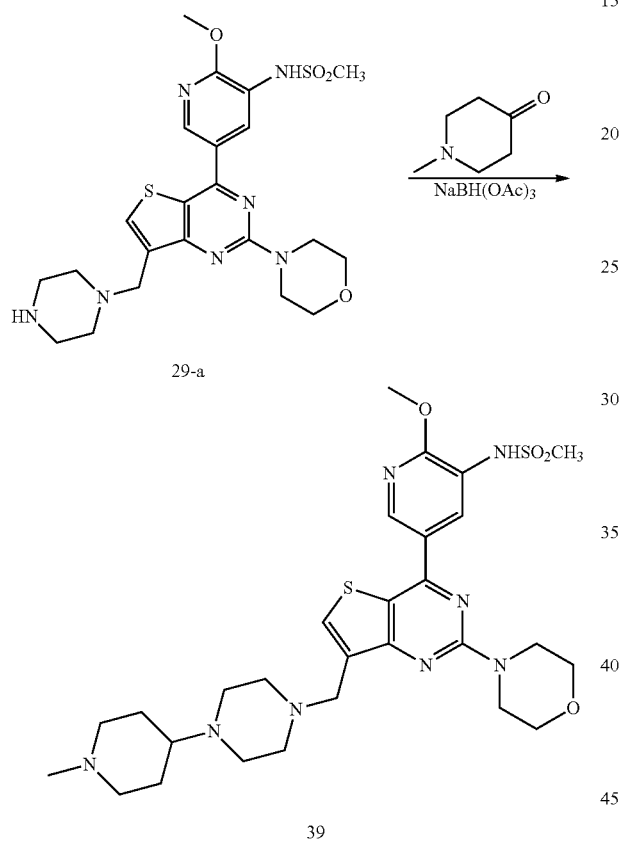

39

Synthesis of Compound 39

Compound 29-a (70 mg, 0.135 mmol), N-methyl-4-piperidone (305 mg, 2.69 mmol) was dissolved in dichloromethane (5 mL), and a drop of acetic acid and sodium triacetoxyborohydride (570 mg, 2.69 mmol) were added. The reaction mixture was stirred at room temperature overnight, diluted with dichloromethane (50 mL), and washed with water (10 mL). The organic layer was separated, dried over anhydrous sodium sulfate, and concentrated under reduced pressure. The residue was purified by Prep-HPLC to obtain target compound 39 (15 mg, 18%), as a yellow solid. LC-MS (ESI): m/z 617 (M+H)$^+$. $^1$H-NMR (400 MHz, CDCl$_3$): δ 8.78 (d, J=2.0 Hz, 1H), 8.58 (d, J=2 Hz, 1H), 7.78 (s, 1H), 4.12 (s, 3H), 3.92-3.94 (m, 4H), 3.82-3.84 (m, H), 3.08 (s, 3H), 2.92 (d, J=12.0 Hz, 2H), 2.63 (br, 8H), 2.17 (s, 4H), 1.94-1.97 (m, 2H), 1.80-1.83 (m, 2H), 1.60-1.63 (m, 2H).

Synthetic Route of Compound 40

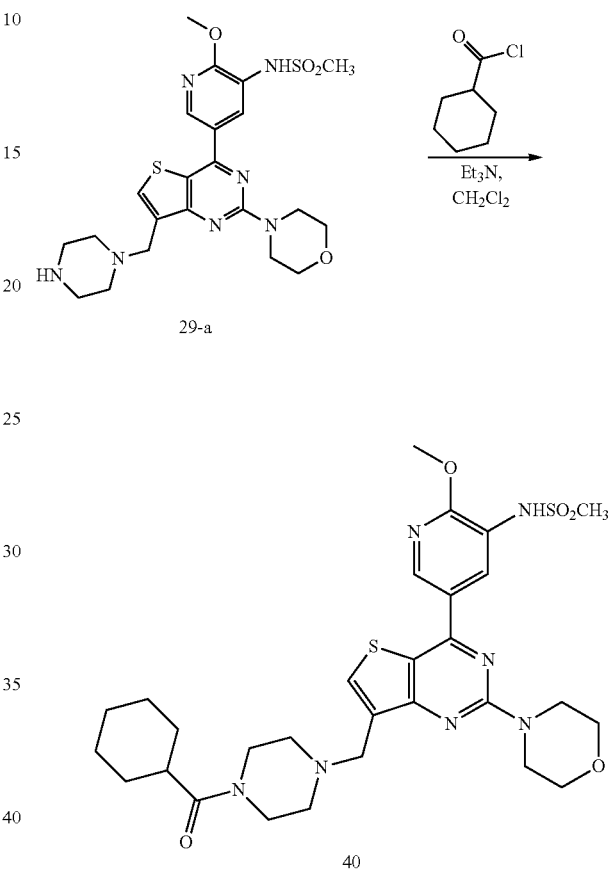

40

Synthesis of Compound 40

Triethylamine (40 μL) was dripped into a solution of compound 29-a (70 mg, 0.135 mmol) in dichloromethane (1 mL). The reaction liquid was cooled to 0° C., and cyclohexylcarbonyl chloride (30 mg, 0.203 mmol) was added dropwise. The reaction mixture was stirred for 30 minutes, quenched with water (5 mL), and extracted with dichloromethane (15 mL). The organic layer was dried over anhydrous sodium sulfate, and concentrated under reduced pressure. The residue was purified by Prep-HPLC to obtain target compound 40 (12 mg, 14%), as a yellow solid. LC-MS (ESI): m/z 630 (M+H)$^+$. $^1$H-NMR (400 MHz, CDCl$_3$): δ 8.78 (d, J=2.0 Hz, 1H), 8.59 (d, J=2.0 Hz, 1H), 7.78 (s, 1H), 6.83 (s, 1H), 4.12 (s, 3H), 3.94 (m, 4H), 3.84 (m, 6H), 3.65 (br, 2H), 3.54 (br, 2H), 3.08 (s, 3H), 2.57 (brs, 4H), 2.43-2.50 (m, 1H), 1.71-1.83 (m, 5H), 1.48-1.56 (m, 2H), 1.22-1.32 (m, 3H).

Synthetic Route of Compound 41

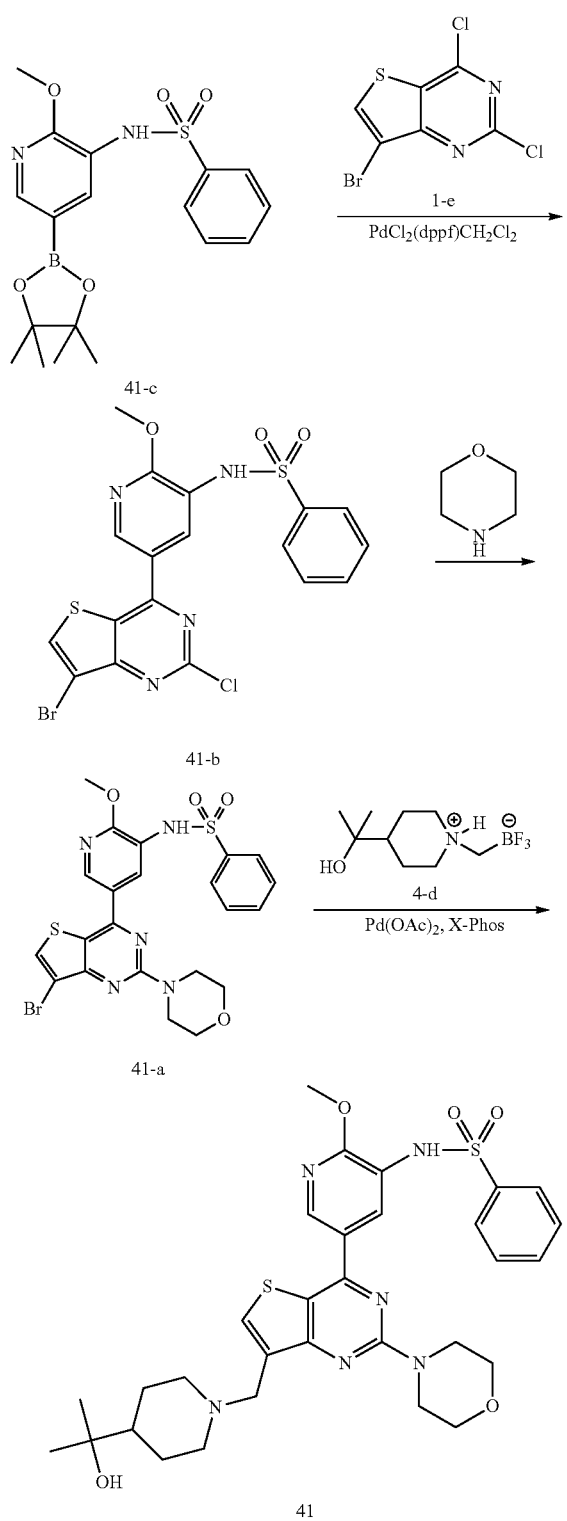

Synthesis of Compound 41-b

To a reaction flask were added compound 1-e (318 mg, 1.1 mmol), compound 41-c (prepared according to the method disclosed in: WO 2012/037108 A1) (400 mg, 1.0 mmol), PdCl$_2$(dppf) (82 mg, 0.1 mmol), Na$_2$CO$_3$ (318 mg, 3.0 mmol), dioxane (10 mL) and water (1 mL). The reaction solution was reacted under nitrogen atmosphere at 80° C. overnight. Then the reaction mixture was cooled to room temperature, and concentrated under reduced pressure. the resultant residue was partitioned between water (20 mL) and ethyl acetate (30 mL). The organic layer was separated, and the aqueous layer was extracted with ethyl acetate (2×30 mL). The organic phases were combined, and dried over (Na$_2$SO$_4$), and concentrated under reduced pressure. The residue was purified by silica gel column chromatography (elution system: petroleum ether/ethyl acetate=2/1) to obtain target compound 41-b (250 mg, yield 49%), as a yellow solid. LC-MS (ESI): m/z 512 (M+H)$^+$.

Synthesis of Compound 41-a

A mixture of compound 41-b (200 mg, 0.4 mmol), morpholine (2.0 mmol) and ethylene glycol dimethyl ether (15 mL) was heated to 80° C. to react for 2 hrs. The reaction mixture was cooled, and concentrated under reduced pressure. The residue was purified by silica gel column chromatography (elution system: petroleum ether/ethyl acetate=2/1) to obtain target compound 41-a (80 mg, 36%). LC-MS (ESI): m/z 562 (M+H)$^+$.

Synthesis of Compound 41

Compound 41-a (80 mg, 0.14 mmol), compound 4-d (0.42 mmol), cesium carbonate (137 mg, 0.42 mmol), X-Phos (13 mg, 0.028 mmol), palladium acetate (3 mg, 0.014 mmol) and a mixed liquid of dioxane and water (10/1, v/v, 1.1 mL) were added into a microwave tube. The mixture was stirred under nitrogen atmosphere at 80° C. overnight. The reaction solution was cooled to room temperature, and then partitioned between water (10 mL) and ethyl acetate (20 mL). The organic layer was separated, and the aqueous layer was extracted with ethyl acetate (2×10 mL). The organic phases were combined, and then dried over (Na$_2$SO$_4$), and concentrated under reduced pressure. The residue was purified by Prep-HPLC to yield compound 41 (10 mg, 11%), as a yellow solid. LC-MS (ESI): m/z 639 (M+H)$^+$. $^1$H NMR (400 MHz, CDCl$_3$): δ 8.70 (t, J=2.0 Hz, 1H), 8.56 (d, J=2.0 Hz, 1H), 7.87-7.89 (m, 3H), 7.54-7.56 (m, 1H), 7.44-7.48 (m, 2H), 3.83-3.94 (m, 13H), 3.14 (d, J=11.4 Hz, 2H), 2.13 (t, J=11.6 Hz, 2H), 1.76 (d, J=12.4 Hz, 2H), 1.27-1.38 (m, 3H), 1.18 (s, 6H).

Synthetic Route of Compound 42

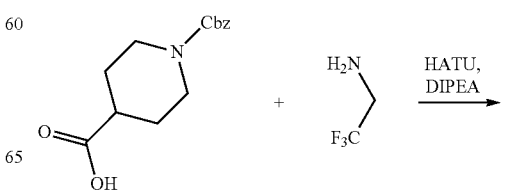

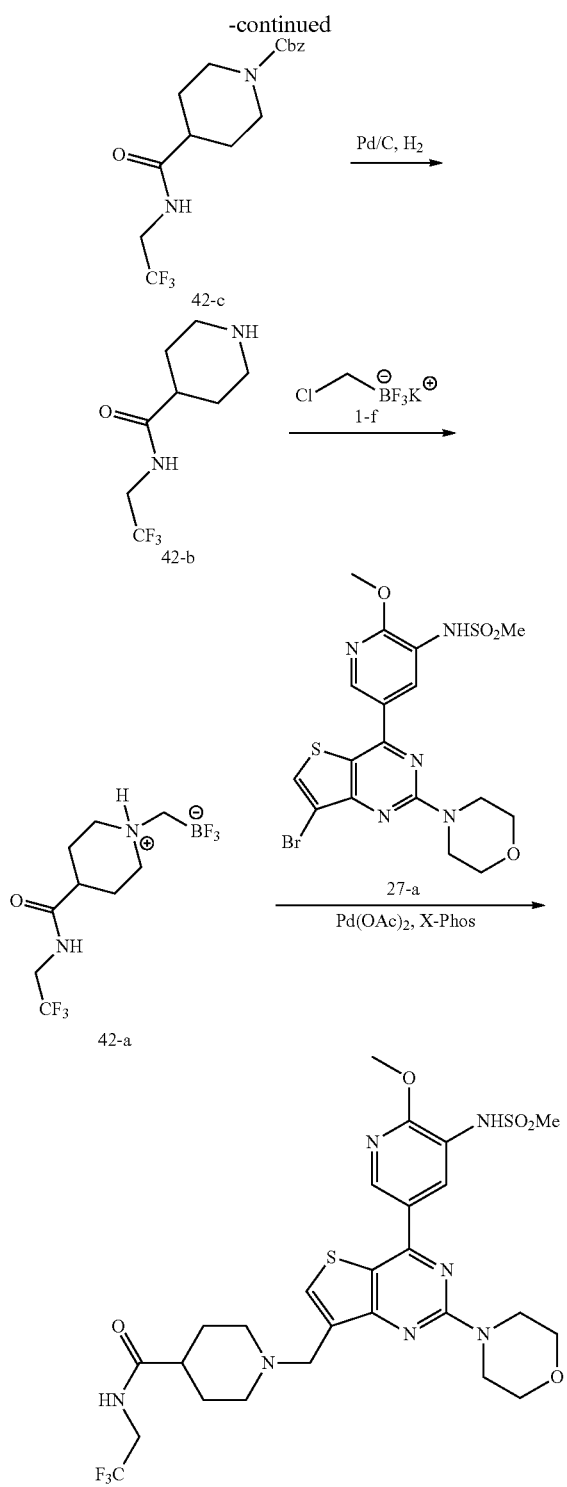

overnight, and then concentrated under reduced pressure. The residue was dissolved in ethyl acetate, sequentially washed with water, saturated brine, dried over anhydrous sodium sulfate, and concentrated under reduced pressure. The residue was purified by Prep-HPLC to yield compound 42-c (2 g, 58%). LC-MS (ESI): m/z=344.9 (M+H)$^+$.

Synthesis of Compound 42-b

A mixture of compound 42-c (600 mg, 1.74 mmol), Pd-C (60 mg) and methanol (10 mL) was stirred under hydrogen atmosphere at room temperature overnight, and concentrated under reduced pressure to obtain a colorless oil, i.e., compound 42-b (300 mg, 82%). LC-MS (ESI): m/z=210.9 (M+H)$^+$.

Synthesis of Compound 42-a

Compound 42-b (300 mg, 1.43 mmol), 1-f (221 mg, 1.41 mmol), cyclopentyl methyl ether (3 mL) and tert-amyl alcohol (1 mL) were added into a sealed tube, and stirred under nitrogen atmosphere at a temperature of 110° C. overnight. The reaction solution was cooled to room temperature, and concentrated under reduced pressure, and to the residue was added acetone and refluxed, followed by slow addition of diethyl ether to allow precipitation and filtration, the filter cake was dried to obtain compound 42-a (280 mg, 68%). $^1$H NMR (400 MHz, DMSO-d$_6$): δ 8.65 (t, J=6.3 Hz, 1H), 3.84-3.93 (m, 2H), 3.38 (d, J=12.4 Hz, 2H), 3.28-2.97 (m, 1H), 2.78-2.80 (m, 2H), 2.41 (dd, J=11.8, 6.7 Hz, 1H), 2.00-1.72 (m, 6H).

Synthesis of Compound 42

A mixture of compound 42-a (70 mg, 0.24 mmol), 27-a (40 mg, 0.08 mmol), palladium acetate (0.52 mg, 0.0024 mmol), X-Phos (2.28 mg, 0.0048 mmol), cesium carbonate (80 mg, 0.24 mmol), tetrahydrofuran (6 mL) and water (0.6 mL) was stirred under nitrogen atmosphere at 80° C. overnight. The reaction solution was cooled to room temperature, and then partitioned between water (10 mL) and ethyl acetate (20 mL). The organic layer was separated, and the aqueous layer was extracted with ethyl acetate (2×10 mL). The organic phases were combined, and then dried over (Na$_2$SO$_4$), and concentrated under reduced pressure. The residue was purified by Prep-HPLC to yield compound 42 (20 mg, 39%). LC-MS (ESI): m/z=643.9 (M+H)$^+$. $^1$H NMR (400 MHz, CDCl$_3$): δ 8.75 (t, J=2.4 Hz, 1H), 8.55 (d, J=2.1 Hz, 1H), 8.32 (s, 1H), 6.91 (d, J=5.1 Hz, 1H), 5.99 (s, 1H), 4.47 (s, 2H), 4.13 (d, J=1.3 Hz, 3H), 4.05-3.73 (m, 11H), 3.62 (d, J=11.6 Hz, 1H), 3.41 (s, 2H), 3.09 (s, 3H), 2.93 (s, 1H), 2.33-2.09 (m, 4H).

Synthetic Routes of Compounds 43 and 52

Synthesis of Compound 42-c

N-Cbz-piperidine-4-carboxylic acid (3.19 g, 12.1 mmol), 2, 2, 2-trifluoroethylamine (1 g, 10.1 mmol), HATU (7.68 g, 20.2 mmol), N, N-diisopropylethylamine (3.5 mL, 20.2 mmol) and dichloromethane (15 mL) were added into a reaction flask. The mixture was stirred at room temperature

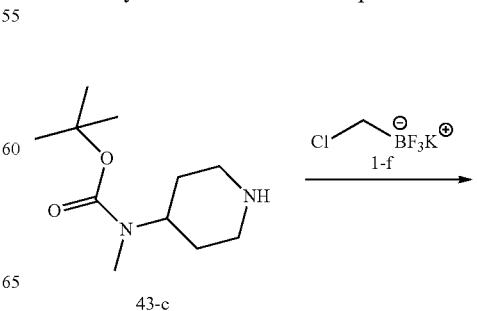

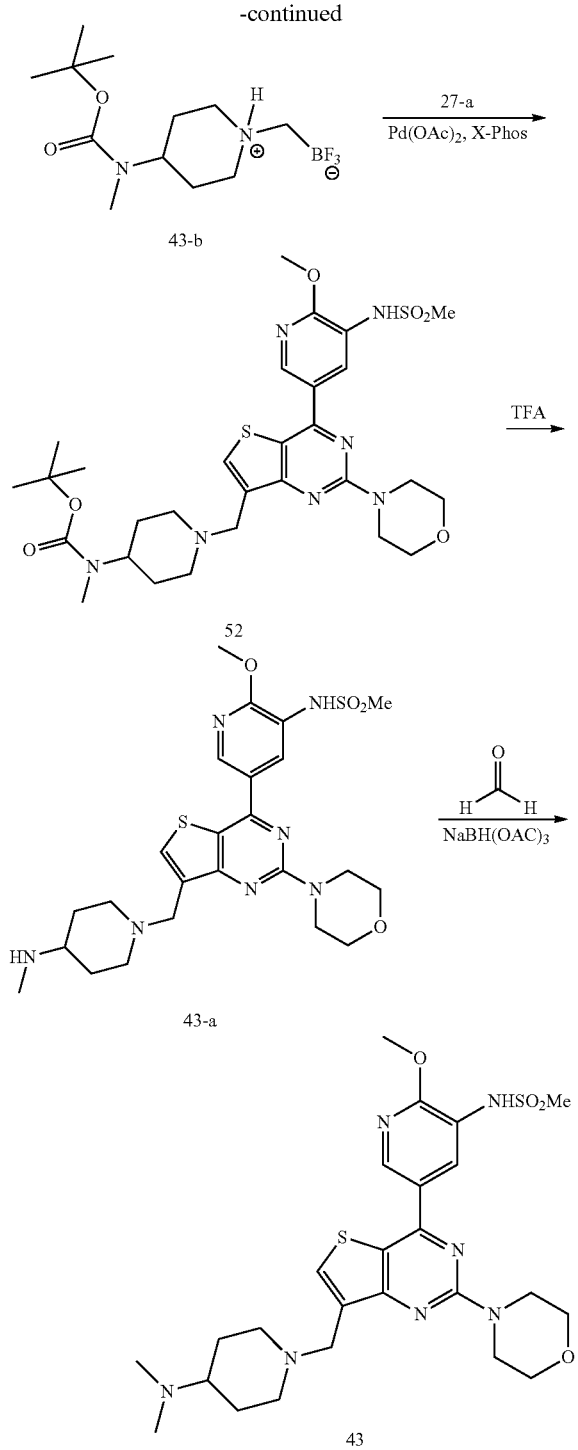

Synthesis of Compound 52

Compound 43-b (118 mg, 0.40 mmol), compound 27-a (100 mg, 0.20 mmol), palladium acetate (5 mg, 0.03 mmol), X-Phos (10 mg, 0.03 mmol) and cesium carbonate (196 mg, 0.6 mmol) were added into a microwave tube containing THF (2.0 mL) and water (0.2 mL). The reacting compounds were reacted under nitrogen atmosphere at 80° C. overnight. The reaction mixture was cooled, filtered, and rinsed with THF. The filtrate and the rinsing liquid were combined, and concentrated under reduced pressure. The residue was purified by silica gel column chromatography (elution system: dichloromethane/methanol=10/1) to obtain target compound 52 (67 mg, 52%), as a yellow solid. LC-MS (ESI): m/z 648 (M+H)$^+$. $^1$H-NMR (400 MHz, CDCl$_3$) δ 8.78 (d, J=2.0 Hz, 1H), 8.59 (d, J=2.0 Hz, 1H), 7.77 (s, 1H), 4.12 (s, 3H), 3.92-3.95 (m, 4H), 3.81-3.85 (m, 6H), 3.03-3.09 (m, 5H), 2.74 (s, 3H), 2.15-2.24 (m, 2H), 1.61-1.78 (m, 5H).

Synthesis of Compound 43-a

Compound 52 (67 mg, 0.33 mmol) was dissolved in dichloromethane (1 mL), and trifluoroacetic acid (0.5 mL) was added. The mixture was stirred at room temperature for 3 hrs, and then concentrated under reduced pressure. The residue was partitioned between dichloromethane (50 mL) and saturated sodium carbonate (5 mL). The organic layer was separated, dried over anhydrous sodium sulfate, and concentrated under reduced pressure to obtain compound 43-a (38 mg, yield 67%), as a pale yellow solid. LC-MS (ESI): m/z 548 (M+H)$^+$.

Synthesis of Compound 43

Compound 43-a (38 mg, 0.069 mmol) and 37% formaldehyde (3 mL, 1.39 mmol) were dissolved in dichloromethane (5 mL), and a drop of acetic acid and sodium triacetoxyborohydride (295 mg, 1.39 mmol) were added, and then stirred at room temperature overnight. The reaction mixture was partitioned between dichloromethane (50 mL) and water (10 mL). The organic layer was separated, dried over anhydrous sodium sulfate, and concentrated under reduced pressure. The residue was purified by Prep-HPLC to yield compound 43 (7 mg, 18%), as a yellow solid. LC-MS (ESI): m/z 562 (M+H)$^+$. $^1$H-NMR (400 MHz, CDCl$_3$): δ 8.78 (d, J=2.0 Hz, 1H), 8.58 (d, J=2.0 Hz, 1H), 7.78 (s, 1H), 4.12 (s, 3H), 3.93-3.95 (m, 4H), 3.84-3.85 (m, 6H), 3.08 (s, 3H), 3.07 (m, 2H), 2.33 (s, 6H), 2.11-2.17 (m, 3H), 1.80-1.90 (m, 2H), 1.60-1.70 (m, 2H).

Synthetic Route of Compound 44

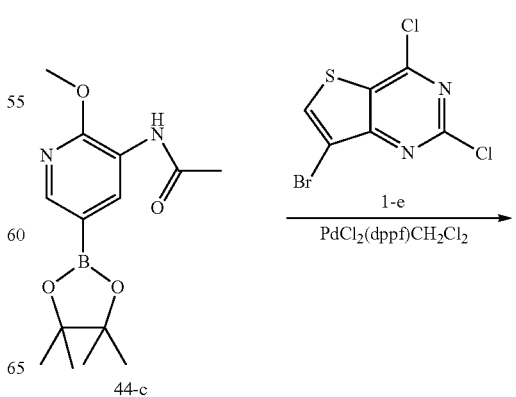

Synthesis of Compound 43-b

A mixture of compound 43-c (500 mg, 2.34 mmol), compound 1-f (365 mg, 2.34 mmol), methyl cyclopentyl ether (3 mL) and tert-amyl alcohol (3 mL) was heated to 110° C. to react overnight, and then concentrated under reduced pressure. The residue was washed with diethyl ether (2×10 mL), and dried under vacuum to obtain compound 43-b (370 mg, 54%).

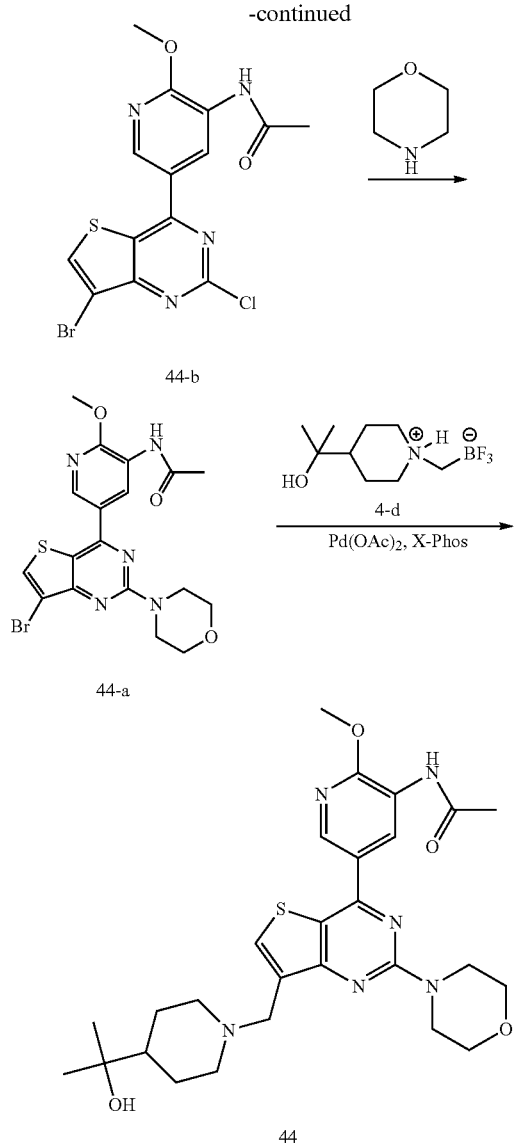

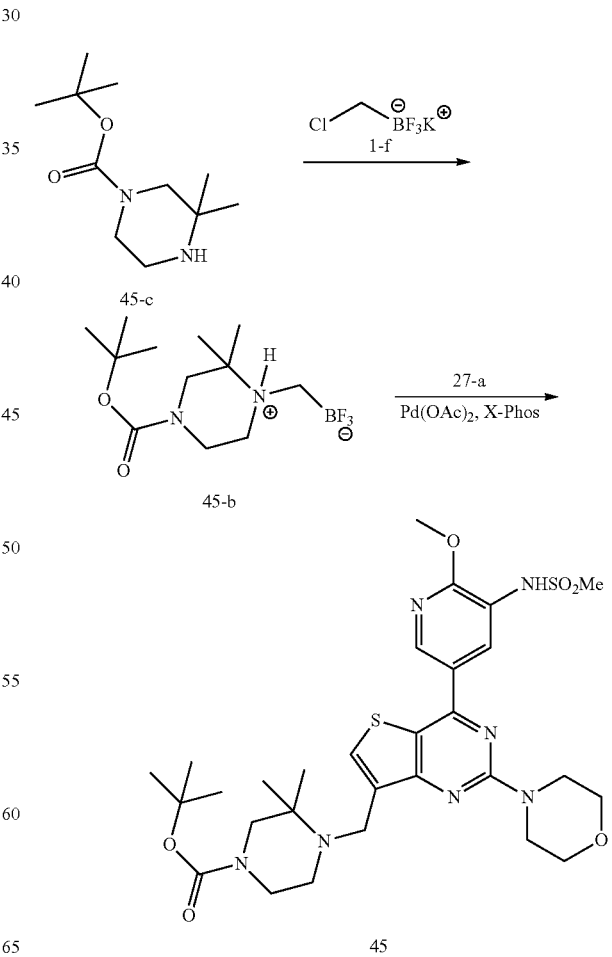

Synthesis of Compound 44-b

Compound 44-c (prepared according to the method disclosed in: WO 2010/139731 A1) (2.1 g, 7.19 mmol), compound 1-e (1.84 g, 6.5 mmol), Pd(dppf)$_2$Cl$_2$ (533 mg, 0.70 mmol), sodium carbonate (2.2 g, 21 mmol), dioxane (40 mL) and water (8 mL) were added into a 100 mL round-bottomed flask. The mixture was stirred under nitrogen atmosphere at 80° C. overnight. The reaction solution was concentrated under reduced pressure, and then dissolved in ethyl acetate, and filtered through celite. The filtrate was washed sequentially with water, saturated brine, dried over anhydrous sodium sulfate, and concentrated under reduced pressure. The residue was purified by silica gel column chromatography (elution system: ethyl acetate/petroleum ether=1/3~1/1) to yield compound 44-b (0.8 g, 27%), as a yellow solid. LC-MS (ESI): m/z=412.9 (M+H)$^+$.

Synthesis of Compound 44-a

Compound 44-b (0.8 g, 1.94 mmol), morpholine (8.44 g, 9.7 mmol) and ethylene glycol dimethyl ether (30 mL) were added into a 100 mL round-bottomed flask. The mixture was heated to 90° C., and stirred to react for 4 hrs. The reaction solution was cooled, filtered, and the filter cake was washed with methanol and water. The filtrate was concentrated under reduced pressure to yield compound 44-a (0.6 g, 67%), as a yellow solid. LC-MS (ESI): m/z=463.9 (M+H)$^+$.

Synthesis of Compound 44

Compound 44-a (93 mg, 0.2 mmol), compound 4-d (113 mg, 0.5 mmol), palladium acetate (4.5 mg, 0.02 mmol), X-Phos (9.5 mg, 0.02 mmol), cesium carbonate (163 mmol, 0.6 mmol), THF (20 mL) and water (2 mL) were added into a 50 mL round-bottomed flask. The mixture was reacted under nitrogen atmosphere at 80° C. overnight. The reaction solution was cooled, filtered, and concentrated under reduced pressure. The residue was purified by Prep-HPLC to yield compound 44 (25 mg, 23%). LC-MS (ESI): m/z=541.1 (M+H)$^+$. $^1$H NMR (400 MHz, CDCl3): δ9.46 (d, J=2.0 Hz, 1H), 8.72 (d, J=1.6 Hz, 1H), 7.78 (s, 1H), 7.74 (s, 1H), 4.11 (s, 3H), 3.95 (t, J=4.4H, 4H), 3.84 (d, J=5.6 HZ, 6H), 3.11 (d, J=11.2 Hz, 2H), 2.27 (s, 3H), 2.09 (t, J=11.2 Hz, 2H), 1.75 (d, J=12 Hz, 2H), 1.49-1.41 (m, 2H), 1.31-1.18 (m, 2H), 1.15 (s, 6H).

Synthetic Route of Compound 45

Synthesis of Compound 45-b

According to the method for preparing compound 43-b, compound 45-c was used in the preparation to yield compound 45-b (890 mg, 89.5%), as a white solid. $^1$H NMR (400 MHz, DMSO-$d_6$): δ9.08 (1H, brs), 4.77 (1H, brs), 4.53 (1H, brs), 4.20 (1H, d, J=12.8 Hz), 4.14 (1H, s), 4.00 (1H, brs), 3.70 (1H, brs), 2.89 (1H, brs), 2.41 (1H, brs), 2.21 (9H, s), 2.06 (3H, s), 1.94 (3H, s).

Synthesis of Compound 45

According to the method for preparing compound 52, compound 45-b was used in the preparation to yield compound 45 (25 mg, 25%), as a yellow solid. LC-MS (ESI): m/z=648.3 (M+H)$^+$. $^1$H NMR (400 MHz, CDCl$_3$): δ 8.71 (1H, d, J=2.0 Hz), 8.52 (1H, d, J=2.0 Hz), 7.70 (1H, s), 4.05 (3H, s), 3.85-3.88 (4H, m), 3.75-3.78 (4H, m), 3.68 (2H, s), 3.36 (2H, s), 3.16 (2H, s), 3.01 (3H, s), 2.52 (2H, s), 1.40 (9H, s), 1.09 (6H, brs).

Synthesis of Compound 46

According to the method for preparing compound 40, isovaleryl chloride was used in the preparation to yield compound 46 (33 mg, 47.8%), as a yellow solid. LC-MS (ESI): m/z=604.2 (M+H)$^+$. $^1$H NMR (400 MHz, CDCl$_3$): δ 8.71 (1H, d, J=2.0 Hz), 8.52 (1H, d, J=2.0 Hz), 7.71 (1H, s), 6.76 (1H, s), 4.04 (3H, s), 3.86 (4H, t, J=4.8 Hz), 3.76 (6H, t, J=4.4 Hz), 3.61 (4H, s), 3.02 (3H, s), 2.50 (4H, t, J=4.8 Hz), 1.20 (9H, s).

Synthesis of Compound 47

According to the method for preparing compound 40, isobutyryl chloride was used in the preparation to yield compound 47 (22 mg, 28%), as a yellow solid. LC-MS (ESI): m/z=590 (M+H)$^+$. $^1$H NMR (400 MHz, CDCl$_3$): δ 8.78 (d, J=2.0 Hz, 1H), 8.59 (d, J=2.0 Hz, 1H), 7.78 (s, 1H), 6.83 (s, 1H), 4.12 (s, 3H), 3.92-3.94 (m, 4H), 3.82-3.88 (m, 6H), 3.53-3.66 (m, 4H), 3.08 (s, 3H), 2.73-2.78 (m, 1H), 2.57 (br, 4H), 1.12 (d, J=6.8 Hz, 6H).

Synthetic Route of Compound 48

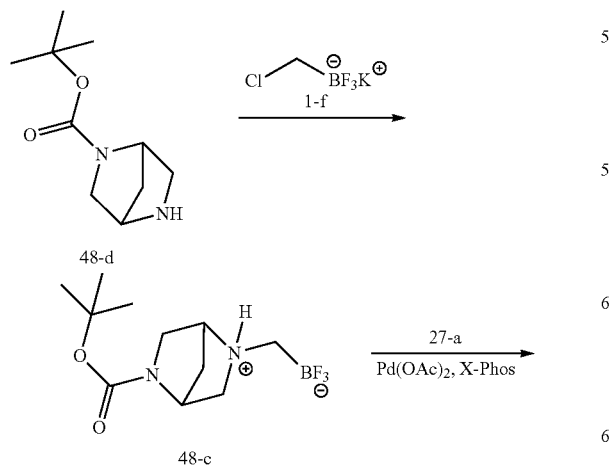

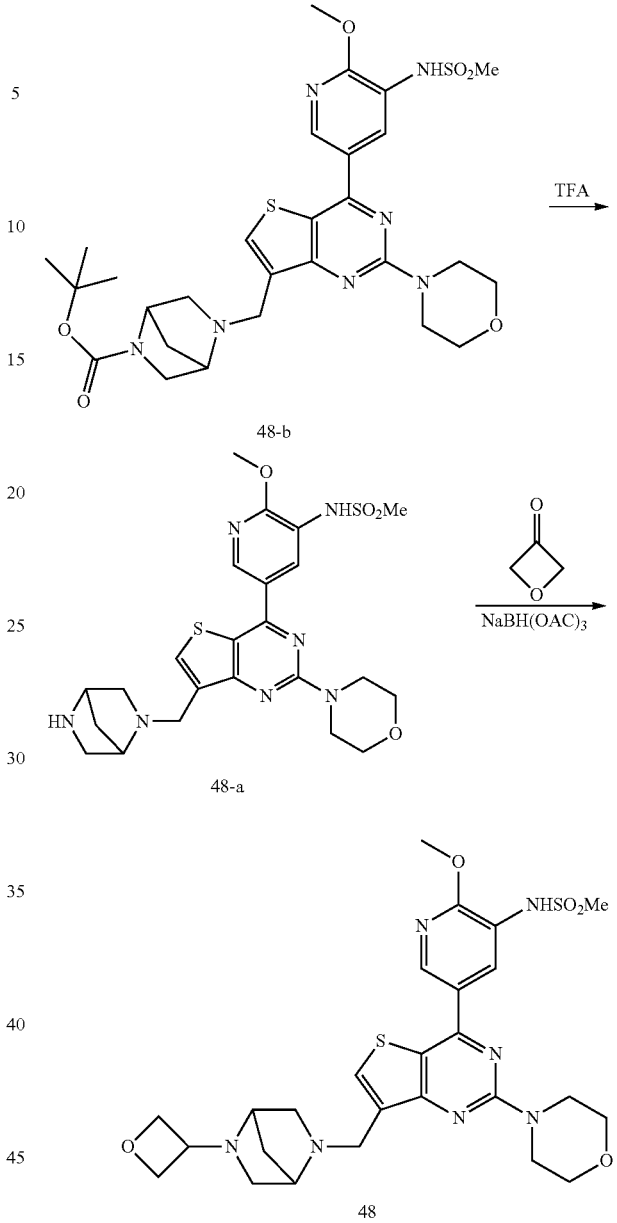

Synthesis of Compound 48-c

According to the method for preparing compound 43-b, compound 48-d was used in the preparation to yield compound 48-c (1.78 g, 99%), as a white solid. $^1$H NMR (400 MHz, DMSO-$d_6$): δ4.25 (s, 1H), 2.69 (t, J=12.2 Hz, 2H), 1.90 (d, J=5.0 Hz, 2H), 1.74 (d, J=13.3 Hz, 2H), 1.36-1.51 (m, 4H), 1.02 (s, 9H).

Synthesis of Compound 48-b

According to the method for preparing compound 52, compound 48-c was used in the preparation to yield compound 48-b (80 mg, 32%), as a yellow solid. LC-MS (ESI): m/z=631.8 (M+H)$^+$.

Synthesis of Compound 48-a

According to the method for preparing compound 29-a, compound 48-b was used in the preparation to yield compound 48-a (60 mg, 90%), as a yellow solid. LC-MS (ESI): m/z=531.8 (M+H)$^+$.

Synthesis of Compound 48

According to the method for preparing compound 29, compound 48-a was used in the preparation to yield compound 48 (20 mg, 36%). LC-MS (ESI): m/z=588 (M+H)$^+$. $^1$H NMR (400 MHz, CDCl$_3$) δ 8.78 (d, J=2.1 Hz, 1H), 8.59 (d, J=2.1 Hz, 1H), 7.80 (s, 1H), 4.58-4.77 (m, 3H), 4.57 (t, J=6.0 Hz, 1H), 4.12 (s, 3H), 4.05-3.96 (m, 2H), 3.96-3.89 (m, 5H), 3.89-3.71 (m, 5H), 3.46 (s, 1H), 3.29 (s, 1H), 3.08 (s, 3H), 3.06 (d, J=9.9 Hz, 1H), 2.79 (s, 1H), 2.68 (dd, J=9.7, 2.2 Hz, 1H), 2.02 (d, J=5.8 Hz, 1H), 1.82 (d, J=9.7 Hz, 1H), 1.71 (d, J=9.8 Hz, 1H).

Synthetic Route of Compound 49

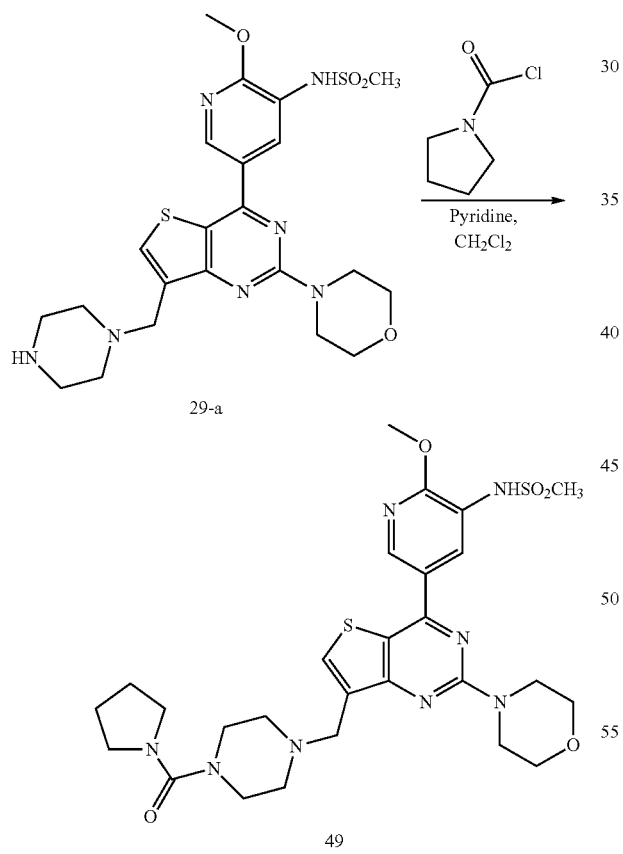

Synthesis of Compound 49

Compound 29-a (40 mg, 0.077 mmol), 1-pyrrolidinylcarbonyl chloride (15 mg, 0.013 mL, 0.115 mmol), pyridine (0.019 mL, 0.231 mmol) and dichloromethane (5 mL) were added into a reaction flask. The reaction mixture was stirred at normal temperature overnight, and then the liquid was concentrated under reduced pressure. The residue was purified by Prep-HPLC to obtain target compound 49 (20 mg, 42%), as a yellow solid. LC-MS (ESI): m/z=617.0 (M+H)$^+$. $^1$H NMR (400 MHz, CDCl$_3$): δ 8.78 (d, J=2.2 Hz, 1H), 8.58 (d, J=2.2 Hz, 1H), 7.82 (s, 1H), 4.12 (s, 3H), 3.96-3.91 (m, 4H), 3.87 (s, 2H), 3.86-3.81 (m, 4H), 3.35 (s, 7H), 3.09 (s, 3H), 2.65-2.54 (m, 4H), 2.01 (s, 2H), 1.81 (t, J=6.5 Hz, 4H).

Synthetic Route of Compound 50

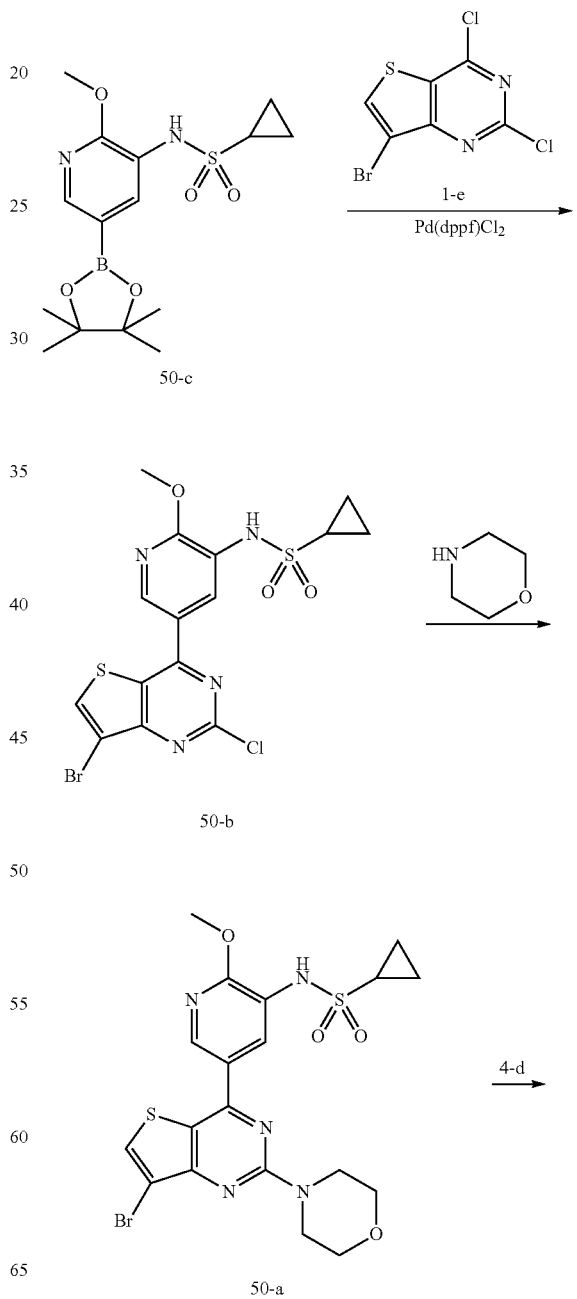

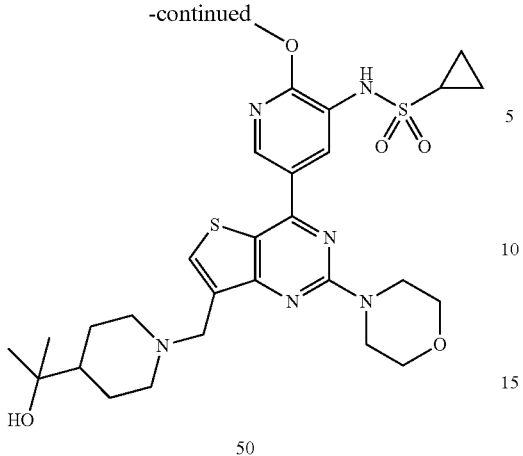

50

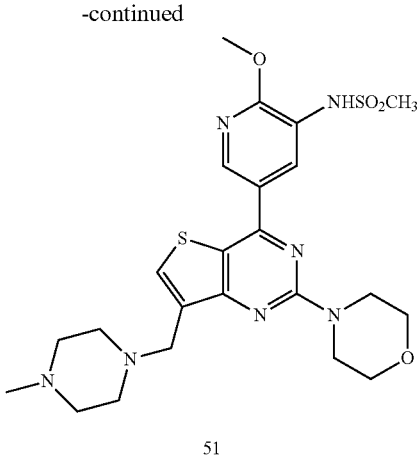

51

Synthesis of Compound 50-b

According to the method for preparing compound 27-b, compound 50-c (prepared according to the method disclosed in: WO 2012/037108 A1) was used in the preparation to yield compound 50-b (300 mg, 45%), as a yellow solid. LC-MS (ESI): m/z=476 (M+H)$^+$.

Synthesis of Compound 50-a

According to the method for preparing compound 27-a, compound 50-b was used in the preparation to yield compound 50-a (120 mg, 37%), as a yellow solid. LC-MS (ESI): m/z=526 (M+H)$^+$.

Synthesis of Compound 50

According to the method for preparing compound 35, compound 50-a was used in the preparation to yield compound 50 (20 mg, 28%), as a yellow solid. LC-MS (ESI): m/z=603 (M+H)$^+$. $^1$H NMR (400 MHz, CDCl$_3$): δ 8.77 (d, J=2.0 Hz, 1H), 8.61 (d, J=2.4 Hz, 1H), 7.77 (s, 1H), 4.11 (s, 3H), 3.93-3.95 (m, 4H), 3.82-3.85 (m, 6H), 3.10 (d, J=11.2 Hz, 2H), 2.50-2.60 (m, 1H), 2.07 (t, J=11.2 Hz, 2H), 1.74 (d, J=12.4 Hz, 2H), 1.25-1.50 (m, 5H), 1.18 (s, 6H), 0.99-1.02 (m, 2H).

Synthetic Route of Compound 51

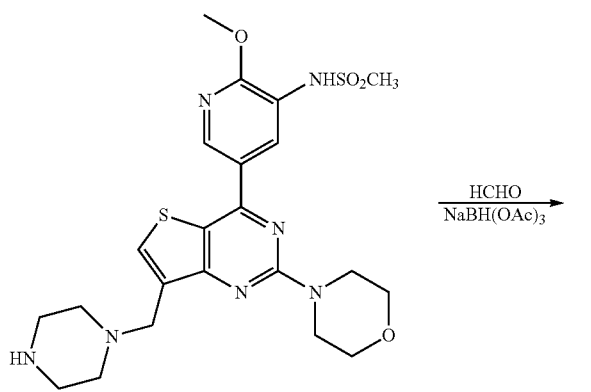

29-a

Synthesis of Compound 51

Compound 29-a (38 mg, 0.073 mmol), 37% formaldehyde (3 mL, 1.39 mmol) were dissolved in dichloromethane (5 mL), and a drop of acetic acid and sodium triacetoxyborohydride (295 mg, 1.39 mmol) were added. The reaction mixture was stirred at room temperature overnight, diluted with dichloromethane (50 mL), and washed with water (10 mL). The organic layer was separated, dried over anhydrous sodium sulfate, and concentrated under reduced pressure. The residue was purified by Prep-HPLC to obtain target compound 51 (28 mg, 24%), as a yellow solid. LC-MS (ESI): m/z 534 (M+H)$^+$. $^1$H-NMR (400 MHz, CDCl$_3$): δ 8.78 (d, J=2.0 Hz, 1H), 8.58 (d, J=2.0 Hz, 1H), 7.79 (s, 1H), 4.12 (s, 3H), 3.92-3.95 (m, 4H), 3.82-3.85 (m, 6H), 3.08 (s, 3H), 2.63 (br, 4H), 2.54 (br, 4H), 2.33 (s, 3H).

Synthetic Route of Compound 53

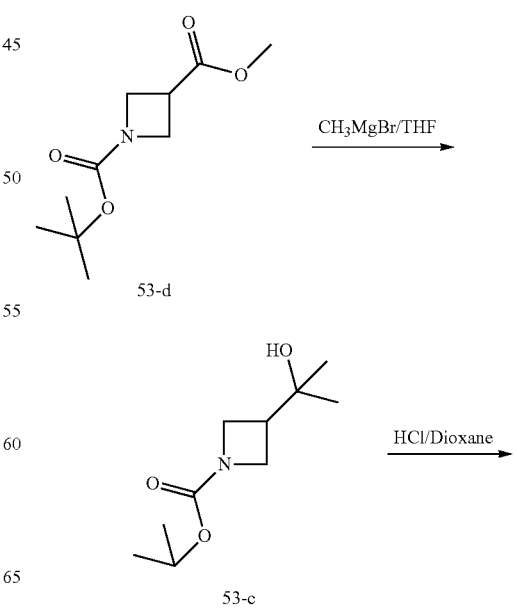

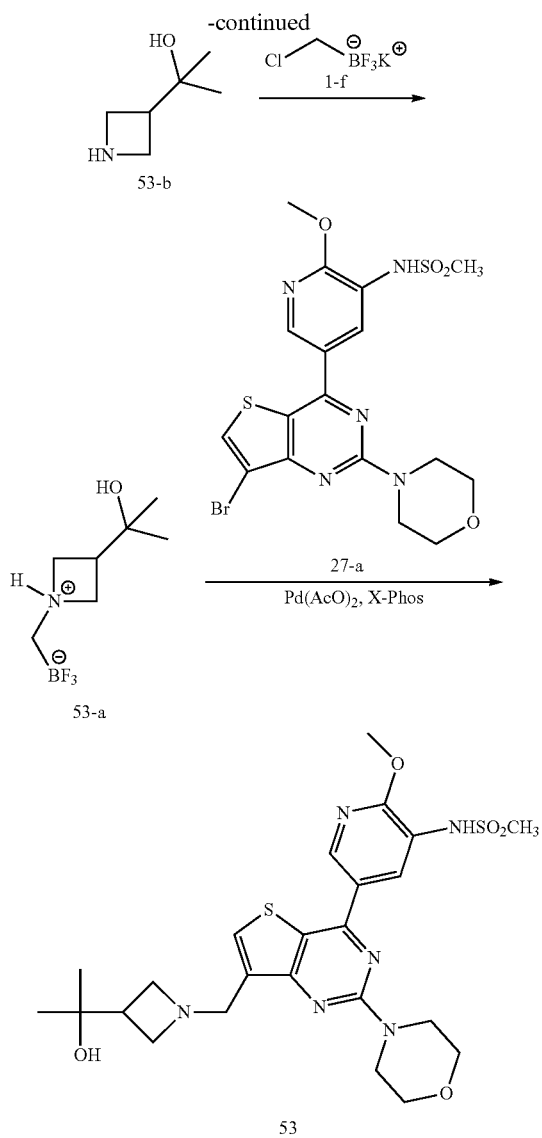

Synthesis of Compound 53-c

Compound 53-d (3.23 g, 15 mmol) and dry THF (60 mL) were added into a 100 mL three-necked flask. The mixture was cooled to −78° C., and a solution of methylmagnesium bromide (35 mmol) in tetrahydrofuran was added dropwise, and then stirred overnight. The reaction mixture was quenched with water, and extracted with ethyl acetate (3×40 mL). The organic phases were combined, dried over anhydrous sodium sulfate, and concentrated under reduced pressure to yield a colorless solid 53-c (3.0 g, 93%). LC-MS (ESI): m/z=238 (M+Na)$^+$.

Synthesis of Compound 53-b

A mixture of compound 53-c (3.0 g, 14 mmol) and HCl dioxane solution (4 M, 25 mL) was stirred at room temperature for 5 hrs. The reaction mixture was filtered, and the filter cake was washed with dioxane, and dried under vacuum to yield compound 53-b (1.7 g, 81%), as a white solid of HCl salt. LC-MS (ESI): m/z=116.1 (M+H)$^+$.

Synthesis of Compound 53-a

Compound 53-b HCl salt (300 mg, 2.0 mmol), sodium hydroxide (100 mg, 2.5 mmol), acetonitrile (15 mL) and water (3 mL) were added into a 50 mL round-bottomed flask, and stirred at room temperature overnight. The reaction mixture was concentrated under reduced pressure. A mixture of the residue, compound 1-f (310 mg, 2.0 mmol), cyclopentyl methyl ether (CPME, 2.0 mL) and tert-amyl alcohol (0.7 mL) was sealed and heated to 110° C., and stirred overnight. The reaction mixture was concentrated under reduced pressure, and the residue was refluxed in 25 mL acetone for 1 hr, and filtered. The filtrate was concentrated under reduced pressure to yield compound 53-a (300 mg, 76%).

Synthesis of Compound 53

Compound 27-a (100 mg, 0.2 mmol), 53-a (200 mg, 1.0 mmol), palladium acetate (4.5 mg, 0.02 mmol), X-Phos (9.5 mg, 0.02 mmol), cesium carbonate (163 mg, 0.5 mmol), THF (20 mL) and water (2 mL) were added into a 50 mL round-bottomed flask, and reacted under nitrogen atmosphere at 80° C. overnight. The reaction solution was filtered, and concentrated under reduced pressure. The residue was purified by silica gel column chromatography (elution system: petroleum ether/ethyl acetate=1/1~0/1, followed by dichloromethane/methanol=10/1), to yield compound 53 (18 mg, 15%), as a yellow solid. LC-MS (ESI): m/z=549.3 (M+H)$^+$. $^1$H NMR (400 MHz, CDCl$_3$): δ8.74 (d, J=2.0 Hz, 1H), 8.60 (s, 1H), 8.55 (d, J=2.0 Hz, 1H), 4.21 (s, 2H), 4.17-4.16 (m, 4H), 4.13 (s, 3H), 3.97 (t, J=4.6 Hz, 4H), 3.85 (t, J=4.6 Hz, 4H), 3.09 (s, 3H), 2.92-2.83 (m, 1H), 1.15 (s, 6H).

Synthetic Route of Compound 54

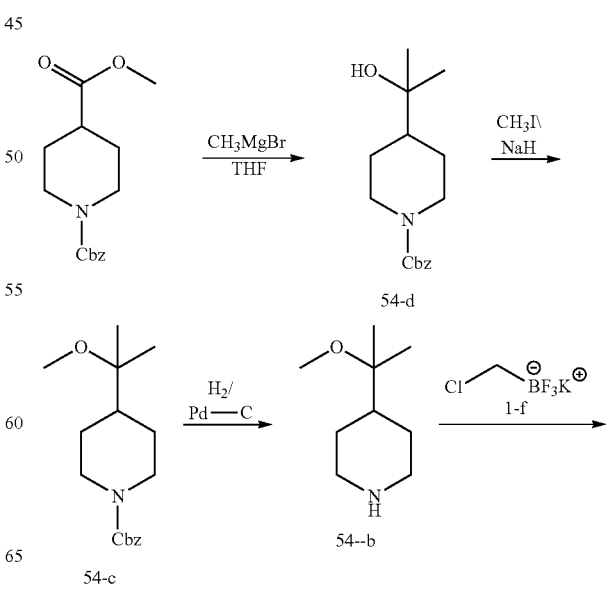

147

-continued

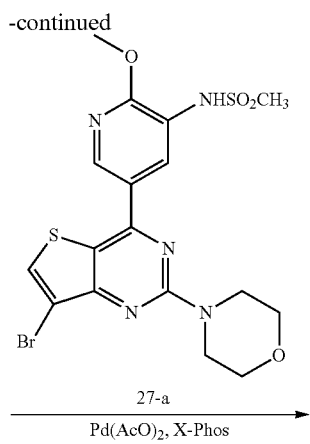

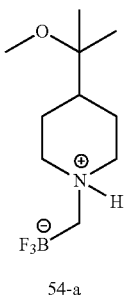

54-a

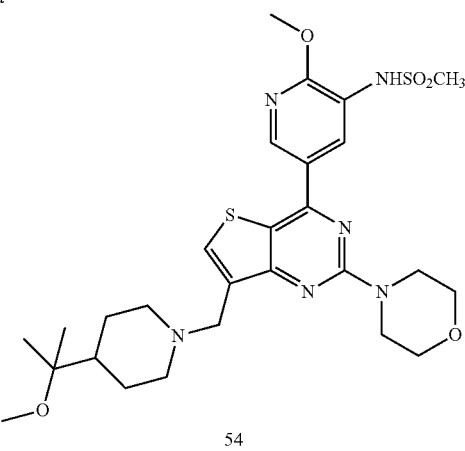

54

Synthesis of Compound 54-d

A solution of methyl N-Cbz-4-piperidinecarboxylate (3.86 g, 13.935 mmol) in tetrahydrofuran (30 mL) was cooled to −78° C., followed by slow dropwise addition of methylmagnesium bromide Grignard reagent (14 mL, 3.0 M in THF), and stirred for 2 hrs, and then naturally warmed to room temperature and continued stirring for 1 hr. The reaction solution was quenched with 1 M HCl (100 mL), and the resultant suspension was extracted with ethyl acetate (3×100 mL). The organic phases were combined, washed with saturated brine, dried over anhydrous sodium sulfate, and concentrated under reduced pressure to yield compound 54-d (3.56 g, 92%). LC-MS (ESI): m/z=278.1 (M+H)+.

Synthesis of Compound 54-c

NaH (0.77 g, 19.278 mmol) and methyl iodide (2.7 g, 19.278 mmol) were added batchwise into a solution of compound 54-d (3.56 g, 12.852 mmol) in tetrahydrofuran (20 mL), and then heated to 50° C., stirred to react for 1 day. The reaction solution was quenched with saturated ammonium chloride aqueous solution (50 mL), and extracted with ethyl acetate (3×40 mL). The organic phases were combined, washed with saturated brine, dried over anhydrous sodium sulfate, and concentrated under reduced pressure.

148

The residue was separated and purified by silica gel column chromatography (elution system: dichloromethane/methanol=50/1), to yield compound 54-c (2.0 g, 53%). LC-MS (ESI): m/z=292.2 (M+H)+.

Synthesis of Compound 54-b

A suspension of compound 54-c (1.0 g, 3.44 mmol) and 10% Pd-C (150 mg) in methanol (15 mL) was stirred under hydrogen atmosphere at room temperature for one night, and then filtered. The filtrate was concentrated under reduced pressure to yield product 54-b (0.54 g, 100%). LC-MS (ESI): m/z=158.3 (M+H)+.

Synthesis of Compound 54-a

A suspension (10 mL) of compound 54-b (0.54 g, 3.44 mmol) and compound 1-f (0.71 g, 4.586 mmol) in methoxycyclopentyl ether and tert-amyl alcohol (60 mL, 2/1) was heated under reflux for 12 hrs, and then concentrated under reduced pressure, and to the residue was added tetrahydrofuran, and filtered off insolubles. The filtrate was diluted with diethyl ether, and the precipitated solid was product 54-a (0.5 g, 52%).

Synthesis of Compound 54

Compound 27-a (80 mg, 0.147 mmol), compound 54-a (65 mg, 0.295 mmol), Pd (OAc)$_2$ (5 mg), cesium carbonate (145 mg, 0.444 mmol), X-Phos (10 mg, 0.021 mmol), tetrahydrofuran (2 mL) and water (0.3 mL) were added into a microwave tube, and the mixture was stirred to react under nitrogen atmosphere at 90° C. with microwave for 2 hrs. The reaction mixture was filtered through celite, and the filtrate was concentrated under reduced pressure. The residue was purified by silica gel preparation plate chromatography (developing system: dichloromethane/methanol=20/1) to yield compound 54 (10 mg, 11%). LC-MS (ESI): m/z=591.0 (M+H)+. $^1$H NMR (400 MHz, CDCl$_3$) δ 8.71 (d, J=2.0 Hz, 1H), 8.52 (d, J=2.0 Hz, 1H), 7.71 (s, 1H), 4.05 (s, 3H), 3.75-3.89 (m, 10H), 3.10 (s, 3H), 3.03 (d, J=11.2 Hz, 2H), 3.02 (s, 3H), 2.00 (t, J=10.8 Hz, 2H), 1.60 (d, J=8.4 Hz, 2H), 1.35-1.37 (m, 3H), 1.03 (s, 6H).

Synthetic Route of Compound 55

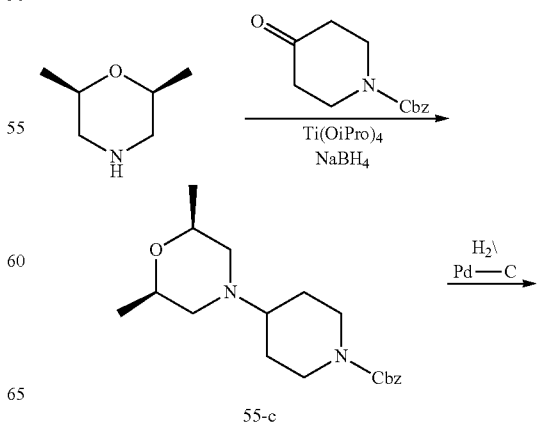

55-c

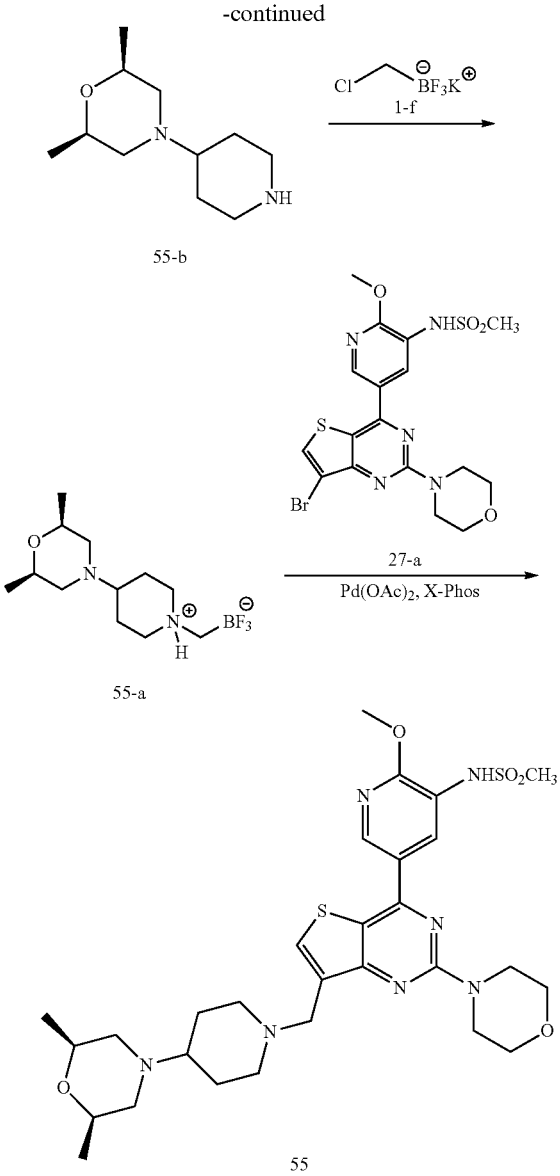

The mixture was filtered, and the filtrate was concentrated under reduced pressure to yield compound 55-b (1.0 g, 100%). LC-MS (ESI): m/z=199.2 (M+H)$^+$.

Synthesis of Compound 55-a

A suspension (10 mL) of compound 55-b (1.0 g, 5.051 mmol), compound 1-f (0.58 g, 3.718 mmol) in methoxycyclopentyl ether and tert-amyl alcohol (60 mL, 2/1) was heated under reflux for 12 hrs, and concentrated under reduced pressure, and to the residue was added acetone (50 mL) and heated and stirred under reflux, and filtered while hot. The resultant solid was product 55-a (1.1 g, 52%).

Synthesis of Compound 55

Compound 27-a (80 mg, 0.147 mmol), compound 55-a (115 mg, 0.444 mmol), Pd (OAc)$_2$ (5 mg), cesium carbonate (145 mg, 0.444 mmol), X-Phos (10 mg, 0.021 mmol), tetrahydrofuran (2 mL) and water (0.3 mL) were added into a microwave tube, and the mixture was stirred to react under nitrogen atmosphere at 90° C. with microwave for 2 hrs. The reaction mixture was filtered through celite, and the filtrate was concentrated under reduced pressure. The residue was purified by silica gel preparation plate chromatography (developing system: dichloromethane/methanol=20/1) to yield compound 55 (21 mg, 21%). LC-MS (ESI): m/z=632.0 (M+H)$^+$. $^1$H NMR (400 MHz, CDCl$_3$): δ 8.71 (d, J=2.4 Hz, 1H), 8.52 (d, J=2.4 Hz, 1H), 7.69 (s, 1H), 4.05 (s, 3H), 3.74-3.88 (m, 10H), 3.55-3.63 (m, 2H), 3.02 (s, 3H), 3.00 (d, J=11.2 Hz, 2H), 2.67 (d, J=10.8 Hz, 2H), 2.01-2.18 (m, 3H), 1.84 (t, J=10.8 Hz, 2H), 1.74 (d, J=11.6 Hz, 2H), 1.49-1.57 (m, 2H), 1.08 (d, J=6.0 Hz, 6H).

Synthesis of Compound 56

According to the method for preparing compound 43, acetaldehyde was used in the preparation to yield compound 56 (15 mg, 41%), as a yellow solid. LC-MS (ESI): m/z 576.0 (M+H)$^+$. $^1$H NMR (400 MHz, CDCl$_3$) δ 8.78 (d, J=2.0 Hz, 1H), 8.58 (d, J=2.0 Hz, 1H), 7.77 (s, 1H), 4.12 (s, 3H), 3.92-3.94 (m, 4H), 3.82-3.84 (m, 6H), 3.08 (s, 3H), 3.05-3.07 (m, 2H), 2.52-2.54 (m, 2H), 2.26 (s, 3H), 2.08-2.20 (m, 2H), 1.52-1.77 (m, 5H), 1.04 (t, J=7.0 Hz, 3H).

Synthesis of Compound 55-c

Titanium tetraisopropanolate (5.68 g, 20.0 mmol) was added into a solution of 2, 6-dimethylmorpholine (1.15 g, 10.0 mmol) and N-Cbz-piperidin-4-one (2.34 g, 10.0 mmol) in anhydrous ethanol (15 mL). The reaction mixture was stirred at room temperature overnight, followed by slow addition of sodium borohydride (0.42 g, 11.0 mmol), and then continually stirred for 2 hrs. The insolubles were removed by filtration, and the filtrate was concentrated under reduced pressure. The residue was separated and purified by silica gel column chromatography to yield compound 55-c (2.49 g, 75%). LC-MS (ESI): m/z=333.3 (M+H)$^+$.

Synthesis of Compound 55-b

A suspension of compound 55-c (1.77 g, 5.331 mmol) and 10% Pd-C (180 mg) in methanol (15 mL) was stirred under hydrogen atmosphere at room temperature for one night.

Synthetic Route of Compound 57

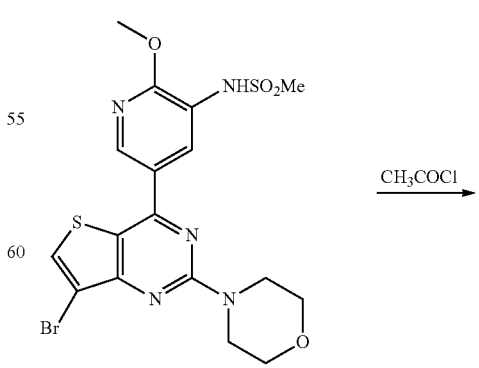

-continued

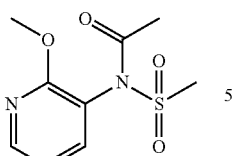

57-b

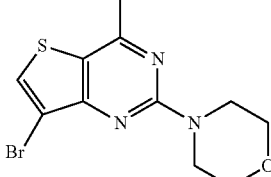

57-e

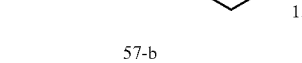

57-d

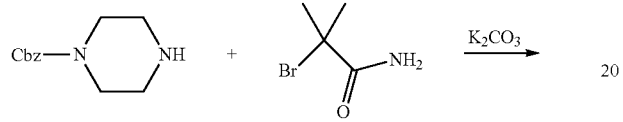

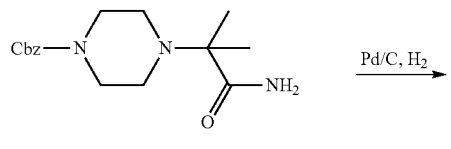

57-c

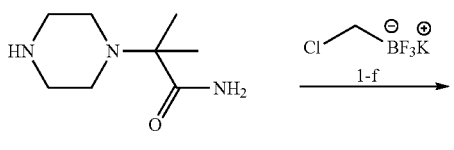

57-b

-continued

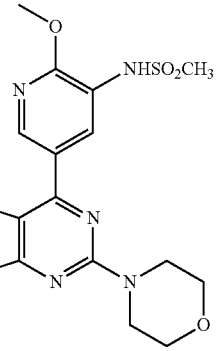

57

Synthesis of Compound 57-b

Triethylamine (0.25 mL, 1.79 mmol) and acetyl chloride (0.085 mL, 1.19 mmol) were sequentially added into a solution of compound 27-a (300 mg, 0.6 mmol) in dichloromethane (10 mL). The reaction solution was stirred at normal temperature overnight, and then diluted with dichloromethane. The organic layer was separated out, and sequentially washed with sodium bicarbonate aqueous solution and saturated sodium chloride aqueous solution, dried over anhydrous sodium sulfate, and concentrated under reduced pressure, to obtain compound 57-b (320 mg, 98%). LC-MS (ESI): m/z=543 (M+H)$^+$.

Synthesis of Compound 57-e

A mixture of 1-Cbz piperazine (1 g, 4.55 mmol), 2-bromo-2-methylpropionamide (751 mg, 4.55 mmol), potassium carbonate (942 mg, 6.83 mmol) and acetonitrile (10 mL) was stirred at 80° C. overnight. The reaction mixture was filtered, and the filtrate was concentrated under reduced pressure. The residue was purified by silica gel column chromatography to obtain 57-e (1.05 g, 76%). LC-MS (ESI): m/z 306.3 (M+H)$^+$.

Synthesis of Compound 57-d

A suspension of compound 57-e (1.05 g, 3.44 mmol) and 10% Pd-C (150 mg) in ethanol (15 mL) was stirred under hydrogen atmosphere at room temperature overnight. The mixture was filtered, and the filtrate was concentrated under reduced pressure to yield compound 57-d (1.0 g, 100%). LC-MS (ESI): m/z=172 (M+H)$^+$.

Synthesis of Compound 57-c

According to the method for preparing compound 4-d, compound 57-d was used in the preparation to yield compound 57-c (520 mg, 90%), as a white solid. $^1$H NMR (400 MHz, DMSO-d$_6$): δ 8.48 (1H, brs), 7.29 (1H, s), 7.01 (1H, s), 3.23-3.33 (2H, m), 2.95 (2H, q, J=10.0 Hz), 2.72 (2H, d, J=12.8 Hz), 2.37-2.50 (2H, m), 1.92 (2H, t, J=4.8 Hz), 1.06 (6H, s).

Synthesis of Compound 57-a

Compound 57-c (93 mg, 0.369 mmol), compound 57-b (100 mg, 0.184 mmol), cesium carbonate (177 mg, 0.54 mmol), X-Phos (18 mg, 0.0369 mmol), palladium acetate (4 mg, 0.0184 mmol), tetrahydrofuran (1 mL) and water (0.1 mL) were added into a microwave tube, and the mixture was stirred under nitrogen atmosphere at 80° C. overnight. The reaction solution was cooled to room temperature, and filtered. The filtrate was concentrated under reduced pressure to yield compound 57-a (110 mg, 92.4%), and crude product was directly used in the next reaction without further purification. LC-MS (ESI): m/z=649.3 (M+H)+.

Synthesis of Compound 57

A mixture of compound 57-a (110 mg, 0.170 mmol), methanol (4.0 mL) and 10% potassium carbonate aqueous solution (2.0 mL) was stirred at room temperature overnight. The reaction solution was diluted with water (20 mL), and the pH value of the solution was adjusted with 1 N HCl to 7-8, and then extracted with dichloromethane (2×20 mL). The organic phases were combined, dried over sodium sulfate, and concentrated under reduced pressure. The residue was purified by Prep-HPLC to obtain target compound 57 (25 mg, 24.4%). LC-MS (ESI): m/z=605.3 (M+H)+. $^1$H NMR (400 MHz, CDCl$_3$): δ 8.71 (1H, d, J=2.0 Hz), 8.52 (1H, d, J=2.0 Hz), 7.69 (1H, s), 7.05 (1H, d, J=5.2 Hz), 5.37 (1H, d, J=4.8 Hz), 4.05 (3H, s), 3.86-3.88 (4H, m), 3.76-3.78 (6H, m), 3.02 (3H, s), 2.51 (8H, s), 1.14 (6H, s).

Synthesis of Compound 58

According to the method for preparing compound 43, acetone was used in the preparation to yield compound 58 (10 mg, 17%), as a yellow solid. LC-MS (ESI): m/z 590 (M+H)+. $^1$H NMR (400 MHz, CDCl$_3$) δ 8.78 (d, J=2.0 Hz, 1H), 8.58 (d, J=2.0 Hz, 1H), 7.77 (s, 1H), 4.12 (s, 3H), 3.92-3.95 (m, 4H), 3.81-3.85 (m, 6H), 3.08 (s, 3H), 3.04-3.06 (m, 3H), 2.22 (s, 3H), 2.09-2.15 (m, 2H), 1.73-1.79 (m, 2H), 1.64-1.69 (m, 2H), 1.03 (d, J=7.0 Hz, 6H).

Synthetic Route of Compound 59

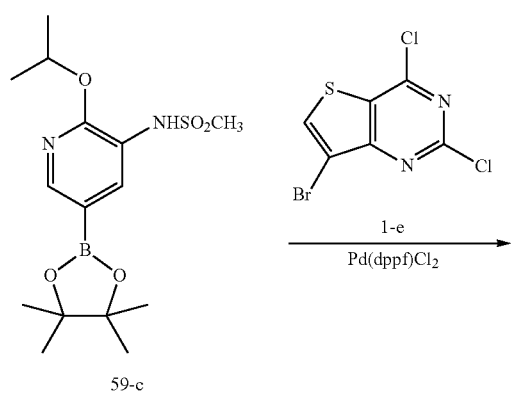

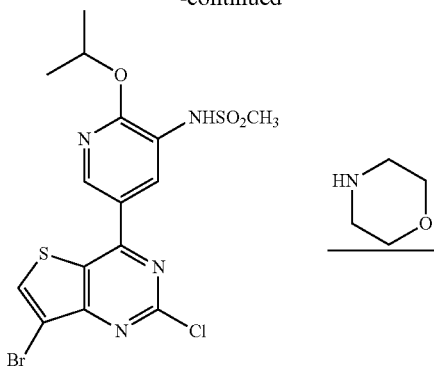

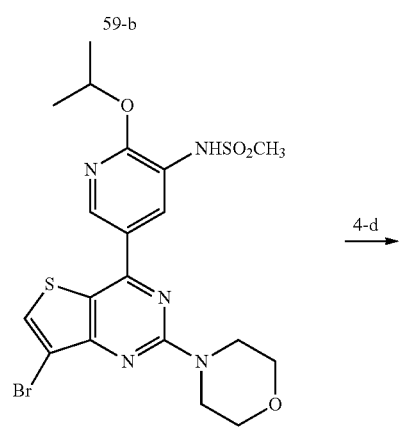

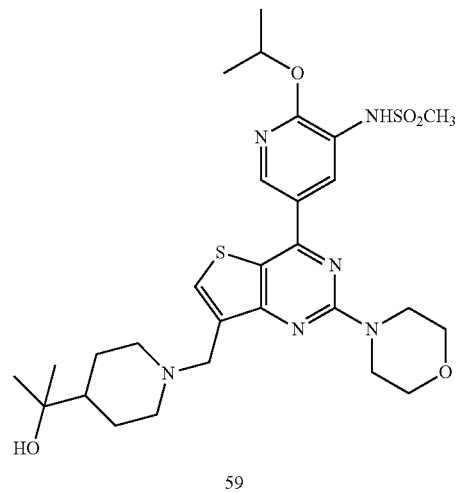

Synthesis of Compound 59-b

According to the method for preparing compound 27-b, compound 59-c (prepared according to the method disclosed in: WO 2012/037108 A1) was used in the preparation to yield compound 59-b (100 mg, 15%), as a yellow solid. LC-MS (ESI): m/z 478 (M+H)+.

Synthesis of Compound 59-a

According to the method for preparing compound 27-a, compound 59-b was used in the preparation to yield compound 59-a (100 mg, 91%), as a yellow solid. LC-MS (ESI): m/z 528 (M+H)+.

Synthesis of Compound 59

According to the method for preparing compound 35, compound 59-a was used in the preparation to yield compound 59 (8 mg, 8%), as a yellow solid. LC-MS (ESI): m/z 605 (M+H)+. 1H-NMR (400 MHz, CDCl3): δ 8.77 (d, J=2.0 Hz, 1H), 8.57 (d, J=2.0 Hz, 1H), 7.76 (s, 1H), 5.50-5.60 (m, 1H), 3.92-3.95 (m, 4H), 3.81-3.84 (m, 6H), 3.07-3.11 (m, 5H), 2.07 (t, J=11.2 Hz, 2H), 1.74 (d, J=12.0 Hz, 3H), 1.42-1.48 (m, 8H), 1.17 (s, 6H).

Synthetic Route of Compound 60

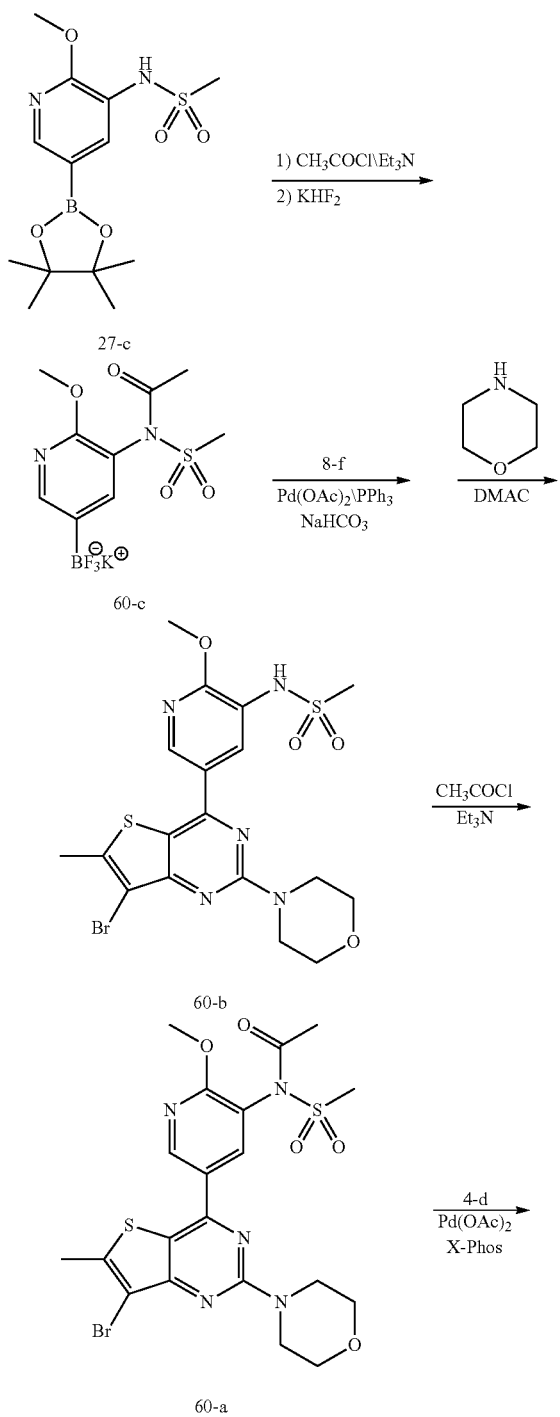

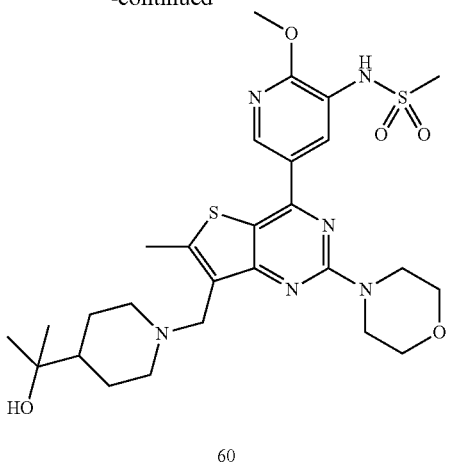

60

Synthesis of Compound 60-c

Acetyl chloride (0.62 g, 7.93 mmol) was added dropwise into a solution of compound 27-c (1.3 g, 3.96 mmol) and triethylamine (5 mL) in dichloromethane (15 mL). The reaction mixture was stirred at room temperature for 10 minutes, and then diluted with dichloromethane. The organic layer was separated out, washed with saturated brine, and concentrated under reduced pressure. The residue was dissolved in methanol (20 mL), and then to the methanol solution was added potassium bifluoride (0.78 g, 10.06 mmol) and 1 mL water. The mixture was heated to 60° C., and then stirred for an hour. The reaction mixture was cooled, and filtered, and the resultant filter cake was washed with dichloromethane several times. The filter cake was dried to obtain compound 60-c (1.99 g), and the crude was directly used in the next step without further purification. LC-MS (ESI): m/z=293.0 (M+H)+.

Synthesis of Compound 60-b

Compound 60-c (1.5 g), compound 8-f (0.8 g, 2.68 mmol), sodium bicarbonate (0.9 g, 10.72 mmol), triphenylphosphine (0.14 g, 0.536 mmol), palladium acetate (62 mg, 0.277 mmol), tetrahydrofuran (9 mL) and water (1 mL) were added into a microwave tube. The mixture was stirred to react under nitrogen atmosphere at 90° C. with microwave for 2 hrs. The reaction mixture was filtered through a short silica gel column, and eluted with petroleum ether/ethyl acetate (1:1), the filtrate was concentrated under reduced pressure. A mixture of the residue, morpholine (0.32 g, 3.678 mmol) and N,N-dimethylacetamide (2 mL) was stirred to react at 90° C. for half an hour. The reaction mixture was cooled, and diluted with dichloromethane. The organic layer was separated out, washed with saturated brine, dried over anhydrous sodium sulfate, and concentrated under reduced pressure. The residue was separated and purified by silica gel column chromatography (elution system: petroleum ether/ethyl acetate=1:1) to yield compound 60-b (0.65 g, 47%). LC-MS (ESI): m/z=513.8 (M+H)+.

Synthesis of Compound 60-a

Acetyl chloride (0.20 g, 2.534 mmol) was added dropwise into a solution of compound 60-b (0.65 g, 1.267 mmol) and triethylamine (1 mL) in dichloromethane (20 mL). The reaction solution was stirred at room temperature for 10 minutes, then diluted with dichloromethane. The organic layer was separated out, washed with saturated brine, dried over anhydrous sodium sulfate, and concentrated under reduced pressure to yield compound 60-a (0.69 g, 98%). LC-MS (ESI): m/z=555.9 (M+H)$^+$.

Synthesis of Compound 60

Compound 60-a (100 mg, 0.180 mmol), compound 4-d (76 mg, 0.289 mmol), Pd (OAc)$_2$ (4 mg, 0.180 mmol), cesium carbonate (176 mg, 0.540 mmol), X-Phos (17 mg, 0.036 mmol), tetrahydrofuran (5 mL) and water (0.5 mL) were added to a microwave tube. The mixture was stirred to react under nitrogen atmosphere at 90° C. with microwave for 2 hrs. The reaction mixture was filtered through celite, and concentrated under reduced pressure. The residue was separated and purified by silica gel preparation plate chromatography (developing system: dichloromethane/methanol=20/1) to yield compound 60 (30 mg, 28%). LC-MS (ESI): m/z=591.3 (M+H)$^+$. $^1$H NMR (400 MHz, CDCl$_3$): δ 8.68 (d, J=2.0 Hz, 1H), 8.49 (d, J=2.0 Hz, 1H), 4.04 (s, 3H), 3.75-3.86 (m, 8H), 3.69 (s, 2H), 3.01 (s, 3H), 2.95 (d, J=10.8 Hz, 2H), 2.58 (s, 3H), 2.00 (t, J=10.8 Hz, 2H), 1.63 (d, J=12.0 Hz, 2H), 1.24-1.34 (m, 2H), 1.18-1.20 (m, 1H), 1.09 (s, 6H).

Synthetic Route of Compound 61

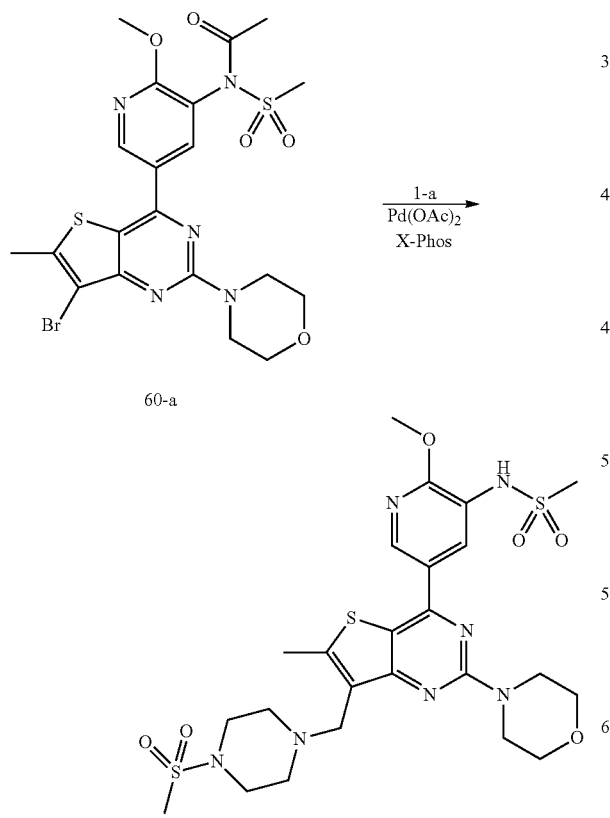

Synthesis of Compound 61

According to the method for preparing compound 60, compound 1-a was used in the preparation to yield compound 61 (10 mg, 30%) as a yellow solid. LC-MS (ESI): m/z 611.9 (M+H)$^+$. $^1$H-NMR (400 MHz, CDCl$_3$): δ δ 8.68 (d, J=2.4 Hz, 1H), 8.48 (d, J=2.4 Hz, 1H), 4.04 (s, 3H), 3.75-3.85 (m, 8H), 3.72 (s, 2H), 3.12-3.15 (m, 4H), 3.01 (s, 3H), 2.69 (s, 3H), 2.55-2.57 (m, 7H).

Synthetic Route of Compound 62

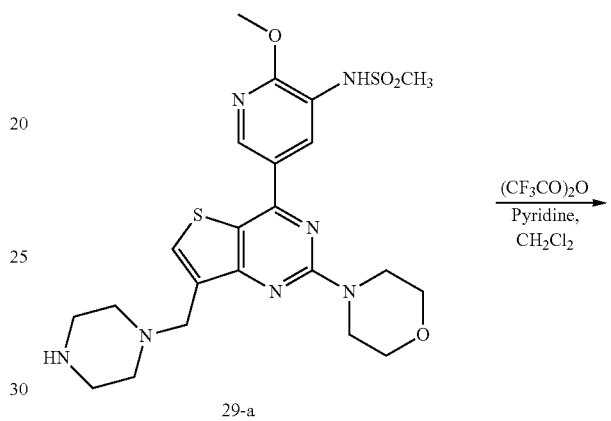

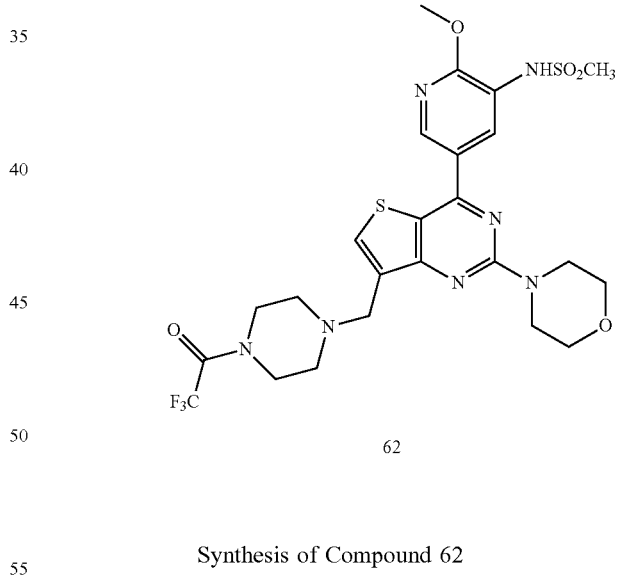

Synthesis of Compound 62

Compound 29-a (80 mg, 0.154 mmol), trifluoroacetyl anhydride (0.024 mL, 0.169 mmol), pyridine (0.062 mL, 0.77 mmol) and dichloromethane (5 mL) were added into a reaction flask. The mixture was stirred at normal temperature overnight, and concentrated under reduced pressure. The residue was purified by Prep-HPLC to obtain target compound 62 (60 mg, 63%), as a yellow solid. LC-MS (ESI): m/z=616.0 (M+H)$^+$. $^1$H-NMR (400 MHz, CD$_3$OD): δ 8.66 (d, J=2.1 Hz, 1H), 8.45 (d, J=2.1 Hz, 1H), 8.37 (s, 1H), 4.53 (s, 2H), 4.02 (s, 3H), 3.93-3.77 (m, 8H), 3.73-3.69 (m, 4H), 3.41 (s, 4H), 2.95 (s, 3H).

Synthetic Route of Compound 63

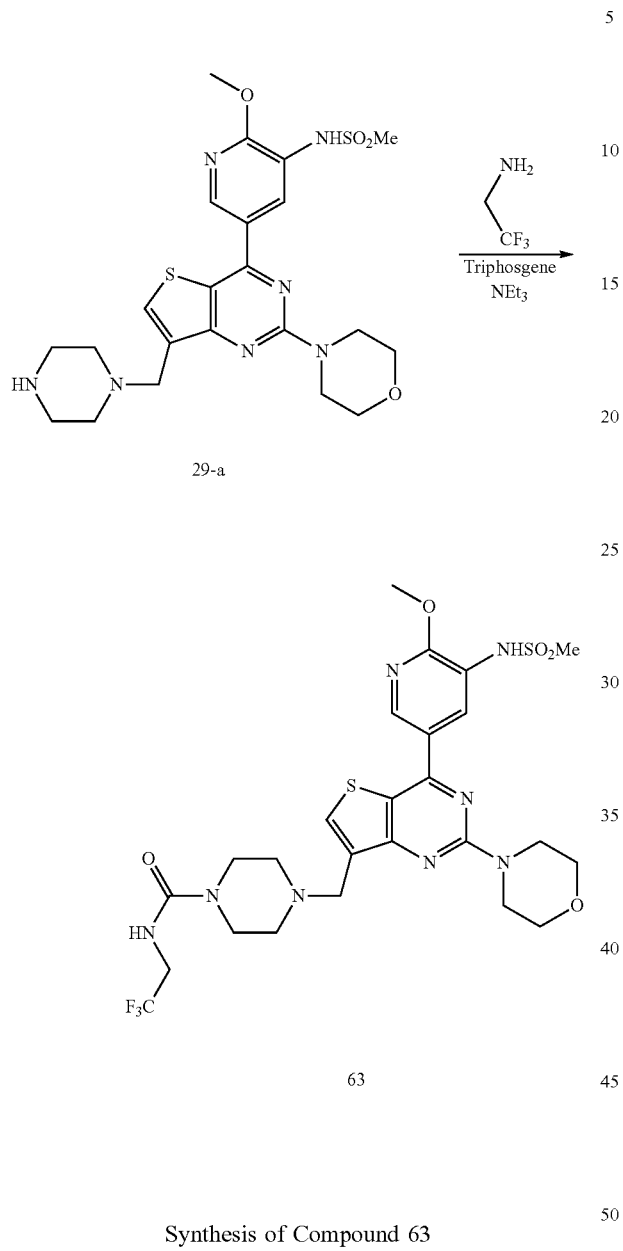

Synthetic Route of Compound 64

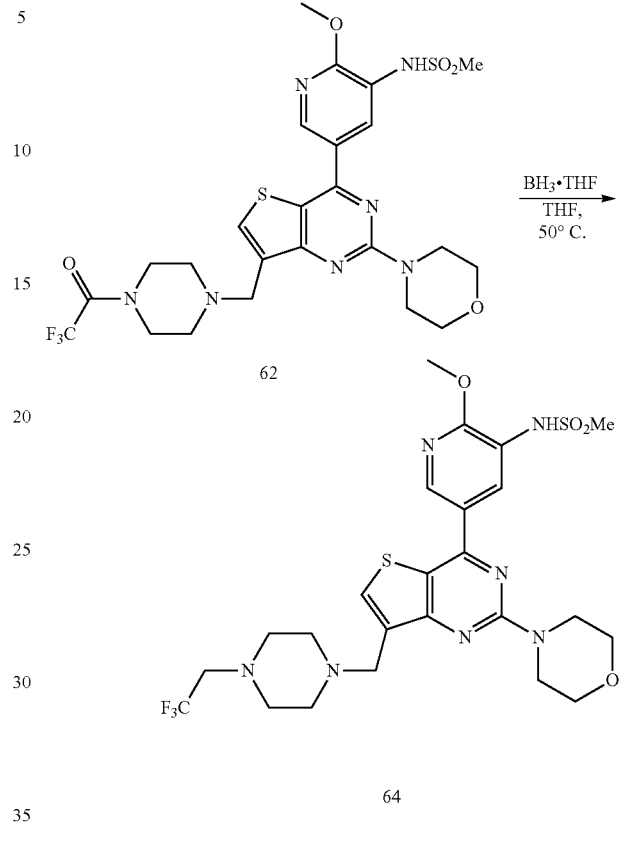

Synthesis of Compound 64

A mixture of compound 62 (20 mg, 0.032 mmol), 1 M borane-tetrahydrofuran solution (0.324 mL, 0.324 mmol) and tetrahydrofuran (3 mL) was stirred to react at 50° C. overnight, and concentrated under reduced pressure. The residue was purified by Prep-HPLC to obtain target compound 64 (6 mg, 30%), as a yellow solid. LC-MS (ESI): m/z=602.2 (M+H)$^+$. $^1$H NMR (400 MHz, CD$_3$OD): δ 8.61 (d, J=2.1 Hz, 1H), 8.52 (d, J=2.2 Hz, 1H), 8.04 (s, 1H), 4.08 (s, 3H), 3.99-3.93 (m, 4H), 3.88 (s, 2H), 3.86-3.80 (m, 4H), 3.07 (d, J=9.8 Hz, 2H), 3.01 (s, 3H), 2.74 (d, J=4.0 Hz, 4H), 2.66 (s, 4H).

Synthesis of Compound 63

Tetrahydrofuran (4 mL), triphosgene (52 mg, 0.173 mmol), 2, 2, 2-trifluoroethylamine (0.041 mL, 0.52 mmol) and triethylamine (0.072 mL, 0.52 mmol) were added into a reaction flask cooled with an ice-water bath. The mixture was warmed to room temperature and stirred for 1 hr, and then compound 29-a (30 mg, 0.058 mmol) was added. The reaction solution was stirred at room temperature overnight, and concentrated under reduced pressure to obtain compound 63 (15 mg, 41%). LC-MS (ESI): m/z=644.9 (M+H)$^+$. $^1$H NMR (400 MHz, CD$_3$OD): δ 8.79 (d, J=2.2 Hz, 1H), 8.60 (d, J=2.2 Hz, 1H), 8.06 (s, 1H), 4.13 (s, 3H), 3.99-3.91 (m, 4H), 3.91-3.78 (m, 8H), 3.54-3.44 (m, 4H), 3.07 (s, 3H), 2.65-2.53 (m, 4H).

Synthetic Route of Compound 65

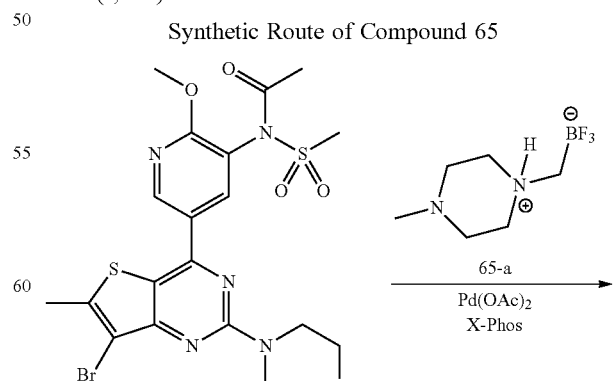

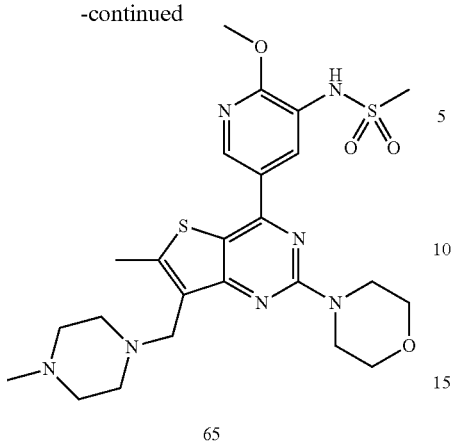

65

Synthesis of Compound 65

According to the method for preparing compound 60, compound 65-a (prepared according to the method disclosed in reference: J. Org. Chem. 2011, 76, 2762-2769) was used in the preparation to yield compound 65 (33 mg, 33%), as a yellow solid. LC-MS (ESI): m/z 548.2 (M+H)$^+$. $^1$H NMR (400 MHz, CDCl$_3$): δ 8.67 (d, J=2.0 Hz, 1H), 8.48 (d, J=2.0 Hz, 1H), 4.04 (s, 3H), 3.74-3.85 (m, 8H), 3.71 (s, 2H), 3.00 (s, 3H), 2.40-2.60 (m, 11H), 2.30 (s, 3H).

Synthetic Route of Compound 66

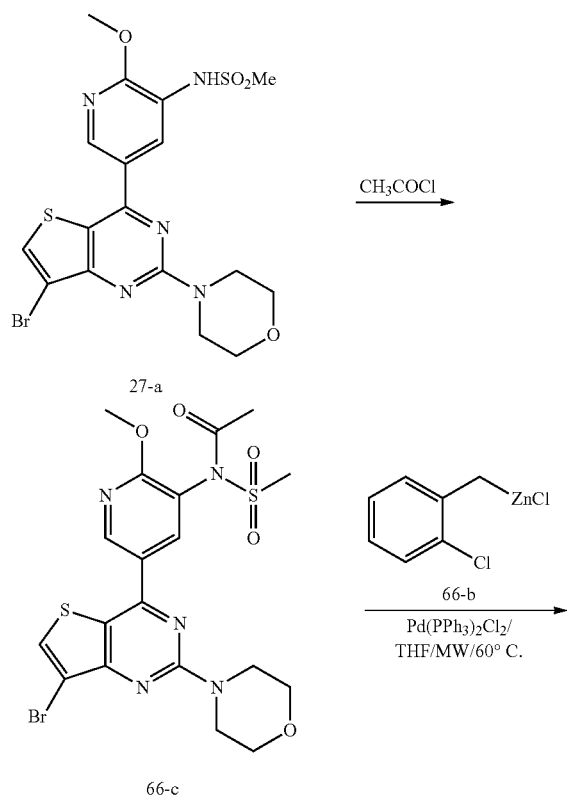

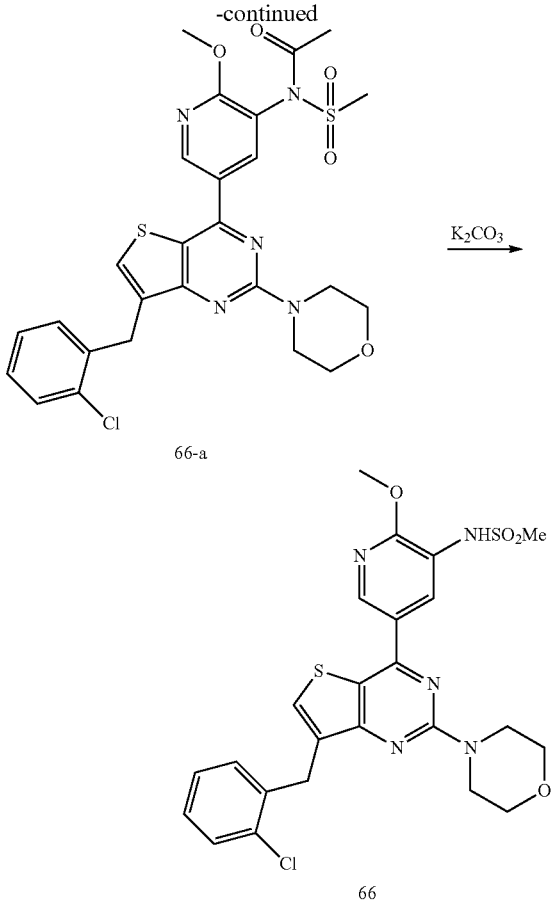

Synthesis of Compound 66-c

According to the method for preparing compound 60-a, compound 27-a was used in the preparation to yield compound 66-c (320 mg, 98%), as a yellow solid. LC-MS (ESI): m/z 543 (M+H)$^+$.

Synthesis of Compound 66-a

Compound 66-c (200 mg, 0.37 mmol), THF (1.5 mL), a solution of 66-b in THF (prepared according to the method disclosed in reference: Chemical Communication, 2008, 5824-5826) (0.5 M, 1.5 mL, 0.75 mmol) and PdCl$_2$(PPh$_3$)$_2$ (20 mg) were added to a 5 mL microwave tube. The reaction solution was reacted under nitrogen atmosphere at 60° C. with microwave for 15 minutes. The reaction liquid was adjusted with 1 M HCl solution to a pH value near 7, and then extracted with dichloromethane. The organic phase was separated out, sequentially washed with water, saturated NaCl aqueous solution, dried over anhydrous sodium sulfate, and concentrated under reduced pressure. The residue was purified by silica gel column chromatography to obtain compound 66-a (145 mg, 67%). LC-MS (ESI): m/z 588 (M+H)$^+$.

Synthesis of Compound 66

10% Potassium carbonate aqueous solution (4 mL) was added dropwise into a solution of compound 66-a (135 mg, 0.23 mmol) in methanol (7 mL), and the reaction solution was stirred at 25° C. overnight. The reaction solution was adjusted with 1 MHCl solution to a pH value near 7, and then extracted with dichloromethane. The organic phase was separated out, sequentially washed with water, saturated NaCl aqueous solution, dried over anhydrous sodium sulfate, and concentrated under reduced pressure. The residue was purified by Prep-HPLC to obtain target compound 66 (31 mg, 25%), as a yellow solid. LC-MS (ESI): m/z=546.1 (M+H)$^+$. $^1$H NMR (400 MHz, CDCl$_3$): δ 8.77 (1H, d, J=2.0 Hz), 8.58 (1H, d, J=2.0 Hz), 7.31-7.48 (3H, m), 7.12-7.24 (2H, m), 6.84 (1H, s), 4.29 (2H, s), 4.11 (3H, s), 3.89-4.02 (4H, m), 3.72-3.88 (4H, m), 3.07 (3H, s).

Synthetic Route of Compound 67

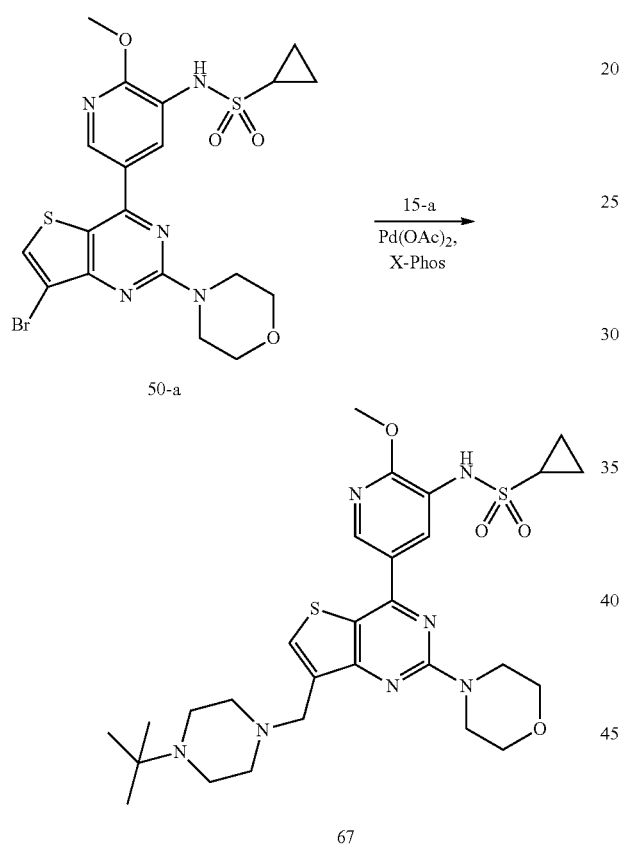

Synthesis of Compound 67

A mixture of compound 50-a (100 mg, 0.19 mmol), compound 15-a (128 mg, 0.57 mmol), Cs$_2$CO$_3$ (185 mg, 0.57 mmol), Pd (OAc)$_2$ (4 mg, 0.019 mmol), X-Phos (18 mg, 0.038 mmol), dioxane (10 mL) and water (1 mL) was reacted at 80° C. overnight. The reaction mixture was cooled to room temperature, diluted by adding water (10 mL), and extracted with ethyl acetate (3×20 mL). The organic layers were combined, dried over anhydrous sodium sulfate, and concentrated under reduced pressure. The residue was purified by Prep-HPLC to obtain target compound 67 (20 mg, 18%), as a yellow solid. LC-MS (ESI): m/z=602 (M+H)$^+$. $^1$H NMR (400 MHz, CDCl$_3$): δ 8.76 (d, J=2.0 Hz, 1H), 8.59 (d, J=2.0 Hz, 1H), 4.11 (s, 3H), 3.92-3.94 (m, 4H), 3.82-3.86 (m, 6H), 3.68 (s, 2H), 2.70-2.88 (m, 8H), 2.56-2.60 (m, 1H), 1.24-1.27 (m, 2H), 1.00-1.01 (m, 2H).

Synthetic Route of Compound 68

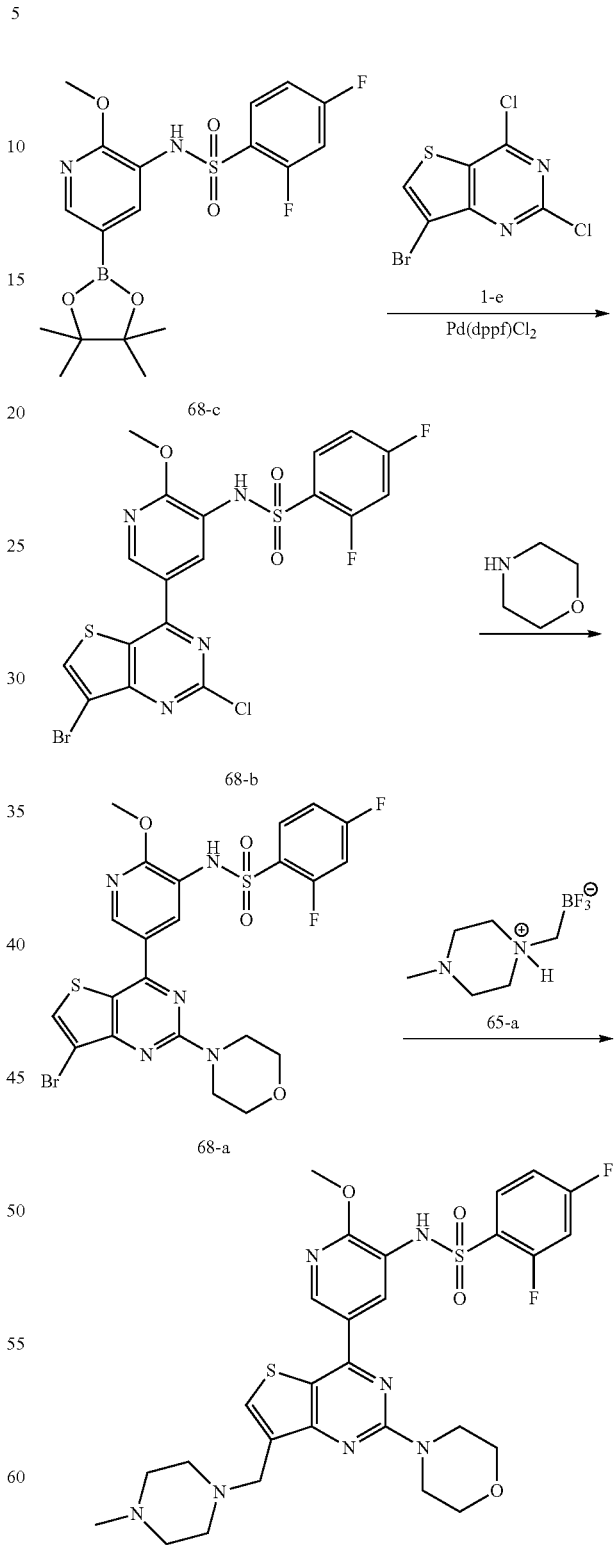

Synthesis of Compound 68-b

According to the method for preparing compound 27-b, compound 68-c (prepared according to the method disclosed in: WO 2012/037108 A1) was used in the preparation to yield compound 68-b (400 mg, 54%), as a yellow solid. LC-MS (ESI): m/z=548 (M+H)+.

Synthesis of Compound 68-a

According to the method for preparing compound 27-a, compound 68-b was used in the preparation to yield compound 68-a (90 mg, 79%), as a yellow solid. LC-MS (ESI): m/z=598 (M+H)+.

Synthesis of Compound 68

According to the method for preparing compound 27, compound 68-a and compound 65-a were used in the preparation to yield compound 68 (10 mg, 10%), as a yellow solid. LC-MS (ESI): m/z=632 (M+H)+. $^1$H NMR (400 MHz, CDCl$_3$): δ8.69 (d, J=2.0 Hz, 1H), 8.49 (d, J=2.4 Hz, 1H), 7.91-7.93 (m, 1H), 7.77 (s, 1H), 6.92-6.94 (m, 2H), 4.00 (s, 3H), 3.90-3.93 (m, 4H), 3.82-3.86 (m, 6H), 2.62 (s, 3H), 2.48 (s, 5H), 2.23 (s, 3H).

Synthesis of Compound 69

According to the method for preparing compound 50, compound 65-a was used in the preparation to yield compound 69 (10 mg, 18%), as a yellow solid. LC-MS (ESI): m/z=560 (M+H)+. $^1$H NMR (400 MHz, CDCl$_3$): δ 8.76 (d, J=2.4 Hz, 1H), 8.60 (d, J=2.4 Hz, 1H), 7.78 (s, 1H), 4.11 (s, 3H), 3.92-3.94 (m, 4H), 3.81-3.84 (m, 6H), 2.52-2.66 (m, 8H), 2.31 (s, 3H), 1.24-1.27 (m, 3H), 0.99-1.01 (m, 2H).

Synthetic Route of Compound 70

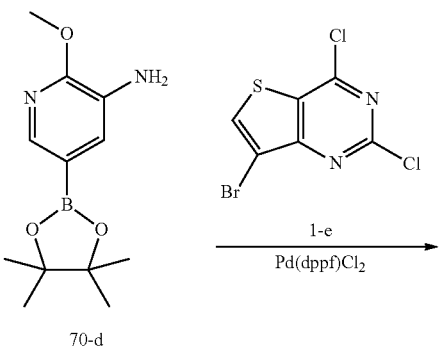

Synthetic Route of Compound 69

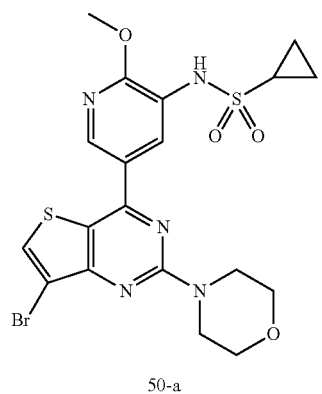
50-a

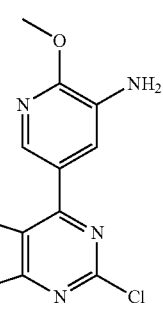
70-c

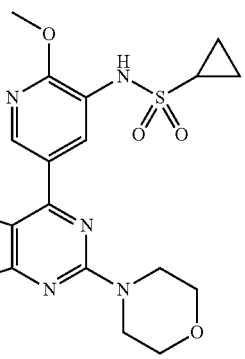
69

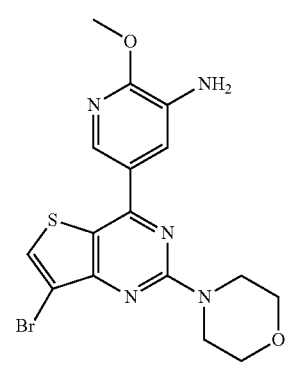
70-b

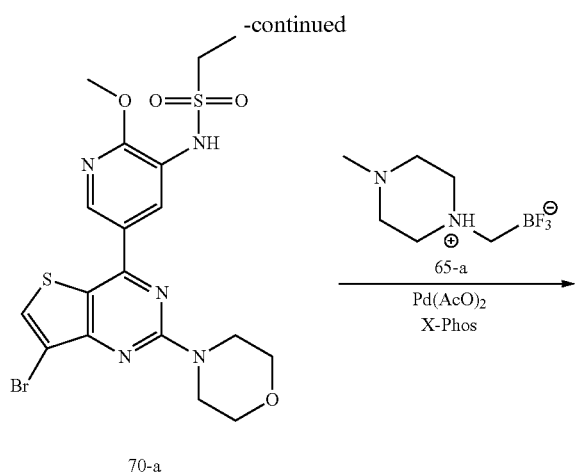

70-a

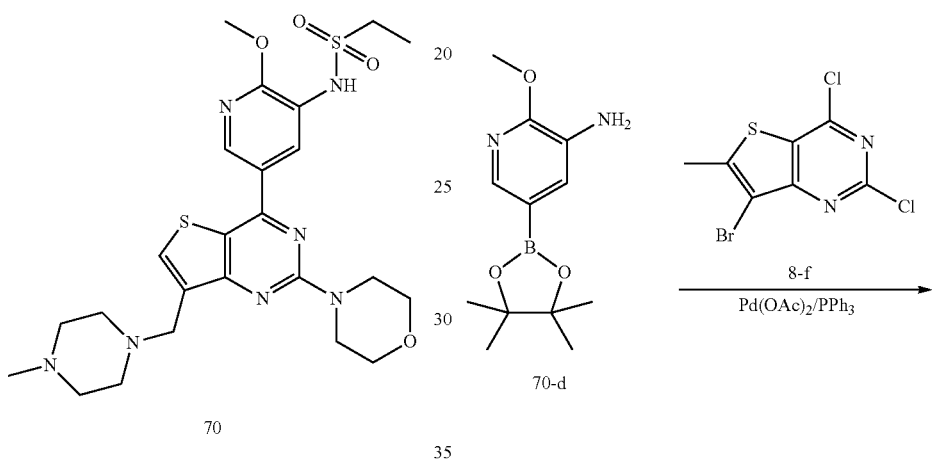

70

Synthesis of Compound 70-c

According to the method for preparing compound 27-b, compound 70-d (prepared according to the method disclosed in: WO 2009/147187 A1) was used in the preparation to yield compound 70-c (1.0 g, 27%), as a yellow solid. LC-MS (ESI): m/z=370.9 (M+H)+.

Synthesis of Compound 70-b

According to the method for preparing compound 27-a, compound 70-c was used in the preparation to yield compound 70-b (0.9 g, 79%), as a yellow solid. LC-MS (ESI): m/z=422 (M+H)+.

Synthesis of Compound 70-a

In a 50 mL round-bottomed flask, were added compound 70-b (0.25 mmol), ethylsulfonyl chloride (1.0 mmol), pyridine (5 mL) and dichloromethane (10 mL). The reaction mixture was heated to 25° C. and stirred overnight. The reaction mixture was concentrated under reduced pressure, and the residue was partitioned between water and dichloromethane. The organic layer was separated out, dried over anhydrous sodium sulfate, and concentrated under reduced pressure. The residue was separated and purified by silica gel column chromatography (petroleum ether/ethyl acetate=5/1~2/1) to yield compound 70-a (65 mg, 51%), as a yellow solid. LC-MS (ESI): m/z=513.8 (M+H)+.

Synthesis of Compound 70

According to the method for preparing compound 27, compound 70-a and compound 65-a were used in the preparation to yield compound 70 (26 mg, 25%), as a yellow solid. LC-MS (ESI): m/z=548 (M+H)+. 1H NMR (400 MHz, CDCl3): δ8.75 (d, J=2.0 Hz, 1H), 8.59 (d, J=2.4 Hz, 1H), 7.84 (s, 1H), 4.12 (s, 3H), 3.93 (t, J=4.8 Hz, 6H), 3.83 (t, J=4.6 Hz, 4H), 3.19 (q, J=7.3 Hz, 2H), 2.77 (brs, 8H), 2.44 (s, 3H), 1.41 (t, J=7.4 Hz, 3H).

Synthetic Routes of Compounds 71 and 96

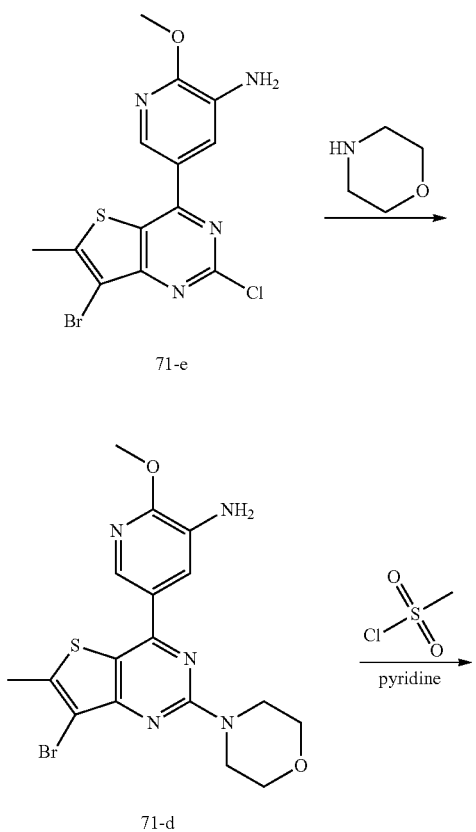

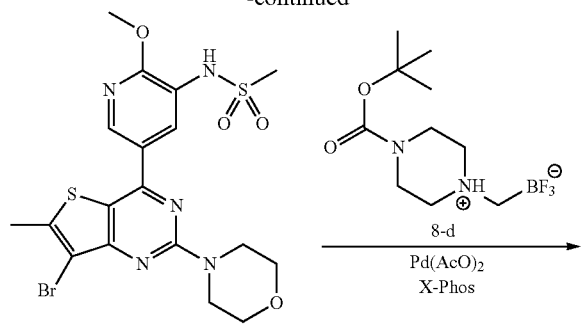

71-c

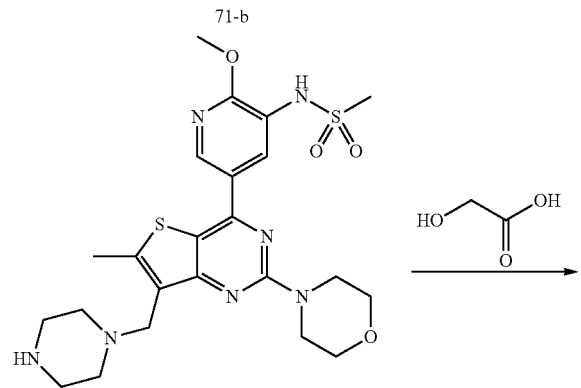

71-b

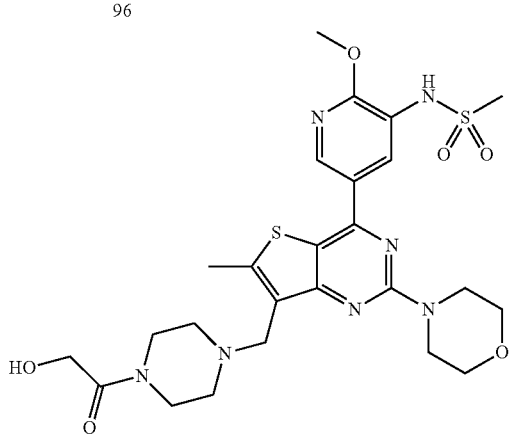

96

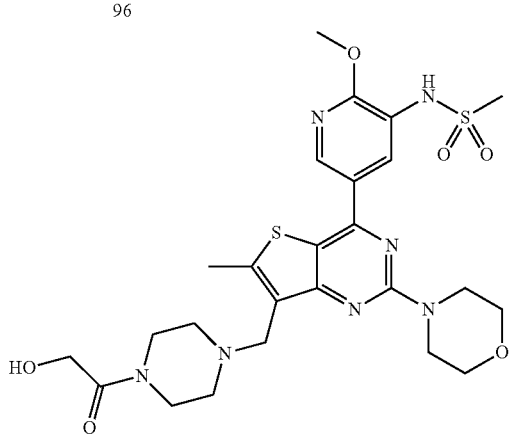

71

Synthesis of Compound 71-e

A mixture of compound 8-f (2.0 g, 6.71 mmol), 70-d (1.68 g, 6.72 mmol), triphenylphosphine (0.4 g, 1.52 mmol), palladium acetate (0.18 g, 0.80 mmol), THF (40 mL) and saturated sodium bicarbonate aqueous solution (4 mL) was stirred under nitrogen atmosphere at 90° C. overnight. Then the reaction mixture was cooled to room temperature, and diluted with THF, and then filtered through celite. The filtrate was concentrated under reduced pressure. The residue was separated and purified by silica gel column chromatography (elution system: petroleum ether/ethyl acetate=3/1~1/1) to obtain compound 71-e (1.19 g, 46%). LC-MS (ESI): m/z=384.9 (M+H)$^+$.

Synthesis of Compound 71-d

Morpholine (1 mL, 11.36 mmol) was added to a solution of compound 71-e (1.32 g, 3.42 mmol) in N,N-dimethylacetamide (DMAC) (30 mL), and then the reaction solution was stirred at 94° C. overnight. The reaction solution was cooled to room temperature, and diluted with water (60 mL). The precipitated solids were filtered, washed sequentially with water, methanol, and dried to obtain compound 71-d (1.30 g, 87%). LC-MS (ESI): m/z=436.0 (M+H)$^+$.

Synthesis of Compound 71-c

Compound 71-d (1.1 g, 2.5 mmol), methylsulfonyl chloride (1.1 g, 10 mmol), pyridine (4 mL), N,N-dimethylaminopyridine (DMAP) (153 mg, 1.25 mmol) and dichloromethane (50 mL) were added to a 50 mL round-bottomed flask. The reaction mixture was stirred at room temperature overnight. The reaction mixture was concentrated under reduced pressure, and the residue was partitioned between dichloromethane and saturated sodium bicarbonate aqueous solution. The organic layer was separated out, washed with water once, dried over anhydrous sodium sulfate, and concentrated under reduced pressure. The residue was separated and purified by silica gel column chromatography (dichloromethane/methanol=50/1) to yield compound 71-c (1.0 g, 77%), as a yellow solid. LC-MS (ESI): m/z=514.0 (M+H)$^+$.

Synthesis of Compound 71-b

According to the method for preparing compound 28, compound 71-c was used in the preparation to yield compound 71-b (585 mg, 55%), as a yellow solid. LC-MS (ESI): m/z=634 (M+H)$^+$.

Synthesis of Compound 96

According to the method for preparing compound 29-a, compound 71-b was used in the preparation to yield compound 96 (164 mg, 93%), as a yellow solid. LC-MS (ESI): m/z=534 (M+H)$^+$.

Synthesis of Compound 71

2-(7-azabenzotriazole)-N,N,N',N'-tetramethyluronium hexafluorophosphate (HATU) (20 mg, 0.053 mmol) was added to a solution of compound 96 (10 mg, 0.018 mmol), hydroxyl acetic acid (15 mg, 0.197 mmol) and diisopropylethylamine (0.1 mL) in DMF (1 mL). The reaction solution was stirred at room temperature for 1 hr, and diluted with dichloromethane (20 mL). The organic layer was separated out, washed with saturated brine, dried over anhydrous sodium sulfate, and concentrated under reduced pressure. The residue was separated and purified by silica gel plate chromatography to yield compound 71 (5 mg, 47%), as a yellow solid. LC-MS (ESI): m/z=592.3 (M+H)+. 1H NMR (400 MHz, CDCl3): δ 8.68 (d, J=2.4 Hz, 1H), 8.48 (d, J=2.4 Hz, 1H), 4.06 (s, 2H), 4.04 (s, 3H), 3.75-3.85 (m, 8H), 3.71 (s, 2H), 3.58 (t, J=4.8 Hz, 2H), 3.17 (t, J=4.8 Hz, 2H), 3.01 (s, 3H), 2.58 (s, 3H), 2.42-2.48 (m, 4H).

Synthetic Route of Compound 72

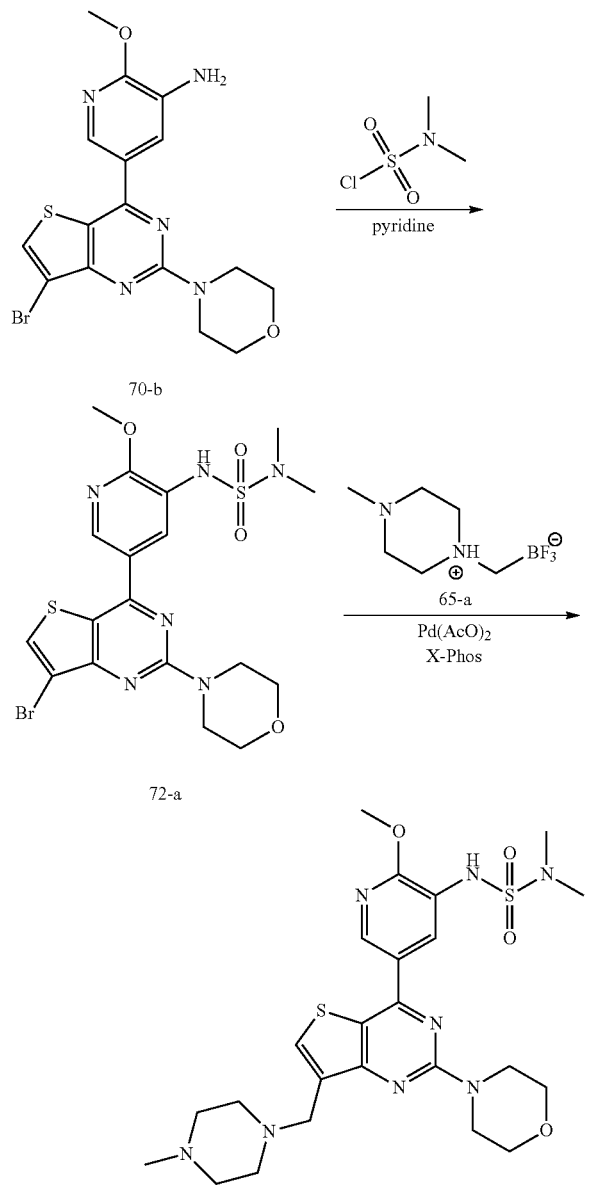

to yield compound 72-a (55 mg, 42%), as a yellow solid. LC-MS (ESI): m/z=528.8 (M+H)+.

Synthesis of Compound 72

According to the method for preparing compound 27, compound 72-a and compound 65-a were used in the preparation to yield compound 72 (21.4 mg, 20%), as a yellow solid. LC-MS (ESI): m/z=563.1 (M+H)+. 1H NMR (400 MHz, CDCl3): δ8.72 (s, 1H), 8.50 (s, 1H), 7.81 (s, 1H), 4.12 (s, 3H), 3.94 (t, J=4.6 Hz, 4H), 3.87 (s, 2H), 3.83 (t, J=4.6 Hz, 4H), 2.90 (s, 6H), 2.63 (brs, 8H), 2.35 (s, 3H).

Synthesis of Compound 73

According to the method for preparing compound 71, D-lactic acid was used in the preparation to yield compound 73 (5.2 mg, 48%), as a yellow solid. LC-MS (ESI): m/z=606.3 (M+H)+. 1H NMR (400 MHz, CDCl3): δ8.68 (d, J=2.4 Hz, 1H), 8.48 (d, J=2.4 Hz, 1H), 4.37 (q, J=6.4 Hz, 1H), 4.04 (s, 3H), 3.75-3.85 (m, 8H), 3.71 (s, 2H), 3.65 (s, 1H), 3.49 (s, 1H), 3.28-3.32 (m, 2H), 3.01 (s, 3H), 2.58 (s, 3H), 2.42-2.48 (m, 4H), 1.23 (d, J=6.8 Hz, 3H).

Synthesis of Compound 74

According to the method for preparing compound 71, L-lactic acid was used in the preparation to yield compound 74 (5.5 mg, 51%), as a yellow solid. LC-MS (ESI): m/z=606.3 (M+H)+. 1H NMR (400 MHz, CDCl3): δ8.68 (d, J=2.0 Hz, 1H), 8.48 (d, J=2.0 Hz, 1H), 4.36 (q, J=6.4 Hz, 1H), 4.04 (s, 3H), 3.75-3.85 (m, 8H), 3.71 (s, 2H), 3.65 (s, 1H), 3.49 (s, 1H), 3.28-3.32 (m, 2H), 3.01 (s, 3H), 2.58 (s, 3H), 2.42-2.48 (m, 4H), 1.23 (d, J=6.8 Hz, 3H).

Synthetic Route of Compound 75

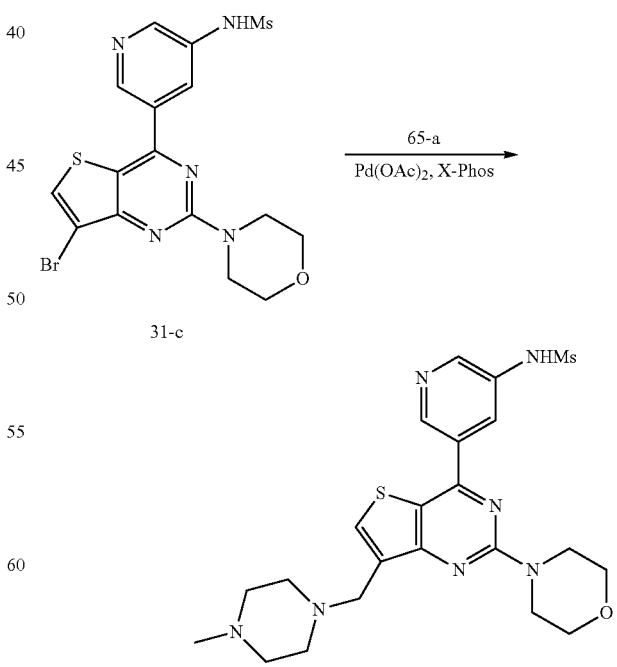

Synthesis of Compound 72-a

According to the method for preparing compound 70-a, dimethylaminosulfonyl chloride was used in the preparation

Synthesis of Compound 75

According to the method for preparing compound 31-b, compound 65-a was used in the preparation to yield compound 75 (19 mg, 31%), as a yellow solid. LC-MS (ESI): m/z=504.1 (M+H)+. 1H NMR (400 MHz, CDCl3): δ9.03 (1H, s), 8.47 (1H, d, J=2.0 Hz), 8.45 (1H, d, J=2.0 Hz), 7.83 (1H, s), 3.85-4.01 (4H, m), 3.82 (2H, s), 3.69-3.82 (4H, m), 3.04 (3H, s), 2.41-2.85 (8H, m), 2.31 (3H, s).

Synthetic Route of Compound 76

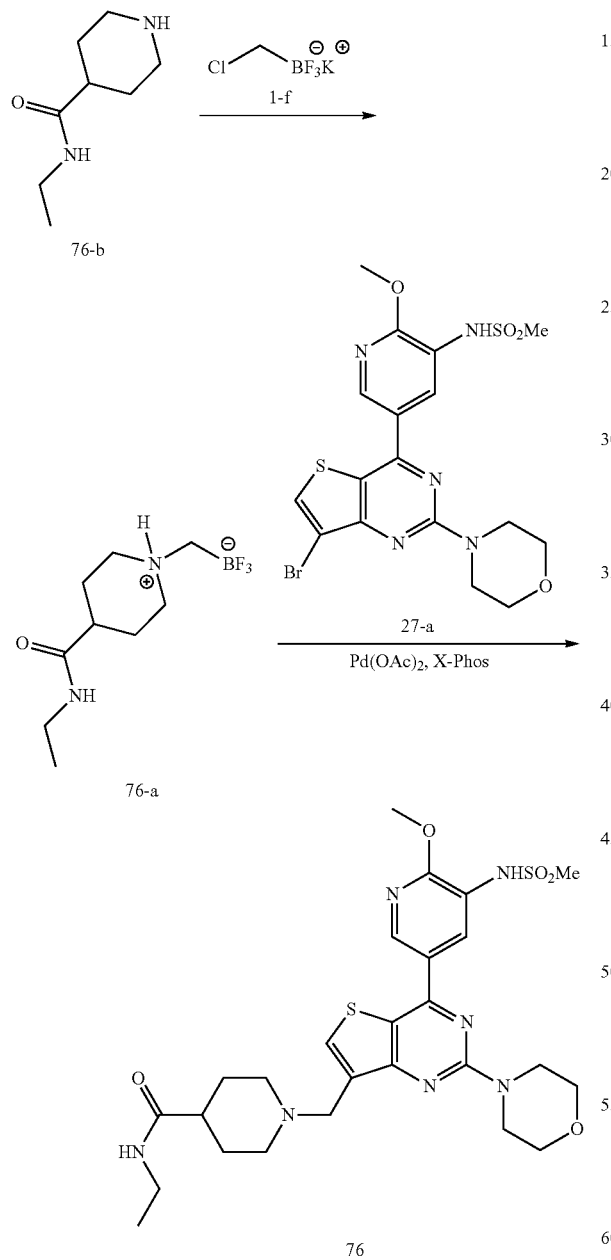

Synthesis of Compound 76-a

According to the method for preparing compound 1-a, purchased compound 76-b was used in the preparation to yield compound 76-a (170 mg, 59%), as a white solid. 1H NMR (400 MHz, DMSO-d6): δ 8.38 (s, 1H), 7.91 (s, 1H), 3.38 (s, 1H), 3.13-2.96 (m, 3H), 2.76 (s, 2H), 2.31-2.19 (m, 1H), 1.93 (s, 2H), 1.78 (s, 4H), 0.99 (t, J=7.1 Hz, 3H).

Synthesis of Compound 76

According to the method for preparing compound 27, compound 76-a was used in the preparation to yield compound 76 (19 mg, 27%), as a yellow solid. LC-MS (ESI): m/z=590.3 (M+H)+. 1H NMR (400 MHz, CD3OD): δ 8.76 (d, J=2.1 Hz, 1H), 8.58 (d, J=2.1 Hz, 1H), 8.03 (s, 1H), 4.13 (s, 3H), 3.97-3.89 (m, 4H), 3.87 (s, 2H), 3.85-3.79 (m, 4H), 3.36-3.31 (m, 4H), 3.23-3.14 (m, 2H), 3.07 (s, 4H), 1.78 (d, J=5.2 Hz, 4H), 1.11 (t, J=7.3 Hz, 3H).

Synthetic Route of Compound 77

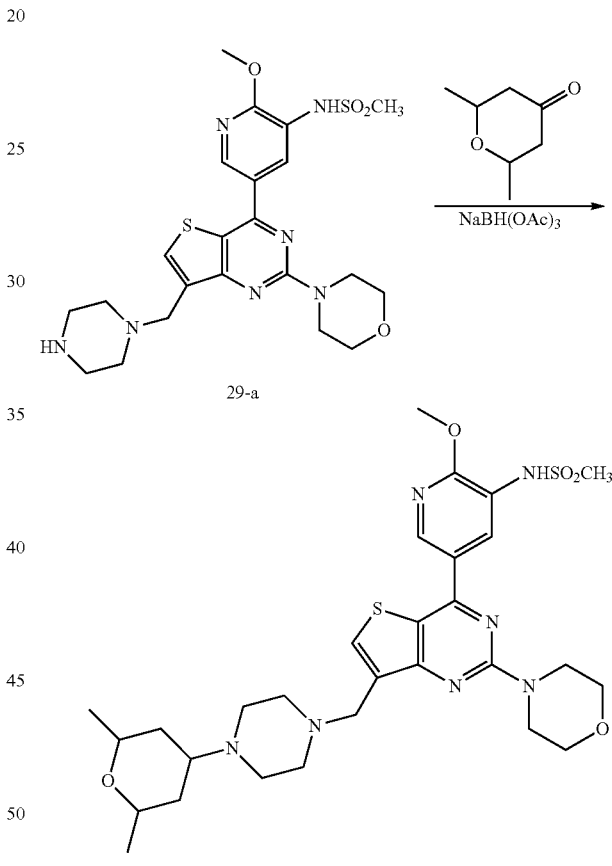

Synthesis of Compound 77

According to the method for preparing compound 33, 2,6-dimethyltetrahydro-4H-pyran-4-one was used in the preparation to yield compound 77 (7 mg, 36%), as a yellow solid. LC-MS (ESI): m/z=632 (M+H)+. 1H NMR (400 MHz, CDCl3): δ 8.78 (d, J=2.0 Hz, 1H), 8.58 (d, J=2.0 Hz, 1H), 7.78 (s, 1H), 4.12 (s, 3H), 3.92-3.94 (m, 4H), 3.82-3.84 (m, 6H), 3.43-3.47 (m, 2H), 3.08 (s, 3H), 2.63 (br, 8H), 2.44-2.48 (m, 1H), 1.78-1.80 (m, 2H), 1.21 (d, J=6.0 Hz, 6H), 1.08-1.17 (m, 2H).

Synthetic Route of Compound 78

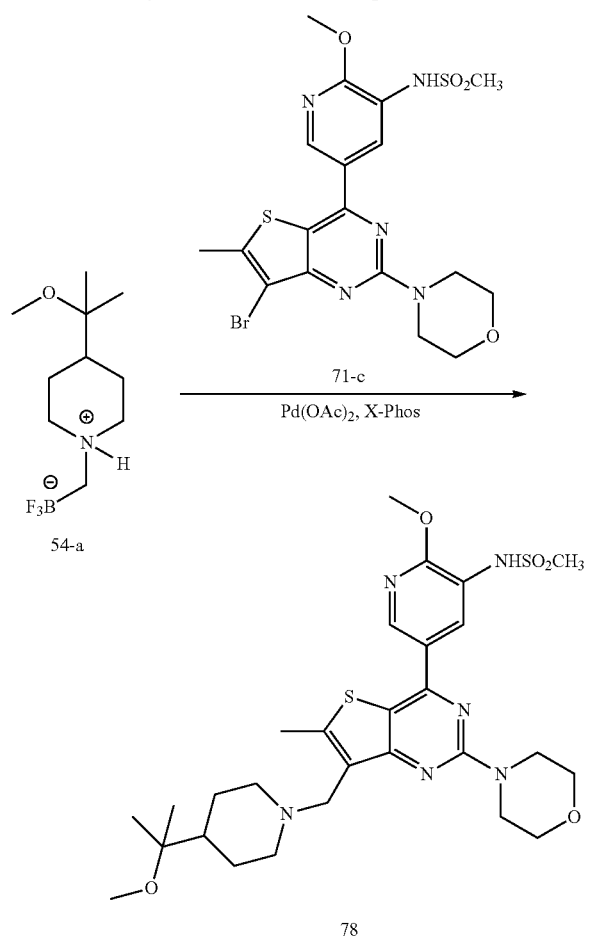

Synthesis of Compound 78

According to the method for preparing compound 54, compound 71-c was used in the preparation to yield compound 78 (33 mg, 30%), as a yellow solid. LC-MS (ESI): m/z=605.3 (M+H)+. 1H NMR (400 MHz, CDCl3) δ 8.74 (d, J=2.4 Hz, 1H), 8.54 (d, 2.4 Hz, 1H), 4.11 (s, 3H), 3.82-3.95 (m, 10H), 3.18 (d, J=10.8 Hz, 2H), 3.15 (s, 3H), 3.08 (s, 3H), 2.70 (s, 3H), 2.28 (t, J=10.8 Hz, 2H), 1.68 (d, J=12.0 Hz, 2H), 1.54-1.57 (m, 2H), 1.40-1.43 (m, 1H), 1.08 (s, 6H).

Synthetic Route of Compound 79

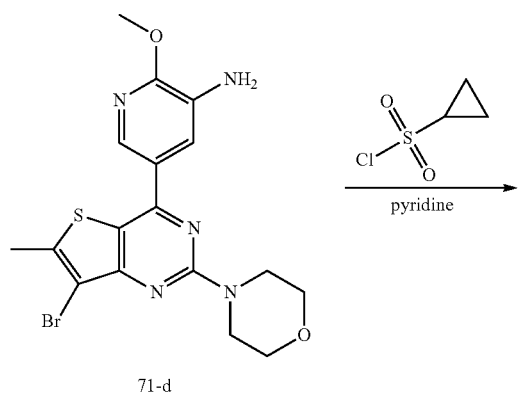

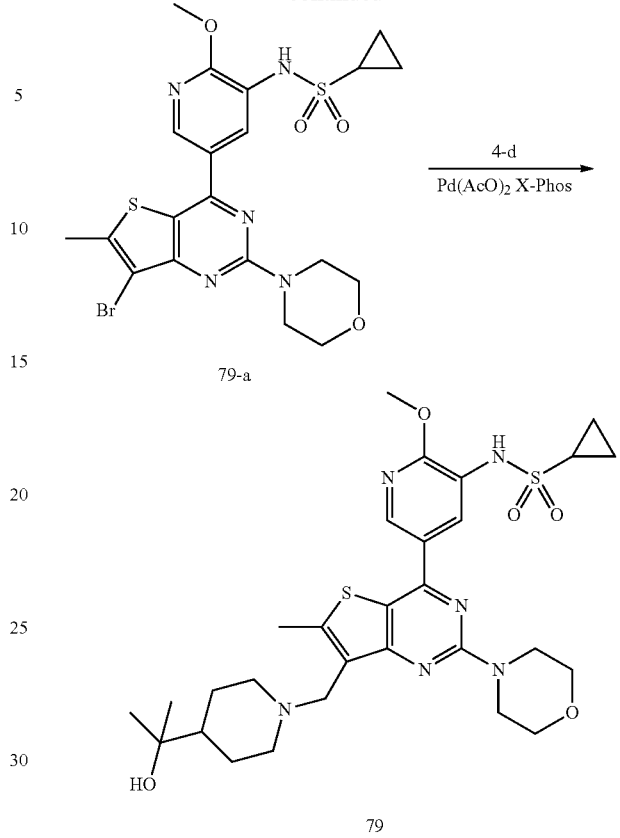

Synthesis of Compound 79-a

Cyclopropylsulfonyl chloride (1 mL) was added dropwise to a mixture of compound 71-d (1.11 g, 2.54 mmol), pyridine (20 mL) and DMAP (50 mg), and then the reaction solution was stirred at 70° C. overnight. The reaction mixture was concentrated under reduced pressure, and the residue was partitioned between dichloromethane and saturated sodium bicarbonate aqueous solution. The organic layer was separated out, washed with water once, dried over anhydrous sodium sulfate, and concentrated under reduced pressure. The residue was separated and purified by silica gel column chromatography (dichloromethane/methanol=50/1) to yield compound 79-a (0.9 g, 66%), as a yellow solid. LC-MS (ESI): m/z=539.9 (M+H)+.

Synthesis of Compound 79

According to the method for preparing compound 4, compound 79-a was used in the preparation to yield compound 79 (20 mg, 18%), as a yellow solid. LC-MS (ESI): m/z=617.3 (M+H)+. 1H NMR (400 MHz, CDCl3) δ 8.74 (1H, d, J=2.4 Hz), 8.58 (1H, d, J=2.4 Hz), 4.11 (3H, s), 3.87-3.96 (4H, m), 3.78-3.87 (4H, m), 3.75 (2H, s), 3.01 (2H, d, J=11.2 Hz), 2.65 (3H, s), 2.49-2.59 (1H, m), 1.98-2.14 (2H, m), 1.69 (2H, d, J=12.0 Hz), 1.29-1.44 (2H, m), 1.18-1.29 (4H, m), 1.15 (6H, s), 0.93-1.05 (2H, m).

Synthetic Route of Compound 80

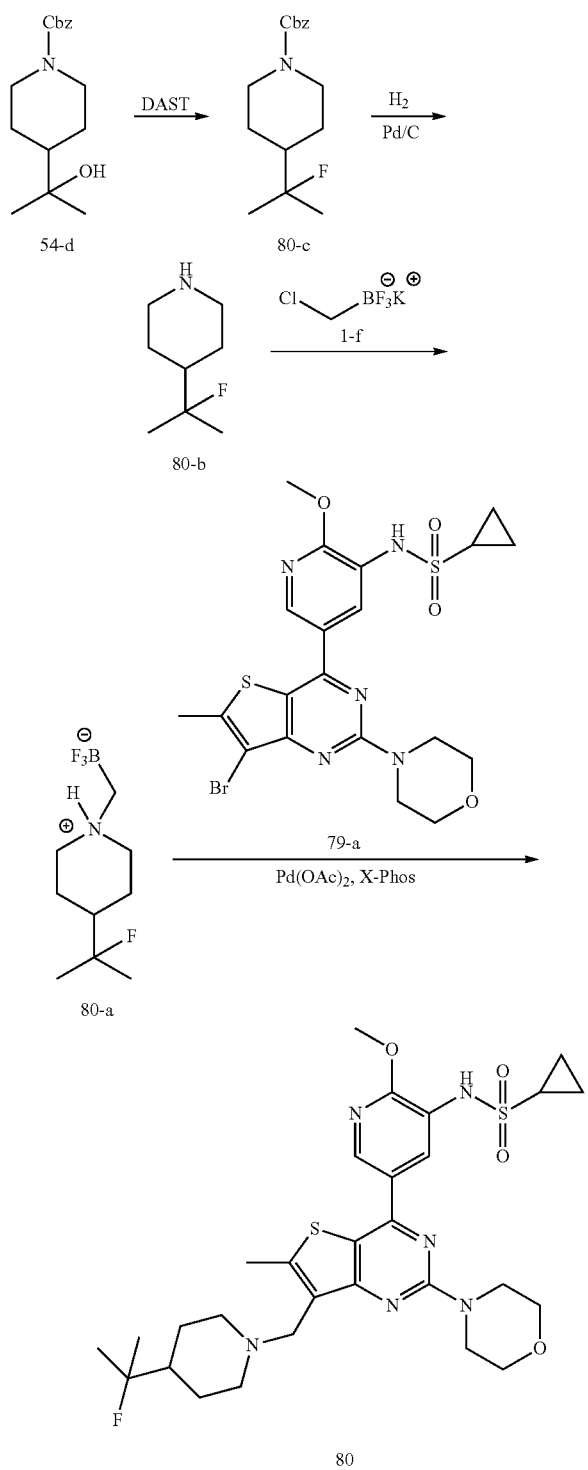

Synthesis of Compound 80-c

A solution of compound 54-d (1.05 g, 3.79 mmol) in dichloromethane (30 mL) was cooled with dry ice bath, and under nitrogen atmosphere to the solution was slowly added dropwise diethylaminosulfur trifluoride (DAST) (1.22 g, 7.58 mmol), and with the dry ice bath cooling continuously reacted for 45 minutes, and then slowly warmed up to room temperature. The reaction solution was diluted with water (50 mL), and extracted with dichloromethane (2×50 mL). The organic layers were combined, dried over sodium sulfate, and concentrated under reduced pressure. The residue was separated and purified by silica gel preparation plate chromatography (developing system: petroleum ether/ethyl acetate=4/1) to obtain compound 80-c (770 mg, 68.1%). LC-MS (ESI): m/z=280.1 (M+H)$^+$, 302.0 (M+Na)$^+$.

Synthesis of Compound 80-b

According to the method for preparing compound 54-b, compound 80-c was used in the preparation to yield compound 80-b (285 mg, 71.3%). LC-MS (ESI): m/z=146.1 (M+H)$^+$.

Synthesis of Compound 80-a

According to the method for preparing compound 1-a, compound 80-b was used in the preparation to yield compound 80-a (440 mg, 98.6%), as a white solid. $^1$H NMR (400 MHz, D$_2$O): δ3.48 (2H, d, J=12.0 Hz), 2.79 (2H, t, J=12.0 Hz), 2.10 (2H, s), 1.72-1.90 (3H, s), 1.45-1.54 (2H, m), 1.28 (3H, s), 1.17 (3H, s).

Synthesis of Compound 80

Compound 80-a (84 mg, 0.37 mmol), compound 79-a (100 mg, 0.185 mmol), cesium carbonate (182 mg, 0.56 mmol), X-Phos (18 mg, 0.037 mmol), palladium acetate (4 mg, 0.0185 mmol), tetrahydrofuran (1 mL) and water (0.1 mL) were added to a microwave tube, and the mixture was stirred under nitrogen atmosphere at 80° C. overnight. The reaction solution was cooled to room temperature, and filtered through celite, and the filtrate was concentrated under reduced pressure. The residue was purified by Prep-HPLC to obtain target compound 80 (18 mg, 15.8%). LC-MS (ESI): m/z=619.3 (M+H)$^+$. $^1$H NMR (400 MHz, CDCl$_3$): δ 8.67 (1H, d, J=2.0 Hz), 8.51 (1H, d, J=1.6 Hz), 4.04 (3H, s), 3.84-3.85 (4H, m), 3.70-3.77 (6H, m), 2.95 (2H, d, J=10.8 Hz), 2.58 (3H, s), 2.46-2.50 (1H, m), 2.02 (2H, t, J=10.8 Hz), 1.60 (2H, d, J=11.6 Hz), 1.31-1.40 (3H, m), 1.24 (3H, m), 1.18-1.21 (5H, m), 0.90-094 (2H, m).

Synthetic Route of Compound 81

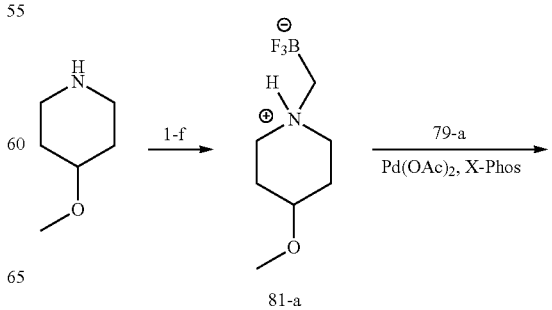

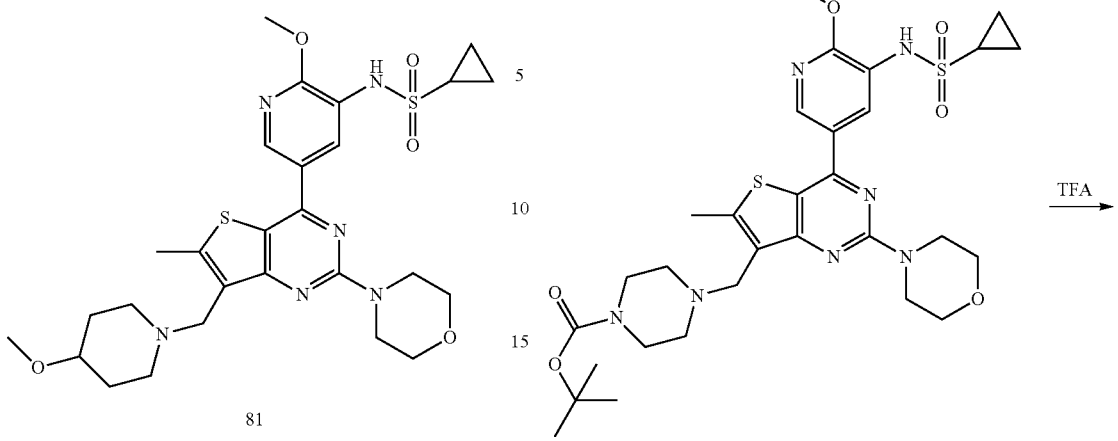

81

Synthesis of Compound 81-a

According to the method for preparing compound 1-a, purchased 4-methoxy piperidine was used in the preparation to yield compound 81-a (800 mg, 78%), as a white solid. $^1$H NMR (400 MHz, DMSO-$d_6$): δ 8.29 (s, 1H), 3.23 (s, 6H), 2.48 (s, 1H), 2.12 (s, 1H), 1.92 (d, J=4.9 Hz, 4H), 1.86 (s, 2H).

Synthesis of Compound 81

According to the method for preparing compound 80, compound 81-a was used in the preparation to yield compound 81 (27 mg, 50%), as a yellow solid. LC-MS (ESI): m/z=589.1 (M+H)$^+$. $^1$H NMR (400 MHz, CD$_3$OD): δ 8.60 (d, J=2.2 Hz, 1H), 8.45 (d, J=2.2 Hz, 1H), 4.51 (s, 1H), 4.01 (s, 3H), 3.80 (d, J=7.8 Hz, 6H), 3.73-3.67 (m, 4H), 3.22 (s, 3H), 2.85 (s, 2H), 2.57 (s, 3H), 2.44 (s, 2H), 1.80 (s, 2H), 1.54 (d, J=8.7 Hz, 2H), 1.18 (s, 1H), 0.97 (dd, J=7.3, 3.5 Hz, 2H), 0.87 (dd, J=7.5, 2.3 Hz, 2H).

Synthetic Route of Compound 82

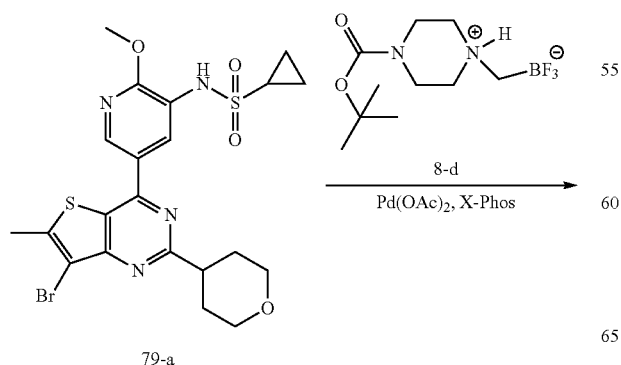

Synthesis of Compound 82-b

Compound 8-d (193 mg, 0.72 mmol), compound 79-a (130 mg, 0.24 mmol), cesium carbonate (234 mg, 0.72 mmol), X-Phos (18 mg, 0.037 mmol), palladium acetate (16 mg, 0.072 mmol), tetrahydrofuran (7 mL) and water (0.7 mL) were added to a reaction flask, and the mixture was stirred under nitrogen atmosphere at 80° C. overnight. The reaction solution was cooled to room temperature, and concentrated under reduced pressure. The residue was partitioned into ethyl acetate and water. The organic layer was separated out, sequentially washed with water, saturated brine, dried over anhydrous sodium sulfate, and concentrated under reduced pressure. The residue was separated and purified by silica gel column chromatography (elution system: dichloromethane:methanol=10:1) to obtain target compound 82-b (150 mg, 69%), as a yellow solid. LC-MS (ESI): m/z=660.2 (M+H)$^+$.

Synthesis of Compound 82-a

A mixture of compound 82-b (140 mg, 0.212 mmol), trifluoroacetic acid (1 mL) and dichloromethane (3 mL) was stirred at room temperature overnight, and afterwards diluted by adding water, and then extracted with dichloromethane (3×10 mL). The organic phases were combined, dried over anhydrous sodium sulfate, and concentrated under reduced pressure to obtain compound 82-a (110 mg, 70%). LC-MS (ESI): m/z=560.2 (M+H)$^+$.

Synthesis of Compound 82

A mixture of compound 82-a (80 mg, 0.14 mmol), trifluoroacetyl anhydride (0.024 mL, 0.17 mmol), pyridine (0.057 mL, 0.7 mmol) and dichloromethane (3 mL) was stirred at normal temperature overnight, and concentrated under reduced pressure.
The residue was purified by Prep-HPLC to obtain target compound 82 (28 mg, 30%). LC-MS (ESI): m/z=656.0 (M+H)$^+$. $^1$H NMR (400 MHz, CDCl$_3$): δ 8.74 (d, J=2.2 Hz, 1H), 8.58 (d, J=2.2 Hz, 1H), 4.12 (s, 3H), 3.94-3.89 (m, 4H), 3.86-3.82 (m, 4H), 3.79 (s, 2H), 3.67 (s, 2H), 3.58 (s, 2H), 2.65 (s, 3H), 2.59-2.55 (m, 4H), 1.26 (dd, J=7.7, 3.5 Hz, 4H), 1.00 (dd, J=7.8, 1.9 Hz, 2H).

Synthesis of Compound 83

Compound 71-c (140 mg, 0.27 mmol), compound 81-a (161 mg, 0.82 mmol), palladium acetate (18 mg, 0.082 mmol), X-Phos (39 mg, 0.082 mmol), cesium carbonate (266 mg, 0.82 mmol), tetrahydrofuran (10 mL) and water (1 mL) were added to a reaction flask, and the mixture was stirred under nitrogen atmosphere at 80° C. overnight. The reaction solution was cooled to room temperature, and concentrated under reduced pressure. The residue was partitioned into ethyl acetate and water. The organic layer was separated out, sequentially washed with water, saturated brine, dried over anhydrous sodium sulfate, and concentrated under reduced pressure. The residue was purified by Prep-HPLC to obtain target compound 83 (21 mg, 14%). LC-MS (ESI): m/z=563.1 (M+H)$^+$. $^1$H NMR (400 MHz, CD$_3$OD): δ 8.53 (d, J=2.2 Hz, 1H), 8.41 (d, J=2.2 Hz, 1H), 3.98 (s, 3H), 3.82-3.78 (m, 4H), 3.72-3.68 (m, 4H), 3.66 (s, 2H), 3.21 (s, 3H), 3.14 (s, 1H), 2.92 (s, 3H), 2.55 (s, 3H), 2.25 (s, 2H), 1.91 (s, 2H), 1.15 (dd, J=15.7, 8.5 Hz, 4H).

Synthetic Route of Compound 84

Synthetic Route of Compound 83

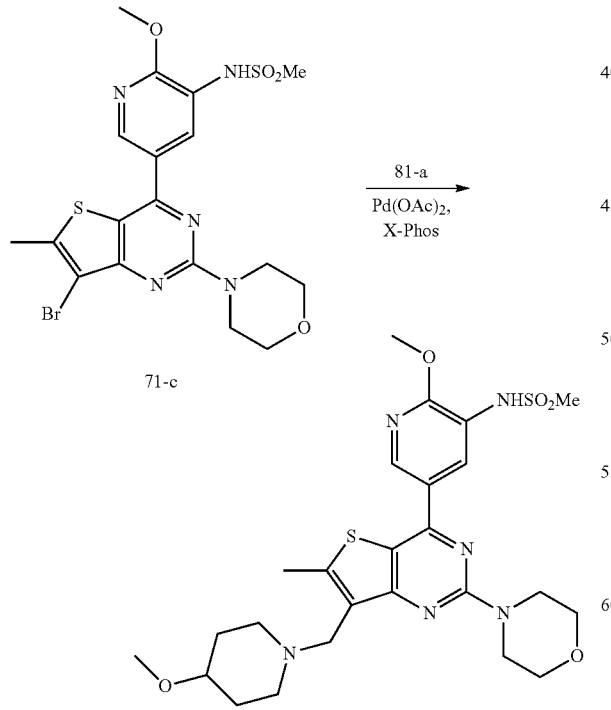

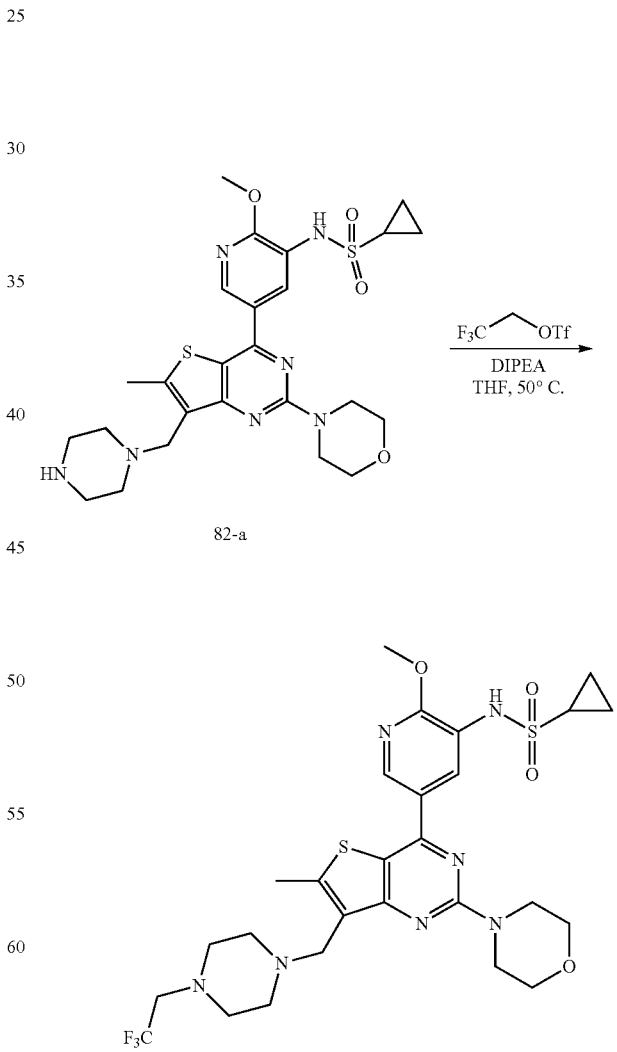

Synthesis of Compound 84

A mixture of compound 82-a (40 mg, 0.07 mmol), 2, 2, 2-trifluoroethyl trifluoromethanesulfonate (0.021 mL, 0.14 mmol), N, N-diisopropylethylamine (0.036 mL, 0.21 mmol) and tetrahydrofuran (3 mL) was stirred at 50° C. overnight, and concentrated under reduced pressure. The residue was purified by Prep-HPLC to obtain target compound 84 (16 mg, 35%). LC-MS (ESI): m/z=642.1 (M+H)$^+$. $^1$H NMR (400 MHz, CD$_3$OD): δ 8.60 (d, J=2.2 Hz, 1H), 8.46 (d, J=2.2 Hz, 1H), 4.00 (s, 3H), 3.83-3.77 (m, 4H), 3.73-3.68 (m, 4H), 3.65 (s, 2H), 3.22-3.20 (m, 4H), 2.92 (d, J=9.8 Hz, 2H), 2.55 (s, 3H), 2.50 (s, 3H), 1.15 (dd, J=15.2, 8.1 Hz, 2H), 1.00-0.95 (m, 2H), 0.87 (dd, J=7.5, 2.3 Hz, 2H).

Synthetic Route of Compound 85

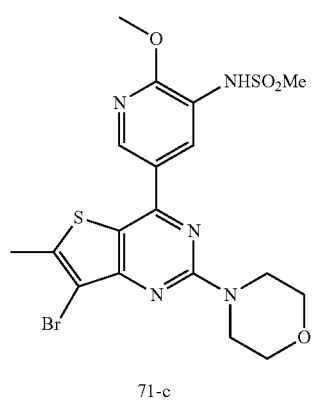

Synthesis of Compound 85

According to the method for preparing compound 80, compound 71-c was used in the preparation to yield compound 85 (43 mg, 37.4%). LC-MS (ESI): m/z=593.3 (M+H)$^+$. $^1$H NMR (400 MHz, CDCl$_3$): δ 8.75 (1H, d, J=2.4 Hz), 8.55 (1H, d, J=2.0 Hz), 4.11 (2H, s), 3.90-3.92 (3H, m), 3.82-3.84 (5H, m), 3.48 (2H, s), 3.08 (4H, s), 2.67 (3H, s), 2.12-2.25 (2H, m), 1.83-1.94 (2H, m), 1.67-1.70 (2H, m), 1.40-1.51 (3H, m), 1.26-1.31 (6H, m).

Synthetic Route of Compound 86

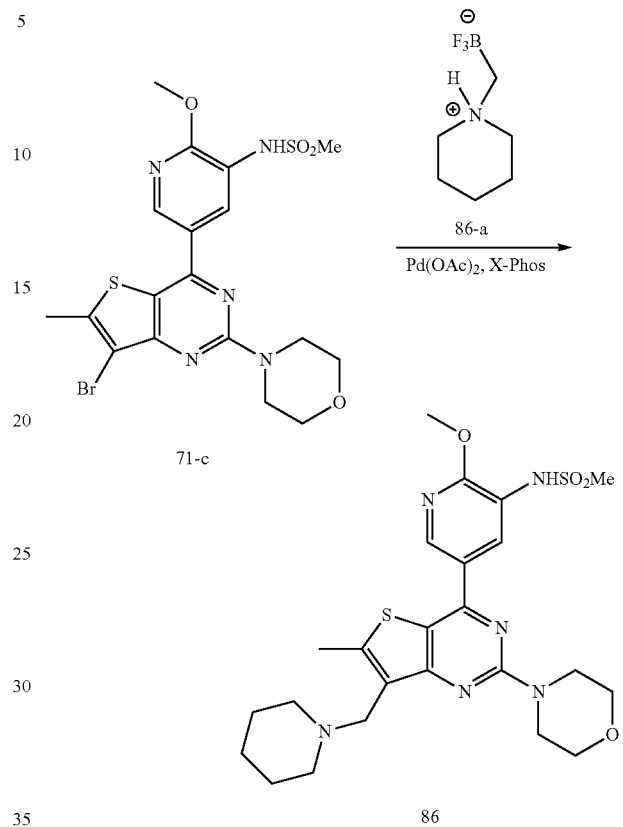

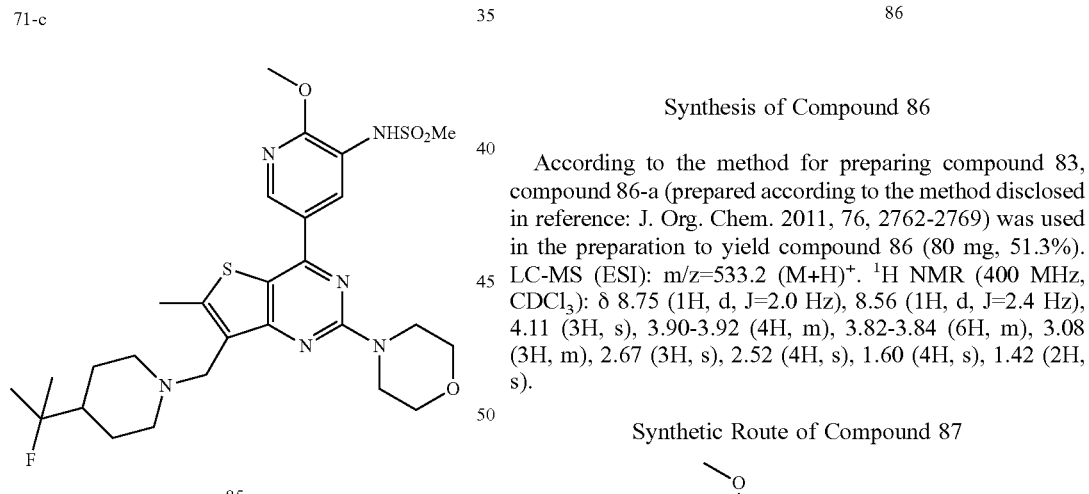

Synthesis of Compound 86

According to the method for preparing compound 83, compound 86-a (prepared according to the method disclosed in reference: J. Org. Chem. 2011, 76, 2762-2769) was used in the preparation to yield compound 86 (80 mg, 51.3%). LC-MS (ESI): m/z=533.2 (M+H)$^+$. $^1$H NMR (400 MHz, CDCl$_3$): δ 8.75 (1H, d, J=2.0 Hz), 8.56 (1H, d, J=2.4 Hz), 4.11 (3H, s), 3.90-3.92 (4H, m), 3.82-3.84 (6H, m), 3.08 (3H, m), 2.67 (3H, s), 2.52 (4H, s), 1.60 (4H, s), 1.42 (2H, s).

Synthetic Route of Compound 87

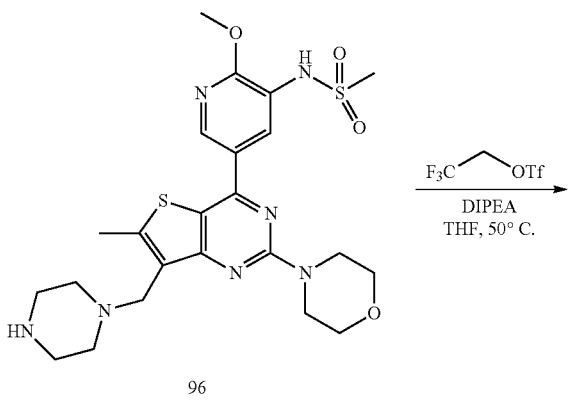

185

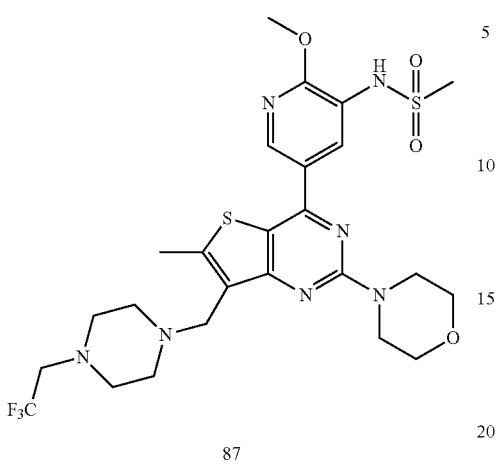

87

Synthesis of Compound 87

According to the method for preparing compound 84, compound 96 was used in the preparation to yield compound 87 (15 mg, 25%). LC-MS (ESI): m/z=616.2 (M+H)+. 1H NMR (400 MHz, CDCl$_3$): δ 8.67 (1H, d, J=2.0 Hz), 8.48 (1H, d, J=2.4 Hz), 4.04 (3H, s), 3.83-3.85 (4H, m), 3.75-3.77 (4H, m), 3.70 (2H, s), 3.01 (3H, s), 2.84-2.91 (2H, m), 2.57-2.60 (7H, m), 2.50 (4H, s).

Synthetic Route of Compound 88

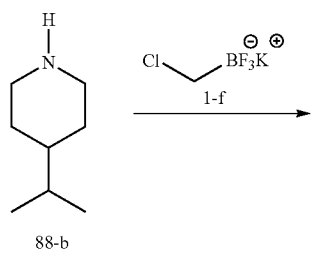

88-b

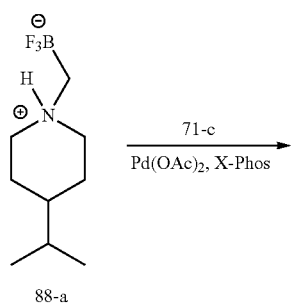

88-a

186

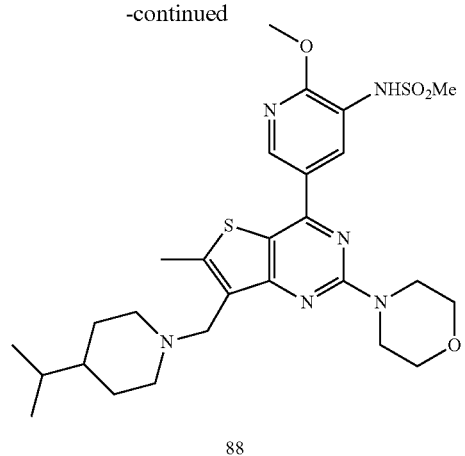

88

Synthesis of Compound 88-a

According to the method for preparing compound 1-a, purchased compound 88-b was used in the preparation to yield compound 88-a (800 mg, 87.9%), as a white solid. 1H NMR (400 MHz, D$_2$O): δ 3.48 (2H, d, J=12.4 Hz), 2.74 (2H, t, J=11.6 Hz), 2.08-2.13 (2H, m), 1.82 (2H, d, J=13.2 Hz), 1.29-1.39 (3H, m), 0.78 (6H, d, J=10.8 Hz).

Synthesis of Compound 88

According to the method for preparing compound 83, compound 88-a was used in the preparation to yield compound 88 (120 mg, 67%), as a yellow solid. LC-MS (ESI): m/z=575.3 (M+H)+. 1H NMR (400 MHz, CDCl$_3$): δ 8.74 (1H, d, J=2.0 Hz), 8.55 (1H, d, J=2.0 Hz), 4.11 (3H, s), 3.90-3.93 (4H, m), 3.82-3.84 (6H, m), 3.08 (5H, s), 2.68 (3H, s), 2.04 (2H, brs), 1.64 (3H, d, J=12.4 Hz), 1.37-1.43 (1H, m), 1.25-1.26 (1H, m), 0.97 (2H, brs), 0.85 (6H, d, J=6.8 Hz).

Synthetic Route of Compound 89

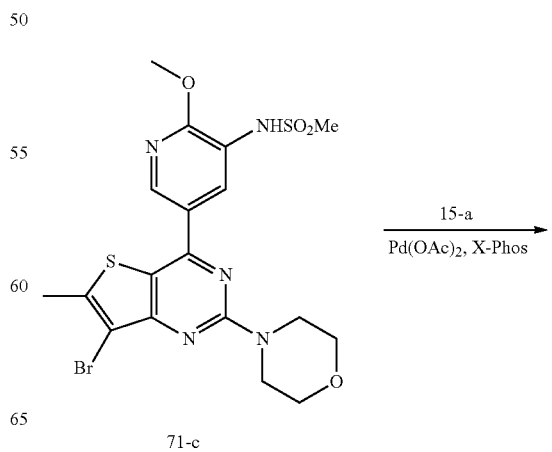

71-c

-continued

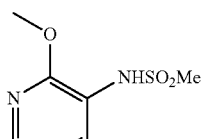

89

Synthesis of Compound 89

According to the method for preparing compound 83, compound 15-a was used in the preparation to yield compound 89 (20 mg, 18%), as a yellow solid. LC-MS (ESI): m/z=590.2 (M+H)+. 1H NMR (400 MHz, CDCl3): δ 8.72 (1H, d, J=2.4 Hz), 8.53 (1H, d, J=2.4 Hz), 4.00 (3H, s), 3.85-3.94 (4H, m), 3.74-3.85 (6H, m), 3.07 (3H, s), 2.66-2.97 (8H, m), 2.62 (3H, s), 1.21 (9H, s).

Synthetic Route of Compound 90

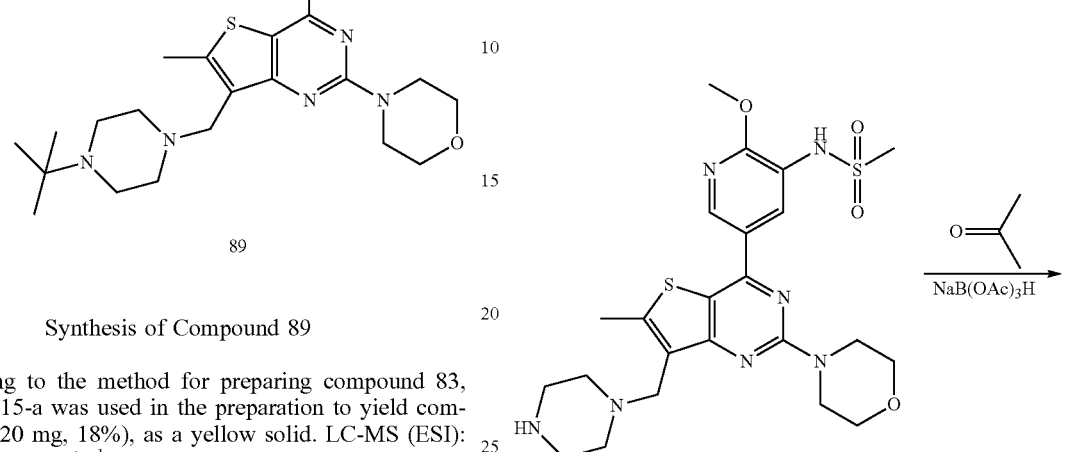

90

Synthesis of Compound 90

According to the method for preparing compound 82, compound 96 was used in the preparation to yield compound 90 (18 mg, 26.5%), as a yellow solid. LC-MS (ESI): m/z=630.1 (M+H)+. 1H NMR (400 MHz, CDCl3): δ 8.68 (1H, d, J=2.4 Hz), 8.48 (1H, d, J=2.4 Hz), 6.80 (1H, s), 4.04 (3H, s), 3.83-3.85 (4H, m), 3.71-3.77 (6H, m), 3.60 (2H, s), 3.51 (2H, s), 3.01 (3H, s), 2.58 (3H, s), 2.50 (4H, s).

Synthetic Route of Compound 91

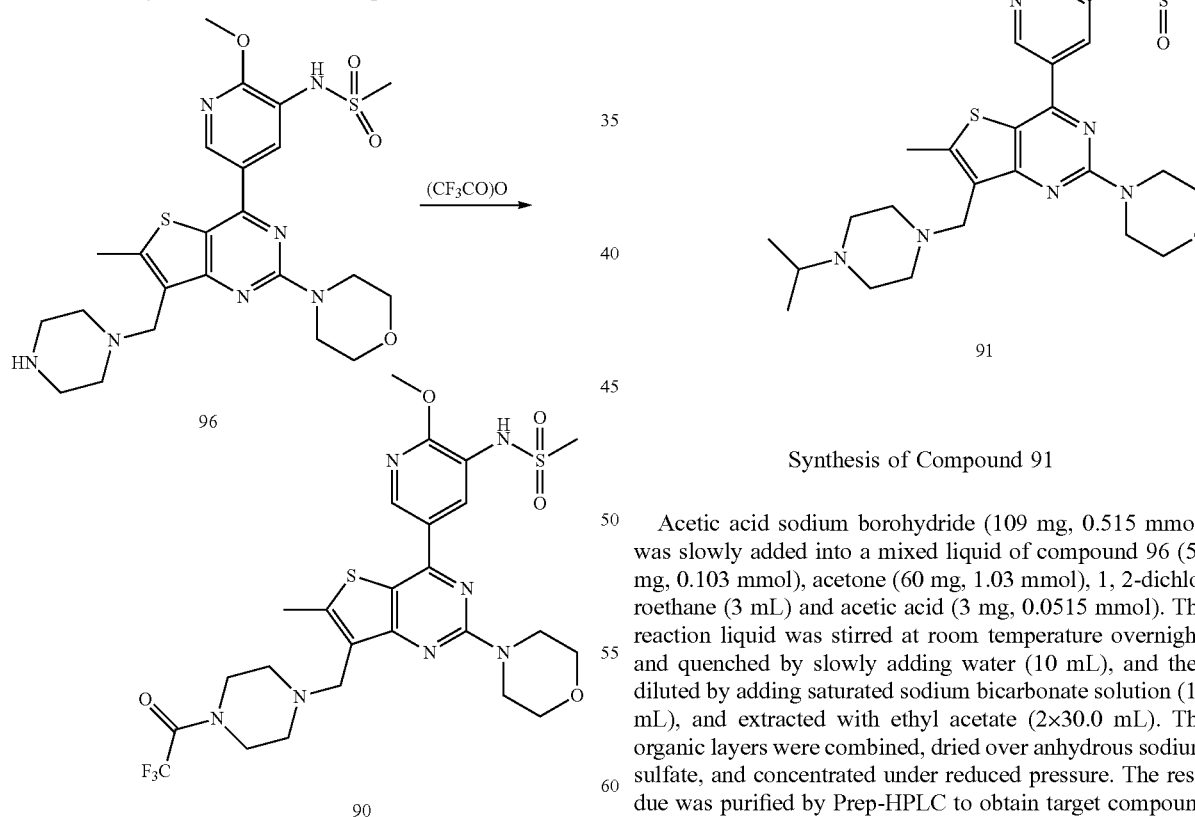

91

Synthesis of Compound 91

Acetic acid sodium borohydride (109 mg, 0.515 mmol) was slowly added into a mixed liquid of compound 96 (55 mg, 0.103 mmol), acetone (60 mg, 1.03 mmol), 1, 2-dichloroethane (3 mL) and acetic acid (3 mg, 0.0515 mmol). The reaction liquid was stirred at room temperature overnight, and quenched by slowly adding water (10 mL), and then diluted by adding saturated sodium bicarbonate solution (10 mL), and extracted with ethyl acetate (2×30.0 mL). The organic layers were combined, dried over anhydrous sodium sulfate, and concentrated under reduced pressure. The residue was purified by Prep-HPLC to obtain target compound 91 (12 mg, 36%), as a yellow solid. LC-MS (ESI): m/z=576.2 (M+H)+. 1H NMR (400 MHz, CDCl3): δ 8.67 (1H, d, J=2.0 Hz), 8.48 (1H, d, J=2.0 Hz), 4.03 (3H, s), 3.82-3.85 (4H, m), 3.71-3.76 (6H, m), 3.01 (3H, s), 2.47-2.57 (11H, m), 1.19 (1H, t, J=7.2 Hz), 8.67 (6H, d, J=6.8 Hz).

Synthetic Routes of Compounds 92 and 93

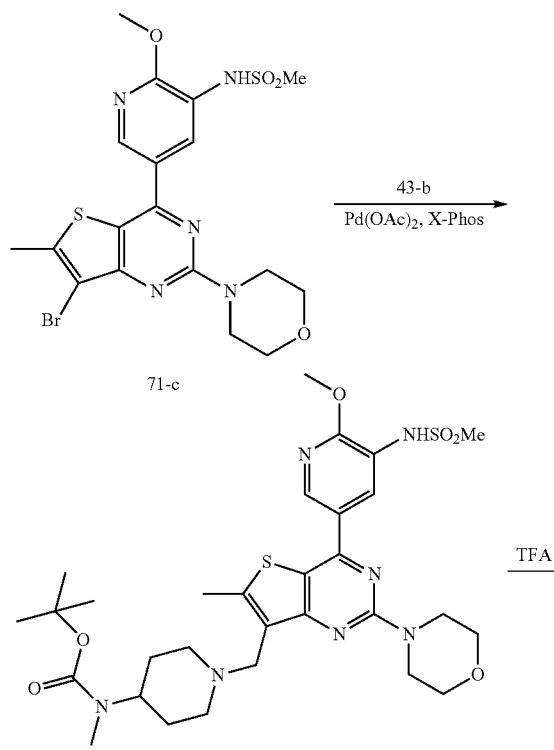

Synthesis of Compound 92-a

According to the method for preparing compound 52, compound 71-c was used in the preparation to yield compound 92-a (18 mg, 26.5%), as a yellow solid. LC-MS (ESI): m/z=662.3 (M+H)$^+$.

Synthesis of Compound 92

According to the method for preparing compound 43-a, compound 92-a was used in the preparation to yield compound 92 (279 mg, 94%), as a yellow solid. LC-MS (ESI): m/z=562.3 (M+H)$^+$. $^1$H NMR (400 MHz, CD$_3$OD): δ 8.57 (1H, d, J=2.0 Hz), 8.41 (1H, d, J=2.4 Hz), 4.00 (3H, s), 3.72-3.82 (4H, m), 3.61-3.72 (6H, m), 2.82-3.02 (6H, m), 2.54 (6H, d, J=12.0 Hz), 2.09-2.22 (2H, m), 1.89-2.01 (2H, m), 1.42-1.58 (2H, m).

Synthesis of Compound 93

According to the method for preparing compound 43, compound 92 was used in the preparation to yield compound 93 (10 mg, 34%), as a yellow solid. LC-MS (ESI): m/z=576.3 (M+H)$^+$. $^1$H NMR (400 MHz, CDCl$_3$): δ 8.75 (1H, d, J=2.0 Hz), 8.55 (1H, d, J=2.0 Hz), 4.11 (3H, s), 3.87-3.96 (4H, m), 3.79-3.87 (4H, m), 3.76 (2H, s), 3.07 (3H, s), 2.98 (2H, d, J=11.2 Hz), 2.64 (3H, s), 2.33 (6H, s), 2.19-2.29 (1H, m), 2.12 (2H, t, J=12.0 Hz), 1.81 (2H, d, J=12.0 Hz), 1.45-1.62 (2H, m).

Synthetic Routes of Compounds 94 and 97

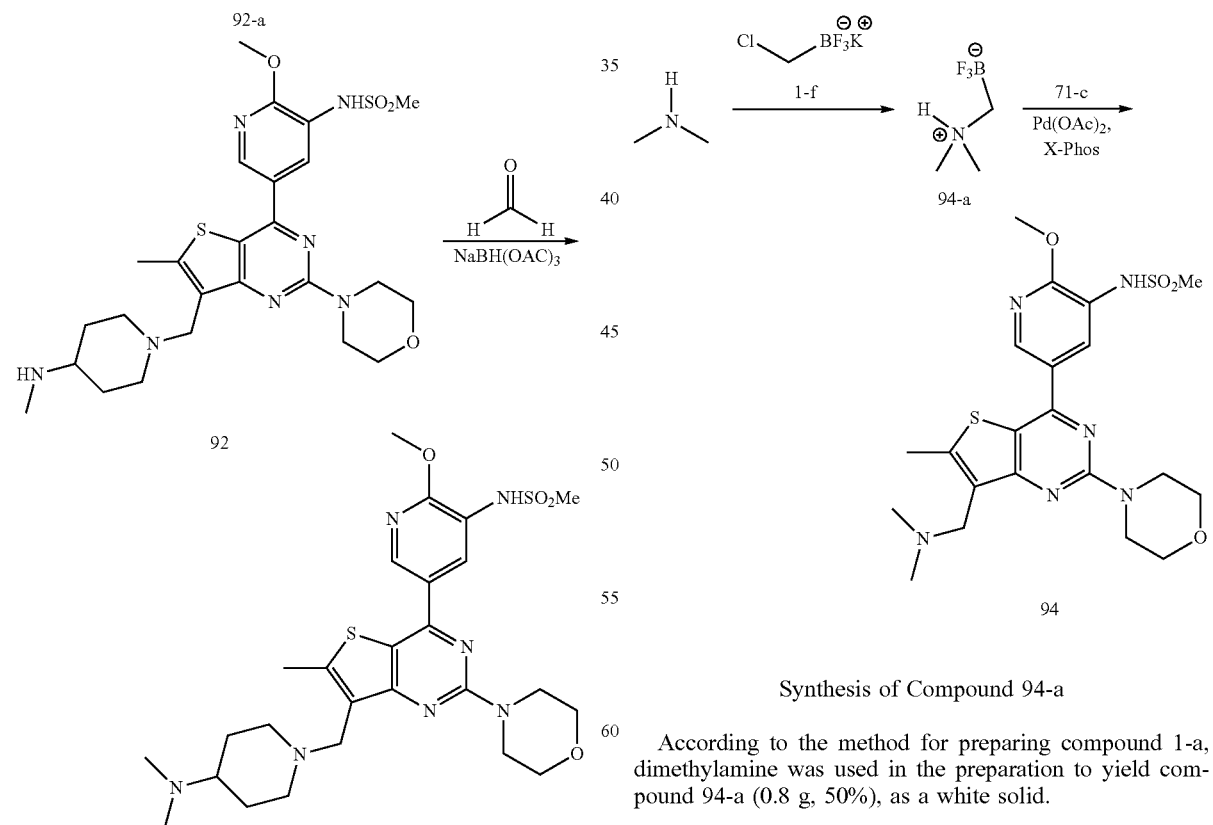

Synthesis of Compound 94-a

According to the method for preparing compound 1-a, dimethylamine was used in the preparation to yield compound 94-a (0.8 g, 50%), as a white solid.

Synthesis of Compounds 94 and 97

Compound 71-c (150 mg, 0.29 mmol), compound 94-a (220 mg, 1.73 mmol), palladium acetate (25 mg, 0.11 mmol), X-Phos (50 mg, 0.11 mmol), cesium carbonate (285 mg, 0.88 mmol), tetrahydrofuran (20 mL) and water (2 mL) were added to a reaction flask, and the mixture was stirred under nitrogen atmosphere at 80° C. overnight. The reaction solution was cooled to room temperature, and concentrated under reduced pressure. The residue was partitioned into ethyl acetate and water. The organic layer was separated out, sequentially washed with water, saturated brine, dried over anhydrous sodium sulfate, and concentrated under reduced pressure. The residue was purified by Prep-HPLC to obtain compound 94 (30 mg, 21%) and compound 97 (10 mg, 8%).

Compound 94: LC-MS (ESI): m/z=493.2 (M+H)$^+$. $^1$H NMR (400 MHz, CDCl$_3$): δ 8.75 (d, J=2.4 Hz, 1H), 8.55 (d, J=2.4 Hz, 1H), 4.11 (s, 3H), 3.92 (t, J=4.6 Hz, 4H), 3.87 (s, 2H), 3.83 (t, J=4.6 Hz, 4H), 3.08 (s, 3H), 2.71 (s, 3H), 2.47 (s, 6H).

Compound 97: LC-MS (ESI): m/z=436.1 (M+H)$^+$. $^1$H NMR (400 MHz, CDCl$_3$): δ 8.76 (d, J=2.4 Hz, 1H), 8.56 (d, J=2.4 Hz, 1H), 6.96 (d, J=1.2 Hz, 1H), 4.11 (s, 3H), 3.90 (t, J=4.6 Hz, 4H), 3.82 (t, J=4.6 Hz, 4H), 3.08 (s, 3H), 2.63 (d, J=1.2 Hz, 3H).

overnight. The reaction mixture was partitioned into dichloromethane (50 mL) and saturated sodium bicarbonate aqueous solution (20 mL). The organic layer was separated, dried over anhydrous sodium sulfate, and concentrated under reduced pressure. The residue was purified by Prep-HPLC to yield compound 95 (33 mg, 30%), as a yellow solid. LC-MS (ESI): m/z 604.3 (M+H)$^+$. $^1$H-NMR (400 MHz, CDCl$_3$): δ 8.74 (1H, d, J=2.4 Hz), 8.55 (1H, d, J=2.4 Hz), 4.73 (1H, brs), 4.10 (3H, s), 3.86-3.96 (4H, m), 3.78-3.86 (4H, m), 3.74 (2H, s), 3.07 (3H, s), 2.88-3.02 (3H, m), 2.64 (3H, s), 2.33-2.47 (1H, m), 2.18 (3H, s), 2.08 (2H, t, J=10.8 Hz), 1.64-1.78 (2H, m), 1.46-1.64 (2H, m), 1.00 (6H, d, J=6.4 Hz).

Synthetic Route of Compound 98

Synthetic Route of Compound 95

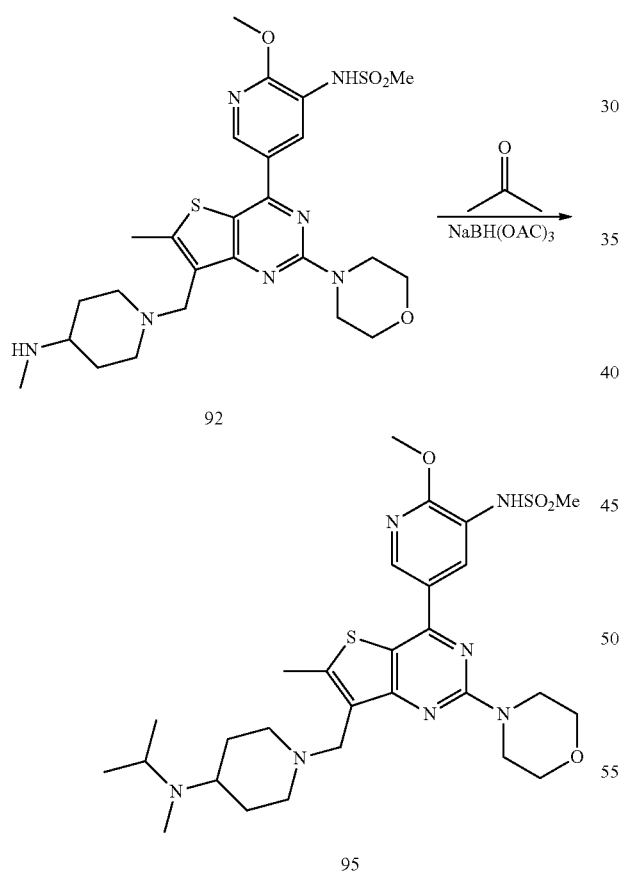

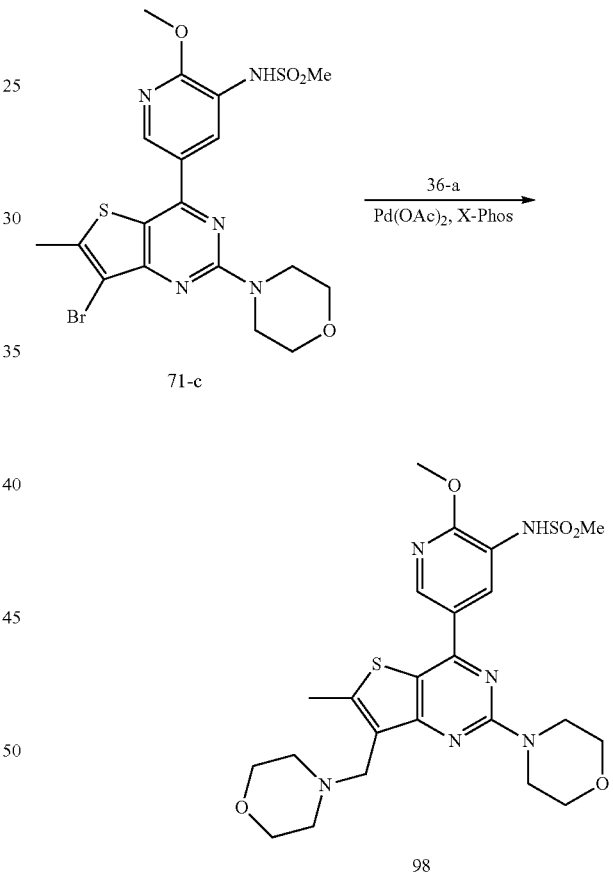

Synthesis of Compound 95

Compound 92 (104 mg, 0.19 mmol) and acetone (5 mL) were dissolved in 1,2-dichloroethane (5 mL), and a drop of acetic acid and sodium triacetoxyborohydride (2 g, 9.44 mmol) were added, and then stirred at room temperature Synthesis of Compound 98

According to the method for preparing compound 83, compound 36-a was used in the preparation to yield compound 98 (32 mg, 61.5%), as a yellow solid. LC-MS (ESI): m/z=535.2 (M+H)$^+$. $^1$H NMR (400 MHz, CDCl$_3$): δ 8.68 (d, J=2.0 Hz, 1H), 8.48 (d, J=2.0 Hz, 1H), 4.04 (s, 3H), 3.82-3.86 (m, 4H), 3.69-3.78 (m, 6H), 3.62 (brs, 4H), 3.01 (s, 3H), 2.60 (s, 3H), 2.46 (brs, 4H).

Synthetic Route of Compound 99

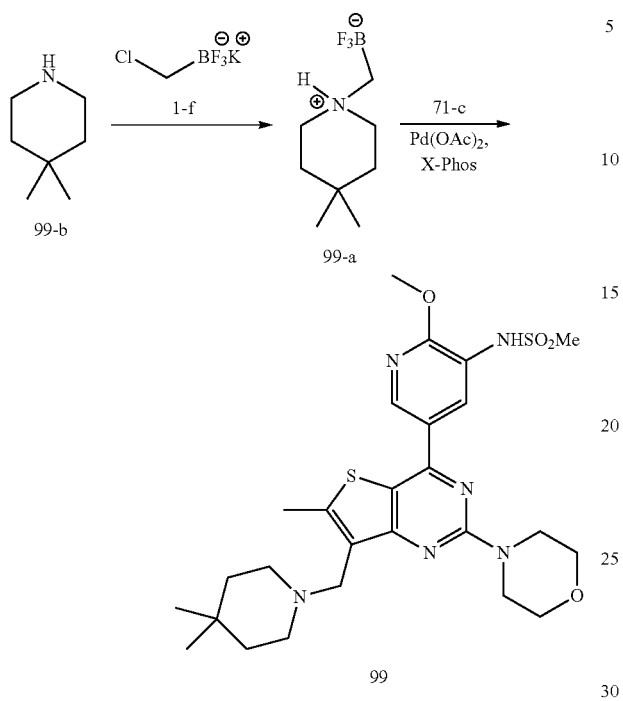

Synthesis of Compound 99-a

According to the method for preparing compound 1-a, purchased compound 99-b was used in the preparation to yield compound 99-a (100 mg, 58%).

Synthesis of Compound 99

According to the method for preparing compound 83, compound 99-a was used in the preparation to yield compound 99 (11 mg, 44%), as a yellow solid. LC-MS (ESI): m/z=561.2 (M+H)+. $^1$H NMR (400 MHz, CDCl$_3$): δ 8.73 (1H, d, J=2.0 Hz), 8.54 (1H, d, J=2.4 Hz), 4.15 (2H, s), 4.11 (3H, s), 3.86-3.95 (4H, m), 3.73-3.86 (4H, m), 3.08 (3H, s), 2.80-3.00 (4H, m), 2.78 (3H, s), 1.47-1.80 (4H, m), 0.95 (6H, s).

Synthetic Route of Compound 100

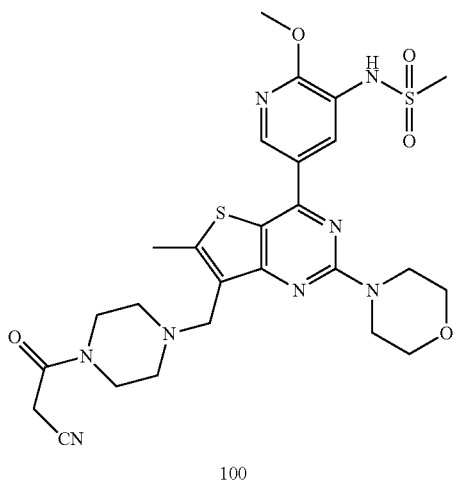

Synthesis of Compound 100

Compound 96 (20 mg, 0.0375 mmol), cyano acetic acid (3.4 mg, 0.045 mmol), HOBt (7.6 mg, 0.0562 mmol), N-methyl morpholine (0.0125 mL, 0.112 mmol), EDCI HCl (10.8 mg, 0.0562 mmol) were dissolved in N, N-dimethylformamide (2 mL), and the reaction mixture was stirred at room temperature overnight. The reaction solution was diluted with dichloromethane (20 mL), and the organic phase was washed with water (20 mL×2). The organic layer was separated, dried over anhydrous sodium sulfate, and concentrated under reduced pressure. The residue was recrystalized from methanol (30 mL) to yield compound 100 (15 mg, 68%). LC-MS (ESI): m/z 601.2 (M+H)+. $^1$H NMR (400 MHz, CDCl$_3$): δ8.68 (d, J=2.0 Hz, 1H), 8.48 (d, J=2.0 Hz, 1H), 4.04 (s, 3H), 3.83-3.85 (m, 4H), 3.75-3.77 (m, 4H), 3.71 (s, 2H), 3.55 (t, J=4.8 Hz, 2H), 3.36 (t, J=4.8 Hz, 2H), 3.01 (s, 3H), 2.89 (s, 1H), 2.81 (s, 1H), 2.57 (s, 3H), 2.45-2.51 (m, 4H).

Synthetic Route of Compound 101

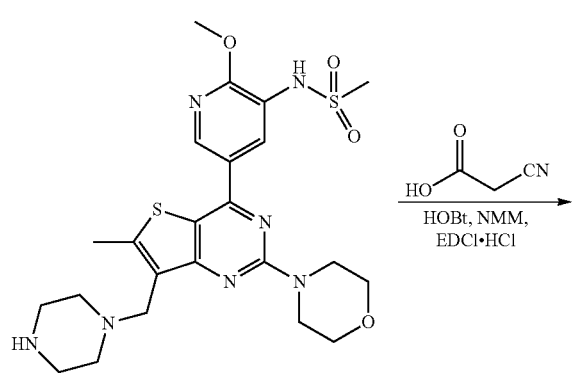

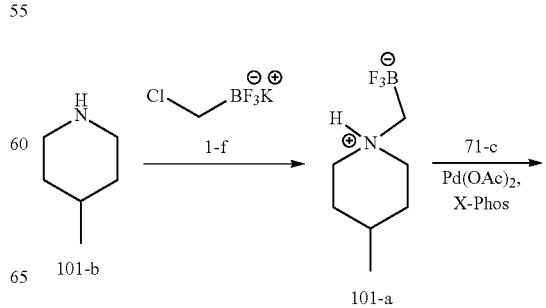

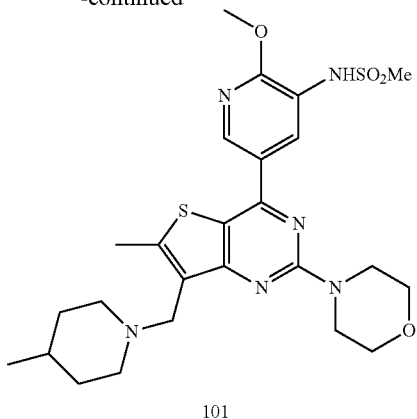

101

Synthesis of Compound 101-a

According to the method for preparing compound 1-a, purchased compound 101-b was used in the preparation to yield compound 101-a (120 mg, 85%).

Synthesis of Compound 101

According to the method for preparing compound 83, compound 101-a was used in the preparation to yield compound 101 (17 mg, 26.6%). LC-MS (ESI): m/z=547.3 (M+H)+. $^1$H NMR (400 MHz, CDCl$_3$): δ 8.74 (d, J=2.0 Hz, 1H), 8.55 (d, J=2.0 Hz, 1H), 4.11 (s, 3H), 3.82-3.91 (m, 10H), 3.05-3.08 (m, 5H), 2.70 (s, 3H), 2.28 (s, 2H), 1.64 (d, J=10.0 Hz, 2H), 1.40 (s, 3H), 0.92 (d, J=4.8 Hz, 3H).

Synthetic Route of Compound 102

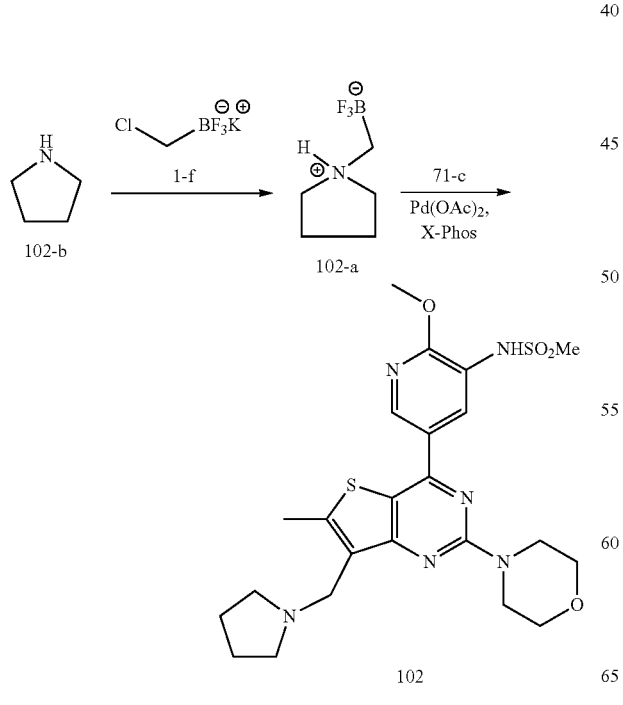

102

Synthesis of Compound 102-a

According to the method for preparing compound 1-a, purchased compound 102-b was used in the preparation to yield compound 102-a (500 mg, 80%).

Synthesis of Compound 102

According to the method for preparing compound 83, compound 102-a was used in the preparation to yield compound 102 (27 mg, 20.5%). LC-MS (ESI): m/z=519.2 (M+H)+. $^1$H NMR (400 MHz, CDCl$_3$): δ 8.63 (d, J=2.4 Hz, 1H), 8.44 (d, J=2.0 Hz, 1H), 4.15 (s, 2H), 4.03 (s, 3H), 3.81-3.84 (m, 4H), 3.70-3.72 (m, 4H), 2.95-3.02 (m, 7H), 2.62 (s, 3H), 1.87 (brs, 4H).

Synthetic Route of Compound 103

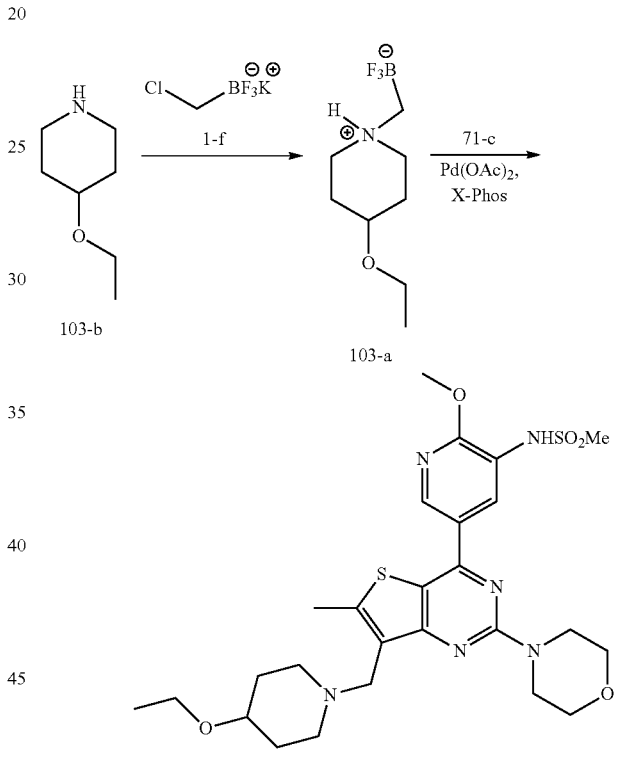

103

Synthesis of Compound 103-a

According to the method for preparing compound 1-a, purchased compound 103-b was used in the preparation to yield compound 103-a (810 mg, 64%).

Synthesis of Compound 103

According to the method for preparing compound 83, compound 103-a was used in the preparation to yield compound 103 (29 mg, 26%), as a yellow solid. LC-MS (ESI): m/z=577.2 (M+H)+. $^1$H NMR (400 MHz, CDCl$_3$): δ 8.75 (d, 1H, J=2.0 Hz), 8.55 (d, 1H, J=2.0 Hz), 4.10 (s, 3H), 3.92 (t, 4H, J=4.0 Hz), 3.84 (t, 4H, J=4.0 Hz), 3.75 (s, 2H), 3.51 (q, 2H, J=7.2 Hz), 3.28 (dd, 1H, J=8.4, 4.4 Hz), 3.07 (s, 3H), 2.82 (d, 2H, J=11.2 Hz), 2.64 (s, 3H), 2.24 (t, 2H, J=10.0 Hz), 1.88 (d, 2H, J=10.0 Hz), 1.60-1.55 (m, 2H), 1.20 (t, 3H, J=6.8 Hz).

Synthetic Route of Compound 104

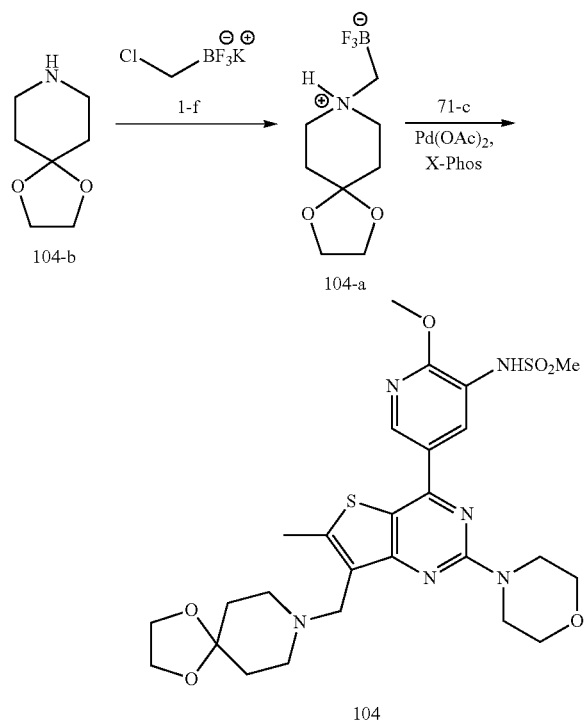

Synthesis of Compound 104-a

According to the method for preparing compound 1-a, purchased compound 104-b was used in the preparation to yield compound 104-a (7.5 g, 76.5%). ¹H NMR (400 MHz, D₂O): δ3.98 (s, 4H), 3.48 (brs, 1H), 3.45 (brs, 1H), 2.99-3.07 (m, 2H), 2.14-2.18 (m, 2H), 1.92-1.94 (m, 4H). Synthesis of compound 104

According to the method for preparing compound 83, compound 104-a was used in the preparation. The residue was purified by silica gel column chromatography (elution system: dichloromethane/methanol=60/1) to yield compound 104 (975 mg, 76.4%), as a yellow solid. LC-MS (ESI): m/z=591.2 (M+H)⁺. ¹H NMR (400 MHz, CDCl₃): δ9.52 (s, 1H), 8.71 (d, J=2.4 Hz, 1H), 8.34 (d, J=2.0 Hz, 1H), 4.04 (s, 3H), 3.80-3.83 (m, 8H), 3.72-3.74 (m, 6H), 3.10 (s, 3H), 2.64 (s, 3H), 2.49-2.51 (m, 4H), 1.57-1.59 (m, 4H).

Synthetic Route of Compound 105

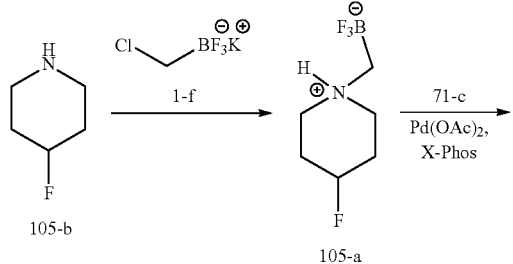

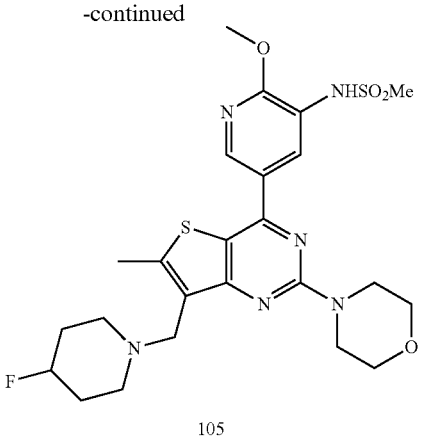

Synthesis of Compound 105-a

According to the method for preparing compound 1-a, purchased compound 105-b was used in the preparation to yield compound 105-a (125 mg, 42%).

Synthesis of Compound 105

According to the method for preparing compound 83, compound 105-a was used in the preparation to yield compound 105 (30 mg, 28%), as a yellow solid. LC-MS (ESI): m/z=551.2 (M+H)⁺. ¹H NMR (400 MHz, CDCl₃): δ 8.74 (1H, d, J=2.0 Hz), 8.55 (1H, d, J=2.0 Hz), 4.51-4.77 (1H, m), 4.10 (3H, s), 3.86-3.94 (4H, m), 3.78-3.86 (4H, m), 3.76 (2H, s), 3.07 (3H, s), 2.64-2.72 (2H, m), 2.64 (3H, s), 2.36-2.52 (2H, m), 1.72-1.97 (4H, m).

Synthetic Route of Compound 106

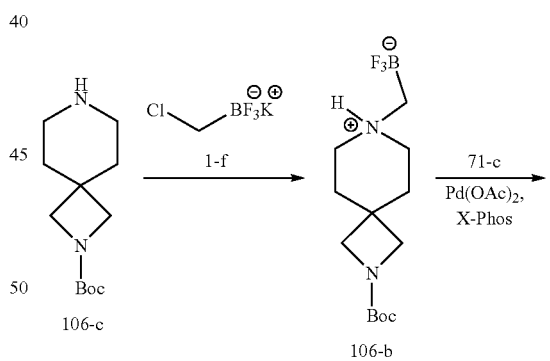

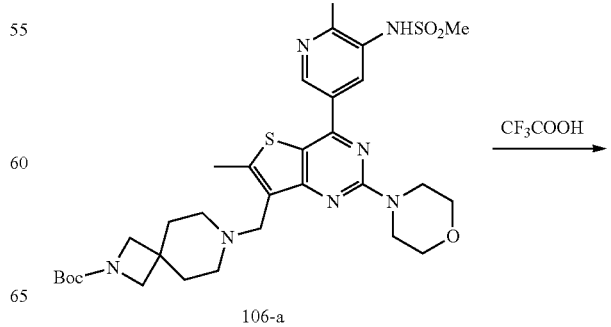

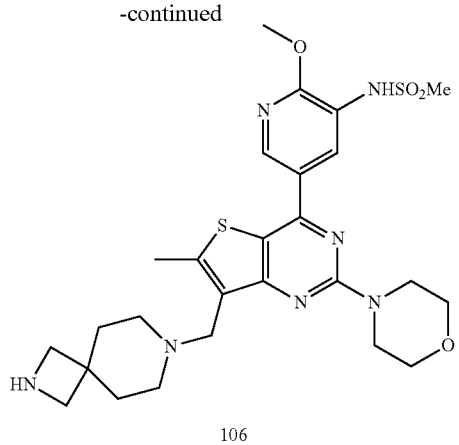

106

Synthesis of Compound 106-b

According to the method for preparing compound 1-a, purchased compound 106-c was used in the preparation to yield compound 106-b (900 mg, 85%).

Synthesis of Compound 106-a

According to the method for preparing compound 83, compound 106-b was used in the preparation to yield compound 106-a (57 mg, 44%), as a yellow solid. LC-MS (ESI): m/z=674.2 (M+H)$^+$. $^1$H NMR (400 MHz, CDCl$_3$): δ 8.75 (d, 1H, J=2.4 Hz), 8.55 (d, 1H, J=2.0 Hz), 4.10 (s, 3H), 3.94 (t, 4H, J=4.0 Hz), 3.86 (t, 6H, J=4.4 Hz), 3.30 (t, 4H, J=5.6 Hz), 3.11 (s, 4H), 3.07 (s, 3H), 2.64 (s, 3H), 1.67 (t, 4H, J=5.6 Hz), 1.43 (s, 9H).

Synthesis of Compound 106

According to the method for preparing compound 43-a, compound 106-a was used in the preparation to yield compound 106 (25 mg, 58%), as a yellow solid. LC-MS (ESI): m/z=574.2 (M+H)$^+$. $^1$H NMR (400 MHz, DMSO-d$_6$): δ 8.35 (d, 1H, J=2.0 Hz), 8.16 (d, 1H, J=2.4 Hz), 3.91 (s, 3H), 3.84 (t, 4H, J=4.0 Hz), 3.76 (s, 2H), 3.73 (t, 4H, J=4.0 Hz), 2.99 (s, 4H), 2.86 (s, 3H), 2.76 (t, 4H, J=5.6 Hz), 2.60 (s, 3H), 1.66 (t, 4H, J=5.6 Hz).

Synthetic Routes of Compounds 107 and 108

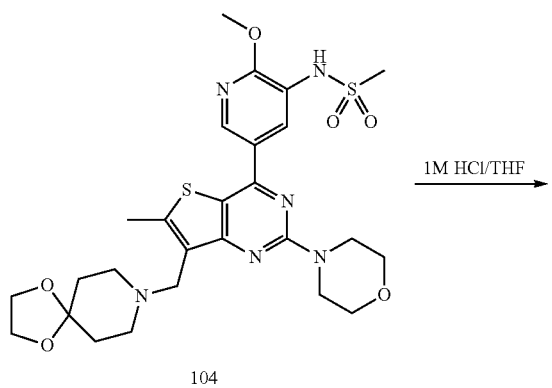

104

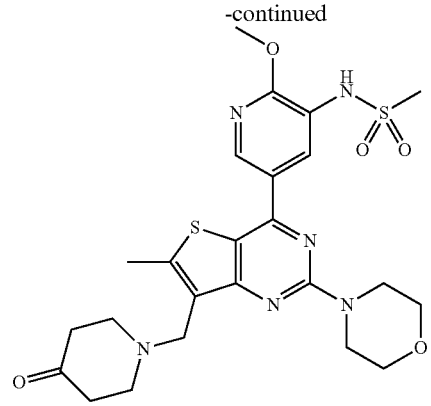

107

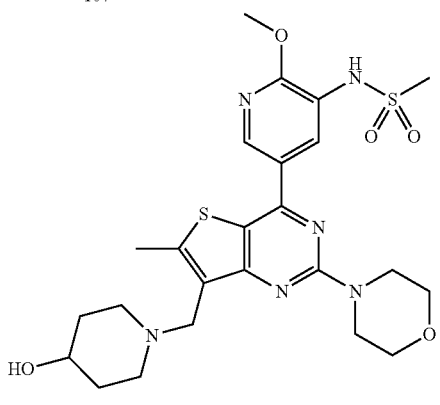

108

Synthesis of Compound 107

At normal temperature, 1 MHCl solution (4 mL) was added dropwise into a suspension of compound 104 (174 mg, 0.30 mmol) in tetrahydrofuran (4 mL). The reaction mixture was stirred at 90° C. overnight. The reaction solution was cooled, and then the mixed liquid was adjusted with sodium bicarbonate aqueous solution to weak basicity, and extracted with dichloromethane. The organic phases were combined, dried over anhydrous sodium sulfate, filtered, and concentrated. The residue was purified by silica gel preparation plate chromatography (developing system: dichloromethane/methanol=10/1) to obtain compound 107 (59 mg, 37%). LC-MS (ESI): m/z=547.2 (M+H)$^+$. $^1$H NMR (400 MHz, CDCl$_3$): δ 8.75 (1H, d, J=2.0 Hz), 8.55 (1H, d, J=2.4 Hz), 6.85 (1H, brs), 4.11 (3H, s), 3.85-3.95 (6H, m), 3.77-3.85 (4H, m), 3.07 (3H, s), 2.76-2.92 (4H, m), 2.69 (3H, s), 2.35-2.53 (4H, m).

Synthesis of Compound 108

At normal temperature, sodium borohydride (10 mg, 0.26 mmol) was added into a solution of compound 107 (43 mg, 0.08 mmol) in methanol (3 mL), and stirred for 1 hr. Then to the reaction solution was added 1 MHCl solution (3 mL), and stirred for 10 minutes. The mixed liquid was adjusted with sodium bicarbonate aqueous solution to weak basicity, and extracted with dichloromethane. The organic phases were combined, dried over anhydrous sodium sulfate, filtered, and concentrated. The residue was purified by silica gel preparation plate chromatography (developing system: dichloromethane/methanol=10/1) to obtain compound 108 (40 mg, 93%). LC-MS (ESI): m/z=549.2 (M+H)⁺. ¹H NMR (400 MHz, CDCl₃): δ8.71 (1H, d, J=2.0 Hz), 8.51 (1H, d, J=2.0 Hz), 4.09 (3H, s), 3.95 (2H, s), 3.83-3.90 (4H, m), 3.68-3.83 (5H, m), 3.06 (3H, s), 2.92-3.03 (2H, m), 2.69 (3H, s), 2.45-2.64 (2H, m), 1.92-2.09 (2H, m), 1.58-1.76 (2H, m).

Synthetic Route of Compound 109

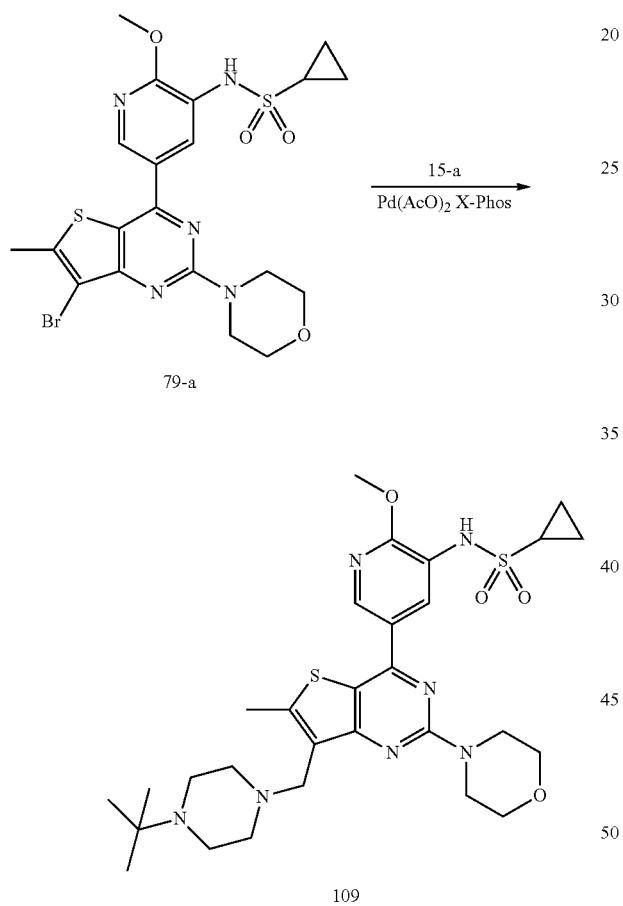

Synthesis of Compound 109

According to the method for preparing compound 80, compound 15-a was used in the preparation to yield compound 109 (27 mg, 33.7%), as a yellow solid. LC-MS (ESI): m/z=616.3 (M+H)⁺. ¹H NMR (400 MHz, CDCl₃): δ8.74 (d, J=2.1 Hz, 1H), 8.57 (d, J=2.1 Hz, 1H), 4.11 (s, 3H), 3.93-3.89 (m, 4H), 3.85-3.81 (m, 4H), 3.80 (s, 2H), 2.64 (s, 3H), 2.62 (s, 1H), 2.56 (m, 8H), 1.26 (dd, J=4.8, 1.9 Hz, 2H), 1.06 (s, 9H), 1.01 (d, J=2.0 Hz, 1H), 0.99 (d, J=1.9 Hz, 1H).

Synthetic Route of Compound 110

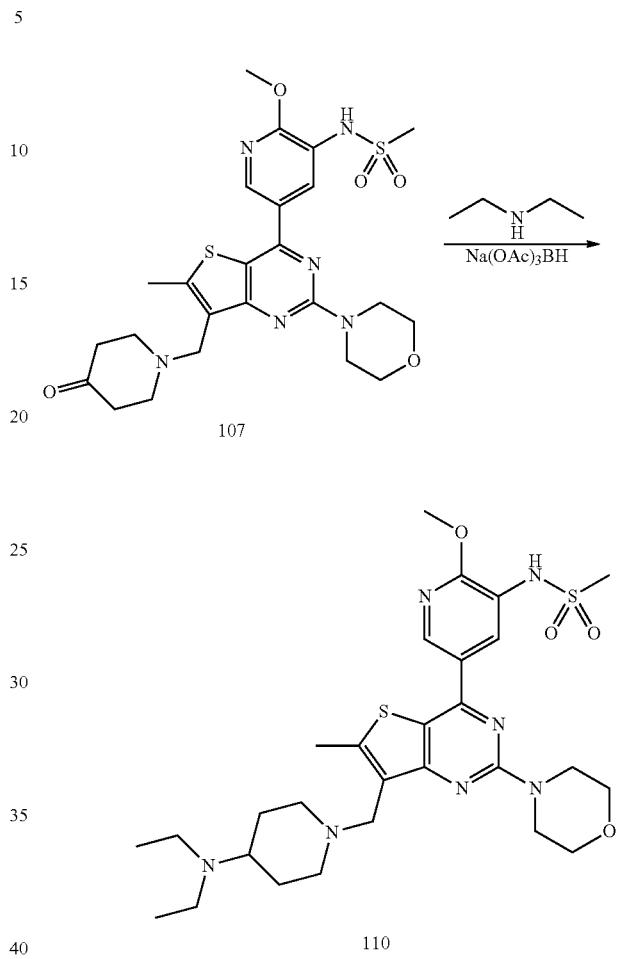

Synthesis of Compound 110

A reaction mixture of compound 107 (50 mg, 0.092 mmol), diethylamine (67 mg, 0.92 mmol), dichloroethane (5.0 mL) and acetic acid (0.02 mL) was stirred at room temperature for 30 minutes, and acetic acid sodium borohydride (97.5 mg, 0.46 mmol) was slowly added, and then stirred at room temperature overnight. The reaction mixture was diluted with saturated sodium carbonate solution (25 mL), and the aqueous phase was extracted with dichloromethane (25 mL×2). The organic phases were combined, dried over anhydrous sodium sulfate, filtered, and concentrated under reduced pressure. The residue was purified by Prep-HPLC to yield compound 110 (8 mg, 14.5%), as a yellow solid. LC-MS (ESI): m/z=604.3 (M+H)⁺. ¹H NMR (400 MHz, CDCl₃): δ8.75 (d, J=2.0 Hz, 1H), 8.56 (d, J=2.4 Hz, 1H), 4.11 (s, 3H), 3.89-3.93 (m, 4H), 3.82-3.86 (m, 4H), 3.75 (s, 2H), 3.08 (s, 3H), 2.97 (d, J=11.6 Hz, 2H), 2.64 (s, 3H), 2.49-2.60 (m, 5H), 2.06-2.11 (m, 2H), 1.72 (d, J=12.0 Hz, 2H), 1.53-1.60 (m, 2H), 1.04 (t, J=7.2 Hz, 6H).

203
Synthetic Route of Compound 111

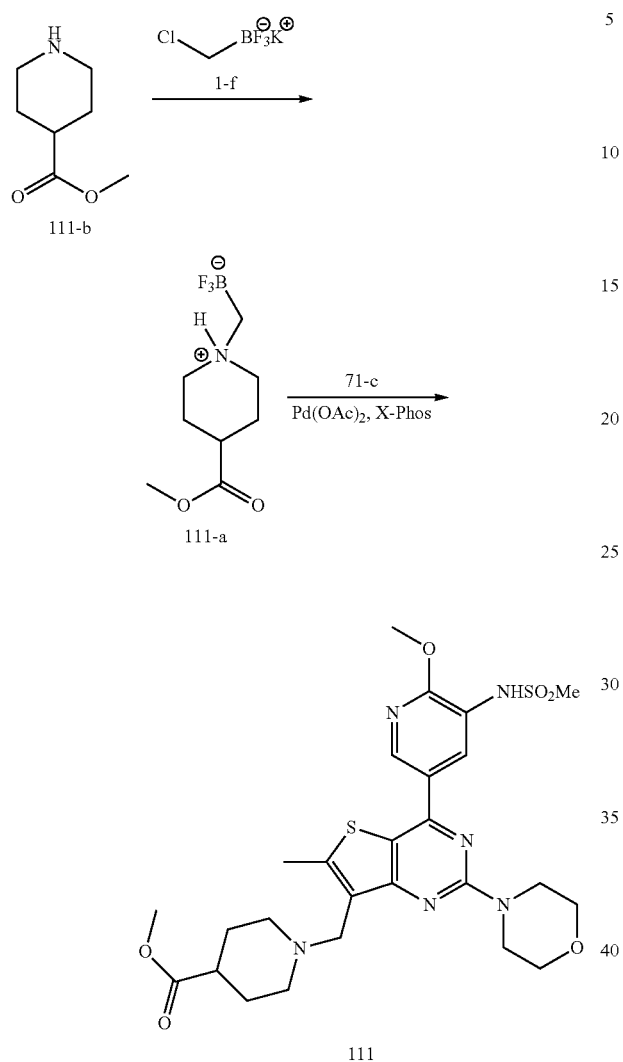

204
Synthetic Route of Compound 112

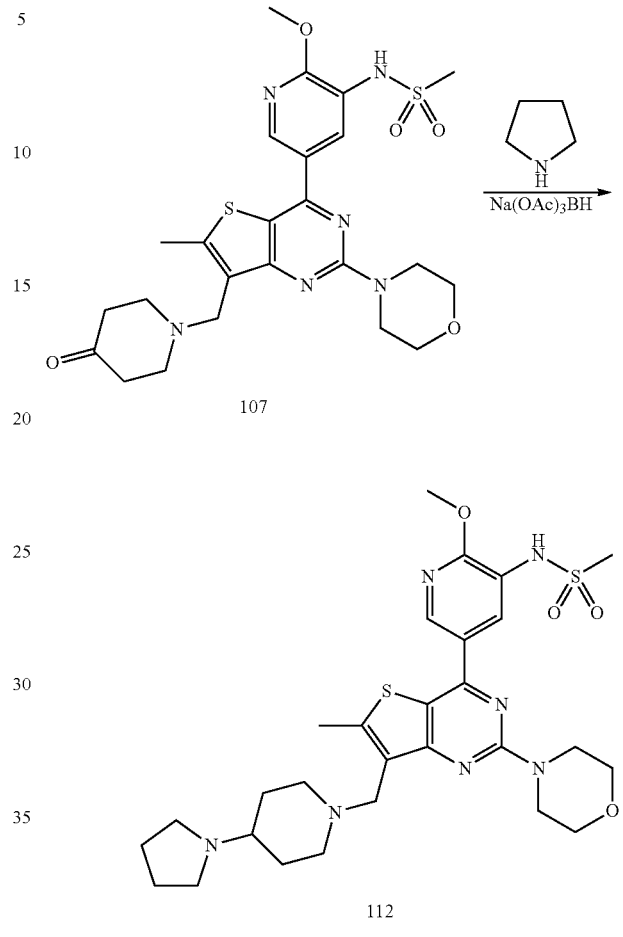

Synthesis of Compound 111-a

According to the method for preparing compound 1-a, purchased compound 111-b was used in the preparation to yield compound 111-a (750 mg, 33%).

Synthesis of Compound 111

According to the method for preparing compound 83, compound 111-a was used in the preparation to yield compound 111 (65 mg, 19%), as a yellow solid. LC-MS (ESI): m/z=591.2 (M+H)+. $^1$H NMR (400 MHz, CDCl$_3$): δ 8.75 (1H, d, J=2.0 Hz), 8.55 (1H, d, J=2.0 Hz), 4.10 (3H, s), 3.87-3.95 (4H, m), 3.78-3.86 (4H, m), 3.74 (2H, s), 3.66 (3H, s), 3.07 (3H, s), 2.80-2.96 (2H, m), 2.64 (3H, s), 2.21-2.34 (1H, m), 2.04-2.22 (2H, m), 1.80-1.92 (2H, m), 1.61-1.79 (2H, m).

Synthesis of Compound 112

According to the method for preparing compound 110, pyrrolidinyl was used in the preparation to yield compound 112 (25 mg, 36.2%), as a yellow solid. LC-MS (ESI): m/z=602.3 (M+H)+. $^1$H NMR (400 MHz, CDCl$_3$): δ 8.74 (d, J=2.4 Hz, 1H), 8.55 (d, J=2.0 Hz, 1H), 4.11 (s, 3H), 3.89-3.93 (m, 4H), 3.82-3.86 (m, 4H), 3.75 (s, 2H), 3.08 (s, 3H), 2.91 (d, J=12.0 Hz, 2H), 2.54-2.64 (m, 7H), 1.98-2.13 (m, 3H), 1.79-1.86 (m, 6H), 1.52-1.61 (m, 2H).

Synthetic Route of Compound 113

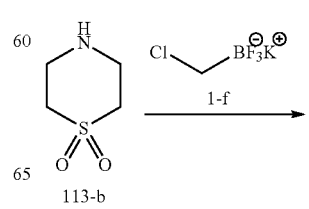

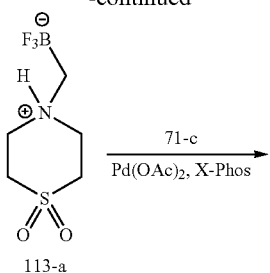

113-a

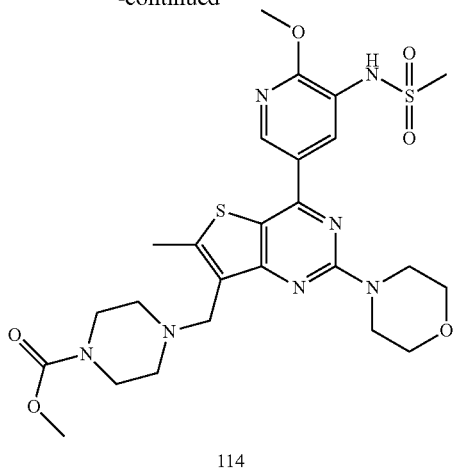

114

Synthesis of Compound 113-a

According to the method for preparing compound 1-a, purchased compound 113-b was used in the preparation to yield compound 113-a (950 mg, 86%).

Synthesis of Compound 113

According to the method for preparing compound 83, compound 113-a was used in the preparation to yield compound 113 (23 mg, 21%), as a yellow solid. LC-MS (ESI): m/z=583.2 (M+H)$^+$. $^1$H NMR (400 MHz, CDCl$_3$): δ 8.74 (d, 1H, J=2.0 Hz), 8.54 (d, 1H, J=2.4 Hz), 6.88 (s, 1H), 4.11 (s, 3H), 3.91 (t, 6H, J=4.4 Hz), 3.84 (t, 4H, J=4.8 Hz), 3.07 (s, 11H), 2.64 (s, 3H).

Synthesis of Compound 114

A mixture of compound 96 (45 mg, 0.084 mmol), methyl chloroformate (8 mg, 0.084 mmol), pyridine (0.033 mL, 0.42 mmol) and dichloromethane (3 mL) was stirred to react at room temperature for 4 hrs. The reaction solution was diluted with dichloromethane (20 mL), and the organic phase was washed with water (10 mL×2). The organic layer was separated, dried over anhydrous sodium sulfate, and concentrated under reduced pressure. The residue was purified by silica gel preparation plate chromatography (developing system: dichloromethane/methanol=10/1) to obtain compound 114 (20 mg, 40%). LC-MS (ESI): m/z=592.2 (M+H)$^+$. $^1$H NMR (400 MHz, CDCl$_3$): δ 8.68 (d, J=2.2 Hz, 1H), 8.48 (d, J=2.2 Hz, 1H), 4.04 (s, 3H), 3.86-3.80 (m, 4H), 3.79-3.73 (m, 4H), 3.69 (s, 2H), 3.61 (s, 3H), 3.38 (s, 4H), 3.01 (s, 3H), 2.57 (s, 3H), 2.40 (s, 4H).

Synthetic Route of Compound 115

Synthetic Route of Compound 114

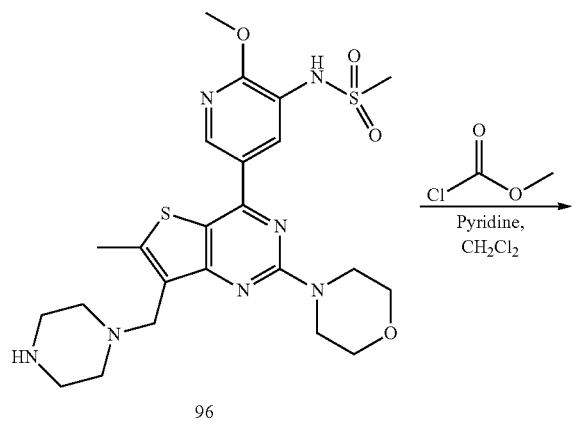

96

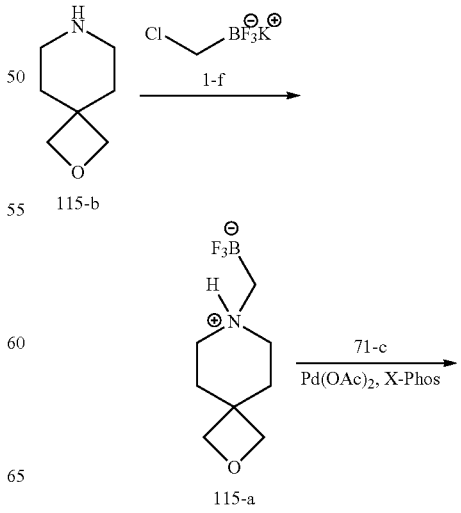

115-b 115-a

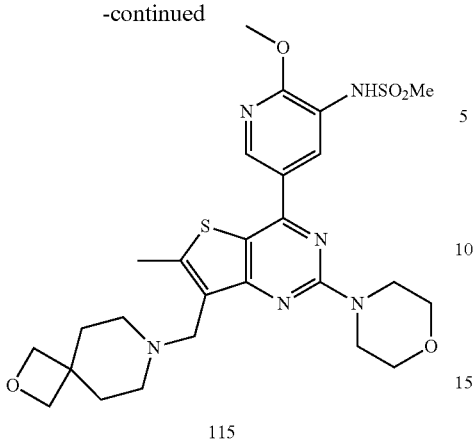

115

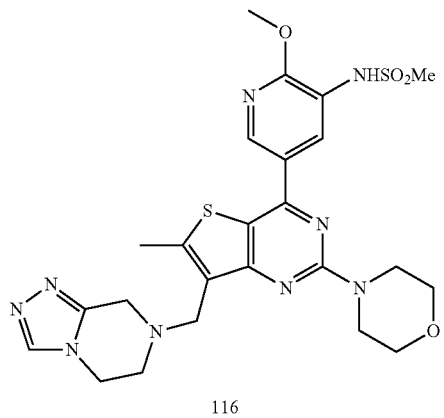

116

Synthesis of Compound 115-a

According to the method for preparing compound 1-a, purchased compound 115-b was used in the preparation to yield compound 115-a (220 mg, 95%).

Synthesis of Compound 115

According to the method for preparing compound 83, compound 115-a was used in the preparation to yield compound 115 (22 mg, 20%), as a yellow solid. LC-MS (ESI): m/z=575.2 (M+H)+. $^1$H NMR (400 MHz, CDCl$_3$): δ 8.74 (1H, d, J=2.4 Hz), 8.55 (1H, d, J=2.4 Hz), 4.39 (4H, s), 4.10 (3H, s), 3.86-3.94 (4H, m), 3.77-3.86 (4H, m), 3.69 (2H, s), 3.07 (3H, s), 2.63 (3H, s), 2.27-2.48 (4H, m), 1.75-1.91 (4H, m).

Synthetic Route of Compound 116

Synthesis of Compound 116-a

According to the method for preparing compound 1-a, purchased compound 116-b was used in the preparation to yield compound 116-a (390 mg, 71%).

Synthesis of Compound 116

According to the method for preparing compound 83, compound 116-a was used in the preparation to yield compound 116 (11 mg, 48%), as a yellow solid. LC-MS (ESI): m/z=572.2 (M+H)+. $^1$H NMR (400 MHz, CDCl$_3$): δ 8.73 (1H, d, J=2.0 Hz), 8.54 (1H, d, J=2.0 Hz), 8.08 (1H, s), 4.10 (3H, s), 4.04 (2H, t, J=5.2 Hz), 3.97 (2H, s), 3.91 (2H, s), 3.85-3.91 (4H, m), 3.75-3.85 (4H, m), 3.07 (3H, s), 2.96 (2H, t, J=5.2 Hz), 2.64 (3H, s).

Synthetic Route of Compound 117

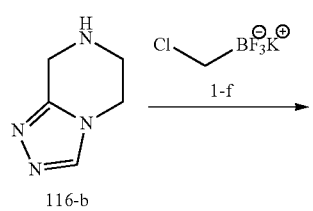

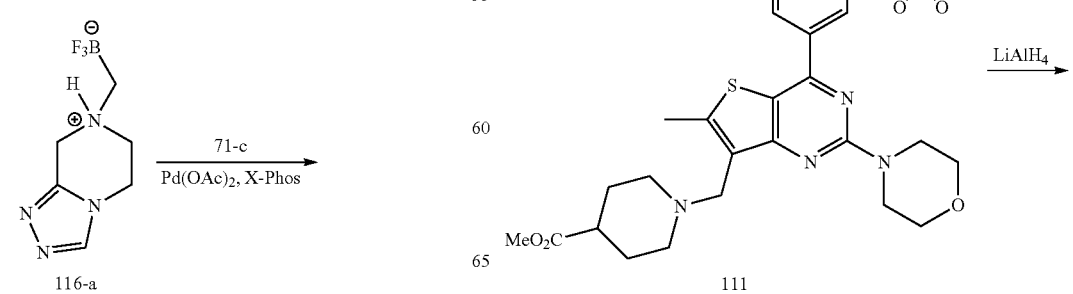

209

-continued

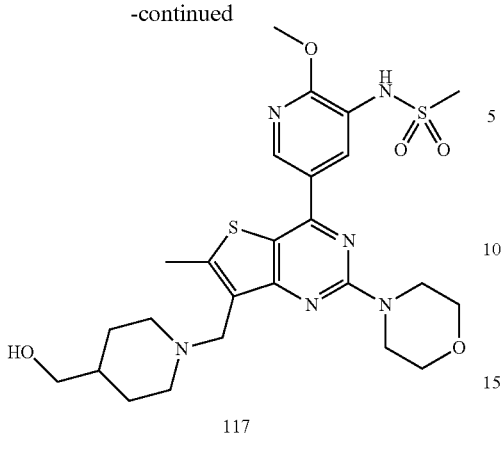

117

Synthesis of Compound 117

A solution of compound 111 (27 mg, 0.046 mmol) in tetrahydrofuran (1.5 mL) was added dropwise into a mixture of lithium aluminium hydride (18 mg, 0.46 mmol) in tetrahydrofuran (2 mL) at −20° C., and then stirred at ice-water bath for 1 hr. The reaction was quenched by adding a little sodium sulfate decahydrate. The reaction solution was sequentially adjusted to acidity by adding HCl/1, 4-dioxane solution, and the reaction solution was adjusted to basicity by adding sodium bicarbonate solid. The mixed liquid was diluted with dichloromethane (20 mL), and the organic phase was washed with water (10 mL×2). The organic layer was separated, dried over anhydrous sodium sulfate, and concentrated under reduced pressure. The residue was purified by silica gel preparation plate chromatography (developing system: dichloromethane/methanol=10/1) to obtain compound 117 (25 mg, 95%). LC-MS (ESI): m/z=563.2 (M+H)$^+$. $^1$H NMR (400 MHz, CD$_3$OD): δ8.67 (1H, d, J=2.0 Hz), 8.51 (1H, d, J=2.4 Hz), 4.10 (3H, s), 3.85-3.96 (4H, m), 3.84 (2H, s), 3.70-3.82 (4H, m), 3.32-3.43 (2H, m), 3.06-3.15 (2H, m), 3.04 (3H, s), 2.65 (3H, s), 2.31 (2H, t, J=11.2 Hz), 1.65-1.87 (2H, m), 1.39-1.53 (1H, m), 1.21-1.35 (2H, m).

Synthetic Route of Compound 118

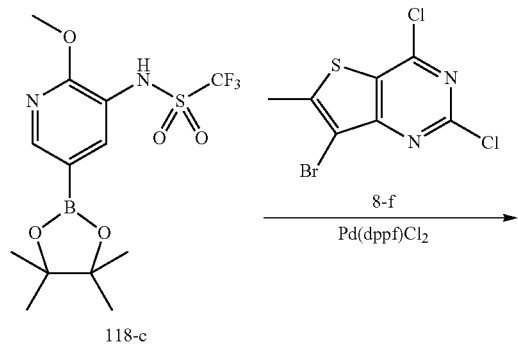

118-c

210

-continued

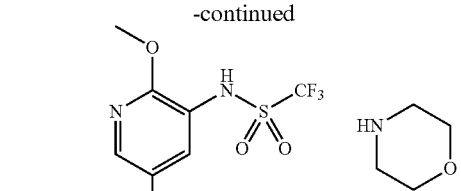

118-b

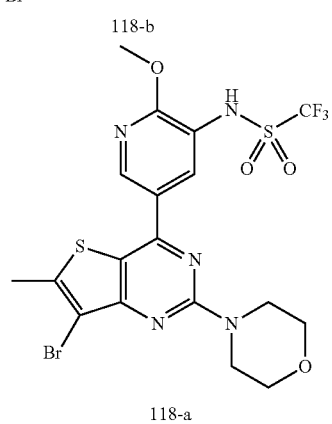

118-a

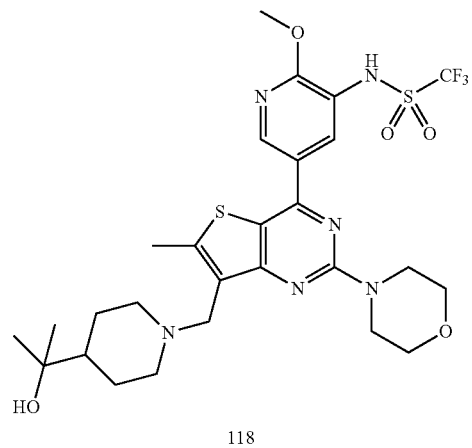

118

Synthesis of Compound 118-b

According to the method for preparing compound 27-b, compound 8-f and compound 118-c (prepared according to the method disclosed in: WO 2012/037108 A1) were used in the preparation to yield compound 118-b (244 mg, 75%), as a yellow solid. LC-MS (ESI): m/z=516.9 (M+H)$^+$.

Synthesis of Compound 118-a

According to the method for preparing compound 27-a, compound 118-b was used in the preparation to yield compound 118-a (250 mg, 93%), as a yellow oil. LC-MS (ESI): m/z=568 (M+H)$^+$.

Synthesis of Compound 118

According to the method for preparing compound 35, compound 118-a was used in the preparation to yield compound 118 (20 mg, 22%). LC-MS (ESI): m/z=645.1 (M+H)+. 1H NMR (400 MHz, DMSO-d6): δ9.02 (1H, s), 8.34 (1H, d, J=2.4 Hz), 8.17 (1H, d, J=2.0 Hz), 4.40 (2H, s), 4.31 (1H, s), 3.86-3.78 (7H, m), 3.73 (4H, t, J=4.8 Hz), 3.58-3.54 (2H, m), 3.09-3.01 (2H, m), 2.73 (3H, s), 1.87-1.81 (2H, m), 1.50-1.45 (3H, m), 1.03 (6H, s).

Synthetic Route of Compound 119

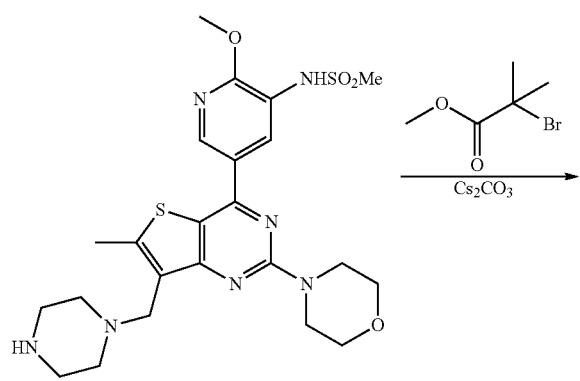

Synthesis of Compound 119-a

A mixture of compound 96 (50 mg, 0.094 mmol.), compound methyl α-bromoisobutyrate (25 mg, 0.14 mmol), cesium carbonate (92 mg, 0.282 mmol) and N, N-dimethylformamide (3 mL) was stirred at 70° C. overnight. The reaction mixture was cooled, and concentrated under reduced pressure. The residue was purified by silica gel preparation plate chromatography (developing system: dichloromethane/methanol=20/1) to obtain compound 119-a (77 mg, 52%). LC-MS (ESI): m/z=634.3 (M+H)+.

Synthesis of Compound 119

According to the method for preparing compound 117, compound 119-a was used in the preparation. The residue was purified by Prep-HPLC to yield compound 119 (12 mg, 18%). LC-MS (ESI): m/z=606.3 (M+H)+. 1H NMR (400 MHz, CDCl3): δ 8.75 (d, J=2.2 Hz, 1H), 8.55 (s, 1H), 4.11 (s, 3H), 3.91 (d, J=4.7 Hz, 4H), 3.84 (d, J=4.7 Hz, 4H), 3.77 (s, 2H), 3.30 (s, 2H), 3.08 (s, 3H), 2.64 (s, 3H), 2.56 (s, 8H), 1.01 (s, 6H).

Synthetic Route of Compound 120

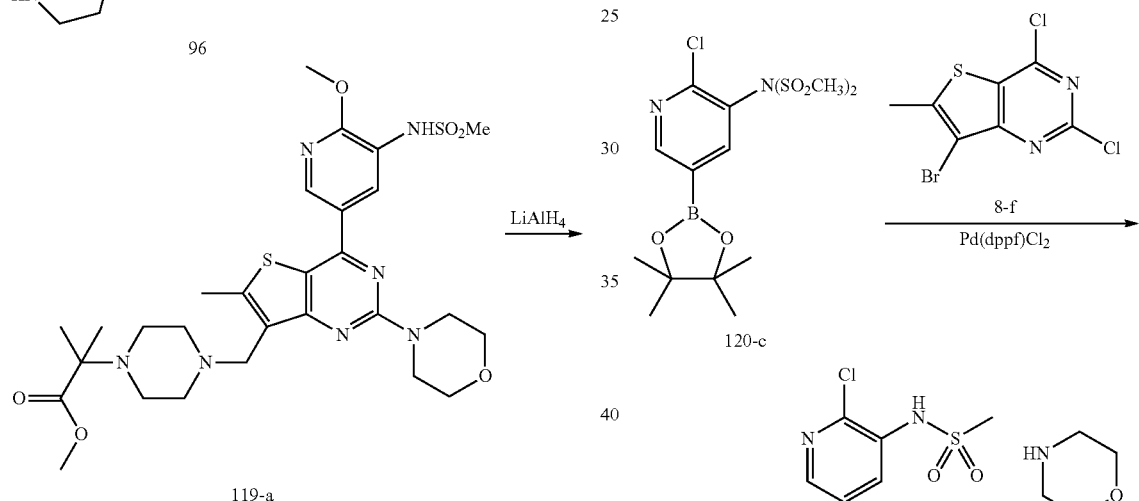

-continued

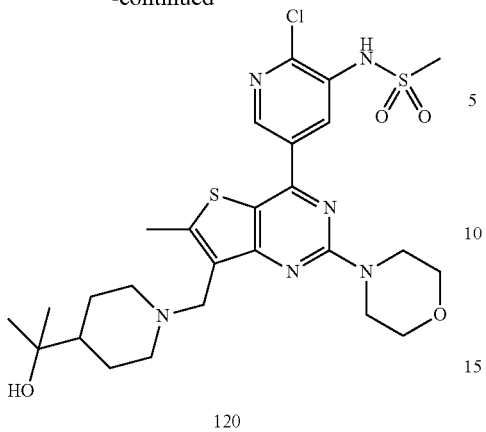

120

Synthesis of Compound 120-b

According to the method for preparing compound 27-b, compound 8-f and compound 120-c (prepared according to the method disclosed in: WO 2010/008847 A2) were used in the preparation to yield compound 120-b (1.36 g, 59%). LC-MS (ESI): m/z=468 (M+H)$^+$.

Synthesis of Compound 120-a

According to the method for preparing compound 27-a, compound 120-b was used in the preparation to yield compound 120-a (1.03 g, 83%). LC-MS (ESI): m/z=519 (M+H)$^+$.

Synthesis of Compound 120

According to the method for preparing compound 35, compound 120-a was used in the preparation to yield compound 120 (8 mg, 16%). LC-MS (ESI): m/z=595.2 (M+H)$^+$. $^1$H NMR (400 MHz, CDCl$_3$): δ8.94 (d, J=2.2 Hz, 1H), 8.72 (d, J=2.2 Hz, 1H), 3.94-3.89 (m, 4H), 3.86-3.82 (m, 4H), 3.78 (s, 2H), 3.14 (s, 3H), 3.03 (d, J=11.2 Hz, 2H), 2.67 (s, 3H), 2.06 (d, J=12.6 Hz, 2H), 1.70 (d, J=12.6 Hz, 2H), 1.40-1.32 (m, 2H), 1.30-1.24 (m, 1H), 1.15 (s, 6H).

Synthetic Route of Compound 121

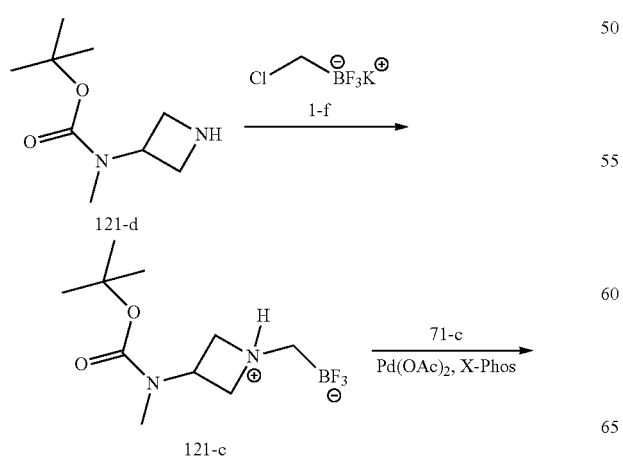

-continued

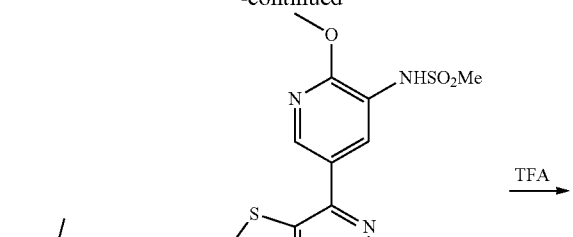

121-b

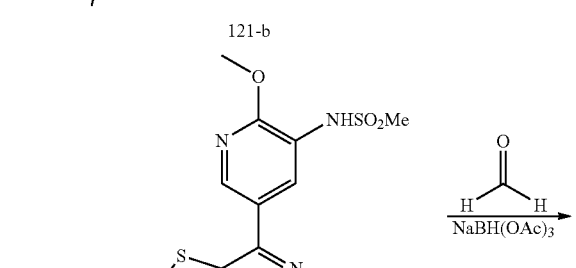

121-a

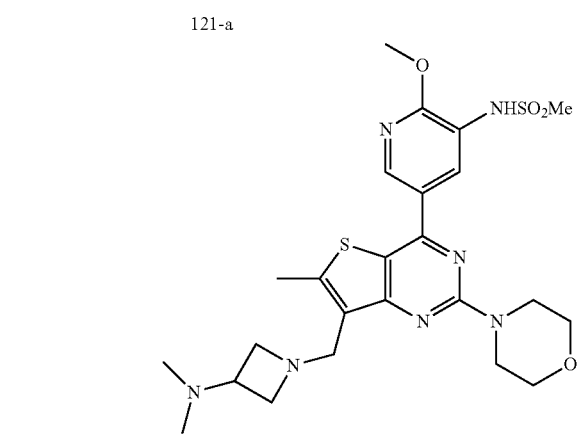

121

Synthesis of Compound 121-c

According to the method for preparing compound 1-a, purchased compound 121-d was used in the preparation to yield compound 121-c (450 mg, 95%).

Synthesis of Compound 121-b

According to the method for preparing compound 83, compound 121-c was used in the preparation to yield compound 121-b (208 mg, 91%). LC-MS (ESI): m/z=634.2 (M+H)$^+$.

215

Synthesis of Compound 121-a

According to the method for preparing compound 43-a, compound 121-b was used in the preparation to yield compound 121-a (175 mg, 100%). LC-MS (ESI): m/z=534.2 (M+H)+.

Synthesis of Compound 121

According to the method for preparing compound 43, compound 121-a was used in the preparation to yield compound 121 (80 mg, 49%). LC-MS (ESI): m/z=548.2 (M+H)+. 1H NMR (400 MHz, CDCl3): δ 8.74 (d, J=2.2 Hz, 1H), 8.55 (d, J=2.2 Hz, 1H), 4.11 (s, 3H), 3.96-3.91 (m, 4H), 3.84 (dd, J=12.1, 7.0 Hz, 6H), 3.55 (s, 2H), 3.13 (s, 2H), 3.08 (s, 3H), 2.89-2.83 (m, 1H), 2.65 (s, 3H), 2.09 (s, 6H).

Synthetic Route of Compound 122

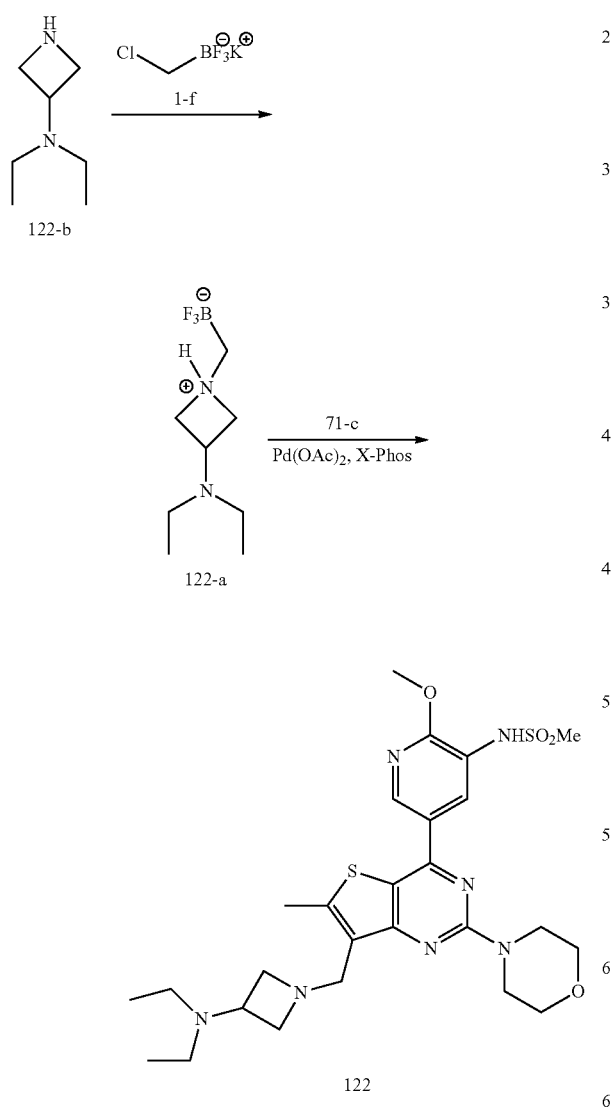

216

Synthesis of Compound 122-a

According to the method for preparing compound 1-a, purchased compound 122-b was used in the preparation to yield compound 122-a (402 mg, 85%).

Synthesis of Compound 122

According to the method for preparing compound 83, compound 122-a was used in the preparation to yield compound 122 (21 mg, 21%), as a yellow solid. LC-MS (ESI): m/z=576.2 (M+H)+. 1H NMR (400 MHz, CDCl3): δ 8.74 (1H, d, J=2.4 Hz), 8.54 (1H, d, J=2.4 Hz), 4.10 (3H, s), 3.87-3.97 (4H, m), 3.76-3.86 (6H, m), 3.53 (2H, t, J=6.4 Hz), 3137-3.29 (1H, m), 3.11 (2H, t, J=6.8 Hz), 3.07 (3H, s), 2.63 (3H, s), 2.46 (4H, q, J=7.2 Hz), 0.96 (6H, t, J=7.2 Hz).

Synthetic Route of Compound 123

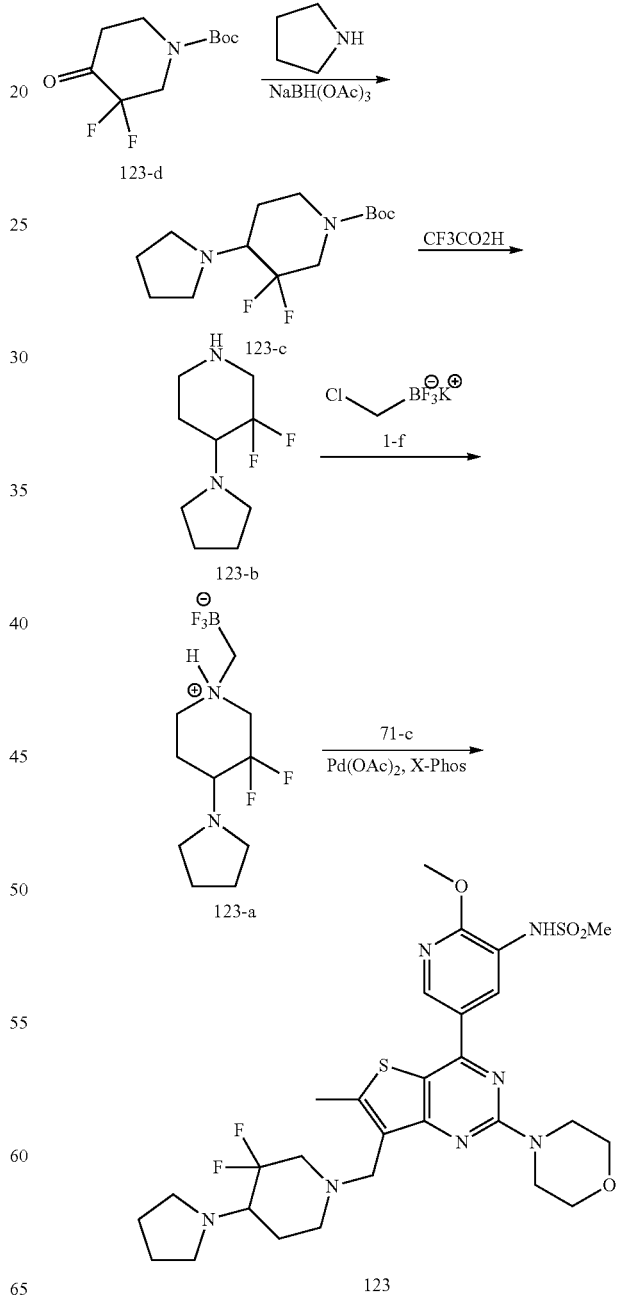

Synthesis of Compound 123-c

A reaction mixture of purchased compound 123-d (370 mg, 1.57 mmol), pyrrolidine (240 mg, 3.14 mmol), 1,2-dichloroethane (20 mL) and acetic acid (0.05 mL) was stirred at room temperature for 30 minutes, and acetic acid sodium borohydride (1.6 g, 7.85 mmol) was slowly added, and then stirred at room temperature overnight. The reaction mixture was diluted with water (10 mL), and extracted with dichloromethane (30 mL×3). The organic phases were combined, dried over anhydrous sodium sulfate, filtered, and concentrated under reduced pressure. The residue was separated and purified by silica gel column chromatography (elution system: with petroleum ether/ethyl acetate=1:1) to yield compound 123-c (350 mg, 76.7%). LC-MS (ESI): m/z=291.3 (M+H)$^+$.

Synthesis of Compound 123-b

A reaction mixture of compound 123-c (350 mg, 1.2 mmol), dichloromethane (10 mL), and trifluoroacetic acid (10 mL) was stirred at room temperature for 2 hrs, and then concentrated under reduced pressure. The residue was partitioned into saturated sodium bicarbonate solution (30 mL) and ethyl acetate (50 mL). The organic phase was separated out, dried over anhydrous sodium sulfate, filtered, and concentrated under reduced pressure to yield compound 123-b (88 mg, 35.9%). LC-MS (ESI): m/z=191.2 (M+H)$^+$.

Synthesis of Compound 123-a

According to the method for preparing compound 1-a, compound 123-b was used in the preparation to yield compound 123-a (110 mg, 88.4%).

Synthesis of Compound 123

According to the method for preparing compound 83, compound 123-a was used in the preparation to yield compound 123 (10 mg, 10.9%). LC-MS (ESI): m/z=638.2 (M+H)$^+$. $^1$H NMR (400 MHz, CDCl$_3$): δ8.75 (1H, d, J=2.0 Hz), 8.56 (1H, d, J=2.0 Hz), 4.11 (3H, s), 3.93-3.90 (4H, m), 3.85-3.82 (6H, m), 3.75-3.70 (1H, m), 3.08 (3H, s), 2.65 (3H, s), 1.77-1.60 (6H, m), 1.38-1.29 (8H, m).

Synthetic Route of Compound 124

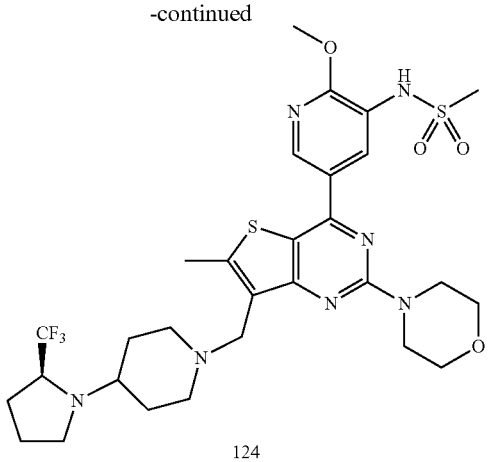

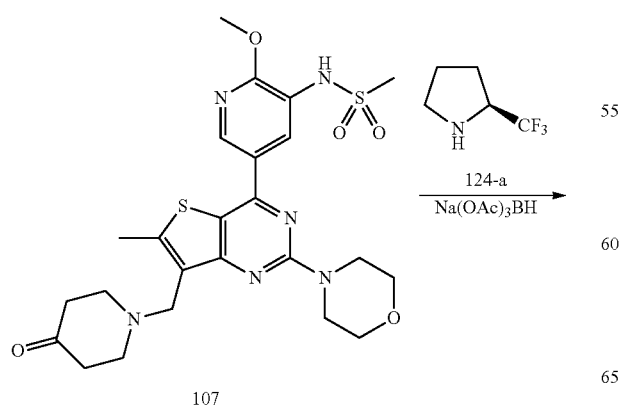

Synthesis of Compound 124

According to the method for preparing compound 110, purchased 124-a was used in the preparation to yield compound 124 (30 mg, 55%), as a yellow solid. LC-MS (ESI): m/z=670.2 (M+H)$^+$. $^1$H NMR (400 MHz, CDCl$_3$): δ 8.74 (1H, d, J=2.0 Hz), 8.54 (1H, d, J=2.0 Hz), 4.01 (3H, s), 3.86-3.97 (4H, m), 3.78-3.86 (4H, m), 3.74 (2H, s), 3.23-3.43 (1H, m), 3.07 (3H, s), 2.89-3.03 (3H, m), 2.66-2.74 (1H, m), 2.63 (3H, s), 2.51-2.62 (1H, m), 2.00-2.19 (2H, m), 1.89-1.99 (1H, m), 1.69-1.89 (4H, m), 1.47-1.69 (3H, m).

Synthetic Route of Compound 125

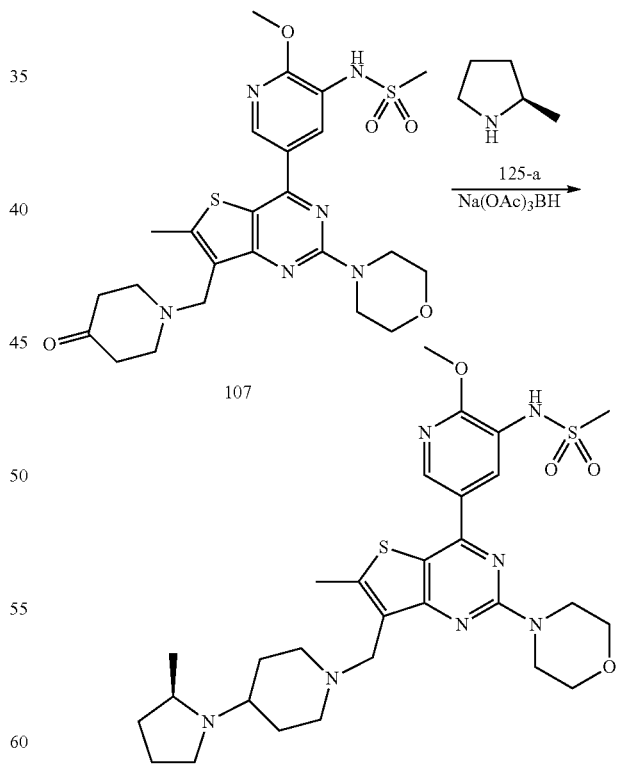

Synthesis of Compound 125

According to the method for preparing compound 110, purchased 125-a was used in the preparation to yield compound 125 (19 mg, 49%), as a yellow solid. LC-MS (ESI): m/z=616.3 (M+H)+. 1H NMR (400 MHz, CDCl3): δ 8.73 (1H, d, J=2.4 Hz), 8.54 (1H, d, J=2.0 Hz), 4.09 (3H, s), 3.86-3.96 (4H, m), 3.78-3.86 (4H, m), 3.75 (2H, s), 3.07 (3H, s), 2.90-3.00 (2H, m), 2.76-2.90 (2H, m), 2.64 (3H, s), 2.41-2.58 (2H, m), 2.00-2.18 (2H, m), 1.80-1.93 (1H, m), 1.57-1.80 (5H, m), 1.45-1.57 (1H, m), 1.32-1.45 (1H, m), 1.02 (3H, d, J=6.0 Hz).

Synthetic Route of Compound 126

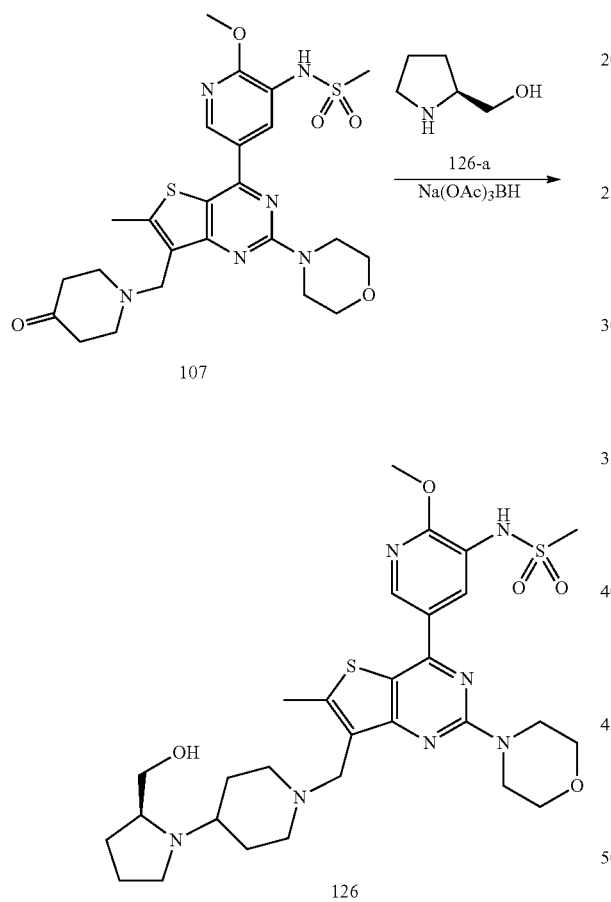

Synthesis of Compound 126

According to the method for preparing compound 110, purchased 126-a was used in the preparation to yield compound 126 (22 mg, 42.3%), as a yellow solid. LC-MS (ESI): m/z=632.3 (M+H)+. 1H NMR (400 MHz, CDCl3): δ 8.75 (1H, d, J=2.0 Hz), 8.55 (1H, d, J=2.0 Hz), 4.11 (3H, s), 3.92 (4H, t, J=4.0 Hz), 3.84 (4H, t, J=4.0 Hz), 3.74 (2H, s), 3.58-3.55 (1H, m), 3.42-3.40 (1H, m), 3.08 (5H, s), 2.98 (2H, t, J=8.4 Hz), 2.64 (5H, s), 2.15-2.06 (2H, m), 1.86-1.69 (6H, m), 1.66-1.57 (2H, m).

Synthetic Route of Compound 127

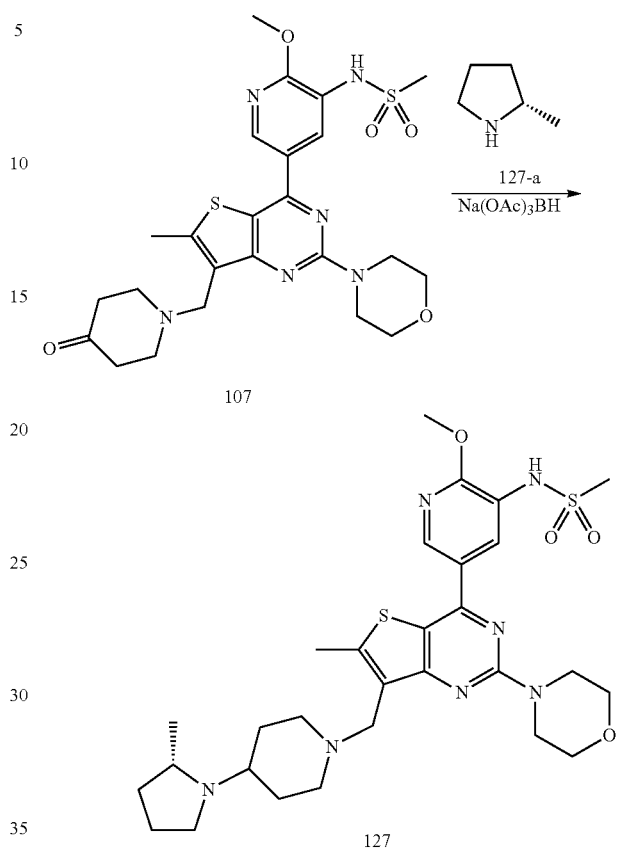

Synthesis of Compound 127

According to the method for preparing compound 110, purchased 127-a was used in the preparation to yield compound 127 (20 mg, 42.6%), as a yellow solid. LC-MS (ESI): m/z=616.3 (M+H)+. 1H NMR (400 MHz, CDCl3): δ 8.75 (d, J=2.0 Hz, 1H), 8.55 (d, J=2.0 Hz, 1H), 4.11 (s, 3H), 3.89-3.93 (m, 4H), 3.82-3.86 (m, 4H), 3.76 (s, 2H), 3.08 (s, 3H), 2.98-3.00 (m, 4H), 2.60-2.69 (m, 5H), 2.07-2.17 (m, 2H), 1.84-1.98 (m, 3H), 1.51-1.76 (m, 5H), 1.14 (d, J=6.4 Hz, 3H).

Synthetic Route of Compound 128

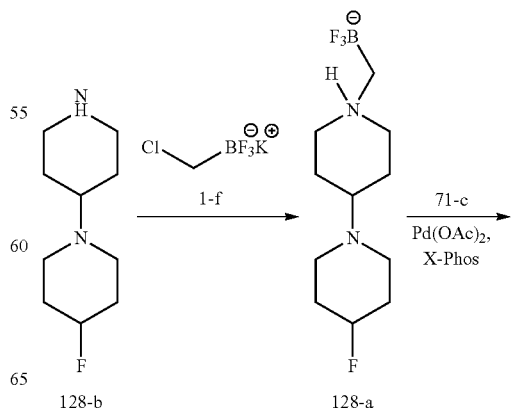

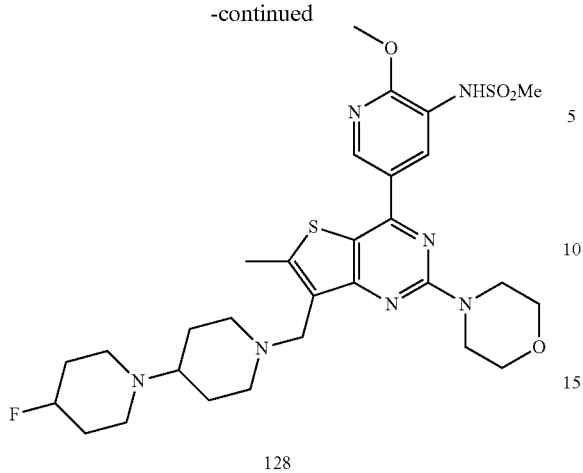

128

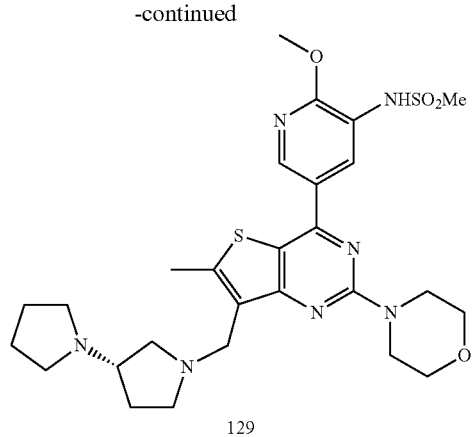

129

Synthesis of Compound 128-a

According to the method for preparing compound 1-a, purchased compound 128-b was used in the preparation to yield compound 128-a (340 mg, 82%).

Synthesis of Compound 128

According to the method for preparing compound 83, compound 128-a was used in the preparation to yield compound 128 (34 mg, 26.6%), as a yellow solid. LC-MS (ESI): m/z=633.3 (M+H)+. $^1$H NMR (400 MHz, CDCl$_3$): δ 8.68 (d, J=2.4 Hz, 1H), 8.49 (d, J=2.4 Hz, 1H), 4.52-4.65 (m, 1H), 4.04 (s, 3H), 3.83-3.86 (m, 4H), 3.75-3.78 (m, 4H), 3.67 (s, 2H), 3.01 (s, 3H), 2.91 (d, J=11.6 Hz, 2H), 2.57-2.63 (m, 5H), 2.39-2.41 (m, 2H), 2.18-2.37 (m, 1H), 2.02 (t, J=11.2 Hz, 2H), 1.77-1.86 (m, 4H), 1.68 (d, J=11.6 Hz, 2H), 1.44-1.53 (m, 2H).

Synthetic Route of Compound 129

Synthesis of Compound 129-a

According to the method for preparing compound 1-a, purchased compound 129-b was used in the preparation to yield compound 129-a (1.5 g, 95%).

Synthesis of Compound 129

According to the method for preparing compound 83, compound 129-a was used in the preparation to yield compound 129 (41 mg, 39%), as a yellow solid. LC-MS (ESI): m/z=588.3 (M+H)+. $^1$H NMR (400 MHz, CDCl$_3$): δ 8.75 (d, 1H, J=2.4 Hz), 8.55 (d, 1H, J=2.0 Hz), 4.10 (s, 3H), 3.92 (t, 4H, J=5.2 Hz), 3.86 (s, 2H), 3.83 (t, 4H, J=5.2 Hz), 3.07 (s, 3H), 2.97 (dd, 1H, J=8.8, 7.2 Hz), 2.80-2.74 (m, 2H), 2.63 (s, 3H), 2.62 (t, 1H, J=8.0 Hz), 2.50-2.41 (m, 5H), 2.04-1.97 (m, 1H), 1.75-1.71 (m, 5H).

Synthetic Route of Compound 130

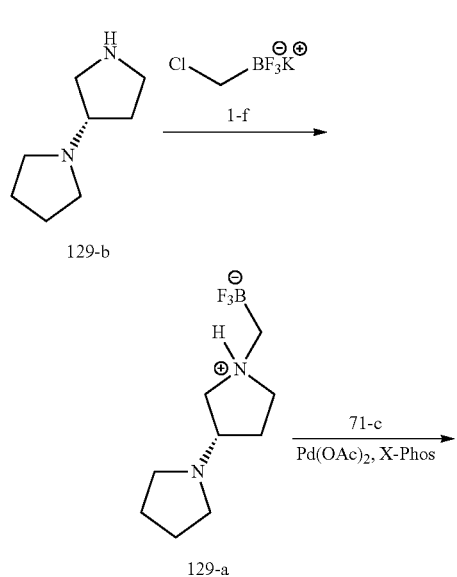

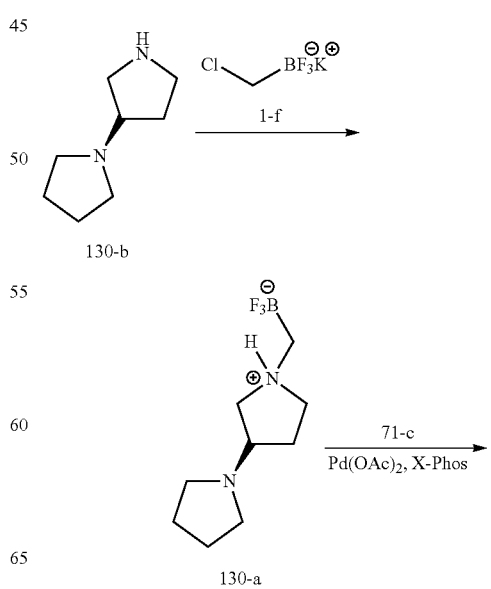

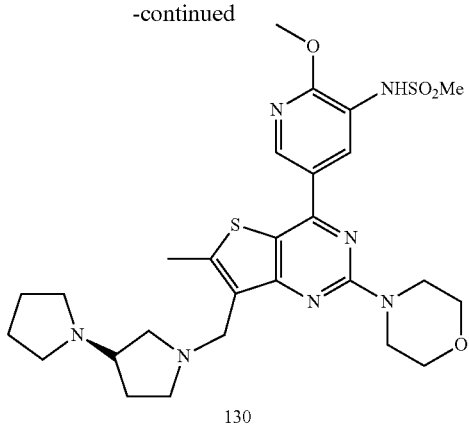

130

Synthesis of Compound 130-a

According to the method for preparing compound 1-a, purchased compound 130-b was used in the preparation to yield compound 130-a (1.63 g, 93%).

Synthesis of Compound 130

According to the method for preparing compound 83, compound 130-a was used in the preparation to yield compound 130 (27 mg, 26%), as a yellow solid. LC-MS (ESI): m/z=588.3 (M+H)+. 1H NMR (400 MHz, CDCl3): δ 8.75 (d, 1H, J=2.4 Hz), 8.55 (d, 1H, J=2.0 Hz), 4.10 (s, 3H), 3.92 (t, 4H, J=5.2 Hz), 3.86 (s, 2H), 3.83 (t, 4H, J=5.2 Hz), 3.07 (s, 3H), 2.97 (dd, 1H, J=8.8, 7.2 Hz), 2.80-2.77 (m, 2H), 2.63 (s, 3H), 2.60 (t, 1H, J=9.2 Hz), 2.50-2.42 (m, 5H), 2.02-1.97 (m, 1H), 1.76-1.70 (m, 5H).

Synthetic Route of Compound 131

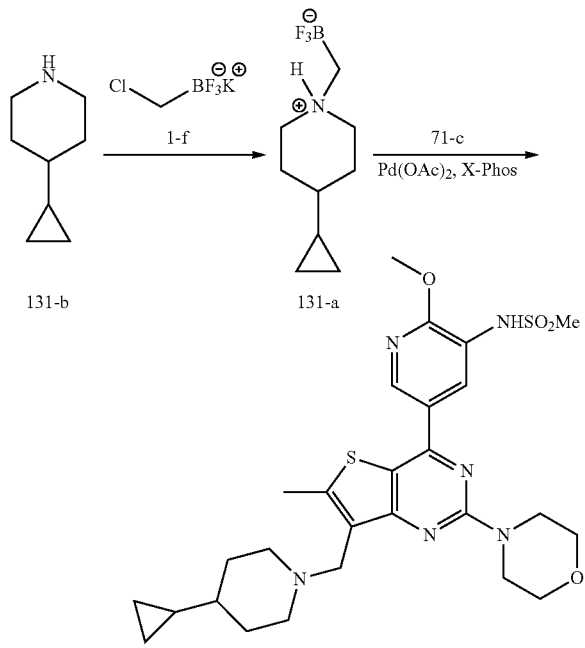

131

Synthesis of Compound 131-a

According to the method for preparing compound 1-a, purchased compound 131-b was used in the preparation to yield compound 131-a (300 mg, 92%).

Synthesis of Compound 131

According to the method for preparing compound 83, compound 131-a was used in the preparation to yield compound 131 (10 mg, 18%). LC-MS (ESI): m/z=573.3 (M+H)+. 1H NMR (400 MHz, CDCl3): δ 8.75 (1H, d, J=2.0 Hz), 8.55 (1H, d, J=2.0 Hz), 4.10 (3H, s), 3.87-3.97 (4H, m), 3.77-3.86 (4H, m), 3.74 (2H, s), 3.07 (3H, s), 2.83-2.98 (2H, m), 2.65 (3H, s), 1.94-2.08 (2H, m), 1.60-1.75 (2H, m), 1.30-1.45 (2H, m), 0.39-0.56 (2H, m), 0.30-0.39 (2H, m), 0.03-0.05 (2H, m).

Synthetic Route of Compound 132

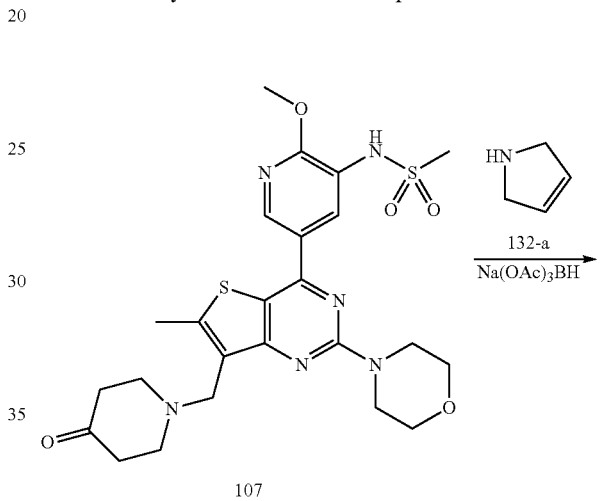

107

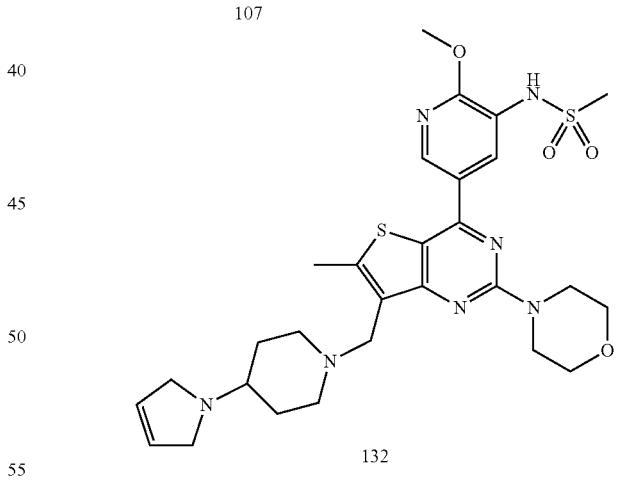

132

Synthesis of Compound 132

According to the method for preparing compound 110, purchased compound 132-a was used in the preparation to yield compound 132 (22 mg, 16%). LC-MS (ESI): m/z=634.2 (M+H)+. 1H NMR (400 MHz, CDCl3): δ 8.68 (d, J=2.4 Hz, 1H), 8.48 (d, J=2.0 Hz, 1H), 5.73 (s, 2H), 4.04 (s, 3H), 3.83-3.86 (m, 4H), 3.75-3.77 (m, 4H), 3.72 (s, 2H), 3.43 (s, 4H), 3.01 (s, 3H), 2.84-2.87 (m, 2H), 2.58 (s, 3H), 2.05-2.30 (m, 3H), 1.75-1.77 (m, 2H), 1.49-1.52 (m, 2H).

225
Synthetic Route of Compound 133

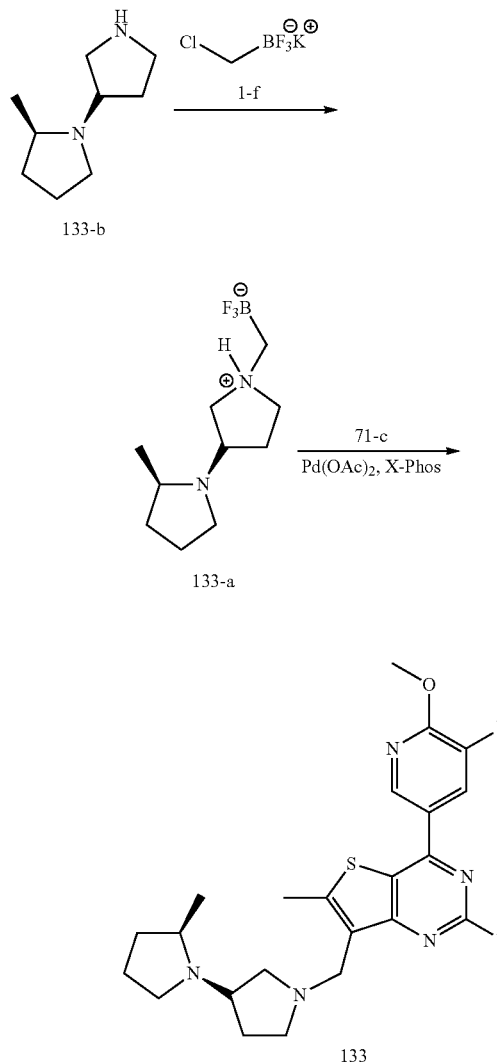

133-b 133-a

133

Synthesis of Compound 133-a

According to the method for preparing compound 1-a, purchased compound 133-b was used in the preparation to yield compound 133-a (732 mg, 95%).

Synthesis of Compound 133

According to the method for preparing compound 83, compound 133-a was used in the preparation to yield compound 133 (15 mg, 14%), as a yellow solid. LC-MS (ESI): m/z=602.2 (M+H)$^+$. $^1$H NMR (400 MHz, CDCl$_3$): δ 8.75 (d, 1H, J=2.4 Hz), 8.55 (d, 1H, J=2.4 Hz), 4.11 (s, 3H), 3.92-3.85 (m, 6H), 3.83 (t, 4H, J=4.8 Hz), 3.44-3.43 (m, 1H), 3.08 (s, 4H), 2.97 (dd, 1H, J=9.2, 7.2 Hz), 2.83-2.82 (m, 1H), 2.70-2.65 (m, 4H), 2.63 (s, 3H), 1.97-1.92 (m, 2H), 1.84-1.79 (m, 2H), 1.74-1.72 (m, 1H), 1.56-1.50 (m, 1H), 1.14 (d, 3H, J=6.0 Hz).

226
Synthetic Route of Compound 134

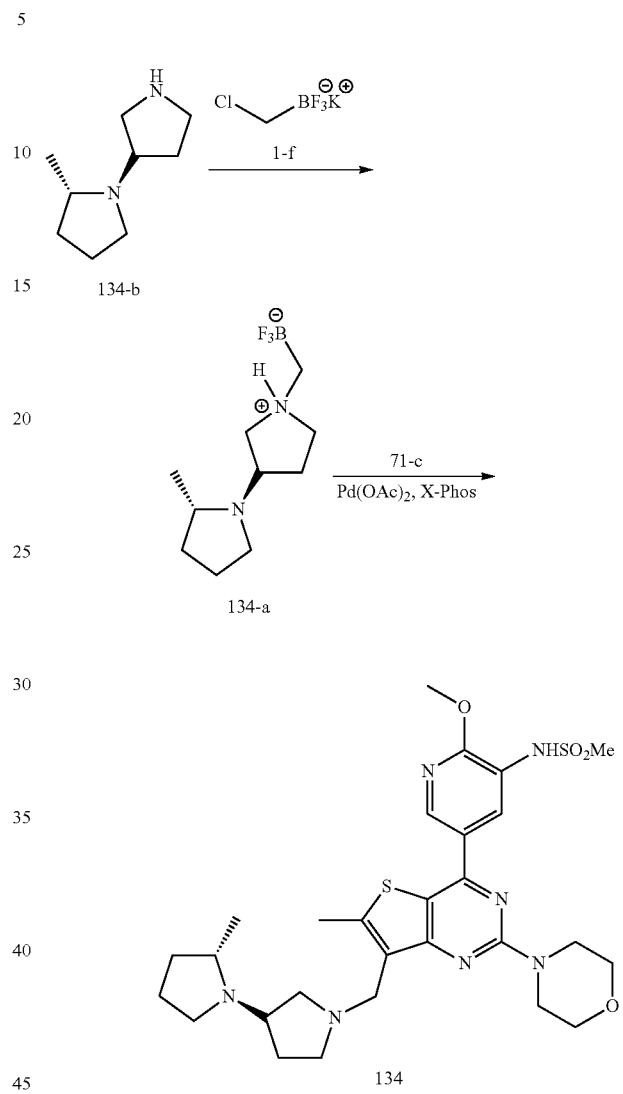

134-b 134-a

134

Synthesis of Compound 134-a

According to the method for preparing compound 1-a, purchased compound 134-b was used in the preparation to yield compound 134-a (830 mg, 93%).

Synthesis of Compound 134

According to the method for preparing compound 83, compound 134-a was used in the preparation to yield compound 134 (19 mg, 20%), as a yellow solid. LC-MS (ESI): m/z=602.2 (M+H)$^+$. $^1$H NMR (400 MHz, CDCl$_3$): δ 8.75 (d, 1H, J=2.4 Hz), 8.55 (d, 1H, J=2.4 Hz), 4.10 (s, 3H), 3.92 (t, 4H, J=4.4 Hz), 3.85-3.80 (m, 6H), 3.27-3.23 (m, 1H), 3.07 (s, 3H), 2.89-2.88 (m, 1H), 2.77-2.73 (m, 1H), 2.69-2.59 (m, 6H), 2.57-2.53 (m, 1H), 2.52-2.46 (m, 1H), 2.04-2.00 (m, 1H), 1.79-1.66 (m, 4H), 1.43-1.38 (m, 1H), 1.07 (d, 3H, J=6.0 Hz).

Synthetic Route of Compound 135

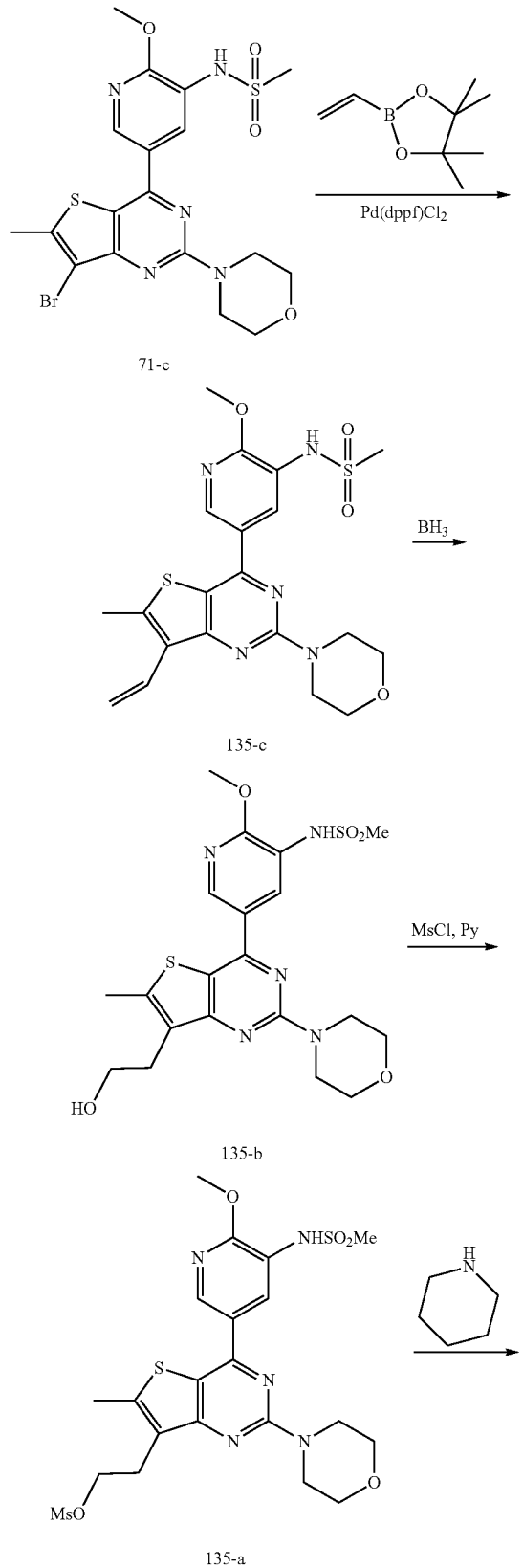

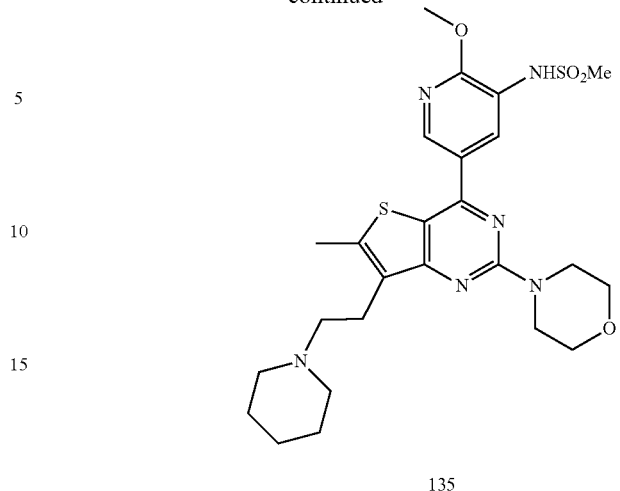

Synthesis of Compound 135-c

Compound 71-c (452 mg, 0.88 mmol), vinyl boronic acid pinacol ester (0.186 mL, 1.06 mmol), PdCl$_2$(dppf) CH$_2$Cl$_2$ (36 mg, 0.44 mmol), potassium carbonate (365 mg, 2.64 mmol), 1,4-dioxane (4.0 mL) and water (1.0 mL) were added to a microwave tube, and under nitrogen atmosphere heated with microwave (110° C.) to react for half an hour. The reaction solution was cooled, filtered, and washed with dichloromethane. The filtrate was concentrated under reduced pressure, and the residue was partitioned into dichloromethane (50 mL) and saturated sodium bicarbonate solution (50 mL), and the organic phase was separated. The organic phase was washed with saturated brine (50 mL), dried over anhydrous sodium sulfate, and concentrated under reduced pressure. The residue was separated and purified by Prep-thin layer plate chromatography (developing system: dichloromethane/methanol=50/1) to obtain compound 135-c (323 mg, 80%), as a pale yellow solid. LC-MS (ESI): m/z 462.1 (M+H)$^+$.

Synthesis of Compound 135-b

In an ice bath and under nitrogen atmosphere, a solution of compound 135-c (223 mg, 0.48 mmol) in tetrahydrofuran (10 mL) was added into 1 M BH$_3$/THF (1.45 mL, 1.45 mmol). The reaction solution was slowly warmed up to room temperature and stirred for 3 hrs, and then hydrogen peroxide (3 mL) and 20% sodium hydroxide solution (3 mL) were added, and stirred overnight. The reaction solution was neutralized with 1N HCl, and then the reaction solution was adjusted with saturated sodium bicarbonate solution to weak basicity, and extracted with dichloromethane (3×20 mL). The organic layers were combined, washed with saturated brine (50 mL), dried over anhydrous sodium sulfate, and concentrated under reduced pressure. The residue was separated and purified by Prep-thin layer plate chromatography (developing system: dichloromethane/methanol=10/1) to obtain compound 135-b (72 mg, 31%), as a pale yellow solid. LC-MS (ESI): m/z 480.1 (M+H)$^+$; $^1$H NMR (400 MHz, CDCl$_3$): δ8.75 (d, 1H, J=2.0 Hz), 8.55 (d, 1H, J=2.0 Hz), 6.88 (s, 1H), 4.11 (s, 3H), 3.90-3.83 (m, 10H), 3.08-3.05 (m, 5H), 2.55 (s, 3H).

Synthesis of Compound 135-a

In an ice bath, pyridine (1 mL) was added to a solution of compound 135-b (32 mg, 0.067 mmol) in dichloromethane (5 mL), and then to the reaction liquid was slowly added methylsulfonyl chloride (16 μL, 0.201 mmol). The reaction solution was slowly warmed to room temperature and stirred for 1 hr. The reaction solution was concentrated under reduced pressure, and the residue was partitioned into dichloromethane (20 mL) and saturated sodium bicarbonate solution (10 mL), and the organic phase was separated. The organic phase was washed with saturated brine (10 mL), dried over anhydrous sodium sulfate, and concentrated under reduced pressure to obtain crude compound 135-a (40 mg, >100%), as a yellow oil, used directly in the next reaction. LC-MS (ESI): m/z 558.1 (M+H)$^+$.

Synthesis of Compound 135

Compound 135-a (40 mg, 0.072 mmol) and piperidine (1.5 mL) were placed into a microwave tube, and heated with microwave (90° C.) and reacted for 15 minutes. The reaction solution was concentrated under reduced pressure, and the residue was partitioned into dichloromethane (20 mL) and saturated sodium bicarbonate solution (10 mL), and the organic phase was separated. The organic phase was washed with saturated brine (10 mL), dried over anhydrous sodium sulfate, and concentrated under reduced pressure. The residue was separated and purified by Prep-thin layer plate chromatography (developing system: dichloromethane/methanol=10/1) to obtain compound 135 (27 mg, two-step 75%), as a pale yellow solid. LC-MS (ESI): m/z 547.2 (M+H)$^+$; $^1$H NMR (400 MHz, CDCl$_3$): δ8.75 (d, 1H, J=2.0 Hz), 8.56 (d, 1H, J=2.4 Hz), 4.10 (s, 3H), 3.93 (t, 4H, J=4.4 Hz), 3.84 (t, 4H, J=4.4 Hz), 3.07 (s, 3H), 3.04-2.99 (m, 2H), 2.59-2.56 (m, 9H), 1.68-1.63 (m, 4H), 1.49-1.48 (m, 2H).

Synthetic Route of Compound 136

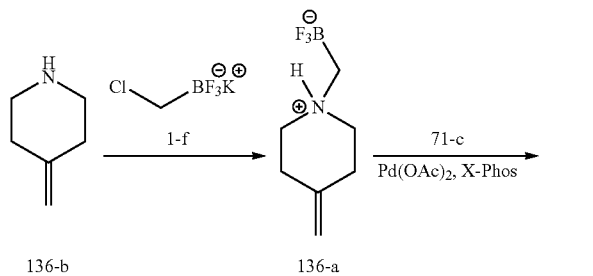

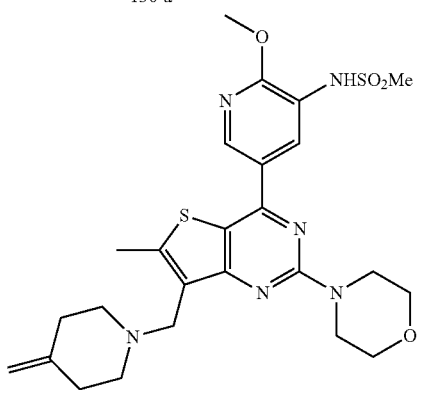

136

Synthesis of Compound 136-a

According to the method for preparing compound 1-a, purchased compound 136-b was used in the preparation to yield compound 115-a (450 mg, 98%).

Synthesis of Compound 136

According to the method for preparing compound 83, compound 136-a was used in the preparation to yield compound 136 (40 mg, 59%). LC-MS (ESI): m/z=545.2 (M+H)$^+$. $^1$H NMR (400 MHz, CDCl$_3$): δ8.75 (1H, d, J=2.4 Hz), 8.55 (1H, d, J=2.0 Hz), 4.63 (2H, s), 4.10 (3H, s), 3.91 (4H, t, J=4.0 Hz), 3.82 (4H, t, J=4.8 Hz), 3.78 (2H, s), 3.07 (3H, s), 2.66 (3H, s), 2.53 (4H, t, J=5.6 Hz), 2.22 (4H, t, J=5.6 Hz).

Synthetic Route of Compound 137

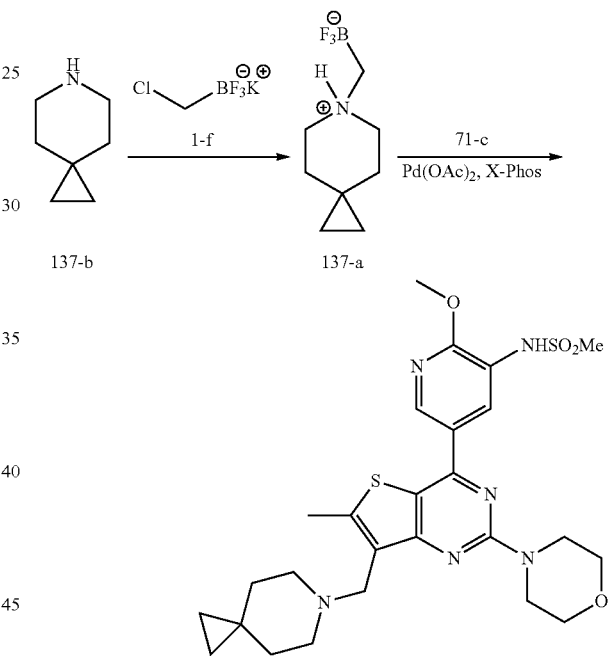

137

Synthesis of Compound 137-a

According to the method for preparing compound 1-a, purchased compound 137-b was used in the preparation to yield compound 137-a (620 mg, 92%).

Synthesis of Compound 137

According to the method for preparing compound 83, compound 137-a was used in the preparation to yield compound 137 (25 mg, 23%). LC-MS (ESI): m/z=559.2 (M+H)$^+$. $^1$H NMR (400 MHz, CDCl$_3$): δ 8.75 (1H, d, J=2.4 Hz), 8.56 (1H, d, J=2.0 Hz), 4.11 (3H, s), 2.87-2.97 (4H, m), 3.81-3.87 (4H, m), 3.79 (2H, s), 3.08 (3H, s), 2.66 (3H, s), 2.44-2.59 (4H, m), 1.21-1.55 (4H, m), 0.24 (4H, s).

Synthetic Route of Compound 138

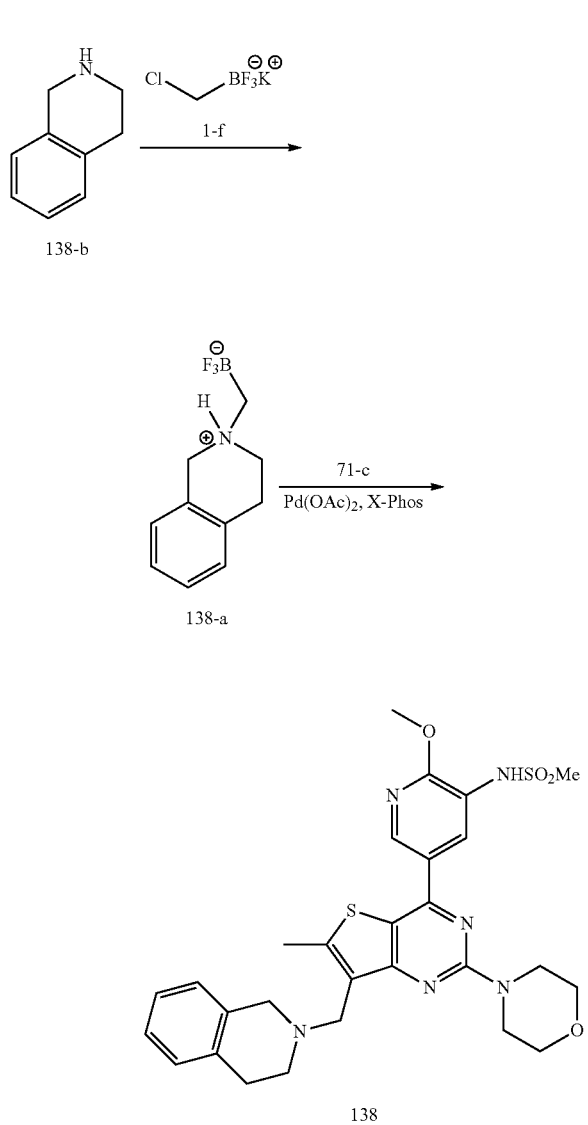

Synthesis of Compound 138-a

According to the method for preparing compound 1-a, purchased compound 138-b was used in the preparation to yield compound 138-a (600 mg, 45.1%).

Synthesis of Compound 138

According to the method for preparing compound 83, compound 138-a was used in the preparation to yield compound 138 (38 mg, 33.6%). LC-MS (ESI): m/z=581.2 (M+H)+. ¹H NMR (400 MHz, CDCl$_3$): δ 8.76 (d, J=2.4 Hz, 1H), 8.57 (d, J=2.0 Hz, 1H), 7.10-7.12 (m, 3H), 6.97-7.00 (m, 1H), 4.11 (s, 3H), 3.90-3.98 (m, 6H), 3.76-3.84 (m, 6H), 3.08 (s, 3H), 2.91 (brs, 4H), 2.71 (s, 3H).

Synthetic Route of Compound 139

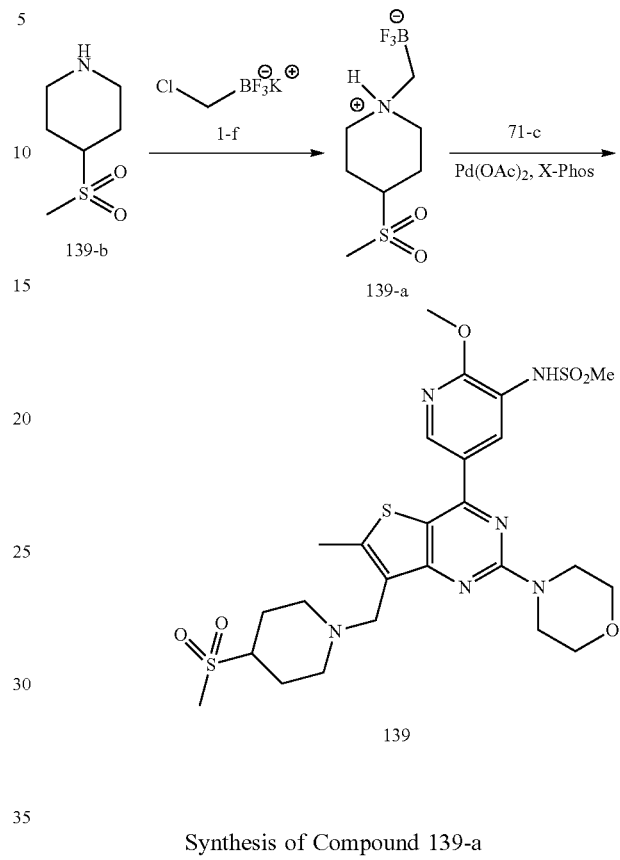

Synthesis of Compound 139-a

According to the method for preparing compound 1-a, purchased compound 139-b was used in the preparation to yield compound 139-a (126 mg, 32%).

Synthesis of Compound 139

According to the method for preparing compound 83, compound 139-a was used in the preparation to yield compound 139 (20 mg, 28%), as a pale yellow solid. LC-MS (ESI): m/z=611.2 (M+H)+. ¹H NMR (400 MHz, CDCl$_3$): δ 8.75 (d, 1H, J=2.0 Hz), 8.55 (d, 1H, J=2.4 Hz), 6.86 (s, 1H), 4.11 (s, 3H), 3.92 (t, 4H, J=4.0 Hz), 3.84 (t, 4H, J=4.0 Hz), 3.78 (s, 2H), 3.08 (s, 5H), 2.81 (s, 4H), 2.65 (s, 3H), 2.16-2.09 (m, 4H), 1.86-1.84 (m, 2H).

Synthetic Route of Compound 140

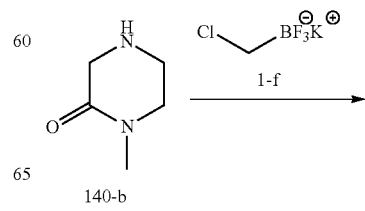

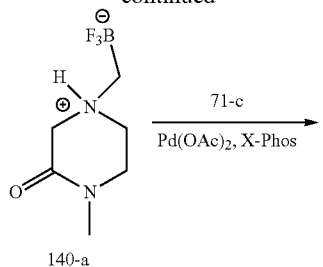

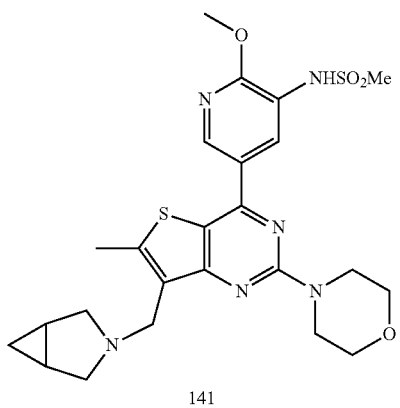

Synthesis of Compound 140-a

According to the method for preparing compound 1-a, purchased compound 140-b was used in the preparation to yield compound 140-a (516 mg, 95%).

Synthesis of Compound 140

According to the method for preparing compound 83, compound 140-a was used in the preparation to yield compound 140 (23 mg, 21%), as a pale yellow solid. LC-MS (ESI): m/z=562.2 (M+H)$^+$. $^1$H NMR (400 MHz, CDCl$_3$): δ 8.74 (d, 1H, J=2.4 Hz), 8.55 (d, 1H, J=2.0 Hz), 6.88 (s, 1H), 4.11 (s, 3H), 3.92 (t, 4H, J=4.0 Hz), 3.84 (t, 4H, J=4.4 Hz), 3.79 (s, 2H), 3.30 (t, 2H, J=5.2 Hz), 3.21 (s, 2H), 3.08 (s, 3H), 2.93 (s, 3H), 2.78 (t, 2H, J=5.2 Hz), 2.64 (s, 3H).

Synthetic Route of Compound 141

Synthesis of Compound 141-a

According to the method for preparing compound 1-a, purchased compound 141-b was used in the preparation to yield compound 141-a (1.0 g, 96%).

Synthesis of Compound 141

According to the method for preparing compound 83, compound 141-a was used in the preparation to yield compound 141 (40 mg, 25.8%). LC-MS (ESI): m/z=531.2 (M+H)$^+$. $^1$H NMR (400 MHz, CDCl$_3$): δ 8.67 (d, J=2.0 Hz, 1H), 8.48 (d, J=2.0 Hz, 1H), 4.02 (s, 3H), 3.74-3.85 (m, 10H), 3.00 (s, 3H), 2.82 (d, J=8.8 Hz, 2H), 2.52 (s, 3H), 2.43 (d, J=8.0 Hz, 2H), 1.18-1.22 (m, 2H), 0.61-0.64 (m, 1H), 0.21-0.25 (m, 1H).

Synthetic Route of Compound 142

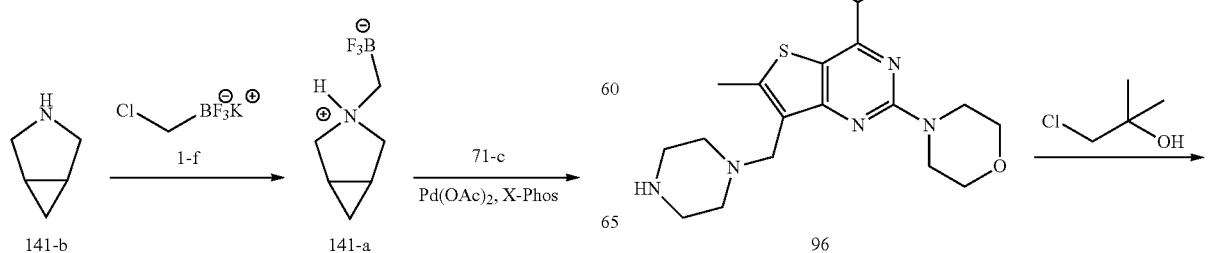

235

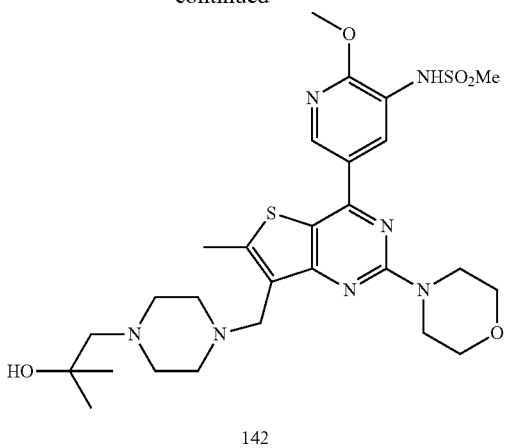

142

Synthesis of Compound 142

According to the method for preparing compound 13, compound 96 was used in the preparation to yield compound 142 (28 mg, 25%). LC-MS (ESI): m/z=606.2 (M+H)+. 1H NMR (400 MHz, CDCl3): δ8.75 (d, J=2.1 Hz, 1H), 8.55 (d, J=2.1 Hz, 1H), 4.10 (s, 3H), 3.94-3.90 (m, 4H), 3.86-3.82 (m, 4H), 3.76 (s, 2H), 3.08 (s, 3H), 2.64 (s, 7H), 2.55 (s, 4H), 2.30 (s, 2H), 1.14 (s, 6H).

Synthetic Route of Compound 143

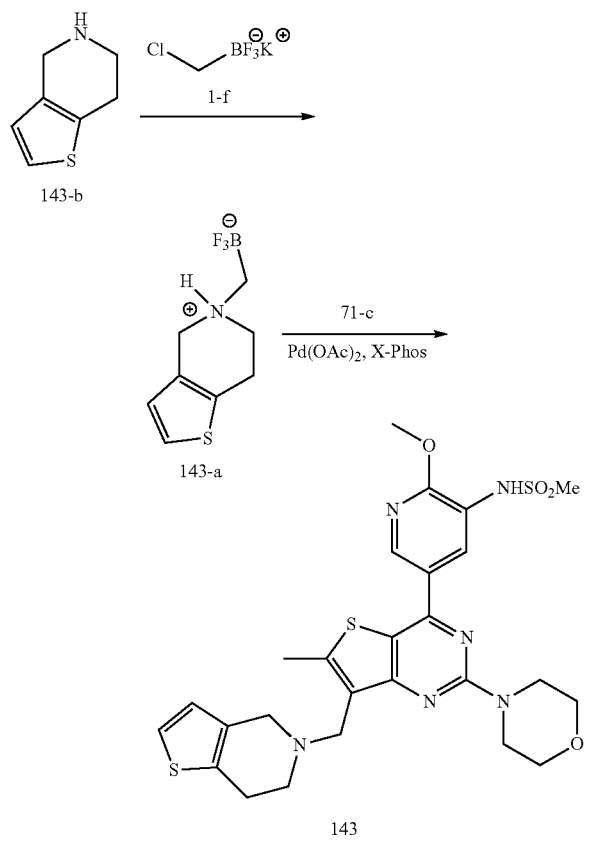

143

236

Synthesis of Compound 143-a

According to the method for preparing compound 1-a, purchased compound 143-b was used in the preparation to yield compound 143-a (700 mg, 90%).

Synthesis of Compound 143

According to the method for preparing compound 83, compound 143-a was used in the preparation to yield compound 143 (70 mg, 74.7%). LC-MS (ESI): m/z=587.2 (M+H)+. 1H NMR (400 MHz, CDCl3): δ 8.76 (d, J=2.4 Hz, 1H), 8.57 (d, J=2.4 Hz, 1H), 7.07 (d, J=4.8 Hz, 1H), 6.82 (brs, 1H), 6.70 (d, J=5.2 Hz, 1H), 4.11 (s, 3H), 3.98 (brs, 2H), 3.90-3.94 (m, 4H), 3.82-3.84 (m, 4H), 3.68 (brs, 2H), 3.08 (s, 3H), 2.93 (brs, 4H), 2.70 (s, 3H).

Synthetic Route of Compound 144

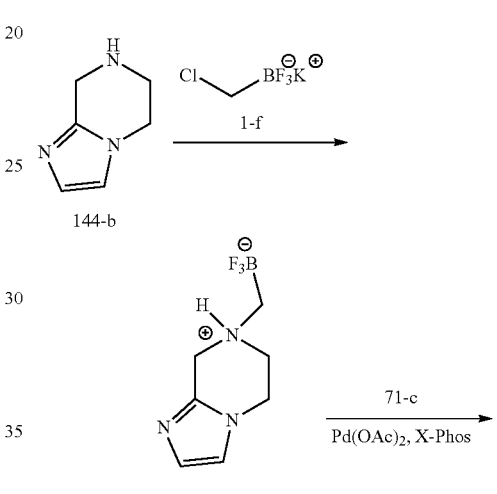

144

Synthesis of Compound 144-a

According to the method for preparing compound 1-a, purchased Compound 144-b was used in the preparation to yield compound 144-a (260 mg, 93%).

Synthesis of Compound 144

According to the method for preparing compound 83, compound 144-a was used in the preparation to yield compound 144 (50 mg, 45%). LC-MS (ESI): m/z=571 (M+H)+. 1H NMR (400 MHz, CDCl3): δ 8.75 (d, J=1.6 Hz, 1H), 8.56 (d, J=1.6 Hz, 1H), 6.90 (brs, 2H), 4.11 (s, 3H), 3.83-3.95 (m, 14H), 3.08 (s, 3H), 2.95 (s, 2H), 2.66 (s, 3H).

Synthetic Route of Compound 145

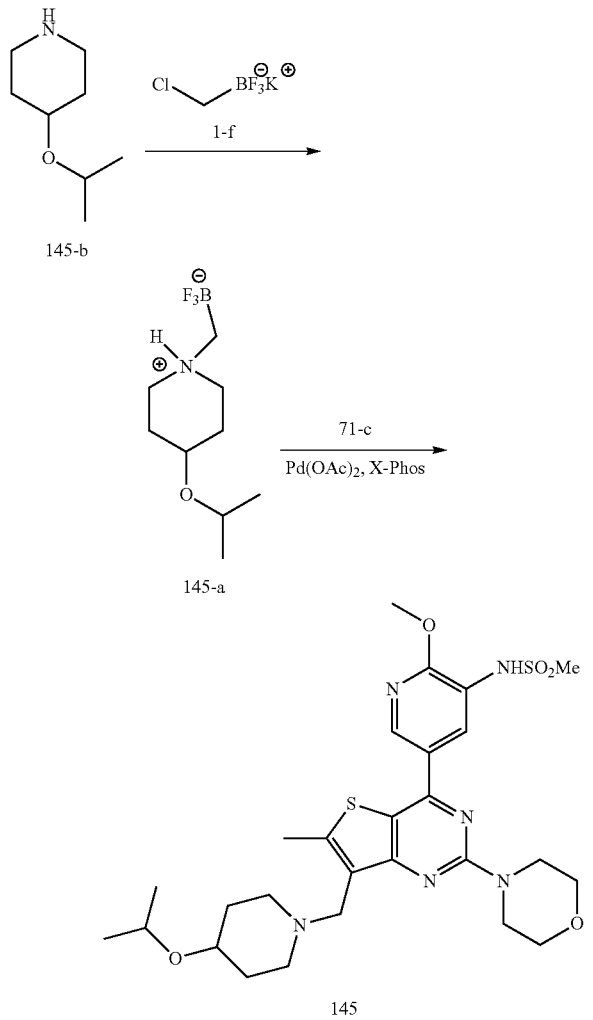

Synthesis of Compound 145-a

According to the method for preparing compound 1-a, purchased compound 145-b was used in the preparation to yield compound 145-a (800 mg, 94%).

Synthesis of Compound 145

According to the method for preparing compound 83, compound 145-a was used in the preparation to yield compound 145 (15 mg, 15%). LC-MS (ESI): m/z=591.3 (M+H)+. 1H NMR (400 MHz, CDCl3): δ 8.72 (d, J=2.2 Hz, 1H), 8.53 (d, J=2.2 Hz, 1H), 4.83 (s, 1H), 4.41 (s, 2H), 4.12 (s, 3H), 3.93-3.89 (m, 4H), 3.85-3.82 (m, 4H), 3.65-3.58 (m, 1H), 3.39 (d, J=11.4 Hz, 2H), 3.25 (t, J=11.4 Hz, 2H), 3.08 (s, 3H), 2.73 (s, 3H), 2.07 (d, J=12.6 Hz, 2H), 1.88 (d, J=15.0 Hz, 2H), 1.14-1.11 (m, 6H).

Synthetic Route of Compound 146

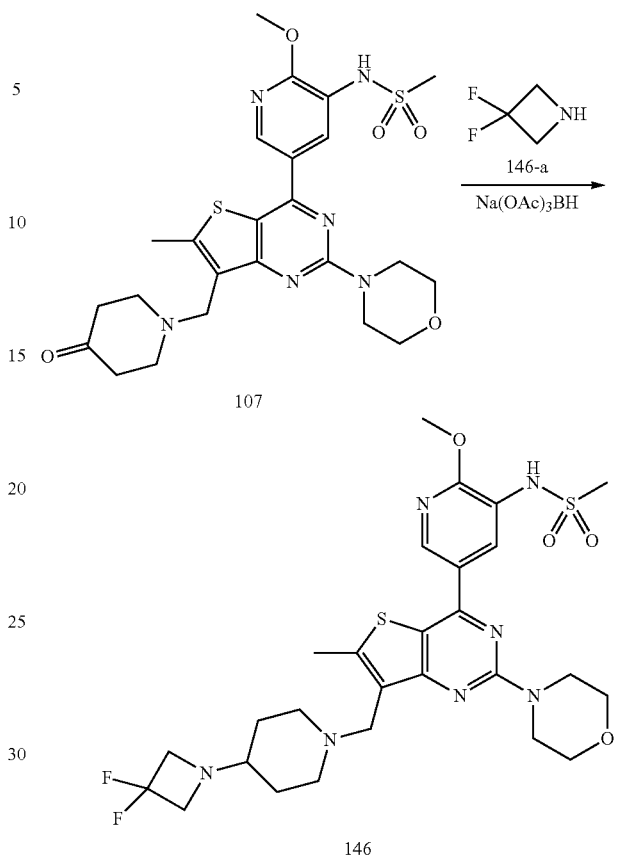

Synthesis of Compound 146

According to the method for preparing compound 110, purchased compound 146-a was used in the preparation to yield compound 146 (40 mg, 43.7%). LC-MS (ESI): m/z=624.3 (M+H)+. 1H NMR (400 MHz, CDCl3): δ8.74 (1H, d, J=2.0 Hz), 8.55 (1H, d, J=2.0 Hz), 4.10 (3H, s), 3.86-3.96 (4H, m), 3.78-3.86 (4H, m), 3.75 (2H, s), 3.52 (4H, t, J=12.0 Hz), 3.07 (3H, s), 2.76-2.89 (2H, m), 2.63 (3H, s), 2.02-2.21 (3H, m), 1.54-1.70 (2H, m), 1.28-1.45 (2H, m).

Synthetic Route of Compound 147

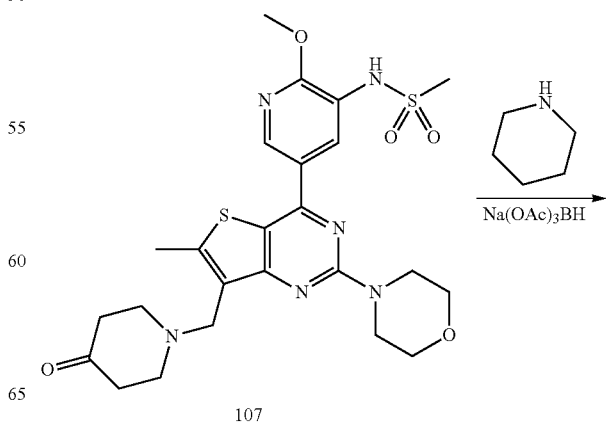

Synthesis of Compound 147

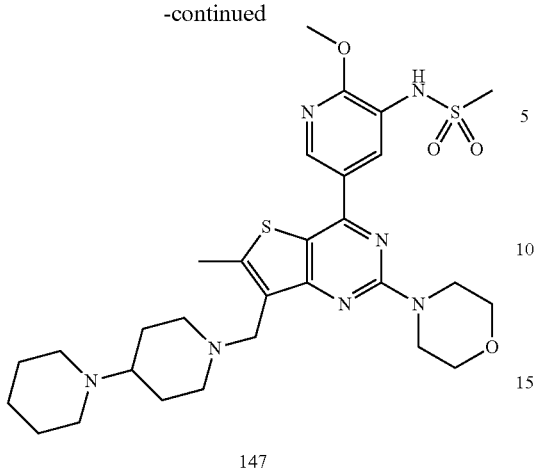

147

According to the method for preparing compound 110, piperidine was used in the preparation to yield compound 147 (44 mg, 48.6%). LC-MS (ESI): m/z=616.3 (M+H)⁺. ¹H NMR (400 MHz, CDCl₃): δ8.72 (1H, d, J=2.0 Hz), 8.53 (1H, d, J=2.0 Hz), 4.09 (3H, s), 3.85-3.97 (4H, m), 3.70-3.85 (4H, m), 3.72 (2H, s), 3.06 (3H, s), 2.97 (2H, d, J=11.6 Hz), 2.62 (3H, s), 2.42-2.55 (4H, m), 2.19-2.32 (1H, m), 2.01-2.15 (2H, m), 1.71-1.83 (2H, m), 1.48-1.64 (6H, m), 1.35-1.47 (2H, m).

Synthetic Route of Compound 148

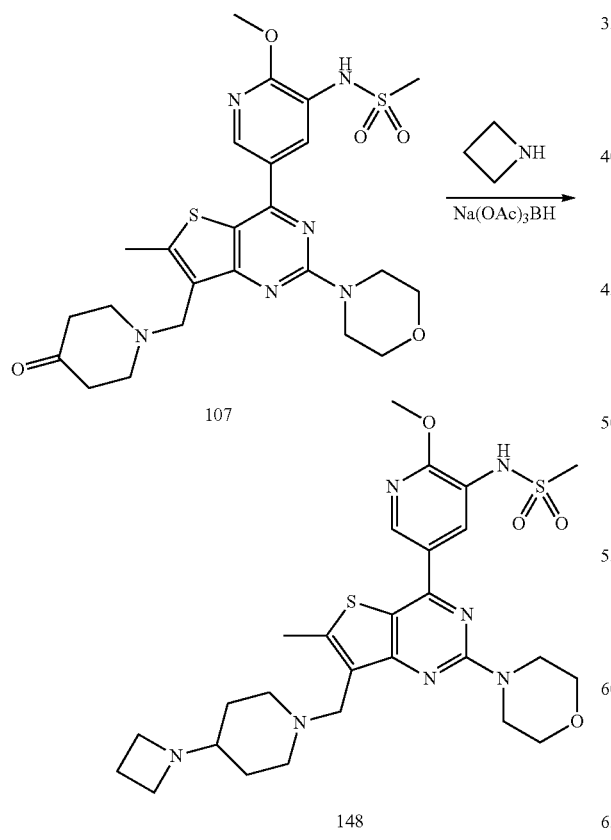

Synthesis of Compound 148

According to the method for preparing compound 110, azetidine was used in the preparation to yield compound 148 (30 mg, 57%). LC-MS (ESI): m/z=588.3 (M+H)⁺. ¹H NMR (400 MHz, DMSO-d₆): δ8.73 (d, 1H, J=2.0 Hz), 8.53 (d, 1H, J=2.4 Hz), 4.08 (s, 3H), 3.90 (t, 4H, J=4.0 Hz), 3.83 (t, 4H, J=4.0 Hz), 3.73 (s, 2H), 3.17 (t, 4H, J=6.8 Hz), 3.06 (s, 3H), 2.85 (d, 2H, J=12.0 Hz), 2.61 (s, 3H), 2.09-2.00 (m, 5H), 1.64 (d, 2H, J=11.2 Hz), 1.28-1.26 (m, 2H).

Synthetic Route of Compound 149

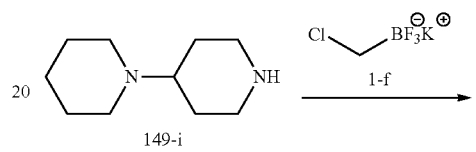

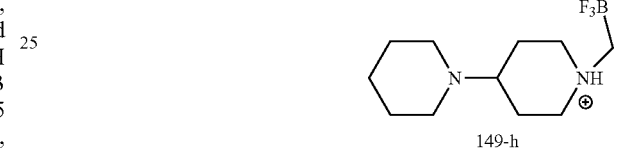

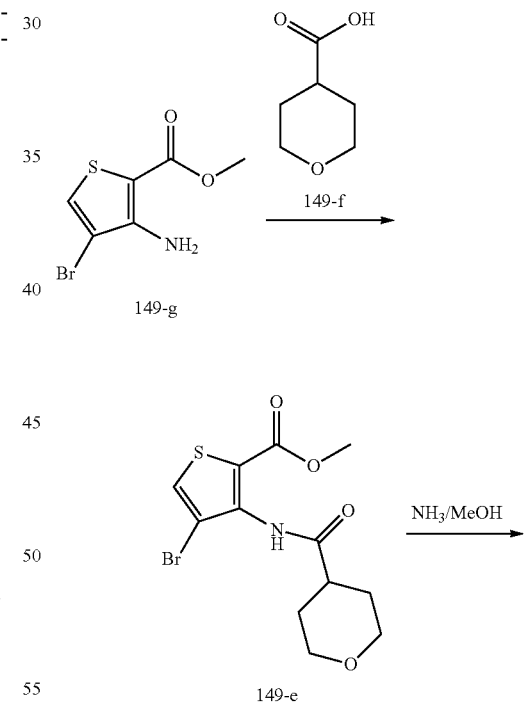

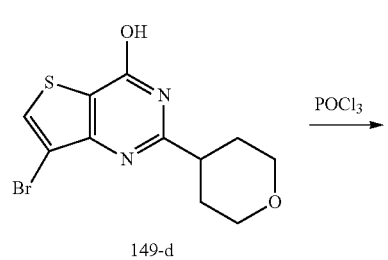

241

-continued

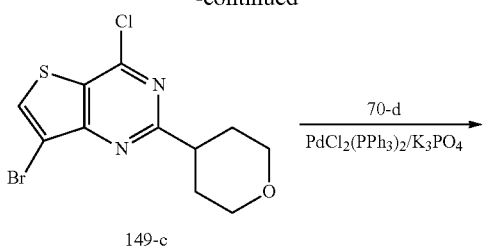

149-c

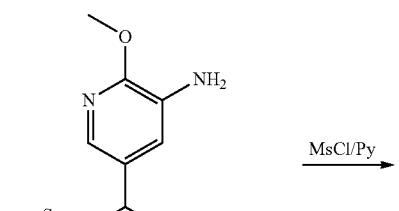

149-b

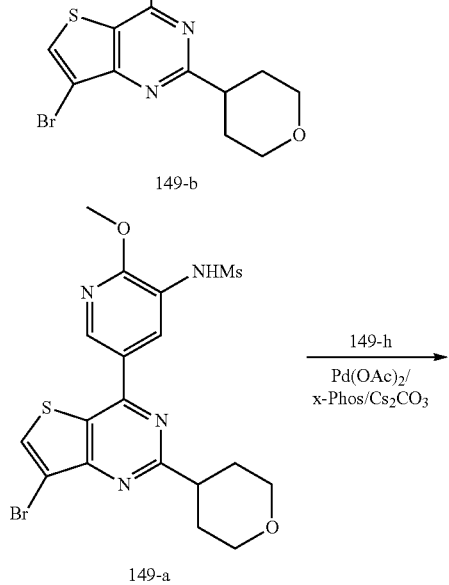

149-a

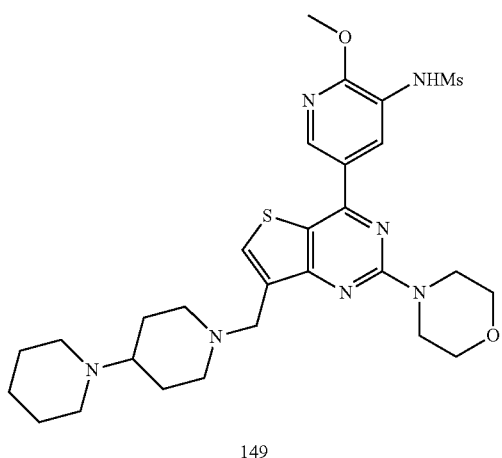

149

Synthesis of Compound 149-h

According to the method for preparing compound 1-a, purchased compound 149-i was used in the preparation to yield compound 149-h (700 mg, 89%).

242

Synthesis of Compound 149-e

At normal temperature, N-methyl morpholine (4.55 mL, 41.34 mmol) and isopropyl chloroformate (3.3 mL, 23.77 mmol) were added to a solution of purchased compound 149-f (2.69 g, 20.67 mmol) in acetonitrile (70 mL). The mixture was cooled with an ice-water bath, and a solution of purchased compound 149-g (4.88 g, 20.67 mmol) in acetonitrile (20 mL) was slowly added. The reaction solution was stirred at room temperature overnight, and then the reaction was quenched by adding water, and the reaction solution was extracted with dichloromethane. The organic phases were combined, dried over anhydrous sodium sulfate, and concentrated under reduced pressure. The residue was purified by silica gel column chromatography to obtain compound 149-e (1.1 g, 16%).

Synthesis of Compound 149-d

Compound 149-e (1.1 g, 3.16 mmol) and 7 M ammoniamethanol solution (5 mL) were mixed in a microwave tube, and stirred at 100° C. for 3 days. The reaction solution was concentrated, and to the residue was added ethyl acetate, and heated to reflux, and filtered to obtain compound 149-d (0.92 g, 92%), as a white solid. LC-MS (ESI): m/z=315.0 (M+H)$^+$.

Synthesis of Compound 149-c

A mixture of compound 149-d (0.92 g, 2.92 mmol) and phosphoric trichloride (10 mL) was stirred at 110° C. overnight. The reaction mixture was concentrated under reduced pressure, and the residue was purified by silica gel column chromatography to obtain compound 149-c (0.7 g, 72%), as a white solid. LC-MS (ESI): m/z=333.0 (M+H)$^+$.

Synthesis of Compound 149-b

Compound 149-c (100 mg, 0.3 mmol), compound 70-d (83 mg, 0.33 mmol), potassium phosphate (95 mg, 0.45 mmol), bis(triphenylphosphine)palladium dichloride (10 mg), DMF (1.1 mL) and water (0.05 mL) were added into a 5 mL microwave tube. The mixture was heated under nitrogen atmosphere, microwave (150 W, 100° C.) and reacted for 1 hr. The reaction mixture was concentrated under reduced pressure, and the residue was dissolved in dichloromethane, and filtered through celite. The filtrate was concentrated under reduced pressure, and the residue was purified by Prep-TLC to obtain compound 149-b (12 mg, 9.5%). LC-MS (ESI): m/z=421.0 (M+H)$^+$.

Synthesis of Compound 149-a

At normal temperature, to a solution of compound 149-b (10 mg, 0.02 mmol) in pyridine (2 mL) was added methylsulfonyl chloride (50 μL, 0.65 mmol), and then stirred at room temperature overnight. The reaction solution was concentrated under reduced pressure, and the residue was dissolved in dichloromethane. The dichloromethane solution was washed with water, dried over anhydrous sodium sulfate, and concentrated under reduced pressure. The residue was purified by Prep-HPLC to obtain compound 149-a (10 mg, 84%). LC-MS (ESI): m/z=499.0 (M+H)$^+$.

Synthesis of Compound 149

Compound 149-a (10 mg, 0.02 mmol), compound 149-h (30 mg, 0.12 mmol), cesium carbonate (25 mg, 0.08 mmol), X-Phos (10 mg, 0.02 mmol), Pd (OAc)$_2$ (5 mg, 0.02 mmol), THF (1.0 mL) and water (0.1 mL) were added to a 5 mL microwave tube. The mixture was heated under nitrogen atmosphere, microwave (150 W, 90° C.) and reacted for 1 hr. The reaction mixture was filtered through celite, and washed with THF. The filtrate was concentrated under reduced pressure. The residue was purified by Prep-HPLC to obtain compound 149 (3 mg, 25%). LC-MS (ESI): m/z=601.3 (M+H)$^+$; $^1$H NMR (400 MHz, CDCl$_3$): δ8.83 (1H, d, J=2.0 Hz), 8.62 (1H, d, J=2.4 Hz), 7.92 (1H, s), 4.06-4.20 (5H, m), 3.97 (2H, s), 3.55-3.69 (2H, m), 3.23-3.38 (1H, m), 3.11-3.19 (2H, m), 3.11 (3H, s), 2.58-3.03 (4H, m), 2.19-2.25 (1H, m), 2.14-2.19 (2H, m), 2.11-2.14 (1H, m), 1.99-2.11 (5H, m), 1.76-1.98 (8H, m).

Synthetic Route of Compound 150

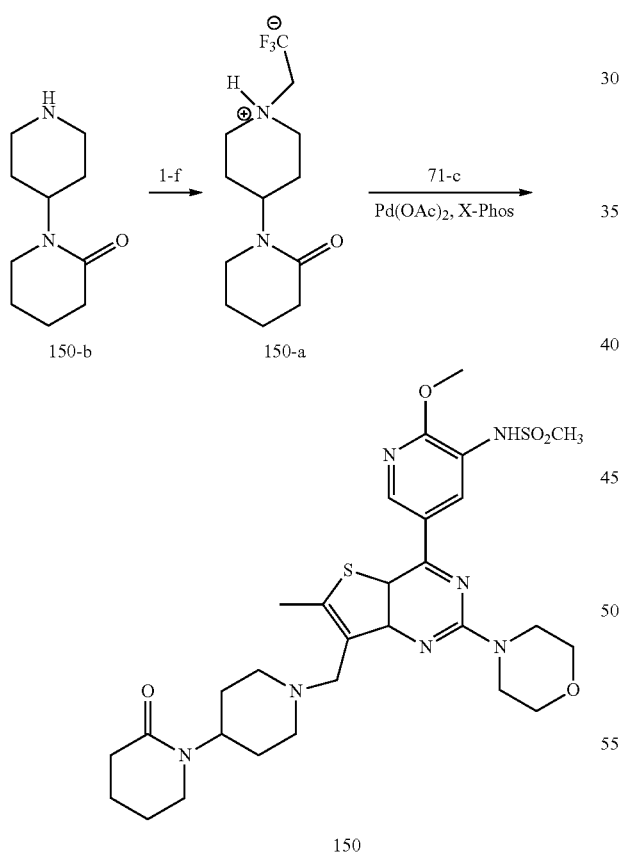

Synthesis of Compound 150-a

According to the method for preparing compound 1-a, purchased compound 150-b was used in the preparation to yield compound 150-a (420 mg, 76%), as a white solid.

Synthesis of Compound 150

According to the method for preparing compound 83, compound 150-a was used in the preparation to yield compound 150 (30 mg, 40.8%). LC-MS (ESI): m/z=630.1 (M+H)$^+$. $^1$H NMR (400 MHz, CDCl$_3$) δ 8.75 (d, J=1.6 Hz, 1H), 8.56 (d, J=2.4 Hz, 1H), 4.48-4.51 (m, 1H), 4.11 (s, 3H), 3.90-3.92 (m, 4H), 3.82-3.84 (m, 4H), 3.75 (s, 2H), 3.16-3.17 (m, 2H), 3.08 (s, 3H), 2.97 (d, J=10.4 Hz, 2H), 2.64 (s, 3H), 2.37-2.40 (m, 2H), 2.27 (d, J=10.8 Hz, 2H), 1.74-1.75 (m, 6H)), 1.54-1.57 (m, 2H).

Synthetic Route of Compound 151

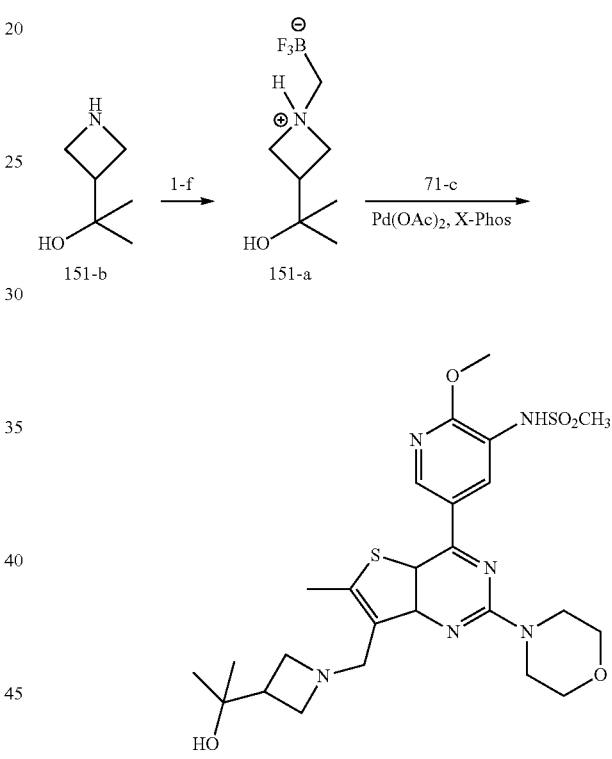

Synthesis of Compound 151-a

According to the method for preparing compound 1-a, purchased compound 151-b was used in the preparation to yield compound 150-a (176 mg, 75%), as a white solid.

Synthesis of Compound 151

According to the method for preparing compound 83, compound 151-a was used in the preparation to yield compound 151 (69 mg, 57%). LC-MS (ESI): m/z=563.2 (M+H)$^+$. $^1$H NMR (400 MHz, CDCl$_3$) δ 8.74 (d, 1H, J=2.0 Hz), 8.55 (d, 1H, J=2.4 Hz), 4.09 (s, 3H), 3.95 (t, 4H, J=4.8 Hz), 3.85 (t, 4H, J=4.8 Hz), 3.78 (s, 2H), 3.35 (t, 2H, J=7.6 Hz), 3.28 (t, 2H, J=7.6 Hz), 3.07 (s, 3H), 2.61 (s, 3H), 2.32-2.29 (m, 1H), 1.13 (s, 6H).

Synthetic Route of Compound 152

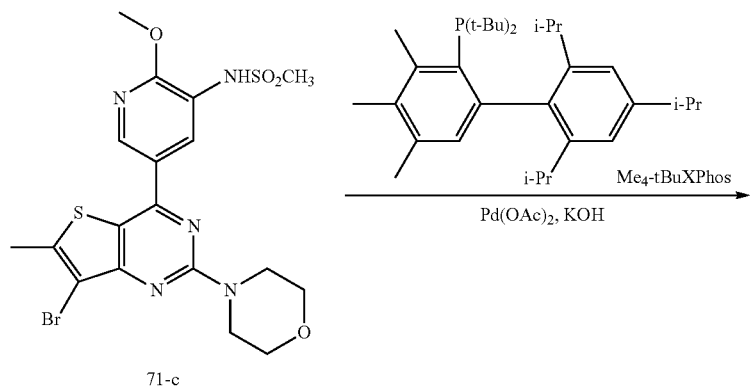

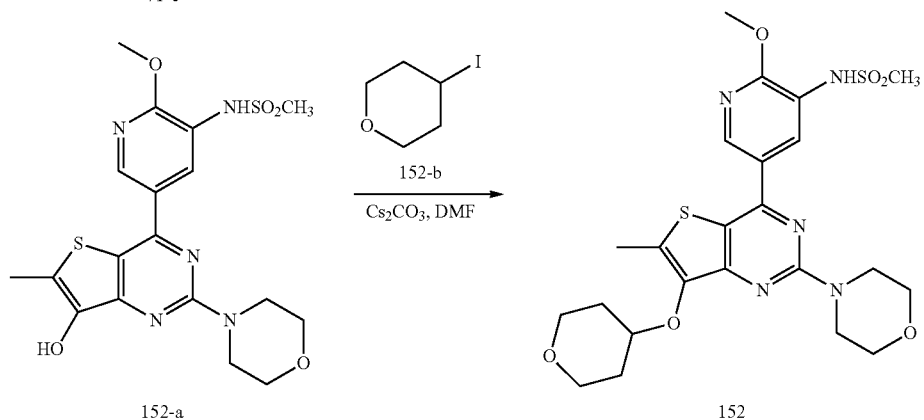

Synthesis of Compound 152-a

Compound 71-c (1 g, 1.94 mmol), Pd₂(dba)₃ (175 mg, 0.19 mmol), Me₄-tBuXPhos (100 mg, 0.21 mmol), potassium hydroxide (1.09 g, 19.43 mmol), 1, 4-dioxane (25 mL) and water (15 mL) were added to a microwave tube, and stirred under nitrogen atmosphere 95° C. overnight. The reaction solution was cooled to room temperature, and acidified with 1 N HCl solution, and then neutralized to PH>7 by adding saturated sodium bicarbonate solution. The mixed liquid was extracted with dichloromethane (50*3 mL). The organic phases were combined, dried over anhydrous sodium sulfate, filtered, and concentrated. The crude was separated and purified by silica gel column chromatography (DCM/MeOH=10/1) to obtain compound 152-a (333 mg, 38%). LC-MS (ESI): m/z=452.0 (M+H)$^+$.

Synthesis of Compound 152

A solution of compound 152-a (50 mg, 0.11 mmol) and cesium carbonate (30 mg, 0.22 mmol) in DMF (4 mL) was stirred at room temperature for 10 minutes, and thereafter compound 152-b (35 mg, 0.17 mmol) was added. The reaction solution was stirred at 70° C. overnight. The reaction solution was quenched with water (20 mL), extracted with ethyl acetate (20 mL), and washed with saturated brine (3*20 mL). The organic phase was dried over anhydrous sodium sulfate, and concentrated. The crude was separated and purified by Prep-HPLC to obtain compound 152 (7 mg, 12%). LC-MS (ESI): m/z=536.2 (M+H)$^+$. $^1$H NMR (400 MHz, CDCl₃): δ8.73 (1H, d, J=2.0 Hz), 8.39 (1H, d, J=2.4 Hz), 6.83 (1H, s), 4.87-4.97 (1H, m), 4.11 (3H, s), 4.01-4.09 (2H, m), 3.86-3.94 (4H, m), 3.79-3.86 (4H, m), 3.53 (1H, dd, J=2.8, 8.8 Hz), 3.51 (1H, dd, J=2.8, 8.8 Hz), 3.08 (3H, s), 2.49 (3H, s), 1.97-2.09 (2H, m), 1.79-1.92 (2H, m).

Synthetic Route of Compound 153

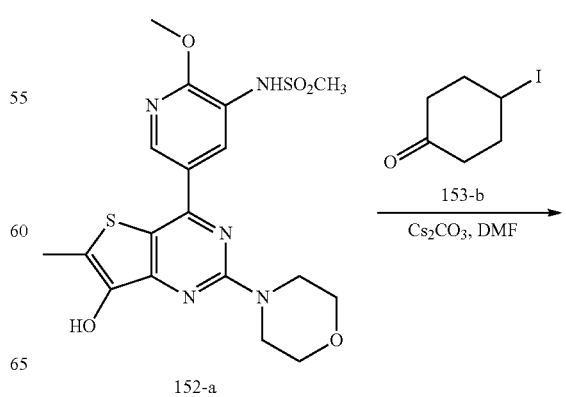

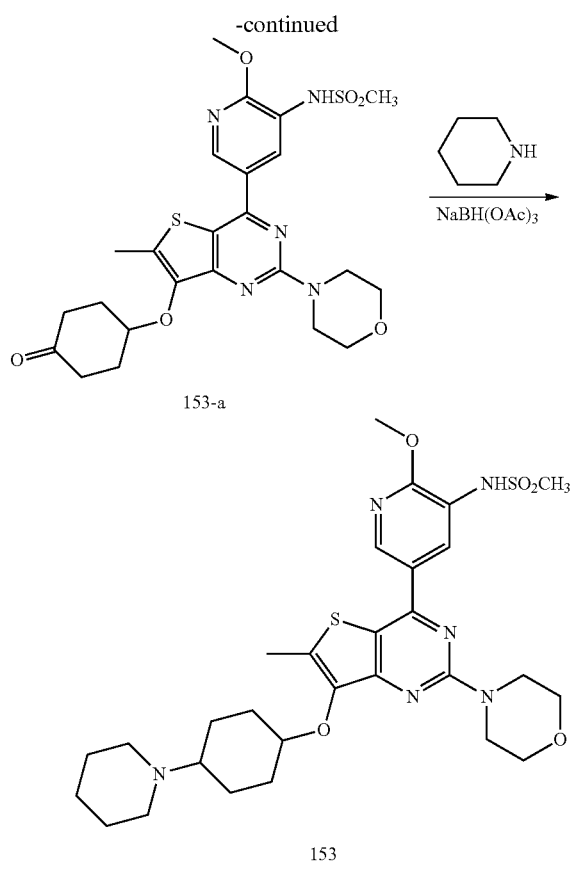

Synthesis of Compound 153-a

According to the method for preparing compound 152, purchased compound 153-b was used in the preparation to yield compound 153-a (30 mg, 6.7%). LC-MS (ESI): m/z=548.2 (M+H)$^+$.

Synthesis of Compound 153

To a reaction flask were added compound 153-a (30 mg, 0.055 mmol), piperidine (0.15 mL, 1.52 mmol), NaBH(OAc)$_3$ (400 mg, 1.89 mmol), glacial acetic acid (2 drops) and 1,2-dichloroethane (5 mL). The mixture was stirred at room temperature overnight, and water (5 mL) was added, and then extracted with dichloromethane (10 mL) 3 times. The organic phases were combined, dried, and concentrated. The residue was separated and purified by Prep-HPLC to obtain compound 153 (5 mg, 15%). LC-MS (ESI): m/z=617.3 (M+H)$^+$.

Effect Example 1

PI3Kα, PI3Kδ, PI3Kβ and PI3Kγ Enzyme Activity Inhibition IC50 Evaluation Assay

1. Buffer preparation: 50 mM HEPES, pH 7.5, 3 mM MgCl$_2$, 1 mM EGTA, 100 mM NaCl, 0.03% CHAPS.
2. Compound was formulated in 100% DMSO in a concentration gradient, and added to a 384-well plate to a final DMSO concentration of 1%.
3. PI3Kα, PI3Kδ, PI3Kβ and PI3Kγ enzymes were diluted to an optimum concentration with the following buffer: 50 mM HEPES, pH 7.5, 3 mM MgCl$_2$, 1 mM EGTA, 100 mM NaCl, 0.03% CHAPS, 2 mM DTT, and transferred to a 384-well plate and incubated with the compound for a certain time.
4. Substrate was diluted to an optimum concentration with the following buffer: 50 mM HEPES, pH 7.5, 3 mM MgCl$_2$, 1 mM EGTA, 100 mM NaCl, 0.03% CHAPS, 2 mM DTT, 50 μM PIP2, 25 μM ATP; then added to a 384-well plate to initiate the reaction, and for PI3Kα, PI3Kβ and PI3Kγ at room temperature reacted for 1 hr, for PI3Kδ at room temperature reacted for 2 hrs. For PI3Kβ and PI3Kγ, it was still necessary to further add 10 μL ADP-Glo Detection Reagent, and then equilibrated at room temperature for 30 minutes.
5. Read Luminescense with FlexStation, and calculate the inhibition rate as the average of two tests.

Table 1 shows the IC$_{50}$ values for PI3Kδ activities and α/δ seletivities for selected compounds. Table 2 shows β/δ and/or γ/δ selectivity values for part of the compounds.

TABLE 1

IC$_{50}$ Values for PI3Kδ Activities and δ/α Seletivities For Part of The Compounds

| Compound No. | PI3Kδ IC50 (nM) | α/δ | Compound No. | PI3Kδ IC50 (nM) | α/δ |
|---|---|---|---|---|---|
| 1 | 105 | 12 | 4 | 35.4 | >282 |
| 6 | 145 | >69 | 8 | 72 | 90 |
| 9 | 50 | >200 | 10 | 25 | >400 |
| 11 | 17 | >588 | 12 | 17 | 133 |
| 13 | 52 | >192 | 14 | 3.8 | 700 |
| 15 | 34 | >294 | 16 | 567 | 18 |
| 17 | 53 | 74 | 18 | 86 | 58 |
| 19 | 87 | 49 | 20 | 66 | 54 |
| 21 | 150.4 | 19 | 23 | 27 | 40 |
| 27 | 99 | 10 | 28 | 35 | 56 |
| 29 | 6.9 | 34 | 30 | 71 | 36 |
| 31 | 4.9 | 10 | 32 | 4.3 | 15 |
| 33 | 4.2 | 51 | 34 | 3.4 | 44 |
| 35 | 4.7 | 95 | 36 | 13 | 23 |
| 37 | 28.9 | 38 | 38 | 108 | 3 |
| 39 | 9.2 | 159 | 40 | 17 | 41 |
| 41 | 11.4 | 323 | 42 | 13 | 152 |
| 43 | 4 | 105 | 46 | 6.1 | 23 |
| 47 | 3.5 | 9 | 48 | 6.9 | 52 |
| 49 | 5.7 | 15 | 50 | 13 | 359 |
| 51 | 11 | 103 | 52 | 36 | 252 |
| 53 | 19 | 110 | 54 | 2.7 | 108 |
| 55 | 5.6 | 224 | 56 | 7.6 | 293 |
| 57 | 2.8 | 103 | 58 | 5.4 | 150 |
| 60 | 7.1 | 147 | 61 | 4.7 | 12 |
| 62 | 5.6 | 104 | 63 | 12 | 27 |
| 64 | 9.1 | 110 | 65 | 17.5 | 174 |
| 67 | 3.6 | 195 | 68 | 71 | 19 |
| 69 | 31 | 79 | 70 | 23 | 87 |
| 71 | 6.8 | 13 | 72 | 60 | 29 |
| 73 | 4.4 | 18 | 74 | 4.4 | 13 |
| 75 | 31 | 19 | 76 | 7.3 | 60 |
| 77 | 7.1 | 52 | 78 | 7.7 | 302 |
| 79 | 9.4 | 582 | 80 | 39 | >256 |
| 81 | 24 | 374 | 82 | 15 | 143 |
| 83 | 11.9 | 257 | 84 | 47 | >213 |
| 85 | 8.6 | 401 | 86 | 12 | 136 |
| 87 | 12.5 | 204 | 88 | 5.8 | 548 |
| 89 | 2.6 | 48 | 90 | 4.9 | 69 |
| 91 | 3.2 | 60 | 92 | 71 | 42 |
| 93 | 10 | 82 | 94 | 32 | 31 |
| 95 | 6.5 | 157 | 96 | 31 | 64 |
| 97 | 190 | 10 | 98 | 12 | 30 |
| 99 | 34 | 152 | 100 | 17 | 17 |
| 101 | 12 | 390 | 102 | 9.3 | 146 |
| 103 | 8.4 | 176 | 104 | 4.3 | 159 |
| 105 | 31 | 77 | 106 | 25.5 | 129 |
| 107 | 11 | 45 | 108 | 13 | 78 |
| 109 | 3.9 | 251 | 110 | 4.1 | 203 |

TABLE 1-continued

IC$_{50}$ Values for PI3Kδ Activities and δ/α Seletivities For Part of The Compounds

| Compound No. | PI3Kδ IC50 (nM) | α/δ | Compound No. | PI3Kδ IC50 (nM) | α/δ |
|---|---|---|---|---|---|
| 111 | 6.5 | 301 | 112 | 7.6 | 108 |
| 113 | 6.6 | 27 | 114 | 5 | 44 |
| 115 | 13 | 67 | 116 | 4.3 | 57 |
| 117 | 7.2 | 213 | 118 | 2.6 | 92 |
| 119 | 5.0 | 84 | 120 | 5.0 | 24 |
| 121 | 16 | 192 | 122 | 9.0 | 172 |
| 123 | 6.8 | 175 | 124 | 3.1 | 430 |
| 125 | 2.6 | 239 | 126 | 4.7 | 170 |
| 127 | 5.8 | 38 | 128 | 6.0 | 223 |
| 129 | 19 | 100 | 130 | 6.7 | 273 |
| 131 | 6.2 | 627 | 132 | 10 | 35 |
| 133 | 7.7 | 185 | 134 | 4.0 | 188 |
| 135 | 6.3 | 226 | 136 | 7.8 | 268 |
| 137 | 11 | 309 | 138 | 34 | 67 |
| 139 | 3.2 | 69 | 140 | 3.2 | 55 |
| 141 | 9.0 | 120 | 142 | 3.7 | 60 |
| 143 | 32 | 107 | 144 | 3.4 | 56 |
| 145 | 3.8 | 287 | 146 | 2.9 | 120 |
| 147 | 4.6 | 225 | 148 | 4.7 | 280 |
| 149 | 134 | 35 | 150 | 9.3 | 39 |
| 151 | 15 | 41 | 152 | 15.6 | 12 |
| 153 | 11 | 42 | CAL-101 | 4.9 | 153 |

TABLE 2

β/δ and γ/δ Selectivity Values For Part of The Compounds

| Compound No. | β/δ | γ/δ | Compound No. | β/δ | γ/δ |
|---|---|---|---|---|---|
| 4 | >282 | >282 | 8 | 27 | 57 |
| 65 | 94 | >571 | 78 | 18 | >1298 |
| 83 | 24 | >840 | 85 | 69 | >1162 |
| 86 | 25 | 402 | 87 | 45 | 498 |
| 88 | 73 | 1202 | 95 | 167 | 532 |
| 99 | 24 | 244 | 101 | 29 | 482 |
| 102 | 16 | 200 | 104 | 19 | 377 |
| 106 | 72 | >392 | 108 | 6 | 262 |
| 109 | 723 | 1296 | 110 | 275 | 1112 |
| 112 | 126 | 611 | 147 | 140 | 567 |
| 148 | 110 | 587 | 150 | 15 | 221 |
| 153 | 418 | >909 | CAL-101 | 66 | 13 |

Effect Example 2

Screening Test for a Drug on Inhibiting TNF-α Generation of Human Raji Cell Induced by Human IgM 1. Raji cell lines (source of human Burkitt's lymphoma) were employed.
2. 1×10$^5$/well Raji cells were plated onto a 96-well cell culture plate.
3. Compounds to be screened were diluted to the corresponding test concentrations and added into the cell culture system 30 minutes before IgM stimulation.
4. 10 μg/ml IgM monoclonal antibody was added into the cell culture system to stimulate the cells generating TNF-α.
5. 24 hrs later, the amount of TNF-α generated by the cell system was measured by ELISA method.
6. The inhibition rate at each compound concentration was calculated and plotted to calculate 50% inhibition rate (IC50), and the specific results were shown in Table 3.

TABLE 3

TNF-α IC50 Values of Part of the Compounds

| Compound No. | TNF-α IC50 (nM) | Compound No. | TNF-α IC50 (nM) |
|---|---|---|---|
| 10 | 28.0 | 11 | 41.1 |
| 14 | 25.6 | 60 | 2.0 |
| 65 | 15.4 | 71 | 8.6 |
| 78 | 10.6 | 79 | 14.5 |
| 81 | 43 | 82 | 76.8 |
| 83 | 6.7 | 84 | 30.4 |
| 85 | 39.1 | 87 | 41.6 |
| 88 | 6.1 | 89 | 1.3 |
| 90 | 31.2 | 91 | 3.4 |
| 95 | 1.1 | 100 | 5.7 |
| 101 | 32.6 | 103 | 9.3 |
| 110 | 3.3 | 112 | 1.1 |
| 121 | 33.7 | 126 | 3.9 |
| 127 | 1.5 | 147 | 3.3 |
| 148 | 7.0 | 150 | 8.6 |
| 153 | 0.6 | CAL-101 | 29.8 |

Based on the above test results, it can be confirmed that the compounds of the present invention possess excellent selective inhibitions against PI3Kδ, and the effects of part of the compound are superior to the positive control compound CAL-101 (idelalisib), which is a kind of selective inhibitor with PI3Kδ inhibitory activity much more than PI3Kα inhibitory activity, and may be an excellent immunosuppressive agent without inducing insulin resistance caused by PI3Kα inhibition, and may be used as prophylactic or therapeutic agents for rejections in various organ transplants, allergic diseases (asthma, atopic dermatitis, etc.), autoimmune diseases (rheumatoid arthritis, psoriasis, ulcerative colitis, Crohn's disease, systemic lupus erythematosus, etc.) and blood tumor, etc.

Although the foregoing has described the specific embodiments of invention, a person skilled in the art should understand that these are only illustrative examples, and various changes and modifications may be made to these embodiments without departing from the principle and substance of the present invention. Therefore, the scope of the present invention should be limited by the attached claims.

What is claimed is:

1. A fused pyrimidine compound represented by formula I, a pharmaceutically acceptable salt, a hydrate, a solvate, an optical isomer or a prodrug thereof,

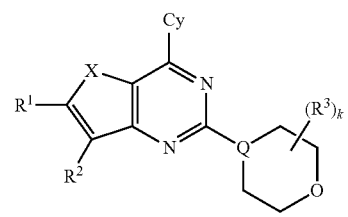

wherein:

X is S or O; Q is C or N;

R$^1$ is selected from a hydrogen, a deuterium, a halogen, an alkyl, an alkoxy, an alkenyl, an alkynyl, a cycloalkyl a heterocycloalkyl, an aryl or a heteroaryl;

R$^2$ is selected from a hydrogen, a deuterium, a halogen, CN, —(CR$^8$R$^9$)$_m$NR$^5$R$^6$, —(CR$^8$R$^9$)$_m$NR$^7$C(=Y)R$^5$, —(CR$^8$R$^9$)$_m$NR$^7$S(O)$_2$R$^5$, —(CR$^8$R$^9$)$_m$OR$^5$, —(CR$^8$R$^9$)$_m$S(O)$_2$R$^5$,—(CR$^8$R$^9$)$_m$S(O)$_2$NR$^5$R$^6$, —C(OR$^5$)R$^6$R$^8$, —C(=Y)R$^5$, —C(=Y)OR$^5$, —C(=Y)NR$^5$R$^6$,—C(=Y)NR$^7$OR$^5$, —C(=O)NR$^7$S(O)$_2$R$^5$, —C(=O)NR$^7$(CR$^8$R$^9$)$_m$NR$^5$R$^6$, —NR$^7$C(=Y)R$^6$,—NR$^7$C(=Y)OR$^6$, —NR$^7$C(=Y)NR$^5$R$^6$, —NR$^7$S(O)$_2$R$^5$, —NR$^7$S(O)$_2$NR$^5$R$^6$, —SR$^5$, —S(O)$_2$R$^5$,—S(O)$_2$NR$^5$R$^6$, —SC(=Y)R$^5$, —SC(=Y)OR$^5$, a C$_1$-C$_{12}$ alkyl, a C$_2$-C$_8$ alkenyl, a C$_2$-C$_8$ alkynyl, a C$_3$-C$_{12}$ carbocyclyl, a C$_2$-C$_{20}$ heterocyclyl, a C$_6$-C$_{20}$ aryl or a C$_1$-C$_{20}$ heteroaryl;

(R$^3$)$_k$ represents that a hydrogen on the heterocycle to which it is attached is substituted by 0 to k occurrences of R$^3$, and at each occurrence R$^3$ is the same or different from one another, and is independently selected from a hydrogen, a deuterium, a halogen, a C$_1$-C$_6$ alkyl, or any two of R$^3$ are linked together by a single bond, a C$_1$-C$_6$ alkylene or a C$_1$-C$_6$ alkylene substituted by one or more heteroatoms, with said heteroatom being O, N or S;

Cy is heterocyclyl selected from:

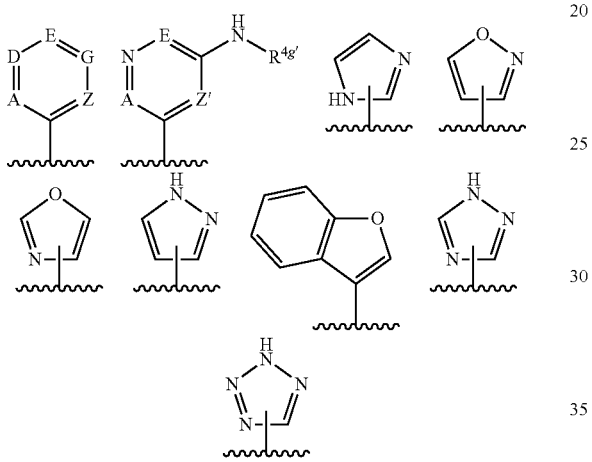

A is N or CR$^{4a}$;
D is N or CR$^{4d}$;
E is N or CR$^{4e}$;
G is N or CR$^{4g}$;
Z is N or CR$^4$;
Z' is N or CR$^{4'}$;
A, D, E, Z and G are not N at the same time;
each of R$^{4a}$, R$^{4d}$, R$^{4e}$ and R$^{4'}$ is independently selected from a hydrogen, a halogen, —CN, an alkyl, an alkoxy, an alkenyl, —NR$^5$R$^6$, —OR$^5$, —SR$^5$, —C(O)R$^5$, —NR$^5$C(O)R$^6$, —N(C(O)R$^6$)$_2$, —NR$^5$C(O)NR$^5$R$^6$, —S(O)R$^5$, —S(O)$_2$R$^5$, —S(O)$_2$NR$^5$R$^6$, —NR$^7$S(O)$_2$R$^5$,—NR$^5$S(O)$_2$NR$^5$R$^6$,—C(=O)OR$^5$ or —C(=O)NR$^5$R$^6$;
R$^{4g'}$ is —S(O)R$^5$, —S(O)$_2$R$^5$, —S(O)$_2$NR$^5$R$^6$ or —C(O)R$^5$;
R$^4$ and R$^{4g}$, together with the atoms to which they are attached form a saturated, unsaturated or partially unsaturated 5-membered or 6-membered heterocycle, and only one of the ring atoms of said 5-membered or 6-membered heterocycle is a heteroatom, and the heteroatom is selected from O, N and S, and said 5-membered or 6-membered heterocycle is fused to the 6-membered ring containing A, D, E, Z and G;
each of R$^5$, R$^{5'}$, R$^6$, R$^7$ and R$^{7'}$ is independently a hydrogen, a C$_1$-C$_{12}$ alkyl, a C$_2$-C$_8$ alkenyl, C$_2$-C$_8$ alkynyl, a C$_3$-C$_{12}$ carbocyclyl, a C$_2$-C$_{20}$ heterocyclyl, a C$_6$-C$_{20}$ aryl, a C$_1$-C$_{20}$ heteroaryl, or a heterocycle formed by R$^5$, R$^6$ together with the nitrogen to which they are directly attached, a spiro ring further formed by the heterocycle formed by R$^5$, R$^6$ together with the nitrogen to which they are directly attached with C$_2$-C$_6$ heterocycle, a spiro ring further formed by the heterocycle formed by R$^5$, R$^6$ together with the nitrogen to which they are directly attached with C$_2$-C$_6$ carbocycle, a fused ring further formed by the heterocycle formed by R$^5$, R$^6$ together with the nitrogen to which they are directly attached with C$_2$-C$_6$ heteroaromatic ring, a bridged ring further formed by the heterocycle formed by R$^5$, R$^6$ together with the nitrogen to which they are directly attached with C$_2$-C$_6$ heteroaromatic ring, a fused ring further formed by the heterocycle formed by R$^5$, R$^6$ together with the nitrogen to which they are directly attached with C$_2$-C$_6$ aromatic ring , a fused ring further formed by the heterocycle formed by R$^5$, R$^6$ together with the nitrogen to which they are directly attached with C$_2$-C$_6$ carbocycle, or a heterocycle formed by R$^5$, R$^6$ together with the nitrogen to which they are directly attached may be optionally substituted by the substituent selected from the group consisting of: oxo, —(CH$_2$)$_m$OR$^7$, —NR$^7$R$^{7'}$, a deuterium, a halogen, —SO$_2$R$^7$, —C(=O)R$^7$, —NR$^7$C(=Y)R$^{7'}$, —NR$^7$S(O)$_2$R$^{7'}$, —C(=Y)NR$^7$R$^{7'}$, a C$_1$-C$_{12}$ alkyl, a C$_2$-C$_8$, alkenyl, a C$_2$-C$_8$ alkynyl, hydroxy(, a C$_3$-C$_{12}$ carbocyclyl, a C$_2$-C$_{20}$ heterocyclyl, a methylsulfonyl, a C$_3$-C$_{20}$ heterocycloalkenyl, a C$_6$-C$_{20}$ aryl, a C$_1$-C$_{20}$ heteroaryl, an amino,

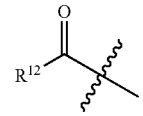

and a substituted or unsubstituted C$_1$-C$_3$ amid, wherein R$^{12}$ is an unsubstituted C$_1$-C$_4$ alkyl, a halogen substituted C$_1$-C$_4$alkyl, a cyano substituted C$_1$-C$_4$ alkyl, a pyrrolyl, a hydroxyl substituted C$_1$-C$_4$ alkyl, an unsubstituted C$_1$-C$_4$ alkoxy or an unsubstituted C$_3$-C$_6$ saturated carbocyclyl;

each of R$^8$ and R$^9$ is independently a hydrogen, a deuterium, a halogen, —CN, a hydroxyl, alkoxy, ar cycloalkoxy, a C$_1$-C$_{12}$ alkyl, a C$_2$-C$_{12}$ alkenyl, a C$_2$-C$_{12}$ alkynyl, a C$_3$-C$_{12}$ cycloalkyl, as C$_6$-C$_{12}$-aryl, a 3-12 membered heterocycloalkyl or a 5-12 membered heteroaryl;

(CR$^8$R$^9$)$_m$ represents that m number of (CR$^8$R$^9$) are linked together, in which each of R$^8$ and R$^9$ are the same or different from one another, and independently is a hydrogen, a deuterium, a halogen, —CN, a hydroxyl, an alkoxy a C$_1$-C$_{12}$ alkyl, a C$_2$-C$_{12}$ alkenyl, a C$_2$-C$_{12}$ alkynyl, a C$_3$-C$_{12}$ cycloalkyl, a C$_6$-C$_{12}$ aryl, a 3-12 membered heterocycloalkyl or a 5-12 memberedheteroaryl; or a saturated or partially unsaturated C$_3$-C$_{12}$ carbocycle or a C$_2$-C$_{20}$ heterocycle formed by R$^8$, R$^9$ together with the atoms to which they are attached;

wherein said alkyl, alkenyl, alkynyl, cycloalkyl, carbocycle, heterocycle, heterocycloalkyl, aryl, or heterocyclyl may optionally be substituted by the substituent selected from the group consisting of: a deuterium, a halogen, —CN, —CF$_3$, —NO$_2$, oxo, R$^5$, —C(=Y)R$^5$, —C(=Y)OR$^5$, —C(=Y)NR$^5$R$^6$, —(CR$^8$R$^9$)$_m$NR$^5$R$^6$, —(CR$^8$R$^9$)$_m$OR$^5$, —NR$^5$R$^6$,—NR$^7$C(=Y)R$^5$, —NR$^7$C(=Y)OR$^6$, —NR$^7$C(=Y)NR$^5$R$^6$, —(CR$^8$R$^9$)$_m$NR$^7$SO$_2$R$^5$, =NR$^7$, OR$^5$, —OC(=Y)R$^5$, —OC(=Y)OR⁵, —OC(=Y)NR⁵R⁶, —OS(O)₂(OR⁵), —OP(=Y)(OR⁵)(OR⁶), —OP(OR⁵)(OR⁶), —SR⁵, —S(O)R⁵, —S(O)₂R⁵, —S(O)₂NR⁵R⁶, —S(O)(OR⁵), —S(O)₂(OR⁵), —SC(=Y)R⁵, —SC(=Y)OR⁵, —SC(=Y)NR⁵R⁶, a C₂-C₈ alkenyl, a C₂-C₈ alkynyl, a C₃-C₁₂ carbocyclyl, a C₂-C₂₀ heterocyclyl, a C₆-C₂₀ aryl and a C₁-C₁₂ heteroaryl;

Y is O, S, or NR⁷;

m and k are independently 0, 1, 2, 3, 4, 5 or 6.

2. The fused pyrimidine compound represented by formula I, the pharmaceutically acceptable salt, the hydrate, the solvate, the optical isomer or the prodrug thereof according to claim 1, wherein,
R¹ is a hydrogen or an alkyl; and when R¹ is an alkyl, said alkyl is an unsubstinated C₁-C₆ alkyl.

3. The fused pyrimidine compound represented by formula I, the pharmaceutically acceptable salt, the hydrate, the solvate, the optical isomer or the prodrug thereof according to claim 2, wherein,
when R¹ is an unsubstituted C₁-C₆ alkyl, said unsubstituted C₁-C₆ alkyl is a methyl, an ethyl, a propyl or an isopropyl.

4. The fused pyrimidine compound represented by formula I, the pharmaceutically acceptable salt, the hydrate, the solvate, the optical isomer or the prodrug thereof according to claim 1, wherein,
when R² is a C₁-C₁₂ alkyl, said C₁-C₁₂ alkyl is a substituted or unsubstituted C₁-C₄ alkyl in which said substituted means being substituted by substituted or unsubstituted aryl, and said substituted in said "substituted or unsubstituted aryl" means being substituted by a halogen and/or an unsubstituted C₁-C₆ alkyl;
and/or,
k is 0.

5. The fused pyrimidine compound represented by formula I, the pharmaceutically acceptable salt, the hydrate, the solvate, the optical isomer or the prodrug thereof according to claim 4, wherein,
when said substituted in said "substituted or unsubstituted aryl" means being substituted by a halogen and/or an unsubstituted C₁-C₆ alkyl, said halogen is F, Cl or Br, and said unsubstituted C₁₋₆ alkyl is a methyl, an ethyl, a propyl, an isopropyl, a butyl, an isobutyl or a tert-butyl;
and/or,
said aryl in said "substituted or unsubstituted aryl" is a phenyl.

6. The fused pyrimidine compound represented by formula I, the pharmaceutically acceptable salt, the hydrate, the solvate, the optical isomer or the prodrug thereof according to claim 4, wherein,
when R² is a substituted or unsubstituted C₁-C₄ alkyl, said "C₁-C₄ alkyl" in said "substituted or unsubstituted C₁-C₄ alkyl" is a methyl.

7. The fused pyrimidine compound represented by formula I, the pharmaceutically acceptable salt, the hydrate, the solvate, the optical isomer or the prodrug thereof according to claim 1, wherein,
when R⁴ᵍ' is —S(O)₂R⁵, said —S(O)₂R⁵ is

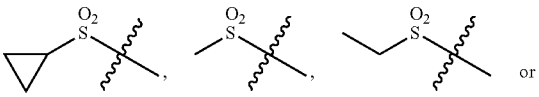

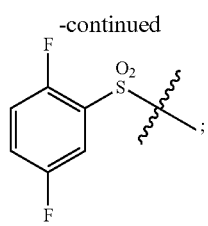

when R⁴ᵍ' is —S(O)₂NR⁵R⁶, said —S(O)₂NR⁵R⁶ is

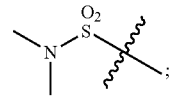

when R⁴ and R⁴ᵍ together with the atoms to which they are attached form an unsaturated or partially unsaturated 5-membered or 6-membered heterocycle, only one of the ring atoms of the 5-membered or 6-membered heterocycle is a heteroatom, and the heteroatom is selected from O, N and S; when the 5-membered or 6-membered heterocycle is fused to the 6-membered ring containing A, D, E, Z and G, the formed Cy is

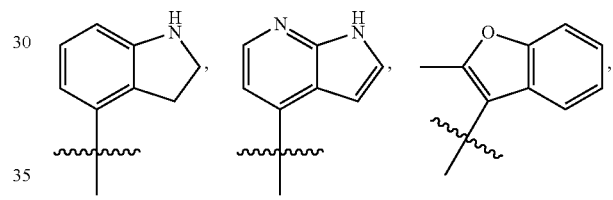

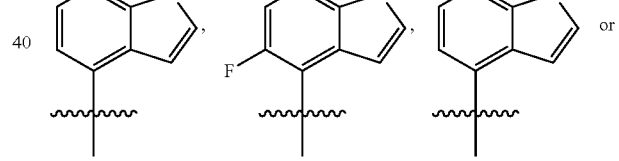

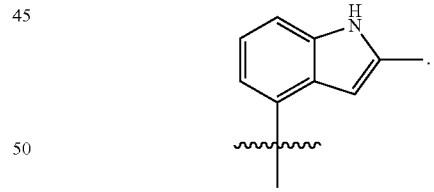

8. The fused pyrimidine compound represented by formula I, the pharmaceutically acceptable salt, the hydrate, the solvate, the optical isomer or the prodrug thereof according to claim 1, wherein,
when each of R⁵, R⁵', R⁶, R⁷ and R⁷' is independently a C₁-C₁₂ alkyl, said C₁-C₁₂ alkyl is a substituted or unsubstituted C₁-C₅ alkyl, said "substituted" in said "substituted or unsubstituted C₁-C₅ alkyl" means being substituted by a hydroxyl and/or an unsubstituted C₁-C₃ alkoxy;
and/or,
when each of R⁵, R⁵', R⁶, R⁷ and R⁷' is independently a C₂-C₈ alkenyl, said C₂-C₈ alkenyl is a substituted or unsubstituted C₂-C₄ alkenyl; said "substituted" in said "substituted or unsubstituted $C_2$-$C_4$ alkenyl" means being substituted by one or more than one unsubstituted $C_1$-$C_6$ alkyl.

9. The fused pyrimidine compound represented by formula I, the pharmaceutically acceptable salt, the hydrate, the solvate, the optical isomer or the prodrug thereof according to claim 8, wherein,
said "$C_1$-$C_5$ alkyl" in said "substituted or unsubstituted $C_1$-$C_5$ alkyl" is a methyl, an ethyl, a propyl, an isopropyl, a n-butyl, an isobutyl, a tert-butyl, a n-pentyl, an isopentyl or a neo-pentyl;
when said "substituted" in said "substituted or unsubstituted $C_1$-$C_5$ alkyl" means being substituted by a hydroxyl and/or an unsubstituted $C_1$-$C_3$ alkoxy, said "unsubstituted $C_1$-$C_3$ alkoxy" is a methoxy;
when said "substituted" in said "substituted or unsubstituted $C_2$-$C_4$ alkenyl" means being substituted by one or more than one unsubstituted $C_1$-$C_6$ alkyl, said "unsubstituted $C_1$-$C_6$ alkyl" is a methyl, an ethyl, a propyl, an isopropyl, a n-butyl, an isobutyl or a tert-butyl.

10. The fused pyrimidine compound represented by formula I, the pharmaceutically acceptable salt, the hydrate, the solvate, the optical isomer or the prodrug thereof according to claim 9, wherein,
said "substituted $C_1$-$C_5$ alkyl" is

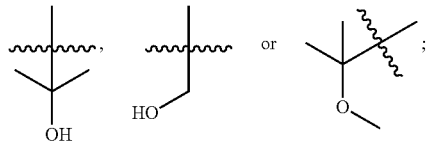

when said "substituted" in said "substituted or unsubstituted $C_2$-$C_4$ alkenyl" means being substituted by an ethyl, said "substituted $C_2$-$C_4$ alkenyl" is

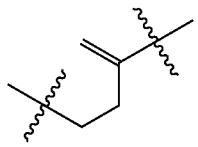

11. The fused pyrimidine compound represented by formula I, the pharmaceutically acceptable salt, the hydrate, the solvate, the optical isomer or the prodrug thereof according to claim 1, wherein,
when each of $R^5$, $R^{5'}$, $R^6$, $R^7$ and $R^{7'}$ is independently a $C_3$-$C_{12}$ carbocyclyl, said $C_3$-$C_{12}$ carbocyclyl is a substituted or unsubstituted $C_3$-$C_6$ saturated carbocyclyl; said "substituted" in said "substituted or unsubstituted $C_3$-$C_6$ saturated carbocyclyl" means being substituted by one or more than one "unsubstituted $C_1$-$C_6$ alkyl" and/or "$C_3$-$C_6$ heterocyclyl containing O or N as heteroatom with a heteroatom number of 1-2;"
when each of $R^5$, $R^{5'}$, $R^6$, $R^7$ and $R^{7'}$ is independently a $C_2$-$C_{20}$ heterocyclyl, said $C_2$-$C_{20}$ heterocyclyl is a substituted or unsubstituted $C_1$-$C_9$ heterocyclyl containing of the heteroatom selected from the group consisting of O, S and N with a heteroatom number of 1-3; in which said "substituted" means being substituted by the substituent selected from the group consisting of an unsubstituted $C_1$-$C_6$ alkyl, a halogen, a halogen substituted alkyl, a hydroxyl substituted alkyl and "$C_2$-$C_4$ hetero-cyclyl containing O, S or N as heteroatom with a heteroatom number of 1-2".

12. The fused pyrimidine compound represented by formula I, the pharmaceutically acceptable salt, the hydrate, the solvate, the optical isomer or the prodrug thereof according to claim 11, wherein,
when said "substituted" in said "substituted or unsubstituted $C_3$-$C_6$ saturated carbocyclyl" means being substituted by one or more than one unsubstituted $C_1$-$C_6$ alkyl, said "unsubstituted $C_1$-$C_6$ alkyl" is a methyl, an ethyl, a propyl, an isopropyl, a n-butyl, an isobutyl or a tert-butyl;
when said "substituted" in said "substituted or unsubstituted $C_3$-$C_6$ saturated carbocyclyl" means being substituted by "$C_3$-$C_6$ heterocyclyl containing O or N as heteroatom with a heteroatom number of 1-2," said "$C_3$-$C_6$ heterocyclyl containing O or N as heteroatom with a heteroatom number of 1-2" is "$C_5$-$C_6$ heterocyclyl containing N as heteroatom with a heteroatom number of 1;"
when said "substituted" in said "substituted or unsubstituted $C_1$-$C_9$ heterocyclyl" means being substituted by unsubstituted $C_1$-$C_6$ alkyl, said "unsubstituted $C_1$-$C_6$ alkyl" is a methyl, an ethyl, a propyl, an isopropyl, a n-butyl, an isobutyl or a tert-butyl;
when said "substituted" in said "substituted or unsubstituted $C_1$-$C_9$ heterocyclyl" means being substituted by halogen, said halogen is F, Cl or Br;
when said "substituted" in said "substituted or unsubstituted $C_1$-$C_9$ heterocyclyl" means being substituted by a halogen-substituted alkyl, said "halogen-substituted alkyl" is trifluoromethyl;
when said "substituted" in said "substituted or unsubstituted $C_1$-$C_9$ heterocyclyl" means being substituted by a hydroxyl-substituted alkyl, said "hydroxyl-substituted alkyl" is hydroxymethyl or

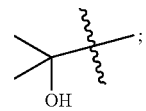 [SMILES: *C(C)(C)O]

when said "substituted" in said "substituted or unsubstituted $C_1$-$C_9$ heterocyclyl" means being substituted by "$C_2$-$C_4$ heterocyclyl containing O, S or N as heteroatom with a heteroatom number of 1-2", said "$C_2$-$C_4$ heterocyclyl" in said "$C_2$-$C_4$ heterocyclyl containing O, S or N as heteroatom with a heteroatom number of 1-2" is a $C_3$ heterocyclyl.

13. The fused pyrimidine compound represented by formula I, the pharmaceutically acceptable salt, the hydrate, the solvate, the optical isomer or the prodrug thereof according to claim 12, wherein,
when said "substituted" in said "substituted or unsubstituted $C_3$-$C_6$ saturated carbocyclyl" means being substituted by a methyl and/or an ethyl, said "substituted $C_3$-$C_6$ saturated carbocyclyl" is

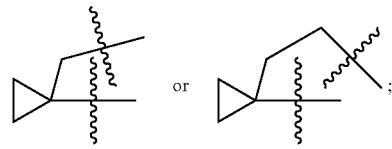 [SMILES: *CC1(*)CC1 ; *CCC1(*)CC1]

when said "substituted" in said "substituted or unsubstituted C₃-C₆ saturated carbocyclyl" means being substituted by "C₅-C₆ heterocyclyl containing N as heteroatom with a heteroatom number of 1," said "C₅-C₆ heterocyclyl containing N as heteroatom with a heteroatom number of 1" is piperidyl;

when said "substituted" in said "substituted or unsubstituted C₁-C₉ heterocyclyl" means being substituted by C₃ heterocyclyl, said "C₃ heterocyclyl" is oxacyclobutyl.

14. The fused pyrimidine compound represented by formula I, the pharmaceutically acceptable salt, the hydrate, the solvate, the optical isomer or the prodrug thereof according to claim 11, wherein,
said "substituted or unsubstituted C₁-C₉ heterocyclyl containing of the heteroatom selected from the group consisting of O, S and N with a heteroatom number of 1-3" is "substituted or unsubstituted C₄-C₅ heterocyclyl containing O or N as heteroatom with a heteroatom number of 1-2".

15. The fused pyrimidine compound represented by formula I, the pharmaceutically acceptable salt, the hydrate, the solvate, the optical isomer or the prodrug thereof according to claim 14, wherein,
when said "substituted or unsubstituted C₁-C₉ heterocyclyl containing the heteroatom selected from the group consisting of O, S and N with a heteroatom number of 1-3" is "substituted or unsubstituted C₄-C₅ heterocyclyl containing O or N as heteroatom with a heteroatom number of 1-2," said "substituted or unsubstituted C₄-C₅ heterocyclyl containing O or N as heteroatom with a heteroatom number of 1-2" is a substituted or unsubstituted tetrahydropyranyl, a substituted or unsubstituted morpholinyl, a substituted or unsubstituted pyrrolyl or a substituted or unsubstituted piperidyl.

16. The fused pyrimidine compound represented by formula I, the pharmaceutically acceptable salt, the hydrate, the solvate, the optical isomer or the prodrug thereof according to claim 15, wherein,
when said "substituted or unsubstituted C₄-C₅ heterocyclyl containing O or N as heteroatom with a heteroatom number of 1-2" is a substituted or unsubstituted tetrahydropyranyl, said "unsubstituted pyranyl" is

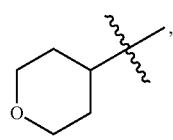

and said "substituted tetrahydropyranyl" is

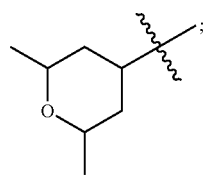 [SMILES: *C1CC(C)OC(C)C1]

when said "substituted or unsubstituted C₄-C₅ heterocyclyl containing O or N as heteroatom with a heteroatom number of 1-2" is a substituted or unsubstituted morpholinyl, said substituted morpholinyl is

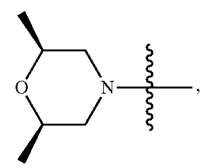 [SMILES: *N1C[C@@H](C)O[C@@H](C)C1]

and said unsubstituted morpholinyl is

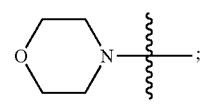

when said "substituted or unsubstituted C₄-C₅ heterocyclyl containing O or N as heteroatom with a heteroatom number of 1-2" is a substituted or unsubstituted pyrrolyl, said substituted pyrrolyl is

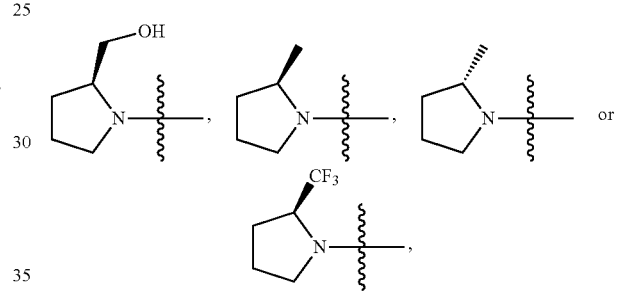

and said unsubstituted pyrrolyl is

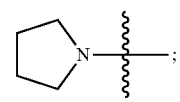 [SMILES: *N1CCCC1]

when said "substituted or unsubstituted C₄-C₅ heterocyclyl containing O or N as heteroatom with a heteroatom number of 1-2" is a substituted or unsubstituted piperidyl, said substituted piperidyl is

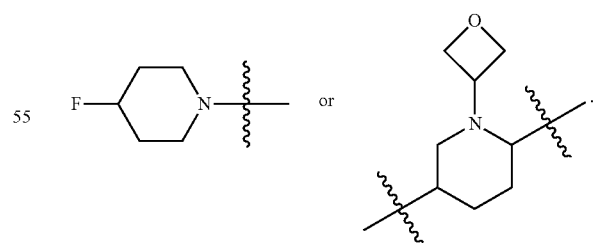

17. The fused pyrimidine compound represented by formula I, the pharmaceutically acceptable salt, the hydrate, the solvate, the optical isomer or the prodrug thereof according to claim 1, wherein,
when the heterocycle formed by R⁵, R⁶ together with the nitrogen to which they are directly attached further forms a spiro ring with C$_2$-C$_6$ heterocycle, said "C$_2$-C$_6$ heterocycle" is "C$_2$-C$_6$ heterocycle containing O, S or N as heteroatom with a heteroatom number of 1-2;"

when the heterocycle formed by R$^5$, R$^6$ together with the nitrogen to which they are directly attached further forms a spiro ring with C$_2$-C$_6$ carbocycle, thus formed spiro ring is

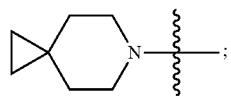 [SMILES: *N1CCC2(CC1)CC2]

when the heterocycle formed by R$^5$, R$^6$ together with the nitrogen to which they are directly attached further forms a fused ring with C$_2$-C$_6$ heteroaromatic ring, said "C$_2$-C$_6$ heteroaromatic ring" is "C$_2$-C$_6$ heteroaromatic ring containing O, S or N as heteroatom with a heteroatom number of 1-2;"

when the heterocycle formed by R$^5$, R$^6$ together with the nitrogen to which they are directly attached further forms a bridged ring with C$_2$-C$_6$ heteroaromatic ring, said "C$_2$-C$_6$ heteroaromatic ring" is "C$_2$-C$_6$ heteroaromatic ring containing O, S or N as heteroatom with a heteroatom number of 1-2;"

when the heterocycle formed by R$^5$, R$^6$ together with the nitrogen to which they are directly attached further forms a fused ring with C$_2$-C$_6$ heteroaromatic ring, said "C$_2$-C$_6$ heteroaromatic ring" is a benzene ring;

when the heterocycle formed by R$^5$, R$^6$ together with the nitrogen to which they are directly attached further forms a fused ring with C$_2$-C$_6$ carbocycle, thus formed the fused ring is

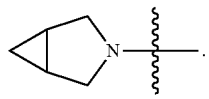

18. The fused pyrimidine compound represented by formula I, the pharmaceutically acceptable salt, the hydrate, the solvate, the optical isomer or the prodrug thereof according to claim 17, wherein, when the heterocycle formed by R$^5$, R$^6$ together with the nitrogen to which they are directly attached further forms a spiro ring with C$_2$-C$_6$ heterocycle, thus formed spiro ring is

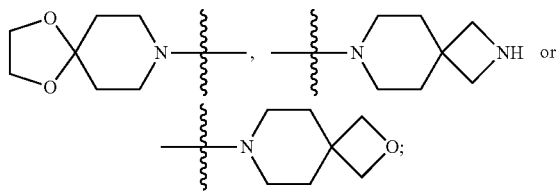

when the heterocycle formed by R$^5$, R$^6$ together with the nitrogen to which they are directly attached further forms a fused ring with C$_2$-C$_6$ heteroaromatic ring, thus formed fused ring is

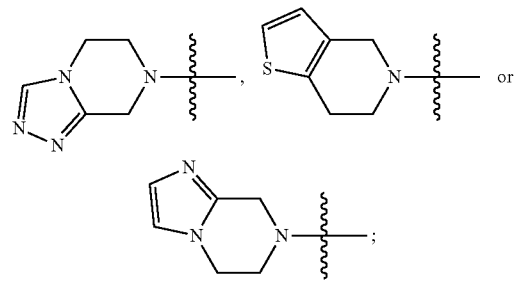

when the heterocycle formed by R$^5$, R$^6$ together with the nitrogen to which they are directly attached further forms a bridged ring with C$_2$-C$_6$ heteroaromatic ring, thus formed bridged ring is

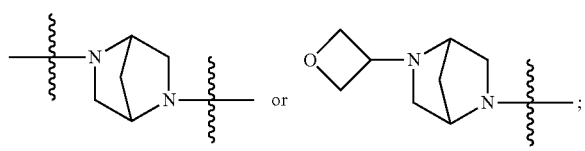 [SMILES: *N1CC2CC1CN2* ; *N1CC2CC1CN2C1COC1]

when the heterocycle formed by R$^5$, R$^6$ together with the nitrogen to which they are directly attached further forms a fused ring with C$_2$-C$_6$ heteroaromatic ring, thus formed fused ring is

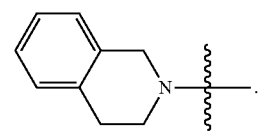

19. The fused pyrimidine compound represented by formula I, the pharmaceutically acceptable salt, the hydrate, the solvate, the optical isomer or the prodrug thereof according to claim 1, wherein, when the heterocycle formed by R$^5$, R$^6$ together with the nitrogen to which they are directly attached is substituted by —(CH$_2$)$_m$OR$^7$, said —(CH$_2$)$_m$OR$^7$ is

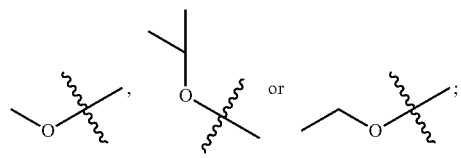

when the heterocycle formed by R$^5$, R$^6$ together with the nitrogen to which they are directly attached is substituted by —NR$^7$R$^{7'}$, said —NR$^7$R$^{7'}$ is

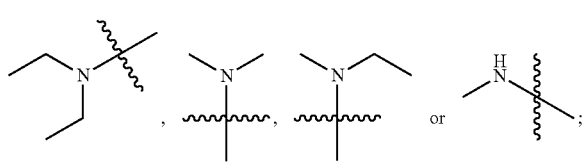

when the heterocycle formed by $R^5$, $R^6$ together with the nitrogen to which they are directly attached is substituted by halogen, said halogen is F, Cl, Br or I;

when the heterocycle formed by $R^5$, $R^6$ together with the nitrogen to which they are directly attached is substituted by —$SO_2R^7$, said —$SO_2R^7$ is

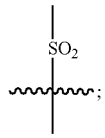

when the heterocycle formed by $R^5$, $R^6$ together with the nitrogen to which they are directly attached is substituted by a $C_1$-$C_{12}$ alkyl, said $C_1$-$C_{12}$ alkyl is a substituted or unsubstituted $C_1$-$C_6$ alkyl in which said "substituted" means being substituted by the substituent selected from the group consisting of hydroxyl,

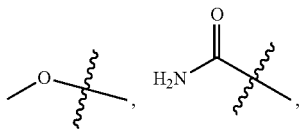

F and a $C_2$-$C_6$ heterocyclyl;

when the heterocycle formed by $R^5$, $R^6$ together with the nitrogen to which they are directly attached is substituted by a $C_2$-$C_8$ alkenyl, and said $C_2$-$C_8$ alkenyl is a substituted or unsubstituted $C_2$-$C_4$ alkenyl, said "substituted" in which means being substituted by one or more than one unsubstituted $C_1$-$C_6$ alkyl;

when the heterocycle formed by $R^5$, $R^6$ together with the nitrogen to which they are directly attached is substituted by a $C_3$-$C_{12}$ carbocyclyl, said $C_3$-$C_{12}$ carbocyclyl is an unsubstituted $C_3$-$C_6$ saturated carbocyclyl;

when the heterocycle formed by $R^5$, $R^6$ together with the nitrogen to which they are directly attached is substituted by a $C_2$-$C_{20}$ heterocyclyl, and said $C_2$-$C_{20}$ heterocyclyl is a substituted or unsubstituted $C_1$-$C_9$ heterocyclyl containing the heteroatom selected from the group consisting of O, S and N as heteroatom with a heteroatom number of 1-3, said "substituted" in which means being substituted by the substituent selected from the group consisting of an unsubstituted $C_1$-$C_6$ alkyl, a halogen, a halogen substituted alkyl, oxo and a hydroxyl substituted alkyl.

20. The fused pyrimidine compound represented by formula I, the pharmaceutically acceptable salt, the hydrate, the solvate, the optical isomer or the prodrug thereof according to claim 19, wherein, when the heterocycle formed by $R^5$, $R^6$ together with the nitrogen to which they are directly attached is substituted by a substituted or unsubstituted $C_1$-$C_6$ alkyl in which said "substituted" means being substituted by a $C_2$-$C_6$ heterocyclyl, said "$C_2$-$C_6$ heterocyclyl" is "$C_2$-$C_6$ heterocycle containing O, S or N as heteroatom with a heteroatom number of 1-2;"

when the heterocycle formed by $R^5$, $R^6$ together with the nitrogen to which they are directly attached is substituted by a substituted or unsubstituted $C_2$-$C_4$ alkenyl in which said "substituted" means being substituted by one or more than one unsubstituted $C_1$-$C_6$ alkyl, said "unsubstituted $C_1$-$C_6$ alkyl" is a methyl, an ethyl, a propyl, an isopropyl, a n-butyl, an isobutyl or a tert-butyl;

when the heterocycle formed by $R^5$, $R^6$ together with the nitrogen to which they are directly attached is substituted by an unsubstituted $C_3$-$C_6$ saturated carbocyclyl, said unsubstituted $C_3$-$C_6$ saturated carbocyclyl is a cyclopropyl;

when the heterocycle formed by $R^5$, $R^6$ together with the nitrogen to which they are directly attached is substituted by a substituted or unsubstituted $C_1$-$C_9$ heterocyclyl containing the heteroatom selected from the group consisting of O, S and N with a heteroatom number of 1-3, said "substituted" in which means being substituted by an unsubstituted $C_1$-$C_6$ alkyl, said unsubstituted $C_1$-$C_6$ alkyl is a methyl, an ethyl, a propyl, an isopropyl, a n-butyl, an isobutyl or a tert-butyl;

when the heterocycle formed by $R^5$, $R^6$ together with the nitrogen to which they are directly attached is substituted by a substituted or unsubstituted $C_1$-$C_9$ heterocyclyl containing the heteroatom selected from the group consisting of O, S and N with a heteroatom number of 1-3 in which said "substituted" means being substituted by a halogen, said halogen is F, Cl, or Br;

when the heterocycle formed by $R^5$, $R^6$ together with the nitrogen to which they are directly attached is substituted by a substituted or unsubstituted $C_1$-$C_9$ heterocyclyl containing the atmosphere selected from the group consisting of O, S and N with a heteroatom number of 1-3 in which said "substituted" means being substituted by a halogen-substituted alkyl, said halogen-substituted alkyl is trifluoromethyl;

when the heterocycle formed by $R^5$, $R^6$ together with the nitrogen to which they are directly attached is substituted by a substituted or unsubstituted $C_1$-$C_9$ heterocyclyl containing the atmosphere selected from the group consisting of O, S and N with a heteroatom number of 1-3 in which said "substituted" means being substituted by a hydroxyl-substituted alkyl, said hydroxyl-substituted alkyl is hydroxymethyl or

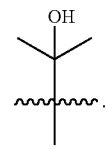 [SMILES: *C(C)(C)O]

21. The fused pyrimidine compound represented by formula I, the pharmaceutically acceptable salt, the hydrate, the solvate, the optical isomer or the prodrug thereof according to claim 20, wherein, when said "$C_2$-$C_6$ heterocyclyl" is a $C_2$-$C_6$ heterocycle containing O, S or N as heteroatom with a heteroatom number of 1-2, said "$C_2$-$C_6$ heterocycle containing O, S or N as heteroatom with a heteroatom number of 1-2" is pyranyl;

when the heterocycle formed by $R^5$, $R^6$ together with the nitrogen to which they are directly attached is substituted by a $C_2$-$C_4$ alkenyl, said "unsubstituted $C_2$-$C_4$ alkenyl" in said "substituted or unsubstituted $C_2$-$C_4$ alkenyl" is

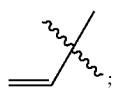

when the heterocycle formed by $R^5$, $R^6$ together with the nitrogen to which they are directly attached is substituted by a $C_2$-$C_4$ alkenyl, said "substituted $C_2$-$C_4$ alkenyl" in said "substituted or unsubstituted $C_2$-$C_4$ alkenyl" is

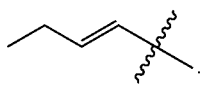 [SMILES: */C=C/CC]

22. The fused pyrimidine compound represented by formula I, the pharmaceutically acceptable salt, the hydrate, the solvate, the optical isomer or the prodrug thereof according to claim 19, wherein,
when said $C_1$-$C_{12}$ alkyl is a substituted or unsubstituted $C_1$-$C_6$ alkyl, said "substituted $C_1$-$C_6$ alkyl" is trifluoromethyl,

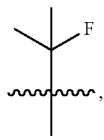

trifluoroethyl,

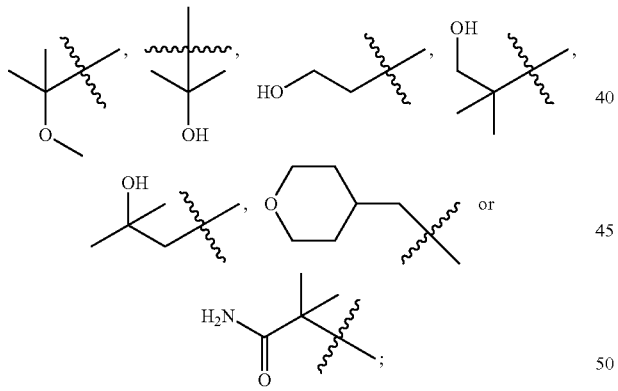

when said $C_1$-$C_{12}$ alkyl is "unsubstituted $C_1$-$C_6$ alkyl", said "unsubstituted $C_1$-$C_6$ alkyl" is a methyl, an ethyl, a propyl, an isopropyl, a n-butyl, an isobutyl, a tert-butyl, a n-pentyl, an isopentyl or a neo-pentyl.

23. The fused pyrimidine compound represented by formula I, the pharmaceutically acceptable salt, the hydrate, the solvate, the optical isomer or the prodrug thereof according to claim 20, wherein,
when the heterocycle formed by $R^5$, $R^6$ together with the nitrogen to which they are directly attached is substituted by a substituted or unsubstituted $C_1$-$C_9$ heterocyclyl containing the heteroatom selected from the group consisting of O, S and N with a heteroatom number of 1-3, said "substituted or unsubstituted $C_1$-$C_9$ heterocyclyl containing the heteroatom selected from the group consisting of O, S and N with a heteroatom number of 1-3" is a substituted or unsubstituted $C_3$-$C_5$ heterocyclyl containing O or N as heteroatom with a heteroatom number of 1-2.

24. The fused pyrimidine compound represented by formula I, the pharmaceutically acceptable salt, the hydrate, the solvate, the optical isomer or the prodrug thereof according to claim 23, wherein,
when the heterocycle formed by $R^5$, $R^6$ together with the nitrogen to which they are directly attached is substituted by a substituted or unsubstituted $C_3$-$C_5$ heterocyclyl containing O or N as heteroatom with a heteroatom number of 1-2, said "substituted or unsubstituted $C_3$-$C_5$ heterocyclyl containing O or N as heteroatom with a heteroatom number of 1-2" is a substituted or unsubstituted pyranyl, a substituted or unsubstituted oxacyclobutyl, a substituted or unsubstituted morpholinyl, a substituted or unsubstituted pyrrolyl, a substituted or unsubstituted piperidyl, or a substituted or unsubstituted azetidinyl.

25. The fused pyrimidine compound represented by formula I, the pharmaceutically acceptable salt, the hydrate, the solvate, the optical isomer or the prodrug thereof according to claim 24, wherein,
when said "substituted or unsubstituted $C_3$-$C_5$ heterocyclyl containing O or N as heteroatom with a heteroatom number of 1-2" is a substituted or unsubstituted pyranyl, said substituted pyranyl is

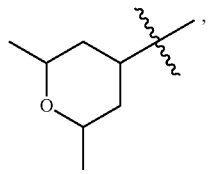 [SMILES: *C1CC(C)OC(C)C1]

and said unsubstituted pyranyl is

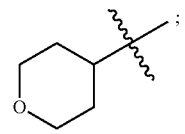 [SMILES: *C1CCOCC1]

when said "substituted or unsubstituted $C_3$-$C_5$ heterocyclyl containing O or N as heteroatom with a heteroatom number of 1-2" is a substituted or unsubstituted oxacyclobutyl, said unsubstituted oxacyclobutyl is

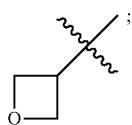 [SMILES: *C1COC1]

when said "substituted or unsubstituted $C_3$-$C_5$ heterocyclyl containing O or N as heteroatom with a heteroatom number of 1-2" is a substituted or unsubstituted morpholinyl, said substituted morpholinyl is

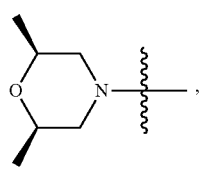

and said unsubstitutedmorpholinyl is

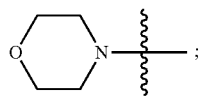

when said "substituted or unsubstituted $C_3$-$C_5$ heterocyclyl containing O or N as heteroatom with a heteroatom number of 1-2" is a substituted or unsubstituted pyrrolyl, said substituted pyrrolyl is

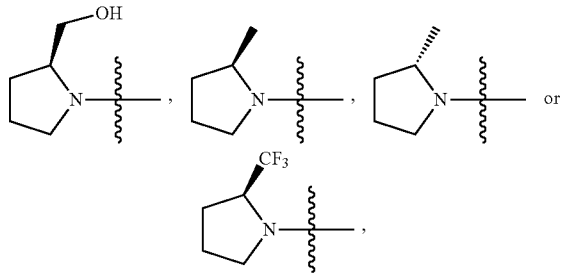

and said unsubstituted pyrrolyl is

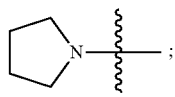

when said "substituted or unsubstituted $C_3$-$C_5$ heterocyclyl containing O or N as heteroatom with a heteroatom number of 1-2" is a substituted or unsubstituted piperidyl, said substituted piperidyl is

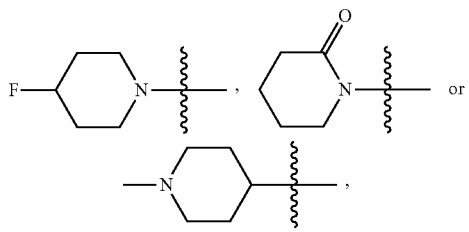

and said unsubstituted piperidyl is

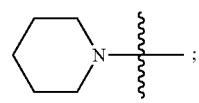

when said "substituted or unsubstituted $C_3$-$C_5$ heterocyclyl containing O or N as heteroatom with a heteroatom number of 1-2" is a substituted or unsubstituted azetidinyl, said substituted azetidinyl is

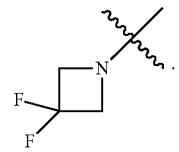

26. The fused pyrimidine compound represented by formula I, the pharmaceutically acceptable salt, the hydrate, the solvate, the optical isomer or the prodrug thereof according to claim 1, wherein, when the heterocycle formed by $R^5$, $R^6$ together with the nitrogen to which they are directly attached is substituted by a methylsulfonyl, said methylsulfonyl is

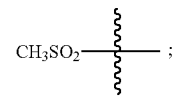

when the heterocycle formed by $R^5$, $R^6$ together with the nitrogen to which they are directly attached is substituted by a $C_3$-$C_{20}$ heterocycloalkenyl, said $C_3$-$C_{20}$ heterocycloalkenyl is a $C_3$-$C_5$ heterocycloalkenyl containing N, O or S as heteroatom with a heteroatom number of 1 or 2;

when the heterocycle formed by $R^5$, $R^6$ together with the nitrogen to which they are directly attached is substituted by a $C_1$-$C_{20}$ heteroaryl, said $C_1$-$C_{20}$ heteroaryl is a substituted or unsubstituted $C_2$-$C_6$ heteroaryl containing O, S or N as heteroatom with a heteroatom number of 1 or 2 in which said substituted means being substituted by the substituent selected from the group consisting of a methyl, an ethyl and a propyl;

when the heterocycle formed by $R^5$, $R^6$ together with the nitrogen to which they are directly attached is substituted by an amino, said amino is the amino substituted by the substituent selected from the group consisting of a methyl, an ethyl, a propyl, an isopropyl, a n-butyl, an isobutyl, a tert-butyl and a tert-butoxycarbonyl;

when the heterocycle formed by $R^5$, $R^6$ together with the nitrogen to which they are directly attached is substituted by

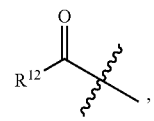

in said

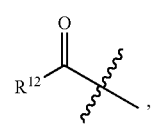

when said $R^{12}$ is an unsubstituted $C_1$-$C_4$ alkyl, said "unsubstituted $C_1$-$C_4$ alkyl" is a methyl, an ethyl, a propyl, an isopropyl or a tert-butyl;

when the heterocycle formed by $R^5$, $R^6$ together with the nitrogen to which they are directly attached is substituted by

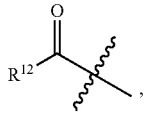

in said

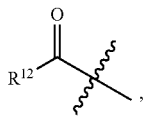

when said $R^{12}$ is a halogen substituted $C_1$-$C_4$ alkyl, said halogen substituted $C_1$-$C_4$ alkyl is trifluoromethyl;

when the heterocycle formed by $R^5$, $R^6$ together with the nitrogen to which they are directly attached is substituted by

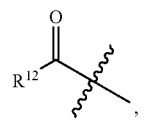

in said

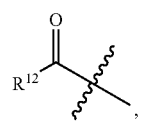

when said $R^{12}$ is a cyano substituted $C_1$-$C_4$ alkyl, said cyano substituted $C_1$-$C_4$ alkyl is

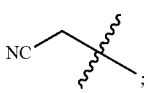 [SMILES: *CC#N]

when the heterocycle formed by $R^5$, $R^6$ together with the nitrogen to which they are directly attached is substituted by

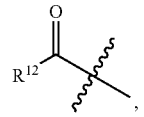

in said

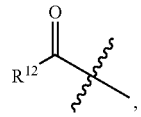

when said $R^{12}$ is a hydroxyl substituted $C_1$-$C_4$ alkyl, said hydroxyl substituted $C_1$-$C_4$ alkyl is hydroxyethyl;

when the heterocycle formed by $R^5$, $R^6$ together with the nitrogen to which they are directly attached is substituted by

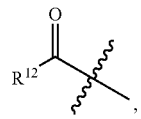

in said

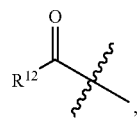

when said $R^{12}$ is an unsubstituted $C_1$-$C_4$ alkoxy, said unsubstituted $C_1$-$C_4$ alkoxy is methoxy or tert-butoxy;

when the heterocycle formed by $R^5$, $R^6$ together with the nitrogen to which they are directly attached is substituted by

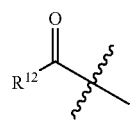

in said

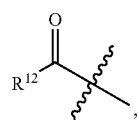

when said $R^{12}$ is an unsubstituted $C_3$-$C_6$ saturated carbocycloalkyl, said unsubstituted $C_3$-$C_6$ saturated carbocyclyl is a cyclopropyl or a cyclohexyl;

when the heterocycle formed by $R^5$, $R^6$ together with the nitrogen to which they are directly attached is substituted by a substituted or unsubstituted $C_1$-$C_3$ amido, said substituted means being substituted by an unsubstituted $C_1$-$C_6$ alkoxy.

27. The fused pyrimidine compound represented by formula I, the pharmaceutically acceptable salt, the hydrate, the solvate, the optical isomer or the prodrug thereof according to claim 26, wherein, when the heterocycle formed by $R^5$, $R^6$ together with the nitrogen to which they are directly attached is substituted by a substituted or unsubstituted $C_1$-$C_3$ amido, in said "substituted or unsubstituted $C_1$-$C_3$ amido", said substituted means being substituted by an unsubstituted $C_1$-$C_6$ alkoxy, said "unsubstituted $C_1$-$C_6$ alkoxy" is a methoxy, an ethoxy, a propoxy, an isopropoxy or a tert-butoxy;

when the heterocycle formed by $R^5$, $R^6$ together with the nitrogen to which they are directly attached is substituted by a $C_3$-$C_5$ heterocycloalkenyl containing N, O or S as heteroatom with a heteroatom number of 1 or 2, said "$C_3$-$C_5$ heterocycloalkenyl containing N, O or S as heteroatom with a heteroatom number of 1 or 2" is

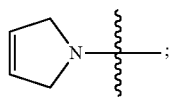 [SMILES: *N1CC=CC1]

when the heterocycle formed by $R^5$, $R^6$ together with the nitrogen to which they are directly attached is substituted by a $C_2$-$C_6$ heteroaryl containing O, S or N as heteroatom with a heteroatom number of 1 or 2, said "$C_2$-$C_6$ heteroaryl containing O, S or N as heteroatom with a heteroatom number of 1 or 2" is a $C_3$ heteroaryl containing S and/or N as heteroatom with a heteroatom number of 2;

when the heterocycle formed by $R^5$, $R^6$ together with the nitrogen to which they are directly attached is substituted by an amino substituted by the substituent selected from the group consisting of a methyl, an ethyl, a propyl, an isopropyl, a n-butyl, an isobutyl, a tert-butyl and a tert-butoxycarbonyl, said "amino substituted by the substituent selected from the group consisting of a methyl, an ethyl, a propyl, an isopropyl, a n-butyl, an isobutyl, a tert-butyl and a tert-butoxycarbonyl" is

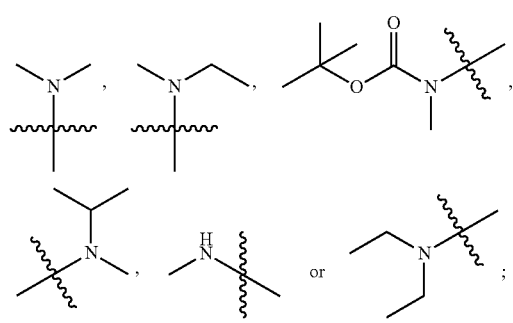

said

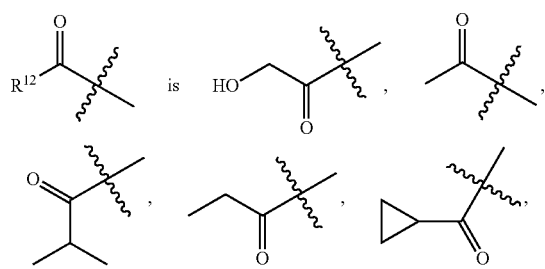

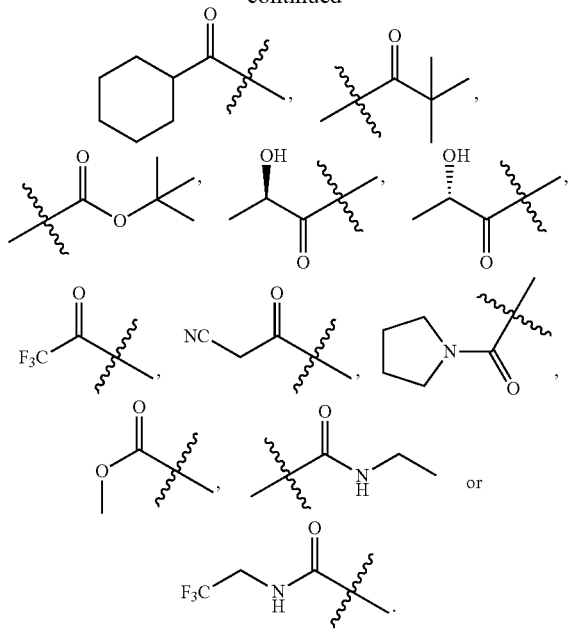

28. The fused pyrimidine compound represented by formula I, the pharmaceutically acceptable salt, the hydrate, the solvate, the optical isomer or the prodrug thereof according to claim 27, wherein, when the heterocycle formed by $R^5$, $R^6$ together with the nitrogen to which they are directly attached is substituted by a substituted or unsubstituted $C_1$-$C_3$ amido, in said "substituted or unsubstituted $C_1$-$C_3$ amido," said substituted means being substituted by tert-butoxy, said "substituted $C_1$-$C_3$ amido" is

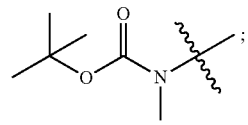 [SMILES: *N(C)C(=O)OC(C)(C)C]

when the heterocycle formed by $R^5$, $R^6$ together with the nitrogen to which they are directly attached is substituted by a $C_3$ heteroaryl containing S and/or N as heteroatom with a heteroatom number of 2, said "$C_3$ heteroaryl containing S and/or N as heteroatom with a heteroatom number of 2" is a substituted thiazolyl.

29. The fused pyrimidine compound represented by formula I, the pharmaceutically acceptable salt, the hydrate, the solvate, the optical isomer or the prodrug thereof according to claim 28, wherein, when the heterocycle formed by $R^5$, $R^6$ together with the nitrogen to which they are directly attached is substituted by a substituted thiazolyl, said substituted thiazolyl is

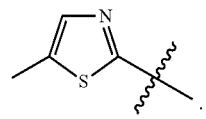 [SMILES: *c1ncc(C)s1]

30. The fused pyrimidine compound represented by formula I, the pharmaceutically acceptable salt, the hydrate, the solvate, the optical isomer or the prodrug thereof according to claim 1, wherein, each of $R^8$ and $R^9$ is independently a hydrogen or a $C_1$-$C_{12}$ alkyl;

when each of $R^8$ and $R^9$ is independently a $C_1$-$C_{12}$ alkyl, said $C_1$-$C_{12}$ alkyl is an unsubstituted $C_1$-$C_6$ alkyl, said "unsubstituted $C_1$-$C_6$ alkyl" is a methyl, an ethyl, a propyl, an isopropyl, a n-butyl, an isobutyl, a tert-butyl, a n-pentyl, an isopentyl or a neo-pentyl.

31. The fused pyrimidine compound represented by formula I, the pharmaceutically acceptable salt, the hydrate, the solvate, the optical isomer or the prodrug thereof according to claim 1, wherein, said fused pyrimidine compound represented by formula I is the compound as shown by formula 2, 3, 4 or 5,

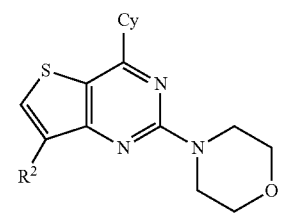

2

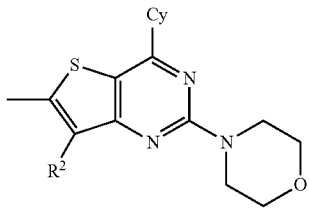

3

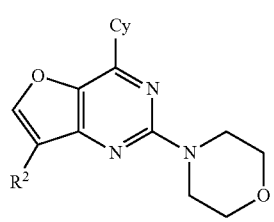

4

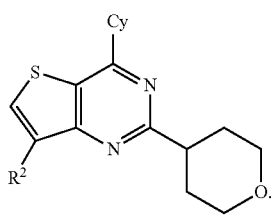

5

32. The fused pyrimidine compound represented by formula I, the pharmaceutically acceptable salt, the hydrate, the solvate, the optical isomer or the prodrug thereof according to claim 31, wherein, in the compound as shown by formula 2 or 3, Cy is a substituent selected from the group consisting of:

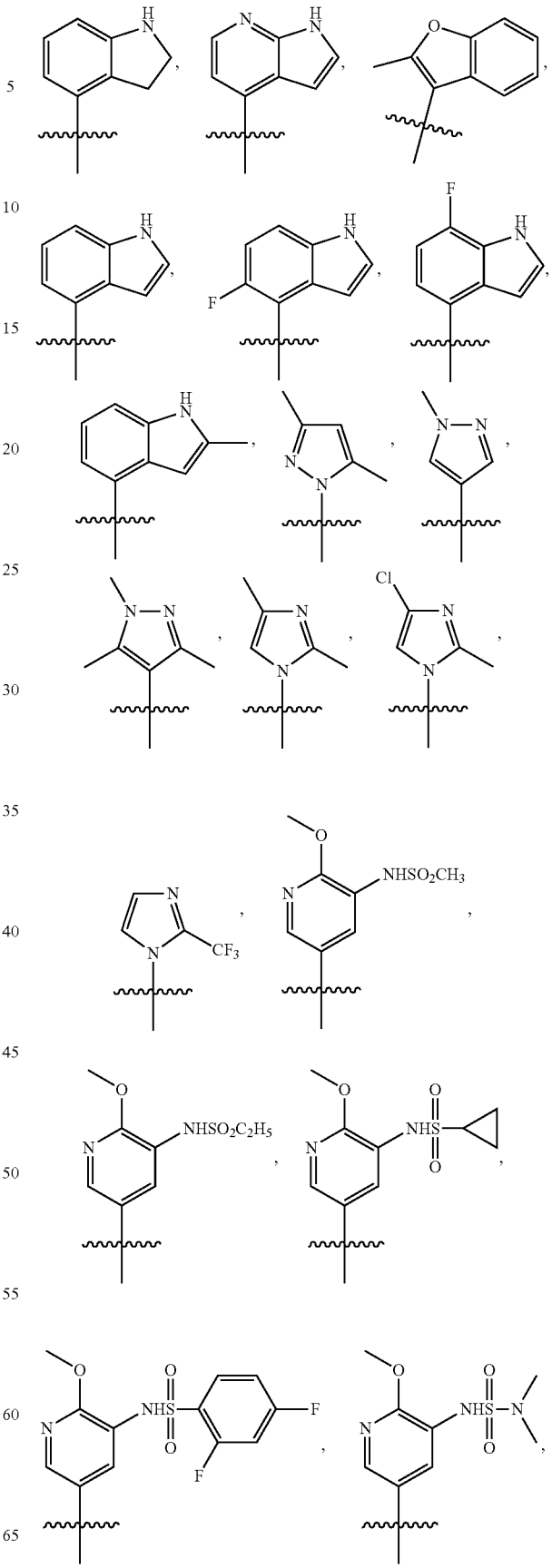

-continued

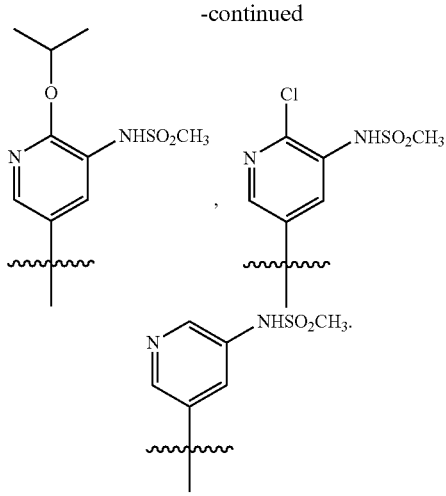

and

33. The fused pyrimidine compound represented by formula I, the pharmaceutically acceptable salt, the hydrate, the solvate, the optical isomer or the prodrug thereof according to claim 31, wherein, in the compound as shown by formula 4 or 5, Cy is the following substituent:

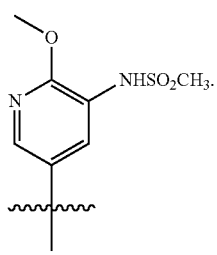

34. The fused pyrimidine compound represented by formula I, the pharmaceutically acceptable salt, the hydrate, the solvate, the optical isomer or the prodrug thereof according to claim 1, wherein, said compound I is a compound selected from the group consisting of:

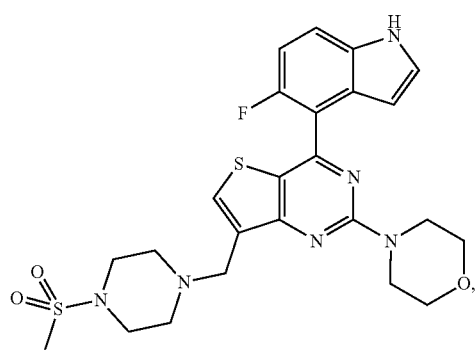

1

-continued

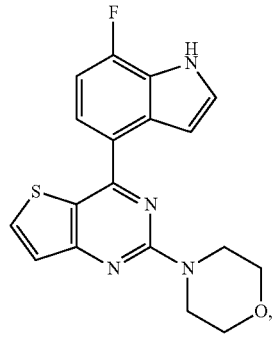

2

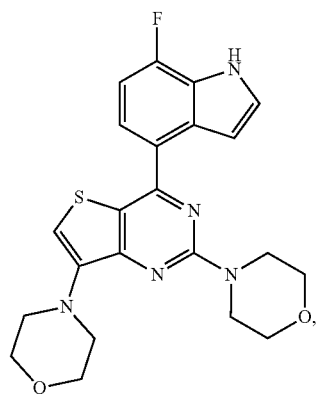

3

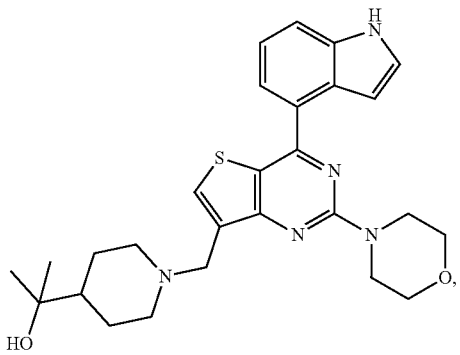

4

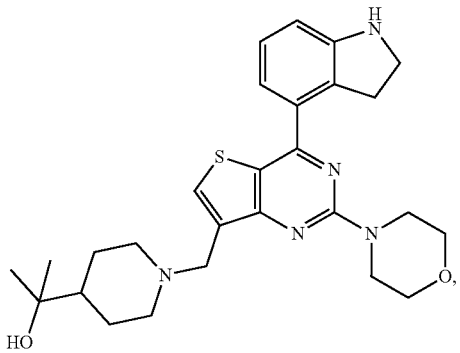

5

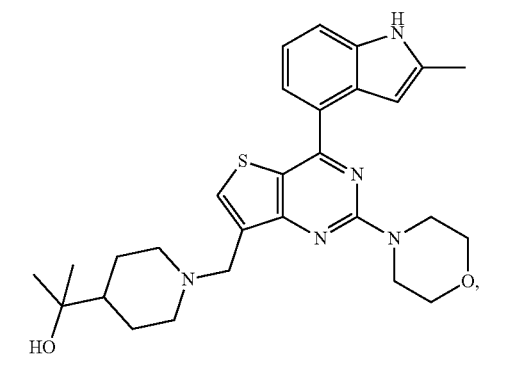
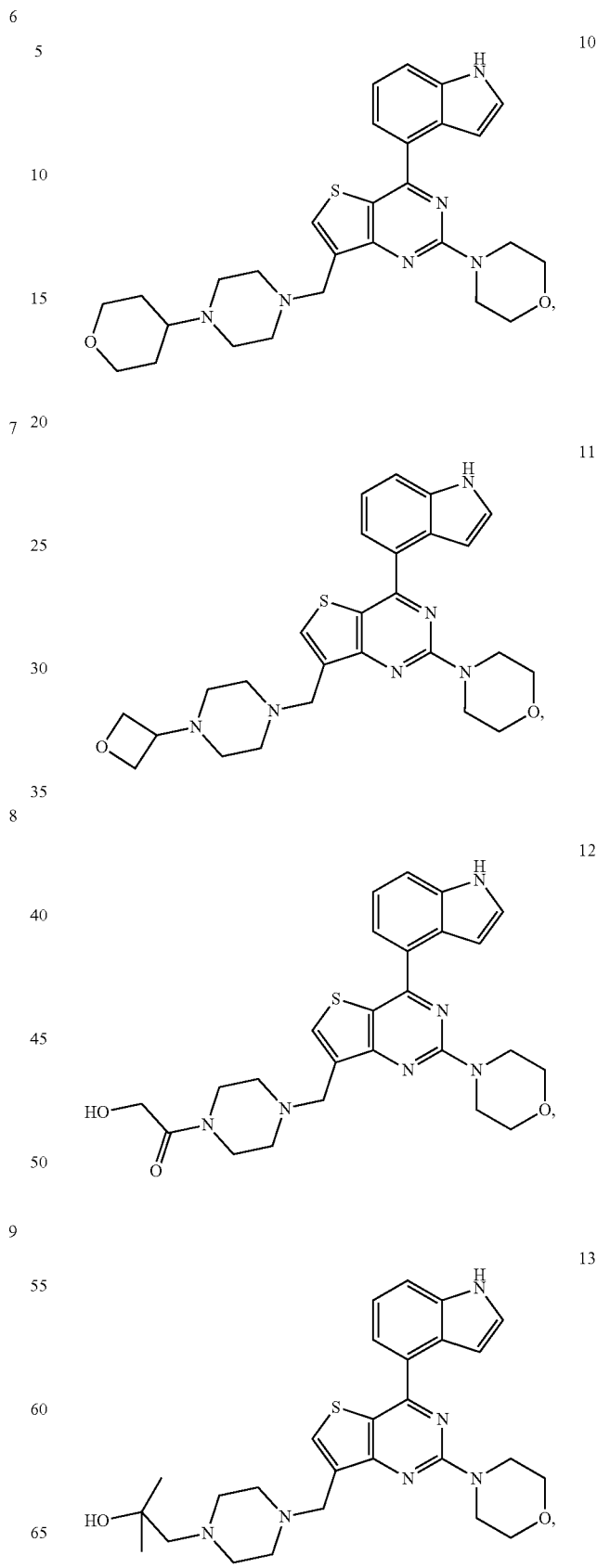

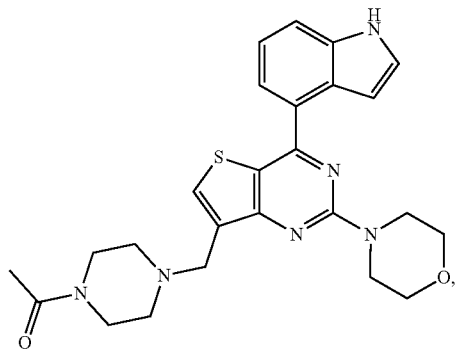
14
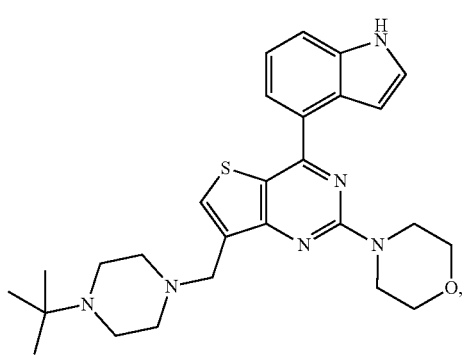
15
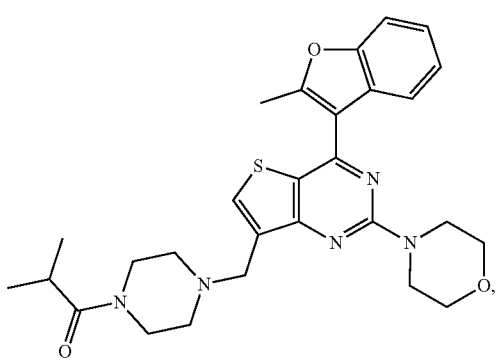
16
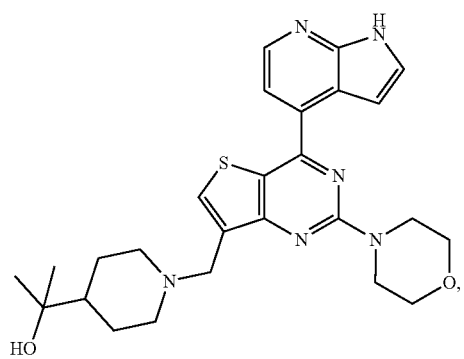
17
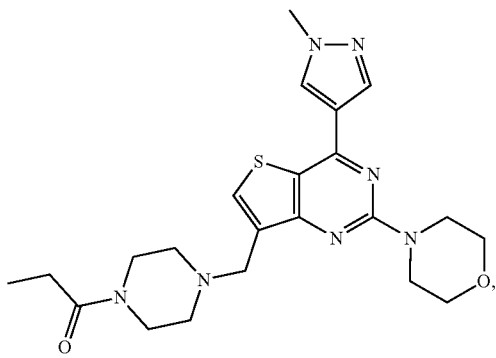
18
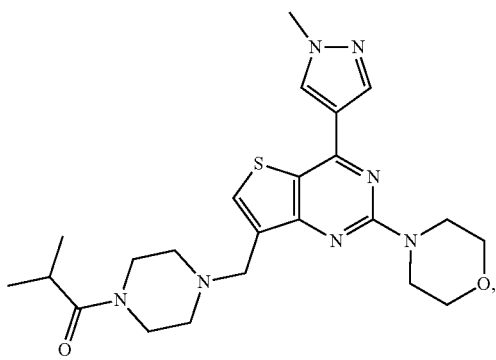
19
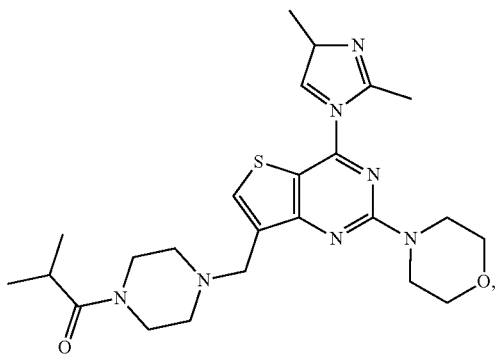
20
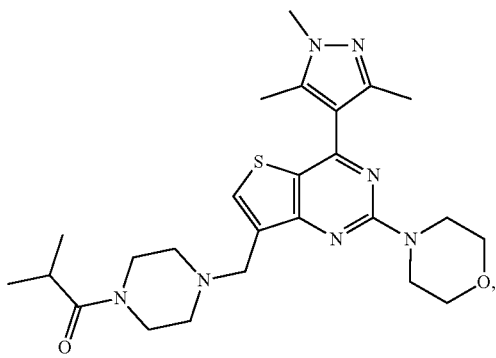
21

22
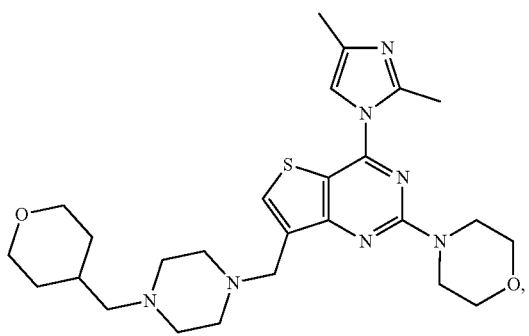
23
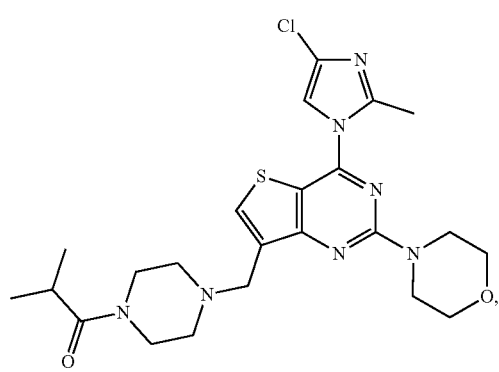
24
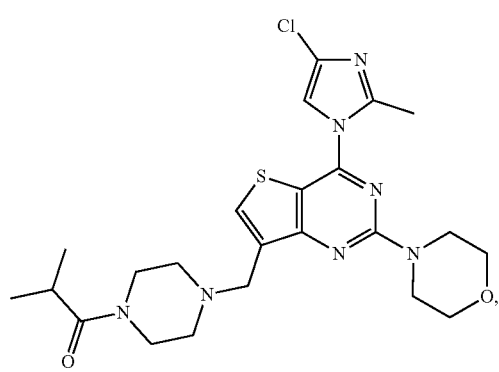
25
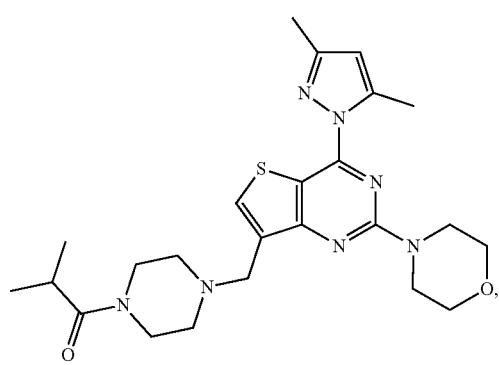
26
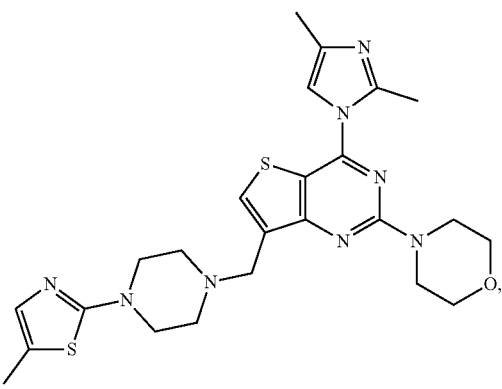
27
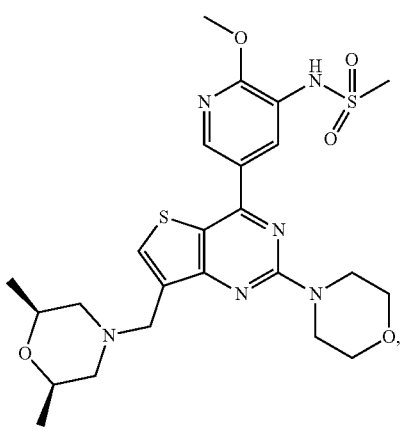
28
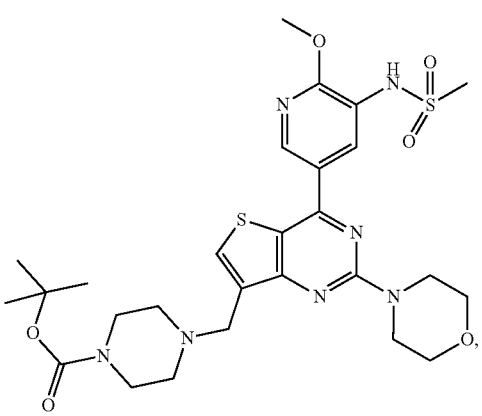
29
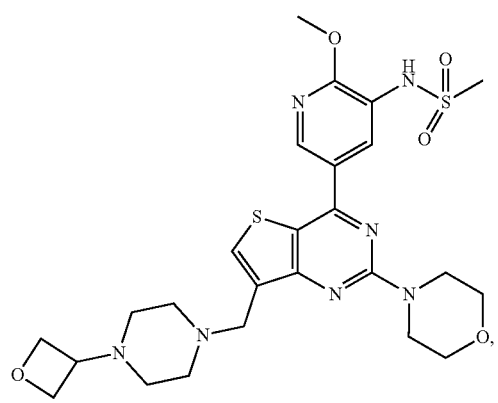

30
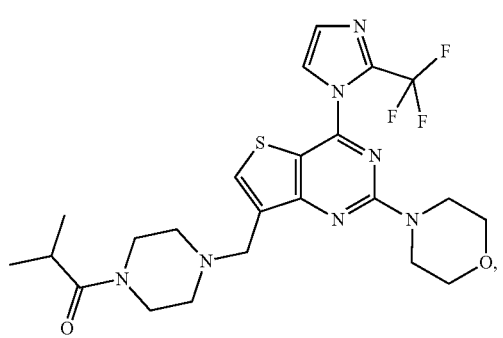
31
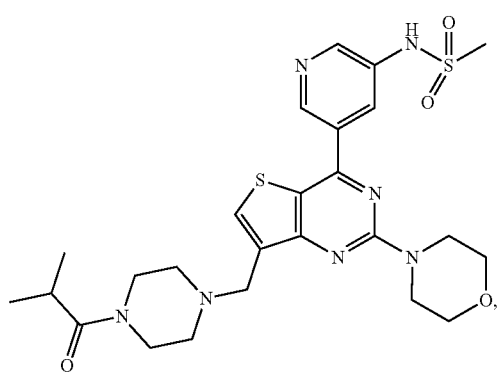
32
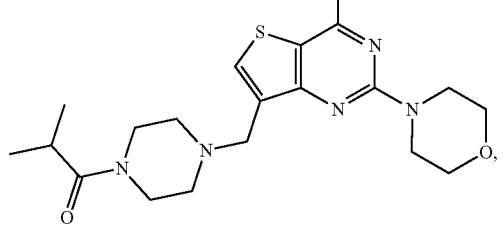
33
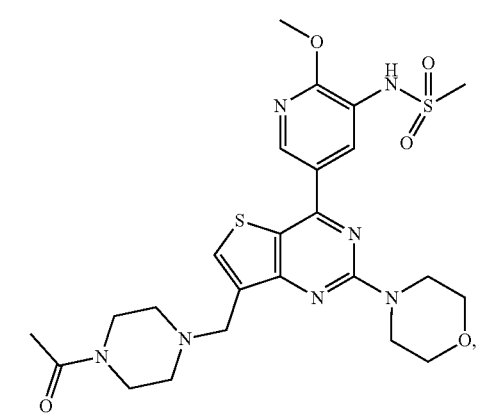
34
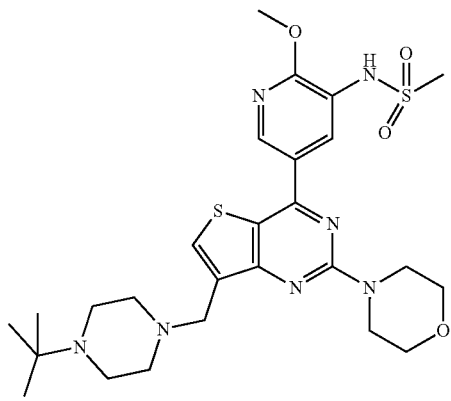
35
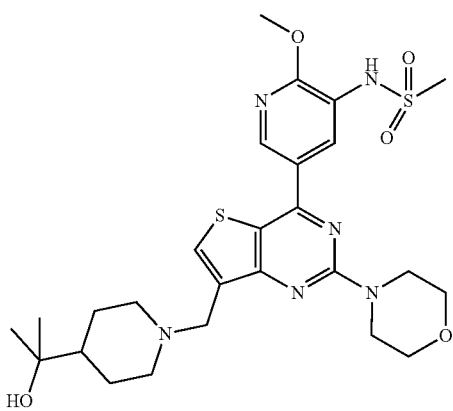
36
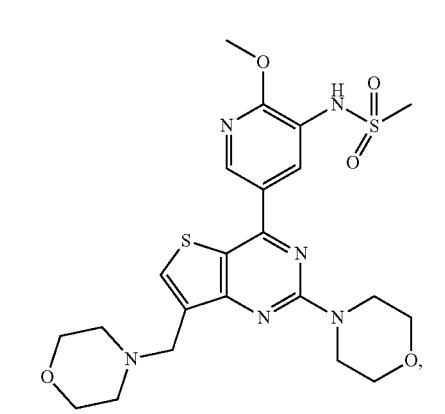
37
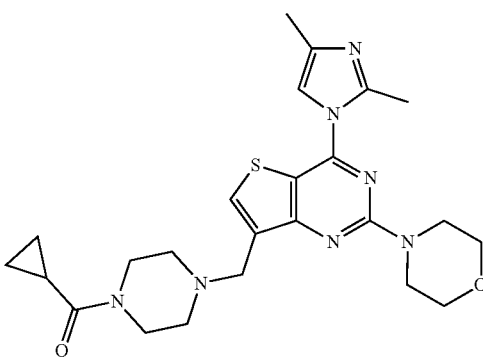

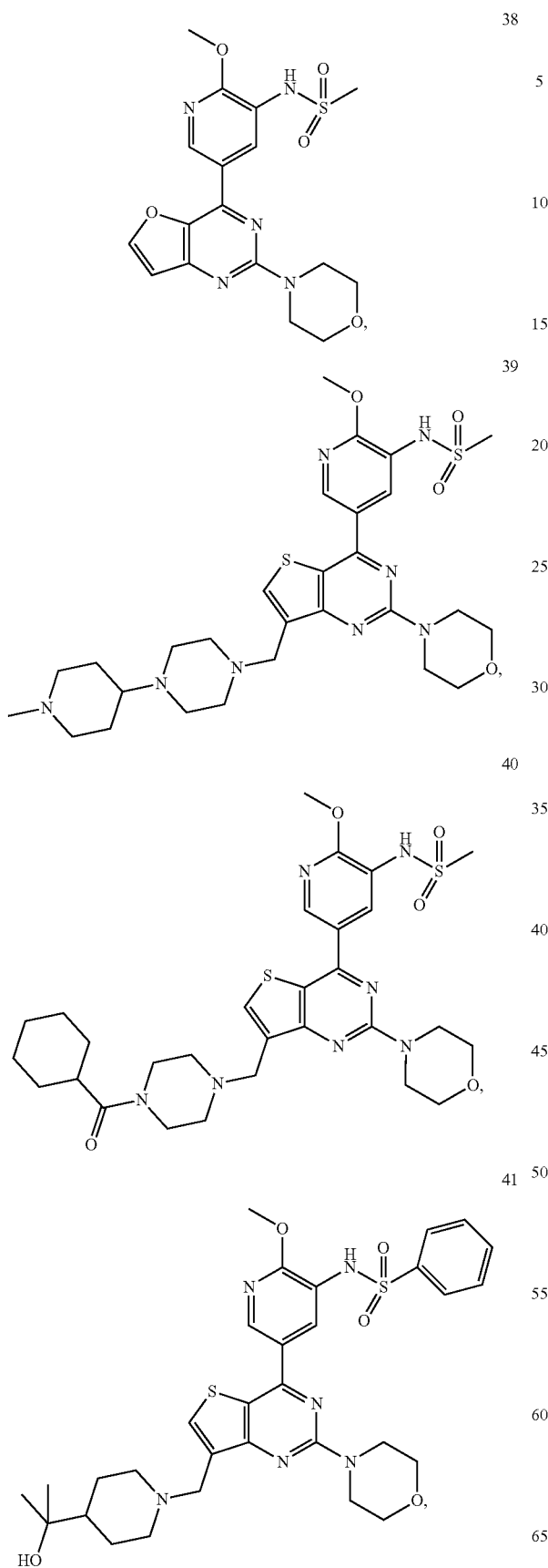
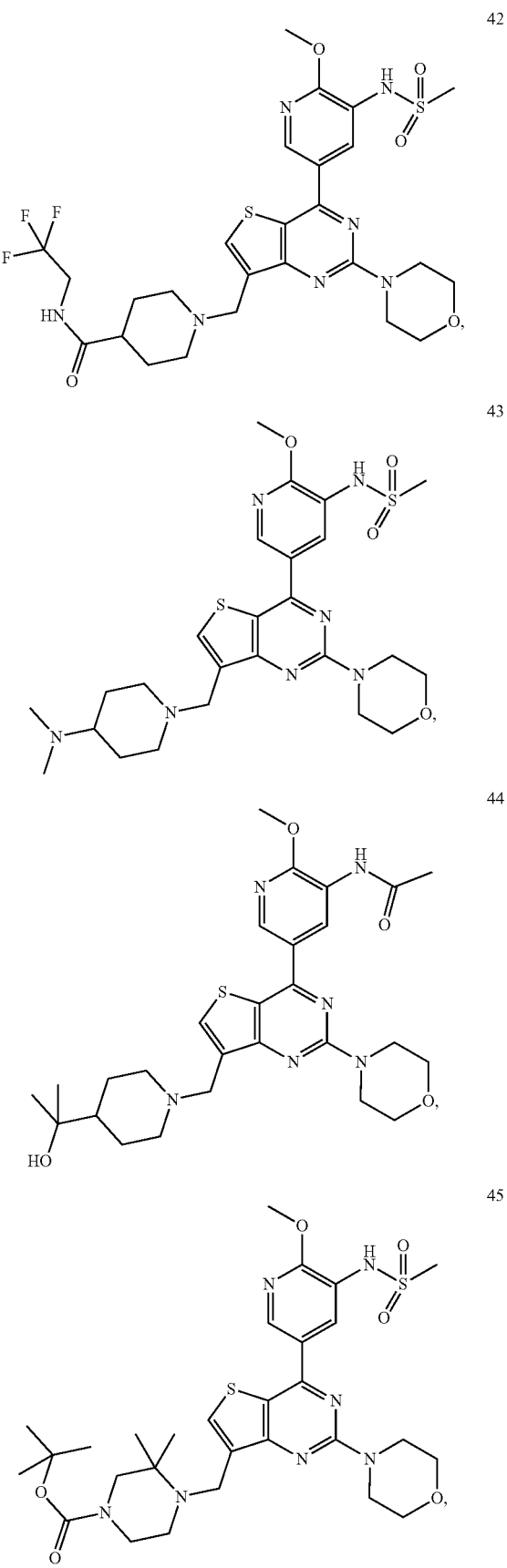

46
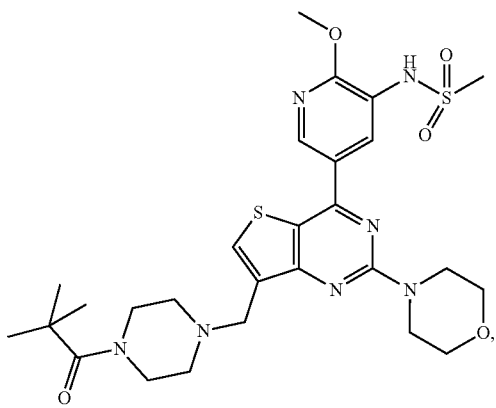
47
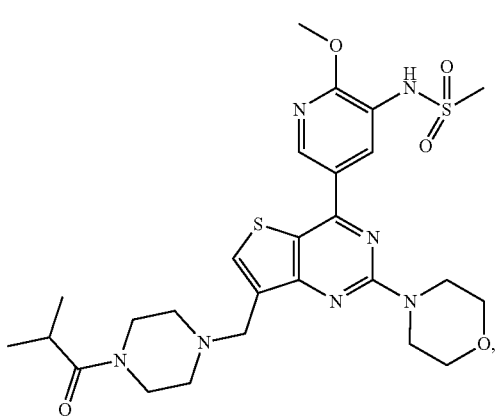
48
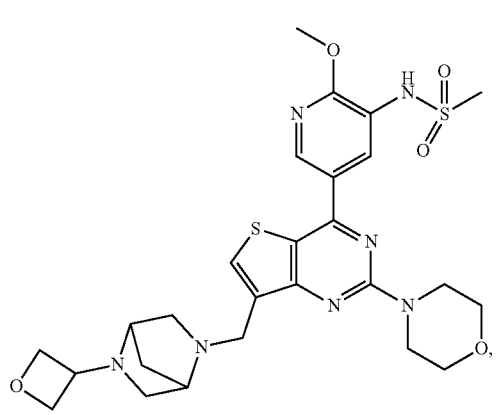
49
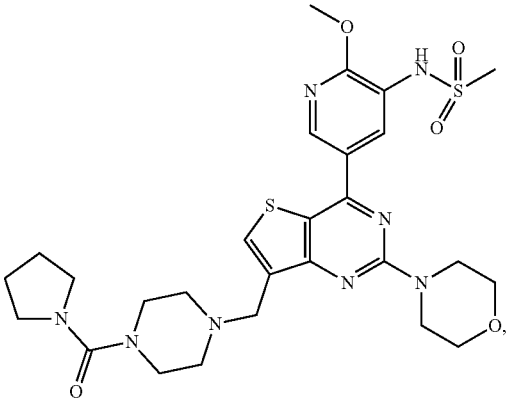
50
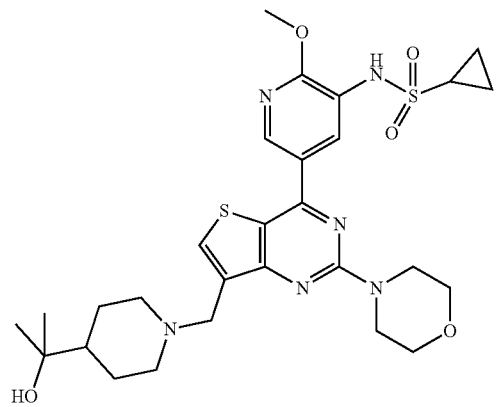
51
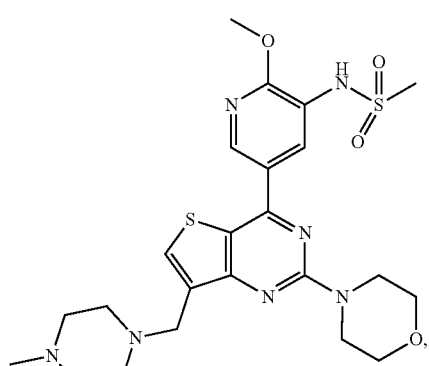
52
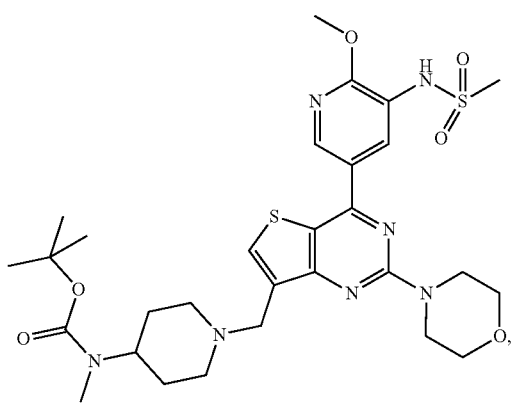
53
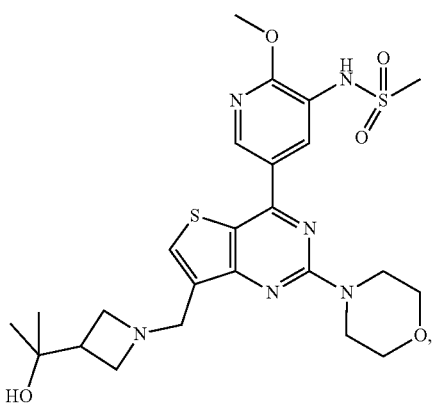

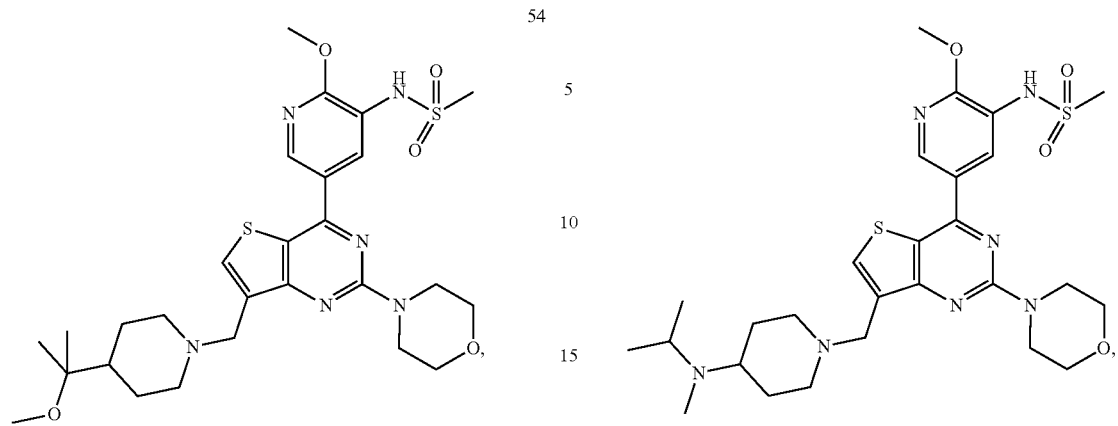

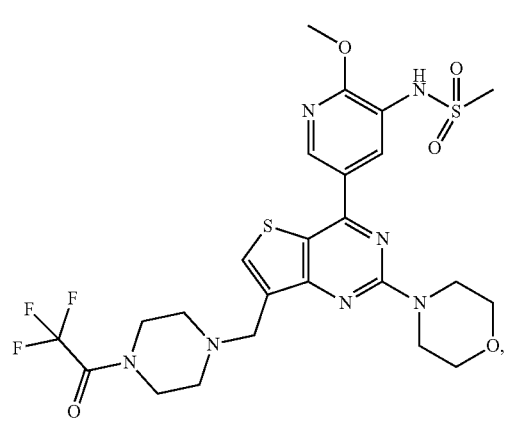
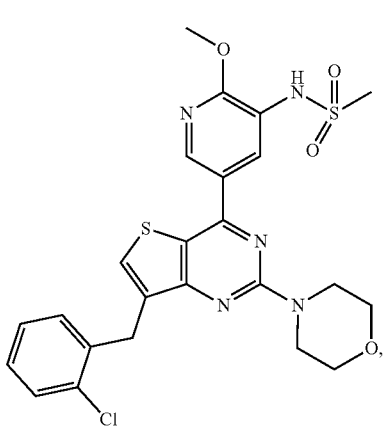
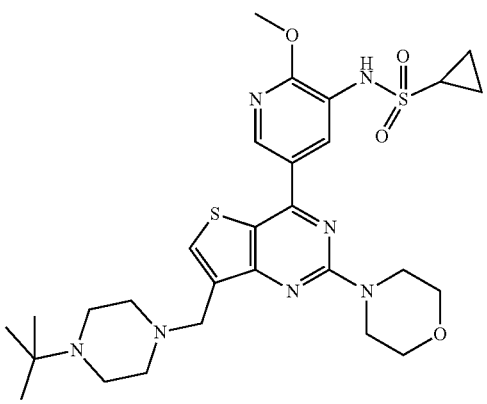
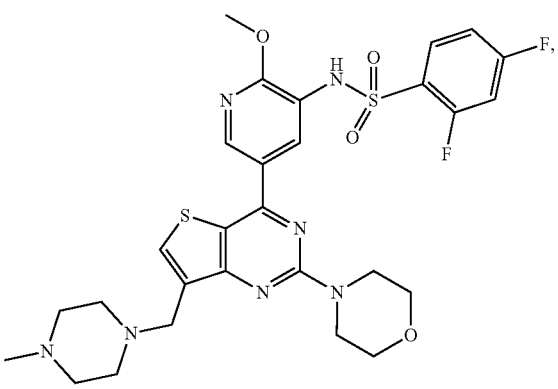
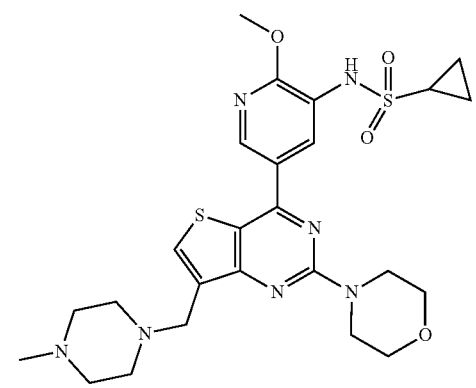

70
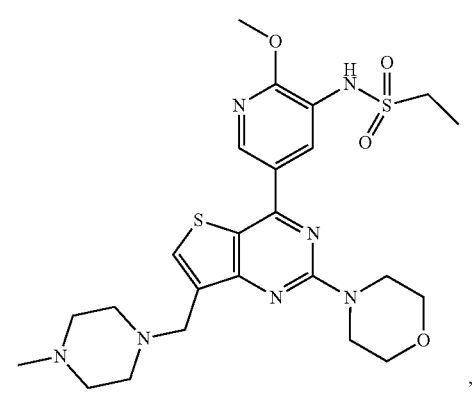
71
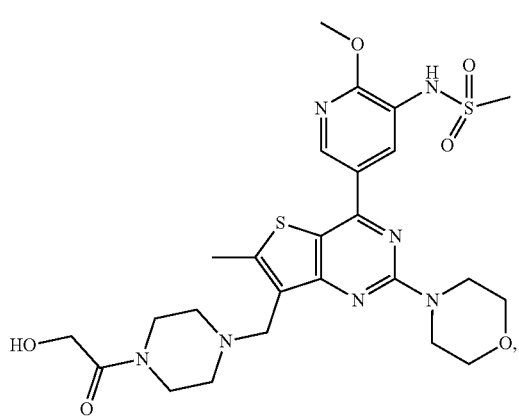
72
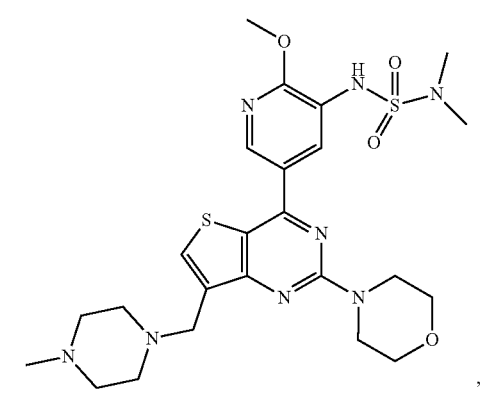
73
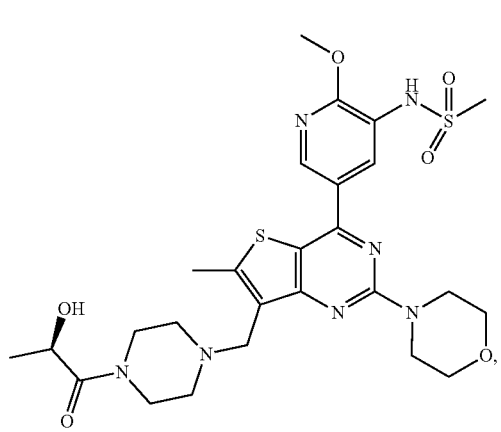
74
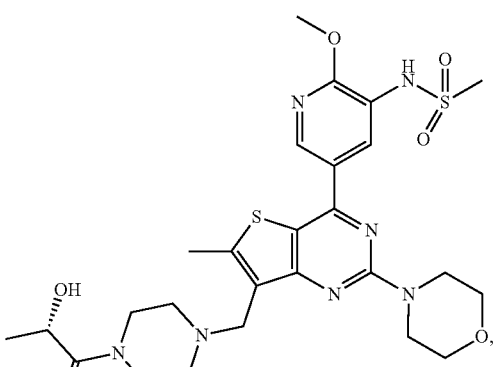
75
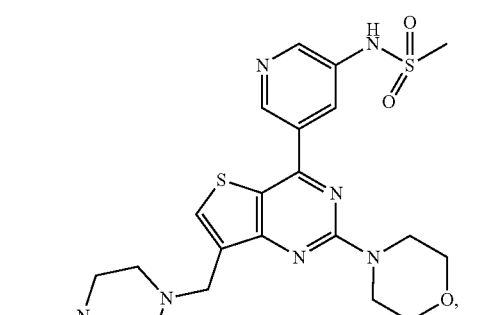
76
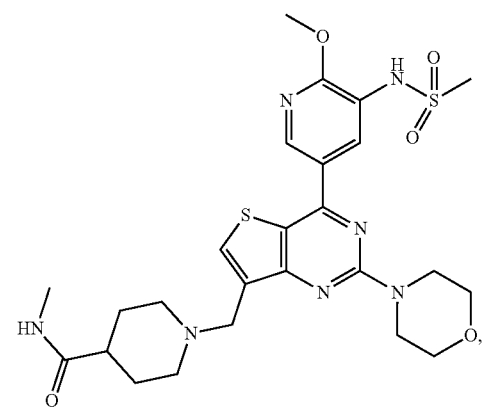
77

293
-continued
78
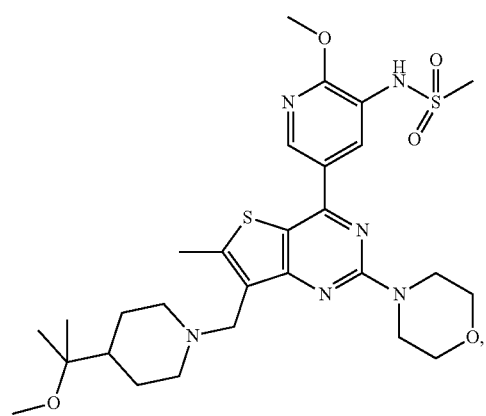
79
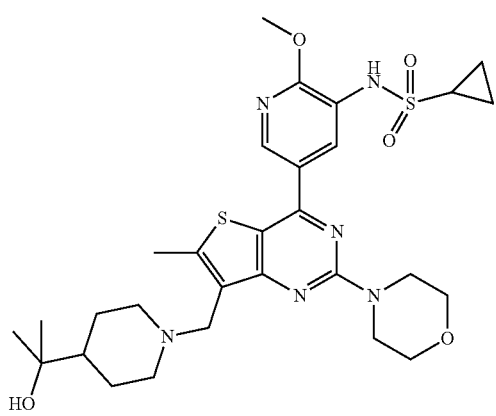
80
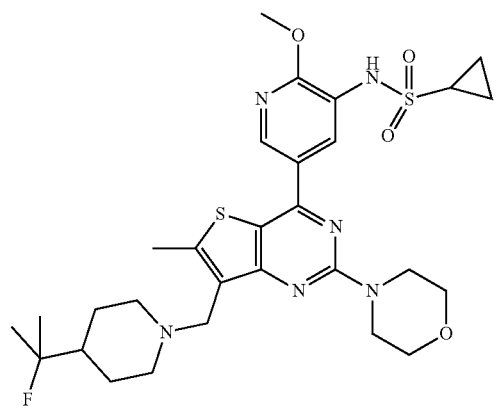
81
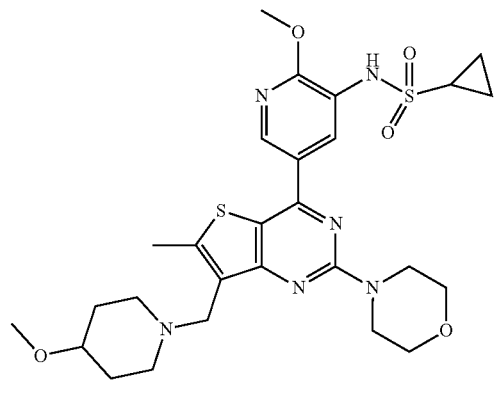
294
-continued
82
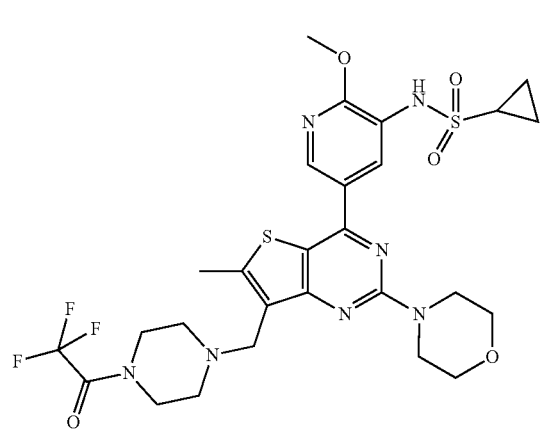
83
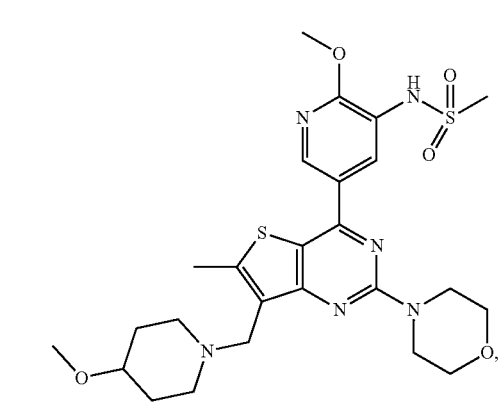
84
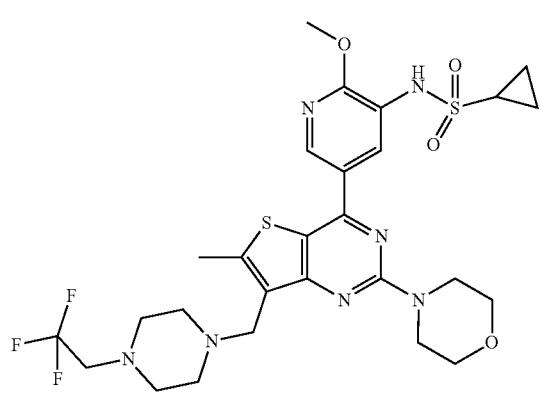
85
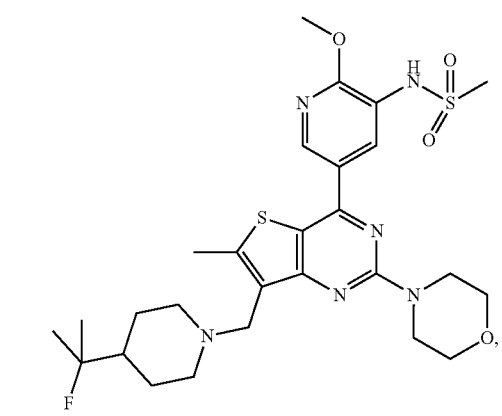

-continued
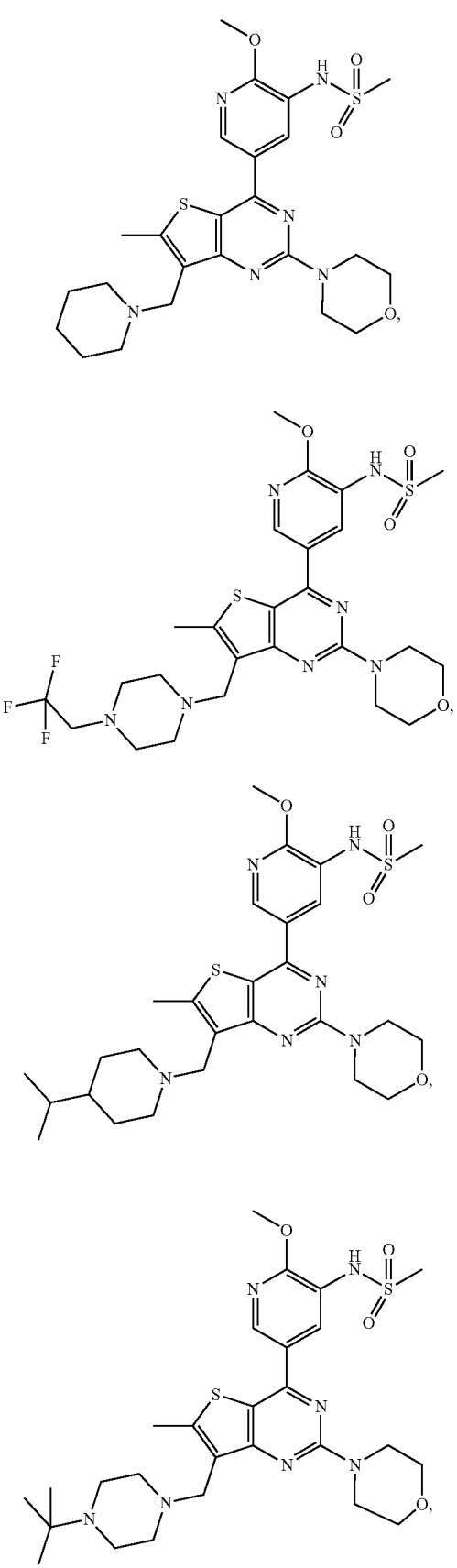
-continued
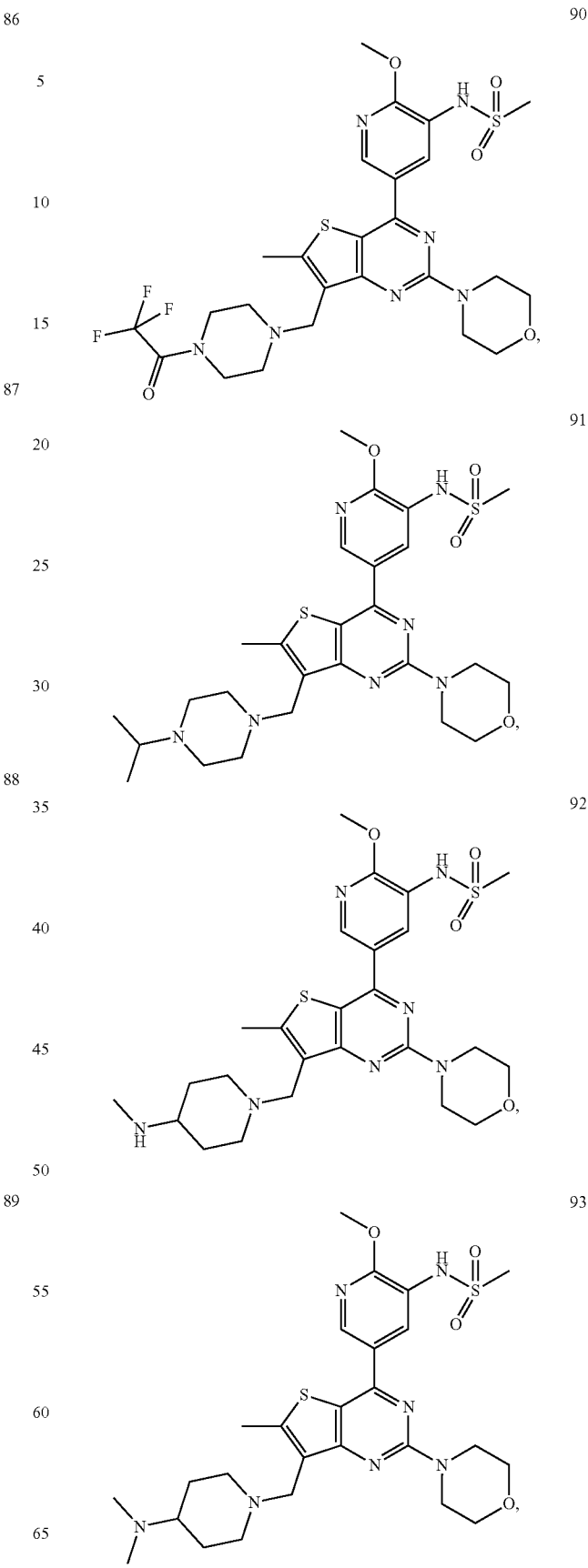

297
-continued
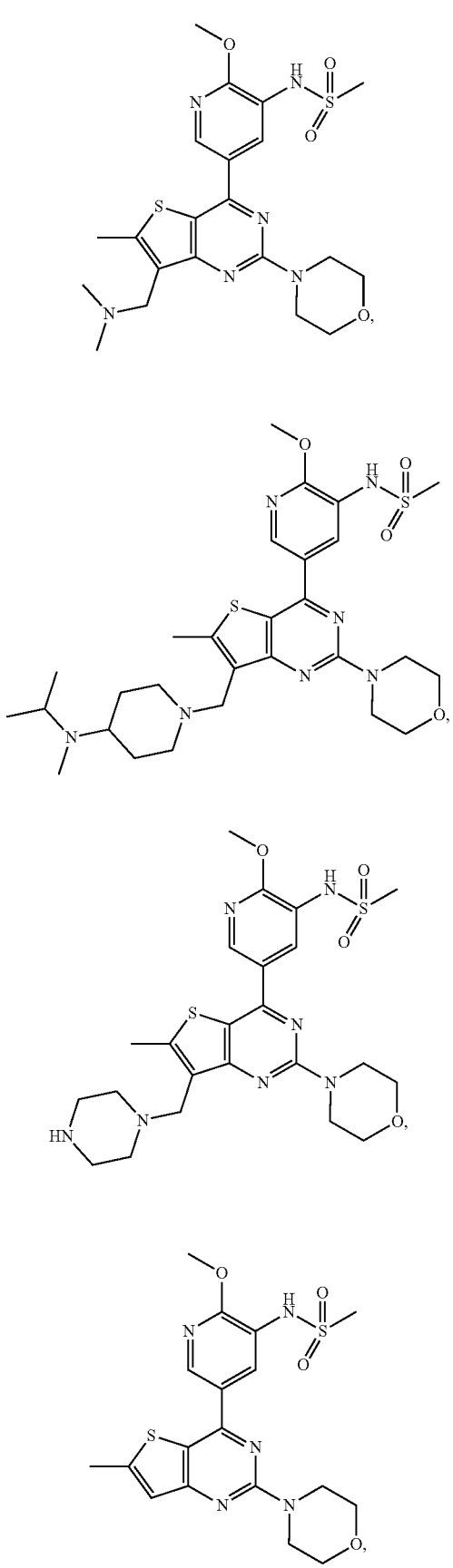
298
-continued
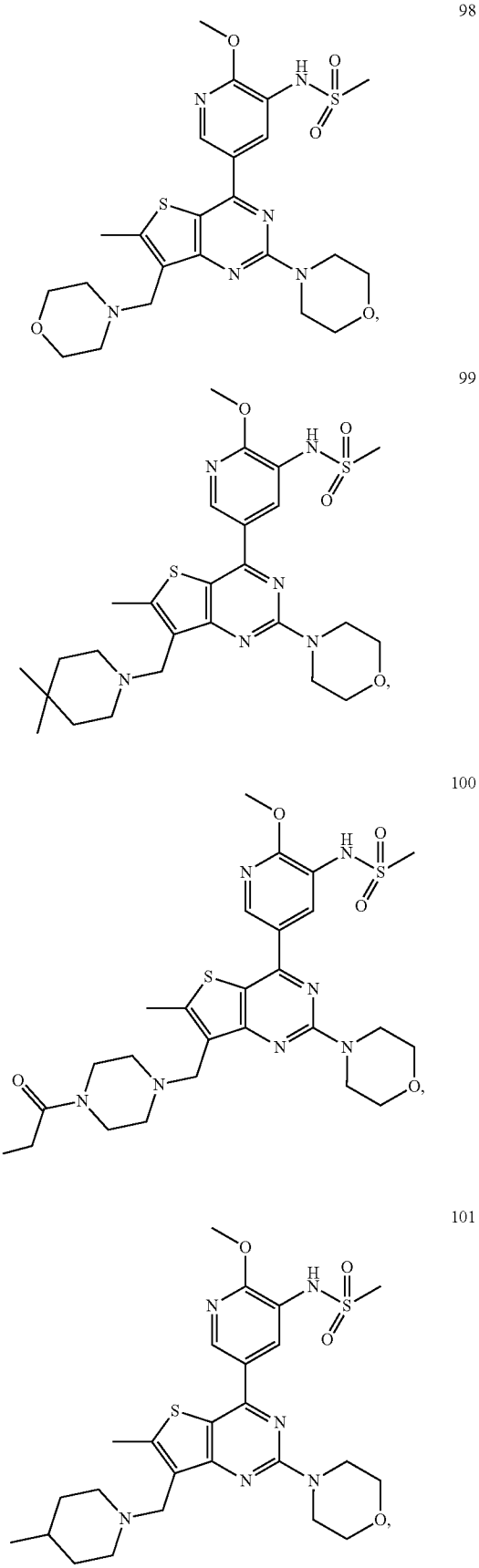

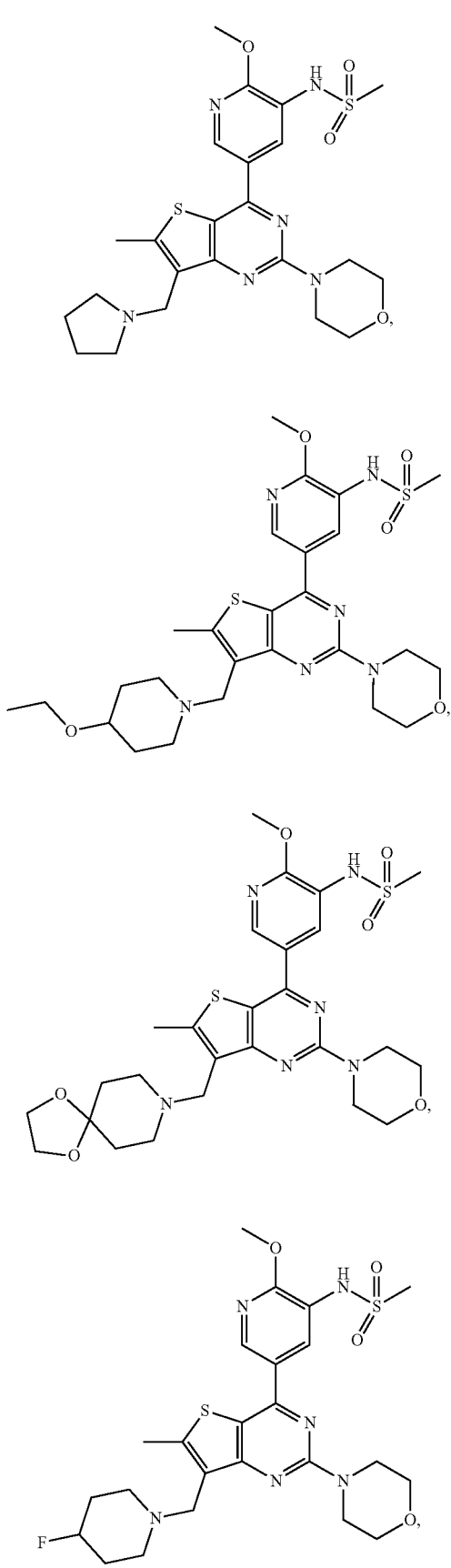
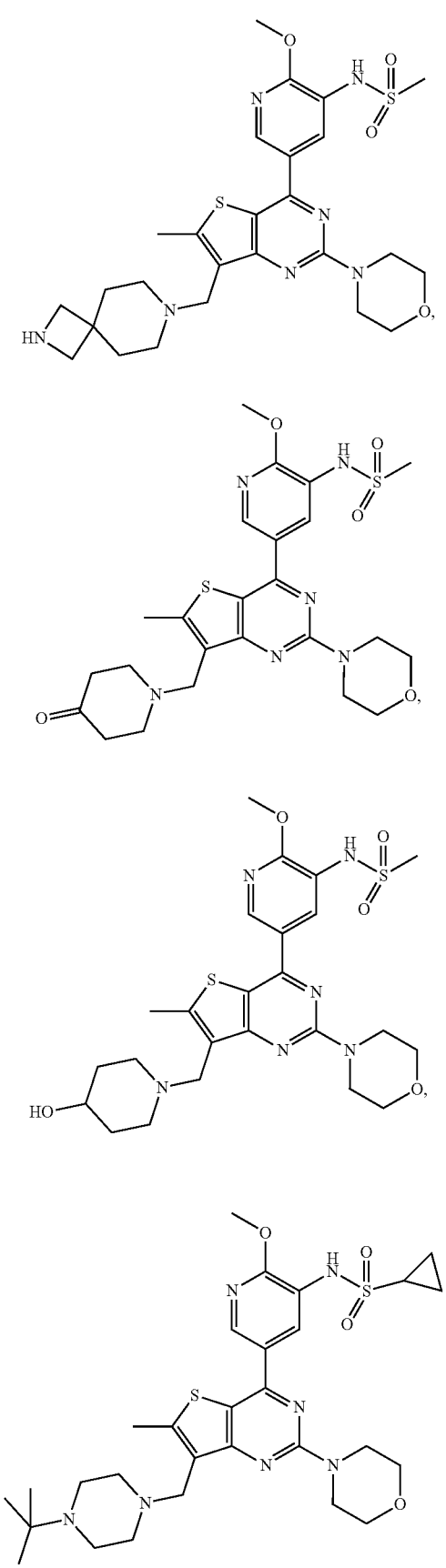

110
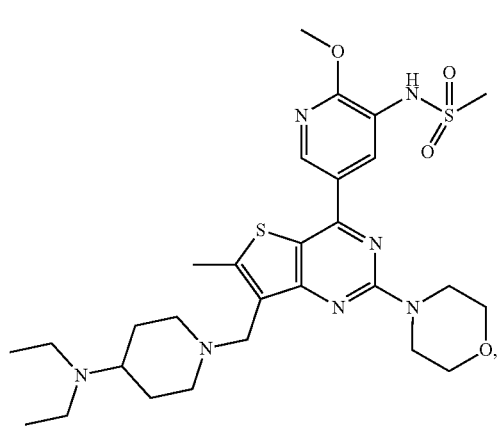
111
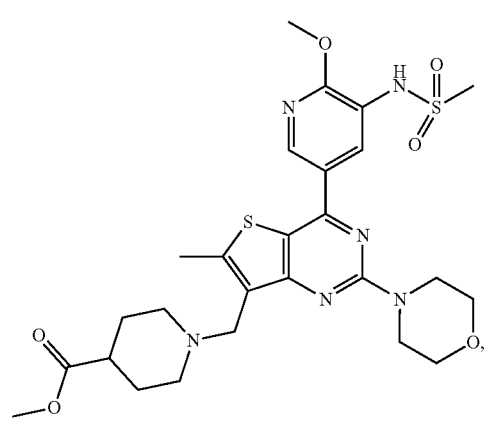
112
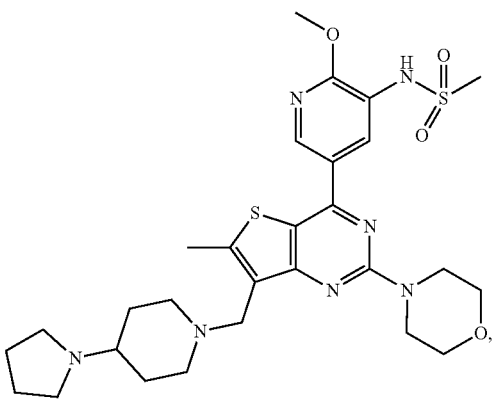
113
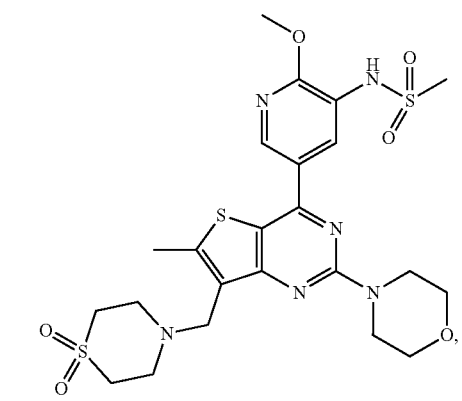
114
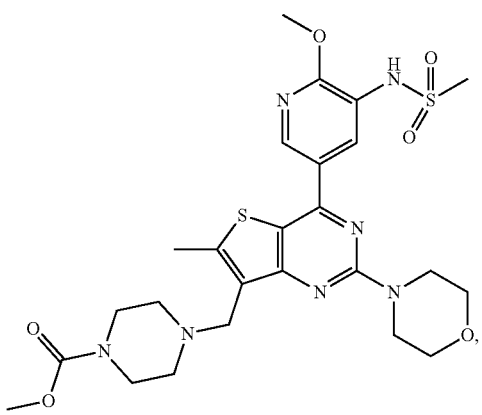
115
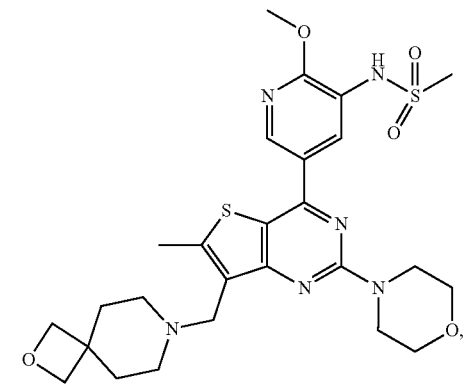
116
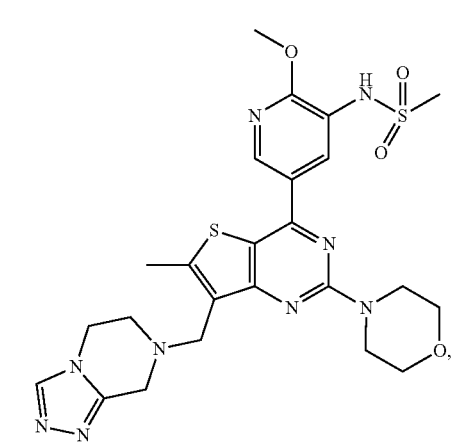
117
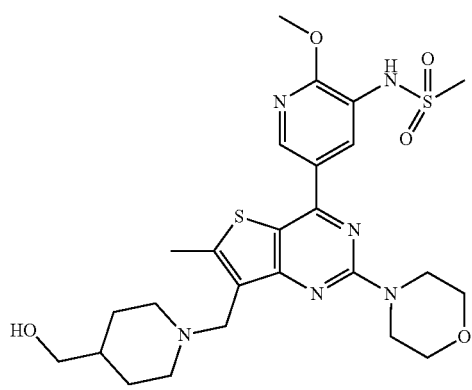

118 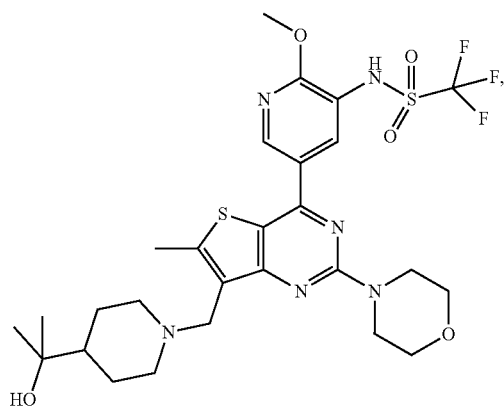
119 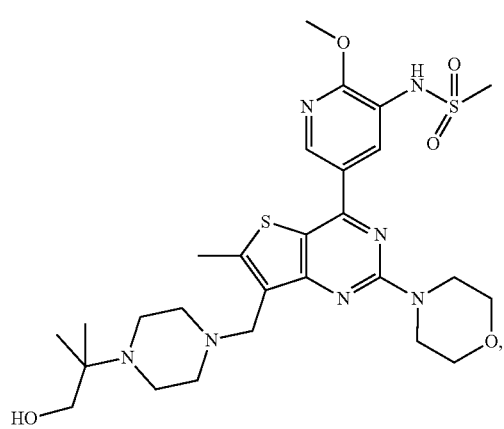
120 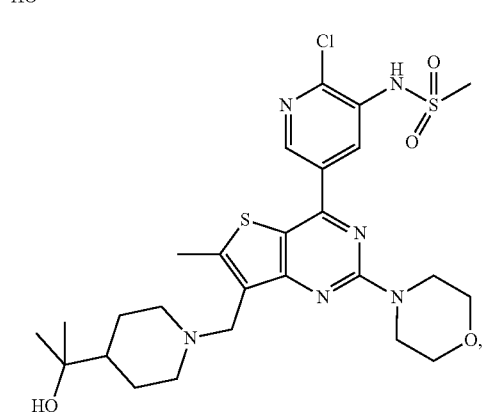
121 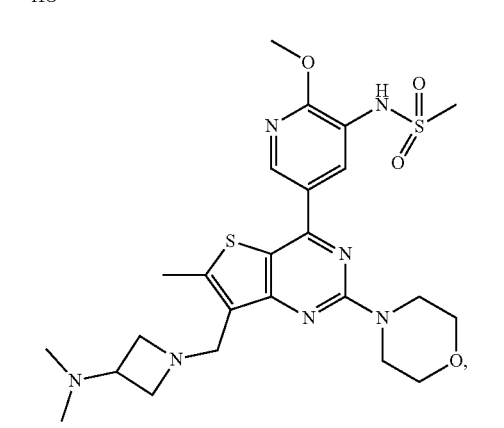
122 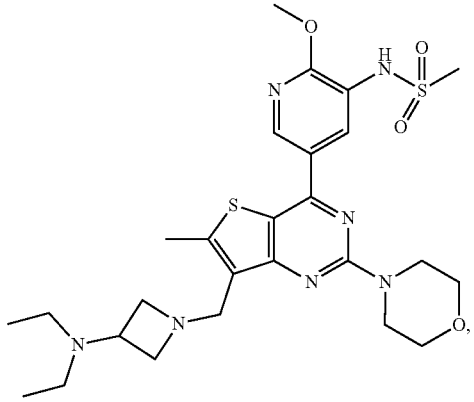
123 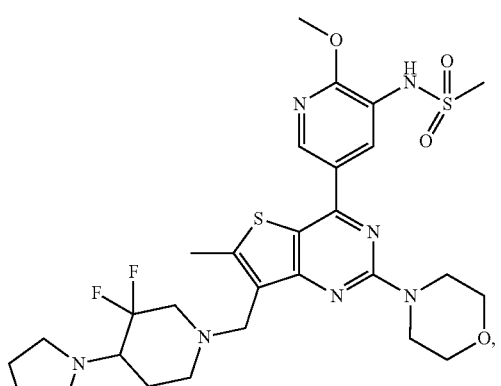
124 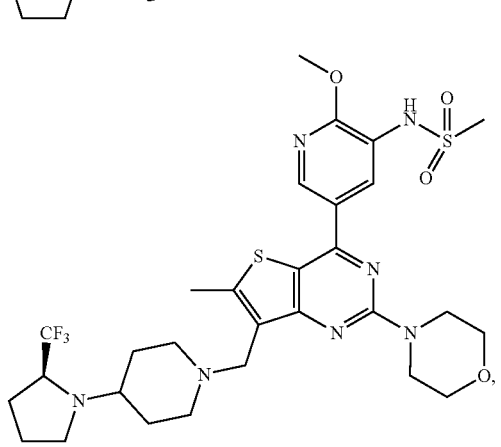
125 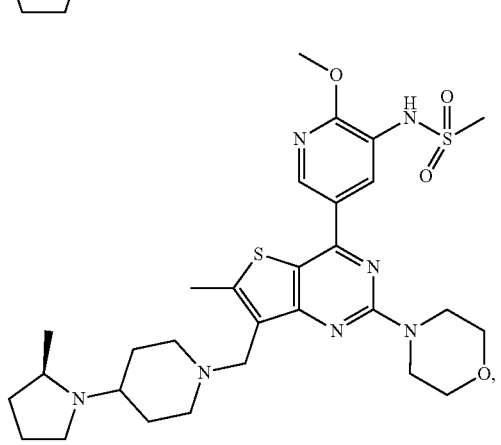

126
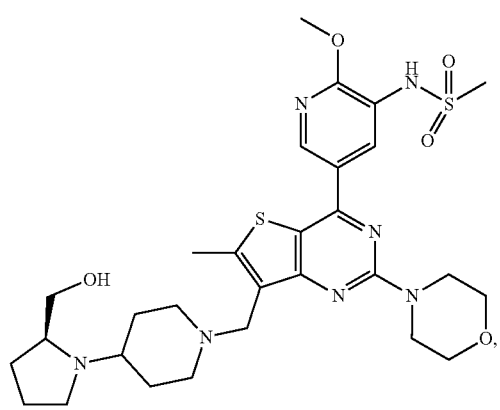
127
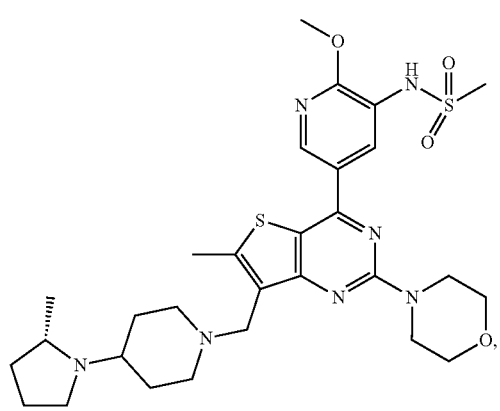
128
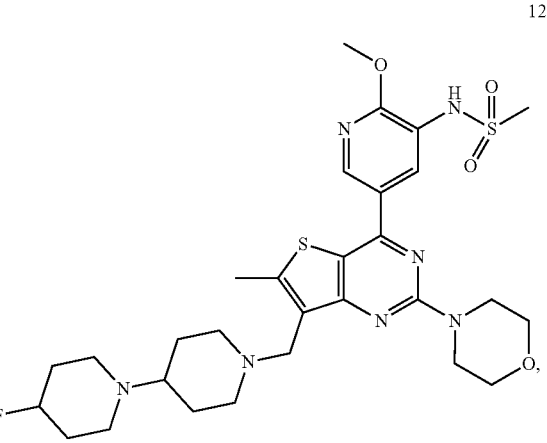
129
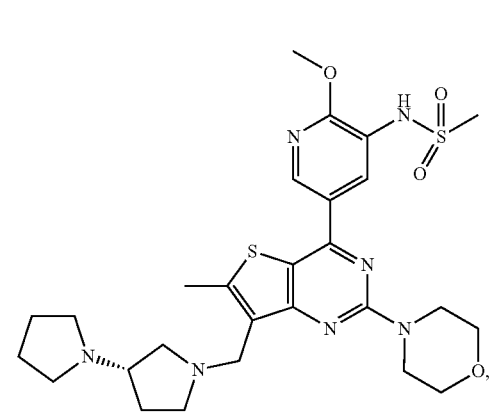
130
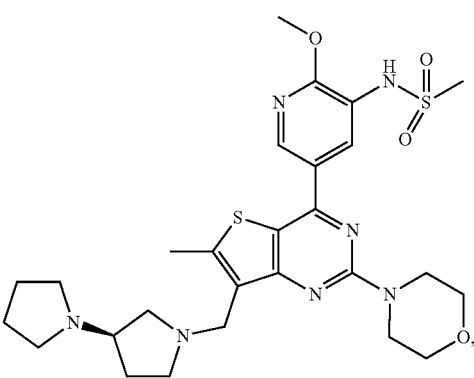
131
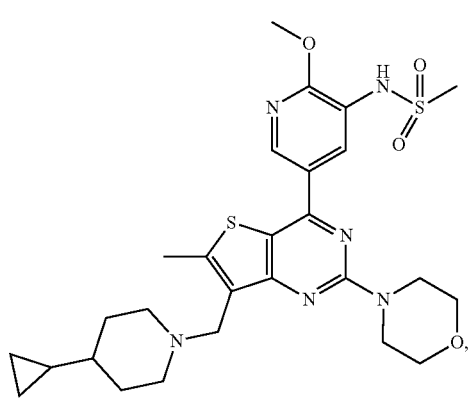
132
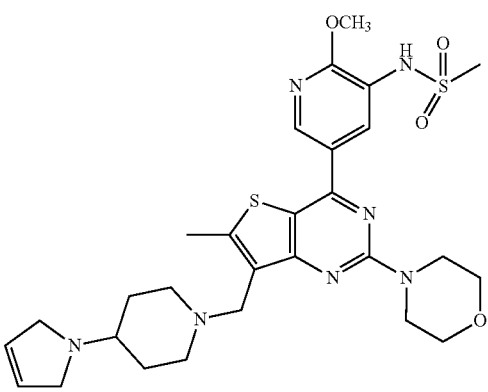
133
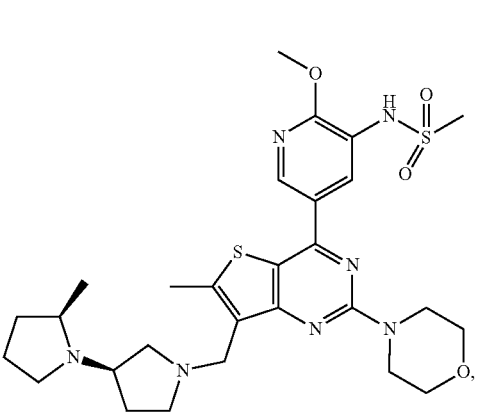

134
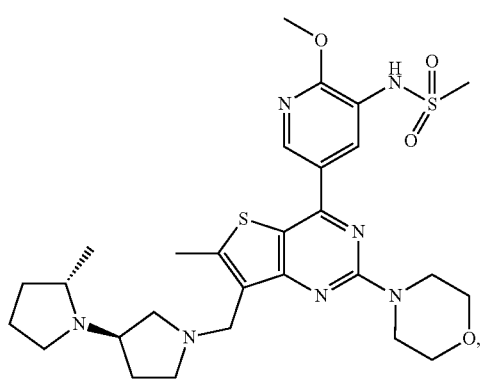
135
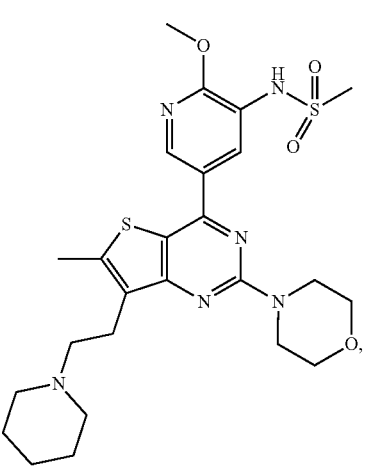
136
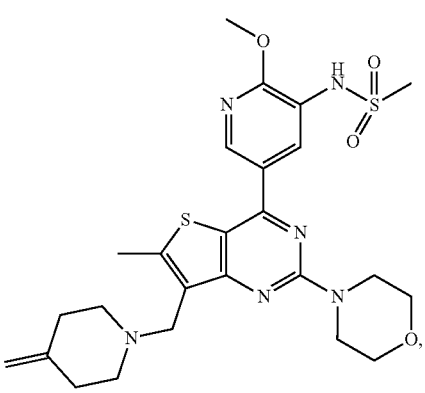
137
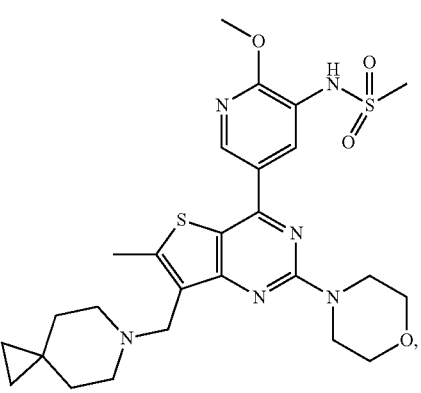
138
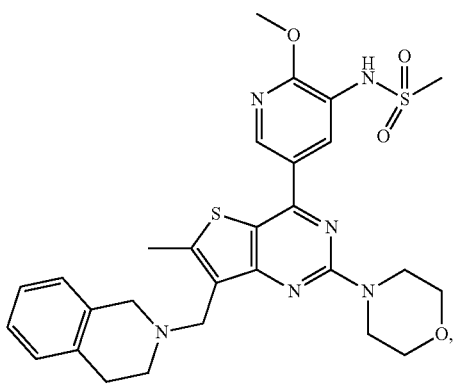
139
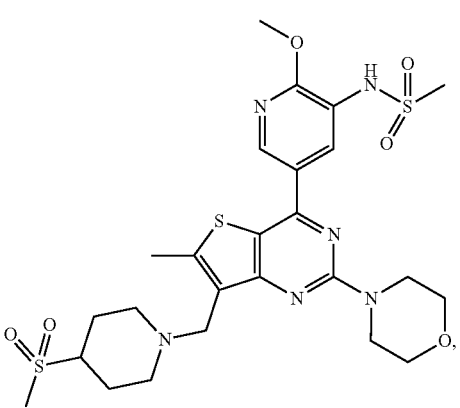
140
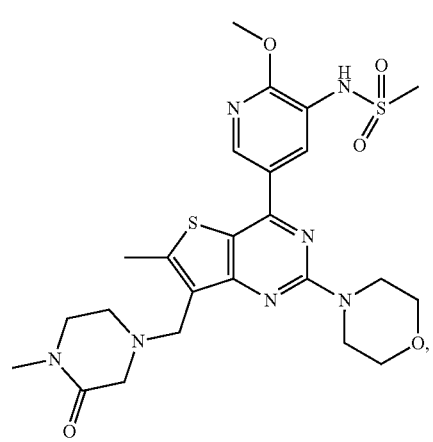
141
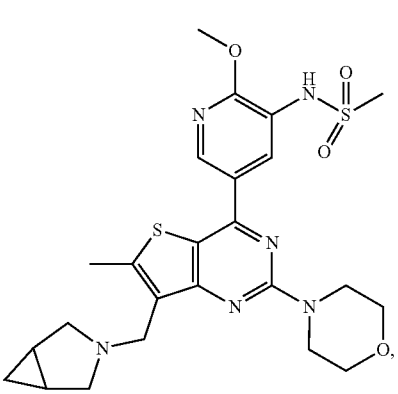

-continued
142
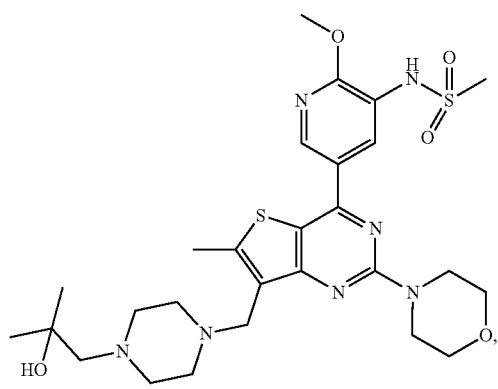
143
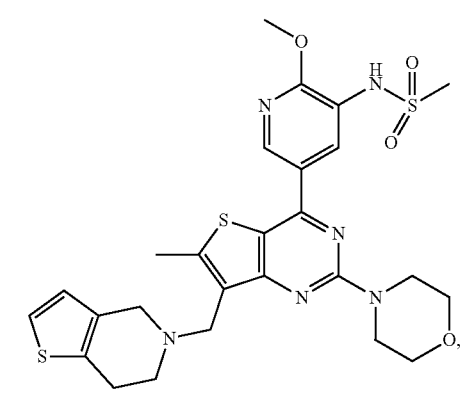
144
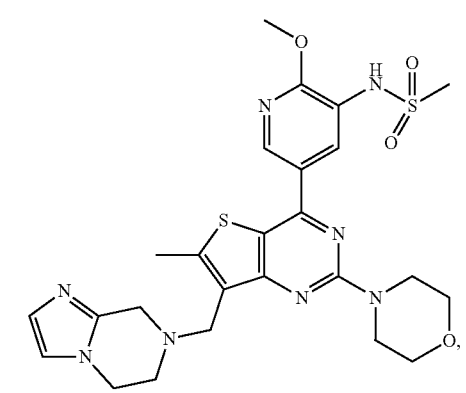
145
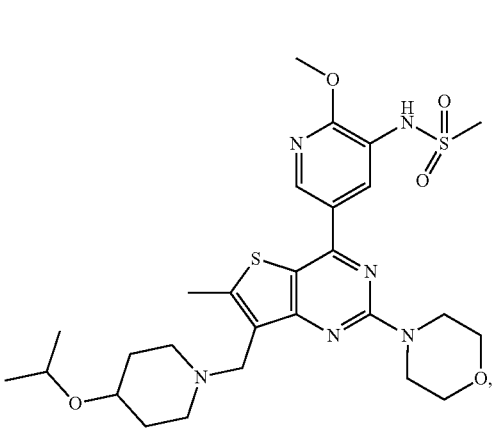
-continued
146
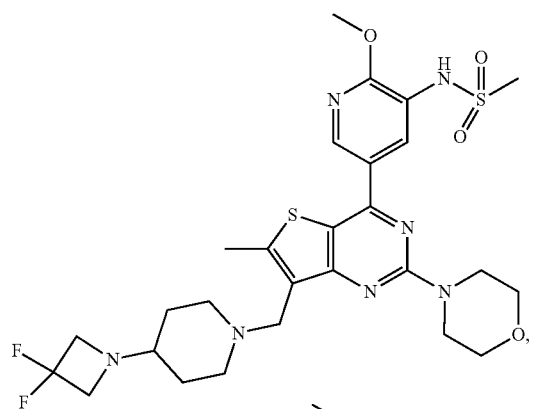
147
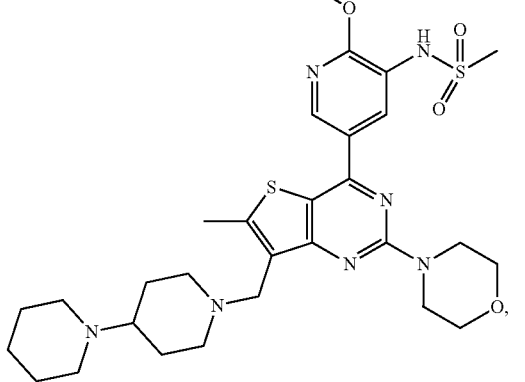
148
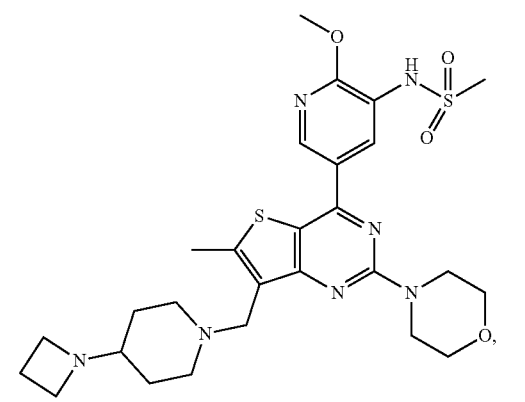
149
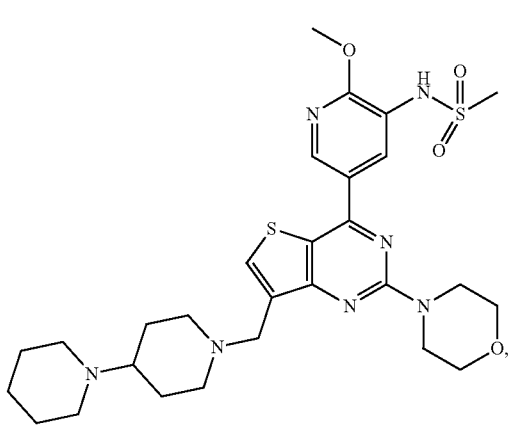

311
-continued

150

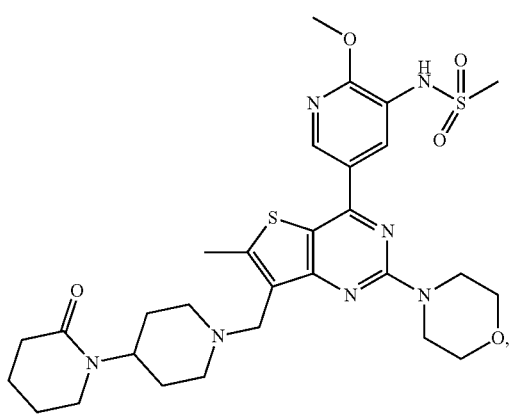

151

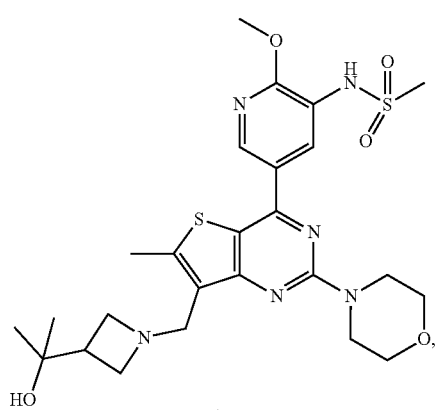

and

152

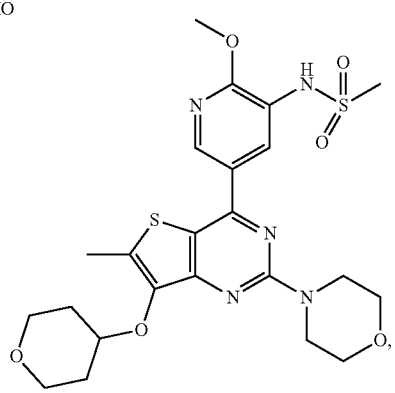

153

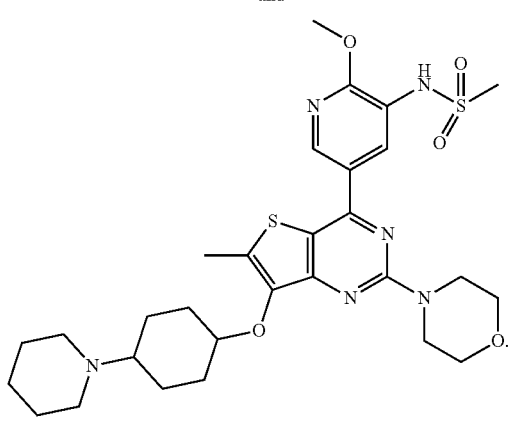

312

35. A method for preparing the fused pyrimidine compound represented by formula I according to claim 1, which is any one of the following Methods I, II, III or IV:

Method I, reacting compound I-a with $R^2BF_3K$, $R^2B(OR^{10})_2$, $R^2ZnX^1$ or $R^2MgX^1$ by the coupling reaction shown below to obtain compound I;

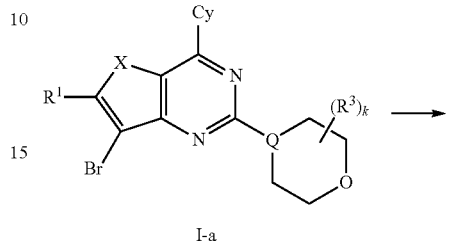

I-a

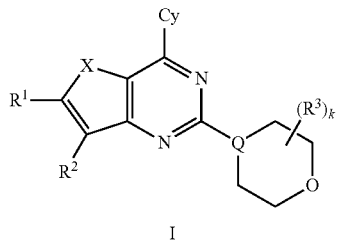

I wherein $R^{10}$ is a hydrogen, a $C_1$-$C_6$ alkyl, or a pinacol borate group formed by two $OR^{10}$ groups together with the boron atom to which they are attached as below;

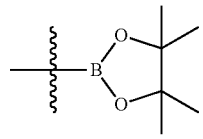 [SMILES: *B1OC(C)(C)C(C)(C)O1]

$X^1$ is Cl, Br or I; $R^1$ is as defined in claim 1; $R^2$ is as defined in claim 1; $R^3$ is as defined in claim 1; Cy is as defined in claim 1; X is as defined in claim 1; k is as defined in claim 1; Q is as defined in claim 1;

Method II: further derivatizing a compound I by deprotecting —$CO_2$t-Bu or after the deprotection, undergoing N-alkylation, N-arylation, reductive amination, or N-acylation reaction, to obtain the target compound I;

the general formula of compound I is as below:

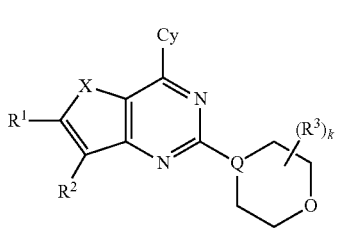

I wherein in the case of compound I as a starting material, $R^2$ is the group shown below, and each of $n_1$ and $n_2$ is independently 0, 1 or 2;

the general formula of compound I is as below:

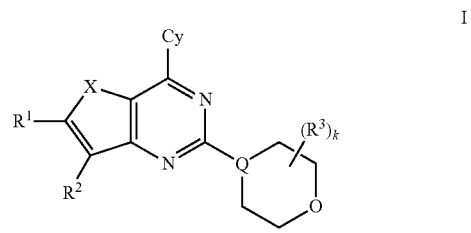

wherein in the case of compound I as a starting material, $R^2$ is the group shown below, and each of $n_1$ and $n_2$ are independently 0, 1 or 2;

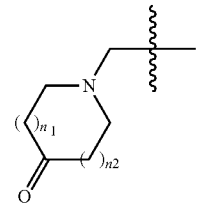

in the case of compound I as a product, $R^2$ is the group shown below: each of $n_1$ and $n_2$ is independently 0, 1 or 2;

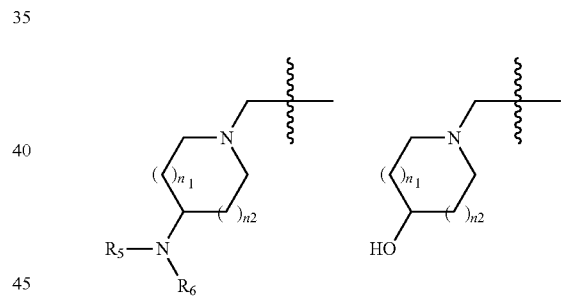

$R^5$ or $R^6$ is as defined in claim 1; Q is as defined in claim 1;

Method IV: allowing compound I-a to undergo Pd-catalyzed hydroxylation reaction to obtain a phenol intermediate I-a', followed by a nucleophilic substitution reaction between I-a' and $R^5$—OTs, $R^5$—OMs or $R^5$—$X^1$, thus to obtain the target compound I;

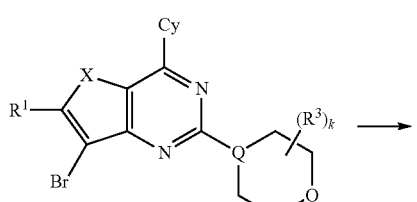

I-a

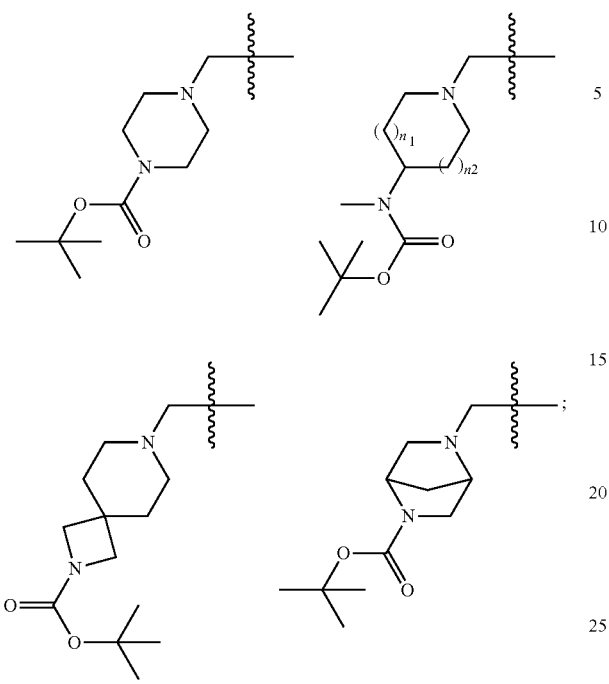

in the case of compound I as a product, $R^2$ is the group shown below:

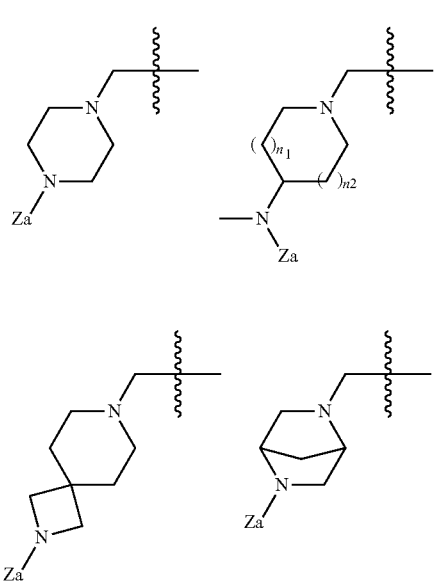

Za is a hydrogen, —C(=Y)$R^5$, —C(=Y)N$R^5R^6$, —S(O)$R^5$, —S(O)$_2R^5$, a $C_1$-$C_{12}$ alkyl, a $C_3$-$C_{12}$ carbocyclyl, a $C_2$-$C_{20}$ heterocyclyl, a $C_6$-$C_{20}$ aryl or a $C_1$-$C_{20}$ heteroaryl; $R^5$ or $R^6$ is as defined in claim 1; Q is as defined in claim 1;

Method III: further derivatizing a Compound I via reduction or reductive amination reaction, to obtain the target compound I;

-continued

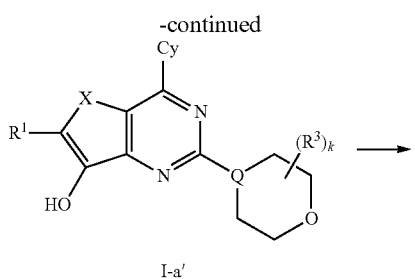

I-a'

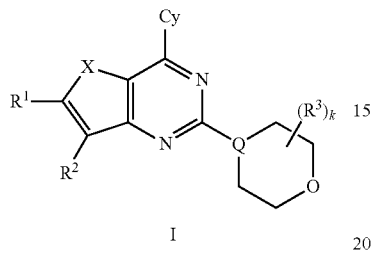

I wherein $R^2$ is —$(CR^8R^9)_mOR^5$, m is 0; $X^1$ is Cl, Br or I; $R^1$ is as defined in claim 1; $R^3$ is as defined in claim 1; Cy is as defined in claim 1; X is as defined in claim 1; k is as defined in claim 1; Q is as defined in claim 1; $R^5$ is a $C_1$-$C_{12}$ alkyl, a $C_3$-$C_{12}$ carbocyclyl or a $C_2$-$C_{20}$ heterocyclyl, and in $R^5$ the carbon atom other than the one α-position to the heteroatom is linked with the oxygen atom in "—$(CR^8R^9)_mOR^5$".

36. Compound according to claim 1, which is a compound I-a, I-c or 152-a, containing a structural formula shown below:

I-a

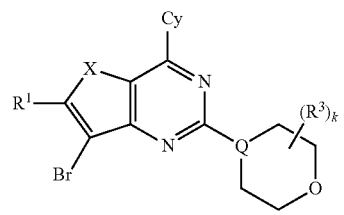

I-c

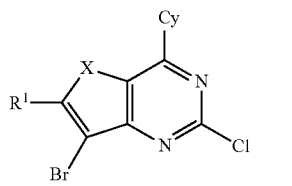

152-a

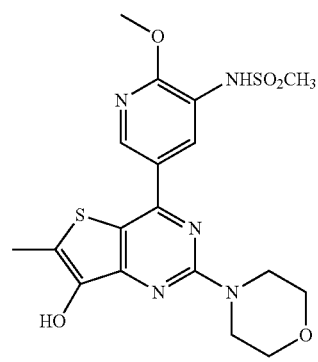

wherein, Q is N; $R^1$ is as defined in claim 1; $R^3$ is as defined in claim 1; Cy is as defined in claim 1; X is as defined in claim 1; k is as defined in claim 1.

37. The compound I-a or I-c according to claim 36, wherein, said compound I-a is a specific compound selected from the group consisting of:

1-b

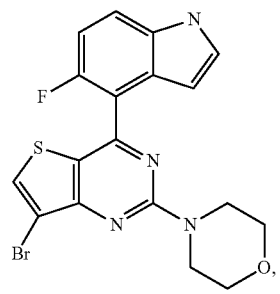

3-a

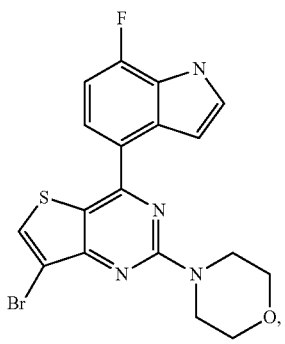

4-a

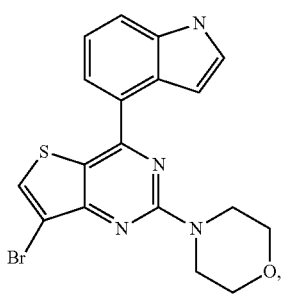

8-c

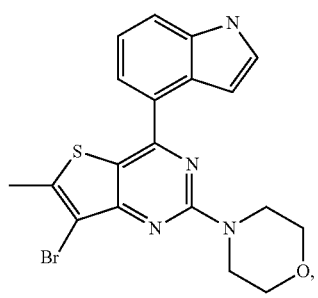

317
-continued
17-a
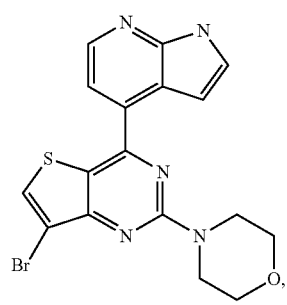
18-c
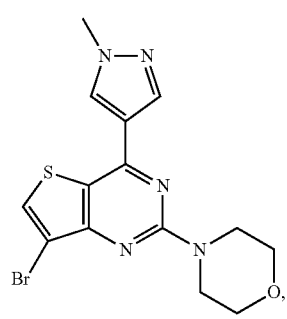
20-c
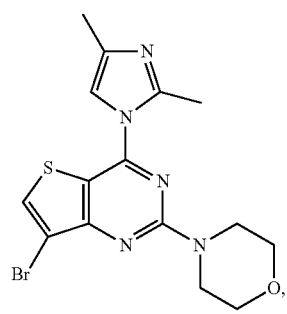
27-a
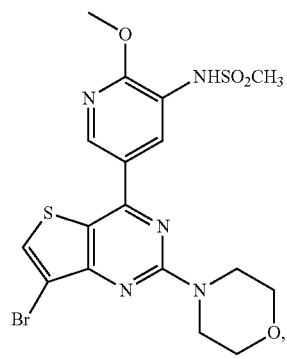
31-c
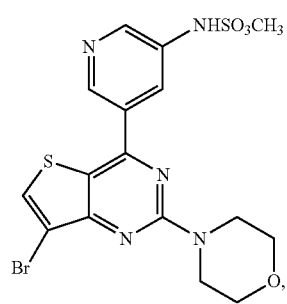
318
-continued
50-a
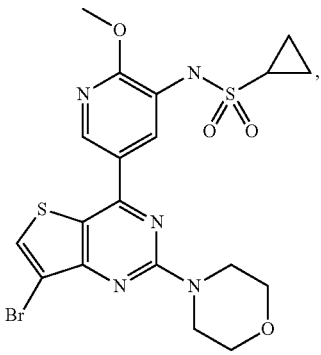
70-a
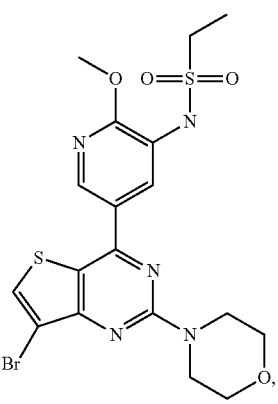
71-c
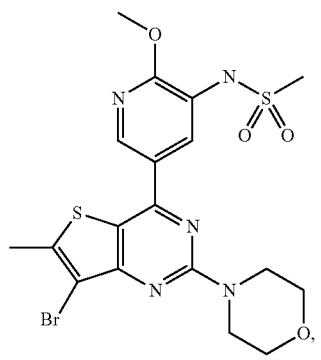
72-a
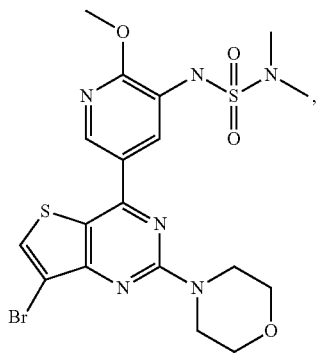

79-a
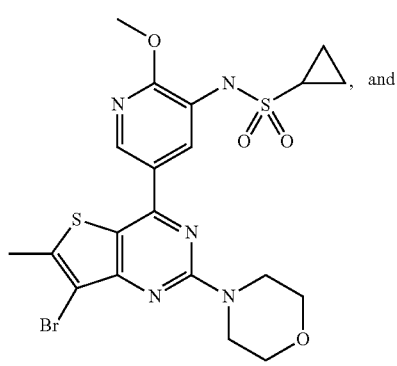
, and
120-a
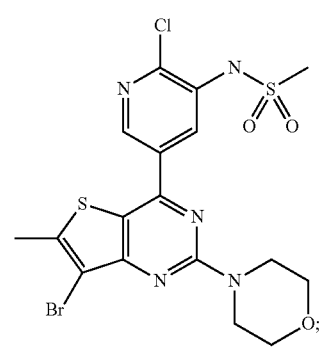
;
said compound I-c is a specific compound selected from the group consisting of:
1-c
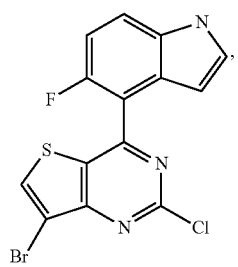
,
3-b
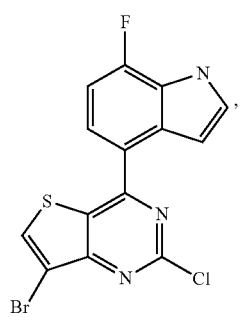
,
4-b
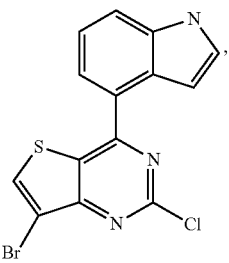
,
8-e
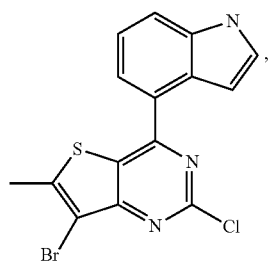
,
17-b
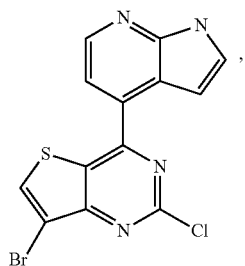
,
18-d
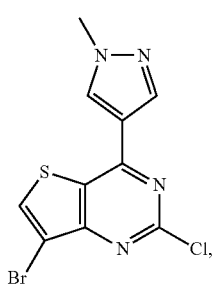
,
27-b
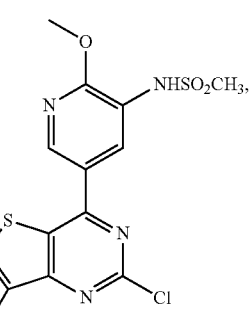
,

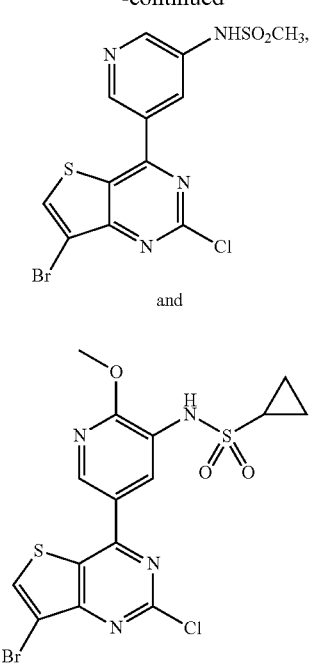

38. A kinase inhibitor, which comprises the fused pyrimidine compound represented by formula I, the pharmaceutically acceptable salt, the hydrate, the solvate, the optical isomer or the prodrug thereof according to claim 1.

39. A method of treating a disease associated with kinase in a subject in need thereof, comprising: administering an effective amount of the fused pyrimidine compound represented by formula I, the pharmaceutically acceptable salt, the hydrate, the solvate, the optical isomer or the prodrug thereof according to claim 1 to the subject.

40. The method according to claim 39, wherein said kinase is PI3 kinase.

41. The method according to claim 40, wherein said PI3 kinase is a p110 δ subtype of the PI3 kinase.

42. The method according to claim 39, wherein said "disease associated with kinase" comprises a disease selected from the group consisting of cancer, immune disease, metabolism and/or endocrine disorder, cardiovascular disease, viral infection and inflammation, and neurological disease.

43. The method according to claim 42, wherein said immune disease comprises a disease selected from the group consisting of rheumatoid arthritis, psoriasis, ulcerative colitis, Crohn's disease and systemic lupus erythematosus; said cardiovascular disease comprises blood tumor; and said viral infection and inflammation comprise asthma and/or atopic dermatitis.

44. A pharmaceutical composition, which comprises a therapeutically effective amount of the fused pyrimidine compound represented by formula I, the pharmaceutically acceptable salt, the hydrate, the solvate, the optical isomer or the prodrug thereof according to claim 1, and a pharmaceutically acceptable carrier.

45. A method for treating a disease associated with kinase, which comprises administering to a patient an effective dosage of the pharmaceutical composition according to claim 44.

* * * * *